United States Patent
Cheung et al.

(10) Patent No.: US 11,787,864 B2
(45) Date of Patent: *Oct. 17, 2023

(54) HETERODIMERIC FC-FUSED PROTEINS

(71) Applicant: Dragonfly Therapeutics, Inc., Waltham, MA (US)

(72) Inventors: Ann F. Cheung, Lincoln, MA (US); Jean-Marie Cuillerot, Somerville, MA (US); Asya Grinberg, Lexington, MA (US); Eva Gutierrez, Waltham, MA (US); William Haney, Wayland, MA (US); Nicolai Wagtmann, Concord, MA (US)

(73) Assignee: Dragonfly Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,282

(22) Filed: Sep. 1, 2022

(65) Prior Publication Data

US 2023/0033425 A1 Feb. 2, 2023

Related U.S. Application Data

(63) Continuation of application No. 17/287,849, filed as application No. PCT/US2019/057721 on Oct. 23, 2019.

(60) Provisional application No. 62/781,898, filed on Dec. 19, 2018, provisional application No. 62/749,489, filed on Oct. 23, 2018, provisional application No. 62/788,499, filed on Jan. 4, 2019, provisional application No. 62/827,347, filed on Apr. 1, 2019, provisional application No. 62/895,889, filed on Sep. 4, 2019.

(51) Int. Cl.
| | | |
|---|---|---|
| *C07K 16/00* | (2006.01) | |
| *C07K 16/28* | (2006.01) | |
| *A61P 35/00* | (2006.01) | |
| *A61K 45/06* | (2006.01) | |
| *A61K 39/00* | (2006.01) | |

(52) U.S. Cl.
CPC .......... *C07K 16/2851* (2013.01); *A61K 45/06* (2013.01); *A61P 35/00* (2018.01); *C07K 16/283* (2013.01); *A61K 2039/505* (2013.01)

(58) Field of Classification Search
None
See application file for complete search history.

(56) References Cited

U.S. PATENT DOCUMENTS

| | | |
|---|---|---|
| 4,722,848 A | 2/1988 | Paoletti et al. |
| 5,173,414 A | 12/1992 | Lebkowski et al. |
| 5,624,821 A | 4/1997 | Winter et al. |
| 5,648,260 A | 7/1997 | Winter et al. |
| 5,807,706 A | 9/1998 | Carter et al. |
| 5,849,589 A | 12/1998 | Tedder et al. |
| 6,194,551 B1 | 2/2001 | Idusogie et al. |
| 6,737,056 B1 | 5/2004 | Presta |
| 6,838,260 B2 | 1/2005 | Gillies et al. |
| 6,864,235 B1 | 3/2005 | Turley et al. |
| 7,226,998 B2 | 6/2007 | Gillies et al. |
| 7,576,193 B2 | 8/2009 | Gillies et al. |
| 7,695,936 B2 | 4/2010 | Carter et al. |
| 7,879,319 B2 | 2/2011 | Gillies et al. |
| 7,943,743 B2 | 5/2011 | Korman et al. |
| 7,951,917 B1 | 5/2011 | Arathoon et al. |
| 8,034,630 B2 | 10/2011 | Terashima et al. |
| 8,044,022 B2 | 10/2011 | Kolodka et al. |
| 8,163,498 B2 | 4/2012 | Fujita |
| 8,192,744 B2 | 6/2012 | Stromblad et al. |
| 8,592,562 B2 | 11/2013 | Kannan et al. |
| 8,674,083 B2 | 3/2014 | Presta |
| 8,679,785 B2 | 3/2014 | Carter et al. |
| 8,765,412 B2 | 7/2014 | Arathoon et al. |
| 8,802,093 B2 | 8/2014 | Johnson et al. |
| 8,871,912 B2 | 10/2014 | Davis et al. |
| 8,945,571 B2 | 2/2015 | Mössner et al. |
| 8,969,526 B2 | 3/2015 | Baehner et al. |
| 9,217,016 B2 | 12/2015 | Panitch et al. |
| 9,248,182 B2 | 2/2016 | De Kruif et al. |
| 9,447,159 B2 | 9/2016 | Ast et al. |

(Continued)

FOREIGN PATENT DOCUMENTS

| | | |
|---|---|---|
| CN | 104955953 A | 9/2015 |
| EP | 2691417 B1 | 8/2018 |

(Continued)

OTHER PUBLICATIONS

U.S. Appl. No. 17/920,174, filed Oct. 20, 2022, Formulation, Dosage Regimen, and Manufacturing Process for Heterodimeric Fc-Fused Proteins.

Schlothauer et al. 2016 "Novel human IgG1 and IgG4 Fc-engineered antibodies with completely abolished immune effector functions," Protein Engineering, Design and Selection, 29(10):457-466.

(Continued)

*Primary Examiner* — Mark Halvorson

(74) *Attorney, Agent, or Firm* — Goodwin Procter LLP

(57) ABSTRACT

The present invention provides Fc-fused protein constructs, which as monovalent dimers have a higher serum half-life compared to a native/natural molecule, and are, therefore, advantageous for achieving higher titers of the proteins during production, higher stability during storage, and improved efficacy when used as a therapeutic. Also provided are Fc-fused protein constructs having mutations in the Fc region that reduce effector functions, which have increased activity to inhibit tumor growth and are, therefore, advantageous when used as a cancer therapy.

13 Claims, 52 Drawing Sheets

Specification includes a Sequence Listing.

(56) References Cited

U.S. PATENT DOCUMENTS

| | | | |
|---|---|---|---|
| 9,493,578 | B2 | 11/2016 | Lazar et al. |
| 9,505,848 | B2 | 11/2016 | Davis et al. |
| 9,562,109 | B2 | 2/2017 | Von Kreudenstein et al. |
| 9,637,557 | B2 | 5/2017 | Scheer et al. |
| 9,751,919 | B2 | 9/2017 | Saward et al. |
| 9,795,686 | B2 | 10/2017 | Lee et al. |
| 9,951,145 | B2 | 4/2018 | Kim et al. |
| 10,011,644 | B2 | 7/2018 | Rueger et al. |
| 10,047,167 | B2 | 8/2018 | Demarest et al. |
| 10,696,722 | B2 | 6/2020 | Kim et al. |
| 10,767,760 | B2 | 9/2020 | Ando |
| 11,078,249 | B2 | 8/2021 | Kim et al. |
| 2002/0055488 | A1 | 5/2002 | Wessels et al. |
| 2007/0259380 | A1 | 11/2007 | Sumida et al. |
| 2010/0015089 | A1 | 1/2010 | Gillies et al. |
| 2010/0256339 | A1 | 10/2010 | Bossenmaier et al. |
| 2010/0286374 | A1 | 11/2010 | Kannan et al. |
| 2011/0054151 | A1 | 3/2011 | Lazar et al. |
| 2012/0149876 | A1 | 6/2012 | Von Kreudenstein et al. |
| 2013/0039913 | A1 | 2/2013 | Labrijn et al. |
| 2014/0072579 | A1 | 3/2014 | De Kruif et al. |
| 2014/0079689 | A1 | 3/2014 | Elliott et al. |
| 2016/0046727 | A1 | 2/2016 | Labrijn et al. |
| 2016/0194389 | A1 | 7/2016 | Regula et al. |
| 2017/0056522 | A1 | 3/2017 | Gerdes et al. |
| 2017/0198038 | A1 | 7/2017 | Gauthier et al. |
| 2017/0260252 | A1 | 9/2017 | Scheer et al. |
| 2017/0342128 | A1 | 11/2017 | Auer et al. |
| 2017/0342167 | A1 | 11/2017 | Moessner et al. |
| 2017/0342168 | A1 | 11/2017 | Schlothauer |
| 2018/0237541 | A1 | 8/2018 | Kim et al. |
| 2018/0258386 | A1 | 9/2018 | Rafii et al. |
| 2018/0282386 | A1 | 10/2018 | Vallera et al. |
| 2018/0346600 | A1 | 12/2018 | Kim et al. |
| 2019/0185584 | A1 | 6/2019 | Scheer et al. |
| 2019/0218282 | A1 | 7/2019 | Dengl et al. |
| 2020/0283524 | A1* | 9/2020 | Xu ..................... C07K 16/2896 |
| 2020/0299347 | A1* | 9/2020 | Gigout ................... C07K 14/50 |
| 2020/0362005 | A1 | 11/2020 | Kim et al. |
| 2022/0119533 | A1 | 4/2022 | Kim et al. |
| 2022/0267460 | A1* | 8/2022 | Lansing .................. A61P 35/00 |

FOREIGN PATENT DOCUMENTS

| | | |
|---|---|---|
| JP | 2021-525423 A | 12/2021 |
| KR | 10-2015-0008012 A | 1/2015 |
| WO | WO 1996/027011 A1 | 9/1996 |
| WO | WO 1999/029732 A2 | 6/1999 |
| WO | WO 2009/089004 A1 | 7/2009 |
| WO | WO 2011/131746 A2 | 10/2011 |
| WO | WO 2012/025530 A1 | 3/2012 |
| WO | WO 2012/032080 A | 3/2012 |
| WO | WO 2014/084607 A1 | 6/2014 |
| WO | WO 2014/145907 A1 | 9/2014 |
| WO | WO 2015/150447 A1 | 10/2015 |
| WO | WO 2017/027422 A1 | 2/2017 |
| WO | WO 2017/065484 A1 | 4/2017 |
| WO | WO 2018/030806 A1 | 2/2018 |
| WO | WO 2018/071919 A1 | 4/2018 |
| WO | WO-2018/152518 A1 | 8/2018 |
| WO | WO-2018/177966 A1 | 10/2018 |
| WO | WO-2019/051308 A1 | 3/2019 |
| WO | WO 2019/077092 A1 | 4/2019 |
| WO | WO 2020/086758 | 4/2020 |

OTHER PUBLICATIONS

Atwell et al., 1997, "Stable heterodimers from remodeling the domain interface of a homodimer using a phage display library", J. Mol. Biol., 270(1):26-35.

Baek et al., 2014, "Construction of a large synthetic human Fab antibody library on yeast cell surface by optimized yeast mating", Journal of Microbiology and Biotechnology, 24(3):408-420.

Brar et al., 2014, "Genomic Evolution of Porcine Reproductive and Respiratory Syndrome Virus (PRRSV) Isolates Revealed by Deep Sequencing," PLOSone 9(4): e88807.

Brekke et al., 1994, "Human IgG isotype-specific amino acid residues affecting complement-mediated cell lysis and phagocytosis," Eur. J. Immunol. 24: 2542-47.

Chan et al., 2010, "Therapeutic antibodies for autoimmunity and inflammation," Nat Rev. Immunol 10(5):301-316.

Choi et al., 2015, "Crystal structures of immunoglobulin Fe heterodimers reveal the molecular basis for heterodimer formation," Mol 1mmunol 65(2):377-383.

Choi et al., 2015, "Engineering of immunoglobin Fc heterodimers using yeast surface-displayed combinatorial Fc library screening", PloS One, vol. 10, article No. 30145349:1-20.

Choi et al., 2013, "A Heterodimeric Fc-Based Bispecific Antibody Simultaneously Targeting VEGFR-2 and Met Exhibits Potent Antitumor Activity,"Mol Cancer Ther, 12(12):2748-2759.

Cunningham et al., 1969, "Subgroups of Amino Acid Sequences in the Variable Regions of 1mmunoglobulin Heaw Chains," Proc. Natl. Acad. Sci. USA 64(3):997-1003.

Davis et al., 2010, "SEEDbodies: fusion proteins based on strand-exchange engineered domain (SEED) CH3 heterodimers in an Fc analogue platform for asymmetric binders or immunofusions and bispecific antibodies, " Protein Engineering Design and Selection, 23(4):195-202.

Doctoral Thesis of Heyji-Choi at Ajou University, "Development of heterodimetic Fc variants for bispecific antibody platform technology," 2015.

Extended European Search Report, European Application No. 17839824. 4, dated Feb. 18, 2020.

Feng et al., 2011, "Design, Expression and Characterization of a Soluble Single-Chain Functional Human Neonatal Fc Receptor," Protein Expression and Purification 79(1):66-71.

Gafner et al., 2006, "An engineered antibody-interleukin-12 fusion protein with enhanced tumor vascular targeting properties," International Journal of Cancer, John Wiley & Sons, Inc., 119(9):2205-2212.

GenBank Accession No. NP_002178.2.

GenBank Accession No. NP_000873.2.

Gillies et al., 1998. "Antibody-IL-12 fusioin proteins are effective in SCID mouse models of prostate and colon carcinoma metastases," Journal of Immunology, 160(12): 6195-6203.

Gunasekaran et al., 2010, "Enhancing antibody Fc heterodimer formation through electrostatic steering effects: applications to bispecific molecules and monovalent IgG (manuscript)," JBC Papers in Press, pp. 1-20.

Ha et al., 2016, "Immunoglobulin Fc Heterodimer Platform Technology: from Design to Applications in Therapeutic Antibodies and Proteins," Frontiers in Immunology, 7(394):1-16.

Holliger et al., 2005, "Engineered antibody fragments and the rise of single domains," Nat. Biotechnol 23(9):1126-1136.

Hu et al., 2013, "Porcine Reproductive and Respiratory Syndrome Virus Vaccines: Current Status and Strategies to a Universal Vaccine," Transboundary and Emerging Diseases (2):109-120.

Idusogie et al., 2000, "Mapping of the C1q Binding Site on Rituxan, a Chimeric antibody with a human IgG1 Fc," Journal of Immunology , 164:4178-84.

International Search Report, PCT/KR2017/008676, dated Nov. 15, 2017.

Isaacs et al., 1998, "Therapy with Monoclonal Antibodies. II. The Contribution of Fcγ Receptor Binding and the Influence of CH1 and CH3 Domains on In Vivo Effector Function," Journal of Immunology, 161: 3862-69.

Jung et al., 2018, "Heterodimeric Fc-fused IL12 shows potent antitumor activity by generating memory CD8 + T cells," OncoImmunology, 7(7):e1438800.

Kim et al., 2007, "Comparative Analyses of Complex Formation and Binding Sites Between Human Tumor Necrosis Factor-Alpha and Its Three Antagonists Elucidate Their Different Neutralizing Mechanisms," J Mol Biol 374:1374-88.

Klein et al., 2012, "Progress in overcoming the chain association issue in bispecific heterodimeric 1gG antibodies," MAbs 4(6):653-663.

(56) References Cited

OTHER PUBLICATIONS

Low et al., 2005, "Oral and pulmonary Delivery of FSH-Fc Fusion Proteins via Neonatal Fc Receptor-mediated Transcytosis," Human Reproduction, 20(7):1805-1813.
Lu et al., 2004, "Simultaneous Blockade of Both the Epidermal Growth Factor Receptor and the Insulin-Like Growth Factor Receptor Signaling Pathways in Cancer Cells with a Fully Human Recombinant Bispecific Antibody," J Biol Chem 279(4):2856-2865.
McBurney et al., 2009, "Human immunodeficiency virus-like particles with consensus envelopes elicited broader cell-mediated peripheral and mucosa I immune responses than polyvalent and monovalent Env vaccines," Vaccine 27(32):4337-4349.
Merchant et al., 1998, "An efficient route to human bispecific IgG", Nature Biotechnology 16:677-681.
Miller et al., 2003, "Design, Construction, and in Vitro Analyses of Multivalent Antibodies," J. lmmunol 170(9):4854-4861.
Milstein et al., 1983, "Hybrid Hybridomas and Their Use in immunohistochemistry," Nature 305: 537-540.
Moore et al., 2011, "A novel bispecific antibody format enables simultaneous bivalent and monovalent co-engagement of distinct target antigens," mAbs 3(6):546-557.
Renukaradhya et al., 2015, "Live porcine reproductive and respiratory syndrome virus vaccines: Current status and future direction," Vaccine 33:4069-4080.
Ridgway et al., 2014, "Knobs-into-Holes' engineering of antibody Ch3 domains for heavy chain heterodimerization," Protein Engineering 9(7):617-621.
Strop et al., 2012, "Generating Bispecific Human IgG1 and IgG2 Antibodies from Any Antibody Pair," J Mol Biol 420:204-219.
Tao et al., 1993, "Structural Features of Human Immunoglobulin G that Determine Isotype-specific Differences in Complement Activation," J. Exp. Med., 178:661-667.
Von Kreudenstein et al., 2013, "Improving Biophysical Properties of a Bispecific Antibody Scaffold to Aid Developability: Quality by Molecular Design," mAbs 5:646-654.
Von Kreudenstein et al., 2014, "Protein Engineering and the Use of Molecular Modeling and Simulation: The Case of Heterodimeric Fe Engineering," Methods 65:77-94.
Vu et al., 2015, "A Synthetic Porcine Reproductive and Respiratory Syndrome Virus Strain Confers Unprecedented Levels of Heterologous Protection," J. Virology 89(23):12070-12083.
Wang et al., 2018, "IgG Fc engineering to modulate antibody effector functions," Protein Cell 9(1):63-73.
Xie et al., 2005, "A new format of bispecific antibody: highly efficient heterodimerization, expression and tumor cell lysis," Journal of Immunological Methods 296(1):95-101.
U.S. Appl. No. 18/323,124, filed May 24, 2023, Heterodimeric Fc-Fused Cytokine and Pharmaceutical Composition Comprising the Same.
De et al. (2015) "Estimation of D-Arabinose by Gas Chromatography/Mass Spectrometry as Surrogate for Mycobacterial Lipoarabinomannan in Human Urine," PLOS One 10(12):e0144088, 17 pages.
Gutierrez et al. (2023) "An Optimized IL-12-Fc expands its therapeutic window, achieving strong activity against mouse tumors at tolerable drug doses," Med 4:1-15 (32 pages).
International Search Report and Written Opinion for PCT/KR2017/008676, dated Nov. 15, 2017 (18 pages).
International Search Report and Written Opinion for PCT/US2019/057721, dated Jan. 15, 2020 (25 pages).
International Search Report and Written Opinion for PCT/US2021/028701, dated Jul. 8, 2021 (11 pages).
Liu et al. (2017) "Fc Engineering for Developing Therapeutic Bispecific Antibodies and Novel Scaffolds," Frontiers in Immunology 3(38), 15 pages.
Lo et al. (2017) "Effector-attenuating Substitutions That Maintain Antibody Stability and Reduce Toxicity in Mice," J. Biol. Chem. 292(9):3900-3908.
Müller et al. (2013) "High-resolution structures of the IgM Fc domains reveal principles of its hexamer formation," PNAS 110(25):10183-10188.
Shields et al. (2001) "High Resolution Mapping of the Binding Site of Human IgG1 for FcγRI, FcγRII, FcγRIII, and FcRn and Design of IgG1 Variants with Improved Binding to the FcγR," The Journal of Biological Chemistry 276(9):6591-6604.

* cited by examiner

FIRST POLYPEPTIDE
(HOLE HETERODIMERIZATION
MUTATIONS)

FIRST POLYPEPTIDE
(KNOB HETERODIMERIZATION
MUTATIONS)

FIRST POLYPEPTIDE
(HOLE HETERODIMERIZATION
MUTATIONS)

FIRST POLYPEPTIDE
(HOLE HETERODIMERIZATION
MUTATIONS)

FIRST POLYPEPTIDE
(KNOB HETERODIMERIZATION
MUTATIONS)

FIRST POLYPEPTIDE
(KNOB HETERODIMERIZATION
MUTATIONS)

FIRST POLYPEPTIDE
(HOLE HETERODIMERIZATION
MUTATIONS)

FIRST POLYPEPTIDE
(HOLE HETERODIMERIZATION
MUTATIONS)

SEQUENCE LISTING

```
Sequence total quantity: 299
SEQ ID NO: 1              moltype = AA  length = 21
FEATURE                   Location/Qualifiers
VARIANT                   19
                          note = Xaa is Leu or Glu
source                    1..21
                          mol_type = protein
                          note = Description of Artificial Sequence: Synthetic peptide
                          organism = synthetic construct
SEQUENCE: 1
RVESKYGPPC PPCPAPEFXG G                                                    21

SEQ ID NO: 2              moltype = AA  length = 21
FEATURE                   Location/Qualifiers
source                    1..21
                          mol_type = protein
                          note = Description of Artificial Sequence: Synthetic peptide
                          organism = synthetic construct
SEQUENCE: 2
RVESKYGPPC PPCPAPEFLG G                                                    21

SEQ ID NO: 3              moltype = AA  length = 36
FEATURE                   Location/Qualifiers
source                    1..36
                          mol_type = protein
                          note = Description of Artificial Sequence: Synthetic
                           polypeptide
                          organism = synthetic construct
SEQUENCE: 3
GGGGSGGGGS GGGGSRVESK YGPPCPPCPA PEFLGG                                    36

SEQ ID NO: 4              moltype = AA  length = 21
FEATURE                   Location/Qualifiers
source                    1..21
                          mol_type = protein
                          note = Description of Artificial Sequence: Synthetic peptide
                          organism = synthetic construct
SEQUENCE: 4
RVESKYGPPC PPCPAPEFEG G                                                    21

SEQ ID NO: 5              moltype = AA  length = 36
FEATURE                   Location/Qualifiers
source                    1..36
                          mol_type = protein
                          note = Description of Artificial Sequence: Synthetic
                           polypeptide
```

```
                                   organism = synthetic construct
SEQUENCE: 5
GGGGSGGGGS GGGGSRVESK YGPPCPPCPA PEFEGG                              36

SEQ ID NO: 6               moltype = AA  length = 22
FEATURE                    Location/Qualifiers
source                     1..22
                           mol_type = protein
                           note = Description of Artificial Sequence: Synthetic peptide
                           organism = synthetic construct
VARIANT                    19
                           note = Xaa is Leu or Ala
VARIANT                    20
                           note = Xaa is Leu, Glu or Ala
VARIANT                    22
                           note = Xaa is Ala or Gly
SEQUENCE: 6
EPKSSDKTHT CPPCPAPEXX GX                                             22

SEQ ID NO: 7               moltype = AA  length = 22
FEATURE                    Location/Qualifiers
source                     1..22
                           mol_type = protein
                           note = Description of Artificial Sequence: Synthetic peptide
                           organism = synthetic construct
SEQUENCE: 7
EPKSSDKTHT CPPCPAPELL GG                                             22

SEQ ID NO: 8               moltype = AA  length = 37
FEATURE                    Location/Qualifiers
source                     1..37
                           mol_type = protein
                           note = Description of Artificial Sequence: Synthetic
                             polypeptide
                           organism = synthetic construct
SEQUENCE: 8
GGGGSGGGGS GGGGSEPKSS DKTHTCPPCP APELLGG                             37

SEQ ID NO: 9               moltype = AA  length = 22
FEATURE                    Location/Qualifiers
source                     1..22
                           mol_type = protein
                           note = Description of Artificial Sequence: Synthetic peptide
                           organism = synthetic construct
SEQUENCE: 9
EPKSSDKTHT CPPCPAPEAA GG                                             22

SEQ ID NO: 10              moltype = AA  length = 37
FEATURE                    Location/Qualifiers
source                     1..37
                           mol_type = protein
                           note = Description of Artificial Sequence: Synthetic
                             polypeptide
                           organism = synthetic construct
SEQUENCE: 10
GGGGSGGGGS GGGGSEPKSS DKTHTCPPCP APEAAGG                             37

SEQ ID NO: 11              moltype = AA  length = 22
FEATURE                    Location/Qualifiers
source                     1..22
                           mol_type = protein
                           note = Description of Artificial Sequence: Synthetic peptide
                           organism = synthetic construct
SEQUENCE: 11
EPKSSDKTHT CPPCPAPEAE GA                                             22

SEQ ID NO: 12              moltype = AA  length = 37
FEATURE                    Location/Qualifiers
source                     1..37
                           mol_type = protein
                           note = Description of Artificial Sequence: Synthetic
                             polypeptide
                           organism = synthetic construct
SEQUENCE: 12
GGGGSGGGGS GGGGSEPKSS DKTHTCPPCP APEAEGA                             37

SEQ ID NO: 13              moltype = AA  length = 26
FEATURE                    Location/Qualifiers
source                     1..26
```

```
                            mol_type = protein
                            note = Description of Artificial Sequence: Synthetic peptide
                            organism = synthetic construct
SEQUENCE: 13
GGGGSRVESK YGPPCPPCPA PEFLGG                                          26

SEQ ID NO: 14           moltype = AA   length = 31
FEATURE                 Location/Qualifiers
source                  1..31
                        mol_type = protein
                        note = Description of Artificial Sequence: Synthetic
                          polypeptide
                        organism = synthetic construct
SEQUENCE: 14
GGGGSGGGGS RVESKYGPPC PPCPAPEFLG G                                    31

SEQ ID NO: 15           moltype = AA   length = 27
FEATURE                 Location/Qualifiers
source                  1..27
                        mol_type = protein
                        note = Description of Artificial Sequence: Synthetic peptide
                        organism = synthetic construct
SEQUENCE: 15
GGGGSEPKSS DKTHTCPPCP APELLGG                                         27

SEQ ID NO: 16           moltype = AA   length = 32
FEATURE                 Location/Qualifiers
source                  1..32
                        mol_type = protein
                        note = Description of Artificial Sequence: Synthetic
                          polypeptide
                        organism = synthetic construct
SEQUENCE: 16
GGGGSGGGGS EPKSSDKTHT CPPCPAPELL GG                                   32

SEQ ID NO: 17           moltype = AA   length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 17
IWELKKDVYV VELDWYPDAP GEMVVLTCDT PEEDGITWTL DQSSEVLGSG KTLTIRVKEF      60
GDAGQYTCHK GGEVLSHSLL LLHKKEDGIW STDILKDQKE PKNKTFLRCE AKNYSGRFTC     120
WWLTTISTDL TFSVKSSRGS SDPQGVTCGA ATLSAERVRG DNKEYEYSVE CQEDSACPAA     180
EESLPIEVMV DAVHKLKYEN YTSSFFIRDI IKPDPPKNLQ LKPLKNSRQV EVSWEYPDTW     240
STPHSYFSLT FCVQVQGKSK REKKDRVFTD KTSATVICRK NASISVRAQD RYYSSSWSEW     300
ASVPCSRVES KYGPPCPPCP APEFLGGPSV FLFPPKPKDT LMISRTPEVT CVVVDVSQED     360
PEVQFNWYVD GVEVHNAKTK PREEQFNSTY RVVSVLTVLH QDWLNGKEYK CKVSNKGLPS     420
SIEKTISKAK GQPREPQVCT LPPSQEEMTK NQVSLTCLVE GFYPSDIAVE WESNGQPENN     480
YKTTPPVLDS DGSFFLYSWL TVDKSRWQEG NVFSCSVMHE ALHNHYTQKS LSLSLG         536

SEQ ID NO: 18           moltype = AA   length = 442
FEATURE                 Location/Qualifiers
source                  1..442
                        mol_type = protein
                        note = Description of Artificial Sequence: Synthetic
                          polypeptide
                        organism = synthetic construct
SEQUENCE: 18
RNLPVATPDP GMFPCLHHSQ NLLRAVSNML QKARQTLEFY PCTSEEIDHV DITKDKTSTV      60
EACLPLELTK NESCLNSRET SFITNGSCLA SRKTSFMMAL CLSSIYEDLK MYQVEFKTMN     120
AKLLMDPKRQ IFLDQNMLAV IDELMQALNF NSETVPQKSS LEEPDFYKTK IKLCILLHAF     180
RIRAVTIDRV MSYLNASGGG GSGGGGSGGG GSRVESKYGP PCPPCPAPEF LGGPSVFLFP     240
PKPKDTLMIS RTPEVTCVVV DVSQEDPEVQ FNWYVDGVEV HNAKTKPREE QFNSTYRVVS     300
VLTVLHQDWL NGKEYKCKVS NKGLPSSIEK TISKAKGQPR EPQVYTLPPC QENMTKNQVS     360
LTCLVKGFYP SDIAVEWESN GQPENNYKTT PPVLSDGSF  TLYSRLTVDK SRWQEGNVFS     420
CSVMHEALHN HYTQKSLSLS LG                                              442

SEQ ID NO: 19           moltype = AA   length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 19
IWELKKDVYV VELDWYPDAP GEMVVLTCDT PEEDGITWTL DQSSEVLGSG KTLTIRVKEF      60
```

```
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSRVES KYGPPCPPCP APEFLGGPSV FLFPPKPKDT LMISRTPEVT CVVVDVSQED    360
PEVQFNWYVD GVEVHNAKTK PREEQFNSTY RVVSVLTVLH QDWLNGKEYK CKVSNKGLPS    420
SIEKTISKAK GQPREPQVCT LPPSQEEMTE NQVSLTCLVK GFYPSDIAVE WESNGQPENN    480
YKTTPPVLDS DGSFFLYSWL TVDKSRWQEG NVFSCSVMHE ALHNHYTQKS LSLSLG        536

SEQ ID NO: 20           moltype = AA  length = 442
FEATURE                 Location/Qualifiers
source                  1..442
                        mol_type = protein
                        note = Description of Artificial Sequence: Synthetic
                          polypeptide
                        organism = synthetic construct
SEQUENCE: 20
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSGGGGSGGG GSRVESKYGP PCPPCPAPEF LGGPSVFLFP    240
PKPKDTLMIS RTPEVTCVVV DVSQEDPEVQ FNWYVDGVEV HNAKTKPREE QFNSTYRVVS    300
VLTVLHQDWL NGKEYKCKVS NKGLPSSIEK TISKAKGQPR EPRVYTLPPC QEEMTKNQVS    360
LTCLVKGFYP SDIAVEWESN GQPENNYKTT PPVLVSDGSF TLYSRLTVDK SRWQEGNVFS    420
CSVMHEALHN HYTQKSLSLS LG                                            442

SEQ ID NO: 21           moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 21
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSRVES KYGPPCPPCP APEFEGGPSV FLFPPKPKDT LMISRTPEVT CVVVDVSQED    360
PEVQFNWYVD GVEVHNAKTK PREEQFNSTY RVVSVLTVLH QDWLNGKEYK CKVSNKGLPS    420
SIEKTISKAK GQPREPQVCT LPPSQEEMTE NQVSLTCLVK GFYPSDIAVE WESNGQPENN    480
YKTTPPVLDS DGSFFLYSWL TVDKSRWQEG NVFSCSVMHE ALHNHYTQKS LSLSLG        536

SEQ ID NO: 22           moltype = AA  length = 442
FEATURE                 Location/Qualifiers
source                  1..442
                        mol_type = protein
                        note = Description of Artificial Sequence: Synthetic
                          polypeptide
                        organism = synthetic construct
SEQUENCE: 22
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSGGGGSGGG GSRVESKYGP PCPPCPAPEF EGGPSVFLFP    240
PKPKDTLMIS RTPEVTCVVV DVSQEDPEVQ FNWYVDGVEV HNAKTKPREE QFNSTYRVVS    300
VLTVLHQDWL NGKEYKCKVS NKGLPSSIEK TISKAKGQPR EPRVYTLPPC QEEMTKNQVS    360
LTCLVKGFYP SDIAVEWESN GQPENNYKTT PPVLVSDGSF TLYSRLTVDK SRWQEGNVFS    420
CSVMHEALHN HYTQKSLSLS LG                                            442

SEQ ID NO: 23           moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 23
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSRVES KYGPPCPPCP APEFEGGPSV FLFPPKPKDT LMISRTPEVT CVVVDVSQED    360
PEVQFNWYVD GVEVHNAKTK PREEQFNSTY RVVSVLTVLH QDWLNGKEYK CKVSNKGLAS    420
SIEKTISKAK GQPREPQVCT LPPSQEEMTE NQVSLTCLVK GFYPSDIAVE WESNGQPENN    480
YKTTPPVLDS DGSFFLYSWL TVDKSRWQEG NVFSCSVMHE ALHNHYTQKS LSLSLG        536
```

```
SEQ ID NO: 24              moltype = AA  length = 442
FEATURE                    Location/Qualifiers
source                     1..442
                           mol_type = protein
                           note = Description of Artificial Sequence: Synthetic
                             polypeptide
                           organism = synthetic construct
SEQUENCE: 24
RNLPVATPDP GMFPCLHHSQ NLLRAVSNML QKARQTLEFY PCTSEEIDHV DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNASGGG GSGGGGSGGG GSRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLASSIEK TISKAKGQPR EPRVYTLPPC QEEMTKNQVS  360
LTCLVKGFYP SDIAVEWESN GQPENNYKTT PPVLVSDGSF TLYSRLTVDK SRWQEGNVFS  420
CSVMHEALHN HYTQKSLSLS LG                                          442

SEQ ID NO: 25              moltype = AA  length = 536
FEATURE                    Location/Qualifiers
source                     1..536
                           mol_type = protein
                           note = Description of Artificial Sequence: Synthetic
                             polypeptide
                           organism = synthetic construct
SEQUENCE: 25
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSRVES KYGPPCPPCP APEFEGGPSV FLFPPKPKDT LMISRTPEVT CVVVDVSQED  360
PEVQFNWYVD GVEVHNAKTK PREEQFNSTY RVVSVLTVLH QDWLNGKEYK CKVSNKGLGS  420
SIEKTISKAK GQPREPQVCT LPPSQEEMTE NQVSLTCLVK GFYPSDIAVE WESNGQPENN  480
YKTTPPVLDS DGSFFLYSWL TVDKSRWQEG NVFSCSVMHE ALHNHYTQKS LSLSLG      536

SEQ ID NO: 26              moltype = AA  length = 442
FEATURE                    Location/Qualifiers
source                     1..442
                           mol_type = protein
                           note = Description of Artificial Sequence: Synthetic
                             polypeptide
                           organism = synthetic construct
SEQUENCE: 26
RNLPVATPDP GMFPCLHHSQ NLLRAVSNML QKARQTLEFY PCTSEEIDHV DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNASGGG GSGGGGSGGG GSRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLGSSIEK TISKAKGQPR EPRVYTLPPC QEEMTKNQVS  360
LTCLVKGFYP SDIAVEWESN GQPENNYKTT PPVLVSDGSF TLYSRLTVDK SRWQEGNVFS  420
CSVMHEALHN HYTQKSLSLS LG                                          442

SEQ ID NO: 27              moltype = AA  length = 537
FEATURE                    Location/Qualifiers
source                     1..537
                           mol_type = protein
                           note = Description of Artificial Sequence: Synthetic
                             polypeptide
                           organism = synthetic construct
SEQUENCE: 27
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSEPKS SDKTHTCPPC PAPELLGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
APIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 28              moltype = AA  length = 443
FEATURE                    Location/Qualifiers
source                     1..443
                           mol_type = protein
                           note = Description of Artificial Sequence: Synthetic
                             polypeptide
                           organism = synthetic construct
SEQUENCE: 28
RNLPVATPDP GMFPCLHHSQ NLLRAVSNML QKARQTLEFY PCTSEEIDHV DITKDKTSTV   60
```

```
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSGGGGSGGG GSEPKSSDKT HTCPPCPAPE LLGGPSVFLF    240
PPKPKDTLMI SRTPEVTCVV VDVSHEDPEV KFNWYVDGVE VHNAKTKPRE EQYNSTYRVV    300
SVLTVLHQDW LNGKEYKCKV SNKALPAPIE KTISKAKGQP REPRVYTLPP CRDELTKNQV    360
SLTCLVKGFY PSDIAVEWES NGQPENNYKT TPPVLVSDGS FTLYSKLTVD KSRWQQGNVF    420
SCSVMHEALH NHYTQKSLSL SPG                                           443

SEQ ID NO: 29              moltype = AA   length = 537
FEATURE                    Location/Qualifiers
source                     1..537
                           mol_type = protein
                           note = Description of Artificial Sequence: Synthetic
                            polypeptide
                           organism = synthetic construct
SEQUENCE: 29
IWELKKDVYV VELDWYPDAP GEMVVLTCDT PEEDGITWTL DQSSEVLGSG KTLTIRVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSEPKS SDKTHTCPPC PAPEAAGGPS VFLFPPPKPK DTLMISRTPEV TCVVVDVSHE    360
DPEVKFNWYV DGVEVHNAKT KPREEQYNST YRVVSVLTVL HQDWLNGKEY KCKVSNKALP    420
APIEKTISKA KGQPREPQVC TLPPSRDELT ENQVSLTCLV KGFYPSDIAV EWESNGQPEN    480
NYKTTPPVLD SDGSFFLYSW LTVDKSRWQQ GNVFSCSVMH EALHNHYTQK SLSLSPG       537

SEQ ID NO: 30              moltype = AA   length = 443
FEATURE                    Location/Qualifiers
source                     1..443
                           mol_type = protein
                           note = Description of Artificial Sequence: Synthetic
                            polypeptide
                           organism = synthetic construct
SEQUENCE: 30
RNLPVATPDP GMFPCLHHSQ NLLRAVSNML QKARQTLEFY PCTSEEIDHV DITKDKTSTV     60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSGGGGSGGG GSEPKSSDKT HTCPPCPAPE AAGGPSVFLF    240
PPKPKDTLMI SRTPEVTCVV VDVSHEDPEV KFNWYVDGVE VHNAKTKPRE EQYNSTYRVV    300
SVLTVLHQDW LNGKEYKCKV SNKALPAPIE KTISKAKGQP REPRVYTLPP CRDELTKNQV    360
SLTCLVKGFY PSDIAVEWES NGQPENNYKT TPPVLVSDGS FTLYSKLTVD KSRWQQGNVF    420
SCSVMHEALH NHYTQKSLSL SPG                                           443

SEQ ID NO: 31              moltype = AA   length = 537
FEATURE                    Location/Qualifiers
source                     1..537
                           mol_type = protein
                           note = Description of Artificial Sequence: Synthetic
                            polypeptide
                           organism = synthetic construct
SEQUENCE: 31
IWELKKDVYV VELDWYPDAP GEMVVLTCDT PEEDGITWTL DQSSEVLGSG KTLTIRVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSEPKS SDKTHTCPPC PAPEAAGGPS VFLFPPPKPK DTLMISRTPEV TCVVVDVSHE    360
DPEVKFNWYV DGVEVHNAKT KPREEQYNST YRVVSVLTVL HQDWLNGKEY KCKVSNKALA    420
APIEKTISKA KGQPREPQVC TLPPSRDELT ENQVSLTCLV KGFYPSDIAV EWESNGQPEN    480
NYKTTPPVLD SDGSFFLYSW LTVDKSRWQQ GNVFSCSVMH EALHNHYTQK SLSLSPG       537

SEQ ID NO: 32              moltype = AA   length = 443
FEATURE                    Location/Qualifiers
source                     1..443
                           mol_type = protein
                           note = Description of Artificial Sequence: Synthetic
                            polypeptide
                           organism = synthetic construct
SEQUENCE: 32
RNLPVATPDP GMFPCLHHSQ NLLRAVSNML QKARQTLEFY PCTSEEIDHV DITKDKTSTV     60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSGGGGSGGG GSEPKSSDKT HTCPPCPAPE AAGGPSVFLF    240
PPKPKDTLMI SRTPEVTCVV VDVSHEDPEV KFNWYVDGVE VHNAKTKPRE EQYNSTYRVV    300
SVLTVLHQDW LNGKEYKCKV SNKALAAPIE KTISKAKGQP REPRVYTLPP CRDELTKNQV    360
SLTCLVKGFY PSDIAVEWES NGQPENNYKT TPPVLVSDGS FTLYSKLTVD KSRWQQGNVF    420
SCSVMHEALH NHYTQKSLSL SPG                                           443

SEQ ID NO: 33              moltype = AA   length = 537
```

```
FEATURE                 Location/Qualifiers
source                  1..537
                        mol_type = protein
                        note = Description of Artificial Sequence: Synthetic
                         polypeptide
                        organism = synthetic construct
SEQUENCE: 33
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSEPKS SDKTHTCPPC PAPEAAGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALG  420
APIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 34           moltype = AA  length = 443
FEATURE                 Location/Qualifiers
source                  1..443
                        mol_type = protein
                        note = Description of Artificial Sequence: Synthetic
                         polypeptide
                        organism = synthetic construct
SEQUENCE: 34
RNLPVATPDP GMFPCLHHSQ NLLRAVSNML QKARQTLEFY PCTSEEIDHV DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNASGGG GSGGGGSGGG GSEPKSSDKT HTCPPCPAPE AAGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALGAPIE KTISKAKGQP REPRVYTLPP CRDELTKNQV  360
SLTCLVKGFY PSDIAVEWES NGQPENNYKT TPPVLSDGS  FTLYSKLTVD KSRWQQGNVF  420
SCSVMHEALH NHYTQKSLSL SPG                                         443

SEQ ID NO: 35           moltype = AA  length = 537
FEATURE                 Location/Qualifiers
source                  1..537
                        mol_type = protein
                        note = Description of Artificial Sequence: Synthetic
                         polypeptide
                        organism = synthetic construct
SEQUENCE: 35
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSEPKS SDKTHTCPPC PAPEAEGAPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
SSIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 36           moltype = AA  length = 443
FEATURE                 Location/Qualifiers
source                  1..443
                        mol_type = protein
                        note = Description of Artificial Sequence: Synthetic
                         polypeptide
                        organism = synthetic construct
SEQUENCE: 36
RNLPVATPDP GMFPCLHHSQ NLLRAVSNML QKARQTLEFY PCTSEEIDHV DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNASGGG GSGGGGSGGG GSEPKSSDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPSSIE KTISKAKGQP REPRVYTLPP CRDELTKNQV  360
SLTCLVKGFY PSDIAVEWES NGQPENNYKT TPPVLSDGS  FTLYSKLTVD KSRWQQGNVF  420
SCSVMHEALH NHYTQKSLSL SPG                                         443

SEQ ID NO: 37           moltype = AA  length = 536
FEATURE                 Location/Qualifiers
source                  1..536
                        mol_type = protein
                        note = Description of Artificial Sequence: Synthetic
                         polypeptide
                        organism = synthetic construct
SEQUENCE: 37
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC  120
```

```
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSRVES KYGPPCPPCP APEFLGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLPS   420
SIEKTISKAK GQPREPQVCT LPPSQEEMTK NQVSLTCLVE GFYPSDIAVE WESNGQPENN   480
YKTTPPVLDS DGSFFLYSWL TVDKSRWQEG NVFSCSVMHE ALHNHYTQKS LSLSLG       536

SEQ ID NO: 38             moltype = AA  length = 427
FEATURE                   Location/Qualifiers
source                    1..427
                          mol_type = protein
                          note = Description of Artificial Sequence: Synthetic
                           polypeptide
                          organism = synthetic construct
SEQUENCE: 38
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASRVE SKYGPPCPPC PAPEFLGGPS VFLPPPKPKD TLMISRTPEV   240
TCVVVDVSQE DPEVQFNWYV DGVEVHNAKT KPREEQFNST YRVVSVLTVL HQDWLNGKEY   300
KCKVSNKGLP SSIEKTISKA KGQPREPQVY TLPPCQENMT KNQVSLTCLV KGFYPSDIAV   360
EWESNGQPEN NYKTTPPVLV SDGSFTLYSR LTVDKSRWQE GNVFSCSVMH EALHNHYTQK   420
SLSLSLG                                                             427

SEQ ID NO: 39             moltype = AA  length = 536
FEATURE                   Location/Qualifiers
source                    1..536
                          mol_type = protein
                          note = Description of Artificial Sequence: Synthetic
                           polypeptide
                          organism = synthetic construct
SEQUENCE: 39
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSRVES KYGPPCPPCP APEFLGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLPS   420
SIEKTISKAK GQPREPQVCT LPPSQEEMTK NQVSLTCLVE GFYPSDIAVE WESNGQPENN   480
YKTTPPVLDS DGSFFLYSWL TVDKSRWQEG NVFSCSVMHE ALHNHYTQKS LSLSLG       536

SEQ ID NO: 40             moltype = AA  length = 432
FEATURE                   Location/Qualifiers
source                    1..432
                          mol_type = protein
                          note = Description of Artificial Sequence: Synthetic
                           polypeptide
                          organism = synthetic construct
SEQUENCE: 40
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSRVESKYGP PCPPCPAPEF LGGPSVFLFP PKPKDTLMIS   240
RTPEVTCVVV DVSQEDPEVQ FNWYVDGVEV HNAKTKPREE QFNSTYRVVS VLTVLHQDWL   300
NGKEYKCKVS NKGLPSSIEK TISKAKGQPR EPQVYTLPPC QENMTKNQVS LTCLVKGFYP   360
SDIAVEWESN GQPENNYKTT PPVLVSDGSF TLYSRLTVDK SRWQEGNVFS CSVMHEALHN   420
HYTQKSLSLS LG                                                       432

SEQ ID NO: 41             moltype = AA  length = 536
FEATURE                   Location/Qualifiers
source                    1..536
                          mol_type = protein
                          note = Description of Artificial Sequence: Synthetic
                           polypeptide
                          organism = synthetic construct
SEQUENCE: 41
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSRVES KYGPPCPPCP APEFLGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLPS   420
SIEKTISKAK GQPREPQVCT LPPSQEEMTK NQVSLTCLVE GFYPSDIAVE WESNGQPENN   480
YKTTPPVLDS DGSFFLYSWL TVDKSRWQEG NVFSCSVMHE ALHNHYTQKS LSLSLG       536

SEQ ID NO: 42             moltype = AA  length = 437
```

```
FEATURE                 Location/Qualifiers
source                  1..437
                        mol_type = protein
                        note = Description of Artificial Sequence: Synthetic
                           polypeptide
                        organism = synthetic construct
SEQUENCE: 42
RNLPVATPDP GMFPCLHHSQ NLLRAVSNML QKARQTLEFY PCTSEEIDHV DITKDKTSTV  60
EACLPLELTK NESCLNSRET SFITNGSCLA SRKTSFMMAL CLSSIYEDLK MYQVEFKTMN 120
AKLLMDPKRQ IFLDQNMLAV IDELMQALNF NSETVPQKSS LEEPDFYKTK IKLCILLHAF 180
RIRAVTIDRV MSYLNASGGG GSGGGGSRVE SKYGPPCPPC PAPEFLGGPS VFLFPPKPKD 240
TLMISRTPEV TCVVVDVSQE DPEVQFNWYV DGVEVHNAKT KPREEQFNST YRVVSVLTVL 300
HQDWLNGKEY KCKVSNKGLP SSIEKTISKA KGQPREPQVY TLPPCQENMT KNQVSLTCLV 360
KGFYPSDIAV EWESNGQPEN NYKTTPPVLV SDGSFTLYSR LTVDKSRWQE GNVFSCSVMH 420
EALHNHYTQK SLSLSLG                                                437

SEQ ID NO: 43           moltype = AA  length = 537
FEATURE                 Location/Qualifiers
source                  1..537
                        mol_type = protein
                        note = Description of Artificial Sequence: Synthetic
                           polypeptide
                        organism = synthetic construct
SEQUENCE: 43
IWELKKDVYV VELDWYPDAP GEMVVLTCDT PEEDGITWTL DQSSEVLGSG KTLTIRVKEF  60
GDAGQYTCHK GGEVLSHSLL LLHKKEDGIW STDILKDQKE PKNKTFLRCE AKNYSGRFTC 120
WWLTTISTDL TFSVKSSRGS SDPQGVTCGA ATLSAERVRG DNKEYEYSVE CQEDSACPAA 180
EESLPIEVMV DAVHKLKYEN YTSSFFIRDI IKPDPPKNLQ LKPLKNSRQV EVSWEYPDTW 240
STPHSYFSLT FCVQVQGKSK REKKDRVFTD KTSATVICRK NASISVRAQD RYYSSSWSEW 300
ASVPCSEPKS SDKTHTCPPC PAPELLGGPS VFLFPPKPKD TLMISRTPEV TCVVVDVSHE 360
DPEVKFNWYV DGVEVHNAKT KPREEQYNST YRVVSVLTVL HQDWLNGKEY KCKVSNKALP 420
APIEKTISKA KGQPREPQVC TLPPSRDELT ENQVSLTCLV KGFYPSDIAV EWESNGQPEN 480
NYKTTPPVLD SDGSFFLYSW LTVDKSRWQQ GNVFSCSVMH EALHNHYTQK SLSLSPG    537

SEQ ID NO: 44           moltype = AA  length = 428
FEATURE                 Location/Qualifiers
source                  1..428
                        mol_type = protein
                        note = Description of Artificial Sequence: Synthetic
                           polypeptide
                        organism = synthetic construct
SEQUENCE: 44
RNLPVATPDP GMFPCLHHSQ NLLRAVSNML QKARQTLEFY PCTSEEIDHV DITKDKTSTV  60
EACLPLELTK NESCLNSRET SFITNGSCLA SRKTSFMMAL CLSSIYEDLK MYQVEFKTMN 120
AKLLMDPKRQ IFLDQNMLAV IDELMQALNF NSETVPQKSS LEEPDFYKTK IKLCILLHAF 180
RIRAVTIDRV MSYLNASEPK SSDKTHTCPP CPAPELLGGP SVFLFPPKPK DTLMISRTPE 240
VTCVVVDVSH EDPEVKFNWY VDGVEVHNAK TKPREEQYNS TYRVVSVLTV LHQDWLNGKE 300
YKCKVSNKAL PAPIEKTISK AKGQPREPRV YTLPPCRDEL TKNQVSLTCL VKGFYPSDIA 360
VEWESNGQPE NNYKTTPPVL VSDGSFTLYS KLTVDKSRWQ QGNVFSCSVM HEALHNHYTQ 420
KSLSLSPG                                                          428

SEQ ID NO: 45           moltype = AA  length = 537
FEATURE                 Location/Qualifiers
source                  1..537
                        mol_type = protein
                        note = Description of Artificial Sequence: Synthetic
                           polypeptide
                        organism = synthetic construct
SEQUENCE: 45
IWELKKDVYV VELDWYPDAP GEMVVLTCDT PEEDGITWTL DQSSEVLGSG KTLTIRVKEF  60
GDAGQYTCHK GGEVLSHSLL LLHKKEDGIW STDILKDQKE PKNKTFLRCE AKNYSGRFTC 120
WWLTTISTDL TFSVKSSRGS SDPQGVTCGA ATLSAERVRG DNKEYEYSVE CQEDSACPAA 180
EESLPIEVMV DAVHKLKYEN YTSSFFIRDI IKPDPPKNLQ LKPLKNSRQV EVSWEYPDTW 240
STPHSYFSLT FCVQVQGKSK REKKDRVFTD KTSATVICRK NASISVRAQD RYYSSSWSEW 300
ASVPCSEPKS SDKTHTCPPC PAPELLGGPS VFLFPPKPKD TLMISRTPEV TCVVVDVSHE 360
DPEVKFNWYV DGVEVHNAKT KPREEQYNST YRVVSVLTVL HQDWLNGKEY KCKVSNKALP 420
APIEKTISKA KGQPREPQVC TLPPSRDELT ENQVSLTCLV KGFYPSDIAV EWESNGQPEN 480
NYKTTPPVLD SDGSFFLYSW LTVDKSRWQQ GNVFSCSVMH EALHNHYTQK SLSLSPG    537

SEQ ID NO: 46           moltype = AA  length = 433
FEATURE                 Location/Qualifiers
source                  1..433
                        mol_type = protein
                        note = Description of Artificial Sequence: Synthetic
                           polypeptide
                        organism = synthetic construct
SEQUENCE: 46
RNLPVATPDP GMFPCLHHSQ NLLRAVSNML QKARQTLEFY PCTSEEIDHV DITKDKTSTV  60
EACLPLELTK NESCLNSRET SFITNGSCLA SRKTSFMMAL CLSSIYEDLK MYQVEFKTMN 120
```

```
AKLLMDPKRQ IFLDQNMLAV IDELMQALNF NSETVPQKSS LEEPDFYKTK IKLCILLHAF   180
RIRAVTIDRV MSYLNASGGG GSEPKSSDKT HTCPPCPAPE LLGGPSVFLF PPKPKDTLMI   240
SRTPEVTCVV VDVSHEDPEV KFNWYVDGVE VHNAKTKPRE EQYNSTYRVV SVLTVLHQDW   300
LNGKEYKCKV SNKALPAPIE KTISKAKGQP REPRVYTLPP CRDELTKNQV SLTCLVKGFY   360
PSDIAVEWES NGQPENNYKT TPPVLVSDGS FTLYSKLTVD KSRWQQGNVF SCSVMHEALH   420
NHYTQKSLSL SPG                                                     433

SEQ ID NO: 47           moltype = AA  length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 47
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSEPKS SDKTHTCPPC PAPELLGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG     537

SEQ ID NO: 48           moltype = AA  length = 438
FEATURE                 Location/Qualifiers
source                  1..438
                        mol_type = protein
                        note = Description of Artificial Sequence: Synthetic
                          polypeptide
                        organism = synthetic construct
SEQUENCE: 48
RNLPVATPDP GMFPCLHHSQ NLLRAVSNML QKARQTLEFY PCTSEEIDHV DITKDKTSTV   60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSGGGGSEPK SSDKTHTCPP CPAPELLGGP SVFLFPPKPK   240
DTLMISRTPE VTCVVVDVSH EDPEVKFNWY VDGVEVHNAK TKPREEQYNS TYRVVSVLTV   300
LHQDWLNGKE YKCKVSNKAL PAPIEKTISK AKGQPREPRV YTLPPCRDEL TKNQVSLTCL   360
VKGFYPSDIA VEWESNGQPE NNYKTTPPVL VSDGSFTLYS KLTVDKSRWQ QGNVFSCSVM   420
HEALHNHYTQ KSLSLSPG                                                438

SEQ ID NO: 49           moltype = AA  length = 443
FEATURE                 Location/Qualifiers
source                  1..443
                        mol_type = protein
                        note = Description of Artificial Sequence: Synthetic
                          polypeptide
                        organism = synthetic construct
SEQUENCE: 49
RNLPVATPDP GMFPCLHHSQ NLLRAVSNML QKARQTLEFY PCTSEEIDHV DITKDKTSTV   60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSGGGGSGGG GSEPKSSDKT HTCPPCPAPE LLGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPQVCTLPP SRDELTENQV   360
SLTCLVKGFY PSDIAVEWES NGQPENNYKT TPPVLDSDGS FFLYSWLTVD KSRWQQGNVF   420
SCSVMHEALH NHYTQKSLSL SPG                                          443

SEQ ID NO: 50           moltype = AA  length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 50
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSEPKS SDKTHTCPPC PAPELLGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPRVY TLPPCRDELT KNQVSLTCLV KGFYPSDIAV EWESNGQPEN   480
NYKTTPPVLV SDGSFTLYSK LTVDKSRWQQ GNVFSCSVMH EALHNHYTQK SLSLSPG     537

SEQ ID NO: 51           moltype = AA  length = 542
FEATURE                 Location/Qualifiers
```

```
source                  1..542
                        mol_type = protein
                        note = Description of Artificial Sequence: Synthetic
                           polypeptide
                        organism = synthetic construct
SEQUENCE: 51
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SEPKSSDKTH TCPPCPAPEL LGGPSVFLFP PKPKDTLMIS RTPEVTCVVV   360
DVSHEDPEVK FNWYVDGVEV HNAKTKPREE QYNSTYRVVS VLTVLHQDWL NGKEYKCKVS   420
NKALPAPIEK TISKAKGQPR EPQVCTLPPS RDELTENQVS LTCLVKGFYP SDIAVEWESN   480
GQPENNYKTT PPVLDSDGSF FLYSWLTVDK SRWQQGNVFS CSVMHEALHN HYTQKSLSLS   540
PG                                                                 542

SEQ ID NO: 52           moltype = AA  length = 433
FEATURE                 Location/Qualifiers
source                  1..433
                        mol_type = protein
                        note = Description of Artificial Sequence: Synthetic
                           polypeptide
                        organism = synthetic construct
SEQUENCE: 52
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSEPKSSDKT HTCPPCPAPE LLGGPSVFLF PPKPKDTLMI   240
SRTPEVTCVV VDVSHEDPEV KFNWYVDGVE VHNAKTKPRE EQYNSTYRVV SVLTVLHQDW   300
LNGKEYKCKV SNKALPAPIE KTISKAKGQP REPRVYTLPP CRDELTKNQV SLTCLVKGFY   360
PSDIAVEWES NGQPENNYKT TPPVLVSDGS FTLYSKLTVD KSRWQQGNVF SCSVMHEALH   420
NHYTQKSLSL SPG                                                     433

SEQ ID NO: 53           moltype = AA  length = 542
FEATURE                 Location/Qualifiers
source                  1..542
                        mol_type = protein
                        note = Description of Artificial Sequence: Synthetic
                           polypeptide
                        organism = synthetic construct
SEQUENCE: 53
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSGGGG SEPKSSDKTH TCPPCPAPEL LGGPSVFLFP PKPKDTLMIS RTPEVTCVVV   360
DVSHEDPEVK FNWYVDGVEV HNAKTKPREE QYNSTYRVVS VLTVLHQDWL NGKEYKCKVS   420
NKALPAPIEK TISKAKGQPR EPQVCTLPPS RDELTENQVS LTCLVKGFYP SDIAVEWESN   480
GQPENNYKTT PPVLDSDGSF FLYSWLTVDK SRWQQGNVFS CSVMHEALHN HYTQKSLSLS   540
PG                                                                 542

SEQ ID NO: 54           moltype = AA  length = 433
FEATURE                 Location/Qualifiers
source                  1..433
                        mol_type = protein
                        note = Description of Artificial Sequence: Synthetic
                           polypeptide
                        organism = synthetic construct
SEQUENCE: 54
RNLPVATPDP GMFPCLHHSQ NLLRAVSNML QKARQTLEFY PCTSEEIDHV DITKDKTSTV    60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSEPKSSDKT HTCPPCPAPE LLGGPSVFLF PPKPKDTLMI   240
SRTPEVTCVV VDVSHEDPEV KFNWYVDGVE VHNAKTKPRE EQYNSTYRVV SVLTVLHQDW   300
LNGKEYKCKV SNKALPAPIE KTISKAKGQP REPRVYTLPP CRDELTKNQV SLTCLVKGFY   360
PSDIAVEWES NGQPENNYKT TPPVLVSDGS FTLYSKLTVD KSRWQQGNVF SCSVMHEALH   420
NHYTQKSLSL SPG                                                     433

SEQ ID NO: 55           moltype = AA  length = 536
FEATURE                 Location/Qualifiers
source                  1..536
                        mol_type = protein
                        note = Description of Artificial Sequence: Synthetic
                           polypeptide
                        organism = synthetic construct
SEQUENCE: 55
IWELKKDVYV VELDWYPDAP GEMVVLTCDT PEEDGITWTL DQSSEVLGSG KTLTIRVKEF    60
```

```
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSRVES KYGPPCPPCP APEFLGGPSV FLFPPKPKDT LMISRTPEVT CVVVDVSQED  360
PEVQFNWYVD GVEVHNAKTK PREEQFNSTY RVVSVLTVLH QDWLNGKEYK CKVSNKGLPS  420
SIEKTISKAK GQPREPQVCT LPPSQEEMTK NQVSLTCLVE GFYPSDIAVE WESNGQPENN  480
YKTTPPVLDS DGSFFLYSWL TVDKSRWQEG NVFSCSVMHE ALHNHYTQKS LSLSLG      536

SEQ ID NO: 56           moltype = AA   length = 442
FEATURE                 Location/Qualifiers
source                  1..442
                        mol_type = protein
                        note = Description of Artificial Sequence: Synthetic
                          polypeptide
                        organism = synthetic construct
SEQUENCE: 56
RNLPVATPDP GMFPCLHHSQ NLLRAVSNML QKARQTLEFY PCTSEEIDHV DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSRVESKYGP PCPPCPAPEF LGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPC QENMTKNQVS  360
LTCLVKGFYP SDIAVEWESN GQPENNYKTT PPVLSDGSF TLYSRLTVDK SRWQEGNVFS  420
CSVMHEALHN HYTQKSLSLS LG                                          442

SEQ ID NO: 57           moltype = AA   length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 57
IWELKKDVYV VELDWYPDAP GEMVVLTCDT PEEDGITWTL DQSSEVLGSG KTLTIRVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSEPKS SDKTHTCPPC PAPEAAGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
APIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 58           moltype = AA   length = 443
FEATURE                 Location/Qualifiers
source                  1..443
                        mol_type = protein
                        note = Description of Artificial Sequence: Synthetic
                          polypeptide
                        organism = synthetic construct
SEQUENCE: 58
RNLPVATPDP GMFPCLHHSQ NLLRAVSNML QKARQTLEFY PCTSEEIDHV DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSEPKSSDKT HTCPPCPAPE AAGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPRVYTLPP CRDELTKNQV  360
SLTCLVKGFY PSDIAVEWES NGQPENNYKT TPPVLSDGSF TLYSKLTVD KSRWQQGNVF  420
SCSVMHEALH NHYTQKSLSL SPG                                         443

SEQ ID NO: 59           moltype = AA   length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 59
IWELKKDVYV VELDWYPDAP GEMVVLTCDT PEEDGITWTL DQSSEVLGSG KTLTIRVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSEPKS SDKTHTCPPC PAPEAAGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALA  420
APIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537
```

```
SEQ ID NO: 60             moltype = AA  length = 443
FEATURE                   Location/Qualifiers
source                    1..443
                          mol_type = protein
                          note = Description of Artificial Sequence: Synthetic
                            polypeptide
                          organism = synthetic construct
SEQUENCE: 60
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALAAPIE KTISKAKGQP REPRVYTLPP CRDELTKNQV   360
SLTCLVKGFY PSDIAVEWES NGQPENNYKT TPPVLVSDGS FTLYSKLTVD KSRWQQGNVF   420
SCSVMHEALH NHYTQKSLSL SPG                                          443

SEQ ID NO: 61             moltype = AA  length = 537
FEATURE                   Location/Qualifiers
source                    1..537
                          mol_type = protein
                          note = Description of Artificial Sequence: Synthetic
                            polypeptide
                          organism = synthetic construct
SEQUENCE: 61
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAEGAPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
SSIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG      537

SEQ ID NO: 62             moltype = AA  length = 443
FEATURE                   Location/Qualifiers
source                    1..443
                          mol_type = protein
                          note = Description of Artificial Sequence: Synthetic
                            polypeptide
                          organism = synthetic construct
SEQUENCE: 62
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AEGAPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPSSIE KTISKAKGQP REPRVYTLPP CRDELTKNQV   360
SLTCLVKGFY PSDIAVEWES NGQPENNYKT TPPVLVSDGS FTLYSKLTVD KSRWQQGNVF   420
SCSVMHEALH NHYTQKSLSL SPG                                          443

SEQ ID NO: 63             moltype = AA  length = 26
FEATURE                   Location/Qualifiers
source                    1..26
                          mol_type = protein
                          note = Description of Artificial Sequence: Synthetic peptide
                          organism = synthetic construct
SEQUENCE: 63
GGGGSRVESK YGPPCPPCPA PEFEGG                                        26

SEQ ID NO: 64             moltype = AA  length = 31
FEATURE                   Location/Qualifiers
source                    1..31
                          mol_type = protein
                          note = Description of Artificial Sequence: Synthetic
                            polypeptide
                          organism = synthetic construct
SEQUENCE: 64
GGGGSGGGGS RVESKYGPPC PPCPAPEFEG G                                  31

SEQ ID NO: 65             moltype = AA  length = 27
FEATURE                   Location/Qualifiers
source                    1..27
                          mol_type = protein
                          note = Description of Artificial Sequence: Synthetic peptide
                          organism = synthetic construct
SEQUENCE: 65
GGGGSEPKSS DKTHTCPPCP APEAAGG                                       27
```

```
SEQ ID NO: 66            moltype = AA   length = 32
FEATURE                  Location/Qualifiers
source                   1..32
                         mol_type = protein
                         note = Description of Artificial Sequence: Synthetic
                           polypeptide
                         organism = synthetic construct
SEQUENCE: 66
GGGGSGGGGS EPKSSDKTHT CPPCPAPEAA GG                                   32

SEQ ID NO: 67            moltype = AA   length = 27
FEATURE                  Location/Qualifiers
source                   1..27
                         mol_type = protein
                         note = Description of Artificial Sequence: Synthetic peptide
                         organism = synthetic construct
SEQUENCE: 67
GGGGSEPKSS DKTHTCPPCP APEAEGA                                         27

SEQ ID NO: 68            moltype = AA   length = 32
FEATURE                  Location/Qualifiers
source                   1..32
                         mol_type = protein
                         note = Description of Artificial Sequence: Synthetic
                           polypeptide
                         organism = synthetic construct
SEQUENCE: 68
GGGGSGGGGS EPKSSDKTHT CPPCPAPEAE GA                                   32

SEQ ID NO: 69            moltype = AA   length = 536
FEATURE                  Location/Qualifiers
source                   1..536
                         mol_type = protein
                         note = Description of Artificial Sequence: Synthetic
                           polypeptide
                         organism = synthetic construct
SEQUENCE: 69
IWELKKDVYV VELDWYPDAP GEMVVLTCDT PEEDGITWTL DQSSEVLGSG KTLTIRVKEF      60
GDAGQYTCHK GGEVLSHSLL LLHKKEDGIW STDILKDQKE PKNKTFLRCE AKNYSGRFTC     120
WWLTTISTDL TFSVKSSRGS SDPQGVTCGA ATLSAERVRG DNKEYEYSVE CQEDSASPAA     180
EESLPIEVMV DAVHKLKYEN YTSSFFIRDI IKPDPPKNLQ LKPLKNSRQV EVSWEYPDTW     240
STPHSYFSLT FCVQVQGKSK REKKDRVFTD KTSATVICRK NASISVRAQD RCYSSSWSEW     300
ASVPCSRVES KYGPPCPPCP APEFLGGPSV FLFPPKPKDT LMISRTPEVT CVVVDVSQED     360
PEVQFNWYVD GVEVHNAKTK PREEQFNSTY RVVSVLTVLH QDWLNGKEYK CKVSNKGLPS     420
SIEKTISKAK GQPREPQVCT LPPSQEEMTK NQVSLTCLVE GFYPSDIAVE WESNGQPENN     480
YKTTPPVLDS DGSFFLYSWL TVDKSRWQEG NVFSCSVMHE ALHNHYTQKS LSLSLG         536

SEQ ID NO: 70            moltype = AA   length = 442
FEATURE                  Location/Qualifiers
source                   1..442
                         mol_type = protein
                         note = Description of Artificial Sequence: Synthetic
                           polypeptide
                         organism = synthetic construct
SEQUENCE: 70
RNLPVATPDP GMFPCLHHSQ NLLRAVSNML QKARQTLEFY PCTSEEIDHV DITKDKTSTV      60
EACLPLELTK NESSLNSRET SFITNGSCLA SRKTSFMMAL CLSSIYEDLK MYQVEFKTMN     120
AKLLMDPKRQ IFLDQNMLAV IDELMQALNF NSETVPQKSS LEEPDFYKTK IKLCILLHAF     180
RIRACTIDRV MSYLNASGGG GSGGGGSGGG GSRVESKYGP PCPPCPAPEF LGGPSVFLFP     240
PKPKDTLMIS RTPEVTCVVV DVSQEDPEVQ FNWYVDGVEV HNAKTKPREE QFNSTYRVVS     300
VLTVLHQDWL NGKEYKCKVS NKGLPSSIEK TISKAKGQPR EPQVYTLPPC QENMTKNQVS     360
LTCLVKGFYP SDIAVEWESN GQPENNYKTT PPVLVSDGSF TLYSRLTVDK SRWQEGNVFS     420
CSVMHEALHN HYTQKSLSLS LG                                              442

SEQ ID NO: 71            moltype = AA   length = 536
FEATURE                  Location/Qualifiers
source                   1..536
                         mol_type = protein
                         note = Description of Artificial Sequence: Synthetic
                           polypeptide
                         organism = synthetic construct
SEQUENCE: 71
IWELKKDVYV VELDWYPDAP GEMVVLTCDT PEEDGITWTL DQSSEVLGSG KTLTIRVKEF      60
GDAGQYTCHK GGEVLSHSLL LLHKKEDGIW STDILKDQKE PKNKTFLRCE AKNYSGRFTC     120
WWLTTISTDL TFSVKSSRGS SDPQGVTCGA ATLSAERVRG DNKEYEYSVE CQEDSASPAA     180
EESLPIEVMV DAVHKLKYEN YTSSFFIRDI IKPDPPKNLQ LKPLKNSRQV EVSWEYPDTW     240
STPHSYFSLT FCVQVQGKSK REKKDRVFTD KTSATVICRK NASISVRAQD RCYSSSWSEW     300
ASVPCSRVES KYGPPCPPCP APEFLGGPSV FLFPPKPKDT LMISRTPEVT CVVVDVSQED     360
```

```
PEVQFNWYVD GVEVHNAKTK PREEQFNSTY RVVSVLTVLH QDWLNGKEYK CKVSNKGLPS    420
SIEKTISKAK GQPREPQVCT LPPSQEEMTE NQVSLTCLVK GFYPSDIAVE WESNGQPENN    480
YKTTPPVLDS DGSFFLYSWL TVDKSRWQEG NVFSCSVMHE ALHNHYTQKS LSLSLG        536

SEQ ID NO: 72              moltype = AA   length = 442
FEATURE                    Location/Qualifiers
source                     1..442
                           mol_type = protein
                           note = Description of Artificial Sequence: Synthetic
                             polypeptide
                           organism = synthetic construct
SEQUENCE: 72
RNLPVATPDP GMFPCLHHSQ NLLRAVSNML QKARQTLEFY PCTSEEIDHV DITKDKTSTV     60
EACLPLELTK NESSLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRACTIDRV MSYLNASGGG GSGGGGSGGG GSRVESKYGP PCPPCPAPEF LGGPSVFLFP    240
PKPKDTLMIS RTPEVTCVVV DVSQEDPEVQ FNWYVDGVEV HNAKTKPREE QFNSTYRVVS    300
VLTVLHQDWL NGKEYKCKVS NKGLPSSIEK TISKAKGQPR ERVYTLPPC QEEMTKNQVS     360
LTCLVKGFYP SDIAVEWESN GQPENNYKTT PPVLVSDGSF TLYSRLTVDK SRWQEGNVFS    420
CSVMHEALHN HYTQKSLSLS LG                                            442

SEQ ID NO: 73              moltype = AA   length = 536
FEATURE                    Location/Qualifiers
source                     1..536
                           mol_type = protein
                           note = Description of Artificial Sequence: Synthetic
                             polypeptide
                           organism = synthetic construct
SEQUENCE: 73
IWELKKDVYV VELDWYPDAP GEMVVLTCDT PEEDGITWTL DQSSEVLGSG KTLTIRVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSASPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RCYSSSWSEW    300
ASVPCSRVES KYGPPCPPCP APEFEGGPSV FLFPPKPKDT LMISRTPEVT CVVVDVSQED    360
PEVQFNWYVD GVEVHNAKTK PREEQFNSTY RVVSVLTVLH QDWLNGKEYK CKVSNKGLPS    420
SIEKTISKAK GQPREPQVCT LPPSQEEMTE NQVSLTCLVK GFYPSDIAVE WESNGQPENN    480
YKTTPPVLDS DGSFFLYSWL TVDKSRWQEG NVFSCSVMHE ALHNHYTQKS LSLSLG        536

SEQ ID NO: 74              moltype = AA   length = 442
FEATURE                    Location/Qualifiers
source                     1..442
                           mol_type = protein
                           note = Description of Artificial Sequence: Synthetic
                             polypeptide
                           organism = synthetic construct
SEQUENCE: 74
RNLPVATPDP GMFPCLHHSQ NLLRAVSNML QKARQTLEFY PCTSEEIDHV DITKDKTSTV     60
EACLPLELTK NESSLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRACTIDRV MSYLNASGGG GSGGGGSGGG GSRVESKYGP PCPPCPAPEF EGGPSVFLFP    240
PKPKDTLMIS RTPEVTCVVV DVSQEDPEVQ FNWYVDGVEV HNAKTKPREE QFNSTYRVVS    300
VLTVLHQDWL NGKEYKCKVS NKGLPSSIEK TISKAKGQPR EPRVYTLPPC QEEMTKNQVS    360
LTCLVKGFYP SDIAVEWESN GQPENNYKTT PPVLVSDGSF TLYSRLTVDK SRWQEGNVFS    420
CSVMHEALHN HYTQKSLSLS LG                                            442

SEQ ID NO: 75              moltype = AA   length = 536
FEATURE                    Location/Qualifiers
source                     1..536
                           mol_type = protein
                           note = Description of Artificial Sequence: Synthetic
                             polypeptide
                           organism = synthetic construct
SEQUENCE: 75
IWELKKDVYV VELDWYPDAP GEMVVLTCDT PEEDGITWTL DQSSEVLGSG KTLTIRVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSASPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RCYSSSWSEW    300
ASVPCSRVES KYGPPCPPCP APEFEGGPSV FLFPPKPKDT LMISRTPEVT CVVVDVSQED    360
PEVQFNWYVD GVEVHNAKTK PREEQFNSTY RVVSVLTVLH QDWLNGKEYK CKVSNKGLAS    420
SIEKTISKAK GQPREPQVCT LPPSQEEMTE NQVSLTCLVK GFYPSDIAVE WESNGQPENN    480
YKTTPPVLDS DGSFFLYSWL TVDKSRWQEG NVFSCSVMHE ALHNHYTQKS LSLSLG        536

SEQ ID NO: 76              moltype = AA   length = 442
FEATURE                    Location/Qualifiers
source                     1..442
                           mol_type = protein
                           note = Description of Artificial Sequence: Synthetic
```

-continued

```
                              polypeptide
                              organism = synthetic construct
SEQUENCE: 76
RNLPVATPDP GMFPCLHHSQ NLLRAVSNML QKARQTLEFY PCTSEEIDHV DITKDKTSTV   60
EACLPLELTK NESSLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLASSIEK TISKAKGQPR EPRVYTLPPC QEEMTKNQVS  360
LTCLVKGFYP SDIAVEWESN GQPENNYKTT PPVLVSDGSF TLYSRLTVDK SRWQEGNVFS  420
CSVMHEALHN HYTQKSLSLS LG                                          442

SEQ ID NO: 77               moltype = AA  length = 536
FEATURE                     Location/Qualifiers
source                      1..536
                            mol_type = protein
                            note = Description of Artificial Sequence: Synthetic
                              polypeptide
                            organism = synthetic construct
SEQUENCE: 77
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSASPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSRVES KYGPPCPPCP APEFEGGPSV FLFPPKPKDT LMISRTPEVT CVVVDVSQED  360
PEVQFNWYVD GVEVHNAKTK PREEQFNSTY RVVSVLTVLH QDWLNGKEYK CKVSNKGLGS  420
SIEKTISKAK GQPREPQVCT LPPSQEEMTE NQVSLTCLVK GFYPSDIAVE WESNGQPENN  480
YKTTPPVLDS DGSFFLYSWL TVDKSRWQEG NVFSCSVMHE ALHNHYTQKS LSLSLG      536

SEQ ID NO: 78               moltype = AA  length = 442
FEATURE                     Location/Qualifiers
source                      1..442
                            mol_type = protein
                            note = Description of Artificial Sequence: Synthetic
                              polypeptide
                            organism = synthetic construct
SEQUENCE: 78
RNLPVATPDP GMFPCLHHSQ NLLRAVSNML QKARQTLEFY PCTSEEIDHV DITKDKTSTV   60
EACLPLELTK NESSLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLGSSIEK TISKAKGQPR EPRVYTLPPC QEEMTKNQVS  360
LTCLVKGFYP SDIAVEWESN GQPENNYKTT PPVLVSDGSF TLYSRLTVDK SRWQEGNVFS  420
CSVMHEALHN HYTQKSLSLS LG                                          442

SEQ ID NO: 79               moltype = AA  length = 537
FEATURE                     Location/Qualifiers
source                      1..537
                            mol_type = protein
                            note = Description of Artificial Sequence: Synthetic
                              polypeptide
                            organism = synthetic construct
SEQUENCE: 79
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSASPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSEPKS SDKTHTCPPC PAPELLGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
APIEKTISKA KGQPREPQVC TLPPSRDELT KNQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 80               moltype = AA  length = 443
FEATURE                     Location/Qualifiers
source                      1..443
                            mol_type = protein
                            note = Description of Artificial Sequence: Synthetic
                              polypeptide
                            organism = synthetic construct
SEQUENCE: 80
RNLPVATPDP GMFPCLHHSQ NLLRAVSNML QKARQTLEFY PCTSEEIDHV DITKDKTSTV   60
EACLPLELTK NESSLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSEPKSSDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPRVYTLPP CRDELTKNQV  360
```

```
SLTCLVKGFY PSDIAVEWES NGQPENNYKT TPPVLVSDGS FTLYSKLTVD KSRWQQGNVF   420
SCSVMHEALH NHYTQKSLSL SPG                                          443

SEQ ID NO: 81           moltype = AA  length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 81
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAAGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG     537

SEQ ID NO: 82           moltype = AA  length = 443
FEATURE                 Location/Qualifiers
source                  1..443
                        mol_type = protein
                        note = Description of Artificial Sequence: Synthetic
                          polypeptide
                        organism = synthetic construct
SEQUENCE: 82
RNLPVATPDP GMFPCLHHSQ NLLRAVSNML QKARQTLEFY PCTSEEIDHV DITKDKTSTV   60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPRVYTLPP CRDELTKNQV   360
SLTCLVKGFY PSDIAVEWES NGQPENNYKT TPPVLVSDGS FTLYSKLTVD KSRWQQGNVF   420
SCSVMHEALH NHYTQKSLSL SPG                                          443

SEQ ID NO: 83           moltype = AA  length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 83
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAAGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALA   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG     537

SEQ ID NO: 84           moltype = AA  length = 443
FEATURE                 Location/Qualifiers
source                  1..443
                        mol_type = protein
                        note = Description of Artificial Sequence: Synthetic
                          polypeptide
                        organism = synthetic construct
SEQUENCE: 84
RNLPVATPDP GMFPCLHHSQ NLLRAVSNML QKARQTLEFY PCTSEEIDHV DITKDKTSTV   60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALAAPIE KTISKAKGQP REPRVYTLPP CRDELTKNQV   360
SLTCLVKGFY PSDIAVEWES NGQPENNYKT TPPVLVSDGS FTLYSKLTVD KSRWQQGNVF   420
SCSVMHEALH NHYTQKSLSL SPG                                          443

SEQ ID NO: 85           moltype = AA  length = 537
FEATURE                 Location/Qualifiers
source                  1..537
                        mol_type = protein
                        note = Description of Artificial Sequence: Synthetic
                          polypeptide
```

```
                            organism = synthetic construct
SEQUENCE: 85
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAAGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALG   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG     537

SEQ ID NO: 86          moltype = AA  length = 443
FEATURE                Location/Qualifiers
source                 1..443
                       mol_type = protein
                       note = Description of Artificial Sequence: Synthetic
                        polypeptide
                       organism = synthetic construct
SEQUENCE: 86
RNLPVATPDP GMFPCLHHSQ NLLRAVSNML QKARQTLEFY PCTSEEIDHV DITKDKTSTV    60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALGAPIE KTISKAKGQP REPRVYTLPP CRDELTKNQV   360
SLTCLVKGFY PSDIAVEWES NGQPENNYKT TPPVLSDGS FTLYSKLTVD KSRWQQGNVF   420
SCSVMHEALH NHYTQKSLSL SPG                                         443

SEQ ID NO: 87          moltype = AA  length = 537
FEATURE                Location/Qualifiers
source                 1..537
                       mol_type = protein
                       note = Description of Artificial Sequence: Synthetic
                        polypeptide
                       organism = synthetic construct
SEQUENCE: 87
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAEGAPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
SSIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG     537

SEQ ID NO: 88          moltype = AA  length = 443
FEATURE                Location/Qualifiers
source                 1..443
                       mol_type = protein
                       note = Description of Artificial Sequence: Synthetic
                        polypeptide
                       organism = synthetic construct
SEQUENCE: 88
RNLPVATPDP GMFPCLHHSQ NLLRAVSNML QKARQTLEFY PCTSEEIDHV DITKDKTSTV    60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AEGAPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPSSIE KTISKAKGQP REPRVYTLPP CRDELTKNQV   360
SLTCLVKGFY PSDIAVEWES NGQPENNYKT TPPVLSDGS FTLYSKLTVD KSRWQQGNVF   420
SCSVMHEALH NHYTQKSLSL SPG                                         443

SEQ ID NO: 89          moltype = AA  length = 536
FEATURE                Location/Qualifiers
source                 1..536
                       mol_type = protein
                       note = Description of Artificial Sequence: Synthetic
                        polypeptide
                       organism = synthetic construct
SEQUENCE: 89
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSRVES KYGPPCPPCP APEFLGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLPS   420
```

```
SIEKTISKAK  GQPREPQVCT  LPPSQEEMTE  NQVSLTCLVK  GFYPSDIAVE  WESNGQPENN   480
YKTTPPVLDS  DGSFFLYSWL  TVDKSRWQEG  NVFSCSVMHE  ALHNHYTQKS  LSLSLG        536

SEQ ID NO: 90               moltype = AA  length = 442
FEATURE                     Location/Qualifiers
source                      1..442
                            mol_type = protein
                            note = Description of Artificial Sequence: Synthetic
                              polypeptide
                            organism = synthetic construct
SEQUENCE: 90
RNLPVATPDP  GMFPCLHHSQ  NLLRAVSNML  QKARQTLEFY  PCTSEEIDHV  DITKDKTSTV    60
EACLPLELTK  NESCLNSRET  SFITNGSCLA  SRKTSFMMAL  CLSSIYEDLK  MYQVEFKTMN   120
AKLLMDPKRQ  IFLDQNMLAV  IDELMQALNF  NSETVPQKSS  LEEPDFYKTK  IKLCILLHAF   180
RIRACTIDRV  MSYLNASGGG  GSGGGGSGGG  GSRVESKYGP  PCPPCPAPEF  LGGPSVFLFP   240
PKPKDTLMIS  RTPEVTCVVV  DVSQEDPEVQ  FNWYVDGVEV  HNAKTKPREE  QFNSTYRVVS   300
VLTVLHQDWL  NGKEYKCKVS  NKGLPSSIEK  TISKAKGQPR  EPRVYTLPPC  QEEMTKNQVS   360
LTCLVKGFYP  SDIAVEWESN  GQPENNYKTT  PPVLVSDGSF  TLYSRLTVDK  SRWQEGNVFS   420
CSVMHEALHN  HYTQKSLSLS  LG                                               442

SEQ ID NO: 91               moltype = AA  length = 536
FEATURE                     Location/Qualifiers
source                      1..536
                            mol_type = protein
                            note = Description of Artificial Sequence: Synthetic
                              polypeptide
                            organism = synthetic construct
SEQUENCE: 91
IWELKKDVYV  VELDWYPDAP  GEMVVLTCDT  PEEDGITWTL  DQSSEVLGSG  KTLTIRVKEF    60
GDAGQYTCHK  GGEVLSHSLL  LLHKKEDGIW  STDILKDQKE  PKNKTFLRCE  AKNYSGRFTC   120
WWLTTISTDL  TFSVKSSRGS  SDPQGVTCGA  ATLSAERVRG  DNKEYEYSVE  CQEDSACPAA   180
EESLPIEVMV  DAVHKLKYEN  YTSSFFIRDI  IKPDPPKNLQ  LKPLKNSRQV  EVSWEYPDTW   240
STPHSYFSLT  FCVQVQGKSK  REKKDRVFTD  KTSATVICRK  NASISVRAQD  RCYSSSWSEW   300
ASVPCSRVES  KYGPPCPPCP  APEFEGGPSV  FLFPPKPKDT  LMISRTPEVT  CVVVDVSQED   360
PEVQFNWYVD  GVEVHNAKTK  PREEQFNSTY  RVVSVLTVLH  QDWLNGKEYK  CKVSNKGLPS   420
SIEKTISKAK  GQPREPQVCT  LPPSQEEMTE  NQVSLTCLVK  GFYPSDIAVE  WESNGQPENN   480
YKTTPPVLDS  DGSFFLYSWL  TVDKSRWQEG  NVFSCSVMHE  ALHNHYTQKS  LSLSLG        536

SEQ ID NO: 92               moltype = AA  length = 442
FEATURE                     Location/Qualifiers
source                      1..442
                            mol_type = protein
                            note = Description of Artificial Sequence: Synthetic
                              polypeptide
                            organism = synthetic construct
SEQUENCE: 92
RNLPVATPDP  GMFPCLHHSQ  NLLRAVSNML  QKARQTLEFY  PCTSEEIDHV  DITKDKTSTV    60
EACLPLELTK  NESCLNSRET  SFITNGSCLA  SRKTSFMMAL  CLSSIYEDLK  MYQVEFKTMN   120
AKLLMDPKRQ  IFLDQNMLAV  IDELMQALNF  NSETVPQKSS  LEEPDFYKTK  IKLCILLHAF   180
RIRACTIDRV  MSYLNASGGG  GSGGGGSGGG  GSRVESKYGP  PCPPCPAPEF  EGGPSVFLFP   240
PKPKDTLMIS  RTPEVTCVVV  DVSQEDPEVQ  FNWYVDGVEV  HNAKTKPREE  QFNSTYRVVS   300
VLTVLHQDWL  NGKEYKCKVS  NKGLPSSIEK  TISKAKGQPR  EPRVYTLPPC  QEEMTKNQVS   360
LTCLVKGFYP  SDIAVEWESN  GQPENNYKTT  PPVLVSDGSF  TLYSRLTVDK  SRWQEGNVFS   420
CSVMHEALHN  HYTQKSLSLS  LG                                               442

SEQ ID NO: 93               moltype = AA  length = 536
FEATURE                     Location/Qualifiers
source                      1..536
                            mol_type = protein
                            note = Description of Artificial Sequence: Synthetic
                              polypeptide
                            organism = synthetic construct
SEQUENCE: 93
IWELKKDVYV  VELDWYPDAP  GEMVVLTCDT  PEEDGITWTL  DQSSEVLGSG  KTLTIRVKEF    60
GDAGQYTCHK  GGEVLSHSLL  LLHKKEDGIW  STDILKDQKE  PKNKTFLRCE  AKNYSGRFTC   120
WWLTTISTDL  TFSVKSSRGS  SDPQGVTCGA  ATLSAERVRG  DNKEYEYSVE  CQEDSACPAA   180
EESLPIEVMV  DAVHKLKYEN  YTSSFFIRDI  IKPDPPKNLQ  LKPLKNSRQV  EVSWEYPDTW   240
STPHSYFSLT  FCVQVQGKSK  REKKDRVFTD  KTSATVICRK  NASISVRAQD  RCYSSSWSEW   300
ASVPCSRVES  KYGPPCPPCP  APEFEGGPSV  FLFPPKPKDT  LMISRTPEVT  CVVVDVSQED   360
PEVQFNWYVD  GVEVHNAKTK  PREEQFNSTY  RVVSVLTVLH  QDWLNGKEYK  CKVSNKGLAS   420
SIEKTISKAK  GQPREPQVCT  LPPSQEEMTE  NQVSLTCLVK  GFYPSDIAVE  WESNGQPENN   480
YKTTPPVLDS  DGSFFLYSWL  TVDKSRWQEG  NVFSCSVMHE  ALHNHYTQKS  LSLSLG        536

SEQ ID NO: 94               moltype = AA  length = 442
FEATURE                     Location/Qualifiers
source                      1..442
                            mol_type = protein
                            note = Description of Artificial Sequence: Synthetic
                              polypeptide
```

```
                        organism = synthetic construct
SEQUENCE: 94
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSRVESKYGP PCPPCPAPEF EGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLASSIEK TISKAKGQPR EPRVYTLPPC QEEMTKNQVS   360
LTCLVKGFYP SDIAVEWESN GQPENNYKTT PPVLVSDGSF TLYSRLTVDK SRWQEGNVFS   420
CSVMHEALHN HYTQKSLSLS LG                                            442

SEQ ID NO: 95           moltype = AA   length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 95
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSRVES KYGPPCPPCP APEFEGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLGS   420
SIEKTISKAK GQPREPQVCT LPPSQEEMTE NQVSLTCLVK GFYPSDIAVE WESNGQPENN   480
YKTTPPVLDS DGSFFLYSWL TVDKSRWQEG NVFSCSVMHE ALHNHYTQKS LSLSLG       536

SEQ ID NO: 96           moltype = AA   length = 442
FEATURE                 Location/Qualifiers
source                  1..442
                        mol_type = protein
                        note = Description of Artificial Sequence: Synthetic
                          polypeptide
                        organism = synthetic construct
SEQUENCE: 96
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSRVESKYGP PCPPCPAPEF EGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLGSSIEK TISKAKGQPR EPRVYTLPPC QEEMTKNQVS   360
LTCLVKGFYP SDIAVEWESN GQPENNYKTT PPVLVSDGSF TLYSRLTVDK SRWQEGNVFS   420
CSVMHEALHN HYTQKSLSLS LG                                            442

SEQ ID NO: 97           moltype = AA   length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 97
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPELLGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG      537

SEQ ID NO: 98           moltype = AA   length = 443
FEATURE                 Location/Qualifiers
source                  1..443
                        mol_type = protein
                        note = Description of Artificial Sequence: Synthetic
                          polypeptide
                        organism = synthetic construct
SEQUENCE: 98
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE LLGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPRVYTLPP CRDELTKNQV   360
SLTCLVKGFY PSDIAVEWES NGQPENNYKT TPPVLVSDGS FTLYSKLTVD KSRWQQGNVF   420
```

```
SCSVMHEALH NHYTQKSLSL SPG                                              443

SEQ ID NO: 99              moltype = AA  length = 537
FEATURE                    Location/Qualifiers
source                     1..537
                           mol_type = protein
                           note = Description of Artificial Sequence: Synthetic
                             polypeptide
                           organism = synthetic construct
SEQUENCE: 99
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSEPKS SDKTHTCPPC PAPEAAGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
APIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 100             moltype = AA  length = 443
FEATURE                    Location/Qualifiers
source                     1..443
                           mol_type = protein
                           note = Description of Artificial Sequence: Synthetic
                             polypeptide
                           organism = synthetic construct
SEQUENCE: 100
RNLPVATPDP GMFPCLHHSQ NLLRAVSNML QKARQTLEFY PCTSEEIDHV DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSEPKSSDKT HTCPPCPAPE AAGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPRVYTLPP CRDELTKNQV  360
SLTCLVKGFY PSDIAVEWES NGQPENNYKT TPPVLVSDGS FTLYSKLTVD KSRWQQGNVF  420
SCSVMHEALH NHYTQKSLSL SPG                                         443

SEQ ID NO: 101             moltype = AA  length = 537
FEATURE                    Location/Qualifiers
source                     1..537
                           mol_type = protein
                           note = Description of Artificial Sequence: Synthetic
                             polypeptide
                           organism = synthetic construct
SEQUENCE: 101
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSEPKS SDKTHTCPPC PAPEAAGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALA  420
APIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 102             moltype = AA  length = 443
FEATURE                    Location/Qualifiers
source                     1..443
                           mol_type = protein
                           note = Description of Artificial Sequence: Synthetic
                             polypeptide
                           organism = synthetic construct
SEQUENCE: 102
RNLPVATPDP GMFPCLHHSQ NLLRAVSNML QKARQTLEFY PCTSEEIDHV DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSEPKSSDKT HTCPPCPAPE AAGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALAAPIE KTISKAKGQP REPRVYTLPP CRDELTKNQV  360
SLTCLVKGFY PSDIAVEWES NGQPENNYKT TPPVLVSDGS FTLYSKLTVD KSRWQQGNVF  420
SCSVMHEALH NHYTQKSLSL SPG                                         443

SEQ ID NO: 103             moltype = AA  length = 537
FEATURE                    Location/Qualifiers
source                     1..537
                           mol_type = protein
                           note = Description of Artificial Sequence: Synthetic
                             polypeptide
                           organism = synthetic construct
```

```
SEQUENCE: 103
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAAGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALG   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG     537

SEQ ID NO: 104          moltype = AA  length = 443
FEATURE                 Location/Qualifiers
source                  1..443
                        mol_type = protein
                        note = Description of Artificial Sequence: Synthetic
                          polypeptide
                        organism = synthetic construct
SEQUENCE: 104
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALGAPIE KTISKAKGQP REPRVYTLPP CRDELTKNQV   360
SLTCLVKGFY PSDIAVEWES NGQPENNYKT TPPVLSDGS FTLYSKLTVD KSRWQQGNVF   420
SCSVMHEALH NHYTQKSLSL SPG                                         443

SEQ ID NO: 105          moltype = AA  length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 105
IWELKKDVYV VELDWYPDAP GEMVVLTCDT PEEDGITWTL DQSSEVLGSG KTLTIRVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAEGAPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
SSIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG     537

SEQ ID NO: 106          moltype = AA  length = 443
FEATURE                 Location/Qualifiers
source                  1..443
                        mol_type = protein
                        note = Description of Artificial Sequence: Synthetic
                          polypeptide
                        organism = synthetic construct
SEQUENCE: 106
RNLPVATPDP GMFPCLHHSQ NLLRAVSNML QKARQTLEFY PCTSEEIDHV DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AEGAPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPSSIE KTISKAKGQP REPRVYTLPP CRDELTKNQV   360
SLTCLVKGFY PSDIAVEWES NGQPENNYKT TPPVLSDGS FTLYSKLTVD KSRWQQGNVF   420
SCSVMHEALH NHYTQKSLSL SPG                                         443

SEQ ID NO: 107          moltype = AA  length = 20
FEATURE                 Location/Qualifiers
source                  1..20
                        mol_type = protein
                        note = Description of Artificial Sequence: Synthetic peptide
                        organism = synthetic construct
SEQUENCE: 107
GGGGSGGGGS GGGGSGGGGS                                              20

SEQ ID NO: 108          moltype = AA  length = 15
FEATURE                 Location/Qualifiers
source                  1..15
                        mol_type = protein
                        note = Description of Artificial Sequence: Synthetic peptide
                        organism = synthetic construct
SEQUENCE: 108
```

```
GGGGSGGGGS GGGGS                                                       15

SEQ ID NO: 109         moltype = AA  length = 10
FEATURE                Location/Qualifiers
source                 1..10
                       mol_type = protein
                       note = Description of Artificial Sequence: Synthetic peptide
                       organism = synthetic construct
SEQUENCE: 109
GGGGSGGGGS                                                             10

SEQ ID NO: 110         moltype = AA  length = 5
FEATURE                Location/Qualifiers
source                 1..5
                       mol_type = protein
                       note = Description of Artificial Sequence: Synthetic peptide
                       organism = synthetic construct
SEQUENCE: 110
GGGGS                                                                  5

SEQ ID NO: 111         moltype = AA  length = 20
FEATURE                Location/Qualifiers
source                 1..20
                       mol_type = protein
                       note = Description of Artificial Sequence: Synthetic peptide
                       organism = synthetic construct
SEQUENCE: 111
GSGSGSGSGS GSGSGSGSGS                                                  20

SEQ ID NO: 112         moltype = AA  length = 30
FEATURE                Location/Qualifiers
source                 1..30
                       mol_type = protein
                       note = Description of Artificial Sequence: Synthetic
                        polypeptide
                       organism = synthetic construct
SEQUENCE: 112
GGSGGSGGSG GSGGSGGSGG SGGSGGSGGS                                       30

SEQ ID NO: 113         moltype = AA  length = 40
FEATURE                Location/Qualifiers
source                 1..40
                       mol_type = protein
                       note = Description of Artificial Sequence: Synthetic
                        polypeptide
                       organism = synthetic construct
SEQUENCE: 113
GGGSGGGSGG GSGGGSGGGS GGGSGGGSGG GSGGGSGGGS                            40

SEQ ID NO: 114         moltype = AA  length = 40
FEATURE                Location/Qualifiers
source                 1..40
                       mol_type = protein
                       note = Description of Artificial Sequence: Synthetic
                        polypeptide
                       organism = synthetic construct
SEQUENCE: 114
GGSGGGSGGG SGGGSGGGSG GGSGGGSGGG SGGGSGGGSG                            40

SEQ ID NO: 115         moltype = AA  length = 50
FEATURE                Location/Qualifiers
source                 1..50
                       mol_type = protein
                       note = Description of Artificial Sequence: Synthetic
                        polypeptide
                       organism = synthetic construct
SEQUENCE: 115
GGSGGGGSGG GGSGGGGSGG GGSGGGSGG GGSGGGGSGG GGSGGGGSGG                  50

SEQ ID NO: 116         moltype = AA  length = 50
FEATURE                Location/Qualifiers
source                 1..50
                       mol_type = protein
                       note = Description of Artificial Sequence: Synthetic
                        polypeptide
                       organism = synthetic construct
SEQUENCE: 116
GGGGSGGGGS GGGGSGGGGS GGGGSGGGGS GGGGSGGGGS GGGGSGGGGS                  50
```

```
SEQ ID NO: 117          moltype = AA  length = 20
FEATURE                 Location/Qualifiers
source                  1..20
                        mol_type = protein
                        note = Description of Artificial Sequence: Synthetic peptide
                        organism = synthetic construct
SEQUENCE: 117
GGGGSGGGGS GGGGSGGGGS                                                    20

SEQ ID NO: 118          moltype = AA  length = 15
FEATURE                 Location/Qualifiers
source                  1..15
                        mol_type = protein
                        note = Description of Artificial Sequence: Synthetic peptide
                        organism = synthetic construct
SEQUENCE: 118
GGGGSGGGGS GGGGS                                                         15

SEQ ID NO: 119          moltype = AA  length = 100
FEATURE                 Location/Qualifiers
source                  1..100
                        mol_type = protein
                        note = Description of Artificial Sequence: Synthetic
                         polypeptide
                        organism = synthetic construct
SEQUENCE: 119
GGGGSGGGGS GGGGSGGGGS GGGGSGGGGS GGGGSGGGGS GGGGSGGGGS GGGGSGGGGS        60
GGGGSGGGGS GGGGSGGGGS GGGGSGGGGS GGGGSGGGGS                             100

SEQ ID NO: 120          moltype = AA  length = 100
FEATURE                 Location/Qualifiers
source                  1..100
                        mol_type = protein
                        note = Description of Artificial Sequence: Synthetic
                         polypeptide
                        organism = synthetic construct
SEQUENCE: 120
GGSGGGGSGG GGSGGGGSGG GGSGGGGSGG GGSGGGGSGG GGSGGGGSGG GGSGGGGSGG        60
GGSGGGGSGG GGSGGGGSGG GGSGGGGSGG GGSGGGGSGG                             100

SEQ ID NO: 121          moltype = AA  length = 306
FEATURE                 Location/Qualifiers
source                  1..306
                        mol_type = protein
                        note = Description of Artificial Sequence: Synthetic
                         polypeptide
                        organism = synthetic construct
SEQUENCE: 121
IWELKKDVYV VELDWYPDAP GEMVVLTCDT PEEDGITWTL DQSSEVLGSG KTLTIRVKEF        60
GDAGQYTCHK GGEVLSHSLL LLHKKEDGIW STDILKDQKE PKNKTFLRCE AKNYSGRFTC       120
WWLTTISTDL TFSVKSSRGS SDPQGVTCGA ATLSAERVRG DNKEYEYSVE CQEDSACPAA       180
EESLPIEVMV DAVHKLKYEN YTSSFFIRDI IKPDPPKNLQ LKPLKNSRQV EVSWEYPDTW       240
STPHSYFSLT FCVQVQGKSK REKKDRVFTD KTSATVICRK NASISVRAQD RYYSSSWSEW       300
ASVPCS                                                                 306

SEQ ID NO: 122          moltype = AA  length = 197
FEATURE                 Location/Qualifiers
source                  1..197
                        mol_type = protein
                        note = Description of Artificial Sequence: Synthetic
                         polypeptide
                        organism = synthetic construct
SEQUENCE: 122
RNLPVATPDP GMFPCLHHSQ NLLRAVSNML QKARQTLEFY PCTSEEIDHV DITKDKTSTV        60
EACLPLELTK NESCLNSRET SFITNGSCLA SRKTSFMMAL CLSSIYEDLK MYQVEFKTMN       120
AKLLMDPKRQ IFLDQNMLAV IDELMQALNF NSETVPQKSS LEEPDFYKTK IKLCILLHAF       180
RIRAVTIDRV MSYLNAS                                                     197

SEQ ID NO: 123          moltype = AA  length = 306
FEATURE                 Location/Qualifiers
source                  1..306
                        mol_type = protein
                        note = Description of Artificial Sequence: Synthetic
                         polypeptide
                        organism = synthetic construct
SEQUENCE: 123
IWELKKDVYV VELDWYPDAP GEMVVLTCDT PEEDGITWTL DQSSEVLGSG KTLTIRVKEF        60
GDAGQYTCHK GGEVLSHSLL LLHKKEDGIW STDILKDQKE PKNKTFLRCE AKNYSGRFTC       120
WWLTTISTDL TFSVKSSRGS SDPQGVTCGA ATLSAERVRG DNKEYEYSVE CQEDSASPAA       180
```

```
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCS                                                              306

SEQ ID NO: 124          moltype = AA   length = 197
FEATURE                 Location/Qualifiers
source                  1..197
                        mol_type = protein
                        note = Description of Artificial Sequence: Synthetic
                         polypeptide
                        organism = synthetic construct
SEQUENCE: 124
RNLPVATPDP GMFPCLHHSQ NLLRAVSNML QKARQTLEFY PCTSEEIDHV DITKDKTSTV   60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNAS                                                  197

SEQ ID NO: 125          moltype = AA   length = 306
FEATURE                 Location/Qualifiers
source                  1..306
                        mol_type = protein
                        note = Description of Artificial Sequence: Synthetic
                         polypeptide
                        organism = synthetic construct
SEQUENCE: 125
IWELKKDVYV VELDWYPDAP GEMVVLTCDT PEEDGITWTL DQSSEVLGSG KTLTIRVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCS                                                              306

SEQ ID NO: 126          moltype = AA   length = 197
FEATURE                 Location/Qualifiers
source                  1..197
                        mol_type = protein
                        note = Description of Artificial Sequence: Synthetic
                         polypeptide
                        organism = synthetic construct
SEQUENCE: 126
RNLPVATPDP GMFPCLHHSQ NLLRAVSNML QKARQTLEFY PCTSEEIDHV DITKDKTSTV   60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNAS                                                  197

SEQ ID NO: 127          moltype = AA   length = 306
FEATURE                 Location/Qualifiers
source                  1..306
                        mol_type = protein
                        organism = Homo sapiens
SEQUENCE: 127
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCS                                                              306

SEQ ID NO: 128          moltype = AA   length = 197
FEATURE                 Location/Qualifiers
source                  1..197
                        mol_type = protein
                        organism = Homo sapiens
SEQUENCE: 128
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNAS                                                  197

SEQ ID NO: 129          moltype = AA   length = 536
FEATURE                 Location/Qualifiers
source                  1..536
                        mol_type = protein
                        note = Description of Artificial Sequence: Synthetic
                         polypeptide
                        organism = synthetic construct
SEQUENCE: 129
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
```

```
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSRVES KYGPPCPPCP APEFLGGPSV FLFPPKPKDT LMISRTPEVT CVVVDVSQED    360
PEVQFNWYVD GVEVHNAKTK PREEQFNSTY RVVSVLTVLH QDWLNGKEYK CKVSNKGLPS    420
SIEKTISKAK GQREPQVCT LPPSQEEMTK NQVSLTCLVE GFYPSDIAVE WESNGQPENN     480
YKTTPPVLDS DGSFFLYSWL TVDKSRWQEG NVFSCSVMHE ALHNHYTQKS LSLSLG        536

SEQ ID NO: 130             moltype = AA   length = 442
FEATURE                    Location/Qualifiers
source                     1..442
                           mol_type = protein
                           note = Description of Artificial Sequence: Synthetic
                             polypeptide
                           organism = synthetic construct
SEQUENCE: 130
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSGGGGSGGG GSRVESKYGP PCPPCPAPEF LGGPSVFLFP    240
PKPKDTLMIS RTPEVTCVVV DVSQEDPEVQ FNWYVDGVEV HNAKTKPREE QFNSTYRVVS    300
VLTVLHQDWL NGKEYKCKVS NKGLPSSIEK TISKAKGQPR EPQVYTLPPC QENMTKNQVS    360
LTCLVKGFYP SDIAVEWESN GQPENNYKTT PPVLSDGSF TLYSRLTVDK SRWQEGNVFS     420
CSVMHEALHN HYTQKSLSLS LG                                            442

SEQ ID NO: 131             moltype = AA   length = 536
FEATURE                    Location/Qualifiers
source                     1..536
                           mol_type = protein
                           note = Description of Artificial Sequence: Synthetic
                             polypeptide
                           organism = synthetic construct
SEQUENCE: 131
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSRVES KYGPPCPPCP APEFLGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLPS   420
SIEKTISKAK GQREPQVCT LPPSQEEMTE NQVSLTCLVK GFYPSDIAVE WESNGQPENN    480
YKTTPPVLDS DGSFFLYSWL TVDKSRWQEG NVFSCSVMHE ALHNHYTQKS LSLSLG       536

SEQ ID NO: 132             moltype = AA   length = 442
FEATURE                    Location/Qualifiers
source                     1..442
                           mol_type = protein
                           note = Description of Artificial Sequence: Synthetic
                             polypeptide
                           organism = synthetic construct
SEQUENCE: 132
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSGGGGSGGG GSRVESKYGP PCPPCPAPEF LGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLPSSIEK TISKAKGQPR EPRVYTLPPC QEEMTKNQVS   360
LTCLVKGFYP SDIAVEWESN GQPENNYKTT PPVLSDGSF TLYSRLTVDK SRWQEGNVFS    420
CSVMHEALHN HYTQKSLSLS LG                                           442

SEQ ID NO: 133             moltype = AA   length = 536
FEATURE                    Location/Qualifiers
source                     1..536
                           mol_type = protein
                           note = Description of Artificial Sequence: Synthetic
                             polypeptide
                           organism = synthetic construct
SEQUENCE: 133
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSRVES KYGPPCPPCP APEFEGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLPS   420
SIEKTISKAK GQREPQVCT LPPSQEEMTE NQVSLTCLVK GFYPSDIAVE WESNGQPENN    480
YKTTPPVLDS DGSFFLYSWL TVDKSRWQEG NVFSCSVMHE ALHNHYTQKS LSLSLG       536

SEQ ID NO: 134             moltype = AA   length = 442
```

```
FEATURE                 Location/Qualifiers
source                  1..442
                        mol_type = protein
                        note = Description of Artificial Sequence: Synthetic
                         polypeptide
                        organism = synthetic construct
SEQUENCE: 134
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSGGGGSGGG GSRVESKYGP PCPPCPAPEF EGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLPSSIEK TISKAKGQPR EPRVYTLPPC QEEMTKNQVS   360
LTCLVKGFYP SDIAVEWESN GQPENNYKTT PPVLSDGSFF TLYSRLTVDK SRWQEGNVFS   420
CSVMHEALHN HYTQKSLSLS LG                                            442

SEQ ID NO: 135          moltype = AA  length = 536
FEATURE                 Location/Qualifiers
source                  1..536
                        mol_type = protein
                        note = Description of Artificial Sequence: Synthetic
                         polypeptide
                        organism = synthetic construct
SEQUENCE: 135
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSRVES KYGPPCPPCP APEFEGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLAS   420
SIEKTISKAK GQPREPQVCT LPPSQEEMTE NQVSLTCLVK GFYPSDIAVE WESNGQPENN   480
YKTTPPVLDS DGSFFLYSWL TVDKSRWQEG NVFSCSVMHE ALHNHYTQKS LSLSLG       536

SEQ ID NO: 136          moltype = AA  length = 442
FEATURE                 Location/Qualifiers
source                  1..442
                        mol_type = protein
                        note = Description of Artificial Sequence: Synthetic
                         polypeptide
                        organism = synthetic construct
SEQUENCE: 136
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSGGGGSGGG GSRVESKYGP PCPPCPAPEF EGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLASSIEK TISKAKGQPR EPRVYTLPPC QEEMTKNQVS   360
LTCLVKGFYP SDIAVEWESN GQPENNYKTT PPVLSDGSFF TLYSRLTVDK SRWQEGNVFS   420
CSVMHEALHN HYTQKSLSLS LG                                            442

SEQ ID NO: 137          moltype = AA  length = 537
FEATURE                 Location/Qualifiers
source                  1..537
                        mol_type = protein
                        note = Description of Artificial Sequence: Synthetic
                         polypeptide
                        organism = synthetic construct
SEQUENCE: 137
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSEPKS SDKTHTCPPC PAPELLGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG      537

SEQ ID NO: 138          moltype = AA  length = 443
FEATURE                 Location/Qualifiers
source                  1..443
                        mol_type = protein
                        note = Description of Artificial Sequence: Synthetic
                         polypeptide
                        organism = synthetic construct
SEQUENCE: 138
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
```

```
AKLLMDPKRQ IFLDQNMLAV IDELMQALNF NSETVPQKSS LEEPDFYKTK IKLCILLHAF 180
RIRAVTIDRV MSYLNASGGG GSGGGGSGGG GSEPKSSDKT HTCPPCPAPE LLGGPSVFLF 240
PPKPKDTLMI SRTPEVTCVV VDVSHEDPEV KFNWYVDGVE VHNAKTKPRE EQYNSTYRVV 300
SVLTVLHQDW LNGKEYKCKV SNKALPAPIE KTISKAKGQP REPRVYTLPP CRDELTKNQV 360
SLTCLVKGFY PSDIAVEWES NGQPENNYKT TPPVLVSDGS FTLYSKLTVD KSRWQQGNVF 420
SCSVMHEALH NHYTQKSLSL SPG 443

SEQ ID NO: 139       moltype = AA  length = 537
FEATURE              Location/Qualifiers
source               1..537
                     mol_type = protein
                     note = Description of Artificial Sequence: Synthetic
                       polypeptide
                     organism = synthetic construct
SEQUENCE: 139
IWELKKDVYV VELDWYPDAP GEMVVLTCDT PEEDGITWTL DQSSEVLGSG KTLTIQVKEF 60
GDAGQYTCHK GGEVLSHSLL LLHKKEDGIW STDILKDQKE PKNKTFLRCE AKNYSGRFTC 120
WWLTTISTDL TFSVKSSRGS SDPQGVTCGA ATLSAERVRG DNKEYEYSVE CQEDSACPAA 180
EESLPIEVMV DAVHKLKYEN YTSSFFIRDI IKPDPPKNLQ LKPLKNSRQV EVSWEYPDTW 240
STPHSYFSLT FCVQVQGKSK REKKDRVFTD KTSATVICRK NASISVRAQD RYYSSSWSEW 300
ASVPCSEPKS SDKTHTCPPC PAPEAAGGPS VFLFPPKPKD TLMISRTPEV TCVVVDVSHE 360
DPEVKFNWYV DGVEVHNAKT KPREEQYNST YRVVSVLTVL HQDWLNGKEY KCKVSNKALP 420
APIEKTISKA KGQPREPQVC TLPPSRDELT ENQVSLTCLV KGFYPSDIAV EWESNGQPEN 480
NYKTTPPVLD SDGSFFLYSW LTVDKSRWQQ GNVFSCSVMH EALHNHYTQK SLSLSPG 537

SEQ ID NO: 140       moltype = AA  length = 443
FEATURE              Location/Qualifiers
source               1..443
                     mol_type = protein
                     note = Description of Artificial Sequence: Synthetic
                       polypeptide
                     organism = synthetic construct
SEQUENCE: 140
RNLPVATPDP GMFPCLHHSQ NLLRAVSNML QKARQTLEFY PCTSEEIDHE DITKDKTSTV 60
EACLPLELTK NESCLNSRET SFITNGSCLA SRKTSFMMAL CLSSIYEDLK MYQVEFKTMN 120
AKLLMDPKRQ IFLDQNMLAV IDELMQALNF NSETVPQKSS LEEPDFYKTK IKLCILLHAF 180
RIRAVTIDRV MSYLNASGGG GSGGGGSGGG GSEPKSSDKT HTCPPCPAPE AAGGPSVFLF 240
PPKPKDTLMI SRTPEVTCVV VDVSHEDPEV KFNWYVDGVE VHNAKTKPRE EQYNSTYRVV 300
SVLTVLHQDW LNGKEYKCKV SNKALPAPIE KTISKAKGQP REPRVYTLPP CRDELTKNQV 360
SLTCLVKGFY PSDIAVEWES NGQPENNYKT TPPVLVSDGS FTLYSKLTVD KSRWQQGNVF 420
SCSVMHEALH NHYTQKSLSL SPG 443

SEQ ID NO: 141       moltype = AA  length = 537
FEATURE              Location/Qualifiers
source               1..537
                     mol_type = protein
                     note = Description of Artificial Sequence: Synthetic
                       polypeptide
                     organism = synthetic construct
SEQUENCE: 141
IWELKKDVYV VELDWYPDAP GEMVVLTCDT PEEDGITWTL DQSSEVLGSG KTLTIQVKEF 60
GDAGQYTCHK GGEVLSHSLL LLHKKEDGIW STDILKDQKE PKNKTFLRCE AKNYSGRFTC 120
WWLTTISTDL TFSVKSSRGS SDPQGVTCGA ATLSAERVRG DNKEYEYSVE CQEDSACPAA 180
EESLPIEVMV DAVHKLKYEN YTSSFFIRDI IKPDPPKNLQ LKPLKNSRQV EVSWEYPDTW 240
STPHSYFSLT FCVQVQGKSK REKKDRVFTD KTSATVICRK NASISVRAQD RYYSSSWSEW 300
ASVPCSEPKS SDKTHTCPPC PAPEAAGGPS VFLFPPKPKD TLMISRTPEV TCVVVDVSHE 360
DPEVKFNWYV DGVEVHNAKT KPREEQYNST YRVVSVLTVL HQDWLNGKEY KCKVSNKALA 420
APIEKTISKA KGQPREPQVC TLPPSRDELT ENQVSLTCLV KGFYPSDIAV EWESNGQPEN 480
NYKTTPPVLD SDGSFFLYSW LTVDKSRWQQ GNVFSCSVMH EALHNHYTQK SLSLSPG 537

SEQ ID NO: 142       moltype = AA  length = 443
FEATURE              Location/Qualifiers
source               1..443
                     mol_type = protein
                     note = Description of Artificial Sequence: Synthetic
                       polypeptide
                     organism = synthetic construct
SEQUENCE: 142
RNLPVATPDP GMFPCLHHSQ NLLRAVSNML QKARQTLEFY PCTSEEIDHE DITKDKTSTV 60
EACLPLELTK NESCLNSRET SFITNGSCLA SRKTSFMMAL CLSSIYEDLK MYQVEFKTMN 120
AKLLMDPKRQ IFLDQNMLAV IDELMQALNF NSETVPQKSS LEEPDFYKTK IKLCILLHAF 180
RIRAVTIDRV MSYLNASGGG GSGGGGSGGG GSEPKSSDKT HTCPPCPAPE AAGGPSVFLF 240
PPKPKDTLMI SRTPEVTCVV VDVSHEDPEV KFNWYVDGVE VHNAKTKPRE EQYNSTYRVV 300
SVLTVLHQDW LNGKEYKCKV SNKALAAPIE KTISKAKGQP REPRVYTLPP CRDELTKNQV 360
SLTCLVKGFY PSDIAVEWES NGQPENNYKT TPPVLVSDGS FTLYSKLTVD KSRWQQGNVF 420
SCSVMHEALH NHYTQKSLSL SPG 443

SEQ ID NO: 143       moltype = AA  length = 537
FEATURE              Location/Qualifiers
```

```
                    source            1..537
                                      mol_type = protein
                                      note = Description of Artificial Sequence: Synthetic
                                       polypeptide
                                      organism = synthetic construct
SEQUENCE: 143
IWELKKDVYV VELDWYPDAP GEMVVLTCDT PEEDGITWTL DQSSEVLGSG KTLTIQVKEF        60
GDAGQYTCHK GGEVLSHSLL LLHKKEDGIW STDILKDQKE PKNKTFLRCE AKNYSGRFTC       120
WWLTTISTDL TFSVKSSRGS SDPQGVTCGA ATLSAERVRG DNKEYEYSVE CQEDSACPAA       180
EESLPIEVMV DAVHKLKYEN YTSSFFIRDI IKPDPPKNLQ LKPLKNSRQV EVSWEYPDTW       240
STPHSYFSLT FCVQVQGKSK REKKDRVFTD KTSATVICRK NASISVRAQD RYYSSSWSEW       300
ASVPCSEPKS SDKTHTCPPC PAPEAEGAPS VFLFPPKPKD TLMISRTPEV TCVVVDVSHE       360
DPEVKFNWYV DGVEVHNAKT KPREEQYNST YRVVSVLTVL HQDWLNGKEY KCKVSNKALP       420
SSIEKTISKA KGQPREPQVC TLPPSRDELT ENQVSLTCLV KGFYPSDIAV EWESNGQPEN       480
NYKTTPPVLD SDGSFFLYSW LTVDKSRWQQ GNVFSCSVMH EALHNHYTQK SLSLSPG          537

SEQ ID NO: 144              moltype = AA  length = 443
FEATURE                     Location/Qualifiers
source                      1..443
                            mol_type = protein
                            note = Description of Artificial Sequence: Synthetic
                             polypeptide
                            organism = synthetic construct
SEQUENCE: 144
RNLPVATPDP GMFPCLHHSQ NLLRAVSNML QKARQTLEFY PCTSEEIDHE DITKDKTSTV        60
EACLPLELTK NESCLNSRET SFITNGSCLA SRKTSFMMAL CLSSIYEDLK MYQVEFKTMN       120
AKLLMDPKRQ IFLDQNMLAV IDELMQALNF NSETVPQKSS LEEPDFYKTK IKLCILLHAF       180
RIRAVTIDRV MSYLNASGGG GSGGGGSGGG GSEPKSSDKT HTCPPCPAPE AEGAPSVFLF       240
PPKPKDTLMI SRTPEVTCVV VDVSHEDPEV KFNWYVDGVE VHNAKTKPRE EQYNSTYRVV       300
SVLTVLHQDW LNGKEYKCKV SNKALPSSIE KTISKAKGQP REPRVYTLPP CRDELTKNQV       360
SLTCLVKGFY PSDIAVEWES NGQPENNYKT TPPVLVSDGS FTLYSKLTVD KSRWQQGNVF       420
SCSVMHEALH NHYTQKSLSL SPG                                               443

SEQ ID NO: 145              moltype = AA  length = 536
FEATURE                     Location/Qualifiers
source                      1..536
                            mol_type = protein
                            note = Description of Artificial Sequence: Synthetic
                             polypeptide
                            organism = synthetic construct
SEQUENCE: 145
IWELKKDVYV VELDWYPDAP GEMVVLTCDT PEEDGITWTL DQSSEVLGSG KTLTIQVKEF        60
GDAGQYTCHK GGEVLSHSLL LLHKKEDGIW STDILKDQKE PKNKTFLRCE AKNYSGRFTC       120
WWLTTISTDL TFSVKSSRGS SDPQGVTCGA ATLSAERVRG DNKEYEYSVE CQEDSACPAA       180
EESLPIEVMV DAVHKLKYEN YTSSFFIRDI IKPDPPKNLQ LKPLKNSRQV EVSWEYPDTW       240
STPHSYFSLT FCVQVQGKSK REKKDRVFTD KTSATVICRK NASISVRAQD RYYSSSWSEW       300
ASVPCSRVES KYGPPCPPCP APEFLGGPSV FLFPPKPKD  LMISRTPEVT CVVVDVSQED       360
PEVQFNWYVD GVEVHNAKTK PREEQFNSTY RVVSVLTVLH QDWLNGKEYK CKVSNKGLPS       420
SIEKTISKAK GQPREPQVCT LPPSQEEMTK NQVSLTCLVE GFYPSDIAVE WESNGQPENN       480
YKTTPPVLDS DGSFFLYSWL TVDKSRWQEG NVFSCSVMHE ALHNHYTQKS LSLSLG           536

SEQ ID NO: 146              moltype = AA  length = 427
FEATURE                     Location/Qualifiers
source                      1..427
                            mol_type = protein
                            note = Description of Artificial Sequence: Synthetic
                             polypeptide
                            organism = synthetic construct
SEQUENCE: 146
RNLPVATPDP GMFPCLHHSQ NLLRAVSNML QKARQTLEFY PCTSEEIDHE DITKDKTSTV        60
EACLPLELTK NESCLNSRET SFITNGSCLA SRKTSFMMAL CLSSIYEDLK MYQVEFKTMN       120
AKLLMDPKRQ IFLDQNMLAV IDELMQALNF NSETVPQKSS LEEPDFYKTK IKLCILLHAF       180
RIRAVTIDRV MSYLNASRVE SKYGPPCPPC PAPEFLGGPS VFLFPPKPKD TLMISRTPEV       240
TCVVVDVSQE DPEVQFNWYV DGVEVHNAKT KPREEQFNST YRVVSVLTVL HQDWLNGKEY       300
KCKVSNKGLP SSIEKTISKA KGQPREPQVY TLPPCQENMT KNQVSLTCLV KGFYPSDIAV       360
EWESNGQPEN NYKTTPPVLV SDGSFTLYSR LTVDKSRWQE GNVFSCSVMH EALHNHYTQK       420
SLSLSLG                                                                 427

SEQ ID NO: 147              moltype = AA  length = 536
FEATURE                     Location/Qualifiers
source                      1..536
                            mol_type = protein
                            note = Description of Artificial Sequence: Synthetic
                             polypeptide
                            organism = synthetic construct
SEQUENCE: 147
IWELKKDVYV VELDWYPDAP GEMVVLTCDT PEEDGITWTL DQSSEVLGSG KTLTIQVKEF        60
GDAGQYTCHK GGEVLSHSLL LLHKKEDGIW STDILKDQKE PKNKTFLRCE AKNYSGRFTC       120
WWLTTISTDL TFSVKSSRGS SDPQGVTCGA ATLSAERVRG DNKEYEYSVE CQEDSACPAA       180
```

```
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSRVES KYGPPCPPCP APEFLGGPSV FLFPPKPKDT LMISRTPEVT CVVVDVSQED    360
PEVQFNWYVD GVEVHNAKTK PREEQFNSTY RVVSVLTVLH QDWLNGKEYK CKVSNKGLPS    420
SIEKTISKAK GQPREPQVCT LPPSQEEMTK NQVSLTCLVE GFYPSDIAVE WESNGQPENN    480
YKTTPPVLDS DGSFFLYSWL TVDKSRWQEG NVFSCSVMHE ALHNHYTQKS LSLSLG        536

SEQ ID NO: 148          moltype = AA  length = 432
FEATURE                 Location/Qualifiers
source                  1..432
                        mol_type = protein
                        note = Description of Artificial Sequence: Synthetic
                          polypeptide
                        organism = synthetic construct
SEQUENCE: 148
RNLPVATPDP GMFPCLHHSQ NLLRAVSNML QKARQTLEFY PCTSEEIDHE DITKDKTSTV     60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSRVESKYGP PCPPCPAPEF LGGPSVFLFP PKPKDTLMIS    240
RTPEVTCVVV DVSQEDPEVQ FNWYVDGVEV HNAKTKPREE QFNSTYRVVS VLTVLHQDWL    300
NGKEYKCKVS NKGLPSSIEK TISKAKGQPR EPQVYTLPPC QENMTKNQVS LTCLVKGFYP    360
SDIAVEWESN GQPENNYKTT PPVLVSDGSF TLYSRLTVDK SRWQEGNVFS CSVMHEALHN    420
HYTQKSLSLS LG                                                        432

SEQ ID NO: 149          moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 149
IWELKKDVYV VELDWYPDAP GEMVVLTCDT PEEDGITWTL DQSSEVLGSG KTLTIQVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSRVES KYGPPCPPCP APEFLGGPSV FLFPPKPKDT LMISRTPEVT CVVVDVSQED    360
PEVQFNWYVD GVEVHNAKTK PREEQFNSTY RVVSVLTVLH QDWLNGKEYK CKVSNKGLPS    420
SIEKTISKAK GQPREPQVCT LPPSQEEMTK NQVSLTCLVE GFYPSDIAVE WESNGQPENN    480
YKTTPPVLDS DGSFFLYSWL TVDKSRWQEG NVFSCSVMHE ALHNHYTQKS LSLSLG        536

SEQ ID NO: 150          moltype = AA  length = 437
FEATURE                 Location/Qualifiers
source                  1..437
                        mol_type = protein
                        note = Description of Artificial Sequence: Synthetic
                          polypeptide
                        organism = synthetic construct
SEQUENCE: 150
RNLPVATPDP GMFPCLHHSQ NLLRAVSNML QKARQTLEFY PCTSEEIDHE DITKDKTSTV     60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSGGGGSRVE SKYGPPCPPC PAPEFLGGPS VFLFPPKPKD    240
TLMISRTPEV TCVVVDVSQE DPEVQFNWYV DGVEVHNAKT KPREEQFNST YRVVSVLTVL    300
HQDWLNGKEY KCKVSNKGLP SSIEKTISKA KGQPREPQVY TLPPCQENMT KNQVSLTCLV    360
KGFYPSDIAV EWESNGQPEN NYKTTPPVLV SDGSFTLYSR LTVDKSRWQE GNVFSCSVMH    420
EALHNHYTQK SLSLSLG                                                   437

SEQ ID NO: 151          moltype = AA  length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 151
IWELKKDVYV VELDWYPDAP GEMVVLTCDT PEEDGITWTL DQSSEVLGSG KTLTIQVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSEPKS SDKTHTCPPC PAPELLGGPS VFLFPPKPKD TLMISRTPEV TCVVVDVSHE    360
DPEVKFNWYV DGVEVHNAKT KPREEQYNST YRVVSVLTVL HQDWLNGKEY KCKVSNKALP    420
APIEKTISKA KGQPREPQVC TLPPSRDELT ENQVSLTCLV KGFYPSDIAV EWESNGQPEN    480
NYKTTPPVLD SDGSFFLYSW LTVDKSRWQQ GNVFSCSVMH EALHNHYTQK SLSLSPG       537

SEQ ID NO: 152          moltype = AA  length = 428
FEATURE                 Location/Qualifiers
```

```
source                     1..428
                           mol_type = protein
                           note = Description of Artificial Sequence: Synthetic
                              polypeptide
                           organism = synthetic construct
SEQUENCE: 152
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNASEPK SSDKTHTCPP CPAPELLGGP SVFLFPPKPK DTLMISRTPE  240
VTCVVVDVSH EDPEVKFNWY VDGVEVHNAK TKPREEQYNS TYRVVSVLTV LHQDWLNGKE  300
YKCKVSNKAL PAPIEKTISK AKGQPREPRV YTLPPCRDEL TKNQVSLTCL VKGFYPSDIA  360
VEWESNGQPE NNYKTTPPVL VSDGSFTLYS KLTVDKSRWQ QGNVFSCSVM HEALHNHYTQ  420
KSLSLSPG                                                          428

SEQ ID NO: 153             moltype = AA  length = 537
FEATURE                    Location/Qualifiers
source                     1..537
                           mol_type = protein
                           note = Description of Artificial Sequence: Synthetic
                              polypeptide
                           organism = synthetic construct
SEQUENCE: 153
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSEPKS SDKTHTCPPC PAPELLGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
APIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 154             moltype = AA  length = 433
FEATURE                    Location/Qualifiers
source                     1..433
                           mol_type = protein
                           note = Description of Artificial Sequence: Synthetic
                              polypeptide
                           organism = synthetic construct
SEQUENCE: 154
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNASGGG GSEPKSSDKT HTCPPCPAPE LLGGPSVFLF PPKPKDTLMI  240
SRTPEVTCVV VDVSHEDPEV KFNWYVDGVE VHNAKTKPRE EQYNSTYRVV SVLTVLHQDW  300
LNGKEYKCKV SNKALPAPIE KTISKAKGQP REPRVYTLPP CRDELTKNQV SLTCLVKGFY  360
PSDIAVEWES NGQPENNYKT TPPVLSDGS FTLYSKLTVD KSRWQQGNVF SCSVMHEALH  420
NHYTQKSLSL SPG                                                    433

SEQ ID NO: 155             moltype = AA  length = 537
FEATURE                    Location/Qualifiers
source                     1..537
                           mol_type = protein
                           note = Description of Artificial Sequence: Synthetic
                              polypeptide
                           organism = synthetic construct
SEQUENCE: 155
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSEPKS SDKTHTCPPC PAPELLGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
APIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 156             moltype = AA  length = 438
FEATURE                    Location/Qualifiers
source                     1..438
                           mol_type = protein
                           note = Description of Artificial Sequence: Synthetic
                              polypeptide
                           organism = synthetic construct
SEQUENCE: 156
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
```

```
RIRAVTIDRV MSYLNASGGG GSGGGGSEPK SSDKTHTCPP CPAPELLGGP SVFLFPPKPK   240
DTLMISRTPE VTCVVVDVSH EDPEVKFNWY VDGVEVHNAK TKPREEQYNS TYRVVSVLTV   300
LHQDWLNGKE YKCKVSNKAL PAPIEKTISK AKGQPREPRV YTLPPCRDEL TKNQVSLTCL   360
VKGFYPSDIA VEWESNGQPE NNYKTTPPVL VSDGSFTLYS KLTVDKSRWQ QGNVFSCSVM   420
HEALHNHYTQ KSLSLSPG                                                 438

SEQ ID NO: 157           moltype = AA  length = 443
FEATURE                  Location/Qualifiers
source                   1..443
                         mol_type = protein
                         note = Description of Artificial Sequence: Synthetic
                          polypeptide
                         organism = synthetic construct
SEQUENCE: 157
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSGGGGSGGG GSEPKSSDKT HTCPPCPAPE LLGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPQVCTLPP SRDELTENQV   360
SLTCLVKGFY PSDIAVEWES NGQPENNYKT TPPVLDSDGS FFLYSWLTVD KSRWQQGNVF   420
SCSVMHEALH NHYTQKSLSL SPG                                           443

SEQ ID NO: 158           moltype = AA  length = 537
FEATURE                  Location/Qualifiers
source                   1..537
                         mol_type = protein
                         note = Description of Artificial Sequence: Synthetic
                          polypeptide
                         organism = synthetic construct
SEQUENCE: 158
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSEPKS SDKTHTCPPC PAPELLGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPRVY TLPPCRDELT KNQVSLTCLV KGFYPSDIAV EWESNGQPEN   480
NYKTTPPVLV SDGSFTLYSK LTVDKSRWQQ GNVFSCSVMH EALHNHYTQK SLSLSPG      537

SEQ ID NO: 159           moltype = AA  length = 542
FEATURE                  Location/Qualifiers
source                   1..542
                         mol_type = protein
                         note = Description of Artificial Sequence: Synthetic
                          polypeptide
                         organism = synthetic construct
SEQUENCE: 159
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SEPKSSDKTH TCPPCPAPEL LGGPSVFLFP PKPKDTLMIS RTPEVTCVVV   360
DVSHEDPEVK FNWYVDGVEV HNAKTKPREE QYNSTYRVVS VLTVLHQDWL NGKEYKCKVS   420
NKALPAPIEK TISKAKGQPR EPQVCTLPPS RDELTENQVS LTCLVKGFYP SDIAVEWESN   480
GQPENNYKTT PPVLDSDGSF FLYSWLTVDK SRWQQGNVFS CSVMHEALHN HYTQKSLSLS   540
PG                                                                  542

SEQ ID NO: 160           moltype = AA  length = 433
FEATURE                  Location/Qualifiers
source                   1..433
                         mol_type = protein
                         note = Description of Artificial Sequence: Synthetic
                          polypeptide
                         organism = synthetic construct
SEQUENCE: 160
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSEPKSSDKT HTCPPCPAPE LLGGPSVFLF PPKPKDTLMI   240
SRTPEVTCVV VDVSHEDPEV KFNWYVDGVE VHNAKTKPRE EQYNSTYRVV SVLTVLHQDW   300
LNGKEYKCKV SNKALPAPIE KTISKAKGQP REPRVYTLPP CRDELTKNQV SLTCLVKGFY   360
PSDIAVEWES NGQPENNYKT TPPVLVSDGS FTLYSKLTVD KSRWQQGNVF SCSVMHEALH   420
NHYTQKSLSL SPG                                                      433

SEQ ID NO: 161           moltype = AA  length = 542
FEATURE                  Location/Qualifiers
```

```
source                  1..542
                        mol_type = protein
                        note = Description of Artificial Sequence: Synthetic
                         polypeptide
                        organism = synthetic construct
SEQUENCE: 161
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSGGGG SEPKSSDKTH TCPPCPAPEL LGGPSVFLFP PKPKDTLMIS RTPEVTCVVV   360
DVSHEDPEVK FNWYVDGVEV HNAKTKPREE QYNSTYRVVS VLTVLHQDWL NGKEYKCKVS   420
NKALPAPIEK TISKAKGQPR EPQVCTLPPS RDELTENQVS LTCLVKGFYP SDIAVEWESN   480
GQPENNYKTT PPVLDSDGSF FLYSWLTVDK SRWQQGNVFS CSVMHEALHN HYTQKSLSLS   540
PG                                                                 542

SEQ ID NO: 162          moltype = AA  length = 433
FEATURE                 Location/Qualifiers
source                  1..433
                        mol_type = protein
                        note = Description of Artificial Sequence: Synthetic
                         polypeptide
                        organism = synthetic construct
SEQUENCE: 162
RNLPVATPDP GMFPCLHHSQ NLLRAVSNML QKARQTLEFY PCTSEEIDHE DITKDKTSTV    60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSEPKSSDKT HTCPPCPAPE LLGGPSVFLF PPKPKDTLMI   240
SRTPEVTCVV VDVSHEDPEV KFNWYVDGVE VHNAKTKPRE EQYNSTYRVV SVLTVLHQDW   300
LNGKEYKCKV SNKALPAPIE KTISKAKGQP REPRVYTLPP CRDELTKNQV SLTCLVKGFY   360
PSDIAVEWES NGQPENNYKT TPPVLSDGSF TLYSKLTVD KSRWQQGNVF SCSVMHEALH    420
NHYTQKSLSL SPG                                                     433

SEQ ID NO: 163          moltype = AA  length = 536
FEATURE                 Location/Qualifiers
source                  1..536
                        mol_type = protein
                        note = Description of Artificial Sequence: Synthetic
                         polypeptide
                        organism = synthetic construct
SEQUENCE: 163
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSRVES KYGPPCPPCP APEFLGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLPS   420
SIEKTISKAK GQPREPQVCT LPPSQEEMTK NQVSLTCLVE GFYPSDIAVE WESNGQPENN   480
YKTTPPVLDS DGSFFLYSWL TVDKSRWQEG NVFSCSVMHE ALHNHYTQKS LSLSLG       536

SEQ ID NO: 164          moltype = AA  length = 442
FEATURE                 Location/Qualifiers
source                  1..442
                        mol_type = protein
                        note = Description of Artificial Sequence: Synthetic
                         polypeptide
                        organism = synthetic construct
SEQUENCE: 164
RNLPVATPDP GMFPCLHHSQ NLLRAVSNML QKARQTLEFY PCTSEEIDHE DITKDKTSTV    60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSRVESKYGP PCPPCPAPEF LGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLPSSIEK TISKAKGQPR EPQVYTLPPC QENMTKNQVS   360
LTCLVKGFYP SDIAVEWESN GQPENNYKTT PPVLDSDGSF TLYSRLTVDK SRWQEGNVFS   420
CSVMHEALHN HYTQKSLSLS LG                                           442

SEQ ID NO: 165          moltype = AA  length = 536
FEATURE                 Location/Qualifiers
source                  1..536
                        mol_type = protein
                        note = Description of Artificial Sequence: Synthetic
                         polypeptide
                        organism = synthetic construct
SEQUENCE: 165
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
```

```
WWLTTISTDL TFSVKSSRGS SDPQGVTCGA ATLSAERVRG DNKEYEYSVE CQEDSASPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSRVES KYGPPCPPCP APEFLGGPSV FLFPPKPKDT LMISRTPEVT CVVVDVSQED  360
PEVQFNWYVD GVEVHNAKTK PREEQFNSTY RVVSVLTVLH QDWLNGKEYK CKVSNKGLPS  420
SIEKTISKAK GQREPQVCT LPPSQEEMTE NQVSLTCLVK GFYPSDIAVE WESNGQPENN  480
YKTTPPVLDS DGSFFLYSWL TVDKSRWQEG NVFSCSVMHE ALHNHYTQKS LSLSLG     536

SEQ ID NO: 166           moltype = AA  length = 442
FEATURE                  Location/Qualifiers
source                   1..442
                         mol_type = protein
                         note = Description of Artificial Sequence: Synthetic
                          polypeptide
                         organism = synthetic construct
SEQUENCE: 166
RNLPVATPDP GMFPCLHHSQ NLLRAVSNML QKARQTLEFY PCTSEEIDHE DITKDKTSTV  60
EACLPLELTK NESSLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSRVESKYGP PCPPCPAPEF LGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPRVYTLPPC QEEMTKNQVS  360
LTCLVKGFYP SDIAVEWESN GQPENNYKTT PPVLVSDGSF TLYSRLTVDK SRWQEGNVFS  420
CSVMHEALHN HYTQKSLSLS LG                                         442

SEQ ID NO: 167           moltype = AA  length = 536
FEATURE                  Location/Qualifiers
source                   1..536
                         mol_type = protein
                         note = Description of Artificial Sequence: Synthetic
                          polypeptide
                         organism = synthetic construct
SEQUENCE: 167
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSASPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSRVES KYGPPCPPCP APEFEGGPSV FLFPPKPKDT LMISRTPEVT CVVVDVSQED  360
PEVQFNWYVD GVEVHNAKTK PREEQFNSTY RVVSVLTVLH QDWLNGKEYK CKVSNKGLPS  420
SIEKTISKAK GQREPQVCT LPPSQEEMTE NQVSLTCLVK GFYPSDIAVE WESNGQPENN  480
YKTTPPVLDS DGSFFLYSWL TVDKSRWQEG NVFSCSVMHE ALHNHYTQKS LSLSLG     536

SEQ ID NO: 168           moltype = AA  length = 442
FEATURE                  Location/Qualifiers
source                   1..442
                         mol_type = protein
                         note = Description of Artificial Sequence: Synthetic
                          polypeptide
                         organism = synthetic construct
SEQUENCE: 168
RNLPVATPDP GMFPCLHHSQ NLLRAVSNML QKARQTLEFY PCTSEEIDHE DITKDKTSTV  60
EACLPLELTK NESSLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPRVYTLPPC QEEMTKNQVS  360
LTCLVKGFYP SDIAVEWESN GQPENNYKTT PPVLVSDGSF TLYSRLTVDK SRWQEGNVFS  420
CSVMHEALHN HYTQKSLSLS LG                                         442

SEQ ID NO: 169           moltype = AA  length = 536
FEATURE                  Location/Qualifiers
source                   1..536
                         mol_type = protein
                         note = Description of Artificial Sequence: Synthetic
                          polypeptide
                         organism = synthetic construct
SEQUENCE: 169
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSASPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSRVES KYGPPCPPCP APEFEGGPSV FLFPPKPKDT LMISRTPEVT CVVVDVSQED  360
PEVQFNWYVD GVEVHNAKTK PREEQFNSTY RVVSVLTVLH QDWLNGKEYK CKVSNKGLAS  420
SIEKTISKAK GQREPQVCT LPPSQEEMTE NQVSLTCLVK GFYPSDIAVE WESNGQPENN  480
YKTTPPVLDS DGSFFLYSWL TVDKSRWQEG NVFSCSVMHE ALHNHYTQKS LSLSLG     536

SEQ ID NO: 170           moltype = AA  length = 442
```

```
FEATURE                 Location/Qualifiers
source                  1..442
                        mol_type = protein
                        note = Description of Artificial Sequence: Synthetic
                         polypeptide
                        organism = synthetic construct
SEQUENCE: 170
RNLPVATPDP GMFPCLHHSQ NLLRAVSNML QKARQTLEFY PCTSEEIDHE DITKDKTSTV    60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSRVESKYGP PCPPCPAPEF EGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLASSIEK TISKAKGQPR EPRVYTLPPC QEEMTKNQVS   360
LTCLVKGFYP SDIAVEWESN GQPENNYKTT PPVLVSDGSF TLYSRLTVDK SRWQEGNVFS   420
CSVMHEALHN HYTQKSLSLS LG                                            442

SEQ ID NO: 171          moltype = AA  length = 537
FEATURE                 Location/Qualifiers
source                  1..537
                        mol_type = protein
                        note = Description of Artificial Sequence: Synthetic
                         polypeptide
                        organism = synthetic construct
SEQUENCE: 171
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPELLGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG      537

SEQ ID NO: 172          moltype = AA  length = 443
FEATURE                 Location/Qualifiers
source                  1..443
                        mol_type = protein
                        note = Description of Artificial Sequence: Synthetic
                         polypeptide
                        organism = synthetic construct
SEQUENCE: 172
RNLPVATPDP GMFPCLHHSQ NLLRAVSNML QKARQTLEFY PCTSEEIDHE DITKDKTSTV    60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE LLGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPRVYTLPP CRDELTKNQV   360
SLTCLVKGFY PSDIAVEWES NGQPENNYKT TPPVLSDGS FTLYSKLTVD KSRWQQGNVF   420
SCSVMHEALH NHYTQKSLSL SPG                                           443

SEQ ID NO: 173          moltype = AA  length = 537
FEATURE                 Location/Qualifiers
source                  1..537
                        mol_type = protein
                        note = Description of Artificial Sequence: Synthetic
                         polypeptide
                        organism = synthetic construct
SEQUENCE: 173
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAAGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG      537

SEQ ID NO: 174          moltype = AA  length = 443
FEATURE                 Location/Qualifiers
source                  1..443
                        mol_type = protein
                        note = Description of Artificial Sequence: Synthetic
                         polypeptide
                        organism = synthetic construct
SEQUENCE: 174
RNLPVATPDP GMFPCLHHSQ NLLRAVSNML QKARQTLEFY PCTSEEIDHE DITKDKTSTV    60
EACLPLELTK NESSLNSRET SFITNGSCLA SRKTSFMMAL CLSSIYEDLK MYQVEFKTMN   120
```

```
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPRVYTLPP CRDELTKNQV   360
SLTCLVKGFY PSDIAVEWES NGQPENNYKT TPPVLVSDGS FTLYSKLTVD KSRWQQGNVF   420
SCSVMHEALH NHYTQKSLSL SPG                                          443

SEQ ID NO: 175          moltype = AA  length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 175
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAAGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALA   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG     537

SEQ ID NO: 176          moltype = AA  length = 443
FEATURE                 Location/Qualifiers
source                  1..443
                        mol_type = protein
                        note = Description of Artificial Sequence: Synthetic
                          polypeptide
                        organism = synthetic construct
SEQUENCE: 176
RNLPVATPDP GMFPCLHHSQ NLLRAVSNML QKARQTLEFY PCTSEEIDHE DITKDKTSTV   60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALAAPIE KTISKAKGQP REPRVYTLPP CRDELTKNQV   360
SLTCLVKGFY PSDIAVEWES NGQPENNYKT TPPVLVSDGS FTLYSKLTVD KSRWQQGNVF   420
SCSVMHEALH NHYTQKSLSL SPG                                          443

SEQ ID NO: 177          moltype = AA  length = 537
FEATURE                 Location/Qualifiers
source                  1..537
                        mol_type = protein
                        note = Description of Artificial Sequence: Synthetic
                          polypeptide
                        organism = synthetic construct
SEQUENCE: 177
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAEGAPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
SSIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG     537

SEQ ID NO: 178          moltype = AA  length = 443
FEATURE                 Location/Qualifiers
source                  1..443
                        mol_type = protein
                        note = Description of Artificial Sequence: Synthetic
                          polypeptide
                        organism = synthetic construct
SEQUENCE: 178
RNLPVATPDP GMFPCLHHSQ NLLRAVSNML QKARQTLEFY PCTSEEIDHE DITKDKTSTV   60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AEGAPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPSSIE KTISKAKGQP REPRVYTLPP CRDELTKNQV   360
SLTCLVKGFY PSDIAVEWES NGQPENNYKT TPPVLVSDGS FTLYSKLTVD KSRWQQGNVF   420
SCSVMHEALH NHYTQKSLSL SPG                                          443

SEQ ID NO: 179          moltype = AA  length = 536
FEATURE                 Location/Qualifiers
```

-continued

```
source                  1..536
                        mol_type = protein
                        note = Description of Artificial Sequence: Synthetic
                         polypeptide
                        organism = synthetic construct
SEQUENCE: 179
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSRVES KYGPPCPPCP APEFLGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLPS   420
SIEKTISKAK GQPREPQVCT LPPSQEEMTK NQVSLTCLVE GFYPSDIAVE WESNGQPENN   480
YKTTPPVLDS DGSFFLYSWL TVDKSRWQEG NVFSCSVMHE ALHNHYTQKS LSLSLG       536

SEQ ID NO: 180          moltype = AA   length = 442
FEATURE                 Location/Qualifiers
source                  1..442
                        mol_type = protein
                        note = Description of Artificial Sequence: Synthetic
                         polypeptide
                        organism = synthetic construct
SEQUENCE: 180
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSRVESKYGP PCPPCPAPEF LGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLPSSIEK TISKAKGQPR EPQVYTLPPC QENMTKNQVS   360
LTCLVKGFYP SDIAVEWESN GQPENNYKTT PPVLVSDGSF TLYSRLTVDK SRWQEGNVFS   420
CSVMHEALHN HYTQKSLSLS LG                                            442

SEQ ID NO: 181          moltype = AA   length = 536
FEATURE                 Location/Qualifiers
source                  1..536
                        mol_type = protein
                        note = Description of Artificial Sequence: Synthetic
                         polypeptide
                        organism = synthetic construct
SEQUENCE: 181
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSRVES KYGPPCPPCP APEFLGGPSV FLFPPKPKDT LMISRTPEVT CVVVDVSQED   360
PEVQFNWYVD GVEVHNAKTK PREEQFNSTY RVVSVLTVLH QDWLNGKEYK CKVSNKGLPS   420
SIEKTISKAK GQPREPQVCT LPPSQEEMTE NQVSLTCLVK GFYPSDIAVE WESNGQPENN   480
YKTTPPVLDS DGSFFLYSWL TVDKSRWQEG NVFSCSVMHE ALHNHYTQKS LSLSLG       536

SEQ ID NO: 182          moltype = AA   length = 442
FEATURE                 Location/Qualifiers
source                  1..442
                        mol_type = protein
                        note = Description of Artificial Sequence: Synthetic
                         polypeptide
                        organism = synthetic construct
SEQUENCE: 182
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSRVESKYGP PCPPCPAPEF LGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLPSSIEK TISKAKGQPR EPRVYTLPPC QEEMTKNQVS   360
LTCLVKGFYP SDIAVEWESN GQPENNYKTT PPVLVSDGSF TLYSRLTVDK SRWQEGNVFS   420
CSVMHEALHN HYTQKSLSLS LG                                            442

SEQ ID NO: 183          moltype = AA   length = 536
FEATURE                 Location/Qualifiers
source                  1..536
                        mol_type = protein
                        note = Description of Artificial Sequence: Synthetic
                         polypeptide
                        organism = synthetic construct
SEQUENCE: 183
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
```

```
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSRVES KYGPPCPPCP APEFEGGPSV FLFPPKPKDT LMISRTPEVT CVVVDVSQED  360
PEVQFNWYVD GVEVHNAKTK PREEQFNSTY RVVSVLTVLH QDWLNGKEYK CKVSNKGLPS  420
SIEKTISKAK GQPREPQVCT LPPSQEEMTE NQVSLTCLVK GFYPSDIAVE WESNGQPENN  480
YKTTPPVLDS DGSFFLYSWL TVDKSRWQEG NVFSCSVMHE ALHNHYTQKS LSLSLG      536

SEQ ID NO: 184          moltype = AA  length = 442
FEATURE                 Location/Qualifiers
source                  1..442
                        mol_type = protein
                        note = Description of Artificial Sequence: Synthetic
                         polypeptide
                        organism = synthetic construct
SEQUENCE: 184
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPRVYTLPPC QEEMTKNQVS  360
LTCLVKGFYP SDIAVEWESN GQPENNYKTT PPVLVSDGSF TLYSRLTVDK SRWQEGNVFS  420
CSVMHEALHN HYTQKSLSLS LG                                          442

SEQ ID NO: 185          moltype = AA  length = 536
FEATURE                 Location/Qualifiers
source                  1..536
                        mol_type = protein
                        note = Description of Artificial Sequence: Synthetic
                         polypeptide
                        organism = synthetic construct
SEQUENCE: 185
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSRVES KYGPPCPPCP APEFEGGPSV FLFPPKPKDT LMISRTPEVT CVVVDVSQED  360
PEVQFNWYVD GVEVHNAKTK PREEQFNSTY RVVSVLTVLH QDWLNGKEYK CKVSNKGLAS  420
SIEKTISKAK GQPREPQVCT LPPSQEEMTE NQVSLTCLVK GFYPSDIAVE WESNGQPENN  480
YKTTPPVLDS DGSFFLYSWL TVDKSRWQEG NVFSCSVMHE ALHNHYTQKS LSLSLG      536

SEQ ID NO: 186          moltype = AA  length = 442
FEATURE                 Location/Qualifiers
source                  1..442
                        mol_type = protein
                        note = Description of Artificial Sequence: Synthetic
                         polypeptide
                        organism = synthetic construct
SEQUENCE: 186
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLASSIEK TISKAKGQPR EPRVYTLPPC QEEMTKNQVS  360
LTCLVKGFYP SDIAVEWESN GQPENNYKTT PPVLVSDGSF TLYSRLTVDK SRWQEGNVFS  420
CSVMHEALHN HYTQKSLSLS LG                                          442

SEQ ID NO: 187          moltype = AA  length = 537
FEATURE                 Location/Qualifiers
source                  1..537
                        mol_type = protein
                        note = Description of Artificial Sequence: Synthetic
                         polypeptide
                        organism = synthetic construct
SEQUENCE: 187
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSEPKS SDKTHTCPPC PAPELLGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
APIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 188          moltype = AA  length = 443
FEATURE                 Location/Qualifiers
```

```
source                   1..443
                         mol_type = protein
                         note = Description of Artificial Sequence: Synthetic
                           polypeptide
                         organism = synthetic construct
SEQUENCE: 188
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE LLGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPRVYTLPP CRDELTKNQV   360
SLTCLVKGFY PSDIAVEWES NGQPENNYKT TPPVLVSDGS FTLYSKLTVD KSRWQQGNVF   420
SCSVMHEALH NHYTQKSLSL SPG                                          443

SEQ ID NO: 189           moltype = AA  length = 537
FEATURE                  Location/Qualifiers
source                   1..537
                         mol_type = protein
                         note = Description of Artificial Sequence: Synthetic
                           polypeptide
                         organism = synthetic construct
SEQUENCE: 189
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAAGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG      537

SEQ ID NO: 190           moltype = AA  length = 443
FEATURE                  Location/Qualifiers
source                   1..443
                         mol_type = protein
                         note = Description of Artificial Sequence: Synthetic
                           polypeptide
                         organism = synthetic construct
SEQUENCE: 190
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNASGGG GSGGGGSGGG GSEPKSSDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPRVYTLPP CRDELTKNQV   360
SLTCLVKGFY PSDIAVEWES NGQPENNYKT TPPVLVSDGS FTLYSKLTVD KSRWQQGNVF   420
SCSVMHEALH NHYTQKSLSL SPG                                          443

SEQ ID NO: 191           moltype = AA  length = 537
FEATURE                  Location/Qualifiers
source                   1..537
                         mol_type = protein
                         note = Description of Artificial Sequence: Synthetic
                           polypeptide
                         organism = synthetic construct
SEQUENCE: 191
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSEPKS SDKTHTCPPC PAPEAAGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALA   420
APIEKTISKA KGQPREPQVC TLPPSRDELT ENQVSLTCLV KGFYPSDIAV EWESNGQPEN   480
NYKTTPPVLD SDGSFFLYSW LTVDKSRWQQ GNVFSCSVMH EALHNHYTQK SLSLSPG      537

SEQ ID NO: 192           moltype = AA  length = 443
FEATURE                  Location/Qualifiers
source                   1..443
                         mol_type = protein
                         note = Description of Artificial Sequence: Synthetic
                           polypeptide
                         organism = synthetic construct
SEQUENCE: 192
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
```

```
RIRACTIDRV MSYLNASGGG GSGGGGSGGG GSEPKSSDKT HTCPPCPAPE AAGGPSVFLF    240
PPKPKDTLMI SRTPEVTCVV VDVSHEDPEV KFNWYVDGVE VHNAKTKPRE EQYNSTYRVV    300
SVLTVLHQDW LNGKEYKCKV SNKALAAPIE KTISKAKGQP REPRVYTLPP CRDELTKNQV    360
SLTCLVKGFY PSDIAVEWES NGQPENNYKT TPPVLVSDGS FTLYSKLTVD KSRWQQGNVF    420
SCSVMHEALH NHYTQKSLSL SPG                                            443

SEQ ID NO: 193            moltype = AA   length = 537
FEATURE                   Location/Qualifiers
source                    1..537
                          mol_type = protein
                          note = Description of Artificial Sequence: Synthetic
                           polypeptide
                          organism = synthetic construct
SEQUENCE: 193
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RCYSSSWSEW    300
ASVPCSEPKS SDKTHTCPPC PAPEAEGAPS VFLFPPKPKD TLMISRTPEV TCVVVDVSHE    360
DPEVKFNWYV DGVEVHNAKT KPREEQYNST YRVVSVLTVL HQDWLNGKEY KCKVSNKALP    420
SSIEKTISKA KGQPREPQVC TLPPSRDELT ENQVSLTCLV KGFYPSDIAV EWESNGQPEN    480
NYKTTPPVLD SDGSFFLYSW LTVDKSRWQQ GNVFSCSVMH EALHNHYTQK SLSLSPG       537

SEQ ID NO: 194            moltype = AA   length = 443
FEATURE                   Location/Qualifiers
source                    1..443
                          mol_type = protein
                          note = Description of Artificial Sequence: Synthetic
                           polypeptide
                          organism = synthetic construct
SEQUENCE: 194
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRACTIDRV MSYLNASGGG GSGGGGSGGG GSEPKSSDKT HTCPPCPAPE AEGAPSVFLF    240
PPKPKDTLMI SRTPEVTCVV VDVSHEDPEV KFNWYVDGVE VHNAKTKPRE EQYNSTYRVV    300
SVLTVLHQDW LNGKEYKCKV SNKALPSSIE KTISKAKGQP REPRVYTLPP CRDELTKNQV    360
SLTCLVKGFY PSDIAVEWES NGQPENNYKT TPPVLVSDGS FTLYSKLTVD KSRWQQGNVF    420
SCSVMHEALH NHYTQKSLSL SPG                                            443

SEQ ID NO: 195            moltype = AA   length = 537
FEATURE                   Location/Qualifiers
source                    1..537
                          mol_type = protein
                          note = Description of Artificial Sequence: Synthetic
                           polypeptide
                          organism = synthetic construct
SEQUENCE: 195
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RCYSSSWSEW    300
ASVPCSEPKS SDKTHTCPPC PAPEAAGGPS VFLFPPKPKD TLMISRTPEV TCVVVDVSHE    360
DPEVKFNWYV DGVEVHNAKT KPREEQYNST YRVVSVLTVL HQDWLNGKEY KCKVSNKALP    420
APIEKTISKA KGQPREPQVC TLPPSRDELT ENQVSLTCLV KGFYPSDIAV EWESNGQPEN    480
NYKTTPPVLD SDGSFFLYSW LTVDKSRWQQ GNVFSCSVMH EALHNHYTQK SLSLSPG       537

SEQ ID NO: 196            moltype = AA   length = 443
FEATURE                   Location/Qualifiers
source                    1..443
                          mol_type = protein
                          note = Description of Artificial Sequence: Synthetic
                           polypeptide
                          organism = synthetic construct
SEQUENCE: 196
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRACTIDRV MSYLNASGGG GSGGGGSGGG GSEPKSSDKT HTCPPCPAPE AAGGPSVFLF    240
PPKPKDTLMI SRTPEVTCVV VDVSHEDPEV KFNWYVDGVE VHNAKTKPRE EQYNSTYRVV    300
SVLTVLHQDW LNGKEYKCKV SNKALPAPIE KTISKAKGQP REPRVYTLPP CRDELTKNQV    360
SLTCLVKGFY PSDIAVEWES NGQPENNYKT TPPVLVSDGS FTLYSKLTVD KSRWQQGNVF    420
SCSVMHEALH NHYTQKSLSL SPG                                            443

SEQ ID NO: 197            moltype = AA   length = 537
FEATURE                   Location/Qualifiers
source                    1..537
```

```
                        mol_type = protein
                        note = Description of Artificial Sequence: Synthetic
                           polypeptide
                        organism = synthetic construct
SEQUENCE: 197
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSEPKS SDKTHTCPPC PAPEAAGGPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALA  420
APIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 198           moltype = AA  length = 443
FEATURE                  Location/Qualifiers
source                   1..443
                        mol_type = protein
                        note = Description of Artificial Sequence: Synthetic
                           polypeptide
                        organism = synthetic construct
SEQUENCE: 198
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSEPKSSDKT HTCPPCPAPE AAGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALAAPIE KTISKAKGQP REPRVYTLPP CRDELTKNQV  360
SLTCLVKGFY PSDIAVEWES NGQPENNYKT TPPVLSDGS FTLYSKLTVD KSRWQQGNVF  420
SCSVMHEALH NHYTQKSLSL SPG                                          443

SEQ ID NO: 199           moltype = AA  length = 537
FEATURE                  Location/Qualifiers
source                   1..537
                        mol_type = protein
                        note = Description of Artificial Sequence: Synthetic
                           polypeptide
                        organism = synthetic construct
SEQUENCE: 199
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RCYSSSWSEW  300
ASVPCSEPKS SDKTHTCPPC PAPEAEGAPS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
SSIEKTISKA KGQPREPQVC TLPPSRDELT ENQVSLTCLV KGFYPSDIAV EWESNGQPEN  480
NYKTTPPVLD SDGSFFLYSW LTVDKSRWQQ GNVFSCSVMH EALHNHYTQK SLSLSPG     537

SEQ ID NO: 200           moltype = AA  length = 443
FEATURE                  Location/Qualifiers
source                   1..443
                        mol_type = protein
                        note = Description of Artificial Sequence: Synthetic
                           polypeptide
                        organism = synthetic construct
SEQUENCE: 200
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRACTIDRV MSYLNASGGG GSGGGGSGGG GSEPKSSDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPSSIE KTISKAKGQP REPRVYTLPP CRDELTKNQV  360
SLTCLVKGFY PSDIAVEWES NGQPENNYKT TPPVLSDGS FTLYSKLTVD KSRWQQGNVF  420
SCSVMHEALH NHYTQKSLSL SPG                                          443

SEQ ID NO: 201           moltype = AA  length = 306
FEATURE                  Location/Qualifiers
source                   1..306
                        mol_type = protein
                        note = Description of Artificial Sequence: Synthetic
                           polypeptide
                        organism = synthetic construct
SEQUENCE: 201
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSASPAA  180
EESLPIEVMV DAVHKLKYEN YTSSFFIRDI IKPDPPKNLQ LKPLKNSRQV EVSWEYPDTW  240
```

```
STPHSYFSLT FCVQVQGKSK REKKDRVFTD KTSATVICRK NASISVRAQD RCYSSSWSEW   300
ASVPCS                                                             306

SEQ ID NO: 202           moltype = AA  length = 197
FEATURE                  Location/Qualifiers
source                   1..197
                         mol_type = protein
                         note = Description of Artificial Sequence: Synthetic
                           polypeptide
                         organism = synthetic construct
SEQUENCE: 202
RNLPVATPDP GMFPCLHHSQ NLLRAVSNML QKARQTLEFY PCTSEEIDHE DITKDKTSTV   60
EACLPLELTK NESSLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNAS                                                 197

SEQ ID NO: 203           moltype = AA  length = 306
FEATURE                  Location/Qualifiers
source                   1..306
                         mol_type = protein
                         note = Description of Artificial Sequence: Synthetic
                           polypeptide
                         organism = synthetic construct
SEQUENCE: 203
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCS                                                             306

SEQ ID NO: 204           moltype = AA  length = 197
FEATURE                  Location/Qualifiers
source                   1..197
                         mol_type = protein
                         note = Description of Artificial Sequence: Synthetic
                           polypeptide
                         organism = synthetic construct
SEQUENCE: 204
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRACTIDRV MSYLNAS                                                 197

SEQ ID NO: 205           moltype = AA  length = 208
FEATURE                  Location/Qualifiers
source                   1..208
                         mol_type = protein
                         note = Description of Unknown: IgG4 Fc wild-type sequence
                         organism = unidentified
SEQUENCE: 205
PSVFLFPPKP KDTLMISRTP EVTCVVVDVS QEDPEVQFNW YVDGVEVHNA KTKPREEQFN   60
STYRVVSVLT VLHQDWLNGK EYKCKVSNKG LPSSIEKTIS KAKGQPREPQ VYTLPPSQEE   120
MTKNQVSLTC VKGFYPSDIA VEWESNGQPE NNYKTTPPVL DSDGSFFLYS KLTVDKSRWQ   180
EGNVFSCSVM HEALHNHYTQ KSLSLSLG                                     208

SEQ ID NO: 206           moltype = AA  length = 208
FEATURE                  Location/Qualifiers
source                   1..208
                         mol_type = protein
                         note = Description of Artificial Sequence: Synthetic
                           polypeptide
                         organism = synthetic construct
SEQUENCE: 206
PSVFLFPPKP KDTLMISRTP EVTCVVVDVS QEDPEVQFNW YVDGVEVHNA KTKPREEQFN   60
STYRVVSVLT VLHQDWLNGK EYKCKVSNKG LPSSIEKTIS KAKGQPREPQ VCTLPPSQEE   120
MTKNQVSLTC VEGFYPSDIA VEWESNGQPE NNYKTTPPVL DSDGSFFLYS WLTVDKSRWQ   180
EGNVFSCSVM HEALHNHYTQ KSLSLSLG                                     208

SEQ ID NO: 207           moltype = AA  length = 209
FEATURE                  Location/Qualifiers
source                   1..209
                         mol_type = protein
                         note = Description of Artificial Sequence: Synthetic
                           polypeptide
                         organism = synthetic construct
SEQUENCE: 207
PSVFLFPPKP KDTLMISRTP EVTCVVVDVS QEDPEVQFNW YVDGVEVHNA KTKPREEQFN   60
STYRVVSVLT VLHQDWLNGK EYKCKVSNKG LPSSIEKTIS KAKGQPREPQ VYTLPPCQEN   120
```

```
MTKNQVSLTC LVKGFYPSDI AVEWESNGQP ENNYKTTPPV LVSDGSFTLY SRLTVDKSRW    180
QEGNVFSCSV MHEALHNHYT QKSLSLSLG                                     209

SEQ ID NO: 208          moltype = AA  length = 209
FEATURE                 Location/Qualifiers
source                  1..209
                        mol_type = protein
                        note = Description of Artificial Sequence: Synthetic
                          polypeptide
                        organism = synthetic construct
SEQUENCE: 208
PSVFLFPPKP KDTLMISRTP EVTCVVVDVS QEDPEVQFNW YVDGVEVHNA KTKPREEQFN    60
STYRVVSVLT VLHQDWLNGK EYKCKVSNKG LPSSIEKTIS KAKGQPREPQ VCTLPPSQEE    120
MTENQVSLTC LVKGFYPSDI AVEWESNGQP ENNYKTTPPV LDSDGSFFLY SWLTVDKSRW    180
QEGNVFSCSV MHEALHNHYT QKSLSLSLG                                     209

SEQ ID NO: 209          moltype = AA  length = 209
FEATURE                 Location/Qualifiers
source                  1..209
                        mol_type = protein
                        note = Description of Artificial Sequence: Synthetic
                          polypeptide
                        organism = synthetic construct
SEQUENCE: 209
PSVFLFPPKP KDTLMISRTP EVTCVVVDVS QEDPEVQFNW YVDGVEVHNA KTKPREEQFN    60
STYRVVSVLT VLHQDWLNGK EYKCKVSNKG LPSSIEKTIS KAKGQPREPQ VYTLPPCQEE    120
MTKNQVSLTC LVKGFYPSDI AVEWESNGQP ENNYKTTPPV LVSDGSFTLY SRLTVDKSRW    180
QEGNVFSCSV MHEALHNHYT QKSLSLSLG                                     209

SEQ ID NO: 210          moltype = AA  length = 209
FEATURE                 Location/Qualifiers
source                  1..209
                        mol_type = protein
                        note = Description of Artificial Sequence: Synthetic
                          polypeptide
                        organism = synthetic construct
SEQUENCE: 210
PSVFLFPPKP KDTLMISRTP EVTCVVVDVS QEDPEVQFNW YVDGVEVHNA KTKPREEQFN    60
STYRVVSVLT VLHQDWLNGK EYKCKVSNKG LASSIEKTIS KAKGQPREPQ VCTLPPSQEE    120
MTENQVSLTC LVKGFYPSDI AVEWESNGQP ENNYKTTPPV LDSDGSFFLY SWLTVDKSRW    180
QEGNVFSCSV MHEALHNHYT QKSLSLSLG                                     209

SEQ ID NO: 211          moltype = AA  length = 209
FEATURE                 Location/Qualifiers
source                  1..209
                        mol_type = protein
                        note = Description of Artificial Sequence: Synthetic
                          polypeptide
                        organism = synthetic construct
SEQUENCE: 211
PSVFLFPPKP KDTLMISRTP EVTCVVVDVS QEDPEVQFNW YVDGVEVHNA KTKPREEQFN    60
STYRVVSVLT VLHQDWLNGK EYKCKVSNKG LASSIEKTIS KAKGQPREPR VYTLPPCQEE    120
MTKNQVSLTC LVKGFYPSDI AVEWESNGQP ENNYKTTPPV LVSDGSFTLY SRLTVDKSRW    180
QEGNVFSCSV MHEALHNHYT QKSLSLSLG                                     209

SEQ ID NO: 212          moltype = AA  length = 209
FEATURE                 Location/Qualifiers
source                  1..209
                        mol_type = protein
                        note = Description of Unknown: IgG1 Fc wild-type sequence
                        organism = unidentified
SEQUENCE: 212
PSVFLFPPKP KDTLMISRTP EVTCVVVDVS HEDPEVKFNW YVDGVEVHNA KTKPREEQYN    60
STYRVVSVLT VLHQDWLNGK EYKCKVSNKA LPAPIEKTIS KAKGQPREPQ VYTLPPSRDE    120
LTKNQVSLTC LVKGFYPSDI AVEWESNGQP ENNYKTTPPV LDSDGSFFLY SKLTVDKSRW    180
QQGNVFSCSV MHEALHNHYT QKSLSLSPG                                     209

SEQ ID NO: 213          moltype = AA  length = 209
FEATURE                 Location/Qualifiers
source                  1..209
                        mol_type = protein
                        note = Description of Artificial Sequence: Synthetic
                          polypeptide
                        organism = synthetic construct
SEQUENCE: 213
PSVFLFPPKP KDTLMISRTP EVTCVVVDVS HEDPEVKFNW YVDGVEVHNA KTKPREEQYN    60
STYRVVSVLT VLHQDWLNGK EYKCKVSNKA LPAPIEKTIS KAKGQPREPQ VCTLPPSRDE    120
LTENQVSLTC LVKGFYPSDI AVEWESNGQP ENNYKTTPPV LDSDGSFFLY SWLTVDKSRW    180
QQGNVFSCSV MHEALHNHYT QKSLSLSPG                                     209
```

```
SEQ ID NO: 214             moltype = AA   length = 209
FEATURE                    Location/Qualifiers
source                     1..209
                           mol_type = protein
                           note = Description of Artificial Sequence: Synthetic
                             polypeptide
                           organism = synthetic construct
SEQUENCE: 214
PSVFLFPPKP KDTLMISRTP EVTCVVVDVS HEDPEVKFNW YVDGVEVHNA KTKPREEQYN    60
STYRVVSVLT VLHQDWLNGK EYKCKVSNKA LPAPIEKTIS KAKGQPREPR VYTLPPCRDE   120
LTKNQVSLTC LVKGFYPSDI AVEWESNGQP ENNYKTTPPV LVSDGSFTLY SKLTVDKSRW   180
QQGNVFSCSV MHEALHNHYT QKSLSLSPG                                    209

SEQ ID NO: 215             moltype = AA   length = 209
FEATURE                    Location/Qualifiers
source                     1..209
                           mol_type = protein
                           note = Description of Artificial Sequence: Synthetic
                             polypeptide
                           organism = synthetic construct
SEQUENCE: 215
PSVFLFPPKP KDTLMISRTP EVTCVVVDVS HEDPEVKFNW YVDGVEVHNA KTKPREEQYN    60
STYRVVSVLT VLHQDWLNGK EYKCKVSNKA LAAPIEKTIS KAKGQPREPQ VCTLPPSRDE   120
LTENQVSLTC LVKGFYPSDI AVEWESNGQP ENNYKTTPPV LDSDGSFFLY SWLTVDKSRW   180
QQGNVFSCSV MHEALHNHYT QKSLSLSPG                                    209

SEQ ID NO: 216             moltype = AA   length = 209
FEATURE                    Location/Qualifiers
source                     1..209
                           mol_type = protein
                           note = Description of Artificial Sequence: Synthetic
                             polypeptide
                           organism = synthetic construct
SEQUENCE: 216
PSVFLFPPKP KDTLMISRTP EVTCVVVDVS HEDPEVKFNW YVDGVEVHNA KTKPREEQYN    60
STYRVVSVLT VLHQDWLNGK EYKCKVSNKA LAAPIEKTIS KAKGQPREPR VYTLPPCRDE   120
LTKNQVSLTC LVKGFYPSDI AVEWESNGQP ENNYKTTPPV LVSDGSFTLY SKLTVDKSRW   180
QQGNVFSCSV MHEALHNHYT QKSLSLSPG                                    209

SEQ ID NO: 217             moltype = AA   length = 209
FEATURE                    Location/Qualifiers
source                     1..209
                           mol_type = protein
                           note = Description of Artificial Sequence: Synthetic
                             polypeptide
                           organism = synthetic construct
SEQUENCE: 217
PSVFLFPPKP KDTLMISRTP EVTCVVVDVS HEDPEVKFNW YVDGVEVHNA KTKPREEQYN    60
STYRVVSVLT VLHQDWLNGK EYKCKVSNKA LPSSIEKTIS KAKGQPREPQ VCTLPPSRDE   120
LTENQVSLTC LVKGFYPSDI AVEWESNGQP ENNYKTTPPV LDSDGSFFLY SWLTVDKSRW   180
QQGNVFSCSV MHEALHNHYT QKSLSLSPG                                    209

SEQ ID NO: 218             moltype = AA   length = 209
FEATURE                    Location/Qualifiers
source                     1..209
                           mol_type = protein
                           note = Description of Artificial Sequence: Synthetic
                             polypeptide
                           organism = synthetic construct
SEQUENCE: 218
PSVFLFPPKP KDTLMISRTP EVTCVVVDVS HEDPEVKFNW YVDGVEVHNA KTKPREEQYN    60
STYRVVSVLT VLHQDWLNGK EYKCKVSNKA LPSSIEKTIS KAKGQPREPR VYTLPPCRDE   120
LTKNQVSLTC LVKGFYPSDI AVEWESNGQP ENNYKTTPPV LVSDGSFTLY SKLTVDKSRW   180
QQGNVFSCSV MHEALHNHYT QKSLSLSPG                                    209

SEQ ID NO: 219             moltype = AA   length = 230
FEATURE                    Location/Qualifiers
source                     1..230
                           mol_type = protein
                           note = Description of Artificial Sequence: Synthetic
                             polypeptide
                           organism = synthetic construct
SEQUENCE: 219
RVESKYGPPC PPCPAPEFLG GPSVFLFPPK PKDTLMISRT PEVTCVVVDV SQEDPEVQFN    60
WYVDGVEVHN AKTKPREEQF NSTYRVVSVL TVLHQDWLNG KEYKCKVSNK GLPSSIEKTI   120
SKAKGQPREP QVYTLPPSQE EMTKNQVSLT CLVKGFYPSD IAVEWESNGQ PENNYKTTPP   180
VLDSDGSFFL YSKLTVDKSR WQEGNVFSCS VMHEALHNHY TQKSLSLSLG              230
```

```
SEQ ID NO: 220            moltype = AA   length = 230
FEATURE                   Location/Qualifiers
source                    1..230
                          mol_type = protein
                          note = Description of Artificial Sequence: Synthetic
                            polypeptide
                          organism = synthetic construct
SEQUENCE: 220
RVESKYGPPC PPCPAPEFLG GPSVFLFPPK PKDTLMISRT PEVTCVVVDV SQEDPEVQFN    60
WYVDGVEVHN AKTKPREEQF NSTYRVVSVL TVLHQDWLNG KEYKCKVSNK GLPSSIEKTI   120
SKAKGQPREP QVCTLPPSQE EMTKNQVSLT CLVEGFYPSD IAVEWESNGQ PENNYKTTPP   180
VLDSDGSFFL YSWLTVDKSR WQEGNVFSCS VMHEALHNHY TQKSLSLSLG              230

SEQ ID NO: 221            moltype = AA   length = 230
FEATURE                   Location/Qualifiers
source                    1..230
                          mol_type = protein
                          note = Description of Artificial Sequence: Synthetic
                            polypeptide
                          organism = synthetic construct
SEQUENCE: 221
RVESKYGPPC PPCPAPEFLG GPSVFLFPPK PKDTLMISRT PEVTCVVVDV SQEDPEVQFN    60
WYVDGVEVHN AKTKPREEQF NSTYRVVSVL TVLHQDWLNG KEYKCKVSNK GLPSSIEKTI   120
SKAKGQPREP QVYTLPPCQE NMTKNQVSLT CLVKGFYPSD IAVEWESNGQ PENNYKTTPP   180
VLVSDGSFTL YSRLTVDKSR WQEGNVFSCS VMHEALHNHY TQKSLSLSLG              230

SEQ ID NO: 222            moltype = AA   length = 230
FEATURE                   Location/Qualifiers
source                    1..230
                          mol_type = protein
                          note = Description of Artificial Sequence: Synthetic
                            polypeptide
                          organism = synthetic construct
SEQUENCE: 222
RVESKYGPPC PPCPAPEFLG GPSVFLFPPK PKDTLMISRT PEVTCVVVDV SQEDPEVQFN    60
WYVDGVEVHN AKTKPREEQF NSTYRVVSVL TVLHQDWLNG KEYKCKVSNK GLPSSIEKTI   120
SKAKGQPREP QVCTLPPSQE EMTENQVSLT CLVKGFYPSD IAVEWESNGQ PENNYKTTPP   180
VLDSDGSFFL YSWLTVDKSR WQEGNVFSCS VMHEALHNHY TQKSLSLSLG              230

SEQ ID NO: 223            moltype = AA   length = 230
FEATURE                   Location/Qualifiers
source                    1..230
                          mol_type = protein
                          note = Description of Artificial Sequence: Synthetic
                            polypeptide
                          organism = synthetic construct
SEQUENCE: 223
RVESKYGPPC PPCPAPEFLG GPSVFLFPPK PKDTLMISRT PEVTCVVVDV SQEDPEVQFN    60
WYVDGVEVHN AKTKPREEQF NSTYRVVSVL TVLHQDWLNG KEYKCKVSNK GLPSSIEKTI   120
SKAKGQPREP RVYTLPPCQE EMTKNQVSLT CLVKGFYPSD IAVEWESNGQ PENNYKTTPP   180
VLVSDGSFTL YSRLTVDKSR WQEGNVFSCS VMHEALHNHY TQKSLSLSLG              230

SEQ ID NO: 224            moltype = AA   length = 230
FEATURE                   Location/Qualifiers
source                    1..230
                          mol_type = protein
                          note = Description of Artificial Sequence: Synthetic
                            polypeptide
                          organism = synthetic construct
SEQUENCE: 224
RVESKYGPPC PPCPAPEFEG GPSVFLFPPK PKDTLMISRT PEVTCVVVDV SQEDPEVQFN    60
WYVDGVEVHN AKTKPREEQF NSTYRVVSVL TVLHQDWLNG KEYKCKVSNK GLPSSIEKTI   120
SKAKGQPREP QVCTLPPSQE EMTENQVSLT CLVKGFYPSD IAVEWESNGQ PENNYKTTPP   180
VLDSDGSFFL YSWLTVDKSR WQEGNVFSCS VMHEALHNHY TQKSLSLSLG              230

SEQ ID NO: 225            moltype = AA   length = 230
FEATURE                   Location/Qualifiers
source                    1..230
                          mol_type = protein
                          note = Description of Artificial Sequence: Synthetic
                            polypeptide
                          organism = synthetic construct
SEQUENCE: 225
RVESKYGPPC PPCPAPEFEG GPSVFLFPPK PKDTLMISRT PEVTCVVVDV SQEDPEVQFN    60
WYVDGVEVHN AKTKPREEQF NSTYRVVSVL TVLHQDWLNG KEYKCKVSNK GLPSSIEKTI   120
SKAKGQPREP RVYTLPPCQE EMTKNQVSLT CLVKGFYPSD IAVEWESNGQ PENNYKTTPP   180
VLVSDGSFTL YSRLTVDKSR WQEGNVFSCS VMHEALHNHY TQKSLSLSLG              230

SEQ ID NO: 226            moltype = AA   length = 230
```

```
FEATURE                 Location/Qualifiers
source                  1..230
                        mol_type = protein
                        note = Description of Artificial Sequence: Synthetic
                         polypeptide
                        organism = synthetic construct
SEQUENCE: 226
RVESKYGPPC PPCPAPEFEG GPSVFLFPPK PKDTLMISRT PEVTCVVVDV SQEDPEVQFN    60
WYVDGVEVHN AKTKPREEQF NSTYRVVSVL TVLHQDWLNG KEYKCKVSNK GLASSIEKTI   120
SKAKGQPREP QVCTLPPSQE EMTENQVSLT CLVKGFYPSD IAVEWESNGQ PENNYKTTPP   180
VLDSDGSFFL YSWLTVDKSR WQEGNVFSCS VMHEALHNHY TQKSLSLSLG              230

SEQ ID NO: 227          moltype = AA   length = 230
FEATURE                 Location/Qualifiers
source                  1..230
                        mol_type = protein
                        note = Description of Artificial Sequence: Synthetic
                         polypeptide
                        organism = synthetic construct
SEQUENCE: 227
RVESKYGPPC PPCPAPEFEG GPSVFLFPPK PKDTLMISRT PEVTCVVVDV SQEDPEVQFN    60
WYVDGVEVHN AKTKPREEQF NSTYRVVSVL TVLHQDWLNG KEYKCKVSNK GLASSIEKTI   120
SKAKGQPREP RVYTLPPCQE EMTKNQVSLT CLVKGFYPSD IAVEWESNGQ PENNYKTTPP   180
VLVSDGSFTL YSRLTVDKSR WQEGNVFSCS VMHEALHNHY TQKSLSLSLG              230

SEQ ID NO: 228          moltype = AA   length = 231
FEATURE                 Location/Qualifiers
source                  1..231
                        mol_type = protein
                        note = Description of Artificial Sequence: Synthetic
                         polypeptide
                        organism = synthetic construct
SEQUENCE: 228
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP G            231

SEQ ID NO: 229          moltype = AA   length = 231
FEATURE                 Location/Qualifiers
source                  1..231
                        mol_type = protein
                        note = Description of Artificial Sequence: Synthetic
                         polypeptide
                        organism = synthetic construct
SEQUENCE: 229
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVCTLPPSR DELTENQVSL TCLVKGFYPS DIAVEWESNG QPENNYKTTP   180
PVLDSDGSFF LYSWLTVDKS RWQQGNVFSC SVMHEALHNH YTQKSLSLSP G            231

SEQ ID NO: 230          moltype = AA   length = 231
FEATURE                 Location/Qualifiers
source                  1..231
                        mol_type = protein
                        note = Description of Artificial Sequence: Synthetic
                         polypeptide
                        organism = synthetic construct
SEQUENCE: 230
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PRVYTLPPCR DELTKNQVSL TCLVKGFYPS DIAVEWESNG QPENNYKTTP   180
PVLVSDGSFT LYSKLTVDKS RWQQGNVFSC SVMHEALHNH YTQKSLSLSP G            231

SEQ ID NO: 231          moltype = AA   length = 231
FEATURE                 Location/Qualifiers
source                  1..231
                        mol_type = protein
                        note = Description of Artificial Sequence: Synthetic
                         polypeptide
                        organism = synthetic construct
SEQUENCE: 231
EPKSSDKTHT CPPCPAPEAA GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVCTLPPSR DELTENQVSL TCLVKGFYPS DIAVEWESNG QPENNYKTTP   180
PVLDSDGSFF LYSWLTVDKS RWQQGNVFSC SVMHEALHNH YTQKSLSLSP G            231

SEQ ID NO: 232          moltype = AA   length = 231
FEATURE                 Location/Qualifiers
```

```
source                   1..231
                         mol_type = protein
                         note = Description of Artificial Sequence: Synthetic
                          polypeptide
                         organism = synthetic construct
SEQUENCE: 232
EPKSSDKTHT CPPCPAPEAA GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT   120
ISKAKGQPRE PRVYTLPPCR DELTKNQVSL TCLVKGFYPS DIAVEWESNG QPENNYKTTP   180
PVLVSDGSFT LYSKLTVDKS RWQQGNVFSC SVMHEALHNH YTQKSLSLSP G           231

SEQ ID NO: 233           moltype = AA  length = 231
FEATURE                  Location/Qualifiers
source                   1..231
                         mol_type = protein
                         note = Description of Artificial Sequence: Synthetic
                          polypeptide
                         organism = synthetic construct
SEQUENCE: 233
EPKSSDKTHT CPPCPAPEAA GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALAAPIEKT   120
ISKAKGQPRE PQVCTLPPSR DELTENQVSL TCLVKGFYPS DIAVEWESNG QPENNYKTTP   180
PVLDSDGSFF LYSWLTVDKS RWQQGNVFSC SVMHEALHNH YTQKSLSLSP G           231

SEQ ID NO: 234           moltype = AA  length = 231
FEATURE                  Location/Qualifiers
source                   1..231
                         mol_type = protein
                         note = Description of Artificial Sequence: Synthetic
                          polypeptide
                         organism = synthetic construct
SEQUENCE: 234
EPKSSDKTHT CPPCPAPEAA GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALAAPIEKT   120
ISKAKGQPRE PRVYTLPPCR DELTKNQVSL TCLVKGFYPS DIAVEWESNG QPENNYKTTP   180
PVLVSDGSFT LYSKLTVDKS RWQQGNVFSC SVMHEALHNH YTQKSLSLSP G           231

SEQ ID NO: 235           moltype = AA  length = 231
FEATURE                  Location/Qualifiers
source                   1..231
                         mol_type = protein
                         note = Description of Artificial Sequence: Synthetic
                          polypeptide
                         organism = synthetic construct
SEQUENCE: 235
EPKSSDKTHT CPPCPAPEAE GAPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPSSIEKT   120
ISKAKGQPRE PQVCTLPPSR DELTENQVSL TCLVKGFYPS DIAVEWESNG QPENNYKTTP   180
PVLDSDGSFF LYSWLTVDKS RWQQGNVFSC SVMHEALHNH YTQKSLSLSP G           231

SEQ ID NO: 236           moltype = AA  length = 231
FEATURE                  Location/Qualifiers
source                   1..231
                         mol_type = protein
                         note = Description of Artificial Sequence: Synthetic
                          polypeptide
                         organism = synthetic construct
SEQUENCE: 236
EPKSSDKTHT CPPCPAPEAE GAPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPSSIEKT   120
ISKAKGQPRE PRVYTLPPCR DELTKNQVSL TCLVKGFYPS DIAVEWESNG QPENNYKTTP   180
PVLVSDGSFT LYSKLTVDKS RWQQGNVFSC SVMHEALHNH YTQKSLSLSP G           231

SEQ ID NO: 237           moltype = AA  length = 21
FEATURE                  Location/Qualifiers
VARIANT                  18
                         note = Xaa is Leu or Ala
VARIANT                  19
                         note = Xaa is Leu, Glu or Ala
VARIANT                  21
                         note = Xaa is Ala or Gly
source                   1..21
                         mol_type = protein
                         note = Description of Artificial Sequence: Synthetic peptide
                         organism = synthetic construct
SEQUENCE: 237
PKSSDKTHTC PPCPAPEXXG X                                              21

SEQ ID NO: 238           moltype = AA  length = 21
```

```
FEATURE              Location/Qualifiers
source               1..21
                     mol_type = protein
                     note = Description of Artificial Sequence: Synthetic peptide
                     organism = synthetic construct
SEQUENCE: 238
PKSSDKTHTC PPCPAPELLG G                                              21

SEQ ID NO: 239       moltype = AA  length = 21
FEATURE              Location/Qualifiers
source               1..21
                     mol_type = protein
                     note = Description of Artificial Sequence: Synthetic peptide
                     organism = synthetic construct
SEQUENCE: 239
PKSSDKTHTC PPCPAPEAAG G                                              21

SEQ ID NO: 240       moltype = AA  length = 21
FEATURE              Location/Qualifiers
source               1..21
                     mol_type = protein
                     note = Description of Artificial Sequence: Synthetic peptide
                     organism = synthetic construct
SEQUENCE: 240
PKSSDKTHTC PPCPAPEAEG A                                              21

SEQ ID NO: 241       moltype = AA  length = 36
FEATURE              Location/Qualifiers
source               1..36
                     mol_type = protein
                     note = Description of Artificial Sequence: Synthetic
                      polypeptide
                     organism = synthetic construct
SEQUENCE: 241
GGGGSGGGGS GGGGSPKSSD KTHTCPPCPA PELLGG                              36

SEQ ID NO: 242       moltype = AA  length = 26
FEATURE              Location/Qualifiers
source               1..26
                     mol_type = protein
                     note = Description of Artificial Sequence: Synthetic peptide
                     organism = synthetic construct
SEQUENCE: 242
GGGGSPKSSD KTHTCPPCPA PELLGG                                         26

SEQ ID NO: 243       moltype = AA  length = 31
FEATURE              Location/Qualifiers
source               1..31
                     mol_type = protein
                     note = Description of Artificial Sequence: Synthetic
                      polypeptide
                     organism = synthetic construct
SEQUENCE: 243
GGGGSGGGGS PKSSDKTHTC PPCPAPELLG G                                   31

SEQ ID NO: 244       moltype = AA  length = 36
FEATURE              Location/Qualifiers
source               1..36
                     mol_type = protein
                     note = Description of Artificial Sequence: Synthetic
                      polypeptide
                     organism = synthetic construct
SEQUENCE: 244
GGGGSGGGGS GGGGSPKSSD KTHTCPPCPA PEAAGG                              36

SEQ ID NO: 245       moltype = AA  length = 26
FEATURE              Location/Qualifiers
source               1..26
                     mol_type = protein
                     note = Description of Artificial Sequence: Synthetic peptide
                     organism = synthetic construct
SEQUENCE: 245
GGGGSPKSSD KTHTCPPCPA PEAAGG                                         26

SEQ ID NO: 246       moltype = AA  length = 31
FEATURE              Location/Qualifiers
source               1..31
                     mol_type = protein
                     note = Description of Artificial Sequence: Synthetic
```

```
                         polypeptide
                         organism = synthetic construct
SEQUENCE: 246
GGGGSGGGGS PKSSDKTHTC PPCPAPEAAG G                                   31

SEQ ID NO: 247           moltype = AA   length = 36
FEATURE                  Location/Qualifiers
source                   1..36
                         mol_type = protein
                         note = Description of Artificial Sequence: Synthetic
                         polypeptide
                         organism = synthetic construct
SEQUENCE: 247
GGGGSGGGGS GGGGSPKSSD KTHTCPPCPA PEAEGA                              36

SEQ ID NO: 248           moltype = AA   length = 26
FEATURE                  Location/Qualifiers
source                   1..26
                         mol_type = protein
                         note = Description of Artificial Sequence: Synthetic peptide
                         organism = synthetic construct
SEQUENCE: 248
GGGGSPKSSD KTHTCPPCPA PEAEGA                                         26

SEQ ID NO: 249           moltype = AA   length = 31
FEATURE                  Location/Qualifiers
source                   1..31
                         mol_type = protein
                         note = Description of Artificial Sequence: Synthetic
                         polypeptide
                         organism = synthetic construct
SEQUENCE: 249
GGGGSGGGGS PKSSDKTHTC PPCPAPEAEG A                                   31

SEQ ID NO: 250           moltype = AA   length = 230
FEATURE                  Location/Qualifiers
source                   1..230
                         mol_type = protein
                         note = Description of Artificial Sequence: Synthetic
                         polypeptide
                         organism = synthetic construct
SEQUENCE: 250
PKSSDKTHTC PPCPAPELLG GPSVFLFPPK PKDTLMISRT PEVTCVVVDV SHEDPEVKFN     60
WYVDGVEVHN AKTKPREEQY NSTYRVVSVL TVLHQDWLNG KEYKCKVSNK ALPAPIEKTI    120
SKAKGQPREP QVYTLPPSRD ELTKNQVSLT CLVKGFYPSD IAVEWESNGQ PENNYKTTPP    180
VLDSDGSFFL YSKLTVDKSR WQQGNVFSCS VMHEALHNHY TQKSLSLSPG               230

SEQ ID NO: 251           moltype = AA   length = 230
FEATURE                  Location/Qualifiers
source                   1..230
                         mol_type = protein
                         note = Description of Artificial Sequence: Synthetic
                         polypeptide
                         organism = synthetic construct
SEQUENCE: 251
PKSSDKTHTC PPCPAPELLG GPSVFLFPPK PKDTLMISRT PEVTCVVVDV SHEDPEVKFN     60
WYVDGVEVHN AKTKPREEQY NSTYRVVSVL TVLHQDWLNG KEYKCKVSNK ALPAPIEKTI    120
SKAKGQPREP QVCTLPPSRD ELTENQVSLT CLVKGFYPSD IAVEWESNGQ PENNYKTTPP    180
VLDSDGSFFL YSWLTVDKSR WQQGNVFSCS VMHEALHNHY TQKSLSLSPG               230

SEQ ID NO: 252           moltype = AA   length = 230
FEATURE                  Location/Qualifiers
source                   1..230
                         mol_type = protein
                         note = Description of Artificial Sequence: Synthetic
                         polypeptide
                         organism = synthetic construct
SEQUENCE: 252
PKSSDKTHTC PPCPAPELLG GPSVFLFPPK PKDTLMISRT PEVTCVVVDV SHEDPEVKFN     60
WYVDGVEVHN AKTKPREEQY NSTYRVVSVL TVLHQDWLNG KEYKCKVSNK ALPAPIEKTI    120
SKAKGQPREP RVYTLPPCRD ELTKNQVSLT CLVKGFYPSD IAVEWESNGQ PENNYKTTPP    180
VLVSDGSFTL YSKLTVDKSR WQQGNVFSCS VMHEALHNHY TQKSLSLSPG               230

SEQ ID NO: 253           moltype = AA   length = 230
FEATURE                  Location/Qualifiers
source                   1..230
                         mol_type = protein
                         note = Description of Artificial Sequence: Synthetic
                         polypeptide
```

```
SEQUENCE: 253
PKSSDKTHTC PPCPAPEAAG GPSVFLFPPK PKDTLMISRT PEVTCVVVDV SHEDPEVKFN      60
WYVDGVEVHN AKTKPREEQY NSTYRVVSVL TVLHQDWLNG KEYKCKVSNK ALPAPIEKTI     120
SKAKGQPREP QVCTLPPSRD ELTKNQVSLT CLVKGFYPSD IAVEWESNGQ PENNYKTTPP    180
VLDSDGSFFL YSWLTVDKSR WQQGNVFSCS VMHEALHNHY TQKSLSLSPG               230

SEQ ID NO: 254          moltype = AA  length = 230
FEATURE                 Location/Qualifiers
source                  1..230
                        mol_type = protein
                        note = Description of Artificial Sequence: Synthetic
                         polypeptide
                        organism = synthetic construct
SEQUENCE: 254
PKSSDKTHTC PPCPAPEAAG GPSVFLFPPK PKDTLMISRT PEVTCVVVDV SHEDPEVKFN      60
WYVDGVEVHN AKTKPREEQY NSTYRVVSVL TVLHQDWLNG KEYKCKVSNK ALPAPIEKTI     120
SKAKGQPREP RVYTLPPCRD ELTKNQVSLT CLVKGFYPSD IAVEWESNGQ PENNYKTTPP    180
VLVSDGSFTL YSKLTVDKSR WQQGNVFSCS VMHEALHNHY TQKSLSLSPG               230

SEQ ID NO: 255          moltype = AA  length = 230
FEATURE                 Location/Qualifiers
source                  1..230
                        mol_type = protein
                        note = Description of Artificial Sequence: Synthetic
                         polypeptide
                        organism = synthetic construct
SEQUENCE: 255
PKSSDKTHTC PPCPAPEAAG GPSVFLFPPK PKDTLMISRT PEVTCVVVDV SHEDPEVKFN      60
WYVDGVEVHN AKTKPREEQY NSTYRVVSVL TVLHQDWLNG KEYKCKVSNK ALAAPIEKTI     120
SKAKGQPREP QVCTLPPSRD ELTENQVSLT CLVKGFYPSD IAVEWESNGQ PENNYKTTPP    180
VLDSDGSFFL YSWLTVDKSR WQQGNVFSCS VMHEALHNHY TQKSLSLSPG               230

SEQ ID NO: 256          moltype = AA  length = 230
FEATURE                 Location/Qualifiers
source                  1..230
                        mol_type = protein
                        note = Description of Artificial Sequence: Synthetic
                         polypeptide
                        organism = synthetic construct
SEQUENCE: 256
PKSSDKTHTC PPCPAPEAAG GPSVFLFPPK PKDTLMISRT PEVTCVVVDV SHEDPEVKFN      60
WYVDGVEVHN AKTKPREEQY NSTYRVVSVL TVLHQDWLNG KEYKCKVSNK ALAAPIEKTI     120
SKAKGQPREP RVYTLPPCRD ELTENQVSLT CLVKGFYPSD IAVEWESNGQ PENNYKTTPP    180
VLVSDGSFTL YSKLTVDKSR WQQGNVFSCS VMHEALHNHY TQKSLSLSPG               230

SEQ ID NO: 257          moltype = AA  length = 230
FEATURE                 Location/Qualifiers
source                  1..230
                        mol_type = protein
                        note = Description of Artificial Sequence: Synthetic
                         polypeptide
                        organism = synthetic construct
SEQUENCE: 257
PKSSDKTHTC PPCPAPEAEG APSVFLFPPK PKDTLMISRT PEVTCVVVDV SHEDPEVKFN      60
WYVDGVEVHN AKTKPREEQY NSTYRVVSVL TVLHQDWLNG KEYKCKVSNK ALPSSIEKTI     120
SKAKGQPREP QVCTLPPSRD ELTENQVSLT CLVKGFYPSD IAVEWESNGQ PENNYKTTPP    180
VLDSDGSFFL YSWLTVDKSR WQQGNVFSCS VMHEALHNHY TQKSLSLSPG               230

SEQ ID NO: 258          moltype = AA  length = 230
FEATURE                 Location/Qualifiers
source                  1..230
                        mol_type = protein
                        note = Description of Artificial Sequence: Synthetic
                         polypeptide
                        organism = synthetic construct
SEQUENCE: 258
PKSSDKTHTC PPCPAPEAEG APSVFLFPPK PKDTLMISRT PEVTCVVVDV SHEDPEVKFN      60
WYVDGVEVHN AKTKPREEQY NSTYRVVSVL TVLHQDWLNG KEYKCKVSNK ALPSSIEKTI     120
SKAKGQPREP RVYTLPPCRD ELTKNQVSLT CLVKGFYPSD IAVEWESNGQ PENNYKTTPP    180
VLVSDGSFTL YSKLTVDKSR WQQGNVFSCS VMHEALHNHY TQKSLSLSPG               230

SEQ ID NO: 259          moltype = AA  length = 536
FEATURE                 Location/Qualifiers
source                  1..536
                        mol_type = protein
                        note = Description of Artificial Sequence: Synthetic
                         polypeptide
                        organism = synthetic construct
```

```
SEQUENCE: 259
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSPKSS DKTHTCPPCP APELLGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG      536

SEQ ID NO: 260          moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 260
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSPKSS DKTHTCPPCP APEAAGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG      536

SEQ ID NO: 261          moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 261
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSPKSS DKTHTCPPCP APEAAGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALAA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG      536

SEQ ID NO: 262          moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 262
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSPKSS DKTHTCPPCP APEAEGAPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPS   420
SIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG      536

SEQ ID NO: 263          moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 263
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSPKSS DKTHTCPPCP APELLGGPSV FLFPPKPKDT LMISRTPEVT CVVVDVSHED   360
```

```
PEVKFNWYVD GVEVHNAKTK PREEQYNSTY RVVSVLTVLH QDWLNGKEYK CKVSNKALPA    420
PIEKTISKAK GQPREPQVCT LPPSRDELTE NQVSLTCLVK GFYPSDIAVE WESNGQPENN    480
YKTTPPVLDS DGSFFLYSWL TVDKSRWQQG NVFSCSVMHE ALHNHYTQKS LSLSPG        536

SEQ ID NO: 264           moltype = AA  length = 536
FEATURE                  Location/Qualifiers
source                   1..536
                         mol_type = protein
                         note = Description of Artificial Sequence: Synthetic
                          polypeptide
                         organism = synthetic construct
SEQUENCE: 264
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSPKSS DKTHTCPPCP APELLGGPSV FLFPPKPKDT LMISRTPEVT CVVVDVSHED    360
PEVKFNWYVD GVEVHNAKTK PREEQYNSTY RVVSVLTVLH QDWLNGKEYK CKVSNKALPA    420
PIEKTISKAK GQPREPQVCT LPPSRDELTE NQVSLTCLVK GFYPSDIAVE WESNGQPENN    480
YKTTPPVLDS DGSFFLYSWL TVDKSRWQQG NVFSCSVMHE ALHNHYTQKS LSLSPG        536

SEQ ID NO: 265           moltype = AA  length = 536
FEATURE                  Location/Qualifiers
source                   1..536
                         mol_type = protein
                         note = Description of Artificial Sequence: Synthetic
                          polypeptide
                         organism = synthetic construct
SEQUENCE: 265
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSPKSS DKTHTCPPCP APELLGGPSV FLFPPKPKDT LMISRTPEVT CVVVDVSHED    360
PEVKFNWYVD GVEVHNAKTK PREEQYNSTY RVVSVLTVLH QDWLNGKEYK CKVSNKALPA    420
PIEKTISKAK GQPREPQVCT LPPSRDELTE NQVSLTCLVK GFYPSDIAVE WESNGQPENN    480
YKTTPPVLDS DGSFFLYSWL TVDKSRWQQG NVFSCSVMHE ALHNHYTQKS LSLSPG        536

SEQ ID NO: 266           moltype = AA  length = 442
FEATURE                  Location/Qualifiers
source                   1..442
                         mol_type = protein
                         note = Description of Artificial Sequence: Synthetic
                          polypeptide
                         organism = synthetic construct
SEQUENCE: 266
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSGGGGSGGG GSPKSSDKTH TCPPCPAPEL LGGPSVFLFP    240
PKPKDTLMIS RTPEVTCVVV DVSHEDPEVK FNWYVDGVEV HNAKTKPREE QYNSTYRVVS    300
VLTVLHQDWL NGKEYKCKVS NKALPAPIEK TISKAKGQPR EPQVCTLPPS RDELTENQVS    360
LTCLVKGFYP SDIAVEWESN GQPENNYKTT PPVLDSDGSF FLYSWLTVDK SRWQQGNVFS    420
CSVMHEALHN HYTQKSLSLS PG                                            442

SEQ ID NO: 267           moltype = AA  length = 541
FEATURE                  Location/Qualifiers
source                   1..541
                         mol_type = protein
                         note = Description of Artificial Sequence: Synthetic
                          polypeptide
                         organism = synthetic construct
SEQUENCE: 267
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SPKSSDKTHT CPPCPAPELL GGPSVFLFPP KPKDTLMISR TPEVTCVVVD    360
VSHEDPEVKF NWYVDGVEVH NAKTKPREEQ YNSTYRVVSV LTVLHQDWLN GKEYKCKVSN    420
KALPAPIEKT ISKAKGQPRE PQVCTLPPSR DELTENQVSL TCLVKGFYPS DIAVEWESNG    480
QPENNYKTTP PVLDSDGSFF LYSWLTVDKS RWQQGNVFSC SVMHEALHNH YTQKSLSLSP    540
G                                                                   541

SEQ ID NO: 268           moltype = AA  length = 541
FEATURE                  Location/Qualifiers
source                   1..541
```

```
                          mol_type = protein
                          note = Description of Artificial Sequence: Synthetic
                            polypeptide
                          organism = synthetic construct
SEQUENCE: 268
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSGGGG SPKSSDKTHT CPPCPAPELL GGPSVFLFPP KPKDTLMISR TPEVTCVVVD   360
VSHEDPEVKF NWYVDGVEVH NAKTKPREEQ YNSTYRVVSV LTVLHQDWLN GKEYKCKVSN   420
KALPAPIEKT ISKAKGQPRE PQVCTLPPSR DELTENQVSL TCLVKGFYPS DIAVEWESNG   480
QPENNYKTTP PVLDSDGSFF LYSWLTVDKS RWQQGNVFSC SVMHEALHNH YTQKSLSLSP   540
G                                                                  541

SEQ ID NO: 269            moltype = AA   length = 536
FEATURE                   Location/Qualifiers
source                    1..536
                          mol_type = protein
                          note = Description of Artificial Sequence: Synthetic
                            polypeptide
                          organism = synthetic construct
SEQUENCE: 269
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APELLGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 270            moltype = AA   length = 536
FEATURE                   Location/Qualifiers
source                    1..536
                          mol_type = protein
                          note = Description of Artificial Sequence: Synthetic
                            polypeptide
                          organism = synthetic construct
SEQUENCE: 270
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APEAAGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 271            moltype = AA   length = 536
FEATURE                   Location/Qualifiers
source                    1..536
                          mol_type = protein
                          note = Description of Artificial Sequence: Synthetic
                            polypeptide
                          organism = synthetic construct
SEQUENCE: 271
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APEAAGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALAA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 272            moltype = AA   length = 536
FEATURE                   Location/Qualifiers
source                    1..536
                          mol_type = protein
                          note = Description of Artificial Sequence: Synthetic
                            polypeptide
                          organism = synthetic construct
SEQUENCE: 272
IWELKKDVYV VELDWYPDAP GEMVVLTCDT PEEDGITWTL DQSSEVLGSG KTLTIQVKEF    60
```

```
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSASPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APEAEGAPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPS   420
SIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 273          moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 273
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APELLGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 274          moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 274
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APEAAGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 275          moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 275
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APEAAGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALAA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 276          moltype = AA  length = 536
FEATURE                 Location/Qualifiers
source                  1..536
                        mol_type = protein
                        note = Description of Artificial Sequence: Synthetic
                          polypeptide
                        organism = synthetic construct
SEQUENCE: 276
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APEAEGAPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPS   420
SIEKTISKAK GQPREPQVCT LPPSRDELTE NQVSLTCLVK GFYPSDIAVE WESNGQPENN   480
```

```
YKTTPPVLDS DGSFFLYSWL TVDKSRWQQG NVFSCSVMHE ALHNHYTQKS LSLSPG       536

SEQ ID NO: 277           moltype = AA   length = 536
FEATURE                  Location/Qualifiers
source                   1..536
                         mol_type = protein
                         note = Description of Artificial Sequence: Synthetic
                          polypeptide
                         organism = synthetic construct
SEQUENCE: 277
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APEAAGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 278           moltype = AA   length = 536
FEATURE                  Location/Qualifiers
source                   1..536
                         mol_type = protein
                         note = Description of Artificial Sequence: Synthetic
                          polypeptide
                         organism = synthetic construct
SEQUENCE: 278
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APEAAGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALAA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 279           moltype = AA   length = 536
FEATURE                  Location/Qualifiers
source                   1..536
                         mol_type = protein
                         note = Description of Artificial Sequence: Synthetic
                          polypeptide
                         organism = synthetic construct
SEQUENCE: 279
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RCYSSSWSEW   300
ASVPCSPKSS DKTHTCPPCP APEAEGAPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPS   420
SIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 280           moltype = AA   length = 19
FEATURE                  Location/Qualifiers
VARIANT                  17
                         note = Xaa is Leu or Glu
source                   1..19
                         mol_type = protein
                         note = Description of Artificial Sequence: Synthetic peptide
                         organism = synthetic construct
SEQUENCE: 280
ESKYGPPCPP CPAPEFXGG                                                19

SEQ ID NO: 281           moltype = AA   length = 18
FEATURE                  Location/Qualifiers
VARIANT                  16
                         note = Xaa is Leu or Glu
source                   1..18
                         mol_type = protein
                         note = Description of Artificial Sequence: Synthetic peptide
                         organism = synthetic construct
SEQUENCE: 281
SKYGPPCPPC PAPEFXGG                                                 18

SEQ ID NO: 282           moltype = AA   length = 19
```

```
FEATURE                 Location/Qualifiers
source                  1..19
                        mol_type = protein
                        note = Description of Artificial Sequence: Synthetic peptide
                        organism = synthetic construct
SEQUENCE: 282
ESKYGPPCPP CPAPEFLGG                                                    19

SEQ ID NO: 283          moltype = AA   length = 18
FEATURE                 Location/Qualifiers
source                  1..18
                        mol_type = protein
                        note = Description of Artificial Sequence: Synthetic peptide
                        organism = synthetic construct
SEQUENCE: 283
SKYGPPCPPC PAPEFLGG                                                     18

SEQ ID NO: 284          moltype = AA   length = 19
FEATURE                 Location/Qualifiers
source                  1..19
                        mol_type = protein
                        note = Description of Artificial Sequence: Synthetic peptide
                        organism = synthetic construct
SEQUENCE: 284
ESKYGPPCPP CPAPEFEGG                                                    19

SEQ ID NO: 285          moltype = AA   length = 18
FEATURE                 Location/Qualifiers
source                  1..18
                        mol_type = protein
                        note = Description of Artificial Sequence: Synthetic peptide
                        organism = synthetic construct
SEQUENCE: 285
SKYGPPCPPC PAPEFEGG                                                     18

SEQ ID NO: 286          moltype = AA   length = 544
FEATURE                 Location/Qualifiers
source                  1..544
                        mol_type = protein
                        note = Description of Artificial Sequence: Synthetic
                         polypeptide
                        organism = synthetic construct
SEQUENCE: 286
MWELEKDVYV VEVDWTPDAP GETVNLTCDT PEEDDITWTS DQRHGVIGSG KTLTITVKEF    60
LDAGQYTCHK GGETLSHSHL LLHKKENGIW STEILKNFKN KTFLKCEAPN YSGRFTCSWL   120
VQRNMDLKFN IKSSSSSPDS RAVTCGMASL SAEKVTLDQR DYEKYSVSCQ EDVTCPTAEE   180
TLPIELALEA RQQNKYENYS TSFFIRDIIK PDPPKNLQMK PLKNSQVEVS WEYPDSWSTP   240
HSYFSLKFFV RIQRKKEKMK ETEEGCNQKG AFLVEKTSTE VQCKGGNVCV QAQDRYYNSS   300
CSKWACVPCR VRSPRGPTIK PCPPCKCPAP NLLGGPSVFI FPPKIKDVLM ISLSPIVTCV   360
VVDVSEDDPD VQISWFVNNV EVHTAQTQTH REDYNSTLRV VSALPIQHQD WMSGKEFKCK   420
VNNKDLPAPI ERTISKPKGS VRAPQVYVLP PPEEEMTEKQ VTLTCMVTDF MPEDIYVEWT   480
NNGKTELNYK NTEPVLDSDG SYFMYSWLRV EKKNWVERNS YSCSVHEGL HNHHTTKSFS   540
RTPG                                                                544

SEQ ID NO: 287          moltype = AA   length = 439
FEATURE                 Location/Qualifiers
source                  1..439
                        mol_type = protein
                        note = Description of Artificial Sequence: Synthetic
                         polypeptide
                        organism = synthetic construct
SEQUENCE: 287
RVIPVSGPAR CLSQSRNLLK TTDDMVKTAR EKLKHYSCTA EDIDHEDITR DQTSTLKTCL    60
PLELHKNESC LATRETSSTT RGSCLPPQKT SLMMTLCLGS IYEDLKMYQT EFQAINAALQ   120
NHNHQQIILD KGMLVAIDEL MQSLNHNGET LRQKPPVGEA DPYRVKMKLC ILLHAFSTRV   180
VTINRVMGYL SSAGGGGSGG GGSGGGGSPR GPTIKPCPPC KCPAPNLLGG PSVFIFPPKI   240
KDVLMISLSP IVTCVVVDVS EDDPDVQISW FVNNVEVHTA QTQTHREDYN STLRVVSALP   300
IQHQDWMSGK EFKCKVNNKD LPAPIERTIS KPKGSVRAPR VYVLPPPEEE MTKKQVTLTC   360
MVTDFMPEDI YVEWTNNGKT ELNYKNTEPV LVSDGSYTMY SKLRVEKKNW VERNSYSCSV   420
VHEGLHNHHT TKSFSRTPG                                                439

SEQ ID NO: 288          moltype = AA   length = 544
FEATURE                 Location/Qualifiers
source                  1..544
                        mol_type = protein
                        note = Description of Artificial Sequence: Synthetic
                         polypeptide
                        organism = synthetic construct
SEQUENCE: 288
```

```
MWELEKDVYV VEVDWTPDAP GETVNLTCDT PEEDDITWTS DQRHGVIGSG KTLTITVKEF    60
LDAGQYTCHK GGETLSHSHL LLHKKENGIW STEILKNFKN KTFLKCEAPN YSGRFTCSWL   120
VQRNMDLKFN IKSSSSSPDS RAVTCGMASL SAEKVTLDQR DYEKYSVSCQ EDVTCPTAEE   180
TLPIELALEA RQQNKYENYS TSFFIRDIIK PDPPKNLQMK PLKNSQVEVS WEYPDSWSTP   240
HSYFSLKFFV RIQRKKEKMK ETEEGCNQKG APLVEKTSTE VQCKGGNVCV QAQDRYYNSS   300
CSKWACVPCR VRSPRGPTIK PCPPCKPAP NAAGGPSVFI FPPKIKDVLM ISLSPIVTCV    360
VVDVSEDDPD VQISWFVNNV EVHTAQTQTH REDYNSTLRV VSALPIQHQD WMSGKEFKCK   420
VNNKDLGAPI ERTISKPKGS VRAPQVYVLP PPEEEMTEKQ VTLTCMVTDF MPEDIYVEWT   480
NNGKTELNYK NTEPVLDSDG SYFMYSWLRV EKKNWVERNS YSCSVVHEGL HNHHTTKSFS   540
RTPG                                                                544

SEQ ID NO: 289          moltype = AA  length = 439
FEATURE                 Location/Qualifiers
source                  1..439
                        mol_type = protein
                        note = Description of Artificial Sequence: Synthetic
                         polypeptide
                        organism = synthetic construct
SEQUENCE: 289
RVIPVSGPAR CLSQSRNLLK TTDDMVKTAR EKLKHYSCTA EDIDHEDITR DQTSTLKTCL    60
PLELHKNESC LATRETSSTT RGSCLPPQKT SLMMTLCLGS IYEDLKMYQT EFQAINAALQ   120
NHNHQQIILD KGMLVAIDEL MQSLNHNGET LRQKPPVGEA DPYRVKMKLC ILLHAFSTRV   180
VTINRVMGYL SSAGGGGSGG GGSGGGGSPR GPTIKPCPPC KCPAPNAAGG PSVFIFPPKI   240
KDVLMISLSP IVTCVVVDVS EDDPDVQISW FVNNVEVHTA QTQTHREDYN STLRVVSALP   300
IQHQDWMSGK EFKCKVNNKD LGAPIERTIS KPKGSVRAPR VYVLPPPEEE MTKKQVTLTC   360
MVTDFMPEDI YVEWTNNGKT ELNYKNTEPV LVSDGSYTMY SKLRVEKKNW VERNSYSCSV   420
VHEGLHNHHT TKSFSRTPG                                                439

SEQ ID NO: 290          moltype = AA  length = 536
FEATURE                 Location/Qualifiers
source                  1..536
                        mol_type = protein
                        note = Description of Artificial Sequence: Synthetic
                         polypeptide
                        organism = synthetic construct
SEQUENCE: 290
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSPKSS DKTHTCPPCP APEAAGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALAA   420
PIEKTISKAK GQPREPQVCT LPPSRDELTE NQVSLTCLVK GFYPSDIAVE WESNGQPENN   480
YKTTPPVLDS DGSFFLYSWL TVDKSRWQQG NVFSCSVMHE ALHNHYTQKS LSLSPG       536

SEQ ID NO: 291          moltype = AA  length = 443
FEATURE                 Location/Qualifiers
source                  1..443
                        mol_type = protein
                        note = Description of Artificial Sequence: Synthetic
                         polypeptide
                        organism = synthetic construct
SEQUENCE: 291
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSGGGGSGGG GSEPKSSDKT HTCPPCPAPE AAGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALAAPIE KTISKAKGQP REPRVYTLPP CRDELTKNQV   360
SLTCLVKGFY PSDIAVEWES NGQPENNYKT TPPVLSDGS FTLYSKLTVD KSRWQQGNVF    420
SCSVMHEALH NHYTQKSLSL SPG                                          443

SEQ ID NO: 292          moltype = AA  length = 558
FEATURE                 Location/Qualifiers
source                  1..558
                        mol_type = protein
                        note = Description of Artificial Sequence: Synthetic
                         polypeptide
                        organism = synthetic construct
SEQUENCE: 292
MDMRVPAQLL GLLLLWLPGA RCIWELKKDV YVVELDWYPD APGEMVVLTC DTPEEDGITW    60
TLDQSSEVLG SGKTLTIQVK EFGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCSPK SSDKTHTCPP CPAPEAAGGP SVFLFPPKPK   360
DTLMISRTPE VTCVVVDVSH EDPEVKFNWY VDGVEVHNAK TKPREEQYNS TYRVVSVLTV   420
LHQDWLNGKE YKCKVSNKAL AAPIEKTISK AKGQPREPQV CTLPPSRDEL TENQVSLTCL   480
```

```
VKGFYPSDIA VEWESNGQPE NNYKTTPPVL DSDGSFFLYS WLTVDKSRWQ QGNVFSCSVM    540
HEALHNHYTQ KSLSLSPG                                                 558

SEQ ID NO: 293         moltype = AA  length = 465
FEATURE                Location/Qualifiers
source                 1..465
                       mol_type = protein
                       note = Description of Artificial Sequence: Synthetic
                        polypeptide
                       organism = synthetic construct
SEQUENCE: 293
MDMRVPAQLL GLLLLWLPGA RCRNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM    120
ALCLSSIYED LKMYQVEFKT MNAKLLMDPK RQIFLDQNML AVIDELMQAL NFNSETVPQK    180
SSLEEPDFYK TKIKLCILLH AFRIRAVTID RVMSYLNASG GGGSGGGGSG GGGSEPKSSD    240
KTHTCPPCPA PEAAGGPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALAAP IEKTISKAKG    360
QPREPRVYTL PPCRDELTKN QVSLTCLVKG FYPSDIAVEW ESNGQPENNY KTTPPVLVSD    420
GSFTLYSKLT VDKSRWQQGN VFSCSVMHEA LHNHYTQKSL SLSPG                    465

SEQ ID NO: 294         moltype = AA  length = 40
FEATURE                Location/Qualifiers
REPEAT                 1..40
                       note = MISC_FEATURE - This sequence may encompass 1-20 "Gly
                        Ser" repeating units
source                 1..40
                       mol_type = protein
                       note = Description of Artificial Sequence: Synthetic
                        polypeptide
                       organism = synthetic construct
SEQUENCE: 294
GSGSGSGSGS GSGSGSGSGS GSGSGSGSGS GSGSGSGSGS                          40

SEQ ID NO: 295         moltype = AA  length = 60
FEATURE                Location/Qualifiers
REPEAT                 1..60
                       note = MISC_FEATURE - This sequence may encompass 1-20 "Gly
                        Gly Ser" repeating units
source                 1..60
                       mol_type = protein
                       note = Description of Artificial Sequence: Synthetic
                        polypeptide
                       organism = synthetic construct
SEQUENCE: 295
GGSGGSGGSG GSGGSGGSGG SGGSGGSGGS GGSGGSGGSG GSGGSGGSGG SGGSGGSGGS    60

SEQ ID NO: 296         moltype = AA  length = 80
FEATURE                Location/Qualifiers
REPEAT                 1..80
                       note = MISC_FEATURE - This sequence may encompass 1-20 "Gly
                        Gly Gly Ser" repeating units
source                 1..80
                       mol_type = protein
                       note = Description of Artificial Sequence: Synthetic
                        polypeptide
                       organism = synthetic construct
SEQUENCE: 296
GGGSGGGSGG GSGGGSGGGS GGGSGGGSGG GSGGGSGGGS GGGSGGGSGG GSGGGSGGGS    60
GGGSGGGSGG GSGGGSGGGS                                               80

SEQ ID NO: 297         moltype = AA  length = 80
FEATURE                Location/Qualifiers
REPEAT                 1..80
                       note = MISC_FEATURE - This sequence may encompass 1-20 "Gly
                        Gly Ser Gly" repeating units
source                 1..80
                       mol_type = protein
                       note = Description of Artificial Sequence: Synthetic
                        polypeptide
                       organism = synthetic construct
SEQUENCE: 297
GGSGGGSGGG SGGGSGGGSG GGGSGGGSGG SGGGSGGGSG GGSGGGSGGG SGGGSGGGSG    60
GGSGGGSGGG SGGGSGGGSG                                               80

SEQ ID NO: 298         moltype = AA  length = 100
FEATURE                Location/Qualifiers
REPEAT                 1..100
                       note = MISC_FEATURE - This sequence may encompass 1-20 "Gly
                        Gly Ser Gly Gly" repeating units
```

```
source          1..100
                mol_type = protein
                note = Description of Artificial Sequence: Synthetic
                 polypeptide
                organism = synthetic construct
SEQUENCE: 298
GGSGGGGSGG GGSGGGGSGG GGSGGGGSGG GGSGGGGSGG GGSGGGGSGG GGSGGGGSGG    60
GGSGGGGSGG GGSGGGGSGG GGSGGGGSGG GGSGGGGSGG                         100

SEQ ID NO: 299        moltype = AA  length = 100
FEATURE               Location/Qualifiers
source                1..100
                      mol_type = protein
                      note = Description of Artificial Sequence: Synthetic
                       polypeptide
                      organism = synthetic construct
REPEAT                1..100
                      note = MISC_FEATURE - This sequence may encompass 1-20 "Gly
                       Gly Gly Gly Ser" repeating units
SEQUENCE: 299
GGGGSGGGGS GGGGSGGGGS GGGGSGGGGS GGGGSGGGGS GGGGSGGGGS GGGGSGGGGS    60
GGGGSGGGGS GGGGSGGGGS GGGGSGGGGS GGGGSGGGGS                        100
```

HETERODIMERIC FC-FUSED PROTEINS

CROSS-REFERENCE TO RELATED APPLICATIONS

This application is a continuation of U.S. Patent Application No. 17/287,849 filed on Apr. 22, 2021, which is a U.S. National Stage Application of International Patent Application No. PCT/US2019/057721, filed Oct. 23, 2019, which claims the benefit of and priority to U.S. Provisional Patent Application No. 62/749,489, filed Oct. 23, 2018; to U.S. Provisional Patent Application No. 62/781,898, filed Dec. 19, 2018; to U.S. Provisional Patent Application No. 62/788,499, filed Jan. 4, 2019; to U.S. Provisional Patent Application No. 62/827,347, filed Apr. 1, 2019; and to U.S. Provisional Patent Application No. 62/895,889, filed Sep. 4, 2019, the disclosures of which are hereby incorporated by reference in their entireties for all purposes.

SEQUENCE LISTING

This application contains a computer readable Sequence Listing which has been submitted in XML file format via Patent Center, the entire content of which is incorporated by reference herein in its entirety. The Sequence Listing XML file submitted via Patent Center is entitled "14247-717-999_SequenceListing.xml", was created on Aug. 31, 2022 and is 434,587 bytes in size.

FIELD OF THE INVENTION

The invention generally relates to heterodimeric Fc-fused proteins and pharmaceutical compositions comprising such proteins, and methods of use in treating a disease or disorder in a human patient.

BACKGROUND

Physiologically active proteins mostly have the disadvantage of having a short in vivo half-life. In order to solve this disadvantage, there has been an attempt to conjugate them to PEG (polyethylene glycol) or the like, or to fuse them to an antibody Fc (crystallizable fragment) region. Proteins composed of two or more different subunits, in which the two or more different subunits form a protein complex to exhibit physiological activity, can be fused to wild-type Fc domains to prepare Fc-fused protein forms, forming a homodimer due to the homodimeric nature of Fc. Proteins composed of two or more different subunits, in which the two or more different subunits form a protein complex to exhibit physiological activity, can also be fused to heterodimeric Fc regions derived not only from IgG1, but also from other isotype antibodies such as IgG2, IgG3 and IgG4, to form a heterodimeric Fc-fused protein. Thus, one or more subunit(s) of the protein, which is composed of two or more different subunits and in which two or more subunits exhibit physiological activity by forming a protein complex, can be fused to the terminus of heterodimeric Fc variant regions to form improved Fc-fused protein forms.

Fc heterodimerization is a technology that induces mutations in two different CH3 domains of Fc by genetic engineering, such that the two Fc fragments form a heterodimer with minimal sequence variations while they have tertiary structures very similar to those of naturally occurring antibodies (see, e.g., U.S. Pat. No. 7,695,936).

The inventions described in the present disclosure provide designs for improving the Fc-fused protein forms, in which the two subunits of a heterodimeric protein are connected to two Fc domains having different heterodimerization domains, by introducing linkers of varying lengths, or mutations in the CH2 and the CH3 domains of the Fc.

SUMMARY

The invention generally relates to heterodimeric Fc-fused proteins and pharmaceutical compositions comprising such proteins.

In one aspect the present invention provides a heterodimeric Fc-fused protein comprising a first polypeptide comprising a first antibody Fc domain polypeptide and a first subunit of a multisubunit protein; and a second polypeptide comprising a second antibody Fc domain polypeptide and a second, different subunit of the multisubunit protein, wherein the first and second antibody Fc domain polypeptides each comprise different mutations promoting heterodimerization, wherein the first and/or second antibody Fc domain polypeptides comprise one or more mutation(s) that reduce(s) an effector function of an Fc, and wherein the first subunit and second, different subunit of the multisubunit protein are bound to each other.

In some embodiments, the effector function comprises the ability of an Fc domain polypeptide to induce antibody-dependent cellular cytotoxicity (ADCC), antibody-dependent cellular phagocytosis (ADCP), and/or complement dependent cytotoxicity (CDC). In some embodiments, the first and second antibody Fc domain polypeptides are human antibody Fc domain polypeptides. In some embodiments, the first and second antibody Fc domain polypeptides are IgG1, IgG2, IgG3, IgG4, IgM, IgA, IgD, or IgE Fc domain polypeptides (e.g., human IgG1, IgG2, IgG3, IgG4, IgM, IgA, IgD, or IgE Fc domain polypeptides). In some embodiments, the first and/or second antibody Fc domain polypeptides comprise one or more mutation(s) at position(s) 233, 234, 235, 236, 237, 297, 318, 320, 322, 329, 330, and/or 331 under EU numbering. In some embodiments, the heterodimeric Fc-fused protein is fucosylated.

In some embodiments, the first and second antibody Fc domain polypeptides are human IgG1 Fc domain polypeptides. In some embodiments, the first and/or second antibody Fc domain polypeptides comprise one or more mutation(s) at position(s) 234, 235, 237, 329, 330, and/or 331 under EU numbering. In some embodiments, the first and/or second antibody Fc domain polypeptides comprise one or more mutation(s) selected from L234A, L235A, L235E, G237A, P329A, A330S, and P331S. In some embodiments, the first and second antibody Fc domain polypeptides each comprise mutations L234A and L235A. In some embodiments, the first and second antibody Fc domain polypeptides each comprise mutations L234A, L235A, and P329A. In some embodiments, the first and second antibody Fc domain polypeptides each comprise mutations L234A, L235E, G237A, A330S, and P331S. In some embodiments, the first and second antibody Fc domain polypeptides each comprise mutation C220S.

In some embodiments, the first and second antibody Fc domain polypeptides are human IgG4 Fc domain polypeptides. In some embodiments, the first and/or second antibody Fc domain polypeptides comprise one or more mutation(s) at position(s) 235 and/or 329 under EU numbering. In some embodiments, the first and/or second antibody Fc domain polypeptides comprise one or more mutation(s) selected from L235E and P329A. In some embodiments, the first and second antibody Fc domain polypeptides each comprise mutation L235E. In some embodiments, the first and second antibody Fc domain polypeptides each comprise mutations L235E and P329A. In some embodiments, the first and second antibody Fc domain polypeptides each comprise mutation S228P.

In another aspect, the present invention provides a heterodimeric Fc-fused protein comprising a first polypeptide comprising the amino acid sequence of SEQ ID NO:290 and a second polypeptide comprising the amino acid sequence of SEQ ID NO:291.

In yet another aspect, the present invention provides a polypeptide comprising a subunit of a multisubunit cytokine and an immunoglobulin Fc domain polypeptide; the Fc domain polypeptide comprises mutations for promoting heterodimerization with a different immunoglobulin Fc domain polypeptide, and one or more mutation(s) that reduce(s) an effector function of an Fc. For example, the Fc domain polypeptide comprising the mutations can be a human IgG1 antibody Fc domain polypeptide.

In some embodiments, the one or more mutation(s) that reduce(s) an effector function of an Fc is selected from L234A, L235A or L235E, G237A, P329A, A330S, and P331S, numbered according to the EU numbering system. For example, in some embodiments the mutations that reduce an effector function of an Fc are L234A, L235A, and P329A, numbered according to the EU numbering system.

In some embodiments, the mutations for promoting heterodimerization are K360E and K409W, numbered according to the EU numbering system. In some other embodiments, the mutations for promoting heterodimerization are Q347R, D399V, and F405T, numbered according to the EU numbering system.

In some embodiments, the Fc domain polypeptide further comprises a mutation for promoting disulfide bond formation with a different immunoglobulin Fc domain polypeptide. For example, when the heterodimerization mutations are K360E and K409W, in some embodiments the mutation for promoting disulfide bond formation is Y349C, numbered according to the EU numbering system. When the heterodimerization mutations are Q347R, D399V, and F405T, in some embodiments the mutation for promoting disulfide bond formation is S354C, numbered according to the EU numbering system.

For example, in some embodiments a polypeptide comprising a subunit of a multisubunit cytokine and an immunoglobulin Fc domain polypeptide comprises an amino acid sequence of SEQ ID NO:290 or an amino acid sequence of SEQ ID NO:291.

In another aspect, the present invention provides a nucleic acid encoding a polypeptide comprising an amino acid sequence of SEQ ID NO:290 or SEQ ID NO:291. In yet another aspect, the present invention provides an expression vector comprising a nucleic acid comprising a sequence encoding a polypeptide comprising an amino acid sequence of SEQ ID NO:290 or SEQ ID NO:291. In one aspect, the present invention provides a cell comprising a nucleic acid encoding a polypeptide comprising an amino acid sequence of SEQ ID NO:290 or SEQ ID NO:291, or an expression vector comprising a nucleic acid comprising a sequence encoding a polypeptide comprising an amino acid sequence of SEQ ID NO:290 or SEQ ID NO:291.

In another aspect, the present invention provides a heterodimeric Fc-fused protein comprising a first Fc domain polypeptide and a second, different Fc domain polypeptide of an immunoglobulin Fc and a first subunit and a second, different subunit of a multisubunit protein wherein the first subunit and the second, different subunit are bound to each other and linked to one or more end(s) of the N-terminus or C-terminus of the first Fc domain polypeptide and/or the second, different Fc domain polypeptide; wherein the first Fc domain polypeptide and the second Fc domain polypeptide are mutated so as to promote heterodimeric Fc formation and to reduce an effector function of an Fc. In some embodiments, the multisubunit protein is IL-12 (e.g., human IL-12), such that in a heterodimeric Fc-fused protein the p35 and p40 subunits of IL-12 are bound to each other and linked to one or more end(s) of the N-terminus or C-terminus of the first Fc domain polypeptide and/or the second Fc domain polypeptide; wherein the first Fc domain polypeptide and the second Fc domain polypeptide are mutated so as to promote heterodimeric Fc formation and to reduce an effector function of an Fc.

In one aspect the present invention provides a heterodimeric Fc-fused protein comprising: a first polypeptide comprising a first antibody Fc domain polypeptide and a second polypeptide comprising a second antibody Fc domain polypeptide bound to the first antibody Fc domain polypeptide, in which the first polypeptide further comprises a first subunit of a multisubunit protein fused by a linker comprising amino acid sequence PKSSDKTHTCPPCPAPEX$_1$X$_2$GX$_3$ (SEQ ID NO:237) or EPKSSDKTHTCPPCPAPEX$_1$X$_2$GX$_3$ (SEQ ID NO:6) to the first antibody Fc domain polypeptide, wherein X$_1$ represents L or A, X$_2$ represents L, E, or A, and X$_3$ represents A or G; a second, different subunit of the multisubunit protein is fused to the second antibody Fc domain polypeptide and the subunits of the multisubunit protein are bound to each other; when X$_1$ represents L and/or X$_2$ represents L, at least one of the first antibody Fc domain polypeptide and the second antibody Fc domain polypeptide comprises a Q347R mutation for promoting heterodimerization.

In some embodiments, within the heterodimeric Fc-fused protein, the linker connecting the first subunit of the multisubunit protein to the first antibody Fc domain polypeptide comprises amino acid sequence PKSSDKTHTCPPCPA-PEAAGG (SEQ ID NO:239) or EPKSSDKTHTCPPCPA-PEAAGG (SEQ ID NO:9). In some embodiments, within the heterodimeric Fc-fused protein, the linker connecting the first subunit of the multisubunit protein to the first antibody Fc domain polypeptide consists of amino acid sequence PKSSDKTHTCPPCPAPEAAGG (SEQ ID NO:239) or EPKSSDKTHTCPPCPAPEAAGG (SEQ ID NO:9).

In some embodiments, within the heterodimeric Fc-fused protein, the second, different subunit of the multisubunit protein is fused to the second antibody Fc domain polypeptide by a linker comprising amino acid sequence GGGGSGGGGSGGGGSEPKSSDKTHTCPPCPA-PEAAGG (SEQ ID NO:10) or GGGGSGGGGSGGGGSPKSSDKTHTCPPCPAPEAAGG (SEQ ID NO:244). In some embodiments, the second, different subunit of the multisubunit protein is fused to the second antibody Fc domain polypeptide by a linker consisting of amino acid sequence

```
                                       (SEQ ID NO: 10)
GGGGSGGGGSGGGGSEPKSSDKTHTCPPCPAPEAAGG
or (SEQ ID NO: 244)
GGGGSGGGGSGGGGSPKSSDKTHTCPPCPAPEAAGG.
```

In some embodiments, within the heterodimeric Fc-fused protein, the linker connecting the first subunit of the multisubunit protein to the first antibody Fc domain polypeptide comprises amino acid sequence PKSSDKTHTCPPCPA- PELLGG (SEQ ID NO:238) or EPKSSDKTHTCPPCPA-PELLGG (SEQ ID NO:7). In some embodiments, within the heterodimeric Fc-fused protein, the linker fusing the first subunit of the multisubunit protein to the first antibody Fc domain polypeptide consists of amino acid sequence PKSSDKTHTCPPCPAPELLGG (SEQ ID NO:238) or EPKSSDKTHTCPPCPAPELLGG (SEQ ID NO:7).

In some embodiments, within the heterodimeric Fc-fused protein, the second, different subunit of the multisubunit protein is fused to the second antibody Fc domain polypeptide by a linker comprising amino acid sequence GGGGSGGGGSGGGGSEPKSSDKTHTCPPCPA-PELLGG (SEQ ID NO:8) or GGGGSGGGGSGGGGSPKSSDKTHTCPPCPAPELLGG (SEQ ID NO:241). In some embodiments, the second, different subunit of the multisubunit protein is fused to the second antibody Fc domain polypeptide by a linker consisting of amino acid sequence

```
                                            (SEQ ID NO: 8)
GGGGSGGGGSGGGGSEPKSSDKTHTCPPCPAPELLGG
or (SEQ ID NO: 241)
GGGGSGGGGSGGGGSPKSSDKTHTCPPCPAPELLGG.
```

In some embodiments, within the heterodimeric Fc-fused protein, the second, different subunit of the multisubunit protein is fused to the second antibody Fc domain polypeptide by a linker comprising amino acid sequence GGGGSEPKSSDKTHTCPPCPAPELLGG (SEQ ID NO:15) or GGGGSPKSSDKTHTCPPCPAPELLGG (SEQ ID NO:242). In some embodiments, the second, different subunit of the multisubunit protein is fused to the second antibody Fc domain polypeptide by a linker consisting of amino acid sequence

```
                                           (SEQ ID NO: 15)
GGGGSEPKSSDKTHTCPPCPAPELLGG
or (SEQ ID NO: 242)
GGGGSPKSSDKTHTCPPCPAPELLGG.
```

In some embodiments, within the heterodimeric Fc-fused protein, the second, different subunit of the multisubunit protein is fused to the second antibody Fc domain polypeptide by a linker comprising amino acid sequence GGGGSGGGGSEPKSSDKTHTCPPCPAPELLGG (SEQ ID NO:16) or GGGGSGGGGSPKSSDKTHTCPPCPA-PELLGG (SEQ ID NO:243). In some embodiments, the second, different subunit of the multisubunit protein is fused to the second antibody Fc domain polypeptide by a linker consisting of amino acid sequence

```
                                           (SEQ ID NO: 16)
GGGGSGGGGSEPKSSDKTHTCPPCPAPELLGG
or (SEQ ID NO: 243)
GGGGSGGGGSPKSSDKTHTCPPCPAPELLGG.
```

In some embodiments, within the heterodimeric Fc-fused protein, the second, different subunit of the multisubunit protein is fused to the second antibody Fc domain polypeptide by a linker comprising amino acid sequence GGGGSEPKSSDKTHTCPPCPAPEAAGG (SEQ ID NO:65) or GGGGSPKSSDKTHTCPPCPAPEAAGG (SEQ ID NO:245). In some embodiments, the second, different subunit of the multisubunit protein is fused to the second antibody Fc domain polypeptide by a linker consisting of amino acid sequence

```
                                           (SEQ ID NO: 65)
GGGGSEPKSSDKTHTCPPCPAPEAAGG
or (SEQ ID NO: 245)
GGGGSPKSSDKTHTCPPCPAPEAAGG.
```

In some embodiments, within the heterodimeric Fc-fused protein, the second, different subunit of the multisubunit protein is fused to the second antibody Fc domain polypeptide by a linker comprising amino acid sequence GGGGSGGGGSEPKSSDKTHTCPPCPAPEAAGG (SEQ ID NO:66) or GGGGSGGGGSPKSSDKTHTCPPCPA-PEAAGG (SEQ ID NO:246). In some embodiments, the second, different subunit of the multisubunit protein is fused to the second antibody Fc domain polypeptide by a linker consisting of amino acid sequence

```
                                           (SEQ ID NO: 66)
GGGGSGGGGSEPKSSDKTHTCPPCPAPEAAGG
or (SEQ ID NO: 246)
GGGGSGGGGSPKSSDKTHTCPPCPAPEAAGG.
```

In some embodiments, within the heterodimeric Fc-fused protein, the linker connecting the first subunit of the multisubunit protein to the first antibody Fc domain polypeptide comprises amino acid sequence EPKSSDKTHTCPPCPA-PEAEGA (SEQ ID NO:11) or PKSSDKTHTCPPCPAPE-AEGA (SEQ ID NO:240). In some embodiments, within the heterodimeric Fc-fused protein, the linker fusing the first subunit of the multisubunit protein to the first antibody Fc domain polypeptide consists of amino acid sequence EPKSSDKTHTCPPCPAPEAEGA (SEQ ID NO:11) or PKSSDKTHTCPPCPAPEAEGA (SEQ ID NO:240).

In some embodiments, within the heterodimeric Fc-fused protein, the second, different subunit of the multisubunit protein is fused to the second antibody Fc domain polypeptide by a linker comprising amino acid sequence GGGGSGGGGSGGGGSEPKSSDKTHTCPPCPAPE-AEGA (SEQ ID NO:12) or GGGGSGGGGSGGGGSPKSSDKTHTCPPCPAPEAEGA (SEQ ID NO:247). In some embodiments, the second, different subunit of the multisubunit protein is fused to the second antibody Fc domain polypeptide by a linker consisting of amino acid sequence

```
                                           (SEQ ID NO: 12)
GGGGSGGGGSGGGGSEPKSSDKTHTCPPCPAPEAEGA
or (SEQ ID NO: 247)
GGGGSGGGGSGGGGSPKSSDKTHTCPPCPAPEAEGA.
```

In some embodiments, within the heterodimeric Fc-fused protein, the second, different subunit of the multisubunit protein is fused to the second antibody Fc domain polypeptide by a linker comprising amino acid sequence GGGGSEPKSSDKTHTCPPCPAPEAEGA (SEQ ID NO:67) or GGGGSPKSSDKTHTCPPCPAPEAEGA (SEQ ID NO:248). In some embodiments, the second, different subunit of the multisubunit protein is fused to the second antibody Fc domain polypeptide by a linker consisting of amino acid sequence

```
                                     (SEQ ID NO: 67)
GGGGSEPKSSDKTHTCPPCPAPEAEGA
or
                                    (SEQ ID NO: 248)
GGGGSPKSSDKTHTCPPCPAPEAEGA.
```

In some embodiments, within the heterodimeric Fc-fused protein, the second, different subunit of the multisubunit protein is fused to the second antibody Fc domain polypeptide by a linker comprising amino acid sequence GGGGSGGGGSEPKSSDKTHTCPPCPAPEAEGA (SEQ ID NO:68) or GGGGSGGGGSPKSSDKTHTCPPCPAPEAEGA (SEQ ID NO:249). In some embodiments, the second, different subunit of the multisubunit protein is fused to the second antibody Fc domain polypeptide by a linker consisting of amino acid sequence

```
                                     (SEQ ID NO: 68)
GGGGSGGGGSEPKSSDKTHTCPPCPAPEAEGA
or
                                    (SEQ ID NO: 249)
GGGGSGGGGSPKSSDKTHTCPPCPAPEAEGA.
```

In another aspect, the present invention provides a heterodimeric Fc-fused protein comprising a subunit of a multisubunit cytokine connected to an immunoglobulin Fc domain polypeptide by a linker comprising an amino acid sequence PKSSDKTHTCPPCPAPEAAGG (SEQ ID NO:239); the Fc domain polypeptide comprises mutations for promoting heterodimerization with a different immunoglobulin Fc domain polypeptide, and L234A, L235A, and P329A substitutions for reducing an effector function of an Fc.

In some embodiments, the present invention provides a heterodimeric Fc-fused protein comprising a p40 subunit of human IL-12 connected to a first human IgG1 (hIgG1) Fc domain polypeptide by a linker comprising or consisting of an amino acid sequence PKSSDKTHTCPPCPAPEAAGG (SEQ ID NO:239), and a p35 subunit of human IL-12 connected to a second hIgG1 Fc domain polypeptide by a linker comprising or consisting of an amino acid sequence GGGGSGGGGSGGGGSEPKSSDKTHTCPPCPAPEAAGG (SEQ ID NO:10); the first and the second Fc domain polypeptides comprise mutations promoting heterodimerization, and L234A, L235A, and P329A substitutions for reducing an effector function of a hIgG1 Fc.

In one aspect the present invention provides a heterodimeric Fc-fused protein comprising: a first polypeptide comprising a first antibody Fc domain polypeptide and a second polypeptide comprising a second antibody Fc domain polypeptide, in which the first polypeptide further comprises a first subunit of a multisubunit protein, in which the protein sequence is fused by a linker comprising amino acid sequence RVESKYGPPCPPCPAPEFXGG (SEQ ID NO:1) to the first antibody Fc domain polypeptide, in which X represents L or E; a second, different subunit of the multisubunit protein is fused to the second antibody Fc domain polypeptide, and the subunits of the multisubunit protein are bound to each other, the first antibody Fc domain polypeptide and the second antibody Fc domain polypeptide each contain different mutations promoting heterodimerization, and the first antibody Fc domain polypeptide and the second antibody Fc domain polypeptide are bound to each other.

In some embodiments, a heterodimeric Fc-fused protein of the present invention comprises a first polypeptide comprising a first antibody Fc domain polypeptide and a second polypeptide comprising a second antibody Fc domain polypeptide, in which the first polypeptide further comprises a first subunit of a multisubunit protein, in which the protein sequence is fused by a linker to the first antibody Fc domain polypeptide; and the second polypeptide further comprises a second, different subunit of a multisubunit protein, in which the protein sequence is fused by a linker to the second antibody Fc domain polypeptide. The linker connecting the protein sequence of the second, different subunit of a multisubunit protein to the second antibody Fc domain polypeptide may include G4S (SEQ ID NO:110), (G4S)$_2$ (SEQ ID NO:109), or (G4S)$_3$ (SEQ ID NO:108).

In some embodiments, within the heterodimeric Fc-fused protein, the linker connecting the subunit of the multisubunit protein to the first antibody Fc domain polypeptide comprises amino acid sequence RVESKYGPPCPPCPAPEFLGG (SEQ ID NO:2). In some embodiments, the linker fusing the first subunit of the multisubunit protein to the first antibody Fc domain polypeptide consists of amino acid sequence

```
                                     (SEQ ID NO: 2)
RVESKYGPPCPPCPAPEFLGG.
```

In some embodiments, the second, different subunit of the multisubunit protein is fused to the second antibody Fc domain polypeptide by a linker comprising amino acid sequence GGGGSGGGGSGGGGSRVESKYGPPCPPCPAPEFLGG (SEQ ID NO:3). In some embodiments, the second, different subunit of the multisubunit protein is fused to the second antibody Fc domain polypeptide by a linker consisting of amino acid sequence

```
                                     (SEQ ID NO: 3)
GGGGSGGGGSGGGGSRVESKYGPPCPPCPAPEFLGG.
```

In some embodiments, the second, different subunit of the multisubunit protein is fused to the second antibody Fc domain polypeptide by a linker comprising amino acid sequence GGGGSRVESKYGPPCPPCPAPEFLGG (SEQ ID NO:13). In some embodiments, the second, different subunit of the multisubunit protein is fused to the second antibody Fc domain polypeptide by a linker consisting of amino acid sequence

```
                                    (SEQ ID NO: 13)
GGGGSRVESKYGPPCPPCPAPEFLGG.
```

In some embodiments, the second, different subunit of the multisubunit protein is fused to the second antibody Fc domain polypeptide by a linker comprising amino acid sequence GGGGSGGGGSRVESKYGPPCPPCPAPEFLGG (SEQ ID NO:14). In some embodiments, the second, different subunit of the multisubunit protein is fused to the second antibody Fc domain polypeptide by a linker consisting of amino acid sequence

```
                                    (SEQ ID NO: 14)
GGGGSGGGGSRVESKYGPPCPPCPAPEFLGG.
```

In some embodiments, within the heterodimeric Fc-fused protein, the linker connecting the subunit of the multisubunit protein to the first antibody Fc domain polypeptide comprises amino acid sequence RVESKYGPPCPPCPAPEFEGG (SEQ ID NO:4). In some embodiments, the linker fusing the first subunit of the multisubunit protein to the first antibody Fc domain polypeptide consists of amino acid sequence (SEQ ID NO: 4)
RVESKYGPPCPPCPAPEFEGG.

In some embodiments, the second, different subunit of the multisubunit protein is fused to the second antibody Fc domain polypeptide by a linker comprising amino acid sequence GGGGSGGGGSGGGGSRVESKYGPPCPPCPAPEFEGG (SEQ ID NO:5). In some embodiments, the second, different subunit of the multisubunit protein is fused to the second antibody Fc domain polypeptide by a linker consisting of amino acid sequence (SEQ ID NO: 5)
GGGGSGGGGSGGGGSRVESKYGPPCPPCPAPEFEGG.

In some embodiments, the second, different subunit of the multisubunit protein is fused to the second antibody Fc domain polypeptide by a linker comprising amino acid sequence GGGGSRVESKYGPPCPPCPAPEFEGG (SEQ ID NO:63). In some embodiments, the second, different subunit of the multisubunit protein is fused to the second antibody Fc domain polypeptide by a linker consisting of amino acid sequence (SEQ ID NO: 63)
GGGGSRVESKYGPPCPPCPAPEFEGG.

In some embodiments, the second, different subunit of the multisubunit protein is fused to the second antibody Fc domain polypeptide by a linker comprising amino acid sequence GGGGSGGGGSRVESKYGPPCPPCPAPEFEGG (SEQ ID NO:64). In some embodiments, the second, different subunit of the multisubunit protein is fused to the second antibody Fc domain polypeptide by a linker consisting of amino acid sequence (SEQ ID NO: 64)
GGGGSGGGGSRVESKYGPPCPPCPAPEFEGG.

Some heterodimeric Fc-fused proteins described herein include a first IgG4 antibody Fc domain polypeptide and a second, different IgG4 antibody Fc domain polypeptide, each mutated to promote heterodimerization with each other. In some embodiments, the first IgG4 antibody Fc domain polypeptide includes one or more mutation(s) selected from K370E and R409W, and the second, different IgG4 antibody Fc domain polypeptide includes one or more mutation(s) selected from E357N, D399V, and F405T. In some embodiments, the first IgG4 antibody Fc domain polypeptide includes one or more mutation(s) selected from E357N, D399V, and F405T, and the second, different IgG4 antibody Fc domain polypeptide includes one or more mutation(s) selected from K370E and R409W. In some embodiments, the first IgG4 antibody Fc domain polypeptide includes mutations K370E and R409W, and the second, different IgG4 antibody Fc domain polypeptide includes mutations E357N, D399V, and F405T, and the second, different IgG4 antibody Fc domain polypeptide includes mutations K370E and R409W. In some embodiments, the first IgG4 Fc domain polypeptide includes one or more mutation(s) selected from K360E and R409W, and the second, different IgG4 Fc domain polypeptide includes one or more mutation(s) selected from Q347R, D399V, and F405T. In some embodiments, the first IgG4 Fc domain polypeptide includes one or more mutation(s) selected from Q347R, D399V, and F405T, and the second, different IgG4 Fc domain polypeptide includes one or more mutation(s) selected from K360E and R409W. In some embodiments, the first IgG4 Fc domain polypeptide includes mutations K360E and R409W, and the second, different IgG4 Fc domain polypeptide includes mutations Q347R, D399V, and F405T. In some embodiments, the first IgG4 Fc domain polypeptide includes mutations Q347R, D399V, and F405T, and the second, different IgG4 Fc domain polypeptide includes mutations K360E and R409W.

Some heterodimeric Fc-fused proteins disclosed herein include a first IgG1 antibody Fc domain polypeptide and a second, different IgG1 antibody Fc domain polypeptide, each mutated to promote heterodimerization with each other. In some embodiments, the first IgG1 Fc domain polypeptide includes one or more mutation(s) selected from K360E and K409W, and the second, different IgG1 Fc domain polypeptide includes one or more mutation(s) selected from Q347R, D399V, and F405T. In some embodiments, the first IgG1 Fc domain polypeptide includes one or more mutation(s) selected from Q347R, D399V, and F405T, and the second, different IgG1 Fc domain polypeptide includes one or more mutation(s) selected from K360E and K409W. In some embodiments, the first IgG1 antibody Fc domain polypeptide includes mutations K360E and K409W, and the second, different IgG1 antibody Fc domain polypeptide includes mutations Q347R, D399V, and F405T. In some embodiments, the first IgG1 antibody Fc domain polypeptide includes mutations Q347R, D399V, and F405T, and the second, different IgG1 antibody Fc domain polypeptide includes mutations K360E and K409W.

In some embodiments, a heterodimeric Fc-fused protein described herein comprises IgG4 or IgG1 Fc domain polypeptides further mutated to reduce effector functions. In some embodiments, the first antibody Fc domain polypeptide and the second antibody Fc domain polypeptide each contain the mutation P329G or P329A. In some embodiments, the first IgG4 antibody Fc domain polypeptide and the second, different IgG4 antibody Fc domain polypeptide each contain the mutation P329G or P329A. In some embodiments, the first IgG1 antibody Fc domain polypeptide and the second, different IgG1 antibody Fc domain polypeptide each contain the mutation P329G or P329A. In some embodiments, the first IgG4 antibody Fc domain polypeptide and the second, different IgG4 antibody Fc domain polypeptide each contain the mutation P329A. In some embodiments, the first IgG1 antibody Fc domain polypeptide and the second, different IgG1 antibody Fc domain polypeptide each contain the mutation P329A.

In some embodiments, a heterodimeric Fc-based fusion described herein incorporates a first IgG1 antibody Fc domain polypeptide and a second, different IgG1 antibody Fc domain polypeptide each containing a mutation selected from A330S and P331S. In some embodiments, a heterodimeric Fc-based fusion described herein incorporates a first IgG1 antibody Fc domain polypeptide and a second, different IgG1 antibody Fc domain polypeptide each containing the mutations A330S and P331S.

In some embodiments, a heterodimeric Fc-based protein described herein incorporates IgG4 or IgG1 Fc domain polypeptides that are further mutated to introduce an interchain disulfide bond. In some embodiments, the first IgG4 or IgG1 Fc domain polypeptide includes mutation Y349C, and the second, different IgG4 or IgG1 Fc domain polypeptide includes mutation S354C. In some embodiments, the first IgG4 or IgG1 Fc domain polypeptide includes mutation S354C, and the second, different IgG4 or IgG1 Fc domain polypeptide includes mutation Y349C.

Some heterodimeric Fc-fused proteins of the present invention include a native disulfide bond between the first subunit of a multisubunit protein and the second, different subunit of the multisubunit protein. For example, in an exemplary embodiment, a heterodimeric Fc-fused protein according to the invention includes a native heterodimer disulfide bond between p35 and p40 subunits of IL-12. Such a protein includes the native disulfide bond between C74 of p35 and C177 of p40.

Some heterodimeric Fc-fused proteins of the present invention include an artificial or engineered heterodimer disulfide bond between the first subunit of a multisubunit protein and the second, different subunit of the multisubunit protein. For example, in an exemplary embodiment, a heterodimeric Fc-fused protein according to the invention includes an artificial or engineered heterodimer disulfide bond between p35 and p40 subunits of IL-12. Such a protein includes an artificial or engineered disulfide bond between V185C of p35 and Y292C of p40.

Some heterodimeric Fc-fused proteins of the present invention include a native disulfide bond between the first subunit of a multisubunit protein and the second, different subunit of the multisubunit protein, and an artificial or engineered heterodimer disulfide bond between the first subunit of a multisubunit protein and the second, different subunit of the multisubunit protein. For example, in an exemplary embodiment, a native heterodimer disulfide bond between p35 and p40 subunits of IL-12, and includes an artificial or engineered heterodimer disulfide bond between p35 and p40 subunits of IL-12. Such a protein includes the native disulfide bond between C74 of p35 and C177 of p40, and an artificial or engineered disulfide bond between V185C of p35 and Y292C of p40.

Some heterodimeric Fc-fused proteins of the present invention are engineered to remove a native disulfide bond, and then substituted with a non-native artificial or engineered disulfide bond. For example, in an exemplary embodiment, a heterodimeric Fc-fused protein according to the invention includes p35 of IL-12 in which the native C74 is mutated to serine, and a p40 of Il-12 in which the native C177 is mutated to serine, thereby removing the native disulfide bond between p35 and p40 subunits of IL-12. To this mutated IL-12, two new mutations are introduced, V185C on p35 and Y292C on p40, thereby introducing a non-native artificial or engineered disulfide bond.

Within a heterodimeric Fc-fused protein of the present invention, a first polypeptide and a second, different polypeptide comprise a first subunit and a second, different subunit of a multisubunit cytokine, respectively. Within a heterodimeric Fc-fused protein of the present invention, a first polypeptide and a second, different polypeptide comprise a second, different subunit and a first subunit of a multisubunit cytokine, respectively. In an exemplary embodiment, the cytokine is IL-12 (e.g., human IL-12). Formulations containing any one of the heterodimeric Fc-fused proteins described herein, cells containing one or more nucleic acid(s) expressing the heterodimeric Fc-fused proteins or vector(s) expressing the heterodimeric Fc-fused protein, and methods of enhancing tumor cell death using the heterodimeric Fc-fused proteins are also provided. In some embodiments, the invention provides a formulation that includes a heterodimeric Fc-fused protein described herein and a pharmaceutically acceptable carrier.

In another aspect, a heterodimeric Fc-fused protein of the present invention further comprises at least one antibody variable domain (e.g., an antibody heavy chain variable domain). In certain embodiments, the at least one antibody heavy chain variable domain binds to an antibody light chain variable region to form an Fab, and the heavy chain variable domain or the light chain variable domain of the Fab is fused at the N-terminus of the first antibody Fc domain polypeptide and/or the second antibody Fc domain polypeptide.

In certain embodiments, the heterodimeric Fc-fused protein comprising at least one antibody variable domain of the present invention has a a first subunit of a multisubunit protein and a second, different subunit of the multisubunit protein connected to the C-terminus of the first antibody Fc domain polypeptide and the second antibody Fc domain polypeptide, respectively.

In certain embodiments, the heterodimeric Fc-fused protein comprising at least one antibody variable domain of the present invention has a a first subunit of a multisubunit protein and a second, different subunit of the multisubunit protein connected to the C-terminus of the second antibody Fc domain polypeptide and the first antibody Fc domain polypeptide, respectively.

In certain embodiments, a heterodimeric Fc-fused protein of the present invention comprises an antibody heavy chain variable domain positioned at the C-terminus to the first antibody Fc domain polypeptide of the first polypeptide. In certain embodiments, a heterodimeric Fc-fused protein of the present invention comprises an antibody heavy chain variable domain positioned C-terminally to the second antibody Fc domain polypeptide of the second polypeptide. In certain embodiments, the antibody heavy chain variable region binds to an antibody light chain variable region to form an scFv. In certain embodiments, a first subunit of a multisubunit protein and the second, different subunit of the multisubunit protein are connected to the N-terminus of the first antibody Fc domain polypeptide and the second antibody Fc domain polypeptide, respectively. In certain embodiments, a first subunit of a multisubunit protein and the second, different subunit of the multisubunit protein are connected to the N-terminus of the second antibody Fc domain polypeptide and the first antibody Fc domain polypeptide, respectively.

In some embodiments, a heterodimeric Fc-fused protein of the present invention does not comprise an antibody variable domain. For example, in some embodiments, the heterodimeric Fc-fused protein consists of or consists essentially of a first subunit of a multisubunit protein (e.g., an IL-12 protein), a linker optionally comprising a spacer peptide, and a first antibody Fc domain polypeptide; and a second, different subunit of the multisubunit protein (e.g., an IL-12 protein), a linker optionally comprising a spacer peptide, and a second antibody Fc domain polypeptide.

In some embodiments, a heterodimeric Fc-fused protein of the present invention further comprises a proteoglycan-binding domain. In some embodiments, the proteoglycan-binding domain binds one or more proteoglycans that are specifically expressed in a tumor. In some embodiments, the proteoglycan-binding domain binds one or more proteoglycans selected from syndecan, serglycin, CSPG4, betaglycan, glypican, perlecan, versican, brevican, and small leucine-rich proteoglycans (SLRPs). In some embodiments, the SLRPs are selected from decorin, biglycan, asporin, fibrodulin, and lumican. In some embodiments, the proteoglycan-binding domain is linked to the C-terminus of the first antibody Fc domain polypeptide. In some embodiments, the proteoglycan-binding domain is linked to the C-terminus of the second antibody Fc domain polypeptide.

In some embodiments, a heterodimeric Fc-fused protein of the present invention further comprises a collagen-binding domain. In some embodiments, the collagen-binding domain binds one or more collagens that are specifically expressed in a tumor. In some embodiments, the collagen-binding domain is linked to the C-terminus of the first antibody Fc domain polypeptide. In some embodiments, the collagen-binding domain is linked to the C-terminus of the second antibody Fc domain polypeptide.

In some embodiments, a heterodimeric Fc-fused protein of the present invention further comprises a hyaluronic acid-binding domain. In some embodiments, the hyaluronic acid-binding domain is linked to the C-terminus of the first antibody Fc domain polypeptide. In some embodiments, the hyaluronic acid-binding domain is linked to the C-terminus of the second antibody Fc domain polypeptide.

Another aspect of the invention provides a method of treating cancer in a patient. The method comprises administering to a patient, for example, a patient in need thereof, an effective amount of a heterodimeric Fc-fused protein described herein or a formulation that includes an effective amount of a multi-specific binding protein described herein. For example, in some embodiments, the method of treating cancer includes administering to a patient, for example, a patient in need of treatment, a formulation that includes an effective amount of a heterodimeric Fc-fused protein described herein and a pharmaceutically acceptable carrier.

In certain embodiments, the present disclosure provides a method of treating cancer, the method comprising administering to a patient only a single dose of a heterodimeric IL-12-Fc-fused protein. In certain embodiments, the single dose is in an amount sufficient to induce a complete response to the cancer. In certain embodiments, the single dose is in an amount sufficient to delay or prevent recurrence of the cancer.

In certain embodiments, the present disclosure provides a method of treating cancer, the method comprising administering to a patient only a single dose of a heterodimeric IL-12-Fc-fused protein comprising a first polypeptide comprising the amino acid sequence of SEQ ID NO:290 and a second polypeptide comprising the amino acid sequence of SEQ ID NO:291, or a formulation comprising the heterodimeric IL-12-Fc-fused protein and a pharmaceutically acceptable carrier. In certain embodiments, a single dose of a heterodimeric IL-12-Fc-fused protein comprising a first polypeptide comprising the amino acid sequence of SEQ ID NO:290 and a second polypeptide comprising the amino acid sequence of SEQ ID NO:291, or a formulation comprising the heterodimeric IL-12-Fc-fused protein and a pharmaceutically acceptable carrier is in an amount sufficient to induce a complete response to the cancer. In certain embodiments, the single dose is in an amount sufficient to delay or prevent recurrence of the cancer.

Another aspect of the invention provides a method of treating acute radiation syndrome, wherein the method comprises administering a heterodimeric Fc-fused protein or a formulation disclosed herein to a patient. In some embodiments, the acute radiation syndrome comprises one or more syndrome(s) selected from hematopoietic radiation syndrome, gastrointestinal radiation syndrome, neurovascular radiation syndrome, and cutaneous radiation syndrome. In some embodiments, the acute radiation syndrome comprises a syndrome selected from the group consisting of hematopoietic radiation syndrome, gastrointestinal radiation syndrome, neurovascular radiation syndrome, and cutaneous radiation syndrome.

In summary, the present invention provides heterodimeric Fc-fused protein constructs of multisubunit proteins. These fusion protein constructs can exhibit a higher serum half-life compared to a native/natural multisubunit protein, improved yield during production, enhanced stability during storage, and/or improved efficacy when used as a therapeutic.

BRIEF DESCRIPTION OF THE DRAWINGS

FIGS. 4A-4D illustrate exemplary Fc-fused proteins including a first scFv linked to the C-terminus of the first antibody Fc domain polypeptide and a second scFv linked to the C-terminus of the second antibody Fc domain polypeptide. The first scFv and the second scFv can be the same or different (e.g., bind to different antigens or different epitopes on a single antigen). The exemplary Fc-fused proteins illustrated in FIG. 4A and FIG. 4C comprise different pairs of heterodimerization Fc variants. The exemplary Fc-fused proteins illustrated in FIG. 4B and FIG. 4D comprise different pairs of heterodimerization Fc variants. For example, where the heterodimerization mutations include "knobs-into-holes" mutations, FIG. 4A and FIG. 4D illustrate exemplary Fc-fused proteins in which the first polypeptide comprises "hole" mutation(s) and the second polypeptide comprises "knob" mutation(s); FIG. 4B and FIG. 4C illustrate exemplary Fc-fused proteins in which the first polypeptide comprises "knob" mutation(s) and the second polypeptide comprises "hole" mutation(s). FIG. 4A and FIG. 4B illustrate exemplary Fc-fused proteins in which the protein sequence of a first subunit of a multisubunit protein is connected to the first polypeptide; FIG. 4C and FIG. 4D illustrate exemplary Fc-fused proteins in which the second, different subunit of the multisubunit protein is connected to the first polypeptide. Heterodimeric Fc-fused proteins with other types of heterodimerization mutations are similarly contemplated.

FIGS. 4E and 4G illustrate exemplary Fc-fused proteins including an scFv linked to the C-terminus of the first antibody Fc domain polypeptide.

FIGS. 4F and 4H illustrate exemplary Fc-fused proteins including an scFv linked to the C-terminus of the second antibody Fc domain polypeptide.

FIGS. 4I-4L illustrate exemplary Fc-fused proteins including a first Fab linked to the N-terminus of the first antibody Fc domain polypeptide and a second Fab linked to the N-terminus of the second antibody Fc domain polypeptide. FIG. 4I and FIG. 4K illustrate exemplary Fc-fused proteins in which a first subunit of a multisubunit protein is connected to the first polypeptide; FIG. 4J and FIG. 4L illustrate exemplary Fc-fused proteins in which the second, different subunit of the multisubunit protein is connected to the first polypeptide. FIG. 4K differs from FIG. 4I in having a longer amino acid sequence (e.g., spacer peptide disclosed herein) that connects the antibody Fc domain polypeptide and the a first subunit of a multisubunit protein; FIG. 4J differs from FIG. 4L in having a longer amino acid sequence (e.g., spacer peptide disclosed herein) that connects the antibody Fc domain polypeptide and the first subunit of a multisubunit protein.

FIG. 15A shows the PK/PD profile of rmIL-12 in naïve Balb/c mice and FIG. 15B shows the PK/PD profile of DF-mIL-12-Fc si in naïve Balb/c mice IL-12. IL-12 and IFNγ levels in serum were analyzed by ELISA.

FIG. 17A shows Kaplan-Meier survival curves. FIG. 17B shows body weights of mice as averages±standard deviation.

FIG. 19A shows Kaplan-Meier survival curves. FIG. 19B shows body weights of mice as averages+standard deviation.

FIG. 26A is a graph showing tumor growth curves of individual mice inoculated with CT26-Tyrp1 tumor cells and treated once (weekly) with either 2 μg mIgG2a isotype control or 1 μg DF-mIL-12-Fc si. FIG. 26B is a graph showing tumor growth curves of individual mice inoculated with CT26-Tyrp1 tumor cells and treated once (weekly) with either 2 μg mIgG2a isotype control or 2 μg DF-mIL-12-Fc si.

FIGS. 29A, 29C and 29E show IFNγ concentrations/levels of expression in cynomolgus monkeys treated with 1 µg/kg, 2 µg/kg, and 4 µg/kg of DF-hIL-12-Fc si, respectively. FIGS. 29B, 29D and 29F show IP10/CXCL10 concentrations/levels of expression in cynomolgus monkeys treated with 1 µg/kg, 2 µg/kg, and 4 µg/kg of DF-hIL-12-Fc si, respectively. 3240, 3241, 3740, 3741 denote individual cynomolgus monkey subjects.

FIG. 31B also shows tumor growth curves of individual mice previously treated with anti-PD-1 antibody that were administered anti-PD-1 antibody (bi-weekly) along with weekly treatment of 1 µg of DF-mIL-12-Fc si.

DETAILED DESCRIPTION

Figure 1A:
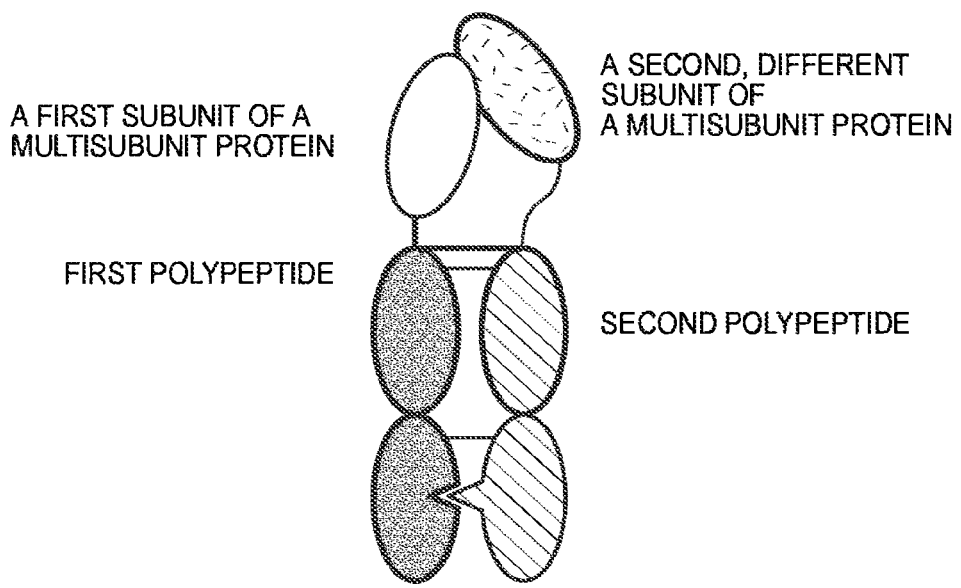
FIG. 1A illustrates an exemplary heterodimeric Fc-fused protein comprising a first subunit of a multisubunit protein connected by a linker to a first antibody Fc domain polypeptide, and a second, different subunit of a multisubunit protein connected by a linker to a second antibody Fc domain polypeptide. The first antibody Fc domain polypeptide and the second antibody Fc domain polypeptide each contain different mutations promoting heterodimerization, and a disulfide bond between the Fc domain polypeptides stabilizes the heterodimer. The linker connecting the additional subunit to the second antibody Fc domain polypeptide may include (G4S)$_3$ sequence (SEQ ID NO:108).
Figure 1B:
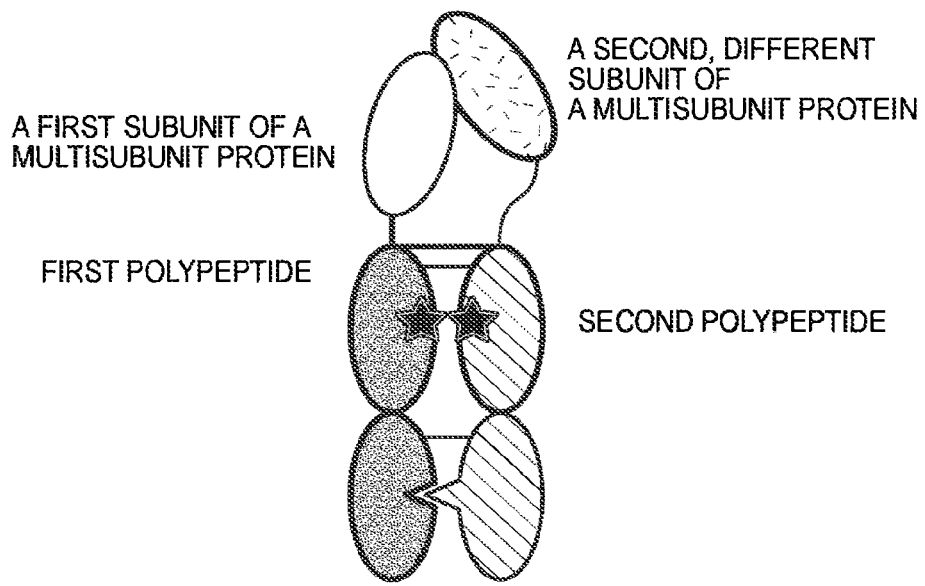
FIG. 1B illustrates an exemplary heterodimeric Fc-fused protein similar to the protein illustrated in FIG. 1A, but also including mutations in the Fc domain polypeptide to reduce FcγR binding.
Figure 1C:
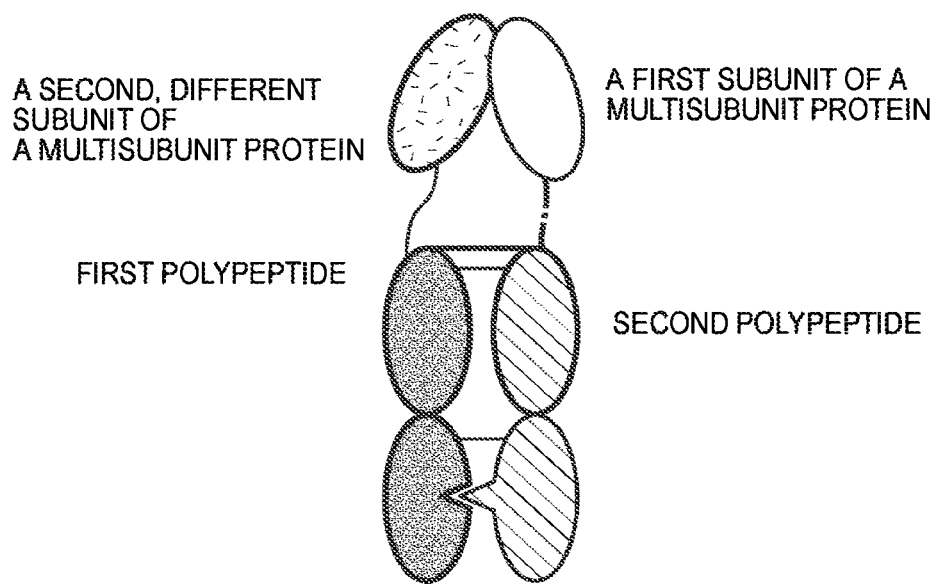
FIG. 1C illustrates an exemplary protein in which the second, different subunit of the multisubunit protein is connected by a linker to the first antibody Fc domain polypeptide, and the other subunit of the multisubunit protein is connected by another linker to the second antibody Fc domain polypeptide.
Figure 1D:
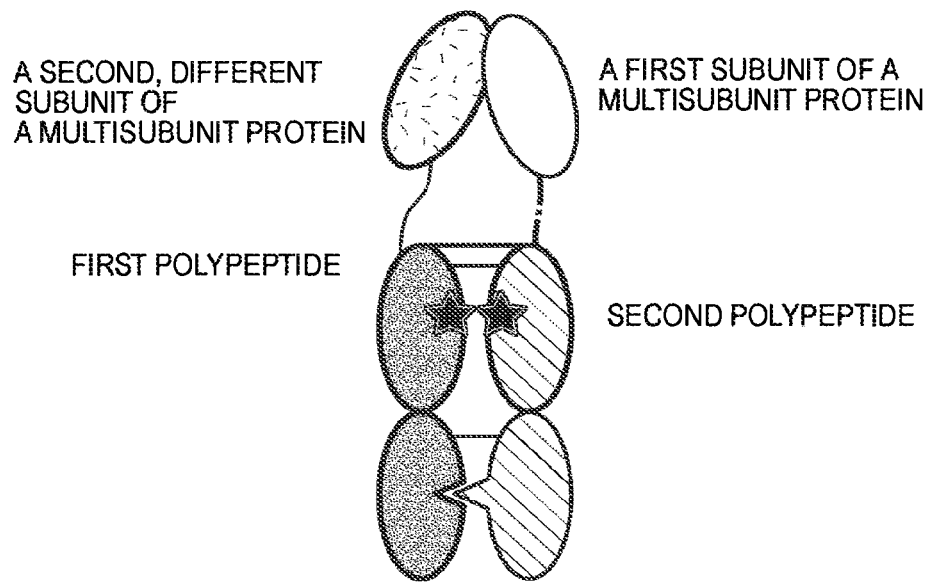
FIG. 1D illustrates an exemplary heterodimeric Fc-fused protein similar to the protein illustrated in FIG. 1C, but also including mutations in the Fc domain polypeptide to reduce FcγR binding.
Figure 1E:
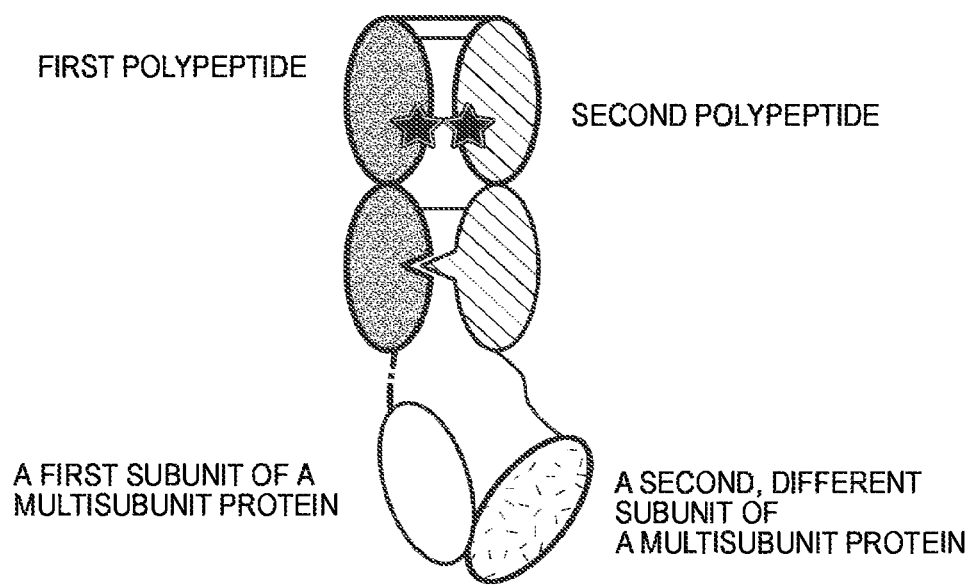
FIG. 1E illustrates an exemplary heterodimeric Fc-fused protein similar to the protein illustrated in FIG. 1B, except that the second, different subunit of a multisubunit protein is positioned at the C-terminus of the second antibody Fc domain polypeptide in the second polypeptide.
Figure 1F:
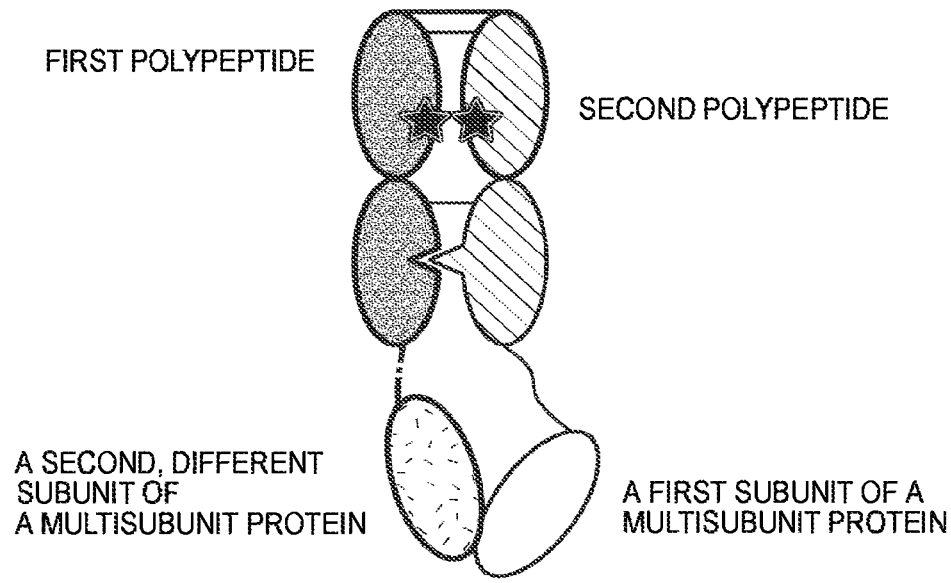
FIG. 1F illustrates an exemplary heterodimeric Fc-fused protein similar to the protein illustrated in FIG. 1E, except that the second, different subunit of a multisubunit protein is positioned at the C-terminus of the first antibody Fc domain polypeptide in the first polypeptide.
Figure 2A:
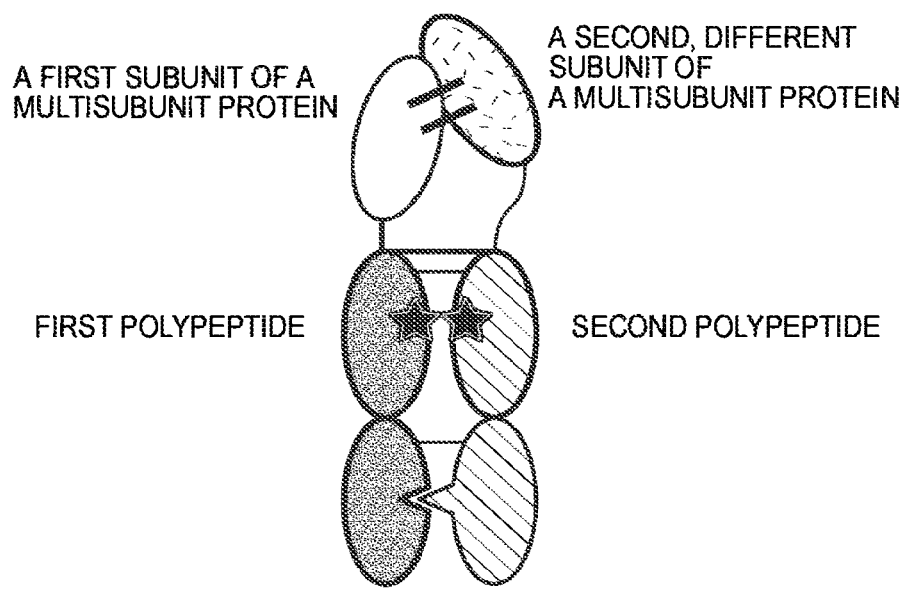
FIG. 2A illustrates an exemplary heterodimeric Fc-fused protein comprising a first subunit of a multisubunit protein connected by a linker to a first antibody Fc domain polypeptide, and a second, different subunit of a multisubunit protein connected by another linker to a second antibody Fc domain polypeptide, in which the subunits are connected by two disulfide bonds. The first antibody Fc domain polypeptide and the second antibody Fc domain polypeptide each contain different mutations promoting heterodimerization, and a disulfide bond between the Fc domain polypeptides stabilizes the heterodimer. The illustrated protein also includes mutations in the Fc domain polypeptide to reduce FcγR binding.
Figure 2B:
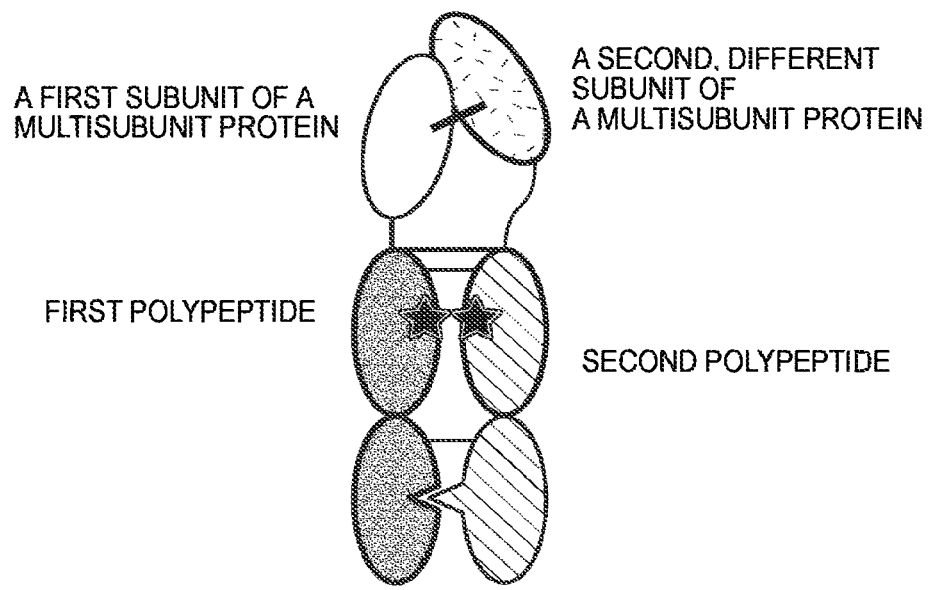
FIG. 2B illustrates an exemplary heterodimeric Fc-fused protein comprising a first subunit of a multisubunit protein connected by a linker to a first antibody Fc domain polypeptide, and a second, different subunit of a multisubunit protein connected by another linker to a second antibody Fc domain polypeptide, in which the subunits are connected by one non-native disulfide bond. In the exemplary protein shown, the native disulfide bond has been removed and replaced with an artificial disulfide bond. For example, an IL-12 construct can incorporate mutations p35-V185C/ C74S and p40-Y292C/C177S. The first antibody Fc domain polypeptide and the second antibody Fc domain polypeptide each contain different mutations promoting heterodimerization, and a disulfide bond between the Fc domain polypeptides stabilizes the heterodimer. The protein also includes mutations in the Fc domain polypeptide to reduce FcγR binding.
Figure 3A:
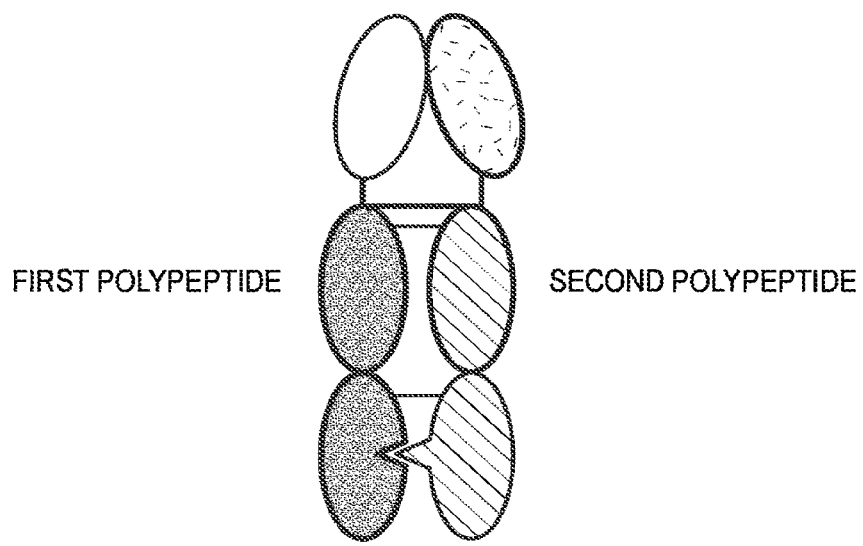
FIG. 3A illustrates an exemplary heterodimeric Fc-fused protein comprising a first subunit of a multisubunit protein connected by a linker to a first antibody Fc domain polypeptide, and a second, different subunit of a multisubunit protein connected by another linker having the same amino acid sequence to a second antibody Fc domain polypeptide. The first antibody Fc domain polypeptide and the second antibody Fc domain polypeptide each contain different mutations promoting heterodimerization, and a disulfide bond between the Fc domain polypeptides stabilizes the heterodimer.
Figure 3B:
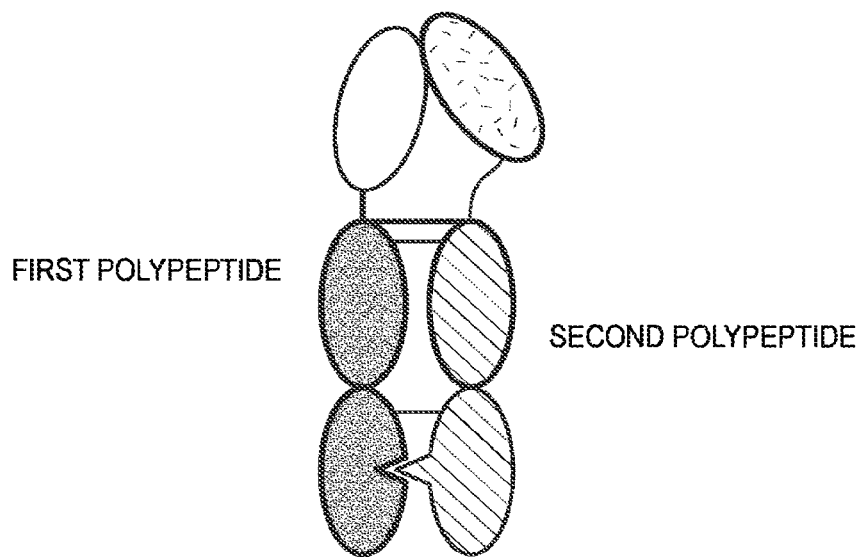
FIG. 3B illustrates an exemplary heterodimeric Fc-fused protein comprising a first subunit of a multisubunit protein connected by a linker to a first antibody Fc domain polypeptide, and a second, different subunit of a multisubunit protein connected by another linker to a second antibody Fc domain polypeptide. The first antibody Fc domain polypeptide and the second antibody Fc domain polypeptide each contain different mutations promoting heterodimerization, and a disulfide bond between the Fc domain polypeptides stabilizes the heterodimer. The linker connecting the second, different subunit of the multisubunit protein to the second antibody Fc domain polypeptide may include a (G4S)$_2$ (SEQ ID NO:109) or G4S (SEQ ID NO:110) sequence.
Figure 4A:
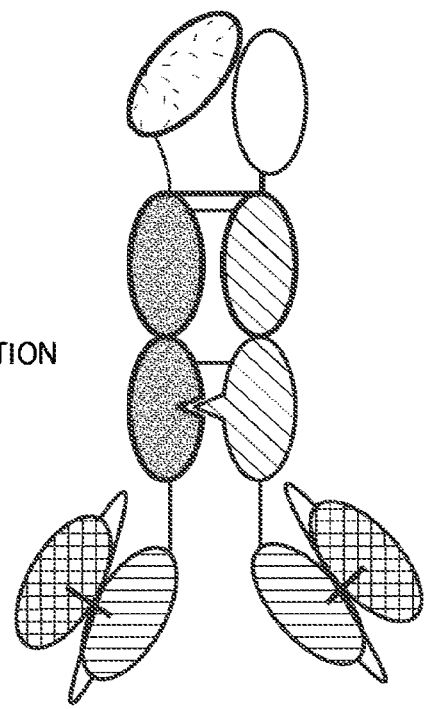
FIGS. 4A-4L illustrate exemplary scFv fusion heterodimeric Fc-fused protein constructs (FIGS. 4A-4H), and mAb fusion heterodimeric Fc-fused protein constructs (FIGS. 4I-4L) in which a first subunit of a multisubunit protein is connected by a linker to a first antibody Fc domain polypeptide, and a second, different subunit of a multisubunit protein is connected by another linker to a second antibody Fc domain polypeptide.
Figure 4B:
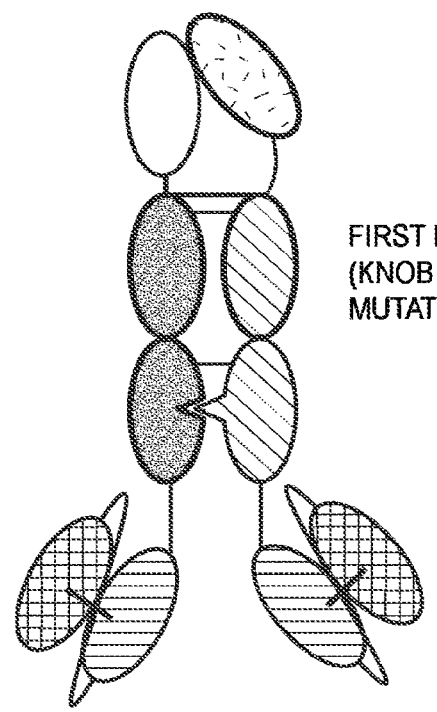
Figure 4C:
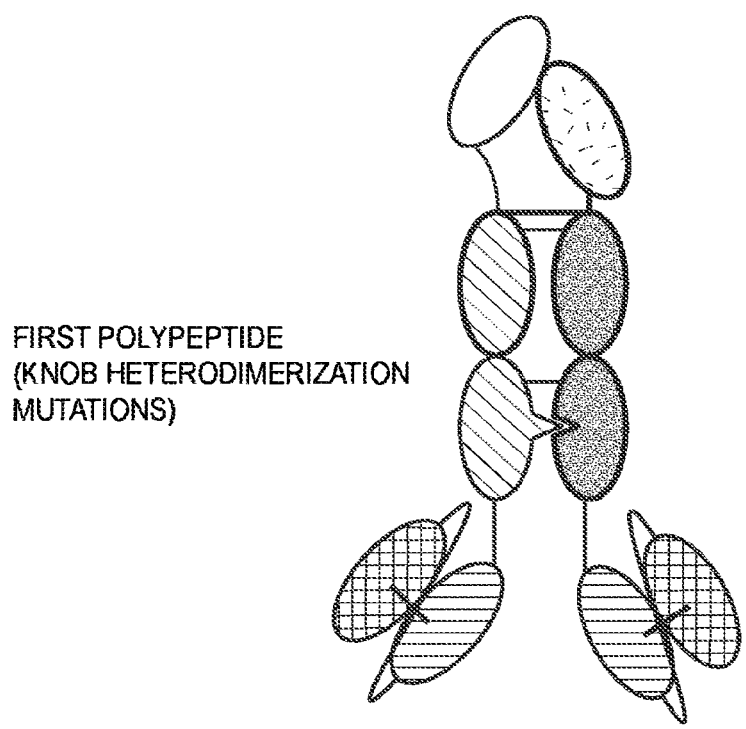
Figure 4D:
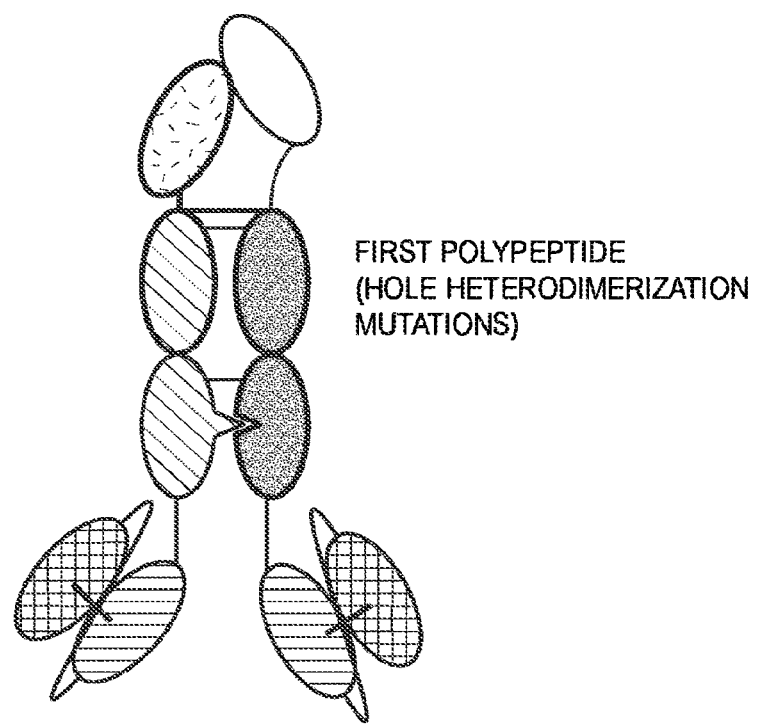
Figure 4E:
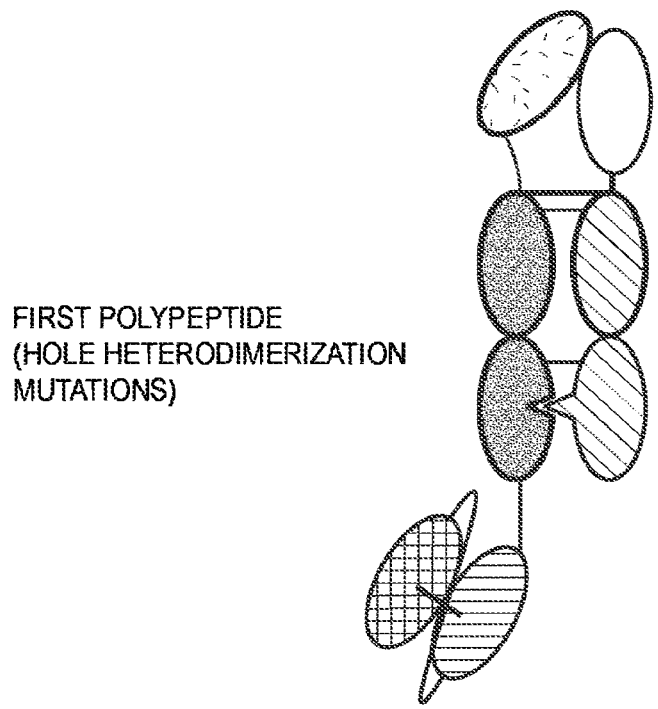
Figure 4F:
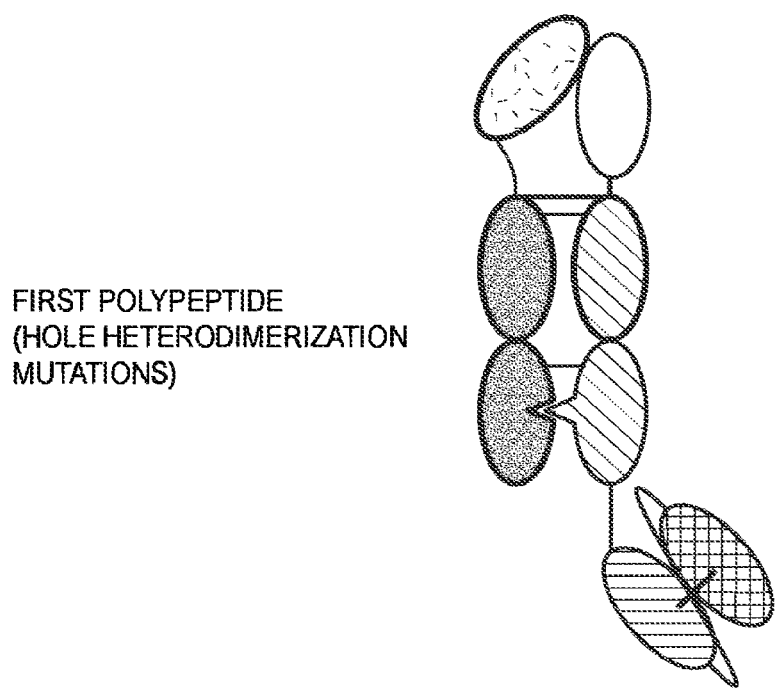
Figure 4G:
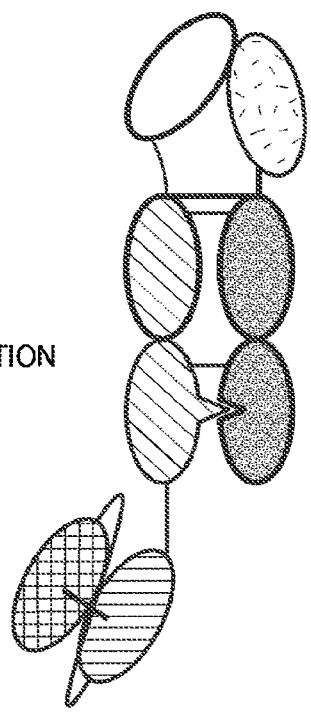
Figure 4H:
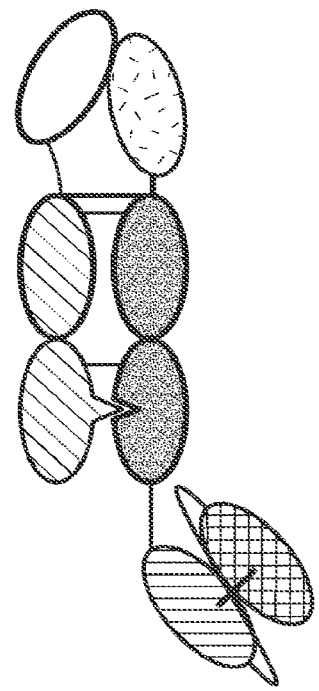
Figure 4I:
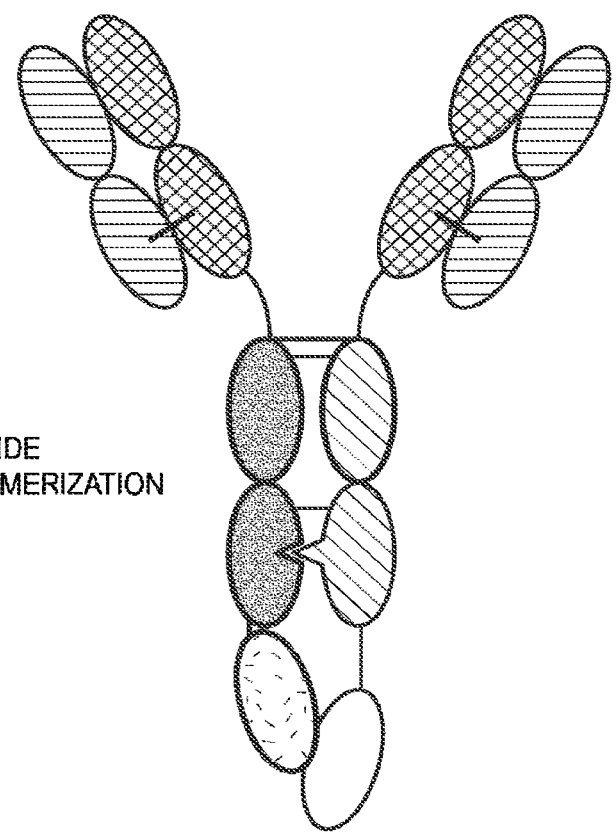
Figure 4J:
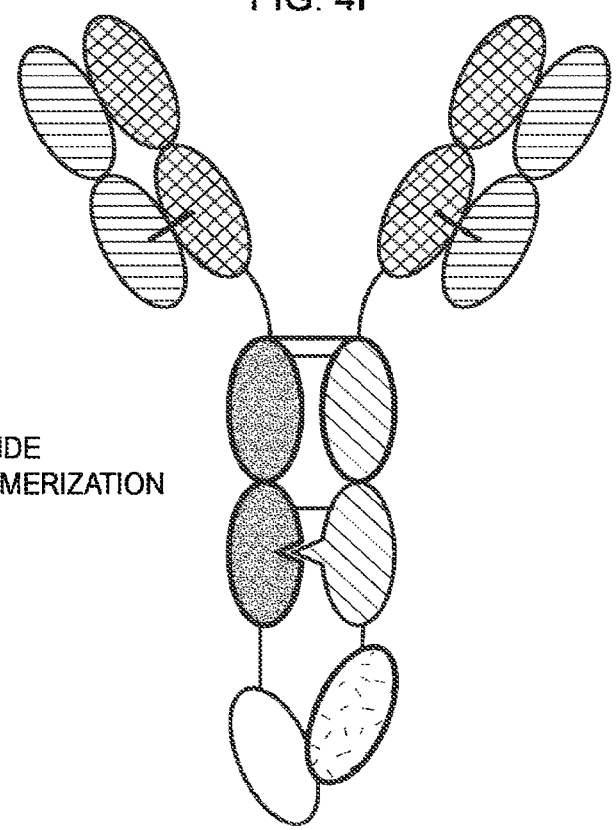
Figure 4K:
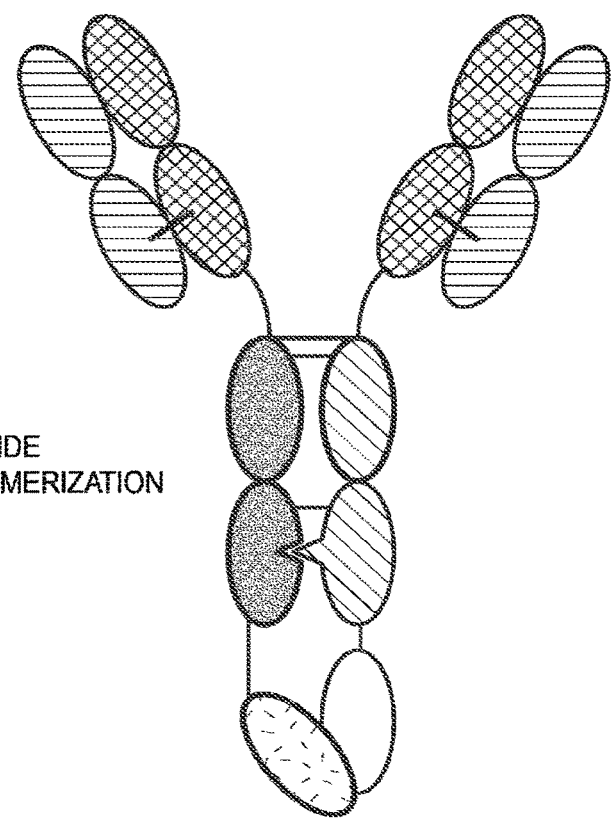
Figure 4L:
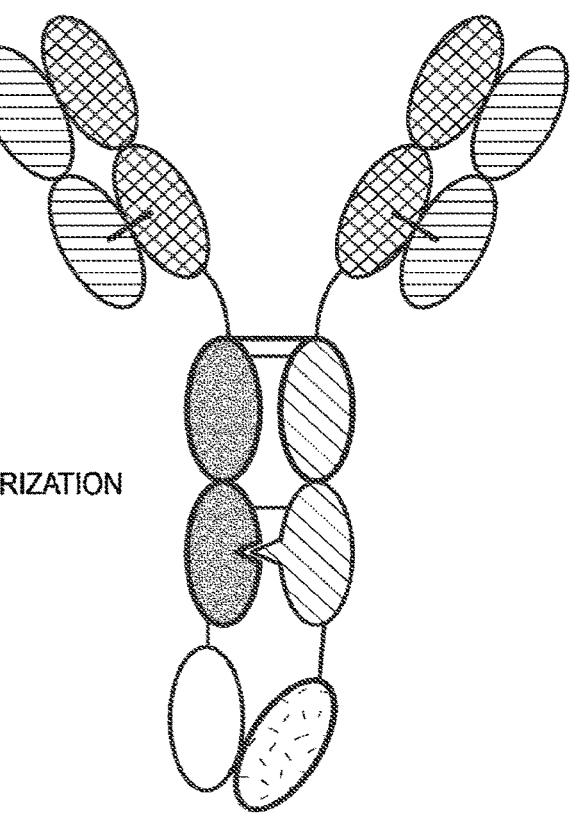

The invention provides improvements on heterodimeric Fc-fused proteins, pharmaceutical compositions comprising such proteins, and therapeutic methods using such proteins and pharmaceutical compositions, including for the treatment of cancer.

To facilitate an understanding of the present invention, a number of terms and phrases are defined below.

The terms "a" and "an" as used herein mean "one or more" and include the plural unless the context is inappropriate.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present invention) sufficient to effect beneficial or desired results (e.g., a desired prophylactic or therapeutic effect). An effective amount can be administered in one or more administration(s), application(s) or dosage(s) and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as Na⁺, NH₄⁺, and NW₄⁺ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Proteins

The present invention provides Fc-fused protein constructs comprising the amino acid sequences of a multisubunit protein. These fusion protein constructs can exhibit a higher serum half-life compared to a native/natural multisubunit protein, improved yield during production, enhanced stability during storage, and/or improved efficacy when used as a therapeutic.

IgG1 Fc-Fused Proteins

In one aspect, the present invention provides a heterodimeric IgG1 Fc-fused protein comprising: a first polypeptide comprising a first antibody IgG1 Fc domain polypeptide and a second polypeptide comprising a second antibody IgG1 Fc domain polypeptide bound to the first antibody Fc domain, in which the first polypeptide further comprises a first subunit of a multisubunit protein fused by a linker comprising amino acid sequence PKSSDKTHTCPPCPAPEX₁X₂GX₃ (SEQ ID NO:237) or EPKSSDKTHTCPPCPAPEX₁X₂GX₃ (SEQ ID NO:6) to the first antibody Fc domain polypeptide, wherein $X_1$ represents L or A, $X_2$ represents L, E, or A, and $X_3$ represents A or G; a second, different subunit of the multisubunit protein is fused to the second antibody Fc domain polypeptide and the subunits of the multisubunit protein are bound to each other; when $X_1$ represents L and/or $X_2$ represents L, at least one of the first antibody Fc domain polypeptide and the second antibody Fc domain polypeptide comprises a Q347R mutation for promoting heterodimerization.

In some embodiments, within the heterodimeric Fc-fused protein, the linker connecting the a first subunit of a multisubunit protein to the first antibody Fc domain polypeptide consists of amino acid sequence PKSSDKTHTCPPCPAPEX₁X₂GX₃ (SEQ ID NO:237) or EPKSSDKTHTCPPCPAPEX₁X₂GX₃ (SEQ ID NO:6), wherein $X_1$ represents L or A, $X_2$ represents L, E, or A, and $X_3$ represents A or G.

In certain embodiments, the linker connecting the first subunit of a multisubunit protein to the first antibody Fc domain polypeptide further comprises a spacer peptide. In certain embodiments, the linker comprises a sequence of SEQ ID NO:237 or SEQ ID NO:6, and a spacer peptide.

In certain embodiments, the second, different subunit of the multisubunit protein is fused to the second antibody Fc domain polypeptide by a linker that comprises a sequence PKSSDKTHTCPPCPAPEX₁X₂GX₃ (SEQ ID NO:237) or EPKSSDKTHTCPPCPAPEX₁X₂GX₃ (SEQ ID NO:6), wherein $X_1$ represents L or A, $X_2$ represents L, E, or A, and $X_3$ represents A or G, and a spacer peptide. In certain embodiments, the second, different subunit of the multisubunit protein is fused to the second antibody Fc domain polypeptide by a linker that consists of the amino acid sequence PKSSDKTHTCPPCPAPEX₁X₂GX₃ (SEQ ID NO:237) or EPKSSDKTHTCPPCPAPEX₁X₂GX₃ (SEQ ID NO:6), wherein $X_1$ represents L or A, $X_2$ represents L, E, or A, and $X_3$ represents A or G. In certain embodiments, the amino acid sequence of the linker connecting the second, different subunit of the multisubunit protein to the second antibody Fc domain polypeptide is identical to the amino acid sequence of the linker connecting the subunit of the multisubunit protein to the first antibody Fc domain polypeptide.

Any spacer peptide described under the heading "Spacer peptides" can be employed. For example, in certain embodiments, the spacer peptide comprises an amino acid sequence set forth in any one of SEQ ID NOs:107-120. In certain embodiments, the spacer peptide consists of an amino acid sequence set forth in any one of SEQ ID NOs:107-120. In certain embodiments, the linker connecting the subunit of a multisubunit protein to the first antibody Fc domain polypeptide consists of, or consists essentially of, a spacer peptide disclosed herein and a peptide having the sequence of SEQ ID NO:237 or SEQ ID NO:6. In certain embodiments, the linker connecting the second, different subunit of the multisubunit protein to the second antibody Fc domain polypeptide consists of, or consists essentially of, a spacer peptide disclosed herein and a peptide having the sequence of SEQ ID NO:237 or SEQ ID NO:6. In certain embodiments, the spacer peptide is N-terminal to the either or both of the linkers.

In some embodiments, within the heterodimeric Fc-fused protein, the linker connecting the first subunit of the multisubunit protein to the first antibody Fc domain polypeptide comprises amino acid sequence PKSSDKTHTCPPCPAPEAAGG (SEQ ID NO:239) or EPKSSDKTHTCPPCPAPEAAGG (SEQ ID NO:9). In some embodiments, within the heterodimeric Fc-fused protein, the linker connecting the first subunit of the multisubunit protein to the first antibody Fc domain polypeptide consists of amino acid sequence PKSSDKTHTCPPCPAPEAAGG (SEQ ID NO:239) or EPKSSDKTHTCPPCPAPEAAGG (SEQ ID NO:9).

In some embodiments, within the heterodimeric Fc-fused protein, the linker connecting the first subunit of the multisubunit protein to the first antibody Fc domain polypeptide comprises amino acid sequence PKSSDKTHTCPPCPAPEAAGG (SEQ ID NO:239). In some embodiments, within the heterodimeric Fc-fused protein, the linker connecting the first subunit of the multisubunit protein to the first antibody Fc domain polypeptide consists of amino acid sequence PKSSDKTHTCPPCPAPEAAGG (SEQ ID NO:239).

In some embodiments, within the heterodimeric Fc-fused protein, the second, different subunit of the multisubunit protein is fused to the second antibody Fc domain polypeptide by a linker comprising amino acid sequence GGGGSGGGGSGGGGSEPKSSDKTHTCPPCPA-
PEAAGG (SEQ ID NO:10) or
GGGGSGGGGSGGGGSPKSSDKTHTCPPCPAPEAAGG
(SEQ ID NO:244). In some embodiments, the second, different subunit of the multisubunit protein is fused to the second antibody Fc domain polypeptide by a linker consisting of amino acid sequence

```
                                       (SEQ ID NO: 10)
GGGGSGGGGSGGGGSEPKSSDKTHTCPPCPAPEAAGG
or
                                      (SEQ ID NO: 244)
GGGGSGGGGSGGGGSPKSSDKTHTCPPCPAPEAAGG.
```

In some embodiments, within the heterodimeric Fc-fused protein, the second, different subunit of the multisubunit protein is fused to the second antibody Fc domain polypeptide by a linker comprising amino acid sequence GGGGSGGGGSGGGGSEPKSSDKTHTCPPCPA-PEAAGG (SEQ ID NO:10). In some embodiments, the second, different subunit of the multisubunit protein is fused to the second antibody Fc domain polypeptide by a linker consisting of amino acid sequence

```
                                       (SEQ ID NO: 10)
GGGGSGGGGSGGGGSEPKSSDKTHTCPPCPAPEAAGG.
```

In some embodiments, within the heterodimeric Fc-fused protein, the linker connecting the subunit of the multisubunit protein to the first antibody Fc domain polypeptide comprises amino acid sequence PKSSDKTHTCPPCPA-PELLGG (SEQ ID NO:238) or EPKSSDKTHTCPPCPA-PELLGG (SEQ ID NO:7). In some embodiments, within the heterodimeric Fc-fused protein, the linker fusing the first subunit of the multisubunit protein to the first antibody Fc domain polypeptide consists of amino acid sequence

```
                                      (SEQ ID NO: 238)
PKSSDKTHTCPPCPAPELLGG
or
                                        (SEQ ID NO: 7)
EPKSSDKTHTCPPCPAPELLGG.
```

In some embodiments, within the heterodimeric Fc-fused protein, the second, different subunit of the multisubunit protein is fused to the second antibody Fc domain polypeptide by a linker comprising amino acid sequence GGGGSGGGGSGGGGSEPKSSDKTHTCPPCPA-PELLGG (SEQ ID NO:8) or GGGGSGGGGSGGGGSPKSSDKTHTCPPCPAPELLGG (SEQ ID NO:241). In some embodiments, the second, different subunit of the multisubunit protein is fused to the second antibody Fc domain polypeptide by a linker consisting of amino acid sequence

```
                                        (SEQ ID NO: 8)
GGGGSGGGGSGGGGSEPKSSDKTHTCPPCPAPELLGG
or
                                      (SEQ ID NO: 241)
GGGGSGGGGSGGGGSPKSSDKTHTCPPCPAPELLGG.
```

In some embodiments, within the heterodimeric Fc-fused protein, the second, different subunit of the multisubunit protein is fused to the second antibody Fc domain polypeptide by a linker comprising amino acid sequence GGGGSEPKSSDKTHTCPPCPAPELLGG (SEQ ID NO:15) or GGGGSPKSSDKTHTCPPCPAPELLGG (SEQ ID NO:242). In some embodiments, the second, different subunit of the multisubunit protein is fused to the second antibody Fc domain polypeptide by a linker consisting of amino acid sequence

```
                                       (SEQ ID NO: 15)
GGGGSEPKSSDKTHTCPPCPAPELLGG
or
                                      (SEQ ID NO: 242)
GGGGSPKSSDKTHTCPPCPAPELLGG.
```

In some embodiments, within the heterodimeric Fc-fused protein, the second, different subunit of the multisubunit protein is fused to the second antibody Fc domain polypeptide by a linker comprising amino acid sequence GGGGSGGGGSEPKSSDKTHTCPPCPAPELLGG (SEQ ID NO:16) or GGGGSGGGGSPKSSDKTHTCPPCPA-PELLGG (SEQ ID NO:243). In some embodiments, the second, different subunit of the multisubunit protein is fused to the second antibody Fc domain polypeptide by a linker consisting of amino acid sequence

```
                                       (SEQ ID NO: 16)
GGGGSGGGGSEPKSSDKTHTCPPCPAPELLGG
or
                                      (SEQ ID NO: 243)
GGGGSGGGGSPKSSDKTHTCPPCPAPELLGG.
```

In some embodiments, within the heterodimeric Fc-fused protein, the second, different subunit of the multisubunit protein is fused to the second antibody Fc domain polypeptide by a linker comprising amino acid sequence GGGGSEPKSSDKTHTCPPCPAPEAAGG (SEQ ID NO:65) or GGGGSPKSSDKTHTCPPCPAPEAAGG (SEQ ID NO:245). In some embodiments, the second, different subunit of the multisubunit protein is fused to the second antibody Fc domain polypeptide by a linker consisting of amino acid sequence

```
                                       (SEQ ID NO: 65)
GGGGSEPKSSDKTHTCPPCPAPEAAGG
or
                                      (SEQ ID NO: 245)
GGGGSPKSSDKTHTCPPCPAPEAAGG.
```

In some embodiments, within the heterodimeric Fc-fused protein, the second, different subunit of the multisubunit protein is fused to the second antibody Fc domain polypeptide by a linker comprising amino acid sequence GGGGSGGGGSEPKSSDKTHTCPPCPAPEAAGG (SEQ ID NO:66) or GGGGSGGGGSPKSSDKTHTCPPCPA-PEAAGG (SEQ ID NO:246). In some embodiments, the second, different subunit of the multisubunit protein is fused to the second antibody Fc domain polypeptide by a linker consisting of amino acid sequence

```
                                       (SEQ ID NO: 66)
GGGGSGGGGSEPKSSDKTHTCPPCPAPEAAGG
or
                                      (SEQ ID NO: 246)
GGGGSGGGGSPKSSDKTHTCPPCPAPEAAGG.
```

In some embodiments, within the heterodimeric Fc-fused protein, the linker connecting the first subunit of the multi-subunit protein to the first antibody Fc domain polypeptide comprises amino acid sequence EPKSSDKTHTCPPCPAPEAEGA (SEQ ID NO:11) or PKSSDKTHTCPPCPAPEAEGA (SEQ ID NO:240). In some embodiments, within the heterodimeric Fc-fused protein, the linker fusing the first subunit of the multisubunit protein to the first antibody Fc domain polypeptide consists of amino acid sequence EPKSSDKTHTCPPCPAPEAEGA (SEQ ID NO:11) or PKSSDKTHTCPPCPAPEAEGA (SEQ ID NO:240).

In some embodiments, within the heterodimeric Fc-fused protein, the second, different subunit of the multisubunit protein is fused to the second antibody Fc domain polypeptide by a linker comprising amino acid sequence GGGGSGGGGSGGGGSEPKSSDKTHTCPPCPAPEAEGA (SEQ ID NO:12) or GGGGSGGGGSGGGGSPKSSDKTHTCPPCPAPEAEGA (SEQ ID NO:247). In some embodiments, the second, different subunit of the multisubunit protein is fused to the second antibody Fc domain polypeptide by a linker consisting of amino acid sequence

```
                                              (SEQ ID NO: 12)
GGGGSGGGGSGGGGSEPKSSDKTHTCPPCPAPEAEGA
or (SEQ ID NO: 247)
GGGGSGGGGSGGGGSPKSSDKTHTCPPCPAPEAEGA.
```

In some embodiments, within the heterodimeric Fc-fused protein, the second, different subunit of the multisubunit protein is fused to the second antibody Fc domain polypeptide by a linker comprising amino acid sequence GGGGSEPKSSDKTHTCPPCPAPEAEGA (SEQ ID NO:67) or GGGGSPKSSDKTHTCPPCPAPEAEGA (SEQ ID NO:248). In some embodiments, the second, different subunit of the multisubunit protein is fused to the second antibody Fc domain polypeptide by a linker consisting of amino acid sequence

```
                                              (SEQ ID NO: 67)
GGGGSEPKSSDKTHTCPPCPAPEAEGA
or (SEQ ID NO: 248)
GGGGSPKSSDKTHTCPPCPAPEAEGA.
```

In some embodiments, within the heterodimeric Fc-fused protein, the second, different subunit of the multisubunit protein is fused to the second antibody Fc domain polypeptide by a linker comprising amino acid sequence GGGGSGGGGSEPKSSDKTHTCPPCPAPEAEGA (SEQ ID NO:68) or GGGGSGGGGSPKSSDKTHTCPPCPAPEAEGA (SEQ ID NO:249). In some embodiments, the second, different subunit of the multisubunit protein is fused to the second antibody Fc domain polypeptide by a linker consisting of amino acid sequence

```
                                              (SEQ ID NO: 68)
GGGGSGGGGSEPKSSDKTHTCPPCPAPEAEGA
or (SEQ ID NO: 249)
GGGGSGGGGSPKSSDKTHTCPPCPAPEAEGA.
```

In certain embodiments the Fc domain polypeptide is that of an IgG1 Fc. In some embodiments, a protein of the current invention includes, a first antibody Fc domain polypeptide and a second antibody Fc domain polypeptide, which are both mutated IgG1 Fc domain polypeptides that promote heterodimerization with each other. For example, if the Fc domain is derived from the Fc of a human IgG1, the Fc domain can comprise an amino acid sequence at least 90% identical to amino acids 234-332 of a human IgG1 antibody, and differ at one or more position(s) selected from the group consisting of Q347, Y349, L351, S354, E356, E357, K360, Q362, S364, T366, L368, K370, N390, K392, T394, D399, S400, D401, F405, Y407, K409, T411, and K439.

In some embodiments, the antibody constant domain can comprise an amino acid sequence at least 90% identical to amino acids 234-332 of a human IgG1 antibody, and differ by one or more substitution(s) selected from the group consisting of Q347E, Q347R, Y349S, Y349K, Y349T, Y349D, Y349E, Y349C, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, D399R, D399K, D399V, S400K, S400R, D401K, F405A, F405T, Y407A, Y407I, Y407V, K409F, K409W, K409D, T411D, T411E, K439D, and K439E. All the amino acid positions in an Fc domain or hinge region disclosed herein are numbered according to EU numbering.

In some embodiments, the first antibody IgG1 Fc domain polypeptide includes one or more mutation(s) selected from K360E and K409W, and the second antibody IgG1 Fc domain polypeptide includes one or more mutation(s) selected from Q347R, D399V, and F405T. In some embodiments, the first antibody IgG1 Fc domain polypeptide includes one or more mutation(s) selected from Q347R, D399V, and F405T, and the second antibody IgG1 Fc domain polypeptide includes one or more mutation(s) selected from K360E and K409W. In some embodiments, the first antibody IgG1 Fc domain polypeptide includes mutations K360E and K409W, and the second antibody IgG1 Fc domain polypeptide includes mutations Q347R, D399V, and F405T. In some embodiments, the first antibody IgG1 Fc domain polypeptide includes mutations Q347R, D399V, and F405T, and the second antibody IgG1 Fc domain polypeptide includes mutations K360E and K409W.

In some embodiments, a heterodimeric Fc-fused protein of the present invention with an IgG1 Fc includes one or more mutation(s) to reduce binding to an FcγR (e.g., FcγRI, FcγRIIA, FcγRIIB, FcγRIIIA, or FcγRIIIB) or a complement component (e.g., C1q) in the first and/or second polypeptides. Such mutations are useful for reducing effector functions. For example, a protein of the present disclosure includes LALA (L234A and L235A) mutations, LALAPA (L234A, L235A, and P329A) mutations, LALAPG (L234A, L235A, and P329G) mutations, or LALEGAASPS (L234A, L235E, G237A, A330S, and P331S) mutations.

In some embodiments, a heterodimeric Fc-fused protein according to the invention includes a first antibody IgG4 or IgG1 Fc domain polypeptide and the second antibody IgG4 or IgG1 Fc domain polypeptide each containing the mutation P329G or P329A. In specific embodiments, a heterodimeric Fc-fused protein according to the invention comprises a first antibody IgG4 or IgG1 Fc domain polypeptide and a second antibody IgG4 or IgG1 Fc domain polypeptide each comprising the mutation P329A.

In some embodiments, the first IgG1 antibody Fc domain polypeptide and the second, different IgG1 antibody Fc domain polypeptide each contain a mutation selected from A330S and P331S. In some embodiments, the first IgG1 antibody Fc domain polypeptide and the second, different IgG1 antibody Fc domain polypeptide each contain the mutations A330S and P331S.

In certain embodiments, an additional disulfide bond between IgG1 Fc monomers is introduced, which improves the stability of the heterodimer. In an exemplary embodiment, the first antibody Fc domain polypeptide fused to the first subunit of a multisubunit protein includes a Y349C substitution in the CH3 domain, which forms a disulfide bond with an S354C substitution on the second antibody Fc domain polypeptide fused to the second, different subunit of a multisubunit protein. Alternatively, the first antibody Fc domain polypeptide fused to the first subunit of a multisubunit protein includes an S354C substitution in the CH3 domain, which forms a disulfide bond with a Y349C substitution on the second antibody Fc domain polypeptide fused to the second, different subunit of a multisubunit protein.

Any of the IgG1 antibody Fc domain polypeptides provided in Table 2 below can be employed in combination with any of the IgG1 hinge sequences (which, in the current invention, is part or the entirety of a linker connecting the protein sequence of the first subunit of the multisubunit protein to the first IgG1 antibody Fc domain polypeptide, or a linker connecting the additional subunit to the second, different IgG1 antibody Fc domain polypeptide) provided in Table 1 below. Exemplary IgG1 hinge-Fc domain polypeptides are provided in Table 3 below. In certain embodiments, the first and second polypeptides of the Fc-fused protein comprise the amino acid sequences of SEQ ID NOs: 212 and 212; 213 and 214; 215 and 216; 217 and 218; 214 and 213; 216 and 215; or 218 and 217, respectively. In certain embodiments, the first and second polypeptides of the Fc-fused protein comprise the amino acid sequences of SEQ ID NOs:228 and 228; 229 and 230; 231 and 232; 233 and 234; 235 and 236; 230 and 229; 232 and 231; 234 and 233; 236 and 235; 228 and 250; 250 and 228; 250 and 250; 229 and 252; 252 and 229; 251 and 230; 230 and 251; 253 and 232; 232 and 253; 231 and 254; 254 and 231; 255 and 234; 234 and 255; 233 and 256; 256 and 233; 257 and 236; 236 and 257; 258 and 235; or 235 and 258, respectively.

IgG4 Fc-Fused Proteins

In one aspect, the current invention provides an improvement on a multisubunit protein. In one aspect the present invention provides a heterodimeric IgG4 Fc-fused protein comprising: a first polypeptide comprising a first antibody IgG4 Fc domain polypeptide and a second polypeptide comprising a second, different antibody IgG4 Fc domain polypeptide bound to the first antibody Fc domain polypeptide, in which the first polypeptide further comprises a first subunit of a multisubunit protein fused by a linker comprising amino acid sequence RVESKYGPPCPPCPAPEFXGG (SEQ ID NO:1) to the first antibody IgG4 Fc domain polypeptide, in which X represents L or E; a second, different subunit of the multisubunit protein is fused to the second antibody IgG4 Fc domain polypeptide and the subunits of the multisubunit protein are bound to each other; the first antibody Fc domain polypeptide and the second antibody IgG4 Fc domain polypeptide each contain different mutations promoting heterodimerization.

In some embodiments, within the heterodimeric IgG4 Fc-fused protein, the linker connecting the a first subunit of a multisubunit protein to the first antibody Fc domain polypeptide consists of amino acid sequence RVESKYGPPCPPCPAPEFXGG, wherein X represents L or E (SEQ ID NO:1).

In certain embodiments, the linker connecting the protein sequence of a first subunit of a multisubunit protein to the first antibody Fc domain polypeptide further comprises a spacer peptide. In certain embodiments, the linker comprises a sequence of SEQ ID NO:1 and a spacer peptide.

In certain embodiments, the second, different subunit of the multisubunit protein is fused to the second antibody Fc domain polypeptide by a linker that comprises a sequence RVESKYGPPCPPCPAPEFXGG, wherein X represents L or E (SEQ ID NO:1), and a spacer peptide. In certain embodiments, the second, different subunit of the multisubunit protein is fused to the second antibody Fc domain polypeptide by a linker that consists of the amino acid sequence RVESKYGPPCPPCPAPEFXGG, wherein X represents L or E (SEQ ID NO:1). In certain embodiments, the amino acid sequence of the linker connecting the second, different subunit of the multisubunit protein to the second antibody Fc domain polypeptide is identical to the amino acid sequence of the linker connecting the subunit of the multisubunit protein to the first antibody Fc domain polypeptide.

Any spacer peptide described under the heading "Spacer peptides" can be employed. For example, in certain embodiments, the spacer peptide comprises an amino acid sequence set forth in any one of SEQ ID NOs: 107-120. In certain embodiments, the spacer peptide consists of an amino acid sequence set forth in any one of SEQ ID NOs: 107-120. In certain embodiments, the linker connecting the subunit of the multisubunit protein to the first antibody Fc domain polypeptide consists of, or consists essentially of, a spacer peptide disclosed herein and SEQ ID NO:1. In certain embodiments, the linker consists of, or consists essentially of, a spacer peptide disclosed herein and SEQ ID NO:1. In certain embodiments, the spacer peptide is N-terminal to the first linker and/or the second linker.

In some embodiments, within the heterodimeric Fc-fused protein, the linker connecting the subunit of the multisubunit protein to the first antibody Fc domain polypeptide comprises amino acid sequence RVESKYGPPCPPCPAPEFLGG (SEQ ID NO:2). In some embodiments, the linker fusing the first subunit of the multisubunit protein to the first antibody Fc domain polypeptide consists of amino acid sequence (SEQ ID NO: 2)
RVESKYGPPCPPCPAPEFLGG.

In some embodiments, the second, different subunit of the multisubunit protein is fused to the second antibody Fc domain polypeptide by a linker comprising amino acid sequence GGGGSGGGGSGGGGSRVESKYGPPCPPCPAPEFLGG (SEQ ID NO:3). In some embodiments, the second, different subunit of the multisubunit protein is fused to the second antibody Fc domain polypeptide by a linker consisting of amino acid sequence (SEQ ID NO: 3)
GGGGSGGGGSGGGGSRVESKYGPPCPPCPAPEFLGG.

In some embodiments, the second, different subunit of the multisubunit protein is fused to the second antibody Fc domain polypeptide by a linker comprising amino acid sequence GGGGSRVESKYGPPCPPCPAPEFLGG (SEQ ID NO:13). In some embodiments, the second, different subunit of the multisubunit protein is fused to the second antibody Fc domain polypeptide by a linker consisting of amino acid sequence (SEQ ID NO: 13)
GGGGSRVESKYGPPCPPCPAPEFLGG.

In some embodiments, the second, different subunit of the multisubunit protein is fused to the second antibody Fc domain polypeptide by a linker comprising amino acid sequence GGGGSGGGGSRVESKYGPPCPPCPAPEFLGG (SEQ ID NO:14). In some embodiments, the second, different subunit of the multisubunit protein is fused to the second antibody Fc domain polypeptide by a linker consisting of amino acid sequence (SEQ ID NO: 14)
GGGGSGGGGSRVESKYGPPCPPCPAPEFLGG.

In some embodiments, within the heterodimeric Fc-fused protein, the linker connecting the first subunit of the multisubunit protein to the first antibody Fc domain polypeptide comprises amino acid sequence RVESKYGPPCPPCPAPEFEGG (SEQ ID NO:4). In some embodiments, the linker fusing the first subunit of the multisubunit protein to the first antibody Fc domain polypeptide consists of amino acid sequence RVESKYGPPCPPCPAPEFEGG (SEQ ID NO:4).

(SEQ ID NO: 4)
RVESKYGPPCPPCPAPEFEGG.

In some embodiments, the second, different subunit of the multisubunit protein is fused to the second antibody Fc domain polypeptide by a linker comprising amino acid sequence GGGGSGGGGSGGGGSRVESKYGPPCPPCPAPEFEGG (SEQ ID NO:5). In some embodiments, the second, different subunit of the multisubunit protein is fused to the second antibody Fc domain polypeptide by a linker consisting of amino acid sequence (SEQ ID NO: 5)
GGGGSGGGGSGGGGSRVESKYGPPCPPCPAPEFEGG.

In some embodiments, the second, different subunit of the multisubunit protein is fused to the second antibody Fc domain polypeptide by a linker comprising amino acid sequence GGGGSRVESKYGPPCPPCPAPEFEGG (SEQ ID NO:63). In some embodiments, the second, different subunit of the multisubunit protein is fused to the second antibody Fc domain polypeptide by a linker consisting of amino acid sequence (SEQ ID NO: 63)
GGGGSRVESKYGPPCPPCPAPEFEGG.

In some embodiments, the second, different subunit of the multisubunit protein is fused to the second antibody Fc domain polypeptide by a linker comprising amino acid sequence GGGGSGGGGSRVESKYGPPCPPCPAPEFEGG (SEQ ID NO:64). In some embodiments, the second, different subunit of the multisubunit protein is fused to the second antibody Fc domain polypeptide by a linker consisting of amino acid sequence (SEQ ID NO: 64)
GGGGSGGGGSRVESKYGPPCPPCPAPEFEGG.

In certain embodiments the Fc domain polypeptide is that of an IgG4 Fc. IgG4 is an unstable dimer that can undergo a Fab-arm exchange and pair with other IgG4 antibodies in the body. In certain embodiments, a S228P mutation is introduced within the hinge (which, in the current invention, is part or the entirety of a linker connecting the first subunit of the multisubunit protein to the first IgG4 antibody Fc domain polypeptide, or a linker connecting the additional subunit to the second, different IgG4 antibody Fc domain polypeptide), which increases the stability of the hinge region and reduces the chance for Fab-arm exchange. In certain embodiments, an additional disulfide bond between Fc domain polypeptide monomers is introduced, which improves the stability of the heterodimer. In an exemplary embodiment, the first antibody Fc domain polypeptide linked to the first subunit of the multisubunit protein includes a Y349C substitution in the CH3 domain, which forms a disulfide bond with an S354C substitution on the second antibody Fc domain polypeptide linked to the second, different subunit of the multisubunit protein second antibody Fc domain polypeptide. Alternatively, the first antibody Fc domain polypeptide linked to the first subunit of the multisubunit protein includes an S354C substitution in the CH3 domain, which forms a disulfide bond with a Y349C substitution on the the second antibody Fc domain polypeptide linked to the second, different subunit of the multisubunit protein.

In some embodiments, a protein of the current invention includes, a first antibody Fc domain polypeptide and a second antibody Fc domain polypeptide, which are both mutated IgG4 Fc domain polypeptides that promote heterodimerization with each other.

In some embodiments, the first antibody IgG4 Fc domain polypeptide includes one or more mutation(s) selected from K360E, K370E, and R409W, and the second antibody IgG4 Fc domain polypeptide includes one or more mutation(s) selected from E357N, Q347R, D399V, and F405T. In some embodiments, the first antibody IgG4 Fc domain polypeptide includes mutations K370E and R409W, and the second antibody IgG4 Fc domain polypeptide includes mutations E357N, D399V, and F405T. In some embodiments, the first antibody IgG4 Fc domain polypeptide includes mutations E357N, D399V, and F405T, and the second antibody IgG4 Fc domain polypeptide includes mutations K370E and R409W. In some embodiments, the first antibody IgG4 Fc domain polypeptide includes mutations K360E and R409W, and the second antibody IgG4 Fc domain polypeptide includes mutations Q347R, D399V, and F405T. In some embodiments, the first antibody IgG4 Fc domain polypeptide includes mutations Q347R, D399V, and F405T, and the second antibody IgG4 Fc domain polypeptide includes mutations K360E and R409W.

In some embodiments, a heterodimeric Fc-fused protein of the present invention with an IgG4 Fc includes one or more mutation(s) to reduce binding to an FcγR (e.g., FcγRI, FcγRIIA, FcγRIIB, FcγRIIIA, or FcγRIIIB) or a complement component (e.g., C1q) in the first and/or second polypeptide (s). Such mutations are useful for reducing effector functions. For example, a protein of the present disclosure includes SPLE (S228P and L235E) mutations, SPLEPA (S228P, L235E, and P329A) mutations, or SPLEPG (S228P, L235E, and P329G) mutations.

Any of the IgG4 antibody Fc domain polypeptides provided in Table 2 can be employed in combination with any of the IgG4 hinge sequences (which, in the current invention, is part or the entirety of a linker connecting the first subunit of the multisubunit protein to the first IgG4 antibody Fc domain polypeptide, or a linker connecting the second, different subunit of the multisubunit protein to the second, different IgG4 antibody Fc domain polypeptide) provided in Table 1. Exemplary IgG4 hinge-Fc domain polypeptides are provided in Table 3. In certain embodiments, the first and second polypeptides of the Fc-fused protein comprise the amino acid sequences of SEQ ID NOs:205 and 205; 206 and 207; 208 and 209; 210 and 211; 207 and 206; 209 and 208; or 211 and 210, respectively. In certain embodiments, the first and second polypeptides of the Fc-fused protein comprise the amino acid sequences of SEQ ID NOs:219 and 219; 220 and 221; 222 and 223; 224 and 225; 226 and 227; 221 and 220; 223 and 222; 225 and 224; or 227 and 226, respectively.

Disulfide Bonds

Some heterodimeric Fc-fused proteins of the present invention include the native heterodimer disulfide bond between the first subunit of a multisubunit protein and the second, different subunit of the multisubunit protein. For example, in an exemplary embodiment, a heterodimeric Fc-fused protein according to the invention includes a native heterodimer disulfide bond between p35 and p40 subunits of IL-12. Such a protein includes the native disulfide bond between C74 of p35 and C177 of p40.

Some heterodimeric Fc-fused proteins of the present invention include an artificial or engineered heterodimer disulfide bond between the first subunit of a multisubunit protein and the second, different subunit of the multisubunit protein. For example, in an exemplary embodiment, a heterodimeric Fc-fused protein according to the invention includes an artificial or engineered heterodimer disulfide bond between p35 and p40 subunits of IL-12. Such a protein includes an artificial or engineered disulfide bond between V185C of p35 and Y292C of p40.

Some heterodimeric Fc-fused proteins of the present invention include the native heterodimer disulfide bond between the first subunit of a multisubunit protein and the second, different subunit of the multisubunit protein, and an artificial or engineered heterodimer disulfide bond between the first subunit of a multisubunit protein and the second, different subunit of the multisubunit protein. For example, in an exemplary embodiment, a native heterodimer disulfide bond between p35 and p40 subunits of IL-12, and includes an artificial or engineered heterodimer disulfide bond between p35 and p40 subunits of IL-12. Such a protein includes the native disulfide bond between C74 of p35 and C177 of p40, and an artificial or engineered disulfide bond between V185C of p35 and Y292C of p40.

Some heterodimeric Fc-fused proteins of the present invention are engineered to remove the native disulfide bond, and to replace it with a non-native artificial or engineered disulfide bond. For example, in an exemplary embodiment, a heterodimeric Fc-fused protein according to the invention includes p35 of IL-12 in which the native C74 is mutated to serine, and a p40 of IL-12 in which the native C177 is mutated to serine, thereby removing the native disulfide bond between p35 and p40 subunits of IL-12. To this mutated IL-12, two new mutations are introduced, V185C on p35 and Y292C on p40, thereby introducing a non-native artificial or engineered disulfide bond.

Sequences of Components of Fc-Fused Polypeptides

Exemplary heterodimeric Fc-fused proteins of the present invention are constructed with any one of the IgG1 or IgG4 Fc variant sequences and any one of the corresponding linker sequences described in the Tables 1-2 below. The fusion protein constructs of the present invention can confer a higher serum half-life compared to a native/natural multisubunit protein, improve yield of the proteins during production, enhance stability during storage, and/or improve efficacy when used as a therapeutic.

Tables 4 and 5 list amino acid sequences of exemplary protein constructs of the present invention. All mutations/substitutions in the Fc domain polypeptides are numbered according to the EU numbering system. Mutations in p35 and p40 subunits are numbered starting from the respective N-terminal amino acids of these subunits.

Any of the IgG4 antibody Fc variant domain polypeptides provided in Table 2 below can be employed in combination with any of the IgG4 hinge sequences provided in Table 1 below. Similarly, any of the IgG1 antibody Fc variant domain polypeptides provided in Table 2 below can be employed in combination with any of the IgG1 hinge sequences provided in Table 1 below. Exemplary IgG1 hinge-Fc domain polypeptides are provided in Table 3 below.

TABLE 1

| Linker Variants | |
|---|---|
| Hinge | Amino Acid Sequence |
| IgG4 hinge consensus | RVESKYGPPCPPCPAPEFXGG wherein X is L or E (SEQ ID NO: 1) |
| IgG4 hinge S228P | RVESKYGPPCPPCPAPEFLGG (SEQ ID NO: 2) |
| IgG4 hinge S228P/ L235E | RVESKYGPPCPPCPAPEFEGG (SEQ ID NO: 4) |
| IgG1 hinge consensus | EPKSSDKTHTCPPCPAPEX$_1$X$_2$GX$_3$ wherein X$_1$ is L or A; X$_2$ is L, E, or A; and X$_3$ is A or G (SEQ ID NO: 6) |
| IgG1 hinge C220S | EPKSSDKTHTCPPCPAPELLGG (SEQ ID NO: 7) |
| IgG1 hinge C220S/ L234A/L235A | EPKSSDKTHTCPPCPAPEAAGG (SEQ ID NO: 9) |
| IgG1 hinge C220S/ L234A/L235E/ G237A | EPKSSDKTHTCPPCPAPEAEGA (SEQ ID NO: 11) |

TABLE 1-continued

Linker Variants

| Hinge | Amino Acid Sequence |
|---|---|
| IgG1 hinge ΔE216 | PKSSDKTHTCPPCPAPEX$_1$X$_2$GX$_3$ wherein X$_1$ is L or A; X$_2$ is L, E, or A; and X$_3$ is A or G (SEQ ID NO: 237) |
| IgG1 hinge ΔE216/C220S | PKSSDKTHTCPPCPAPELLGG (SEQ ID NO: 238) |
| IgG1 hinge ΔE216/C220S/ L234A/L235A | PKSSDKTHTCPPCPAPEAAGG (SEQ ID NO: 239) |
| IgG1 hinge ΔE216/C220S/ L234A/L235E/ G237A | PKSSDKTHTCPPCPAPEAEGA (SEQ ID NO: 240) |

TABLE 2

IgG4 Fc and IgG1 Fc Wild-type Sequences; and Exemplary IgG4 Antibody Fc Variant and IgG1 Antibody Fc Variant Sequences (amino acid substitutions are indicated in bold)

| Fc domain | Amino Acid Sequence* |
|---|---|
| IgG4 Fc wild-type | PSVFLFPPKPKDTLMISRTPEVTCVVVDVSQEDPEVQFNWYVDG VEVHNAKTKPREEQFNSTYRVVSVLTVLHQDWLNGKEYKCKV SNKGLPSSIEKTISKAKGQPREPQVYTLPPSQEEMTKNQVSLTCV KGFYPSDIAVEWESNGQPENNYKTTPPVLDSDGSFFLYSKLTVD KSRWQEGNVFSCSVMHEALHNHYTQKSLSLSLG (SEQ ID NO: 205) |
| IgG4 Fc Y349C/ K370E/R409W | PSVFLFPPKPKDTLMISRTPEVTCVVVDVSQEDPEVQFNWYVDG VEVHNAKTKPREEQFNSTYRVVSVLTVLHQDWLNGKEYKCKV SNKGLPSSIEKTISKAKGQPREPQVCTLPPSQEEMTKNQVSLTCV EGFYPSDIAVEWESNGQPENNYKTTPPVLDSDGSFFLYSWLTVD KSRWQEGNVFSCSVMHEALHNHYTQKSLSLSLG (SEQ ID NO: 206) |
| IgG4 Fc S354C/ E357N/D399V/ F405T | PSVFLFPPKPKDTLMISRTPEVTCVVVDVSQEDPEVQFNWYVDG VEVHNAKTKPREEQFNSTYRVVSVLTVLHQDWLNGKEYKCKV SNKGLPSSIEKTISKAKGQPREPQVYTLPPCQENMTKNQVSLTCL VKGFYPSDIAVEWESNGQPENNYKTTPPVLVSDGSFTLYSRLTV DKSRWQEGNVFSCSVMHEALHNHYTQKSLSLSLG (SEQ ID NO: 207) |
| IgG4 Fc Y349C/ K360E/R409W | PSVFLFPPKPKDTLMISRTPEVTCVVVDVSQEDPEVQFNWYVDG VEVHNAKTKPREEQFNSTYRVVSVLTVLHQDWLNGKEYKCKV SNKGLPSSIEKTISKAKGQPREPQVCTLPPSQEEMTENQVSLTCL VKGFYPSDIAVEWESNGQPENNYKTTPPVLDSDGSFFLYSWLTV DKSRWQEGNVFSCSVMHEALHNHYTQKSLSLSLG (SEQ ID NO: 208) |
| IgG4 Fc Q347R/ S354C/D399V/ F405T | PSVFLFPPKPKDTLMISRTPEVTCVVVDVSQEDPEVQFNWYVDG VEVHNAKTKPREEQFNSTYRVVSVLTVLHQDWLNGKEYKCKV SNKGLPSSIEKTISKAKGQPREPRVYTLPPCQEEMTKNQVSLTCL VKGFYPSDIAVEWESNGQPENNYKTTPPVLVSDGSFTLYSRLTV DKSRWQEGNVFSCSVMHEALHNHYTQKSLSLSLG (SEQ ID NO: 209) |
| IgG4 Fc P329A/ Y349C/K360E/ R409W | PSVFLFPPKPKDTLMISRTPEVTCVVVDVSQEDPEVQFNWYVDG VEVHNAKTKPREEQFNSTYRVVSVLTVLHQDWLNGKEYKCKV SNKGLASSIEKTISKAKGQPREPQVCTLPPSQEEMTENQVSLTCL VKGFYPSDIAVEWESNGQPENNYKTTPPVLDSDGSFFLYSWLTV DKSRWQEGNVFSCSVMHEALHNHYTQKSLSLSLG (SEQ ID NO: 210) |
| IgG4 Fc P329A/ S354C/Q347R/ D399V/F405T | PSVFLFPPKPKDTLMISRTPEVTCVVVDVSQEDPEVQFNWYVDG VEVHNAKTKPREEQFNSTYRVVSVLTVLHQDWLNGKEYKCKV SNKGLASSIEKTISKAKGQPREPRVYTLPPCQEEMTKNQVSLTCL VKGFYPSDIAVEWESNGQPENNYKTTPPVLVSDGSFTLYSRLTV DKSRWQEGNVFSCSVMHEALHNHYTQKSLSLSLG (SEQ ID NO: 211) |

TABLE 2-continued

IgG4 Fc and IgG1 Fc Wild-type Sequences; and Exemplary IgG4
Antibody Fc Variant and IgG1 Antibody Fc Variant Sequences
(amino acid substitutions are indicated in bold)

| Fc domain | Amino Acid Sequence* |
|---|---|
| IgG1 Fc wild-type | PSVFLFPPKPKDTLMISRTPEVTCVVVDVSHEDPEVKFNWYVDG VEVHNAKTKPREEQYNSTYRVVSVLTVLHQDWLNGKEYKCKV SNKALPAPIEKTISKAKGQPREPQVYTLPPSRDELTKNQVSLTCL VKGFYPSDIAVEWESNGQPENNYKTTPPVLDSDGSFFLYSKLTV DKSRWQQGNVFSCSVMHEALHNHYTQKSLSLSPG (SEQ ID NO: 212) |
| IgG1 Fc Y349C/ K360E/K409W | PSVFLFPPKPKDTLMISRTPEVTCVVVDVSHEDPEVKFNWYVDG VEVHNAKTKPREEQYNSTYRVVSVLTVLHQDWLNGKEYKCKV SNKALPAPIEKTISKAKGQPREPQVCTLPPSRDELTENQVSLTCL VKGFYPSDIAVEWESNGQPENNYKTTPPVLDSDGSFFLYSWLTV DKSRWQQGNVFSCSVMHEALHNHYTQKSLSLSPG (SEQ ID NO: 213) |
| IgG1 Fc Q347R/ S354C/D399V/ F405T | PSVFLFPPKPKDTLMISRTPEVTCVVVDVSHEDPEVKFNWYVDG VEVHNAKTKPREEQYNSTYRVVSVLTVLHQDWLNGKEYKCKV SNKALPAPIEKTISKAKGQPREPRVYTLPPCRDELTKNQVSLTCL VKGFYPSDIAVEWESNGQPENNYKTTPPVLVSDGSFTLYSKLTV DKSRWQQGNVFSCSVMHEALHNHYTQKSLSLSPG (SEQ ID NO: 214) |
| IgG1 Fc P329A/ Y349C/K360E/ K409W | PSVFLFPPKPKDTLMISRTPEVTCVVVDVSHEDPEVKFNWYVDG VEVHNAKTKPREEQYNSTYRVVSVLTVLHQDWLNGKEYKCKV SNKALAAPIEKTISKAKGQPREPQVCTLPPSRDELTENQVSLTCL VKGFYPSDIAVEWESNGQPENNYKTTPPVLDSDGSFFLYSWLTV DKSRWQQGNVFSCSVMHEALHNHYTQKSLSLSPG (SEQ ID NO: 215) |
| IgG1 Fc P329A/ Q347R/S354C/ D399V/F405T | PSVFLFPPKPKDTLMISRTPEVTCVVVDVSHEDPEVKFNWYVDG VEVHNAKTKPREEQYNSTYRVVSVLTVLHQDWLNGKEYKCKV SNKALAAPIEKTISKAKGQPREPRVYTLPPCRDELTKNQVSLTCL VKGFYPSDIAVEWESNGQPENNYKTTPPVLVSDGSFTLYSKLTV DKSRWQQGNVFSCSVMHEALHNHYTQKSLSLSPG (SEQ ID NO: 216) |
| IgG1 Fc A330S/ P331S/Y349C/ K360E/K409W | PSVFLFPPKPKDTLMISRTPEVTCVVVDVSHEDPEVKFNWYVDG VEVHNAKTKPREEQYNSTYRVVSVLTVLHQDWLNGKEYKCKV SNKALPSSIEKTISKAKGQPREPQVCTLPPSRDELTENQVSLTCLV KGFYPSDIAVEWESNGQPENNYKTTPPVLDSDGSFFLYSWLTVD KSRWQQGNVFSCSVMHEALHNHYTQKSLSLSPG (SEQ ID NO: 217) |
| IgG1 Fc A330S/ P331S/Q347R/ S354C/D399V/ F405T | PSVFLFPPKPKDTLMISRTPEVTCVVVDVSHEDPEVKFNWYVDG VEVHNAKTKPREEQYNSTYRVVSVLTVLHQDWLNGKEYKCKV SNKALPSSIEKTISKAKGQPREPRVYTLPPCRDELTKNQVSLTCL VKGFYPSDIAVEWESNGQPENNYKTTPPVLVSDGSFTLYSKLTV DKSRWQQGNVFSCSVMHEALHNHYTQKSLSLSPG (SEQ ID NO: 218) |

*The amino acid sequences can further comprise a lysine (K) at the C-terminus.

TABLE 3

S228P mutated IgG4 Hinge-Fc (wild-type); Exemplary S228P mutated IgG4
Hinge-Fc Variants or Hinge Portion-Fc Variants; C220S mutated IgG1 Hinge-Fc
(wild-type); Exemplary C220S mutated IgG1 Hinge-Fc Variants or Hinge
Portion-Fc Variants

| Linker-Fc | Amino Acid Sequence* |
|---|---|
| IgG4 hinge-Fc S228P | RVESKYGPPCPPCPAPEFLGGPSVFLFPPKPKDTLMISRTPEVTCV VVDVSQEDPEVQFNWYVDGVEVHNAKTKPREEQFNSTYRVVS VLTVLHQDWLNGKEYKCKVSNKGLPSSIEKTISKAKGQPREPQV YTLPPSQEEMTKNQVSLTCLVKGFYPSDIAVEWESNGQPENNYK TTPPVLDSDGSFFLYSKLTVDKSRWQEGNVFSCSVMHEALHNH YTQKSLSLSLG (SEQ ID NO: 219) |
| IgG4 hinge-Fc S228P/Y349C/ K370E/R409W | RVESKYGPPCPPCPAPEFLGGPSVFLFPPKPKDTLMISRTPEVTCV VVDVSQEDPEVQFNWYVDGVEVHNAKTKPREEQFNSTYRVVS VLTVLHQDWLNGKEYKCKVSNKGLPSSIEKTISKAKGQPREPQV CTLPPSQEEMTKNQVSLTCLVEGFYPSDIAVEWESNGQPENNYK |

TABLE 3-continued

S228P mutated IgG4 Hinge-Fc (wild-type); Exemplary S228P mutated IgG4 Hinge-Fc Variants or Hinge Portion-Fc Variants; C220S mutated IgG1 Hinge-Fc (wild-type); Exemplary C220S mutated IgG1 Hinge-Fc Variants or Hinge Portion-Fc Variants

| Linker-Fc | Amino Acid Sequence* |
|---|---|
| | TTPPVLDSDGSFFLYSWLTVDKSRWQEGNVFSCSVMHEALHNH YTQKSLSLSLG (SEQ ID NO: 220) |
| IgG4 hinge-Fc S228P/S354C/ E357N/D399V/ F405T | RVESKYGPPCPPCPAPEFLGGPSVFLFPPKPKDTLMISRTPEVTCV VVDVSQEDPEVQFNWYVDGVEVHNAKTKPREEQFNSTYRVVS VLTVLHQDWLNGKEYKCKVSNKGLPSSIEKTISKAKGQPREPQV YTLPPCQENMTKNQVSLTCLVKGFYPSDIAVEWESNGQPENNY KTTPPVLVSDGSFTLYSRLTVDKSRWQEGNVFSCSVMHEALHN HYTQKSLSLSLG (SEQ ID NO: 221) |
| IgG4 hinge-Fc S228P/Y349C/ K360E/R409W | RVESKYGPPCPPCPAPEFLGGPSVFLFPPKPKDTLMISRTPEVTCV VVDVSQEDPEVQFNWYVDGVEVHNAKTKPREEQFNSTYRVVS VLTVLHQDWLNGKEYKCKVSNKGLPSSIEKTISKAKGQPREPQV CTLPPSQEEMTENQVSLTCLVKGFYPSDIAVEWESNGQPENNYK TTPPVLDSDGSFFLYSWLTVDKSRWQEGNVFSCSVMHEALHNH YTQKSLSLSLG (SEQ ID NO: 222) |
| IgG4 hinge-Fc S228P/Q347R/ S354C/D399V/ F405T | RVESKYGPPCPPCPAPEFLGGPSVFLFPPKPKDTLMISRTPEVTCV VVDVSQEDPEVQFNWYVDGVEVHNAKTKPREEQFNSTYRVVS VLTVLHQDWLNGKEYKCKVSNKGLPSSIEKTISKAKGQPREPRV YTLPPCQEEMTKNQVSLTCLVKGFYPSDIAVEWESNGQPENNY KTTPPVLVSDGSFTLYSRLTVDKSRWQEGNVFSCSVMHEALHN HYTQKSLSLSLG (SEQ ID NO: 223) |
| IgG4 hinge-Fc S228P/L235E/ Y349C/K360E/ R409W | RVESKYGPPCPPCPAPEFEGGPSVFLFPPKPKDTLMISRTPEVTCV VVDVSQEDPEVQFNWYVDGVEVHNAKTKPREEQFNSTYRVVS VLTVLHQDWLNGKEYKCKVSNKGLPSSIEKTISKAKGQPREPQV CTLPPSQEEMTENQVSLTCLVKGFYPSDIAVEWESNGQPENNYK TTPPVLDSDGSFFLYSWLTVDKSRWQEGNVFSCSVMHEALHNH YTQKSLSLSLG (SEQ ID NO: 224) |
| IgG4 hinge-Fc S228P/L235E/ S354C/Q347R/ D399V/F405T | RVESKYGPPCPPCPAPEFEGGPSVFLFPPKPKDTLMISRTPEVTCV VVDVSQEDPEVQFNWYVDGVEVHNAKTKPREEQFNSTYRVVS VLTVLHQDWLNGKEYKCKVSNKGLPSSIEKTISKAKGQPREPRV YTLPPCQEEMTKNQVSLTCLVKGFYPSDIAVEWESNGQPENNY KTTPPVLVSDGSFTLYSRLTVDKSRWQEGNVFSCSVMHEALHN HYTQKSLSLSLG (SEQ ID NO: 225) |
| IgG4 hinge-Fc S228P/L235E/ P329A/Y349C/ K360E/R409W | RVESKYGPPCPPCPAPEFEGGPSVFLFPPKPKDTLMISRTPEVTCV VVDVSQEDPEVQFNWYVDGVEVHNAKTKPREEQFNSTYRVVS VLTVLHQDWLNGKEYKCKVSNKGLASSIEKTISKAKGQPREPQ VCTLPPSQEEMTENQVSLTCLVKGFYPSDIAVEWESNGQPENNY KTTPPVLDSDGSFFLYSWLTVDKSRWQEGNVFSCSVMHEALHN HYTQKSLSLSLG (SEQ ID NO: 226) |
| IgG4 hinge-Fc S228P/L235E/ P329A/S354C/ Q347R/D399V/ F405T | RVESKYGPPCPPCPAPEFEGGPSVFLFPPKPKDTLMISRTPEVTCV VVDVSQEDPEVQFNWYVDGVEVHNAKTKPREEQFNSTYRVVS VLTVLHQDWLNGKEYKCKVSNKGLASSIEKTISKAKGQPREPR VYTLPPCQEEMTKNQVSLTCLVKGFYPSDIAVEWESNGQPENN YKTTPPVLVSDGSFTLYSRLTVDKSRWQEGNVFSCSVMHEALH NHYTQKSLSLSLG (SEQ ID NO: 227) |
| IgG1 hinge-Fc C220S | EPKSSDKTHTCPPCPAPELLGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHN HYTQKSLSLSPG (SEQ ID NO: 228) |
| IgG1 hinge-Fc AE216/C220S | PKSSDKTHTCPPCPAPELLGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHN HYTQKSLSLSPG (SEQ ID NO: 250) |
| IgG1 hinge-Fc C220S/Y349C/ K360E/K409W | EPKSSDKTHTCPPCPAPELLGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPREPQ VCTLPPSRDELTENQVSLTCLVKGFYPSDIAVEWESNGQPENNY KTTPPVLDSDGSFFLYSWLTVDKSRWQQGNVFSCSVMHEALHN HYTQKSLSLSPG (SEQ ID NO: 229) |

TABLE 3-continued

S228P mutated IgG4 Hinge-Fc (wild-type); Exemplary S228P mutated IgG4 Hinge-Fc Variants or Hinge Portion-Fc Variants; C220S mutated IgG1 Hinge-Fc (wild-type); Exemplary C220S mutated IgG1 Hinge-Fc Variants or Hinge Portion-Fc Variants

| Linker-Fc | Amino Acid Sequence* |
|---|---|
| IgG1 hinge-Fc AE216/C220S/ Y349C/K360E/ K409W | PKSSDKTHTCPPCPAPELLGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VCTLPPSRDELTENQVSLTCLVKGFYPSDIAVEWESNGQPENNY KTTPPVLDSDGSFFLYSWLTVDKSRWQQGNVFSCSVMHEALHN HYTQKSLSLSPG (SEQ ID NO: 251) |
| IgG1 hinge-Fc C220S/Q347R/ S354C/D399V/ F405T | EPKSSDKTHTCPPCPAPELLGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPREPR VYTLPPCRDELTKNQVSLTCLVKGFYPSDIAVEWESNGQPENNY KTTPPVLVSDGSFTLYSKLTVDKSRWQQGNVFSCSVMHEALHN HYTQKSLSLSPG (SEQ ID NO: 230) |
| IgG1 hinge-Fc AE216/C220S/ Q347R/S354C/ D399V/F405T | PKSSDKTHTCPPCPAPELLGGPSVFLFPPKPKDTLMISRTPEVTCV WDVSHEDPEVKFNWYVDGVEVHNAKTKPREEQYNSTYRVVS VLTVLHQDWLNGKEYKCKVSNKALPAPIEKTISKAKGQPREPR VYTLPPCRDELTKNQVSLTCLVKGFYPSDIAVEWESNGQPENNY KTTPPVLVSDGSFTLYSKLTVDKSRWQQGNVFSCSVMHEALHN HYTQKSLSLSPG (SEQ ID NO: 252) |
| IgG1 hinge-Fc C220S/L234A/ L235A/Y349C/ K360E/K409W | EPKSSDKTHTCPPCPAPEAAGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPREPQ VCTLPPSRDELTENQVSLTCLVKGFYPSDIAVEWESNGQPENNY KTTPPVLDSDGSFFLYSWLTVDKSRWQQGNVFSCSVMHEALHN HYTQKSLSLSPG (SEQ ID NO: 231) |
| IgG1 hinge-Fc AE216/C220S/ L234A/L235A/ Y349C/K360E/ K409W | PKSSDKTHTCPPCPAPEAAGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPREPQ VCTLPPSRDELTENQVSLTCLVKGFYPSDIAVEWESNGQPENNY KTTPPVLDSDGSFFLYSWLTVDKSRWQQGNVFSCSVMHEALHN HYTQKSLSLSPG (SEQ ID NO: 253) |
| IgG1 hinge-Fc C220S/L234A/ L235A/Q347R/ S354C/D399V/ F405T | EPKSSDKTHTCPPCPAPEAAGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPREPR VYTLPPCRDELTKNQVSLTCLVKGFYPSDIAVEWESNGQPENNY KTTPPVLVSDGSFTLYSKLTVDKSRWQQGNVFSCSVMHEALHN HYTQKSLSLSPG (SEQ ID NO: 232) |
| IgG1 hinge-Fc AE216/C220S/ L234A/L235A/ Q347R/S354C/ D399V/F405T | PKSSDKTHTCPPCPAPEAAGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPREPR VYTLPPCRDELTKNQVSLTCLVKGFYPSDIAVEWESNGQPENNY KTTPPVLVSDGSFTLYSKLTVDKSRWQQGNVFSCSVMHEALHN HYTQKSLSLSPG (SEQ ID NO: 254) |
| IgG1 hinge-Fc C220S/L234A/ L235A/P329A/ Y349C/K360E/ K409W | EPKSSDKTHTCPPCPAPEAAGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALAAPIEKTISKAKGQPREP QVCTLPPSRDELTENQVSLTCLVKGFYPSDIAVEWESNGQPENN YKTTPPVLDSDGSFFLYSWLTVDKSRWQQGNVFSCSVMHEALH NHYTQKSLSLSPG (SEQ ID NO: 233) |
| IgG1 hinge-Fc AE216/C220S/ L234A/L235A/ P329A/Y349C/ K360E/K409W | PKSSDKTHTCPPCPAPEAAGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALAAPIEKTISKAKGQPREP QVCTLPPSRDELTENQVSLTCLVKGFYPSDIAVEWESNGQPENN YKTTPPVLDSDGSFFLYSWLTVDKSRWQQGNVFSCSVMHEALH NHYTQKSLSLSPG (SEQ ID NO: 255) |
| IgG1 hinge-Fc C220S/L234A/ L235A/P329A/ Q347R/S354C/ D399V/F405T | EPKSSDKTHTCPPCPAPEAAGGPSVFLFPPKPKDTLMISRTPEVTC VWDVSHEDPEVKFNWYVDGVEVHNAKTKPREEQYNSTYRVV SVLTVLHQDWLNGKEYKCKVSNKALAAPIEKTISKAKGQPREP RVYTLPPCRDELTKNQVSLTCLVKGFYPSDIAVEWESNGQPENN YKTTPPVLVSDGSFTLYSKLTVDKSRWQQGNVFSCSVMHEALH NHYTQKSLSLSPG (SEQ ID NO: 234) |
| IgG1 hinge-Fc AE216/C220S/ L234A/L235A/ | PKSSDKTHTCPPCPAPEAAGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALAAPIEKTISKAKGQPREP |

TABLE 3-continued

S228P mutated IgG4 Hinge-Fc (wild-type); Exemplary S228P mutated IgG4 Hinge-Fc Variants or Hinge Portion-Fc Variants; C220S mutated IgG1 Hinge-Fc (wild-type); Exemplary C220S mutated IgG1 Hinge-Fc Variants or Hinge Portion-Fc Variants

| Linker-Fc | Amino Acid Sequence* |
|---|---|
| P329A/Q347R/<br>S354C/D399V/<br>F405T | RVYTLPPCRDELTKNQVSLTCLVKGFYPSDIAVEWESNGQPENN<br>YKTTPPVLVSDGSFTLYSKLTVDKSRWQQGNVFSCSVMHEALH<br>NHYTQKSLSLSPG (SEQ ID NO: 256) |
| IgG1 hinge-Fc<br>C220S/L234A/<br>L235E/G237A/<br>A330S/P331S/<br>Y349C/K360E/<br>K409W | EPKSSDKTHTCPPCPAPEAEGAPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPSSIEKTISKAKGQPREPQ<br>VCTLPPSRDELTENQVSLTCLVKGFYPSDIAVEWESNGQPENNY<br>KTTPPVLDSDGSFFLYSWLTVDKSRWQQGNVFSCSVMHEALHN<br>HYTQKSLSLSPG (SEQ ID NO: 235) |
| IgG1 hinge-Fc<br>AE216/C220S/<br>L234A/L235E/<br>G237A/A330S/<br>P331S/Y349C/<br>K360E/K409W | PKSSDKTHTCPPCPAPEAEGAPSVFLFPPKPKDTLMISRTPEVTCV<br>VVDVSHEDPEVKFNWYVDGVEVHNAKTKPREEQYNSTYRVVS<br>VLTVLHQDWLNGKEYKCKVSNKALPSSIEKTISKAKGQPREPQV<br>CTLPPSRDELTENQVSLTCLVKGFYPSDIAVEWESNGQPENNYK<br>TTPPVLDSDGSFFLYSWLTVDKSRWQQGNVFSCSVMHEALHNH<br>YTQKSLSLSPG (SEQ ID NO: 257) |
| IgG1 hinge-Fc<br>C220S/L234A/<br>L235E/G237A/<br>A330S/P331S/<br>Q347R/S354C/<br>D399V/F405T | EPKSSDKTHTCPPCPAPEAEGAPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPSSIEKTISKAKGQPREPR<br>VYTLPPCRDELTKNQVSLTCLVKGFYPSDIAVEWESNGQPENNY<br>KTTPPVLVSDGSFTLYSKLTVDKSRWQQGNVFSCSVMHEALHN<br>HYTQKSLSLSPG (SEQ ID NO: 236) |
| IgG1 hinge-Fc<br>AE216/C220S/<br>L234A/L235E/<br>G237A/A330S/<br>P331S/Q347R/<br>S354C/D399V/<br>F405T | PKSSDKTHTCPPCPAPEAEGAPSVFLFPPKPKDTLMISRTPEVTCV<br>VVDVSHEDPEVKFNWYVDGVEVHNAKTKPREEQYNSTYRVVS<br>VLTVLHQDWLNGKEYKCKVSNKALPSSIEKTISKAKGQPREPRV<br>YTLPPCRDELTKNQVSLTCLVKGFYPSDIAVEWESNGQPENNYK<br>TTPPVLVSDGSFTLYSKLTVDKSRWQQGNVFSCSVMHEALHNH<br>YTQKSLSLSPG (SEQ ID NO: 258) |

*The amino acid sequences can further comprise a lysine (K) at the C-terminus.

TABLE 4

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| Construct 101 | | |
| RVESKYGPP<br>CPPCPAPEFL<br>GG (SEQ ID<br>NO: 2) | IWELKKDVYV VELDWYPDAP GEMVVLTCDT<br>PEEDGITWTL DQSSEVLGSG KTLTIQVKEF<br>GDAGQYTCHK GGEVLSHSLL LLHKKEDGIW<br>STDILKDQKE PKNKTFLRCE AKNYSGRFTC<br>WWLTTISTDL TFSVKSSRGS SDPQGVTCGA<br>ATLSAERVRG DNKEYEYSVE CQEDSACPAA<br>EESLPIEVMV DAVHKLKYEN YTSSFFIRDI<br>IKPDPPKNLQ LKPLKNSRQV EVSWEYPDTW<br>STPHSYFSLT FCVQVQGKSK REKKDRVFTD<br>KTSATVICRK NASISVRAQD RYYSSSWSEW<br>ASVPCSRVES KYGPPCPPCP APEFLGGPSV<br>FLFPPKPKDT LMISRTPEVT CVVVDVSQED<br>PEVQFNWYVD GVEVHNAKTK PREEQFNSTY<br>RVVSVLTVLH QDWLNGKEYK CKVSNKGLPS<br>SIEKTISKAK GQPREPQVCT LPPSQEEMTK<br>NQVSLTCLVE GFYPSDIAVE WESNGQPENN<br>YKTTPPVLDS DGSFFLYSWL TVDKSRWQEG<br>NVFSCSVMHE ALHNHYTQKS LSLSLG | IgG4 (IL-12 p40)<br>Heterodimerization mutations:<br>K370E/R409W<br>Substitution for stabilizing disulfide bond: Y349C<br>Substitution for preventing Fab-arm exchange and improving thermostability: S228P |
| GGGGSGGG<br>GSGGGGSRV<br>ESKYGPPCPP<br>CPAPEFLGG<br>(SEQ ID<br>NO: 3) | (SEQ ID NO: 130)<br>RNLPVATPDP GMFPCLHHSQ NLLRAVSNML<br>QKARQTLEFY PCTSEEIDHE DITKDKTSTV<br>EACLPLELTK NESCLNSRET SFITNGSCLA<br>SRKTSFMMAL CLSSIYEDLK MYQVEFKTMN<br>AKLLMDPKRQ IFLDQNMLAV IDELMQALNF<br>NSETVPQKSS LEEPDFYKTK IKLCILLHAF | IgG4 (IL-12 p35)<br>Heterodimerization mutations:<br>E357N/D399V/F405T<br>Substitution for stabilizing disulfide bond: S354C |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | RIRAVTIDRV MSYLNASGGG GSGGGGSGGG GSRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPQVYTLPPC QENMTKNQVS LTCLVKGFYP SDIAVEWESN GQPENNYKTT PPVLVSDGSF TLYSRLTVDK SRWQEGNVFS CSVMHEALHN HYTQKSLSLS LG | Substitution for preventing Fab-arm exchange and improving thermostability: S228P |

Construct 102

| RVESKYGPP CPPCPAPEFL GG (SEQ ID NO: 2) | (SEQ ID NO: 131) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W Substitution for stabilizing disulfide bond: Y349C Substitution for preventing Fab-arm exchange and improving thermostability: S228P |
| GGGGSGGG GSGGGGSRV ESKYGPPCPP CPAPEFLGG (SEQID NO: 3) | (SEQ ID NO: 132) RNLPVATPDP GMFPCLHHSQ NLLRAVSNML QKARQTLEFY PCTSEEIDHE DITKDKTSTV EACLPLELTK NESCLNSRET SPITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T Substitution for stabilizing disulfide bond: S354C Substitution for preventing Fab-arm exchange and improving thermostability: S228P |

Construct 103

| RVESKYGPP CPPCPAPEFE GG (SEQ ID NO: 4) | (SEQ ID NO: 133) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W Substitution for stabilizing disulfide bond: Y349C Substitution for preventing Fab-arm exchange and improving thermostability: S228P Substitutions for reducing FcγR binding: S228P and L235E |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| GGGGSGGG GSGGGGSRV ESKYGPPCPP CPAPEFEGG (SEQ ID NO: 5) | (SEQ ID NO: 134) RNLPVATPDP GMFPCLHHSQ NLLRAVSNML QKAROTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T Substitution for stabilizing disulfide bond: S354C Substitution for preventing Fab-arm exchange and improving thermostability: S228P Substitutions for reducing FcγR binding: S228P and L235E |

Construct 104

| Linker Sequence | Sequences of Heterodimeric Fc-fused Proteins* | Type of IgG (IL-12 subunit); mutations/substitutions |
|---|---|---|
| RVESKYGPP CPPCPAPEFE GG (SEQ ID NO: 4) | (SEQ ID NO: 135) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLAS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W Substitution for stabilizing disulfide bond: Y349C Substitution for preventing Fab-arm exchange and improving thermostability: S228P Substitutions for reducing FcγR binding: S228P, L235E, P329A |
| GGGGSGGG GSGGGGSRV ESKYGPPCPP CPAPEFEGG (SEQ ID NO: 5) | (SEQ ID NO: 136) RNLPVATPDP GMFPCLHHSQ NLLRAVSNML QKAROTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLASSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T Substitution for stabilizing disulfide bond: S354C Substitution for preventing Fab-arm exchange and improving thermostability: S228P Substitutions for reducing FcγR binding: S228P, L235E, P329A |

Construct 106

| Linker Sequence | Sequences of Heterodimeric Fc-fused Proteins* | Type of IgG (IL-12 subunit); mutations/substitutions |
|---|---|---|
| EPKSSDKTH TCPPCPAPEL LGG (SEQ ID NO: 7) OR PKSSDKTHT CPPCPAPELL GG (SEQ ID NO: 238) | (SEQ ID NO: 137) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN | IgG1 (IL-12 p40) Heterodimerization mutations: K360E/K409W Substitution for stabilizing disulfide bond: Y349C C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | NYKTTPPVLD SDGSFFLYSWLTVDKSRWQQ GNVFSCSVMH EALHNHYTQK SLSLSPG OR (SEQ ID NO: 259) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCS PKSS DKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | |
| GGGGSGGG GSGGGGSEP KSSDKTHTC PPCPAPELLG G (SEQ ID NO: 8) | (SEQ ID NO: 138) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GS EPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGSFTLYSKLTVD KSRWQQGNVF SCSVMHEALHNHYTQKSLSL SPG | IgG1 (IL-12 p35) Heterodimerization mutations: Q347R/D399V/F405T Substitution for stabilizing disulfide bond: S354C C220 in the upper hinge is mutated to S |

Construct 107

| EPKSSDKTH TCPPCPAPEA AGG (SEQ ID NO: 9) OR PKSSDKTHT CPPCPAPEA AGG (SEQ ID NO: 239) | (SEQ ID NO: 139) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS DKTHTCPPC PAPEAAGGPS VFLFPPKPKD TLMISRTPEV TCVVVDVSHE DPEVKFNWYV DGVEVHNAKT KPREEQYNST YRVVSVLTVLHQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 260) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCS PKSS DKTHTCPPC PAPEAAGGPS VFLFPPKPKD TLMISRTPEV TCVVVDVSHE | IgG1FcSilent (IL-12 p40) Heterodimerization mutations: K360E/K409W Substitution for stabilizing disulfide bond: Y349C Substitutions for reducing FcγR binding: L234A, L235A C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| GGGGSGGG GSGGGGSEP KSSDKTHTC PPCPAPEAA GG (SEQ ID NO: 10) | DPEVKFNWYV DGVEVHNAKT KPREEQYNST YRVVSVLTVLHQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG (SEQ ID NO: 140) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALHNHYTQKSLSL SPG | IgG1FcSilent (IL-12 p35) Heterodimerization mutations: Q347R/D399V/F405T Substitution for stabilizing disulfide bond: S354C Substitutions for reducing FcγR binding: L234A, L235A C220 in the upper hinge is mutated to S |

Construct 108

| Linker Sequence | Sequences of Heterodimeric Fc-fused Proteins* | Type of IgG (IL-12 subunit); mutations/substitutions |
|---|---|---|
| EPKSSDKTH TCPPCPAPEA AGG (SEQ ID NO: 9) OR PKSSDKTHT CPPCPAPEA AGG (SEQ ID NO: 239) | (SEQ ID NO: 141) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPEAAGGPS VFLFPPKPKD TLMISRTPEVTCVVVDSHE DPEVKFNWYV DGVEVHNAKT KPREEQYNST YRVVSVLTVL HQDWLNGKEYKCKVSNKALA APIEKTISKA KGQPREPQVC TLPPSRDELTENQVSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 261) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCS PKSSDKTHTCPPC PAPEAAGGPS VFLFPPKPKD TLMISRTPEVTCVVVDSHE DPEVKFNWYV DGVEVHNAKT KPREEQYNST YRVVSVLTVL HQDWLNGKEYKCKVSNKALA APIEKTISKA KGQPREPQVC TLPPSRDELTENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1FcSilent (IL-12 p40) Heterodimerization mutations: K360E/K409W Substitution for stabilizing disulfide bond: Y349C Substitutions for reducing FcγR binding: L234A, L235A, P329A C220 in the upper hinge is mutated to S |
| GGGGSGGG GSGGGGSEP KSSDKTHTC PPCPAPEAA GG (SEQ ID NO: 10) | (SEQ ID NO: 142) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG | IgG1FcSilent (IL-12 p35) Heterodimerization mutations: Q347R/D399V/F405T Substitution for stabilizing disulfide bond: S354C |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALAAPIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | Substitutions for reducing FcγR binding: L234A, L235A, P329A C220 in the upper hinge is mutated to S |

Construct 110

| EPKSSDKTH TCPPCPAPEA EGA (SEQ ID NO: 11) OR PKSSDKTHT CPPCPAPEAE GA (SEQ ID NO: 240) | (SEQ ID NO: 143) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPEAEGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP SSIEKTISKA KGQPREPQVC TLPPSRDELT ENQVSLTCLV KGFYPSDIAV EWESNGQPEN NYKTTPPVLD SDGSFFLYSW LTVDKSRWQQ GNVFSCSVMH EALHNHYTQK SLSLSPG OR (SEQ ID NO: 262) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCS PKSS DKTHTCPPC PAPEAEGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP SSIEKTISKA KGQPREPQVC TLPPSRDELT ENQVSLTCLV KGFYPSDIAV EWESNGQPEN NYKTTPPVLD SDGSFFLYSW LTVDKSRWQQ GNVFSCSVMH EALHNHYTQK SLSLSPG | IgG1 Fc (IL-12 p40) Heterodimerization mutations: K360E/K409W Substitution for stabilizing disulfide bond: Y349C Substitutions for reducing FcγR and C1q binding: L234A, L235E, G237A, A330S, P331S |
| GGGGSGGG GSGGGGSEP KSSDKTHTC PPCPAPEAEG A (SEQ ID NO: 12) | (SEQ ID NO: 144) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGGGSGGGGSGGG GSEPKSSDKT HTCPPCPAPE AEGAPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPSSIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 Fc (IL-12 p35) Heterodimerization mutations: Q347R/D399V/F405T Substitution for stabilizing disulfide bond: S354C Substitutions for reducing FcγR and C1q binding: L234A, L235E, G237A, A330S, P331S |

Construct 111

| RVESKYGPP CPPCPAPEFL GG (SEQ ID NO: 2) | (SEQ ID NO: 145) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC | IgG4 Fc (IL-12 p40) Heterodimerization mutations: K370E/R409W |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | Substitution for stabilizing disulfide bond: Y349C Substitution for preventing Fab-arm exchange and improving thermostability: S228P |
| RVESKYGPP CPPCPAPEFL GG (SEQ ID NO: 2) | (SEQ ID NO: 146) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRVMSYLNASRVESKYGPPCPPC PAPEFLGGPSVFLFPPKPKDTLMISRTPEVTCV VVDVSQEDPEVQFNWYV DGVEVHNAKT KPREEQFNST YRVVSVLTVL HQDWLNGKEY KCKVSNKGLPSSIEKTISKAKGQPREPQVYTLP PCQENMT KNQVSLTCLVKGFYPSDIAV EWESNGQPEN NYKTTPPVLV SDGSFTLYSR LTVDKSRWQEGNVFSCSVMH EALHNHYTQK SLSLSLG | IgG4 Fc (IL-12 p35) Heterodimerization mutations: E357N/D399V/F405T Substitution for stabilizing disulfide bond: S354C Substitution for preventing Fab-arm exchange and improving thermostability: S228P |

Construct 112

| Linker Sequence | Sequences of Heterodimeric Fc-fused Proteins* | Type of IgG (IL-12 subunit); mutations/substitutions |
|---|---|---|
| RVESKYGPP CPPCPAPEFL GG (SEQ ID NO: 2) | (SEQ ID NO: 147) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | IgG4 Fc (IL-12 p40) Heterodimerization mutations: K370E/R409W Substitution for stabilizing disulfide bond: Y349C Substitution for preventing Fab-arm exchange and improving thermostability: S228P |
| GGGGSRVES KYGPPCPPCP APEFLGG (SEQ ID NO: 13) | (SEQ ID NO: 148) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPQVYTLPPC QENMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 Fc (IL-12 p35) Heterodimerization mutations: E357N/D399V/F405T Substitution for stabilizing disulfide bond: S354C Substitution for preventing Fab-arm exchange and improving thermostability: S228P |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | Construct 113 | |
| RVESKYGPP CPPCPAPEFL GG (SEQ ID NO: 2) | (SEQ ID NO: 149) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | IgG4Fc (IL-12 p40) Heterodimerization mutations: K370E/R409W Substitution for stabilizing disulfide bond: Y349C Substitution for preventing Fab-arm exchange and improving thermostability: S228P |
| GGGGSGGG GSRVESKYG PPCPPCPAPE FLGG (SEQ ID NO: 14) | (SEQ ID NO: 150) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGGGSGGGGSRVE SKYGPPCPPC PAPEFLGGPS VFLFPPKPKD TLMISRTPEVTCVVVDVSQE DPEVQFNWYV DGVEVHNAKT KPREEQFNST YRVVSVLTVL HQDWLNGKEYKCKVSNKGLPS SIEKTISKA KGQPREPQVYTLPPCQENMTKNQVSLTCLV KGFYPSDIAVEWESNGQPEN NYKTTPPVLV SDGSFTLYSRLTVDKSRWQE GNVFSCSVMH EALHNHYTQK SLSLSLG | IgG4 Fc (IL-12 p35) Heterodimerization mutations: E357N/D399V/F405T Substitution for stabilizing disulfide bond: S354C Substitution for preventing Fab-arm exchange and improving thermostability: S228P |
| | Construct 114 | |
| EPKSSDKTH TCPPCPAPEL LGG (SEQ ID NO: 7) OR PKSSDKTHT CPPCPAPELL GG (SEQ ID NO: 238) | (SEQ ID NO: 151) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPELLGGPS VFLFPPKPKD TLMISRTPEVTCVVVDVSHE DPEVKFNWYV DGVEVHNAKT KPREEQYNST YRVVSVLTVLHDWLNGKEY CKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 263) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSPKS SDKTHTCPPC PAPELLGGPS VFLFPPKPKD TLMISRTPEVTCVVVDVSHE DPEVKFNWYV DGVEVHNAKT KPREEQYNST YRVVSVLTVLHQDWLNGKEY KCKVSNKALP | IgG1 Fc (IL-12 p40) Heterodimerization mutations: K360E/K409W Substitution for stabilizing disulfide bond: Y349C C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| EPKSSDKTH TCPPCPAPEL LGG (SEQ ID NO: 7) | APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG<br>(SEQ ID NO: 152)<br>RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASEPKSSDKTHTCPP CPAPELLGGP SVFLFPPKPK DTLMISRTPE VTCVVVDVSH EDPEVKFNWYVDGVEVHNAK TKPREEQYNS TYRVVSVLTV LHQDWLNGKE YKCKVSNKALPAPIEKTISKAKGQPREPRVYTL PPCRDELTKNQVSLTCLVKGFYPSDIAVEWES NGQPENNYKTTPPVLVSDGSFTLYSKLTVDKS RWQQGNVFSCSVM HEALHNHYTQ KSLSLSPG | IgG1 Fc (IL-12 p35) Heterodimerization mutations: Q347R/D399V/F405T Substitution for stabilizing disulfide bond: S354C C220 in the upper hinge is mutated to S |

Construct 115

| | | |
|---|---|---|
| EPKSSDKTH TCPPCPAPEL LGG (SEQ ID NO: 7) OR PKSSDKTHT CPPCPAPELL GG (SEQ ID NO: 238) | (SEQ ID NO: 153)<br>IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPELLGGPS VFLFPPKPKD TLMISRTPEVTCVVVDVSHE DPEVKFNWYV DGVEVHNAKT KPREEQYNST YRVVSVLTVLHQDWLNGKEY KCKVSNKALP APIEKTISKA KGQPREPQVCTLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG<br>OR<br>(SEQ ID NO: 264)<br>IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSPKS SDKTHTCPPC PAPELLGGPS VFLFPPKPKD TLMISRTPEVTCVVVDVSHE DPEVKFNWYV DGVEVHNAKT KPREEQYNST YRVVSVLTVLHQDWLNGKEY KCKVSNKALP APIEKTISKA KGQPREPQVCTLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 Fc (IL-12 p40) Heterodimerization mutations: K360E/K409W Substitution for stabilizing disulfide bond: Y349C C220 in the upper hinge is mutated to S |
| GGGGSEPKS SDKTHTCPP CP APE LLGG (SEQID NO: 15) | (SEQ ID NO: 154)<br>RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGGGSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP | IgG1 Fc (IL-12 p35) Heterodimerization mutations: Q347R/D399V/F405T Substitution for stabilizing disulfide bond: S354C C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | REPRVYTLPP CRDELTKNQV SLTCLVKGFY PSDIAVEWES NGQPENNYKT TPPVLSDGS FTLYSKLTVD KSRWQQGNVF SCSVMHEALH NHYTQKSLSL SPG | |

Construct 116

| Linker Sequence | Sequences of Heterodimeric Fc-fused Proteins* | Type of IgG (IL-12 subunit); mutations/substitutions |
|---|---|---|
| EPKSSDKTH TCPPCPAPEL LGG (SEQ ID NO: 7) OR PKSSDKTHT CPPCPAPELL GG (SEQ ID NO: 238) | (SEQ ID NO: 155) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPELLGGPS VFLFPPKPKD TLMISRTPEVTCVVVDVSHE DPEVKFNWYV DGVEVHNAKT KPREEQYNST YRVVSVLTVLHQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 265) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSPKS SDKTHTCPPC PAPELLGGPS VFLFPPKPKD TLMISRTPEVTCVVVDVSHE DPEVKFNWYV DGVEVHNAKT KPREEQYNST YRVVSVLTVLHQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 Fc (IL-12 p40) Heterodimerization mutations: K360E/K409W Substitution for stabilizing disulfide bond: Y349C C220 in the upper hinge is mutated to S |
| GGGGSGGG GSEPKSSDK THTCPPCPAP ELLGG (SEQ ID NO: 16) | (SEQ ID NO: 156) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRVMSYLNASGGG GSGGGGSEPK SSDKTHTCPPCPAPELLGGP SVFLFPPKPK DTLMISRTPEVTC VVVDVSH EDPEVKFNWY VDGVEVHNAK TKPREEQYNS TYRVVSVLTVLHQDWLNGKE YKCKVSNKAL PAPIEKTISK AKGQPREPRV YTLPPCRDELTKNQVSLTCL VKGFYPSDIA VEWESNGQPE NNYKTTPPVL VSDGSFTLYSKLTVDKSRWQ QGNVFSCSVM HEALHNHYTQ KSLSLSPG | IgG1 Fc (IL-12 p35) Heterodimerization mutations: Q347R/D399V/F405T Substitution for stabilizing disulfide bond: S354C C220 in the upper hinge is mutated to S |

Construct 117

| Linker Sequence | Sequences of Heterodimeric Fc-fused Proteins* | Type of IgG (IL-12 subunit); mutations/substitutions |
|---|---|---|
| GGGGSGGG GSGGGGSEP KSSDKTHTC PPCPAPELLG G (SEQ ID NO: 8) OR GGGGSGGG | (SEQ ID NO: 157) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG | IgG1 Fc (IL-12 p35) Heterodimerization mutations: K360E/K409W Substitution for stabilizing disulfide |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| GSGGGGSPK SSDKTHTCPP CPAPELLGG (SEQ ID NO: 241) | GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVCTLPPSRDELTENQV SLTCLVKGFY PSDIAVEWES NGQPENNYKT TPPVLDSDGS FFLYSWLTVD KSRWQQGNVF SCSVMHEALHNHYTQKSLSL SPG OR (SEQ ID NO: 266) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GS PKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVCTLPPSRDELTENQV SLTCLVKGFY PSDIAVEWES NGQPENNYKT TPPVLDSDGS FFLYSWLTVD KSRWQQGNVF SCSVMHEALHNHYTQKSLSL SPG | bond: Y349C C220 in the upper hinge is mutated to S |
| EPKSSDKTH TCPPCPAPEL LGG (SEQ ID NO: 7) | (SEQ ID NO: 158) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPRVY TLPPCRDELT KNQVSLTCLV KGFYPSDIAV EWESNGQPEN NYKTTPPVLV SDGSFTLYSK LTVDKSRWQQ GNVFSCSVMH EALHNHYTQK SLSLSPG | IgG1 Fc (IL-12 p40) Heterodimerization mutations: Q347R/D399V/F405T Substitution for stabilizing disulfide bond: S354C C220 in the upper hinge is mutated to S |

Construct 118

| GGGGSEPKS SDKTHTCPP CPAPELLGG (SEQ ID NO: 15) OR GGGGSPKSS DKTHTCPPC PAPELLGG (SEQ ID NO: 242) | (SEQID NO: 159) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSGGGG SEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVCTLPPS RDELTENQVS LTCLVKGFYP SDIAVEWESN GQPENNYKTT PPVLDSDGSF FLYSWLTVDK SRWQQGNVFS CSVMHEALHN HYTQKSLSLS PG OR (SEQ ID NO: 267) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA | IgG1 (IL-12 p40) Heterodimerization mutations: K360E/K409W Substitution for stabilizing disulfide bond: Y349C C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSGGGGS PKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVCTLPPS RDELTENQVS LTCLVKGFYP SDIAVEWESN GQPENNYKTT PPVLDSDGSF FLYSWLTVDK SRWQQGNVFS CSVMHEALHN HYTQKSLSLS PG | |
| GGGGSEPKS SDKTHTCPP CPAPELLGG (SEQ ID NO: 15) | (SEQID NO: 160) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNAS GGG GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T Substitution for stabilizing disulfide bond: S354C C220 in the upper hinge is mutated to S |
| | Construct 119 | |
| GGGGSEPKS SDKTHTCPP CPAPELLGG (SEQ ID NO: 15) OR GGGGSPKSS DKTHTCPPC PAPELLGG (SEQ ID NO: 242) | (SEQ ID NO: 161) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCS GGGG SEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVCTLPPS RDELTENQVS LTCLVKGFYP SDIAVEWESN GQPENNYKTT PPVLDSDGSF FLYSWLTVDK SRWQQGNVFS CSVMHEALHN HYTQKSLSLS PG OR (SEQ ID NO: 268) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCS GGGGS PKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVCTLPPS RDELTENQVS LTCLVKGFYP SDIAVEWESN GQPENNYKTT PPVLDSDGSF FLYSWLTVDK SRWQQGNVFS CSVMHEALHN HYTQKSLSLS PG | IgG1 (IL-12 p40) Heterodimerization mutations: K360E/K409W p40 substitutions: C177S, Y292C (native disulfide bond between subunits is deleted) |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| GGGGSEPKS SDKTHTCPP CP APE LLGG (SEQID NO: 15) | (SEQ ID NO: 162) RNLPVATPDP GMFPCLHHSQ NLLRAVSNML QKARQTLEFY PCTSEEIDHE DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGGGSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPP CRDELTKNQV SLTCLVKGFY PSDIAVEWES NGQPENNYKT TPPVLSDGS FTLYSKLTVD KSRWQQGNVF SCSVMHEALH NHYTQKSLSL SPG | IgG1 (IL-12 p35) Heterodimerization mutations: Q347R/D399V/F405T p35 substitutions: C74S V185C (native disulfide bond between subunits is deleted) |

Construct 119-1

| RVESKYGPP CPPCPAPEFL GG (SEQ ID NO: 2) | (SEQ ID NO: 163) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCS RVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K370E/R409W p40 substitutions: C177S, Y292C (native disulfide bond between subunits is deleted) Substitution for preventing Fab-arm exchange and improving thermostability: S228P |
| GGGGSGGG GSGGGGSRV ESKYGPPCPP CPAPEFLGG (SEQ ID NO: 3) | (SEQ ID NO: 164) RNLPVATPDP GMFPCLHHSQ NLLRAVSNML QKARQTLEFY PCTSEEIDHE DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGPPCPPCPAPEFLGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPQVYTLPPCQENMTKNQVS LTCLVKGFYP SDIAVEWESN GQPENNYKTT PPVLSDGSF TLYSRLTVDK SRWQEGNVFS CSVMHEALHN HYTQKSLSLS LG | IgG4 (IL-12 p35) Heterodimerization mutations: E357N/D399V/F405T p35 substitutions: C74S V185C Substitution for preventing Fab-arm exchange and improving thermostability: S228P |

Construct 119-2

| RVESKYGPP CPPCPAPEFL GG (SEQ ID NO: 2) | (SEQ ID NO: 165) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCS RVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTE NQVSLTCLVK GFYPSDIAVE WESNGQPENN | IgG4 (IL-12 p40) Heterodimerization mutations: K360E/R409W p40 substitutions: C177S, Y292C (native disulfide bond between subunits is deleted) Substitution for preventing Fab-arm exchange and improving thermostability: S228P |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | YKTTPPVLDS DGSFFLYSWL TVDKSRWQEG NVFSCSVMHE ALHNHYTQKS LSLSLG | |
| GGGGSGGG GSGGGGSRV ESKYGPPCPP CPAPEFLGG (SEQ ID NO: 3) | (SEQ ID NO: 166) RNLPVATPDP GMFPCLHHSQ NLLRAVSNML QKARQTLEFY PCTSEEIDHE DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF LGGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T p35 substitutions: C74S V185C Substitution for preventing Fab-arm exchange and improving thermostability: S228P |

Construct 119-3

| RVESKYGPP CPPCPAPEFE GG (SEQ ID NO: 4) | (SEQ ID NO: 167) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCS RVES KYGPPCPPCP APEFEGGPSV FLFPPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W p40 substitutions: C177S, Y292C (native disulfide bond between subunits is deleted) Substitution for preventing Fab-arm exchange and improving thermostability: S228P Substitutions for reducing FcγR binding: S228P and L235E |
| GGGGSGGG GSGGGGSRV ESKYGPPCPP CPAPEFEGG (SEQ ID NO:5) | (SEQ ID NO: 168) RNLPVATPDP GMFPCLHHSQ NLLRAVSNML QKARQTLEFY PCTSEEIDHE DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T p35 substitutions: C74S V185C Substitution for preventing Fab-arm exchange and improving thermostability: S228P Substitutions for reducing FcγR binding: S228P and L235E |

Construct 119-4

| RVESKYGPP CPPCPAPEFE GG (SEQ ID NO:4) | (SEQ ID NO: 169) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFEGGPSV FLFPPPKPKDT LMISRTPEVT CVVVDVSQED PEVQFNWYVD GVEVHNAKTK PREEQFNSTY RVVSVLTVLH QDWLNGKEYK CKVSNKGLAS | IgG4 (IL-12 p40) Heterodimerization mutations: K360E/R409W p40 substitutions: C177S, Y292C (native disulfide bond between subunits is deleted) Substitution for preventing Fab-arm exchange and improving thermostability: S228P Substitutions for |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | reducing FcγR binding: S228P, L235E, P329A |
| GGGGSGGG GSGGGGSRV ESKYGPPCPP CPAPEFEGG (SEQ ID NO:5) | (SEQ ID NO: 170) RNLPVATPDP GMFPCLHHSQ NLLRAVSNML QKARQTLEFY PCTSEEIDHE DITKDKTSTV EACLPLELTK NESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLASSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T p35 substitutions: C74S V185C Substitution for preventing Fab-arm exchange and improving thermostability: S228P Substitutions for reducing FcγR binding: S228P, L235E, P329A |

Construct 119-5

| Linker Sequence | Sequences of Heterodimeric Fc-fused Proteins* | Type of IgG (IL-12 subunit); mutations/substitutions |
|---|---|---|
| EPKSSDKTH TCPPCPAPEL LGG (SEQ ID NO:7) OR PKSSDKTHT CPPCPAPELL GG (SEQ ID NO:238) | (SEQ ID NO: 171) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 269) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitutions: C177S, Y292C (native disulfide bond between subunits is deleted) C220 in the upper hinge is mutated to S |
| GGGGSGGG GSGGGGSEP KSSDKTHTC PPCPAPELLG G (SEQ ID NO:8) | (SEQ ID NO: 172) RNLPVATPDP GMFPCLHHSQ NLLRAVSNML QKARQTLEFY PCTSEEIDHE DITKDKTSTV EACLPLELTK NESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV | IgG1 (IL-12 p35) Heterodimerization mutations: Q347R/D399V/F405T p35 substitutions: C74S V185C C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGSFTLYSKLTVD KSRWQQGNVF SCSVMHEALH NHYTQKSLSL SPG | |

Construct 119-6

| Linker Sequence | Sequences of Heterodimeric Fc-fused Proteins* | Type of IgG (IL-12 subunit); mutations/substitutions |
|---|---|---|
| EPKSSDKTH TCPPCPAPEA AGG (SEQ ID NO:9) OR PKSSDKTHT CPPCPAPEA AGG (SEQ ID NO:239) | (SEQ ID NO: 173) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VFLFPPKPKD TLMISRTPEV TCVVVDVSHE DPEVKFNWYV DGVEVHNAKT KPREEQYNST YRVVSVLTVLHQDWLNGKEY KCKVSNKALP APIEKTISKAKGQPREPQVCTLPPSRDELTENQ VSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 270) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPEAAGGPS VFLFPPKPKD TLMISRTPEV TCVVVDVSHE DPEVKFNWYV DGVEVHNAKT KPREEQYNST YRVVSVLTVLHQDWLNGKEY KCKVSNKALP APIEKTISKAKGQPREPQVCTLPPSRDELTENQ VSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W<br><br>p40 substitutions: C177S, Y292C (native disulfide bond between subunits is deleted) Substitutions for reducing FcγR binding: L234A, L235A C220 in the upper hinge is mutated to S |
| GGGGSGGG GSGGGGSEP KSSDKTHTC PPCPAPEAA GG (SEQ ID NO:10) | (SEQ ID NO: 174) RNLPVATPDP GMFPCLHHSQ NLLRAVSNML QKARQTLEFY PCTSEEIDHE DITKDKTSTV EACLPLELTK NESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALHNHYTQKSLSL SPG | IgG1 (IL-12 p35) Heterodimerization mutations: Q347R/D399V/F405T p35 substitutions: C74S V185C Substitutions for reducing FcγR binding: L234A, L235A C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|

Construct 119-7

| EPKSSDKTH TCPPCPAPEA AGG (SEQ ID NO:9) OR PKSSDKTHT CPPCPAPEA AGG (SEQ ID NO:239) | (SEQ ID NO: 175) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VFLFPPKPKD TLMISRTPEVTCVVVDVSHE DPEVKFNWYV DGVEVHNAKT KPREEQYNST YRVVSVLTVL HQDWLNGKEYKCKVSNKALA APIEKTISKAKGQPREPQVCTLPPSRDELTENQ VSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 271) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPEAAGGPS VFLFPPKPKD TLMISRTPEVTCVVVDVSHE DPEVKFNWYV DGVEVHNAKT KPREEQYNST YRVVSVLTVL HQDWLNGKEYKCKVSNKALA APIEKTISKAKGQPREPQVCTLPPSRDELTENQ VSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitutions: C177S, Y292C (native disulfide bond between subunits is deleted) Substitutions for reducing FcγR binding: L234A, L235A, P329A C220 in the upper hinge is mutated to S |
| GGGGSGGG GSGGGGSEP KSSDKTHTC PPCPAPEAA GG (SEQ ID NO:10) | (SEQ ID NO: 176) RNLPVATPDP GMFPCLHHSQ NLLRAVSNML QKARQTLEFY PCTSEEIDHE DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMISRTPEVTCVV VDVSHEDPEV KFNWYVDGVE VHNAKTKPRE EQYNSTYRVV SVLTVLHQDW LNGKEYKCKV SNKALAAPIE KTISKAKGQP REPRVYTLPP CRDELTKNQV SLTCLVKGFY PSDIAVEWES NGQPENNYKT TPPVLSDGS FTLYSKLTVD KSRWQQGNVF SCSVMHEALHNHYTQKSLSL SPG | IgG1 (IL-12 p35) Heterodimerization mutations: Q347R/D399V/F405T p35 substitutions: C74S, V185C Substitutions for reducing FcγR binding: L234A, L235A, P329A C220 in the upper hinge is mutated to S |

Construct 119-8

| EPKSSDKTH TCPPCPAPEA EGA (SEQ ID NO: 11) OR PKSSDKTHT CPPCPAPEAE GA (SEQ ID NO:240) | (SEQ ID NO: 177) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAEGAPS VFLFPPKPKD TLMISRTPEV TCVVVDVSHE | IgG1 (IL-12 p40) Heterodimerization mutations: K360E/K409W p40 substitutions: C177S, Y292C (native disulfide bond between subunits is deleted) Substitutions for reducing FcγR and C1q binding: L234A, L235E, G237A, |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | DPEVKFNWYV DGVEVHNAKT KPREEQYNST YRVVSVLTVL HQDWLNGKEY KCKVSNKALP SSIEKTISKAKGQPREPQVCTLPPSRDELTENQ VSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 272) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPEAEGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP SSIEKTISKAKGQPREPQVCTLPPSRDELTENQ VSLTCLV KGFYPSDIAV EWESNGQPEN NYKTTPPVLD SDGSFFLYSWLTVDKSRWQQ GNVFSCSVMH EALHNHYTQK SLSLSPG | A330S, P331S C220 in the upper hinge is mutated to S |
| GGGGSGGG GSGGGGSEP KSSDKTHTC PPCPAPEAEG A (SEQ ID NO:12) | (SEQ ID NO: 178) RNLPVATPDP GMFPCLHHSQ NLLRAVSNML QKARQTLEFY PCTSEEIDHE DITKDKTSTV EACLPLELTK NESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AEGAPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPSSIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALHNHYTQKSLSL SPG | IgG1 (IL-12 p35) Heterodimerization mutations: Q347R/D399V/F405T p35 substitutions: C74S, V185C Substitutions for reducing FcγR and C1q binding: L234A, L235E, G237A, A330S, P331S C220 in the upper hinge is mutated to S |

Construct 120

| RVESKYGPP CPPCPAPEFL GG (SEQ ID NO: 2) | (SEQ ID NO: 179) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K370E/R409W p40 substitution: Y292C (native disulfide bond between subunits is preserved) Substitution for preventing Fab-arm exchange and improving thermostability: S228P |
| GGGGSGGG GSGGGGSRV ESKYGPPCPP CPAPEFLGG (SEQ ID NO: 3) | (SEQ ID NO: 180) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF LGGPSVFLFP PKPKDTLMIS RTPEVTCVVV DVSQEDPEVQ | IgG4 (IL-12 p35) Heterodimerization mutations: E357N/D399V/F405T p35 substitution: V185C (native disulfide bond between subunits is preserved) Substitution for preventing Fab-arm |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | FNWYVDGVEV HNAKTKPREE QFNSTYRVVS VLTVLHQDWL NGKEYKCKVS NKGLPSSIEK TISKAKGQPR EPQVYTLPPCQENMTKNQVS LTCLVKGFYP SDIAVEWESN GQPENNYKTT PPVLVSDGSF TLYSRLTVDK SRWQEGNVFS CSVMHEALHN HYTQKSLSLS LG | exchange and improving thermostability: S228P |

Construct 120-1

| RVESKYGPP CPPCPAPEFL GG (SEQ ID NO:2) | (SEQ ID NO: 181) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRVS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W p40 substitution: Y292C (native disulfide bond between subunits is preserved) Substitution for preventing Fab-arm exchange and improving thermostability: S228P |
| GGGGSGGG GSGGGGSRV ESKYGPPCPP CPAPEFLGG (SEQID NO:3) | (SEQ ID NO: 182) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPCQEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T p35 substitution: V185C (native disulfide bond between subunits is preserved) Substitution for preventing Fab-arm exchange and improving thermostability: S228P |

Construct 120-2

| RVESKYGPP CPPCPAPEFE GG (SEQ ID NO:4) | (SEQ ID NO: 183) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRVS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W p40 substitution: Y292C (native disulfide bond between subunits is preserved) Substitution for preventing Fab-arm exchange and improving thermostability: S228P Substitutions for reducing FcγR binding: S228P and L235E |
| GGGGSGGG GSGGGGSRV ESKYGPPCPP CPAPEFEGG (SEQID NO:5) | (SEQ ID NO: 184) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG | IgG4 (IL-12 p35) Heterodimerization mutations: Q347R/D399V/F405T p35 substitution: V185C (native disulfide bond between subunits is preserved) |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | Substitution for preventing Fab-arm exchange and improving thermostability: S228P Substitutions for reducing FcγR binding: S228P and L235E |

Construct 120-3

| RVESKYGPP CPPCPAPEFE GG (SEQ ID NO:4) | (SEQ ID NO: 185) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLAS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W p40 substitution: Y292C (native disulfide bond between subunits is preserved) Substitution for preventing Fab-arm exchange and improving thermostability: S228P Substitutions for reducing FcγR binding: S228P, L235E, P329A |
| GGGGSGGG GSGGGGSRV ESKYGPPCPP CPAPEFEGG (SEQID NO:5) | (SEQ ID NO: 186) RNLPVATPDP GMFPCLHHSQ NLLRAVSNML QKAROTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLASSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T p35 substitution: V185C (native disulfide bond between subunits is preserved) Substitution for preventing Fab-arm exchange and improving thermostability: S228P Substitutions for reducing FcγR binding: S228P, L235E, P329A |

Construct 120-4

| EPKSSDKTH TCPPCPAPEL LGG (SEQ ID NO:7) OR PKSSDKTHT CPPCPAPELL GG (SEQ ID NO:238) | (SEQ ID NO: 187) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 273) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC | IgG1 (IL-12 p40) Heterodimerization mutations: K360E/K409W p40 substitution: Y292C (native disulfide bond between subunits is preserved) C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | |
| GGGGSGGG GSGGGGSEP KSSDKTHTC PPCPAPELLG G (SEQ ID NO:8) | (SEQ ID NO: 188) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGSFTLYSKLTVD KSRWQQGNVF SCSVMHEALHNHYTQKSLSL SPG | IgG1 (IL-12 p35) Heterodimerization mutations: Q347R/D399V/F405T Substitution for stabilizing disulfide bond: S354C p35 substitution: V185C (native disulfide bond between subunits is preserved) C220 in the upper hinge is mutated to S |

Construct 120-5

| Linker Sequence | Sequences of Heterodimeric Fc-fused Proteins* | Type of IgG (IL-12 subunit); mutations/substitutions |
|---|---|---|
| EPKSSDKTH TCPPCPAPEA AGG (SEQ ID NO:9) OR PKSSDKTHT CPPCPAPEA AGG (SEQ ID NO:239) | (SEQ ID NO: 189) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VFLFPPKPKD TLMISRTPEV TCVVVDVSHE DPEVKFNWYV DGVEVHNAKT KPREEQYNST YRVVSVLTVLHQDWLNGKEY KCKVSNKALP APIEKTISKA KGQPREPQVC TLPPSRDELTENQVSLTCLV KGFYPSDIAV EWESNGQPEN NYKTTPPVLD SDGSFFLYSWLTVDKSRWQQ GNVFSCSVMH EALHNHYTQK SLSLSPGPKS OR (SEQ ID NO: 274) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPEAAGGPS VFLFPPKPKD TLMISRTPEV TCVVVDVSHE DPEVKFNWYV DGVEVHNAKT KPREEQYNST YRVVSVLTVLHQDWLNGKEY KCKVSNKALP APIEKTISKA KGQPREPQVC TLPPSRDELTENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitution: Y292C (native disulfide bond between subunits is preserved) Substitutions for reducing FcγR binding: L234A, L235A C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| GGGGSGGG GSGGGGSEP KSSDKTHTC PPCPAPEAA GG (SEQ ID NO:10) | (SEQ ID NO: 190) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALHNHYTQKSLSL SPG | IgG1 (IL-12 p35) Heterodimerization mutations: Q347R/D399V/F405T<br><br>p35 substitution: V185C (native disulfide bond between subunits is preserved) Substitutions for reducing FcγR binding: L234A, L235A C220 in the upper hinge is mutated to S |

Construct 120-6

| Linker Sequence | Sequences of Heterodimeric Fc-fused Proteins* | Type of IgG (IL-12 subunit); mutations/substitutions |
|---|---|---|
| EPKSSDKTH TCPPCPAPEA AGG (SEQ ID NO:9) OR PKSSDKTHT CPPCPAPEA AGG (SEQ ID NO:239) | (SEQ ID NO: 191) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VFLFPPKPKD TLMISRTPEVTCVVVDVSHE DPEVKFNWYV DGVEVHNAKT KPREEQYNST YRVVSVLTVLHQDWLNGKEY KCKVSNKALA APIEKTISKAKGQPREPQVCTLPPSRDELTENQ VSLTCLVKGFYPSDIAVEWESNGQPENNYKTT PPVLDSDGSFFLYSWLTVDKSRWQQGNVFSCS VMH EALHNHYTQK SLSLSPG<br>OR<br>(SEQ ID NO: 275) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPEAAGGPS VFLFPPKPKD TLMISRTPEVTCVVVDVSHE DPEVKFNWYV DGVEVHNAKT KPREEQYNST YRVVSVLTVLHQDWLNGKEY KCKVSNKALA APIEKTISKAKGQPREPQVCTLPPSRDELTENQ VSLTCLVKGFYPSDIAVEWESNGQPENNYKTT PPVLDSDGSFFLYSWLTVDKSRWQQGNVFSCS VMH EALHNHYTQK SLSLSPG | IgG1 (IL-12 p40) Heterodimerization mutations: K360E/K409W p40 substitution: Y292C (native disulfide bond between subunits is preserved) Substitutions for reducing FcγR binding: L234A, L235A, P329A C220 in the upper hinge is mutated to S |
| GGGGSGGG GSGGGGSEP KSSDKTHTC PPCPAPEAA GG (SEQ ID NO:10) | (SEQ ID NO: 192) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGGGSGGGGSGGG GSEPKSSDKT HTCPPCPAPEAAGGPSVFLF PPKPKDTLMISRTPEVTCVVVDVSHEDPEV KFNWYVDGVE VHNAKTKPRE EQYNSTYRVV SVLTVLHQDW LNGKEYKCKV SNKALAAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALHNHYTQKSLSL SPG | IgG1 (IL-12 p35) Heterodimerization mutations: Q347R/D399V/F405T<br><br>p35 substitution: V185C (native disulfide bond between subunits is preserved) Substitutions for reducing FcγR binding: L234A, L235A, P329A C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| Construct 120-7 | | |
| EPKSSDKTH TCPPCPAPEA EGA (SEQ ID NO:11) OR PKSSDKTHT CPPCPAPEAE GA (SEQ ID NO:240) | (SEQ ID NO: 193) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAEGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP SSIEKTISKA KGQPREPQVC TLPPSRDELTENQVSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 276) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPEAEGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP SSIEKTISKA KGQPREPQVC TLPPSRDELTENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitution: Y292C (native disulfide bond between subunits is preserved) Substitutions for reducing FcγR and C1q binding: L234A, L235E, G237A, A330S, P331S C220 in the upper hinge is mutated to S |
| GGGGSGGG GSGGGGSEP KSSDKTHTC PPCPAPEAEG A (SEQ ID NO:12) | (SEQ ID NO: 194) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AEGAPSVFLF PPKPKDTLMISRTPEVTCVV VDVSHEDPEV KFNWYVDGVE VHNAKTKPRE EQYNSTYRVV SVLTVLHQDW LNGKEYKCKV SNKALPSSIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALHNHYTQKSLSL SPG | IgG1 (IL-12 p35) Heterodimerization mutations: Q347R/D399V/F405T p35 substitution: V185C (native disulfide bond between subunits is preserved) Substitutions for reducing FcγR and C1q binding: L234A, L235E, G237A, A330S, P331S C220 in the upper hinge is mutated to S |
| Construct 121 | | |
| EPKSSDKTH TCPPCPAPEA AGG (SEQ ID NO: 9) OR PKSSDKTHT CPPCPAPEA AGG (SEQ ID NO:239) | (SEQ ID NO: 195) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW | IgG1 (IL-12 p40) Heterodimerization mutations: K360E/K409W Substitution for stabilizing disulfide bond: Y349C Substitutions for reducing FcγR binding: L234A, L235A Additional mutation in |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | ASVPCSEPKS SDKTHTCPPC PAPEAAGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSW LTVDKSRWQQ GNVFSCSVMH EALHNHYTQK SLSLSPG OR (SEQ ID NO: 277) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPEAAGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSW LTVDKSRWQQ GNVFSCSVMH EALHNHYTQK SLSLSPG | p40: Y292C to introduce IL-12 stabilizing disulfide bond C220 in the upper hinge is mutated to S |
| GGGGSGGG GSGGGGSEP KSSDKTHTC PPCPAPEAA GG (SEQ ID NO:10) | (SEQ ID NO: 196) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLSDGS FTLYSKLTVD KSRWQQGNVF SCSVMHEALHNHYTQKSLSL SPG | IgG1 (IL-12 p35) Heterodimerization mutations: Q347R/D399V/F405T Substitution for stabilizing disulfide bond: S354C Substitutions for reducing FcγR binding: L234A, L235A Additional mutation in p35: V185C to introduce IL-12 stabilizing disulfide bond C220 in the upper hinge is mutated to S |

Construct 122

| EPKSSDKTH TCPPCPAPEA AGG (SEQ ID NO:9) OR PKSSDKTHT CPPCPAPEA AGG (SEQ ID NO:239) | (SEQ ID NO: 197) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEWASVPCSEPKS SDKTHTCPPC PAPEAAGGPS VFLFPPKPKD TLMISRTPEV TCVVVDVSHEDPEVKFNWYVDGVEVHNAKT KPREEQYNST YRVVSVLTVLHQDWLNGKEY KCKVSNKALA APIEKTISKA KGQPREPQVC TLPPSRDELTENQVSLTCLV KGFYPSDIAV EWESNGQPENNYKTTPPVLDSDGSFFLYSWLT VDKSRWQQ GNVFSCSVMHEALHNHYTQK SLSLSPG OR (SEQ ID NO: 278) IWELKKDVYV VELDWYPDAP GEMVVLTCDT PEEDGITWTL DQSSEVLGSG KTLTIQVKEF GDAGQYTCHK GGEVLSHSLL LLHKKEDGIW | IgG1 (IL-12 p40) Heterodimerization mutations: K360E/K409W Substitution for stabilizing disulfide bond: Y349C Substitutions for reducing FcγR binding: L234A, L235A, P329A Additional mutation Y292C to introduce IL-12 stabilizing disulfide bond C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| | STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPEAAGGPS VFLFPPKPKD TLMISRTPEV TCVVVDVSH EDPEVKFNW YVDGVEVHN AKTKPREEQ YNST YRVVSVLTVLHQDWLNGKEY KCKVSNKALA APIEKTISKA KGQPREPQVC TLPPSRDELTENQVSLTCLV KGFYPSDIAV EWESNGQPENNYKTTPPVLDSDGSFFLYSWLT VDKSRWQQ GNVFSCSVMHEALHNHYTQK SLSLSPG | |
| GGGGSGGG GSGGGGSEP KSSDKTHTC PPCPAPEAA GG (SEQ ID NO:10) | (SEQ ID NO: 198) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMISRTPEVTCVV VDVSHEDPEV KFNWYVDGVEVHNAKTKPREEQYNSTYRVV SVLTVLHQDW LNGKEYKCKV SNKALAAPIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALHNHYTQKSLSL SPG | IgG1 (IL-12 p35) Heterodimerization mutations: Q347R/D399V/F405T Substitution for stabilizing disulfide bond: S354C Substitutions for reducing FcγR binding: L234A, L235A, P329A Additional mutation V185C to introduce IL-12 stabilizing disulfide bond C220 in the upper hinge is mutated to S |

Construct 123

| EPKSSDKTH TCPPCPAPEA EGA (SEQ ID NO:11) OR PKSSDKTHT CPPCPAPEAE GA (SEQ ID NO:240) | (SEQ ID NO: 199) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAEGAPS VFLFPPKPKD TLMISRTPEVTCVVVDVSHE DPEVKFNWYV DGVEVHNAKT KPREEQYNST YRVVSVLTVLHQDWLNGKEY KCKVSNKALP SSIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG OR (SEQ ID NO: 279) IWELKKDVYV VELDWYPDAP GEMVVLTCDT PEEDGITWTL DQSSEVLGSG KTLTIQVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSPKS SDKTHTCPPC PAPEAEGAPS VFLFPPKPKD TLMISRTPEVTCVVVDVSHE DPEVKFNWYV DGVEVHNAKT KPREEQYNST YRVVSVLTVLHQDWLNGKEY KCKVSNKALP SSIEKTISKA KGQPREPQVC TLPPSRDELT ENQVSLTCLV KGFYPSDIAV EWESNGQPEN | IgG1 (IL-12 p40) Heterodimerization mutations: K360E/K409W Substitution for stabilizing disulfide bond: Y349C Substitutions for reducing FcγR and C1q binding: L234A, L235E, G237A, A330S, P331S Additional mutation Y292C to introduce IL-12 stabilizing disulfide bond C220 in the upper hinge is mutated to S |

TABLE 4-continued

Exemplary Heterodimeric Fc-Fused Polypeptide Constructs

| Linker Sequence | Sequences of Heterodimeric Fc-fused Proteins* | Type of IgG (IL-12 subunit); mutations/substitutions |
|---|---|---|
| GGGGSGGG GSGGGGSEP KSSDKTHTC PPCPAPEAEG A (SEQ ID NO:12) | NYKTTPPVLD SDGSFFLYSWLTVDKSRWQQ GNVFSCSVMH EALHNHYTQK SLSLSPG (SEQ ID NO: 200) RNLPVATPDP GMFPCLHHSQ NLLRAVSNML QKARQTLEFY PCTSEEIDHE DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AEGAPSVFLF PPKPKDTLMISRTPEVTCVV VDVSHEDPEV KFNWYVDGVE VHNAKTKPRE EQYNSTYRVV SVLTVLHQDW LNGKEYKCKV SNKALPSSIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALHNHYTQKSLSL SPG | IgG1 (IL-12 p35) Heterodimerization mutations: Q347R/D399V/F405T Substitution for stabilizing disulfide bond: S354C Substitutions for reducing FcγR and C1q binding: L234A, L235E, G237A, A330S, P331S Additional mutation V185C to introduce IL-12 stabilizing disulfide bond C220 in the upper hinge is mutated to S |

*The amino acid sequences can further comprise a lysine (K) at the C-terminus.

TABLE 5

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| Construct 1 | | |
| RVESKYGPP CPPCPAPEFL GG (SEQ ID NO:2) | (SEQ ID NO: 17) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K370E/R409W Substitution for stabilizing disulfide bond: Y349C Substitution for preventing Fab-arm exchange and improving thermostability: S228P |
| GGGGSGGG GSGGGGSRV ESKYGPPCPP CPAPEFLGG (SEQ ID NO: 3) | (SEQ ID NO: 18) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPQVYTLPPC QENMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: E357N/D399V/F405T Substitution for stabilizing disulfide bond: S354C Substitution for preventing Fab-arm exchange and improving thermostability: S228P |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | Construct 2 | |
| RVESKYGPP CPPCPAPEFL GG (SEQ ID NO:2) | (SEQ ID NO: 19) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W Substitution for stabilizing disulfide bond: Y349C Substitution for preventing Fab-arm exchange and improving thermostability: S228P |
| GGGGSGGG GSGGGGSRV ESKYGPPCPP CPAPEFLGG (SEQ ID NO: 3) | (SEQ IDNO: 20) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPC QEEMTKNQVS LTCLVKGFYP SDIAVEWESN GQPENNYKTT PPVLSDGSF TLYSRLTVDK SRWQEGNVFS CSVMHEALHN HYTQKSLSLS LG | IgG4 (IL-12 p35) Heterodimerization mutations: Q347R/D399V/F405T Substitution for stabilizing disulfide bond: S354C Substitution for preventing Fab-arm exchange and improving thermostability: S228P |
| | Construct 3 | |
| RVESKYGPP CPPCPAPEFE GG (SEQ ID NO: 4) | (SEQ ID NO: 21) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W Substitution for stabilizing disulfide bond: Y349C Substitution for preventing Fab-arm exchange and improving thermostability: S228P Substitutions for reducing FcγR binding: S228P and L235E |
| GGGGSGGG GSGGGGSRV ESKYGPPCPP CPAPEFEGG (SEQ ID NO: 5) | (SEQ ID NO: 22) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS | IgG4 (IL-12 p35) Heterodimerization mutations: Q347R/D399V/F405T Substitution for stabilizing disulfide bond: S354C Substitution for preventing Fab-arm exchange and improving |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | VLTVLHQDWL NGKEYKCKVS NKGLPSSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | thermostability: S228P Substitutions for reducing FcγR binding: S228P and L235E |

Construct 4

| RVESKYGPP CPPCPAPEFE GG (SEQ ID NO: 4) | (SEQ ID NO: 23) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLAS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W Substitution for stabilizing disulfide bond: Y349C Substitution for preventing Fab-Arm exchange and improving thermostability: S228P Substitutions for reducing FcγR binding: S228P, L235E, P329A |
| GGGGSGGG GSGGGGSRV ESKYGPPCPP CPAPEFEGG (SEQ ID NO: 5) | (SEQ ID NO: 24) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLASSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T Substitution for stabilizing disulfide bond: S354C Substitution for preventing Fab-Arm exchange and improving thermostability: S228P Substitutions for reducing FcγR binding: S228P, L235E, P329A |

Construct 5

| RVESKYGPP CPPCPAPEFE GG (SEQ ID NO: 4) | (SEQ ID NO: 25) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLGS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W Substitution for stabilizing disulfide bond: Y349C Substitution for preventing Fab-Arm exchange and improving thermostability: S228P Substitutions for reducing FcγR binding: S228P, L235E, P329G |
| GGGGSGGG GSGGGGSRV ESKYGPPCPP CPAPEFEGG (SEQ ID NO: 5) | (SEQ ID NO: 26) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF | IgG4 (IL-12 p35) Heterodimerization mutations: Q347R/D399V/F405T Substitution for stabilizing disulfide |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | NSETVPQKSS LEEPDFYKTK IKLCILLHAF RIRAVTIDRV MSYLNASGGG GSGGGGSGGG GSRVESKYGP PCPPCPAPEF EGGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLGSSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | bond: S354C Substitution for preventing Fab-Arm exchange and improving thermostability: S228P Substitutions for reducing FcγR binding: S228P, L235E, P329G |

Construct 6

| EPKSSDKTH TCPPCPAPEL LGG (SEQ ID NO: 7) | (SEQ ID NO: 27) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W Substitution for stabilizing disulfide bond: Y349C C220 in the upper hinge is mutated to S |
| GGGGSGGG GSGGGGSEP KSSDKTHTC PPCPAPELLG G (SEQ ID NO: 8) | (SEQ ID NO: 28) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGSFTLYSKLTVD KSRWQQGNVF SCSVMHEALH NHYTQKSLSL SPG | IgG1 (IL-12 p35) Heterodimerization mutations: Q347R/D399V/F405T Substitution for stabilizing disulfide bond: S354C C220 in the upper hinge is mutated to S |

Construct 7

| EPKSSDKTH TCPPCPAPEA AGG (SEQ ID NO: 9) | (SEQ ID NO: 29) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPEAAGGPS VFLFPPKPKD TLMISRTPEV TCVVVDVSHE DPEVKFNWYV DGVEVHNAKT KPREEQYNST YRVVSVLTVLHQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1FcSilent (IL-12 p40) Heterodimerization mutations: K360E/K409W Substitution for stabilizing disulfide bond: Y349C Substitutions for reducing FcγR binding: L234A, L235A C220 in the upper hinge is mutated to S |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| GGGGSGGG GSGGGGSEP KSSDKTHTC PPCPAPEAA GG (SEQ ID NO: 10) | (SEQ ID NO: 30) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1FcSilent (IL-12 p35) Heterodimerization mutations: Q347R/D399V/F405T Substitution for stabilizing disulfide bond: S354C Substitutions for reducing FcγR binding: L234A, L235A C220 in the upper hinge is mutated to S |

Construct 8

| Linker Sequence | Sequences of Heterodimeric Fc-fused Proteins* | Type of IgG (IL-12 subunit); mutations/ substitutions |
|---|---|---|
| EPKSSDKTH TCPPCPAPEA AGG (SEQ ID NO: 9) | (SEQ ID NO: 31) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSWSEW ASVPCSEPKS SDKTHTCPPC PAPEAAGGPS VFLFPPKPKD TLMISRTPEVTCVVVDVSHE DPEVKFNWYV DGVEVHNAKT KPREEQYNST YRVVSVLTVL HQDWLNGKEYKCKVSNKALA APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1FcSilent (IL-12 p40) Heterodimerization mutations: K360E/K409W Substitution for stabilizing disulfide bond: Y349C Substitutions for reducing FcγR binding: L234A, L235A, P329A C220 in the upper hinge is mutated to S |
| GGGGSGGG GSGGGGSEP KSSDKTHTC PPCPAPEAA GG (SEQ ID NO: 10) | (SEQ ID NO: 32) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSEPKSSDKT HTCPPCPAPE AAGGPSVFLF PPKPKDTLMISRTPEVTCVV VDVSHEDPEV KFNWYVDGVE VHNAKTKPRE EQYNSTYRVV SVLTVLHQDW LNGKEYKCKV SNKALAAPIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1FcSilent (IL-12 p35) Heterodimerization mutations: Q347R/D399V/F405T Substitution for stabilizing disulfide bond: S354C Substitutions for reducing FcγR binding: L234A, L235A, P329A C220 in the upper hinge is mutated to S |

Construct 9

| Linker Sequence | Sequences of Heterodimeric Fc-fused Proteins* | Type of IgG (IL-12 subunit); mutations/ substitutions |
|---|---|---|
| EPKSSDKTH TCPPCPAPEA AGG (SEQ ID NO: 9) | (SEQ ID NO: 33) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSWSEW ASVPCSEPKS SDKTHTCPPC PAPEAAGGPS VFLFPPKPKD TLMISRTPEVTCVVVDVSHE DPEVKFNWYV DGVEVHNAKT KPREEQYNST | IgG1FcSilent (IL-12 p40) Heterodimerization mutations: K360E/K409W Substitution for stabilizing disulfide bond: Y349C Substitutions for reducing FcγR binding: L234A/L235A/P329G C220 in the upper hinge is mutated to S |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | YRVVSVLTVLHQDWLNGKEY KCKVSNKALG APIEKTISKA KGQPREPQVC TLPPSRDELTENQVSLTCLV KGFYPSDIAV EWESNGQPEN NYKTTPPVLD SDGSFFLYSWLTVDKSRWQQ GNVFSCSVMH EALHNHYTQK SLSLSPG | |
| GGGGSGGG GSGGGGSEP KSSDKTHTC PPCPAPEAA GG (SEQ ID NO: 10) | (SEQ ID NO: 34) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALGAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1FcSilent (IL-12 p35) Heterodimerization mutations: Q347R/D399V/F405T Substitution for stabilizing disulfide bond: S354C Substitutions for reducing FcγR binding: L234A, L235A, P329G C220 in the upper hinge is mutated to S |

Construct 10

| EPKSSDKTH TCPPCPAPEA EGA (SEQ ID NO: 11) | (SEQ ID NO: 35) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPEAEGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP SSIEKTISKA KGQPREPQVC TLPPSRDELT ENQVSLTCLV KGFYPSDIAV EWESNGQPEN NYKTTPPVLD SDGSFFLYSW LTVDKSRWQQ GNVFSCSVMH EALHNHYTQK SLSLSPG | IgG1 Fc (IL-12 p40) Heterodimerization mutations: K360E/K409W Substitution for stabilizing disulfide bond: Y349C Substitutions for reducing FcγR and C1q binding: L234A, L235E, G237A, A330S, P331S |
| GGGGSGGG GSGGGGSEP KSSDKTHTC PPCPAPEAG A (SEQ ID NO: 12) | (SEQ ID NO: 36) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGGGSGGGGSGGG GSEPKSSDKT HTCPPCPAPE AEGAPSVFLF PPKPKDTLMISRTPEVTCVV VDVSHEDPEV KFNWYVDGVE VHNAKTKPRE EQYNSTYRVV SVLTVLHQDW LNGKEYKCKV SNKALPSSIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 Fc (IL-12 p35) Heterodimerization mutations: Q347R/D399V/F405T Substitution for stabilizing disulfide bond: S354C Substitutions for reducing FcγR and C1q binding: L234A, L235E, G237A, A330S, P331S |

Construct 11

| RVESKYGPP CPPCPAPEFL GG (SEQ ID NO: 2) | (SEQ ID NO: 37) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI | IgG4 Fc (IL-12 p40) Heterodimerization mutations: K370E/R409W Substitution for stabilizing disulfide bond: Y349C |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | Substitution for preventing Fab-Arm exchange and improving thermostability: S228P |
| RVESKYGPP CPPCPAPEFL GG (SEQ ID NO: 2) | (SEQ ID NO: 38) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRVMSYLNASRVESKYGPPCPPC PAPEFLGGPSVFLFPPKPKDTLMISRTPEVTCV VVDVSQEDPEVQFNWYV DGVEVHNAKT KPREEQFNST YRVVSVLTVL HQDWLNGKEY KCKVSNKGLPSSIEKTISKAKGQPREPQVYTLP PCQENMT KNQVSLTCLVKGFYPSDIAV EWESNGQPEN NYKTTPPVLV SDGSFTLYSR LTVDKSRWQEGNVFSCSVMH EALHNHYTQK SLSLSLG | IgG4 Fc (IL-12 p35) Heterodimerization mutations: E357N/D399V/F405T Substitution for stabilizing disulfide bond: S354C Substitution for preventing Fab-Arm exchange and improving thermostability: S228P |

Construct 12

| Linker Sequence | Sequences of Heterodimeric Fc-fused Proteins* | Type of IgG (IL-12 subunit); mutations/ substitutions |
|---|---|---|
| RVESKYGPP CPPCPAPEFL GG (SEQ ID NO: 2) | (SEQ ID NO: 39) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | IgG4 Fc (IL-12 p40) Heterodimerization mutations: K370E/R409W Substitution for stabilizing disulfide bond: Y349C Substitution for preventing Fab-Arm exchange and improving thermostability: S228P |
| GGGGSRVES KYGPPCPPCP APEFLGG (SEQ ID NO: 13) | (SEQ ID NO: 40) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPQVYTLPPC QENMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 Fc (IL-12 p35) Heterodimerization mutations: E357N/D399V/F405T Substitution for stabilizing disulfide bond: S354C Substitution for preventing Fab-Arm exchange and improving thermostability: S228P |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| Construct 13 | | |
| RVESKYGPP CPPCPAPEFL GG (SEQ ID NO: 2) | (SEQ ID NO: 41) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | IgG4 Fc (IL-12 p40) Heterodimerization mutations: K370E/R409W Substitution for stabilizing disulfide bond: Y349C Substitution for preventing Fab-Arm exchange and improving thermostability: S228P |
| GGGGSGGG GSRVESKYG PPCPPCPAPE FLGG (SEQ ID NO: 14) | (SEQ ID NO: 42) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGGGSGGGGSRVE SKYGPPCPPC PAPEFLGGPS VFLFPPKPKD TLMISRTPEVTCVVVDVSQE DPEVQFNWYV DGVEVHNAKT KPREEQFNST YRVVSVLTVL HQDWLNGKEYKCKVSNKGLPS SIEKTISKA KGQPREPQVYTLPPCQENMTKNQVSLTCLV KGFYPSDIAVEWESNGQPEN NYKTTPPVLV SDGSFTLYSRLTVDKSRWQE GNVFSCSVMH EALHNHYTQK SLSLSLG | IgG4 Fc (IL-12 p35) Heterodimerization mutations: E357N/D399V/F405T Substitution for stabilizing disulfide bond: S354C Substitution for preventing Fab-Arm exchange and improving thermostability: S228P |
| Construct 14 | | |
| EPKSSDKTH TCPPCPAPEL LGG (SEQ ID NO: 7) | (SEQ ID NO: 43) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPELLGGPS VFLFPPKPKD TLMISRTPEVTCVVVDVSHE DPEVKFNWYV DGVEVHNAKT KPREEQYNST YRVVSVLTVLHQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 Fc (IL-12 p40) Heterodimerization mutations: K360E/K409W Substitution for stabilizing disulfide bond: Y349C C220 in the upper hinge is mutated to S |
| EPKSSDKTH TCPPCPAPEL LGG (SEQ ID NO: 7) | (SEQ ID NO: 44) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASEPKSSDKTHTCPP CPAPELLGGP SVFLFPPKPK DTLMISRTPE VTCVVVDVSH EDPEVKFNWYVDGVEVHNAK TKPREEQYNS TYRVVSVLTV LHQDWLNGKE | IgG1 Fc (IL-12 p35) Heterodimerization mutations: Q347R/D399V/F405T Substitution for stabilizing disulfide bond: S354C C220 in the upper hinge is mutated to S |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | YKCKVSNKALPAPIEKTISKAKGQPREPRVYTL PPCRDELTKNQVSLTCLVKGFYPSDIAVEWES NGQPENNYKTTPPVLVSDGSFTLYSKLTVDKS RWQQGNVFSCSVM HEALHNHYTQ KSLSLSPG | |

Construct 15

| EPKSSDKTH TCPPCPAPEL LGG (SEQ ID NO: 7) | (SEQ ID NO: 45) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPELLGGPS VFLFPPKPKD TLMISRTPEVTCVVVDVSHE DPEVKFNWYV DGVEVHNAKT KPREEQYNST YRVVSVLTVLHQDWLNGKEY KCKVSNKALP APIEKTISKA KGQPREPQVCTLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 Fc (IL-12 p40) Heterodimerization mutations: K360E/K409W Substitution for stabilizing disulfide bond: Y349C C220 in the upper hinge is mutated to S |
| GGGGSEPKS SDKTHTCPP CP APE LLGG (SEQ ID NO: 15) | (SEQ ID NO: 46) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGGGSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 Fc (IL-12 p35) Heterodimerization mutations: Q347R/D399V/F405T Substitution for stabilizing disulfide bond: S354C C220 in the upper hinge is mutated to S |

Construct 16

| EPKSSDKTH TCPPCPAPEL LGG (SEQ ID NO: 7) | (SEQ ID NO: 47) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPELLGGPS VFLFPPKPKD TLMISRTPEVTCVVVDVSHE DPEVKFNWYV DGVEVHNAKT KPREEQYNST YRVVSVLTVLHQDWLNGKEY KCKVSNKALP APIEKTISKA KGQPREPQVC TLPPSRDELT ENQVSLTCLV KGFYPSDIAV EWESNGQPEN nykttppvld SDGSFFLYSWLTVDKSRWQQ GNVFSCSVMH EALHNHYTQK SLSLSPG | IgG1 Fc (IL-12 p40) Heterodimerization mutations: K360E/K409W Substitution for stabilizing disulfide bond: Y349C C220 in the upper hinge is mutated to S |
| GGGGSGGG GSEPKSSDK THTCPPCPAP ELLGG (SEQ ID NO: 16) | (SEQ ID NO: 48) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF | IgG1 Fc (IL-12 p35) Heterodimerization mutations: Q347R/D399V/F405T Substitution for |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | NSETVPQKSS LEEPDFYKTK IKLCILLHAF RIRAVTIDRVMSYLNASGGG GSGGGGSEPK SSDKTHTCPPCPAPELLGGP SVFLFPPKPK DTLMISRTPEVTC VVVDVSH EDPEVKFNWY VDGVEVHNAK TKPREEQYNS TYRWSVLTV LHQDWLNGKE YKCKVSNKAL PAPIEKTISK AKGQPREPRV YTLPPCRDELTKNQVSLTCL VKGFYPSDIA VEWESNGQPE NNYKTTPPVL VSDGSFTLYSKLTVDKSRWQ QGNVFSCSVM HEALHNHYTQ KSLSLSPG | stabilizing disulfide bond: S354C C220 in the upper hinge is mutated to S |

Construct 17

| GGGGSGGG GSGGGGSEP KSSDKTHTC PPCPAPELLG G (SEQ ID NO: 8) | (SEQ ID NO: 49) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSGGGGSGGG GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNK ALPAPIE KTISKAKGQP REPQVCTLPPSRDELTENQV SLTCLVKGFY PSDIAVEWES NGQPENNYKT TPPVLDSDGS FFLYSWLTVD KSRWQQGNVF SCSVMHEALH NHYTQKSLSL SPG | IgG1 Fc (IL-12 p35) Heterodimerization mutations: K360E/K409W Substitution for stabilizing disulfide bond: Y349C C220 in the upper hinge is mutated to S |
| EPKSSDKTH TCPPCPAPEL LGG (SEQ ID NO: 7) | (SEQ ID NO: 50) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSEPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPRVY TLPPCRDELT KNQVSLTCLV KGFYPSDIAV EWESNGQPEN NYKTTPPVLV SDGSFTLYSK LTVDKSRWQQ GNVFSCSVMH EALHNHYTQK SLSLSPG | IgG1 Fc (IL-12 p40) Heterodimerization mutations: Q347R/D399V/F405T Substitution for stabilizing disulfide bond: S354C C220 in the upper hinge is mutated to S |

Construct 18

| GGGGSEPKS SDKTHTCPP CPAPELLGG (SEQ ID NO: 15) | (SEQ ID NO: 51) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RYYSSSWSEW ASVPCSGGGG SEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVCTLPPS RDELTENQVS LTCLVKGFYP SDIAVEWESN GQPENNYKTT PPVLDSDGSF FLYSWLTVDK SRWQQGNVFS CSVMHEALHN HYTQKSLSLS PG | IgG1 (IL-12 p40) Heterodimerization mutations: K360E/K409W Substitution for stabilizing disulfide bond: Y349C C220 in the upper hinge is mutated to S |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| GGGGSEPKS SDKTHTCPP CPAPELLGG (SEQ ID NO: 15) | (SEQ ID NO: 52) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRAVTIDRV MSYLNASGGG GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T Substitution for stabilizing disulfide bond: S354C C220 in the upper hinge is mutated to S |

Construct 19

| GGGGSEPKS SDKTHTCPP CPAPELLGG (SEQ ID NO: 15) | (SEQ ID NO: 53) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSGGGG SEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVCTLPPS RDELTENQVS LTCLVKGFYP SDIAVEWESN GQPENNYKTT PPVLDSDGSF FLYSWLTVDK SRWQQGNVFS CSVMHEALHN HYTQKSLSLS PG | IgG1 (IL-12 p40) Heterodimerization mutations: K360E/K409W p40 substitutions: C177S, Y292C (native disulfide bond between subunits is deleted) |
| GGGGSEPKS SDKTHTCPP CPAPELLGG (SEQ ID NO: 15) | (SEQ ID NO: 54) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGGGSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T p35 substitutions: C74S V185C (native disulfide bond between subunits is deleted) |

Construct 19-1

| RVESKYGPP CPPCPAPEFL GG (SEQ ID NO: 2) | (SEQ ID NO: 69) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY | IgG4 (IL-12 p40) Heterodimerization mutations: K370E/R409W p40 substitutions: C177S, Y292C (native disulfide bond between subunits is deleted) Substitution for preventing Fab-Arm exchange and improving thermostability: S228P |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | |
| GGGGSGGG GSGGGGSRV ESKYGPPCPP CPAPEFLGG (SEQ ID NO: 3) | (SEQ ID NO: 70) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGPPCPPCPAPEFLGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPQVYTLPPCQENMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: E357N/D399V/F405T p35 substitutions: C74S V185C Substitution for preventing Fab-Arm exchange and improving thermostability: S228P |

Construct 19-2

| Linker Sequence | Sequences of Heterodimeric Fc-fused Proteins* | Type of IgG (IL-12 subunit); mutations/ substitutions |
|---|---|---|
| RVESKYGPP CPPCPAPEFL GG (SEQ ID NO: 2) | (SEQ ID NO: 71) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W p40 substitutions: C177S, Y292C (native disulfide bond between subunits is deleted) Substitution for preventing Fab-Arm exchange and improving thermostability: S228P |
| GGGGSGGG GSGGGGSRV ESKYGPPCPP CPAPEFLGG (SEQ ID NO: 3) | (SEQ ID NO: 72) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T p35 substitutions: C74S V185C Substitution for preventing Fab-Arm exchange and improving thermostability: S228P |

Construct 19-3

| Linker Sequence | Sequences of Heterodimeric Fc-fused Proteins* | Type of IgG (IL-12 subunit); mutations/ substitutions |
|---|---|---|
| RVESKYGPP CPPCPAPEFE GG (SEQ ID NO: 4) | (SEQ ID NO: 73) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW | IgG4 (IL-12 p40) Heterodimerization mutations: K360E/R409W p40 substitutions: C177S, Y292C (native disulfide bond between subunits is deleted) |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | STPHSYFSLT FCVQVQGKSK REKKDRVFTD KTSATVICRK NASISVRAQD RCYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | Substitution for preventing Fab-Arm exchange and improving thermostability: S228P Substitutions for reducing FcγR binding: S228P and L235E |
| GGGGSGGG GSGGGGSRV ESKYGPPCPP CPAPEFEGG (SEQ ID NO: 5) | (SEQ ID NO: 74) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPC QEEMTKNQVS LTCLVKGFYP SDIAVEWESN GQPENNYKTT PPVLSDGSF TLYSRLTVDK SRWQEGNVFS CSVMHEALHN HYTQKSLSLS LG | IgG4 (IL-12 p35) Heterodimerization mutations: Q347R/D399V/F405T p35 substitutions: C74S V185C Substitution for preventing Fab-Arm exchange and improving thermostability: S228P Substitutions for reducing FcγR binding: S228P and L235E |

Construct 19-4

| Linker Sequence | Sequences of Heterodimeric Fc-fused Proteins* | Type of IgG (IL-12 subunit); mutations/ substitutions |
|---|---|---|
| RVESKYGPP CPPCPAPEFE GG (SEQ ID NO: 4) | (SEQ ID NO: 75) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLAS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W p40 substitutions: C177S, Y292C (native disulfide bond between subunits is deleted) Substitution for preventing Fab-Arm exchange and improving thermostability: S228P Substitutions for reducing FcγR binding: S228P, L235E, P329A |
| GGGGSGGG GSGGGGSRV ESKYGPPCPP CPAPEFEGG (SEQ ID NO: 5) | (SEQ ID NO: 76) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLASSIEK TISKAKGQPR EPRVYTLPPC QEEMTKNQVS LTCLVKGFYP SDIAVEWESN GQPENNYKTT PPVLSDGSF TLYSRLTVDK SRWQEGNVFS CSVMHEALHN HYTQKSLSLS LG | IgG4 (IL-12 p35) Heterodimerization mutations: Q347R/D399V/F405T p35 substitutions: C74S V185C Substitution for preventing Fab-Arm exchange and improving thermostability: S228P Substitutions for reducing FcγR binding: S228P, L235E, P329A |

Construct 19-5

| Linker Sequence | Sequences of Heterodimeric Fc-fused Proteins* | Type of IgG (IL-12 subunit); mutations/ substitutions |
|---|---|---|
| RVESKYGPP CPPCPAPEFE GG (SEQ ID NO: 4) | (SEQ ID NO: 77) IWELKKDVYV VELDWYPDAP GEMVVLTCDT PEEDGITWTL DQSSEVLGSG KTLTIRVKEF GDAGQYTCHK GGEVLSHSLL LLHKKEDGIW | IgG4 (IL-12 p40) Heterodimerization mutations: K360E/R409W |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLGS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | p40 substitutions: C177S, Y292C (native disulfide bond between subunits is deleted) Substitution for preventing Fab-Arm exchange and improving thermostability: S228P Substitutions for reducing FcγR binding: S228P, L235E, P329G |
| GGGGSGGG GSGGGGSRV ESKYGPPCPP CPAPEFEGG (SEQ ID NO: 5) | (SEQ ID NO: 78) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLGSSIEK TISKAKGQPR EPRVYTLPPC QEEMTKNQVS LTCLVKGFYP SDIAVEWESN GQPENNYKTT PPVLSDGSF TLYSRLTVDK SRWQEGNVFS CSVMHEALHN HYTQKSLSLS LG | IgG4 (IL-12 p35) Heterodimerization mutations: Q347R/D399V/F405T p35 substitutions: C74S V185C Substitution for preventing Fab-Arm exchange and improving thermostability: S228P Substitutions for reducing FcγR binding: S228P, L235E, P329G |

Construct 19-6

| Linker Sequence | Sequences of Heterodimeric Fc-fused Proteins* | Type of IgG (IL-12 subunit); mutations/ substitutions |
|---|---|---|
| EPKSSDKTH TCPPCPAPEL LGG (SEQ ID NO: 7) | (SEQ ID NO: 79) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitutions: C177S, Y292C (native disulfide bond between subunits is deleted) C220 in the upper hinge is mutated to S |
| GGGGSGGG GSGGGGSEP KSSDKTHTC PPCPAPELLG G (SEQ ID NO: 8) | (SEQ ID NO: 80) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLSDGSFTLYSKLTVD KSRWQQGNVF SCSVMHEALH NHYTQKSLSL SPG | IgG1 (IL-12 p35) Heterodimerization mutations: Q347R/D399V/F405T p35 substitutions: C74S V185C C220 in the upper hinge is mutated to S |

TABLE 5-continued

Exemplary Dimeric Fc-fused Proteins

| Linker Sequence | Sequences of Heterodimeric Fc-fused Proteins* | Type of IgG (IL-12 subunit); mutations/substitutions |
|---|---|---|
| | Construct 19-7 | |
| EPKSSDKTH TCPPCPAPEA AGG (SEQ ID NO: 9) | (SEQ ID NO: 81) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VFLFPPKPKD TLMISRTPEV TCVVVDVSHE DPEVKFNWYV DGVEVHNAKT KPREEQYNST YRVVSVLTVLHQDWLNGKEY KCKVSNKALP APIEKTISKAKGQPREPQVCTLPPSRDELTENQ VSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitutions: C177S, Y292C (native disulfide bond between subunits is deleted) Substitutions for reducing FcγR binding: L234A, L235A C220 in the upper hinge is mutated to S |
| GGGGSGGG GSGGGGSEP KSSDKTHTC PPCPAPEAA GG (SEQ ID NO: 10) | (SEQ ID NO: 82) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T p35 substitutions: C74S V185C Substitutions for reducing FcγR binding: L234A, L235A C220 in the upper hinge is mutated to S |
| | Construct 19-8 | |
| EPKSSDKTH TCPPCPAPEA AGG (SEQ ID NO: 9) | (SEQ ID NO: 83) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VFLFPPKPKD TLMISRTPEVTCVVVDVSHE DPEVKFNWYV DGVEVHNAKT KPREEQYNST YRVVSVLTVL HQDWLNGKEYKCKVSNKALA APIEKTISKAKGQPREPQVCTLPPSRDELTENQ VSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitutions: C177S, Y292C (native disulfide bond between subunits is deleted) Substitutions for reducing FcγR binding: L234A, L235A, P329A C220 in the upper hinge is mutated to S |
| GGGGSGGG GSGGGGSEP KSSDKTHTC PPCPAPEAA GG (SEQ ID NO: 10) | (SEQ ID NO: 84) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMISRTPEVTCVV VDVSHEDPEV KFNWYVDGVE VHNAKTKPRE EQYNSTYRVV | IgG1 (IL-12 p35) Heterodimerization mutations: Q347R/D399V/F405T p35 substitutions: C74S, V185C Substitutions for reducing FcγR binding: L234A, L235A, P329A C220 in the upper hinge is mutated to S |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | SVLTVLHQDW LNGKEYKCKV SNKALAAPIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | |

Construct 19-9

| EPKSSDKTH TCPPCPAPEA AGG (SEQ ID NO: 9) | (SEQ ID NO: 85) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VFLFPPKPKD TLMISRTPEVTCVVVDVSHE DPEVKFNWYV DGVEVHNAKT KPREEQYNST YRVVSVLTVLHQDWLNGKEY KCKVSNKALG APIEKTISKAKGQPREPQVCTLPPSRDELTENQ VSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitutions: C177S, Y292C (native disulfide bond between subunits is deleted) Substitutions for reducing FcγR binding: L234A/L235A/P329G C220 in the upper hinge is mutated to S |
| GGGGSGGG GSGGGGSEP KSSDKTHTC PPCPAPEAA GG (SEQ ID NO: 10) | (SEQ ID NO: 86) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALGAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T p35 substitutions: C74S V185C Substitutions for reducing FcγR binding: L234A, L235A, P329G C220 in the upper hinge is mutated to S |

Construct 19-10

| EPKSSDKTH TCPPCPAPEA EGA (SEQ ID NO: 11) | (SEQ ID NO: 87) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSASPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAEGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP SSIEKTISKAKGQPREPQVCTLPPSRDELTENQ VSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitutions: C177S, Y292C (native disulfide bond between subunits is deleted) Substitutions for reducing FcγR and C1q binding: L234A, L235E, G237A, A330S, P331S C220 in the upper hinge is mutated to S |
| GGGGSGGG GSGGGGSEP KSSDKTHTC PPCPAPEAEG A (SEQ ID NO: 12) | (SEQ ID NO: 88) RNLPVATPDP GMFPCLHHSQ NLLRAVSNML QKARQTLEFY PCTSEEIDHV DITKDKTSTV EACLPLELTKNESSLNSRET SFITNGSCLA SRKTSFMMAL CLSSIYEDLK MYQVEFKTMN AKLLMDPKRQ IFLDQNMLAV IDELMQALNF | IgG1 (IL-12 p35) Heterodimerization mutations: Q347R/D399V/F405T p35 substitutions: C74S, V185C |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | NSETVPQKSS LEEPDFYKTK IKLCILLHAF RIRACTIDRV MSYLNASGGG GSGGGGSGGG GSEPKSSDKT HTCPPCPAPE AEGAPSVFLF PPKPKDTLMISRTPEVTCVV VDVSHEDPEV KFNWYVDGVE VHNAKTKPRE EQYNSTYRVV SVLTVLHQDW LNGKEYKCKV SNKALPSSIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | Substitutions for reducing FcγR and C1q binding: L234A, L235E, G237A, A330S, P331S C220 in the upper hinge is mutated to S |

Construct 20

| Linker Sequence | Sequences of Heterodimeric Fc-fused Proteins* | Type of IgG (IL-12 subunit); mutations/ substitutions |
|---|---|---|
| RVESKYGPP CPPCPAPEFL GG (SEQ ID NO: 2) | (SEQ ID NO: 55) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTK NQVSLTCLVE GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K370E/R409W p40 substitution: Y292C (native disulfide bond between subunits is preserved) Substitution for preventing Fab-Arm exchange and improving thermostability: S228P |
| GGGGSGGG GSGGGGSRV ESKYGPPCPP CPAPEFLGG (SEQ ID NO: 3) | (SEQ ID NO: 56) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPQVYTLPPC QENMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: E357N/D399V/F405T p35 substitution: V185C (native disulfide bond between subunits is preserved) Substitution for preventing Fab-Arm exchange and improving thermostability: S228P |

Construct 20-1

| Linker Sequence | Sequences of Heterodimeric Fc-fused Proteins* | Type of IgG (IL-12 subunit); mutations/ substitutions |
|---|---|---|
| RVESKYGPP CPPCPAPEFL GG (SEQ ID NO: 2) | (SEQ ID NO: 89) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W p40 substitution: Y292C (native disulfide bond between subunits is preserved) Substitution for preventing Fab-Arm exchange and improving thermostability: S228P |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| GGGGSGGG GSGGGGSRV ESKYGPPCPP CPAPEFLGG (SEQ ID NO: 3) | (SEQ ID NO: 90) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPCQEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T p35 substitution: V185C (native disulfide bond between subunits is preserved) Substitution for preventing Fab-Arm exchange and improving thermostability: S228P |

Construct 20-2

| Linker Sequence | Sequences of Heterodimeric Fc-fused Proteins* | Type of IgG (IL-12 subunit); mutations/ substitutions |
|---|---|---|
| RVESKYGPP CPPCPAPEFE GG (SEQ ID NO: 4) | (SEQ ID NO: 91) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W p40 substitution: Y292C (native disulfide bond between subunits is preserved) Substitution for preventing Fab-Arm exchange and improving thermostability: S228P Substitutions for reducing FcγR binding: S228P and L235E |
| GGGGSGGG GSGGGGSRV ESKYGPPCPP CPAPEFEGG (SEQ ID NO: 5) | (SEQ ID NO: 92) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T p35 substitution: V185C (native disulfide bond between subunits is preserved) Substitution for preventing Fab-Arm exchange and improving thermostability: S228P Substitutions for reducing FcγR binding: S228P and L235E |

Construct 20-3

| Linker Sequence | Sequences of Heterodimeric Fc-fused Proteins* | Type of IgG (IL-12 subunit); mutations/ substitutions |
|---|---|---|
| RVESKYGPP CPPCPAPEFE GG (SEQ ID NO: 4) | (SEQ ID NO: 93) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY | IgG4 (IL-12 p40) Heterodimerization mutations: K360E/R409W p40 substitution: Y292C (native disulfide bond between subunits is preserved) Substitution for preventing Fab-Arm exchange and improving thermostability: S228P Substitutions for |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | RVVSVLTVLH QDWLNGKEYK CKVSNKGLAS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | reducing FcγR binding: S228P, L235E, P329A |
| GGGGSGGG GSGGGGSRV ESKYGPPCPP CPAPEFEGG (SEQ ID NO: 5) | (SEQ ID NO: 94) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLASSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T p35 substitution: V185C (native disulfide bond between subunits is preserved) Substitution for preventing Fab-Arm exchange and improving thermostability: S228P Substitutions for reducing FcγR binding: S228P, L235E, P329A |

Construct 20-4

| Linker Sequence | Sequences of Heterodimeric Fc-fused Proteins* | Type of IgG (IL-12 subunit); mutations/ substitutions |
|---|---|---|
| RVESKYGPP CPPCPAPEFE GG (SEQ ID NO: 4) | (SEQ ID NO: 95) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSRVES KYGPPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLGS SIEKTISKAK GQPREPQVCT LPPSQEEMTE NQVSLTCLVK GFYPSDIAVE WESNGQPENN YKTTPPVLDS DGSFFLYSWL TVDKSRWQEG NVFSCSVMHE ALHNHYTQKS LSLSLG | IgG4 (IL-12 p40) Heterodimerization mutations: K360E/R409W p40 substitution: Y292C (native disulfide bond between subunits is preserved) Substitution for preventing Fab-Arm exchange and improving thermostability: S228P Substitutions for reducing FcγR binding: S228P, L235E, P329G |
| GGGGSGGG GSGGGGSRV ESKYGPPCPP CPAPEFEGG (SEQ ID NO: 5) | (SEQ ID NO: 96) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSRVESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLGSSIEK TISKAKGQPR EPRVYTLPPC QEEMTKNQVS LTCLVKGFYP SDIAVEWESN GQPENNYKTT PPVLVSDGSF TLYSRLTVDK SRWQEGNVFS CSVMHEALHN HYTQKSLSLS LG | IgG4 (IL-12 p35) Heterodimerization mutations: Q347R/D399V/F405T p35 substitution: V185C (native disulfide bond between subunits is preserved) Substitution for preventing Fab-Arm exchange and improving thermostability: S228P Substitutions for reducing FcγR binding: S228P, L235E, P329G |

Construct 20-5

| Linker Sequence | Sequences of Heterodimeric Fc-fused Proteins* | Type of IgG (IL-12 subunit); mutations/ substitutions |
|---|---|---|
| EPKSSDKTH TCPPCPAPEL LGG (SEQ ID NO: 7) | (SEQ ID NO: 97) IWELKKDVYV VELDWYPDAP GEMVVLTCDT PEEDGITWTL DQSSEVLGSG KTLTIRVKEF GDAGQYTCHK GGEVLSHSLL LLHKKEDGIW | IgG1 (IL-12 p40) Heterodimerization mutations: K360E/K409W |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | p40 substitution: Y292C (native disulfide bond between subunits is preserved) C220 in the upper hinge is mutated to S |
| GGGGSGGG GSGGGGSEP KSSDKTHTC PPCPAPELLG G (SEQ ID NO: 8) | (SEQ ID NO: 98) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGSFTLYSKLTVD KSRWQQGNVF SCSVMHEALH NHYTQKSLSL SPG | IgG1 (IL-12 p35) Heterodimerization mutations: Q347R/D399V/F405T Substitution for stabilizing disulfide bond: S354C p35 substitution: V185C (native disulfide bond between subunits is preserved) C220 in the upper hinge is mutated to S |

Construct 20-6

| Linker Sequence | Sequences of Heterodimeric Fc-fused Proteins* | Type of IgG (IL-12 subunit); mutations/ substitutions |
|---|---|---|
| EPKSSDKTH TCPPCPAPEA AGG (SEQ ID NO: 9) | (SEQ ID NO: 99) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VFLFPPKPKD TLMISRTPEV TCVVVDVSHE DPEVKFNWYV DGVEVHNAKT KPREEQYNST YRVVSVLTVLHQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitution: Y292C (native disulfide bond between subunits is preserved) Substitutions for reducing FcγR binding: L234A, L235A C220 in the upper hinge is mutated to S |
| GGGGSGGG GSGGGGSEP KSSDKTHTC PPCPAPEAA GG (SEQ ID NO: 10) | (SEQ ID NO: 100) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T p35 substitution: V185C (native disulfide bond between subunits is preserved) Substitutions for reducing FcγR binding: L234A, L235A C220 in the upper hinge is mutated to S |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | Construct 20-7 | |
| EPKSSDKTH TCPPCPAPEA AGG (SEQ ID NO: 9) | (SEQ ID NO: 101) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VPLFPPKPKD TLMISRTPEVTCVVVDVSHE DPEVKFNWYV DGVEVHNAKT KPREEQYNST YRVVSVLTVLHQDWLNGKEY KCKVSNKALA APIEKTISKAKGQPREPQVCTLPPSRDELTENQ VSLTCLVKGFYPSDIAVEWESNGQPENNYKTT PPVLDSDGSFFLYSWLTVDKSRWQQGNVFSCS VMH EALHNHYTQK SLSLSPG | IgG1 (IL-12 p40) Heterodimerization mutations: K360E/K409W p40 substitution: Y292C (native disulfide bond between subunits is preserved) Substitutions for reducing FcγR binding: L234A, L235A, P329A C220 in the upper hinge is mutated to S |
| GGGGSGGG GSGGGGSEP KSSDKTHTC PPCPAPEAA GG (SEQ ID NO: 10) | (SEQ ID NO: 102) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGGGSGGGGSGGG GSEPKSSDKT HTCPPCPAPEAAGGPSVFLF PPKPKDTLMISRTPEVTCVVVDVSHEDPEV KFNWYVDGVE VHNAKTKPRE EQYNSTYRVV SVLTVLHQDW LNGKEYKCKV SNKALAAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T p35 substitution: V185C (native disulfide bond between subunits is preserved) Substitutions for reducing FcγR binding: L234A, L235A, P329A C220 in the upper hinge is mutated to S |
| | Construct 20-8 | |
| EPKSSDKTH TCPPCPAPEA AGG (SEQ ID NO: 9) | (SEQ ID NO: 103) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VPLFPPKPKD TLMISRTPEVTCVVVDVSHE DPEVKFNWYV DGVEVHNAKT KPREEQYNST YRVVSVLTVLHQDWLNGKEY KCKVSNKALG APIEKTISKA KGQPREPQVC TLPPSRDELTENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitution: Y292C (native disulfide bond between subunits is preserved) Substitutions for reducing FcγR binding: L234A, L235A, P329G C220 in the upper hinge is mutated to S |
| GGGGSGGG GSGGGGSEP KSSDKTHTC PPCPAPEAA GG (SEQ ID NO: 10) | (SEQ ID NO: 104) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGGGSGGGGSGGG GSEPKSSDKT HTCPPCPAPEAAGGPSVFLF PPKPKDTLMI SRTPEVTCVV VDVSHEDPEV | IgG1 (IL-12 p35) Heterodimerization mutations: Q347R/D399V/F405T p35 substitution: V185C (native disulfide bond between subunits is preserved) Substitutions for reducing FcγR binding: |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | KFNWYVDGVE VHNAKTKPRE EQYNSTYRVV SVLTVLHQDW LNGKEYKCKV SNKALGAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALH NHYTQKSLSL SPG | L234A, L235A, P329G C220 in the upper hinge is mutated to S |

Construct 20-9

| Linker Sequence | Sequences of Heterodimeric Fc-fused Proteins* | Type of IgG (IL-12 subunit); mutations/ substitutions |
|---|---|---|
| EPKSSDKTH TCPPCPAPEA EGA (SEQ ID NO: 11) | (SEQ ID NO: 105) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAEGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP SSIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | IgG1 (IL-12 p40) Heterodimerization mutations: K360E/K409W p40 substitution: Y292C (native disulfide bond between subunits is preserved) Substitutions for reducing FcγR and C1q binding: L234A, L235E, G237A, A330S, P331S C220 in the upper hinge is mutated to S |
| GGGGSGGG GSGGGGSEP KSSDKTHTC PPCPAPEAEG A (SEQ ID NO: 12) | (SEQ ID NO: 106) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AEGAPSVFLF PPKPKDTLMISRTPEVTCVV VDVSHEDPEV KFNWYVDGVE VHNAKTKPRE EQYNSTYRVV SVLTVLHQDW LNGKEYKCKV SNKALPSSIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T p35 substitution: V185C (native disulfide bond between subunits is preserved) Substitutions for reducing FcγR and C1q binding: L234A, L235E, G237A, A330S, P331S C220 in the upper hinge is mutated to S |

Construct 21

| Linker Sequence | Sequences of Heterodimeric Fc-fused Proteins* | Type of IgG (IL-12 subunit); mutations/ substitutions |
|---|---|---|
| EPKSSDKTH TCPPCPAPEA AGG (SEQ ID NO: 9) | (SEQ ID NO: 57) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAAGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSRDELT ENQVSLTCLV KGFYPSDIAV EWESNGQPEN NYKTTPPVLD SDGSFFLYSW LTVDKSRWQQ GNVFSCSVMH EALHNHYTQK SLSLSPG | IgG1 (IL-12 p40) Heterodimerization mutations: K360E/K409W Substitution for stabilizing disulfide bond: Y349C Substitutions for reducing FcγR binding: L234A, L235A Additional mutation in p40: Y292C to introduce IL-12 stabilizing disulfide bond C220 in the upper hinge is mutated to S |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| GGGGSGGG GSGGGGSEP KSSDKTHTC PPCPAPEAA GG (SEQ ID NO: 10) | (SEQ ID NO: 58) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPRVYTLPPCRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T Substitution for stabilizing disulfide bond: S354C Substitutions for reducing FcγR binding: L234A, L235A Additional mutation in p35: V185C to introduce IL-12 stabilizing disulfide bond C220 in the upper hinge is mutated to S |

Construct 22

| Linker Sequence | Sequences of Heterodimeric Fc-fused Proteins* | Type of IgG (IL-12 subunit); mutations/ substitutions |
|---|---|---|
| EPKSSDKTH TCPPCPAPEA AGG (SEQ ID NO: 9) | (SEQ ID NO: 59) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEWASVPCSEPKS SDKTHTCPPC PAPEAAGGPS VFLFPPKPKD TLMISRTPEV TCVVVDVSHEDPEVKFNWYVDGVEVHNAKT KPREEQYNST YRVVSVLTVLHQDWLNGKEY KCKVSNKALA APIEKTISKA KGQPREPQVC TLPPSRDELT ENQVSLTCLV KGFYPSDIAV EWESNGQPENNYKTTPPVLSDGSFFLYSWLT VDKSRWQQ GNVFSCSVMH EALHNHYTQK SLSLSPG | IgG1 (IL-12 p40) Heterodimerization mutations: K360E/K409W Substitution for stabilizing disulfide bond: Y349C Substitutions for reducing FcγR binding: L234A, L235A, P329A Additional mutation Y292C to introduce IL-12 stabilizing disulfide bond C220 in the upper hinge is mutated to S |
| GGGGSGGG GSGGGGSEP KSSDKTHTC PPCPAPEAA GG (SEQ ID NO: 10) | (SEQ ID NO: 60) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AAGGPSVFLF PPKPKDTLMISRTPEVTCVV VDVSHEDPEV KFNWYVDGVEVHNAKTKPREEQYNSTYRVV SVLTVLHQDW LNGKEYKCKV SNKALAAPIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T Substitution for stabilizing disulfide bond: S354C Substitutions for reducing FcγR binding: L234A, L235A, P329A Additional mutation V185C to introduce IL-12 stabilizing disulfide bond C220 in the upper hinge is mutated to S |

Construct 23

| Linker Sequence | Sequences of Heterodimeric Fc-fused Proteins* | Type of IgG (IL-12 subunit); mutations/ substitutions |
|---|---|---|
| EPKSSDKTH TCPPCPAPEA EGA (SEQ ID NO: 11) | (SEQ ID NO: 61) IWELKKDVYV VELDWYPDAP GEMVVLTCDT PEEDGITWTL DQSSEVLGSG KTLTIRVKEF GDAGQYTCHK GGEVLSHSLL LLHKKEDGIW STDILKDQKE PKNKTFLRCE AKNYSGRFTC WWLTTISTDL TFSVKSSRGS SDPQGVTCGA ATLSAERVRG DNKEYEYSVE CQEDSACPAA EESLPIEVMV DAVHKLKYEN YTSSFFIRDI IKPDPPKNLQ LKPLKNSRQV EVSWEYPDTW STPHSYFSLT FCVQVQGKSK REKKDRVFTD KTSATVICRK NASISVRAQD RCYSSSWSEW ASVPCSEPKS SDKTHTCPPC PAPEAEGAPS | IgG1 (IL-12 p40) Heterodimerization mutations: K360E/K409W Substitution for stabilizing disulfide bond: Y349C Substitutions for reducing FcγR and C1q binding: L234A, L235E, G237A, A330S, P331S |

TABLE 5-continued

Exemplary Dimeric Fc-fused Proteins

| Linker Sequence | Sequences of Heterodimeric Fc-fused Proteins* | Type of IgG (IL-12 subunit); mutations/ substitutions |
|---|---|---|
| | VFLFPPKPKD TLMISRTPEVTCVVVDVSHE DPEVKFNWYV DGVEVHNAKT KPREEQYNST YRVVSVLTVLHQDWLNGKEY KCKVSNKALP SSIEKTISKA KGQPREPQVC TLPPSRDELT ENQVSLTCLV KGFYPSDIAV EWESNGQPEN NYKTTPPVLD SDGSFFLYSWLTVDKSRWQQ GNVFSCSVMH EALHNHYTQK SLSLSPG | Additional mutation Y292C to introduce IL-12 stabilizing disulfide bond C220 in the upper hinge is mutated to S |
| GGGGSGGG GSGGGGSEP KSSDKTHTC PPCPAPEAEG A (SEQ ID NO: 12) | (SEQ ID NO: 62) RNLPVATPDP GMFPCLHHSQ NLLRAVSNML QKARQTLEFY PCTSEEIDHV DITKDKTSTV EACLPLELTK NESCLNSRET SFITNGSCLA SRKTSFMMAL CLSSIYEDLK MYQVEFKTMN AKLLMDPKRQ IFLDQNMLAV IDELMQALNF NSETVPQKSS LEEPDFYKTK IKLCILLHAF RIRACTIDRV MSYLNASGGG GSGGGGSGGG GSEPKSSDKT HTCPPCPAPE AEGAPSVFLF PPKPKDTLMISRTPEVTCVV VDVSHEDPEV KFNWYVDGVE VHNAKTKPRE EQYNSTYRVV SVLTVLHQDW LNGKEYKCKV SNKALPSSIE KTISKAKGQP REPRVYTLPP CRDELTKNQV SLTCLVKGFY PSDIAVEWES NGQPENNYKT TPPVLVSDGS FTLYSKLTVD KSRWQQGNVF SCSVMHEALH NHYTQKSLSL SPG | IgG1 (IL-12 p35) Heterodimerization mutations: Q347R/D399V/F405T Substitution for stabilizing disulfide bond: S354C Substitutions for reducing FcγR and C1q binding: L234A, L235E, G237A, A330S, P331S Additional mutation V185C to introduce IL-12 stabilizing disulfide bond C220 in the upper hinge is mutated to S |

*The amino acid sequences can further comprise a lysine (K) at the C-terminus.

IL-12 Subunits

IL-12 is a multi subunit protein including a p40 subunit and a p35 subunit. The amino acid sequence of mature wild-type IL-12 p40 is amino acids 23-328 of the GenBank Accession No. NP_002178.2, set forth in SEQ ID NO: 127 below. The amino acid sequence of mature wild-type IL-12 p35 is amino acids 57-253 of GenBank Accession No. NP_000873.2, set forth in SEQ ID NO: 128 below. The numbering of amino acid residues of p40 and p35 used herein corresponds to the mature wild-type protein sequences. As used herein, an IL-12 p40 subunit comprises an amino acid sequence at least 90% (e.g., at least 91%, 92%, 93%, 94%, 95%, 96%, 97%, 98%, or 99%) identical to SEQ ID NO: 127. As used herein, an IL-12 p35 subunit comprises an amino acid sequence at least 90% (e.g., at least 91%, 92%, 93% 94%, 95%, 96%, 97%, 98%, or 99%) identical to SEQ ID NO: 128.

In certain embodiments of any one of the foregoing aspects, the p40 and p35 subunits of IL-12 comprise the amino acid sequences of SEQ ID NOs: 121 and 122; 127 and 128; 201 and 202; 203 and 204; 123 and 124; or 125 and 126, respectively. In certain embodiments, the first polypeptide comprises the amino acid sequence of a p40 subunit of IL-12, and the second polypeptide comprises the amino acid sequence of a p35 subunit of IL-12. In certain embodiments, the first polypeptide comprises the amino acid sequence of a p35 subunit of IL-12, and the second polypeptide comprises the amino acid sequence of a p40 subunit of IL-12.

In certain embodiments, the present disclosure includes a heterodimeric Fc-fused protein comprising: a first polypeptide comprising a first antibody Fc domain polypeptide and a second polypeptide comprising a second antibody Fc domain polypeptide, wherein the first polypeptide further comprises a first subunit of IL-12 fused to the first antibody Fc domain polypeptide by a linker; and a second, different subunit of IL-12 is fused to the second antibody Fc domain polypeptide, wherein the first and second, different subunits of IL-12 are bound to each other, wherein the first antibody Fc domain polypeptide and the second antibody Fc domain polypeptide each contain different mutations promoting heterodimerization, wherein the first antibody Fc domain polypeptide and the second antibody Fc domain polypeptide are bound to each other, and wherein the first subunit of IL-12 is a p40 subunit with a Y292C substitution, and the second, different subunit of IL-12 is a p35 subunit with a V185C substitution. In certain embodiments, the first subunit and second, different subunit of IL-12 comprise the amino acid sequences of SEQ ID NOs: 125 and 126, respectively.

The first subunit and second, different subunit of IL-12 can be fused to any of the antibody Fc domain polypeptides via any linkers disclosed herein to form Fc-fused proteins having sequences including but not limited to Constructs 120, 120-1, 120-2, 120-3, 120-4, 120-5, 120-6, and 120-7 as described in Table 4 and Constructs 20, 20-1, 20-2, 20-3, 20-4, 20-5, 20-6, 20-7, 20-8, and 20-9 as described in Table 5.

In certain embodiments, the p40 subunit of IL-12 further comprises a replacement of C177, and the p35 subunit of IL-12 further comprises a replacement of C74. In certain embodiments, C177 in the p40 subunit of IL-12 is replaced by S, and C74 in the p35 subunit of IL-12 is replaced by S. In certain embodiments, the p40 and p35 subunits of IL-12 comprise the amino acid sequences of SEQ ID NOs: 123 and 124, respectively.

The first subunit and second, different subunit of IL-12 can be fused to any of the antibody Fc domain polypeptides via any linkers disclosed herein to form Fc-fused proteins having sequences including but not limited to Constructs 119, 119-1, 119-2, 119-3, 119-4, 119-5, 119-6, 119-7, and 119-8 as described in Table 4, and Constructs 19, 19-1, 19-2, 19-3, 19-4, 19-5, 19-6, 19-7, 19-8, 19-9, and 19-10 as described in Table 5.

TABLE 6

Human IL-12 p40 and p35 amino acid sequences

| IL-12 p40 | IL-12 p35 |
|---|---|
| Human IL-12 p40 wild-type<br>IWELKKDVYVVELDWYPDAPGEMVVLT<br>CDTPEEDGITWTLDQSSEVLGSGKTLTIQ<br>VKEFGDAGQYTCHKGGEVLSHSLLLLHK<br>KEDGIWSTDILKDQKEPKNKTFLRCEAK<br>NYSGRFTCWWLTTISTDLTFSVKSSRGSS<br>DPQGVTCGAATLSAERVRGDNKEYEYSV<br>ECQEDSACPAAEESLPIEVMVDAVHKLK<br>YENYTSSFFIRDIIKPDPPKNLQLKPLKNS<br>RQVEVSWEYPDTWSTPHSYFSLTFCVQV<br>QGKSKREKKDRVFTDKTSATVICRKNASI<br>SVRAQDRYYSSSWSEWASVPCS<br>(SEQ ID NO: 127) | Human IL-12 p35 wild-type<br>RNLPVATPDPGMFPCLHHSQNLLRAVSN<br>MLQKARQTLEFYPCTSEEIDHEDITKDKT<br>STVEACLPLELTKNESCLNSRETSFITNGS<br>CLASRKTSFMMALCLSSIYEDLKMYQVEF<br>KTMNAKLLMDPKRQIFLDQNMLAVIDEL<br>MQALNFNSETVPQKS SLEEPDFYKTKIKL<br>CILLHAFRIRAVTIDRVMSYLNAS<br>(SEQ ID NO: 128) |
| Human IL-12 p40 C177S Y292C<br>IWELKKDVYV VELDWYPDAP<br>GEMVVLTCDT PEEDGITWTL<br>DQSSEVLGSG KTLTIQVKEF<br>GDAGQYTCHK GGEVLSHSLL<br>LLHKKEDGIW STDILKDQKE<br>PKNKTFLRCE AKNYSGRFTC<br>WWLTTISTDL TFSVKSSRGS<br>SDPQGVTCGA ATLSAERVRG<br>DNKEYEYSVE CQEDSASPAA<br>EESLPIEVMV DAVHKLKYEN<br>YTSSFFIRDIIKPDPPKNLQ LKPLKNSRQV<br>EVSWEYPDTW STPHSYFSLT<br>FCVQVQGKSK REKKDRVFTD<br>KTSATVICRK NASISVRAQD<br>RCYSSSWSEW ASVPCS<br>(SEQ ID NO: 201) | Human IL-12 p35 C74S V185C<br>RNLPVATPDP GMFPCLHHSQ<br>NLLRAVSNML QKARQTLEFY<br>PCTSEEIDHE DITKDKTSTV<br>EACLPLELTKNESSLNSRET SFITNGSCLA<br>SRKTSFMMAL CLSSIYEDLK<br>MYQVEFKTMN AKLLMDPKRQ<br>IFLDQNMLAV IDELMQALNF<br>NSETVPQKSS LEEPDFYKTK<br>IKLCILLHAF RIRACTIDRV MSYLNAS<br>(SEQ ID NO: 202) |
| Human IL-12 p40 Y292C<br>IWELKKDVYV VELDWYPDAP<br>GEMVVLTCDT PEEDGITWTL<br>DQSSEVLGSG KTLTIQVKEF<br>GDAGQYTCHK GGEVLSHSLL<br>LLHKKEDGIW STDILKDQKE<br>PKNKTFLRCE AKNYSGRFTC<br>WWLTTISTDL TFSVKSSRGS<br>SDPQGVTCGA ATLSAERVRG<br>DNKEYEYSVE CQEDSACPAA<br>EESLPIEVMV DAVHKLKYEN<br>YTSSFFIRDIIKPDPPKNLQ LKPLKNSRQV<br>EVSWEYPDTW STPHSYFSLT<br>FCVQVQGKSK REKKDRVFTD<br>KTSATVICRK NASISVRAQD<br>RCYSSSWSEW ASVPCS<br>(SEQ ID NO: 203) | Human IL-12 p35 V185C<br>RNLPVATPDP GMFPCLHHSQ<br>NLLRAVSNML QKARQTLEFY<br>PCTSEEIDHE DITKDKTSTV<br>EACLPLELTK NESCLNSRET<br>SFITNGSCLA SRKTSFMMAL<br>CLSSIYEDLK MYQVEFKTMN<br>AKLLMDPKRQ IFLDQNMLAV<br>IDELMQALNF NSETVPQKSS<br>LEEPDFYKTK IKLCILLHAF RIRACTIDRV<br>MSYLNAS<br>(SEQ ID NO: 204) |
| Human IL-12 p40 Q56R<br>IWELKKDVYV VELDWYPDAP<br>GEMVVLTCDT PEEDGITWTL<br>DQSSEVLGSG KTLTIRVKEF<br>GDAGQYTCHK GGEVLSHSLL<br>LLHKKEDGIW STDILKDQKE<br>PKNKTFLRCE AKNYSGRFTC<br>WWLTTISTDL TFSVKSSRGS<br>SDPQGVTCGA ATLSAERVRG<br>DNKEYEYSVE CQEDSACPAA<br>EESLPIEVMV DAVHKLKYEN<br>YTSSFFIRDI IKPDPPKNLQ LKPLKNSRQV<br>EVSWEYPDTW STPHSYFSLT<br>FCVQVQGKSK REKKDRVFTD<br>KTSATVICRK NASISVRAQD<br>RYYSSSWSEW ASVPCS<br>(SEQ ID NO: 121) | Human IL-12 p35 E50V<br>RNLPVATPDP GMFPCLHHSQ<br>NLLRAVSNML QKARQTLEFY<br>PCTSEEIDHV DITKDKTSTV<br>EACLPLELTK NESCLNSRET<br>SFITNGSCLA SRKTSFMMAL<br>CLSSIYEDLK MYQVEFKTMN<br>AKLLMDPKRQ IFLDQNMLAV<br>IDELMQALNF NSETVPQKSS<br>LEEPDFYKTK IKLCILLHAF RIRAVTIDRV<br>MSYLNAS<br>(SEQ ID NO: 122) |
| Human IL-12 p40 Q56R C177S Y292C<br>IWELKKDVYV VELDWYPDAP<br>GEMVVLTCDT PEEDGITWTL<br>DQSSEVLGSG KTLTIRVKEF<br>GDAGQYTCHK GGEVLSHSLL<br>LLHKKEDGIW STDILKDQKE<br>PKNKTFLRCE AKNYSGRFTC<br>WWLTTISTDL TFSVKSSRGS | Human IL-12 p35 E50V C74S V185C<br>RNLPVATPDP GMFPCLHHSQ<br>NLLRAVSNML QKARQTLEFY<br>PCTSEEIDHV DITKDKTSTV<br>EACLPLELTK NESSLNSRET SFITNGSCLA<br>SRKTSFMMAL CLSSIYEDLK<br>MYQVEFKTMN AKLLMDPKRQ<br>IFLDQNMLAV IDELMQALNF |

TABLE 6-continued

Human IL-12 p40 and p35 amino acid sequences

| IL-12 p40 | IL-12 p35 |
|---|---|
| SDPQGVTCGA ATLSAERVRG<br>DNKEYEYSVE CQEDSASPAA<br>EESLPIEVMV DAVHKLKYEN<br>YTSSFFIRDI IKPDPPKNLQ LKPLKNSRQV<br>EVSWEYPDTW STPHSYFSLT<br>FCVQVQGKSK REKKDRVFTD<br>KTSATVICRK NASISVRAQD<br>RCYSSSWSEW ASVPCS<br>(SEQ ID NO: 123) | NSETVPQKSS LEEPDFYKTK<br>IKLCILLHAF RIRACTIDRV MSYLNAS<br>(SEQ ID NO: 124) |
| Human IL-12 p40 Q56R Y292C<br>IWELKKDVYV VELDWYPDAP<br>GEMVVLTCDT PEEDGITWTL<br>DQSSEVLGSG KTLTIRVKEF<br>GDAGQYTCHK GGEVLSHSLL<br>LLHKKEDGIW STDILKDQKE<br>PKNKTFLRCE AKNYSGRFTC<br>WWLTTISTDL TFSVKSSRGS<br>SDPQGVTCGA ATLSAERVRG<br>DNKEYEYSVE CQEDSACPAA<br>EESLPIEVMV DAVHKLKYEN<br>YTSSFFIRDIIKPDPPKNLQ LKPLKNSRQV<br>EVSWEYPDTW STPHSYFSLT<br>FCVQVQGKSK REKKDRVFTD<br>KTSATVICRK NASISVRAQD<br>RCYSSSWSEW ASVPCS<br>(SEQ ID NO: 125) | Human IL-12 p35 E50V V185C<br>RNLPVATPDP GMFPCLHHSQ<br>NLLRAVSNML QKARQTLEFY<br>PCTSEEIDHV DITKDKTSTV<br>EACLPLELTK NESCLNSRET<br>SFITNGSCLA SRKTSFMMAL<br>CLSSIYEDLK MYQVEFKTMN<br>AKLLMDPKRQ IFLDQNMLAV<br>IDELMQALNF NSETVPQKSS<br>LEEPDFYKTK IKLCILLHAF RIRACTIDRV<br>MSYLNAS<br>(SEQ ID NO: 126) |

In certain embodiments, a heterodimeric Fc-fused protein of the present invention comprises a first polypeptide comprising the amino acid sequence of SEQ ID NO:290 and a second polypeptide comprising the amino acid sequence of SEQ ID NO:291. In certain embodiments, the heterodimeric Fc-fused protein of the present invention comprising SEQ ID NO:290 and SEQ ID NO:291 comprises a Y349C mutation in the CH3 domain of the first antibody Fc domain polypeptide and a S354C mutation in the CH3 domain of the second antibody Fc domain polypeptide. In certain embodiments, the heterodimeric Fc-fused protein of the present invention comprising SEQ ID NO:290 and SEQ ID NO:291 comprise different mutations in the respective Fc domain polypeptide sequences for promoting heterodimerization between the Fc domains.

In certain embodiments, the first polypeptide sequence comprises a first antibody Fc domain polypeptide (human IgG1) sequence comprising K360E and K409W substitutions. In certain embodiments, the second polypeptide sequence comprises a second antibody Fc domain polypeptide (human IgG1) sequence comprising Q347R, D399V, and F405T substitutions. In certain embodiments, the first polypeptide and second polypeptide amino acid sequences comprise one or more mutations for reducing effector functions. In certain embodiments, the heterodimeric Fc-fused protein of the present invention comprises LALAPA (L234A, L235A, and P329A) mutations.

In certain embodiments, in the first polypeptide of the heterodimeric Fc-fused protein of the present invention (SEQ ID NO:290), the p40 subunit of human IL-12 is fused to the first antibody Fc domain polypeptide by a first linker comprising a first amino acid sequence, and in the second polypeptide of the heterodimeric Fc-fused protein of the present invention (SEQ ID NO:291), the p35 subunit of human IL-12 is fused to the second antibody Fc domain polypeptide by a second linker comprising a second amino acid sequence.

SEQ ID NO:290 is a sequence of p40 subunit of human IL-12 (underlined amino acids) fused to human IgG1 Fc domain polypeptide. Mutations are shown in bold.

(SEQ ID NO: 290)
<u>IWELKKDVYVVELDWYPDAPGEMVVLTCDTPEEDGI</u>

<u>TWTLDQSSEVLGSGKTLTIQVKEFGDAGQYTCHKG</u>

<u>GEVLSHSLLLLHKKEDGIWSTDILKDQKEPKNKTF</u>

<u>LRCEAKNYSGRFTCWWLTTISTDLTFSVKSSRGSS</u>

<u>DPQGVTCGAATLSAERVRGDNKEYEYSVECQEDSA</u>

<u>CPAAEESLPIEVMVDAVHKLKYENYTSSFFIRDII</u>

<u>KPDPPKNLQLKPLKNSRQVEVSWEYPDTWSTPHSY</u>

<u>FSLTFCVQVQGKSKREKKDRVFTDKTSATVICRKN</u>

<u>ASISVRAQDRYYSSSWSEWASVPCSPKSSDKTHTC</u>

PPCPAPEAAGGPSVFLFPPKPKDTLMISRTPEVTC

VVVDVSHEDPEVKFNWYVDGVEVHNAKTKPREEQY

NSTYRVVSVLTVLHQDWLNGKEYKCKVSNKALAAP

IEKTISKAKGQPREPQVCTLPPSRDELTENQVSLT

CLVKGFYPSDIAVEWESNGQPENNYKTTPPVLDSD

GSFFLYSWLTVDKSRWQQGNVFSCSVMHEALHNHY

TQKSLSLSPG

SEQ ID NO:291 is a sequence of p35 subunit of human IL-12 (underlined amino acids) fused to human IgG1 Fc domain polypeptide. Mutations are shown in bold.

(SEQ ID NO: 291)
RNLPVATPDPGMFPCLHHSQNLLRAVSNMLQKARQT

LEFYPCTSEEIDHEDITKDKTSTVEACLPLELTKNE

SCLNSRETSFITNGSCLASRKTSFMMALCLSSIYED

LKMYQVEFKTMNAKLLMDPKRQIFLDQNMLAVIDEL

MQALNFNSETVPQKSSLEEPDFYKTKIKLCILLHAF

RIRAVTIDRVMSYLNASGGGGSGGGGSGGGGSEPKS

SDKTHTCPPCPAPEAAGGPSVFLFPPKPKDTLMISR

TPEVTCVVVDVSHEDPEVKFNWYVDGVEVHNAKTKP

REEQYNSTYRVVSVLTVLHQDWLNGKEYKCKVSNKA

LAAPIEKTISKAKGQPREPRVYTLPPCRDELTKNQV

SLTCLVKGFYPSDIAVEWESNGQPENNYKTTPPVLV

SDGSFTLYSKLTVDKSRWQQGNVFSCSVMHEALHNH

YTQKSLSLSPG

The first and second polypeptides represented by amino acid sequences SEQ ID NO:290 and SEQ ID NO:291, respectively, form a disulfide bond due to a Y349C mutation in the CH3 domain of the first antibody Fc domain polypeptide sequence (human IgG1) in SEQ ID NO:290 (bolded and underlined) and a S354C mutation in the CH3 domain of the second antibody Fc domain polypeptide sequence (human IgG1) in SEQ ID NO:291 (bolded and underlined), which imparts stability to the heterodimeric Fc-fused protein (Fc numbering according to the EU system).

For promoting heterodimerization between the two Fc domain polypeptides of the heterodimeric Fc-fused protein, the first antibody Fc domain polypeptide sequence (human IgG1) in SEQ ID NO:290 includes K360E and K409W substitutions in the CH3 domain, and the second, different Fc domain polypeptide sequence (human IgG1) in SEQ ID NO:291 includes Q347R, D399V, and F405T substitutions in the CH3 domain (Fc numbering according to the EU system).

The first antibody Fc domain polypeptide sequence and the second, different Fc domain polypeptide sequence (human IgG1) in SEQ ID NO:290 and SEQ ID NO:291 also include L234A, L235A, and P329A (LALAPA) mutations for reducing effector functions.

Spacer Peptides

Exemplary spacer peptide sequences are provided in Table 7, and exemplary full length linker sequences are provided in Tables 4 and 5.

Within the first polypeptide of the present invention, a first subunit of a multisubunit protein is fused via a linker to a first antibody Fc domain polypeptide (e.g., an IgG4 antibody Fc variant sequence or an IgG1 antibody Fc variant sequence, as disclosed in Table 2), in an amino-to-carboxyl direction. And within the second polypeptide of the present invention, a second, different subunit of a multisubunit protein is fused via a linker to a second antibody Fc domain polypeptide (e.g., an IgG4 antibody Fc variant sequence or an IgG1 antibody Fc variant sequence, as disclosed in Table 2), in an amino-to-carboxyl direction.

In some embodiments, the first subunit of a multisubunit protein of the present invention is fused via a linker to a first antibody Fc domain sequence, wherein the linker comprises or consists of a spacer peptide $L_1$ and the amino acid sequence of SEQ ID NO:1, 2, 4, 6, 7, 9, 11, 237, 238, 239, or 240. In some embodiments, the second, different subunit of the multisubunit protein is fused to a second antibody Fc domain polypeptide via a linker, wherein the linker comprises or consists of a spacer peptide $L_2$ and the amino acid sequence of SEQ ID NO:1, 2, 4, 6, 7, 9, 11, 237, 238, 239, or 240.

In certain embodiments, $L_1$ and $L_2$ are peptide linkers, for example, $L_1$ and/or $L_2$ include(s) 4-50 amino acid residues. In certain embodiments, $L_1$ consists of 4-50 amino acid residues. In certain embodiments, $L_1$ consists of 4-20 amino acid residues. In certain embodiments, $L_2$ consists of 4-50 amino acid residues. In certain embodiments, $L_2$ consists of about 4-20 amino acid residues. In certain embodiments, $L_1$ and $L_2$ each independently consist of about 4-50 amino acid residues. In certain embodiments, $L_1$ and $L_2$ each independently consist of 4-20 amino acid residues.

In some embodiments, $L_1$ and $L_2$ have an optimized length and/or amino acid composition. In some embodiments, $L_1$ and $L_2$ are of the same length and have the same amino acid composition. In other embodiments, $L_1$ and $L_2$ are different.

In certain embodiments, $L_1$ is of equal number of amino acids to $L_2$; in certain embodiments $L_1$ is longer (i.e., more in the number of amino acids) than $L_2$; in certain embodiments $L_1$ is shorter (i.e., fewer number of amino acids) than $L_2$.

In certain embodiments, $L_1$ and/or $L_2$ are "short," e.g., consist of 0, 1, 2, 3, 4, 5, 6, 7, 8, 9, 10, 11 or 12 amino acid residues. Thus, in certain instances, the spacer peptides consist of about 12 or fewer amino acid residues. In the case of 0 amino acid residues, the spacer peptide is a peptide bond. In certain embodiments, $L_1$ and/or $L_2$ are "long," e.g., consist of 15, 20 or 25 amino acid residues. In some embodiments, the spacer peptides consist of about 3 to about 15, for example 8, 9 or 10 contiguous amino acid residues. Regarding the amino acid composition of $L_1$ and $L_2$, peptides are selected with properties that confer flexibility to first and the second polypeptides of the proteins of the present invention, do not interfere with the binding of the first and the second, different subunits to each other, as well as resist cleavage from proteases. For example, glycine and serine residues generally provide protease resistance. The spacer peptides suitable for linking the first subunit of the multisubunit protein to the amino acid sequence of SEQ ID NO:1, 2, 4, 6, 7, 9, 11, 237, 238, 239, or 240, and/or suitable for linking the second, different subunit of the multisubunit protein to the amino acid sequence of SEQ ID NO:1, 2, 4, 6, 7, 9, 11, 237, 238, 239, or 240 may include, as part of a linker, a $(GS)_n$, $(GGS)_n$, $(GGGS)_n$, $(GGSG)_n$, $(GGSGG)_n$, and $(GGGGS)_n$ sequence, wherein n is 1, 2, 3, 4, 5, 6, 7, 8, 9, 10, 11, 12, 13, 14, 15, 16, 17, 18, 19, or 20. In some embodiments, $L_1$ and/or $L_2$ independently include a $(GGGGS)_4$ (SEQ ID NO:107) or $(GGGGS)_3$ (SEQ ID NO:108) sequence as part of a linker. In other embodiments, $L_1$ and/or $L_2$ independently include a peptide sequence, as part of a linker, as set forth in the sequences selected from: SEQ ID NO:111, SEQ ID NO: 112, SEQ ID NO: 113, SEQ ID NO:114, SEQ ID NO:115, SEQ ID NO:116, SEQ ID NO:117, SEQ ID NO:118, SEQ ID NO:119, and SEQ ID NO:120, as listed in Table 7. In some embodiments, $L_1$ and/or L$_2$ are independently (GGGGS)$_{n=3}$ (SEQ ID NO:108), (GGGGS)$_{n=2}$ (SEQ ID NO:109), or (GGGGS)$_{n=1}$ (SEQ ID NO:110).

TABLE 7

| SEQ ID | Amino Acid Sequence |
| --- | --- |
| SEQ ID NO: 111 | GSGSGSGSGSGSGSGSGSGS |
| SEQ ID NO: 112 | GGSGGSGGSGGSGGSGGSGG SGGSGGSGGS |
| SEQ ID NO: 113 | GGGSGGGSGGGSGGGSGGGS GGGSGGGSGGGSGGGSGGGS |
| SEQ ID NO: 114 | GGSGGSGGGSGGGSGGGSG GGSGGSGGGSGGGSGGGSG |
| SEQ ID NO: 115 | GGSGGGSGGGGSGGGGSGG GGSGGGSGGGGSGGGGSGG GGSGGGSGG |
| SEQ ID NO: 116 | GGGGSGGGGSGGGGSGGGGS GGGGSGGGGSGGGGSGGGG SGGGGSGGGGS |
| SEQ ID NO: 117 | GGGGSGGGGSGGGGSGGGGS |
| SEQ ID NO: 118 | GGGGSGGGGSGGGGS |
| SEQ ID NO: 119 | GGGGSGGGGSGGGGSGGGGS GGGGSGGGGSGGGGSGGGGS GGGGSGGGGSGGGGSGGGGS GGGGSGGGGSGGGGSGGGGS GGGGSGGGGSGGGGSGGGGS |
| SEQ ID NO: 120 | GGSGGGSGGGSGGGSGGGSGG GGSGGGSGGGSGGGSGGGSGG GGSGGGSGGGSGGGSGGGSGG GGSGGGSGGGSGGGSGGGSGG GGSGGGSGGGSGGGSGGGSGG |

In certain embodiments, L$_1$ includes a sequence, as part of a linker, a (GGGGS)$_{n=3}$ (SEQ ID NO: 108) sequence, and L$_2$ includes, as part of a linker, a (GGGGS)$_{n=2}$ (SEQ ID NO: 109), or (GGGGS)$_{n=1}$ (SEQ ID NO:110) sequence. In certain embodiments, L$_2$ includes a sequence, as part of a linker, a (GGGGS)$_{n=3}$ (SEQ ID NO: 108) sequence, and L$_1$ includes, as part of a linker, a (GGGGS)$_{n=2}$ (SEQ ID NO: 109), or (GGGGS)$_{n=1}$ (SEQ ID NO: 110) sequence. In certain embodiments, L$_1$, as part of a linker, does not include a sequence as set forth in SEQ ID NO: 107, SEQ ID NO: 108, SEQ ID NO: 109, SEQ ID NO:110, SEQ ID NO:111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120.

In certain embodiments, only L$_2$, as part of a linker, includes a sequence as set forth in SEQ ID NO: 107, SEQ ID NO: 108, SEQ ID NO: 109, SEQ ID NO:110, SEQ ID NO:111, SEQ ID NO: 112, SEQ ID NO: 113, SEQ ID NO: 114, SEQ ID NO: 115, SEQ ID NO:116, SEQ ID NO:117, SEQ ID NO:118, SEQ ID NO:119, or SEQ ID NO:120. In certain embodiments, neither L$_1$ nor L$_2$, as part of a linker sequence, includes a sequence as set forth in SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, or SEQ ID NO:120.

Some heterodimeric Fc-fused proteins of the present invention comprise a first polypeptide comprising a first subunit of a multisubunit protein and a first antibody Fc domain polypeptide, in which a linker comprising GGGGSGGGGSGGGGS (SEQ ID NO:118; (G4S)$_3$) connects the first subunit of a multisubunit protein to the first antibody Fc domain polypeptide, for example an Fc domain polypeptide of an IgG4 antibody or an Fc domain polypeptide of an IgG1 antibody. Some heterodimeric Fc-fused proteins of the present invention comprise a second polypeptide comprising a second, different subunit of a multisubunit protein and a second antibody Fc domain polypeptide, in which a linker comprising GGGGSGGGGSGGGGS (SEQ ID NO:118; (G4S)$_3$) connects the second, different subunit of a multisubunit protein to the second antibody Fc domain polypeptide, for example an Fc domain polypeptide of an IgG4 antibody or an Fc domain polypeptide of an IgG1 antibody.

In certain embodiments, some heterodimeric Fc-fused proteins of the present invention comprise a first polypeptide comprising a first subunit of a multisubunit protein and a first antibody Fc domain polypeptide, in which a linker comprising GGGGSGGGGSGGGGS (SEQ ID NO:118; (G4S)$_3$) connects the first subunit of a multisubunit protein to the Fc domain polypeptide, and a second polypeptide comprising a second, different subunit of a multisubunit protein and a second antibody Fc domain polypeptide, in which the additional subunit is connected to the second antibody Fc domain polypeptide with a linker that does not comprise GGGGSGGGGSGGGGS (SEQ ID NO:118; (G4S)$_3$).

In certain embodiments, some heterodimeric Fc-fused proteins of the present invention comprise a first polypeptide comprising a first subunit of a multisubunit protein and a first antibody Fc domain polypeptide, in which a linker that does not comprise GGGGSGGGGSGGGGS (SEQ ID NO:118; (G4S)$_3$) connects the first subunit of a multisubunit protein to the Fc domain polypeptide, and a second polypeptide comprising a second, different subunit of a multisubunit protein and a second antibody Fc domain polypeptide, in which the second, different subunit of a multisubunit protein is connected to the second antibody Fc domain polypeptide with a linker comprising GGGGSGGGGSGGGGS (SEQ ID NO:118; (G4S)$_3$).

Some heterodimeric Fc-fused proteins of the present invention comprise a first polypeptide comprising a first subunit of a multisubunit protein and a first antibody Fc domain polypeptide, in which a linker comprising (GGGGS)$_{n=2}$ (SEQ ID NO:109) connects the first subunit of a multisubunit protein to the first antibody Fc domain polypeptide, for example an Fc domain polypeptide of an IgG4 antibody or an Fc domain polypeptide of an IgG1 antibody. Some heterodimeric Fc-fused proteins of the present invention comprise a second polypeptide comprising a second, different subunit of a multisubunit protein and a second antibody Fc domain polypeptide, in which a linker comprising (GGGGS)$_{n=2}$ (SEQ ID NO:109) connects the second, different subunit of a multisubunit protein to the second antibody Fc domain polypeptide, for example an Fc domain polypeptide of an IgG4 antibody or an Fc domain polypeptide of an IgG1 antibody.

Some heterodimeric Fc-fused proteins of the present disclosure include a linker comprising (GGGGS)$_{n=2}$ (SEQ ID NO:109), which connects a first subunit of a multisubunit protein to a first antibody Fc domain polypeptide, for example an Fc domain polypeptide of an IgG4 antibody or an Fc domain polypeptide of an IgG1 antibody, and connects a second, different subunit of a multisubunit protein to a second antibody Fc domain polypeptide, for example an Fc domain polypeptide of an IgG4 antibody or an Fc domain polypeptide of an IgG1 antibody.

In certain embodiments, some heterodimeric Fc-fused proteins of the present invention comprise a first polypeptide comprising a first subunit of a multisubunit protein and a first antibody Fc domain polypeptide, in which a linker comprising $(GGGGS)_{n=2}$ (SEQ ID NO:109) connects the first subunit of a multisubunit protein to the Fc domain polypeptide, and a second polypeptide comprising a second, different subunit of a multisubunit protein and a second antibody Fc domain polypeptide, in which additional subunit of a multisubunit protein is connected to the second antibody Fc domain polypeptide with a linker that does not comprise $(GGGGS)_{n=2}$ (SEQ ID NO:109).

In certain embodiments, some heterodimeric Fc-fused proteins of the present invention comprise a first polypeptide comprising a first subunit of a multisubunit protein and a first antibody Fc domain polypeptide, in which a linker that does not comprise $(GGGGS)_{n=2}$ (SEQ ID NO:109) connects the first subunit of a multisubunit protein to the Fc domain polypeptide, and a second polypeptide comprising a second, different subunit of a multisubunit protein and a second antibody Fc domain polypeptide, in which the second, different subunit of a multisubunit protein is connected to the second antibody Fc domain polypeptide with a linker comprising $(GGGGS)_{n=2}$ (SEQ ID NO:109).

Some heterodimeric Fc-fused proteins of the present invention comprise a first polypeptide comprising a first subunit of a multisubunit protein and a first antibody Fc domain polypeptide, in which a linker comprising $(GGGGS)_{n=1}$ (SEQ ID NO:110) connects the first subunit of a multisubunit protein to the first antibody Fc domain polypeptide, for example an Fc domain polypeptide of an IgG4 antibody or an Fc domain polypeptide of an IgG1 antibody. Some heterodimeric Fc-fused proteins of the present invention comprise a second polypeptide comprising a second, different subunit of a multisubunit protein and a second antibody Fc domain polypeptide, in which a linker comprising $(GGGGS)_{n=1}$ (SEQ ID NO:110) connects the second, different subunit of a multisubunit protein to the second antibody Fc domain polypeptide, for example an Fc domain polypeptide of an IgG4 antibody or an Fc domain polypeptide of an IgG1 antibody.

Some heterodimeric Fc-fused proteins of the present disclosure include a linker comprising $(GGGGS)_{n=1}$ (SEQ ID NO:110), which connects a first subunit of a multisubunit protein to a first antibody Fc domain polypeptide, for example an Fc domain polypeptide of an IgG4 antibody or an Fc domain polypeptide of an IgG1 antibody, and connects a second, different subunit of a multisubunit protein to a second antibody Fc domain polypeptide, for example an Fc domain polypeptide of an IgG4 antibody or an Fc domain polypeptide of an IgG1 antibody.

In certain embodiments, some heterodimeric Fc-fused proteins of the present invention comprise a first polypeptide comprising a first subunit of a multisubunit protein and a first antibody Fc domain polypeptide, in which a linker comprising $(GGGGS)_{n=1}$ (SEQ ID NO:110) connects the first subunit of a multisubunit protein to the Fc domain polypeptide, and a second polypeptide comprising a second, different subunit of a multisubunit protein and a second antibody Fc domain polypeptide, in which the second, different subunit of a multisubunit protein is connected to the second antibody Fc domain polypeptide with a linker that does not comprise $(GGGGS)_{n=1}$ (SEQ ID NO:110).

In certain embodiments, some heterodimeric Fc-fused proteins of the present invention comprise a first polypeptide comprising a first subunit of a multisubunit protein and a first antibody Fc domain polypeptide, in which a linker that does not comprise $(GGGGS)_{n=1}$ (SEQ ID NO:110) connects the first subunit of a multisubunit protein to the Fc domain polypeptide, and a second polypeptide comprising a second, different subunit of a multisubunit protein and a second antibody Fc domain polypeptide, in which the second, different subunit of a multisubunit protein is connected to the second antibody Fc domain polypeptide with a linker comprising $(GGGGS)_{n=1}$ (SEQ ID NO:110).

In certain embodiments, some heterodimeric Fc-fused proteins of the present invention comprise a first polypeptide comprising a first subunit of a multisubunit protein and a first antibody Fc domain polypeptide, in which a linker comprising $(GGGGS)_{n=1}$ (SEQ ID NO:110) sequence connects the first subunit of a multisubunit protein to the Fc domain polypeptide, and a second polypeptide comprising a second, different subunit of a multisubunit protein and a second antibody Fc domain polypeptide, in which the second, different subunit of a multisubunit protein is connected to the second antibody Fc domain polypeptide with a linker comprising $(GGGGS)_{n=2}$ (SEQ ID NO:109) sequence.

In certain embodiments, some heterodimeric Fc-fused proteins of the present invention comprise a first polypeptide comprising a first subunit of a multisubunit protein and a first antibody Fc domain polypeptide, in which a linker comprising $(GGGGS)_{n=2}$ (SEQ ID NO:109) sequence connects the first subunit of a multisubunit protein to the Fc domain polypeptide, and a second polypeptide comprising a second, different subunit of a multisubunit protein and a second antibody Fc domain polypeptide, in which the second, different subunit of a multisubunit protein is connected to the second antibody Fc domain polypeptide with a linker comprising $(GGGGS)_{n=1}$ (SEQ ID NO:110) sequence.

Fc Domain and Substitutions for Promoting Heterodimerization

The assembly of proteins of the present invention can be accomplished by expressing a first polypeptide comprising a first subunit of a multisubunit protein sequence fused to a first antibody Fc domain polypeptide (e.g., an IgG4 antibody Fc variant sequence or an IgG1 antibody Fc variant sequence, as disclosed in Table 2), and a second polypeptide comprising a second, different subunit of a multisubunit protein sequence fused to a second antibody Fc domain polypeptide (e.g., an IgG4 antibody Fc variant sequence or an IgG1 antibody Fc variant sequence, as disclosed in Table 2) in the same cell, which leads to the assembly of a heterodimeric Fc-fused protein according to the invention. The assembled proteins have heterodimeric Fc domain polypeptides with the first antibody Fc domain polypeptide and the second antibody Fc domain polypeptide bound to each other. Promoting the preferential assembly of heterodimers of the Fc can be accomplished by incorporating different mutations in the CH3 domain of each antibody heavy chain constant region as shown in U.S. Ser. No. 13/494,870, U.S. Ser. No. 16/028,850, U.S. Ser. No. 11/533,709, U.S. Ser. No. 12/875,015, U.S. Ser. No. 13/289,934, U.S. Ser. No. 14/773,418, U.S. Ser. No. 12/811,207, U.S. Ser. No. 13/866,756, U.S. Ser. No. 14/647,480, and U.S. Ser. No. 14/830,336. For example, mutations can be made in the CH3 domain based on human IgG1 and incorporating distinct pairs of amino acid substitutions within a first antibody Fc domain polypeptide and a second antibody Fc domain polypeptide that allow these two chains to selectively heterodimerize with each other. The positions of amino acid substitutions illustrated below are all numbered according to the EU index as in Kabat.

In one scenario, an amino acid substitution in the first antibody Fc domain polypeptide replaces the original amino acid with a larger amino acid, selected from arginine (R), phenylalanine (F), tyrosine (Y) or tryptophan (W), and at least one amino acid substitution in the second antibody Fc domain polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one antibody Fc domain polypeptide can incorporate a T366W substitution, and the other can incorporate three substitutions including T366S, L368A, and Y407V.

A first polypeptide comprising a first subunit of a multi-subunit protein sequence or a second polypeptide comprising a second, different subunit of a multisubunit protein sequence of the invention can optionally be coupled to an amino acid sequence at least 90% (e.g., at least 91%, 92%, 93%, 94%, 95%, 96%, 97%, 98%, or 99%) identical to an antibody constant region, such as an IgG constant region including hinge, CH2 and CH3 domains with or without a CH1 domain. In some embodiments, the amino acid sequence of the constant region is at least 90% (e.g., at least 91%, 92%, 93%, 94%, 95%, 96%, 97%, 98%, or 99%) identical to a human antibody constant region, such as a human IgG1 constant region, an IgG2 constant region, an IgG3 constant region, or an IgG4 constant region. In some other embodiments, the amino acid sequence of the constant region is at least 90% (e.g., at least 91%, 92%, 93%, 94%, 95%, 96%, 97%, 98%, or 99%) identical to an antibody constant region from another mammal, such as rabbit, dog, cat, mouse, or horse. One or more mutation(s) can be incorporated into the constant region as compared to the human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394K, T394W, D399R, D399K, D399V, S400K, S400R, D401K, F405A, F405T, Y407A, Y407I, Y407V, K409F, K409W, K409D, T411D, T411E, K439D, and K43Y9E.

In certain embodiments, mutations that can be incorporated into the CH1 of a human IgG1 constant region may be at amino acids V125, F126, P127, T135, T139, A140, F170, P171, and/or V173. In certain embodiments, mutations that can be incorporated into the Cκ of a human IgG1 constant region may be at amino acids E123, F116, S176, V163, S174, and/or T164.

Amino acid substitutions could be selected from the following sets of substitutions shown in Table 8.

TABLE 8

|  | First Polypeptide | Second Polypeptide |
|---|---|---|
| Set 1 | S364E/F405A | Y349K/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |

TABLE 8-continued

|  | First Polypeptide | Second Polypeptide |
|---|---|---|
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 9.

TABLE 9

|  | First Polypeptide | Second Polypeptide |
|---|---|---|
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following set of substitutions shown in Table 10.

TABLE 10

|  | First Polypeptide | Second Polypeptide |
|---|---|---|
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 11.

TABLE 11

| First Polypeptide | Second Polypeptide |
|---|---|
| L351Y, D399R, D399K, S400K, S400R, Y407A, Y407I, Y407V | T366V, T366I, T366L, T366M, N390D, N390E, K392L, K392M, K392V, K392F K392D, K392E, K409F, K409W, T411D and T411E |

Alternatively, at least one amino acid substitutions could be selected from the following set of substitutions in Table 12, where the position(s) indicated in the First Polypeptide column is replaced by any known negatively-charged amino acid, and the position(s) indicated in the Second Polypeptide Column is replaced by any known positively-charged amino acid.

TABLE 12

| First Polypeptide | Second Polypeptide |
|---|---|
| K392, K370, K409, or K439 | D399, E356, or E357 |

Alternatively, at least one amino acid substitutions could be selected from the following set of in Table 13, where the position(s) indicated in the First Polypeptide column is replaced by any known positively-charged amino acid, and the position(s) indicated in the Second Polypeptide Column is replaced by any known negatively-charged amino acid.

TABLE 13

| First Polypeptide | Second Polypeptide |
| --- | --- |
| D399, E356, or E357 | K409, K439, K370, or K392 |

Alternatively, amino acid substitutions could be selected from the following set in Table 14.

TABLE 14

| First Polypeptide | Second Polypeptide |
| --- | --- |
| T350V, L351Y, F405A, and Y407V | T350V, T366L, K392L, and T394W |

Alternatively, or in addition, the structural stability of a heterodimeric Fc-fused protein according to the invention may be increased by introducing S354C on either of the first or second polypeptide chain, and Y349C on the opposing polypeptide chain, which forms an artificial disulfide bond within the interface of the two polypeptides.

In some embodiments, the amino acid sequence of one polypeptide chain of the antibody constant region differs from the amino acid sequence of an IgG1 constant region at position T366, and the amino acid sequence of the other polypeptide chain of the antibody constant region differs from the amino acid sequence of an IgG1 constant region at one or more position(s) selected from T366, L368 and Y407.

In some embodiments, the amino acid sequence of one polypeptide chain of the antibody constant region differs from the amino acid sequence of an IgG1 constant region at one or more position(s) selected from T366, L368 and Y407, and the amino acid sequence of the other polypeptide chain of the antibody constant region differs from the amino acid sequence of an IgG1 constant region at position T366.

In some embodiments, the amino acid sequence of one polypeptide chain of the antibody constant region differs from the amino acid sequence of an IgG1 constant region at one or more position(s) selected from E357, K360, Q362, S364, L368, K370, T394, D401, F405, and T411 and the amino acid sequence of the other polypeptide chain of the antibody constant region differs from the amino acid sequence of an IgG1 constant region at one or more position(s) selected from Y349, E357, S364, L368, K370, T394, D401, F405 and T411.

In some embodiments, the amino acid sequence of one polypeptide chain of the antibody constant region differs from the amino acid sequence of an IgG1 constant region at one or more position(s) selected from Y349, E357, S364, L368, K370, T394, D401, F405 and T411 and the amino acid sequence of the other polypeptide chain of the antibody constant region differs from the amino acid sequence of an IgG1 constant region at one or more position(s) selected from E357, K360, Q362, S364, L368, K370, T394, D401, F405, and T411.

In some embodiments, the amino acid sequence of one polypeptide chain of the antibody constant region differs from the amino acid sequence of an IgG1 constant region at one or more position(s) selected from L351, D399, S400 and Y407 and the amino acid sequence of the other polypeptide chain of the antibody constant region differs from the amino acid sequence of an IgG1 constant region at one or more position(s) selected from T366, N390, K392, K409 and T411.

In some embodiments, the amino acid sequence of one polypeptide chain of the antibody constant region differs from the amino acid sequence of an IgG1 constant region at one or more position(s) selected from T366, N390, K392, K409 and T411 and the amino acid sequence of the other polypeptide chain of the antibody constant region differs from the amino acid sequence of an IgG1 constant region at one or more position(s) selected from L351, D399, S400 and Y407.

In some embodiments, the amino acid sequence of one polypeptide chain of the antibody constant region differs from the amino acid sequence of an IgG1 constant region at one or more position(s) selected from Q347, Y349, K360, and K409, and the amino acid sequence of the other polypeptide chain of the antibody constant region differs from the amino acid sequence of an IgG1 constant region at one or more position(s) selected from Q347, E357, D399 and F405.

In some embodiments, the amino acid sequence of one polypeptide chain of the antibody constant region differs from the amino acid sequence of an IgG1 constant region at one or more position(s) selected from Q347, E357, D399 and F405, and the amino acid sequence of the other polypeptide chain of the antibody constant region differs from the amino acid sequence of an IgG1 constant region at one or more position(s) selected from Y349, K360, Q347 and K409.

In some embodiments, the amino acid sequence of one polypeptide chain of the antibody constant region differs from the amino acid sequence of an IgG1 constant region at one or more position(s) selected from K370, K392, K409 and K439, and the amino acid sequence of the other polypeptide chain of the antibody constant region differs from the amino acid sequence of an IgG1 constant region at one or more position(s) selected from D356, E357 and D399.

In some embodiments, the amino acid sequence of one polypeptide chain of the antibody constant region differs from the amino acid sequence of an IgG1 constant region at one or more position(s) selected from D356, E357 and D399, and the amino acid sequence of the other polypeptide chain of the antibody constant region differs from the amino acid sequence of an IgG1 constant region at one or more position(s) selected from K370, K392, K409 and K439.

In some embodiments, the amino acid sequence of one polypeptide chain of the antibody constant region differs from the amino acid sequence of an IgG1 constant region at one or more position(s) selected from L351, E356, T366 and D399, and the amino acid sequence of the other polypeptide chain of the antibody constant region differs from the amino acid sequence of an IgG1 constant region at one or more position(s) selected from Y349, L351, L368, K392 and K409.

In some embodiments, the amino acid sequence of one polypeptide chain of the antibody constant region differs from the amino acid sequence of an IgG1 constant region at one or more position(s) selected from Y349, L351, L368, K392 and K409, and the amino acid sequence of the other polypeptide chain of the antibody constant region differs from the amino acid sequence of an IgG1 constant region at one or more position(s) selected from L351, E356, T366 and D399.

In some embodiments, the amino acid sequence of one polypeptide chain of the antibody constant region differs from the amino acid sequence of an IgG1 constant region by an S354C substitution and the amino acid sequence of the other polypeptide chain of the antibody constant region differs from the amino acid sequence of an IgG1 constant region by a Y349C substitution.

In some embodiments, the amino acid sequence of one polypeptide chain of the antibody constant region differs from the amino acid sequence of an IgG1 constant region by a Y349C substitution and the amino acid sequence of the other polypeptide chain of the antibody constant region differs from the amino acid sequence of an IgG1 constant region by an S354C substitution.

In some embodiments, the amino acid sequence of one polypeptide chain of the antibody constant region differs from the amino acid sequence of an IgG1 constant region by K360E and K409W substitutions and the amino acid sequence of the other polypeptide chain of the antibody constant region differs from the amino acid sequence of an IgG1 constant region by O347R, D399V and F405T substitutions.

In some embodiments, the amino acid sequence of one polypeptide chain of the antibody constant region differs from the amino acid sequence of an IgG1 constant region by O347R, D399V and F405T substitutions and the amino acid sequence of the other polypeptide chain of the antibody constant region differs from the amino acid sequence of an IgG1 constant region by K360E and K409W substitutions.

In some embodiments, the amino acid sequence of one polypeptide chain of the antibody constant region differs from the amino acid sequence of an IgG1 constant region by a T366W substitutions and the amino acid sequence of the other polypeptide chain of the antibody constant region differs from the amino acid sequence of an IgG1 constant region by T366S, T368A, and Y407V substitutions.

In some embodiments, the amino acid sequence of one polypeptide chain of the antibody constant region differs from the amino acid sequence of an IgG1 constant region by T366S, T368A, and Y407V substitutions and the amino acid sequence of the other polypeptide chain of the antibody constant region differs from the amino acid sequence of an IgG1 constant region by a T366W substitution.

In some embodiments, the amino acid sequence of one polypeptide chain of the antibody constant region differs from the amino acid sequence of an IgG1 constant region by T350V, L351Y, F405A, and Y407V substitutions and the amino acid sequence of the other polypeptide chain of the antibody constant region differs from the amino acid sequence of an IgG1 constant region by T350V, T366L, K392L, and T394W substitutions.

In some embodiments, the amino acid sequence of one polypeptide chain of the antibody constant region differs from the amino acid sequence of an IgG1 constant region by T350V, T366L, K392L, and T394W substitutions and the amino acid sequence of the other polypeptide chain of the antibody constant region differs from the amino acid sequence of an IgG1 constant region by T350V, L351Y, F405A, and Y407V substitutions.

A skilled person in the art would appreciate that during production and/or storage of proteins, N-terminal glutamate (E) or glutamine (Q) can be cyclized to form a lactam (e.g., spontaneously or catalyzed by an enzyme present during production and/or storage). Accordingly, in some embodiments where the N-terminal residue of an amino acid sequence of a polypeptide is E or Q, a corresponding amino acid sequence with the E or Q replaced with pyroglutamate is also contemplated herein.

A skilled person in the art would also appreciate that during protein production and/or storage, the C-terminal lysine (K) of a protein can be removed (e.g., spontaneously or catalyzed by an enzyme present during production and/or storage). Such removal of K is often observed with proteins that comprise a Fc domain at its C-terminus. Accordingly, in some embodiments where the C-terminal residue of an amino acid sequence of a polypeptide (e.g., a Fc domain sequence) is K, a corresponding amino acid sequence with the K removed is also contemplated herein.

Mutations for Reducing Effector Functions

In one aspect, the present invention provides a heterodimeric Fc-fused protein comprising (a) a first polypeptide comprising a first antibody Fc domain polypeptide and a first subunit of a multisubunit protein; and (b) a second polypeptide comprising a second antibody Fc domain polypeptide and a second, different subunit of the multisubunit protein, wherein the first and second antibody Fc domain polypeptides each comprise different mutations promoting heterodimerization, wherein the first and/or second antibody Fc domain polypeptides comprise one or more mutation(s) that reduce(s) an effector function of an Fc, and wherein the first subunit and second, different subunit of the multisubunit protein are bound to each other. In certain embodiments, a heterodimeric Fc-fused protein disclosed herein comprising one or more mutation(s) that reduce(s) an effector function of an Fc has an increased activity to inhibit tumor growth than its counterpart without the Fc mutation(s) that reduce(s) the effector function. The mutations contemplated herein include substitution, insertion, and deletion of amino acid residues. All the amino acid positions in an Fc domain or hinge region disclosed herein are numbered according to EU numbering.

In certain embodiments, the first and/or second antibody Fc domain polypeptides comprise one or more mutation(s) that reduce(s) the ability of the Fc domain polypeptide to induce antibody-dependent cellular cytotoxicity (ADCC) and/or antibody-dependent cellular phagocytosis (ADCP). ADCC and ADCP are typically mediated by an Fc receptor. For example, in certain embodiments, the first and second antibody Fc domain polypeptides are human IgG (e.g., human IgG1, human IgG2, human IgG3, or human IgG4) antibody sequences. The Fc receptors of human IgG, also called Fc gamma receptors (FcγRs), include but are not limited to activating Fc gamma receptors FcγRI (CD64), FcγRIIA (CD32A), FcγRIIIA (CD16 or CD16A), and FcγRIIIB (CD16B), and inhibitor Fc gamma receptor FcγRIIB (CD32B). Accordingly, in some embodiments, a heterodimeric Fc-fused protein of the present invention includes one or more mutation(s) to reduce binding to an activating FcγR (e.g., FcγRI, FcγRIIA, FcγRIIIA, or FcγRIIIB) in the first and/or second polypeptides. In some embodiments, a heterodimeric Fc-fused protein of the present invention includes one or more mutation(s) to increase binding to an inhibitory FcγR (e.g., FcγRIIB) in the first and/or second polypeptides.

Fc mutations that reduce binding to an activating FcγR and/or increase binding to an inhibitory FcγR are known in the art. For example, within the hinge and Fc regions, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al, Nature, 406 (6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

As reviewed in Want et al., Protein Cell (2018) 9(1):63-73, the regions including amino acid positions 232-239, 265-270, 296-299, and 325-332 are implicated in activating FcγR binding according to a crystal structure of human IgG1 Fc. Wang et al. also discloses that L235E and F234A/L235A mutations of human IgG4, L234A/L235A mutations of human IgG1, and N297 mutations (e.g., N297A, N297Q, N297G, or N297D) of IgG antibodies reduce activating FcγR binding. As disclosed in U.S. Pat. No. 8,969,526, mutation at position 329 (e.g., P329A, P329G, or P329R) also reduces activating FcγR binding. Additional amino acid positions and mutations (e.g., E233P mutation) implicated in activating FcγR binding are disclosed in U.S. Pat. No. 7,943,743 and Isaacs et al., J. Immunol. (1998) 161:3862-69.

Accordingly, in certain embodiments, the first and second antibody Fc domain polypeptides comprise a mutation (e.g., substitution relative to wild-type human IgG1) at one or more of positions selected from 233, 234, 235, 297, and 329. In certain embodiments, the first and second antibody Fc domain polypeptides are human IgG1 antibody Fc domain polypeptides comprising mutation(s) E233P; L234A (human IgG1) or F234A (human IgG4); L235A or L235E; N297A, N297Q, N297G, or N297D; and/or P329A, P329G, or P329R. In certain embodiments, the first and second antibody Fc domain polypeptides are human IgG1 antibody Fc domain polypeptides comprising mutations L234A and L235A. In certain embodiments, the first and second antibody Fc domain polypeptides are human IgG1 antibody Fc domain polypeptides comprising mutations L234A, L235A, and P329A. In certain embodiments, the first and second antibody Fc domain polypeptides are human IgG4 antibody Fc domain polypeptides comprising mutation L235E. In certain embodiments, the first and second antibody Fc domain polypeptides are human IgG1 antibody Fc domain polypeptides comprising mutations L235E and P329A.

In certain embodiments, the first and/or second antibody Fc domain polypeptides comprise one or more mutation(s) that reduce(s) the ability of the Fc domain polypeptide to induce complement dependent cytotoxicity (CDC). CDC is typically mediated by a complement component (e.g., C1q). Accordingly, in certain embodiments, a heterodimeric Fc-fused protein of the present invention includes one or more mutation(s) to reduce binding to a complement component (e.g., C1q) in the first and/or second polypeptides.

Fc mutations that reduce binding to C1q are known in the art. For example, as disclosed in U.S. Pat. Nos. 5,648,260 and 5,624,821, the amino acid residues of Fc at positions 234, 235, 236, 237, 297, 318, 320, and 322 are implicated in C1q binding. As disclosed in Tao et al., J. Exp. Med. (1993) 178:661-667 and Brekke et al., Eur. J. Immunol. (1994) 24:2542-47, residue Pro at position 331 is implicated in C1q binding. As disclosed in Idusogie et al., J. Immunol. (2000) 164:4178-84, mutations of Fc at positions 270 (e.g., D270A), 322 (K322A), 329 (e.g., P329A), and 331 (e.g., P331A, P331S, or P331G) reduced C1q binding.

Accordingly, in certain embodiments, the first and second antibody Fc domain polypeptides comprise a mutation (e.g., substitution relative to wild-type human IgG1) at one or more of positions selected from 234, 235, 236, 237, 270, 297, 318, 320, 322, 329, and 331. In certain embodiments, the first and second antibody Fc domain polypeptides are human IgG1 antibody Fc domain polypeptides comprising mutation(s) G237A, A330S, P331S, and/or P329A. In certain embodiments, the first and second antibody Fc domain polypeptides are human IgG1 antibody Fc domain polypeptides comprising mutations G237A, A330S, and P331S. In certain embodiments, the first and second antibody Fc domain polypeptides are human IgG1 antibody Fc domain polypeptides comprising mutation P329A.

The mutations that reduce ADCC and/or ADCP and the mutations that reduce CDC can be combined. In certain embodiments, the first and/or second antibody Fc domain polypeptides comprise one or more mutation(s) that reduce(s) the ability of the Fc domain polypeptide to induce ADCC and/or ADCP and further comprise one or more mutation(s) that reduce(s) the ability of the Fc domain polypeptide to induce CDC. In certain embodiments, the first and second antibody Fc domain polypeptides each comprise one or more mutation(s) that reduce(s) the ability of the Fc domain polypeptide to induce ADCC and/or ADCP and further comprise one or more mutation(s) that reduce(s) the ability of the Fc domain polypeptide to induce CDC.

In some embodiments, a heterodimeric Fc-fused protein of the present invention with an IgG4 Fc includes one or more mutation(s) to reduce binding to an FcγR (e.g., FcγRI, FcγRIIA, FcγRIIB, FcγRIIIA, or FcγRIIIB) or a complement component (e.g., C1q) in the first and/or second polypeptides. Such mutations are useful for reducing effector functions. For example, a protein of the present disclosure can include SPLE (S228P and L235E) mutations, SPLEPA (S228P, L235E, and P329A) mutations, or SPLEPG (S228P, L235E, and P329G) mutations.

In some embodiments, a heterodimeric Fc-fused protein of the present invention with an IgG1 Fc includes one or more mutation(s) to reduce binding to an FcγR (e.g., FcγRI, FcγRIIA, FcγRIIB, FcγRIIIA, or FcγRIIIB) or a complement component (e.g., C1q) in the first and/or second polypeptides. Such mutations are useful for reducing effector functions. For example, a protein of the present disclosure can include LALA (L234A and L235A) mutations, LALAPA (L234A, L235A, and P329A) mutations, LALAPG (L234A, L235A, and P329G) mutations, or LALEGAASPS (L234A, L235E, G237A, A330S, and P331S) mutations.

In some embodiments, a heterodimeric Fc-fused protein according to the invention includes a first antibody IgG4 or IgG1 Fc domain polypeptide and a second antibody IgG4 or IgG1 Fc domain polypeptide each containing the mutation P329G or P329A.

In some embodiments, the first antibody Fc domain polypeptide and the second antibody Fc domain polypeptide each contain a mutation selected from A330S and P331S.

In some embodiments, the first antibody Fc domain polypeptide and the second antibody Fc domain polypeptide each contain the mutations A330S and P331S.

In certain embodiments, in the first polypeptide of the heterodimeric Fc-fused protein of the present invention, the first subunit of the multisubunit protein is fused to the first antibody Fc domain polypeptide by a first linker. In certain embodiments, in the second polypeptide of the heterodimeric Fc-fused protein of the present invention, the second, different subunit of the multisubunit protein is fused to the second antibody Fc domain polypeptide by a second linker. Amino acid sequences of linkers suitable for such use are described under the headings "IgG4 constructs" and "IgG1 constructs." Additional linker sequences suitable for use in the first and/or second polypeptides include but are not limited to wild-type IgG (e.g., human IgG1, human IgG2, human IgG3, or human IgG4) hinge sequences and mutant forms thereof. For example, in certain embodiments, the first and second linkers each comprise amino acid sequence ESKYGPPCPPCPAPEFXGG, wherein X is L or E (SEQ ID NO:280) or SKYGPPCPPCPAPEFXGG, wherein X is L or E (SEQ ID NO:281). In certain embodiments, the first and second linkers each comprise amino acid sequence ESKY-GPPCPPCPAPEFLGG (SEQ ID NO:282) or SKY-GPPCPPCPAPEFLGG (SEQ ID NO:283). In certain embodiments, the first and second linkers each comprise amino acid sequence ESKYGPPCPPCPAPEFEGG (SEQ ID NO:284) or SKYGPPCPPCPAPEFEGG (SEQ ID NO:285).

Serum Half-Life

Heterodimeric Fc-fused proteins according to the invention have pharmacokinetic properties suitable for therapeutic use. For example, in certain embodiments, a heterodimeric Fc-fused protein according to the invention has a serum half-life of at least about 50 hours. In certain embodiments, a heterodimeric Fc-fused protein according to the invention has a serum half-life of at least about 100 hours.

In certain embodiments, 50 hours after intravenous administration to a subject, the serum concentration of the heterodimeric Fc-fused protein according to the invention is at least 10% of the serum concentration of the protein of the present invention 1 hour after the administration in said subject.

In certain embodiments, a heterodimeric Fc-fused protein according to the invention has a serum half-life that is at least 20%, 30%, 40%, 50%, 60%, 70%, 80%, or 90% longer than the multisubunit protein not fused to Fc domain polypeptides. In certain embodiments, a heterodimeric Fc-fused protein comprising a protein sequence of a multisubunit protein according to the present invention has a serum half-life that is at least 2-fold, 3-fold, 4-fold, 5-fold, 6-fold, 7-fold, 8-fold, 9-fold, 10-fold, 15-fold, or 20-fold longer than the multisubunit protein not fused to Fc domain polypeptides.

Tumor Retention

Heterodimeric Fc-fused proteins of the invention can optionally incorporate additional features to enhance retention of the proteins at the tumor site. For example, in certain embodiments of the present invention, the heterodimeric Fc-fused protein further comprises a proteoglycan-binding domain, a collagen-binding domain, and/or a hyaluronic acid-binding domain. In certain embodiments, the heterodimeric Fc-fused protein further comprises a proteoglycan-binding domain that binds one or more proteoglycans (e.g., proteoglycans known in the art, e.g., as disclosed in Lozzo et al., Matrix Bio (2015) 42:11-55; and Nikitovic et al., Frontiers in Endocrinology (2018) 9:69) that are present in a tumor (e.g., on the surface of a tumor cell, in a pericellular matrix in a tumor, or in a extracellular matrix in a tumor). In certain embodiments, the collagen-binding domain binds one or more collagens that are present in a tumor (e.g., on the surface of a tumor cell, in a pericellular matrix in a tumor, or in a extracellular matrix in a tumor). In certain embodiments, the heterodimeric Fc-fused protein further comprises a h acid-binding domain that binds to one ore more hyaluronic acid that are present in a tumor. Such heterodimeric Fc-fused proteins have enhanced retention in tumors and may be administered to a subject intratumorally at a lower dose and/or frequency.

In certain embodiments, the proteoglycan-binding domain comprised in the heterodimeric Fc-fused protein binds one or more proteoglycans that are specifically expressed in a tumor (e.g., on the surface of a tumor cell, in a pericellular matrix in a tumor, or in a extracellular matrix in a tumor). In certain embodiments, the collagen-binding domain comprised in the heterodimeric Fc-fused protein binds one or more collagens that are specifically expressed in a tumor (e.g., on the surface of a tumor cell, in a pericellular matrix in a tumor, or in a extracellular matrix in a tumor). Such heterodimeric Fc-fused proteins may be enriched in tumors after administration (e.g., intravenous, subcutaneous, or pulmonary administration) and have enhanced tumor retention, thereby allowing administration at a lower dose and/or frequency.

In certain embodiments, the heterodimeric Fc-fused protein of the present invention further comprises a proteoglycan-binding domain that binds one or more proteoglycans selected from syndecan, chondroitin sulfate proteoglycan 4 (CSPG4), betaglycan, phosphacan, glypican, perlecan, agrin, collagen (e.g., collagen IX, XII, XV, or XVIII), hyalectan, aggrecan, versican, neurocan, brevican, and a small leucine-rich proteoglycan (SLRP). Proteoglycans implicated in cancer include but are not limited to collagen, syndecan (e.g., syndecan-1 or syndecan-2), serglycin, CSPG4, betaglycan, glypican (e.g., glypican-1 or glypican-3), perlecan, versican, brevican, and SLPR (e.g., decorin, biglycan, asporin, fibrodulin, and lumican). Accordingly, in certain embodiments, the proteoglycan-binding domain comprised in the heterodimeric Fc-fused protein binds one or more proteoglycans selected from syndecan (e.g., syndecan-1 or syndecan-2), serglycin, CSPG4, betaglycan, glypican (e.g., glypican-1 or glypican-3), perlecan, versican, brevican, and a SLPR. In certain embodiments, the proteoglycan-binding domain comprised in the heterodimeric Fc-fused protein binds one or more SLPRs selected from decorin, biglycan, asporin, fibrodulin, and lumican.

The proteoglycan-binding domain comprised in the heterodimeric Fc-fused protein can be a protein (e.g., an antibody or an antigen-binding fragment thereof), a peptide (e.g., a portion of a proteoglycan-binding protein or a variant thereof), an aptamer, a small molecule, or a combination thereof. Proteoglycan-binding domains are also known in the art. For example, syndecan-binding domains are disclosed in U.S. Pat. Nos. 6,566,489, 8,647,828, and 10,124,038; U.S. Patent Application Publication No. 2009/0297479; and PCT Patent Application Publication No. WO2018199176A1. CSPG4-binding domains are disclosed in U.S. Pat. Nos. 9,801,928 and 10,093,745; and U.S. Patent Application Publication Nos. 2016/0032007, 2017/0342151, and 2018/0072811. β-glycan-binding domains are disclosed in U.S. Pat. No. 7,455,839. Glypican-binding domains are disclosed in U.S. Pat. Nos. 7,919,086, 7,776,329, 8,680,247, 8,388,937, 9,260,492, 9,394,364, 9,790,267, 9,522,940, and 9,409,994; U.S. Patent Application Publication Nos. 2004/0236080, 2011/0123998, 2018/0244805, 2018/0230230, and 2018/0346592; European Patent No. 2270509; and PCT Patent Application Publication No. WO2017053619A1, WO2018026533A1, WO2018165344A1, and WO2018199318A1. Perlecan-binding domains are disclosed in U.S. Pat. No. 10,166,304. Decorin-binding domains are disclosed in U.S. Pat. No. 6,517,838 and PCT Patent Application Publication No. WO2000021989A1, WO2000077041A2, and WO2000078800A2.

In certain embodiments, the heterodimeric Fc-fused protein of the present invention further comprises a collagen-binding domain. Collagen is a class of proteins having at least 28 different types identified in vertebrates. Each type of collagen has its unique structural characteristics and distribution pattern, as disclosed in Fang et al., Tumor Biol. (2014) 35:2871-82 and Xiong et al., J. Cancer Metasta. Treat. (2016) 2:357-64. Various types of collagens are implicated in cancer, including but not limited to Col3A1, Col5A2, Col6, Col7A1, Col15A1 Col19A1, and Col22A1.

The collagen-binding domain can be a protein (e.g., an antibody or an antigen-binding fragment thereof), a peptide (e.g., a portion of a collagen-binding protein or a variant thereof), an aptamer, a small molecule, or a combination thereof. Collagen-binding domains are known in the art, and are disclosed in, for example, U.S. Pat. Nos. 5,788,966, 5,587,360, 5,851,794, 5,741,670, 5,849,701, 6,288,214, 6,387,663, 6,908,994, 7,169,902, 7,488,792, 7,820,401, 8,956,612, 8,642,728, and 8,906,649, and U.S. Patent Application Publication Nos. 2007/0161062, 2009/0142345, and 2012/0100106.

In certain embodiments, the heterodimeric Fc-fused protein of the present invention further comprises a hyaluronic acid-binding domain. The hyaluronic acid-binding domain can be a protein (e.g., an antibody or an antigen-binding fragment thereof), a peptide (e.g., a portion of a hyaluronic acid-binding protein or a variant thereof), an aptamer, a small molecule, or a combination thereof. Hyaluronic acid-binding domains are known in the art, and are disclosed in, for example, U.S. Pat. Nos. 6,864,235, 8,192,744, 8,044,022, 8,163,498, 8,034,630, 9,217,016, 9,795,686, and 9,751,919, and U.S. Patent Application Publication Nos. 2002/0055488 and 2007/0259380.

A proteoglycan-binding domain, collagen-binding domain, and/or hyaluronic acid-binding domain, if present, can be at any position of the heterodimeric Fc-fused protein. For example, in certain embodiments, where the IL-12 subunits are positioned N-terminal to the antibody Fc domain polypeptides, a proteoglycan-binding domain, a collagen-binding domain, and/or a hyaluronic acid-binding domain as disclosed herein can be fused to the C-terminus of the first antibody Fc domain polypeptide and/or to the C-terminus of the second antibody Fc domain polypeptide. In certain embodiments, where the IL-12 subunits are positioned C-terminal to the antibody Fc domain polypeptides, a proteoglycan-binding domain, a collagen-binding domain, and/or a hyaluronic acid-binding domain as disclosed herein can be fused to the N-terminus of the first antibody Fc domain polypeptide and/or to the N-terminus of the second antibody Fc domain polypeptide.

A proteoglycan-binding domain, collagen-binding domain, and/or hyaluronic acid-binding domain, if present, can be fused to the rest of the heterodimeric Fc-fused protein through a linker. In certain embodiments, the proteoglycan-binding domain is fused to the rest of the heterodimeric Fc-fused protein through a peptide linker. In certain embodiments, the peptide linker includes a spacer peptide disclosed herein.

II. Methods of Preparation

The proteins of the present invention can be made using recombinant DNA technology well known to a skilled person in the art. For example, a first nucleic acid sequence encoding a first polypeptide comprising a first subunit of a multisubunit protein sequence fused to a first antibody Fc domain polypeptide can be cloned into a first expression vector; a second nucleic acid sequence encoding a second polypeptide comprising a second, different subunit of a multisubunit fused to a second antibody Fc domain polypeptide can be cloned into a second expression vector; and the first and the second expression vectors can be stably transfected together into host cells to produce the multimeric proteins.

To achieve the highest yield of the protein, different ratios of the first and second expression vectors can be explored to determine the optimal ratio for transfection into the host cells. After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the proteins of the present invention. The proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

III. Pharmaceutical Compositions

The present disclosure also features pharmaceutical compositions that contain an effective amount of a protein described herein. The composition can be formulated for use in a variety of drug delivery systems. One or more physiologically acceptable excipient(s) or carrier(s) can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The intravenous drug delivery formulation of the present disclosure may be contained in a bag, a pen, or a syringe. In certain embodiments, the bag may be connected to a channel comprising a tube and/or a needle. In certain embodiments, the formulation may be a lyophilized formulation or a liquid formulation. In certain embodiments, the formulation may freeze-dried (lyophilized) and contained in about 12-60 vials. In certain embodiments, the formulation may be freeze-dried and 45 mg of the freeze-dried formulation may be contained in one vial. In certain embodiments, the about 40 mg-about 100 mg of freeze-dried formulation may be contained in one vial. In certain embodiments, freeze dried formulation from 12, 27, or 45 vials are combined to obtained a therapeutic dose of the protein in the intravenous drug formulation. In certain embodiments, the formulation may be a liquid formulation and stored as about 250 mg/vial to about 1000 mg/vial. In certain embodiments, the formulation may be a liquid formulation and stored as about 600 mg/vial. In certain embodiments, the formulation may be a liquid formulation and stored as about 250 mg/vial.

A heterodimeric Fc-fused protein of the present invention could exist in a liquid aqueous pharmaceutical formulation including an effective amount of the protein in a buffered solution forming a formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including the heterodimeric Fc-fused protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including the heterodimeric Fc-fused protein of the present disclosure in a pH-buffered solution. The buffer of this invention may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g., sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/mL of citric acid (e.g., 1.305 mg/mL), about 0.3 mg/mL of sodium citrate (e.g., 0.305 mg/mL), about 1.5 mg/mL of disodium phosphate dihydrate (e.g., 1.53 mg/mL), about 0.9 mg/mL of sodium dihydrogen phosphate dihydrate (e.g., 0.86), and about 6.2 mg/mL of sodium chloride (e.g., 6.165 mg/mL). In certain embodiments, the buffer system includes 1-1.5 mg/mL of citric acid, 0.25 to 0.5 mg/mL of sodium citrate, 1.25 to 1.75 mg/mL of disodium phosphate dihydrate, 0.7 to 1.1 mg/mL of sodium dihydrogen phosphate dihydrate, and 6.0 to 6.4 mg/mL of sodium chloride. In certain embodiments, the pH of the formulation is adjusted with sodium hydroxide.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g., mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/mL. In certain embodiments, the concentration of mannitol may be about 7.5 to 15 mg/mL. In certain embodiments, the concentration of mannitol may be about 10-14 mg/mL. In certain embodiments, the concentration of mannitol may be about 12 mg/mL. In certain embodiments, the polyol sorbitol may be included in the formulation.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th ed., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In certain embodiments, the protein product of the present disclosure is formulated as a liquid formulation. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments vials may be filled with 61.2 mL of the protein product solution in order to allow an extractable volume of 60 mL. In certain embodiments, the liquid formulation may be diluted with 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 dalton mass decrease of the parent peptide. The subsequent hydrolysis results in an 18 dalton mass increase. Isolation of the succinimide intermediate is difficult due to instability under aqueous conditions. As such, deamidation is typically detectable as a 1 dalton mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation of the present disclosure may be preserved under conditions of pH and humidity to prevent deamination of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% sodium chloride solution before administration. In certain embodiments, the diluted drug product for injection is isotonic and suitable for administration by intravenous infusion.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

The protein of the present disclosure could exist in a lyophilized formulation including the proteins and a lyoprotectant. The lyoprotectant may be sugar, e.g., disaccharides. In certain embodiments, the lyoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing the protein of the present disclosure may be adjusted between 6 to 8. In certain embodiments, the pH range for the lyophilized drug product may be from 7 to 8.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include SWFI, BWFI, a pH buffered solution (e.g., phosphate-buffered saline), sterile saline solution, Ringer's solution or dextrose solution.

In certain embodiments, the lyophilized drug product of the current disclosure is reconstituted with either SWFI, USP or 0.9% sodium chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308: 43-53, 2001; Steimer et al., *Clinica Chimica Acta* 308: 33-41, 2001).

In general, dosages based on body weight are from about 0.01 µg to about 100 mg per kg of body weight, such as about 0.01 µg to about 100 mg/kg of body weight, about 0.01 µg to about 50 mg/kg of body weight, about 0.01 µg to about 10 mg/kg of body weight, about 0.01 µg to about 1 mg/kg of body weight, about 0.01 µg to about 100 µg/kg of body weight, about 0.01 µg to about 50 µg/kg of body weight, about 0.01 µg to about 10 µg/kg of body weight, about 0.01 µg to about 1 µg/kg of body weight, about 0.01 µg to about 0.1 µg/kg of body weight, about 0.1 µg to about 100 mg/kg of body weight, about 0.1 µg to about 50 mg/kg of body weight, about 0.1 µg to about 10 mg/kg of body weight, about 0.1 µg to about 1 mg/kg of body weight, about 0.1 µg to about 100 µg/kg of body weight, about 0.1 µg to about 10 µg/kg of body weight, about 0.1 µg to about 1 µg/kg of body weight, about 1 µg to about 100 mg/kg of body weight, about 1 µg to about 50 mg/kg of body weight, about 1 µg to about 10 mg/kg of body weight, about 1 µg to about 1 mg/kg of body weight, about 1 µg to about 100 µg/kg of body weight, about 1 µg to about 50 µg/kg of body weight, about 1 µg to about 10 µg/kg of body weight, about 10 µg to about 100 mg/kg of body weight, about 10 µg to about 50 mg/kg of body weight, about 10 µg to about 10 mg/kg of body weight, about 10 µg to about 1 mg/kg of body weight, about 10 µg to about 100 µg/kg of body weight, about 10 µg to about 50 µg/kg of body weight, about 50 µg to about 100 mg/kg of body weight, about 50 µg to about 50 mg/kg of body weight, about 50 µg to about 10 mg/kg of body weight, about 50 µg to about 1 mg/kg of body weight, about 50 µg to about 100 µg/kg of body weight, about 100 µg to about 100 mg/kg of body weight, about 100 µg to about 50 mg/kg of body weight, about 100 µg to about 10 mg/kg of body weight, about 100 µg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually. In some embodiments, the heterodimeric Fc-fused protein (e.g., a heterodimeric Fc-fused protein comprising IL-12 subunits) is administered intratumorally. In some embodiments, the heterodimeric Fc-fused protein is administered intratumorally at a lower dose or frequency than when administered systemically. In some embodiments, the heterodimeric Fc-fused protein is administered intratumorally following administration of a local anesthetic. In some embodiments, the heterodimeric Fc-fused protein is administered intratumorally under direct palpation of a tumor mass.

IV. Therapeutic Applications

The invention provides methods for treating cancer using a heterodimeric Fc-fused binding protein described herein and/or a pharmaceutical composition described herein. The methods may be used to treat a variety of cancers by administering to a patient in need thereof an effective amount of a heterodimeric Fc-fused protein described herein. In some embodiments, the cancer that is treated by a method disclosed herein is a locally advanced malignancy. In some embodiments, the locally advanced malignancy can be fully resected. In some embodiments, the locally advanced malignancy has been fully resected, and the treatment is provided subsequent to the resection.

In some embodiments, a heterodimeric Fc-fused protein of the present invention (e.g., a heterodimeric Fc-fused protein comprising IL-12 subunits) is used for treating an advanced malignancy as a monotherapy. In some embodiments, a heterodimeric Fc-fused protein of the present invention (e.g., a heterodimeric Fc-fused protein comprising IL-12 subunits) is used as an adjuvant for active immunotherapy of severe infectious diseases. In some embodiments, a heterodimeric Fc-fused protein of the present invention (e.g., a heterodimeric Fc-fused protein comprising IL-12 subunits) is used as an adjuvant for prophylactic vaccination. In some embodiments, a heterodimeric Fc-fused protein of the present invention is used for treating myelosuppression following radiotherapy.

The present invention also provides a method of reducing hematopoietic toxicity. Hematopoietic toxicity can result from genetic, infective, or environmental causes, including but not limited to irradiation and chemotherapy. For example, in certain embodiments, the present invention provides a method of treating a disease or disorder associated with radiation (e.g., ionizing radiation, alpha radiation, beta radiation, gamma radiation, X radiation, or neutron radiation). For example, in certain embodiments, the present invention provides a method of treating myelosuppression following a radiation therapy, the method comprising administering to a patient in need thereof an effective amount of a heterodimeric Fc-fused protein or a formulation described herein. In certain embodiments, the dose of the radiation therapy is at least 1, 5, 10, 15, or 20 Gy. In certain embodiments, the radiation therapy causes damage in a system, organ, or tissue selected from the group consisting of bone marrow, lymphatic system, immune system, mucosal tissue, mucosal immune system, gastrointestinal system, cardiovascular system, nervous system, reproductive organs, prostate, ovaries, lung, kidney, skin and brain. In certain embodiments, the method of the present invention reduces the damage.

The methods provided herein are useful in treating myelosuppression resulting from radiation. Accordingly, in certain embodiments, the present invention provides a method of treating myelosuppression occurring in the context of an accidental exposure to radiation, the method comprising administering to a patient in need thereof a therapeutically effective amount of a heterodimeric Fc-fused protein or a formulation described herein.

In certain embodiments, the present invention provides a method of treating acute radiation syndrome (ARS), the method comprising administering to a patient in need thereof an effective amount of a heterodimeric Fc-fused protein or a formulation described herein. ARS includes but is not limited to hematopoietic radiation syndrome, gastrointestinal radiation syndrome, neurovascular radiation syndrome, and cutaneous radiation syndrome. For example, hematopoietic radiation syndrome results from, at least in part, depletion of the hematopoietic stem cell pool and shows signs of lymphopenia and granulocytopenia. Gastrointestinal syndrome results from, at least in part, damage of stem cells and progenitor cells located in the crypts and failure to replace the cells in the surface of the villi and shows signs of watery diarrhea, dehydration, electrolyte loss, gastrointestinal bleeding, and perforation. In certain embodiments, the method of treatment provided herein is conducted at the prodromal phase of the ARS. The prodromal phase is the initial phase of acute illness, characterized by the symptoms of nausea, vomiting, anorexia, fever, headache, and/or early skin erythema, typically within 1-3 days after the exposure to radiation. In certain embodiments, the method of treatment provided herein is conducted at the latent phase of the ARS. The latent phase is a phase characterized by improvement of symptoms but exhibition of lymphopenia and granulocytopenia in lab tests, and may last hours to weeks depending on the dose of exposure. Treatment in the prodromal phase or latent phase may mitigate the development of the syndromes in the affected systems, organs, and/or tissues. In certain embodiments, the method of treatment provided herein is conducted at the manifest illness phase of the ARS. Treatment in this phase may still promote recovery from the ARS.

The present invention also provides a method of increasing the survival, proliferation, differentiation, and/or activity of an immune cell, the method comprising contacting the immune cell with a heterodimeric Fc-fused protein or a formulation disclosed herein. In certain embodiments, the immune cell is a T cell (e.g., CD4$^+$ T cells). In certain embodiments, the immune cell is an NK cell.

In certain embodiments, the heterodimeric Fc-fused protein of the present invention (e.g., a heterodimeric Fc-fused protein comprising IL-12 subunits) is used in treating a subject diagnosed with cancer. In certain embodiments, the cancer is bladder cancer, breast cancer, cervical cancer, colorectal cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, non-small cell lung cancer, small cell lung cancer, brain cancer, sarcoma, neuroblastoma, or squamous cell carcinoma of the head and neck cancerous cells. In certain embodiments, the cancer is colon cancer. In certain embodiments, the heterodimeric Fc-fused protein is administered as a monotherapy to a subject diagnosed with colon cancer. In certain embodiments, the cancer is melanoma. In certain embodiments, the heterodimeric Fc-fused protein is administered as a monotherapy to a subject diagnosed with melanoma. In certain embodiments, the cancer is breast cancer. In certain embodiments, the heterodimeric Fc-fused protein is administered as a monotherapy to a subject diagnosed with breast cancer.

In certain embodiments, the present disclosure provides a method of treating cancer, the method comprising administering to a patient only a single dose of a heterodimeric IL-12-Fc-fused protein. In certain embodiments, the single dose is in an amount sufficient to induce a complete response to the cancer. In certain embodiments, the single dose is in an amount sufficient to delay or prevent recurrence of the cancer.

In certain embodiments, the present disclosure provides a method of treating cancer, the method comprising administering to a patient only a single dose of a heterodimeric IL-12-Fc-fused protein comprising a first polypeptide comprising the amino acid sequence of SEQ ID NO:290 and a second polypeptide comprising the amino acid sequence of SEQ ID NO:291, or a formulation comprising the heterodimeric IL-12-Fc-fused protein and a pharmaceutically acceptable carrier.

In certain embodiments, a single dose of a heterodimeric IL-12-Fc-fused protein comprising a first polypeptide comprising the amino acid sequence of SEQ ID NO:290 and a second polypeptide comprising the amino acid sequence of SEQ ID NO:291, or a formulation comprising the heterodimeric IL-12-Fc-fused protein (e.g., comprising SEQ ID NO:290 and SEQ ID NO:291) and a pharmaceutically acceptable carrier is in an amount sufficient to induce a complete response to the cancer. In certain embodiments, the single dose is in an amount sufficient to delay or prevent recurrence of the cancer. In certain embodiments, a recurrence of a completely treated cancer (e.g., complete response after treatment with an IL-12-Fc-fused protein of the present invention) is delayed or prevented by 6 months to 72 months or more (e.g., 6 months, 12 months, 24 months, 36 months, 48 months, 60 months, 72 months, 84 months, or 96 months).

In certain embodiments, the cancer treated with a single dose or more of a heterodimeric IL-12-Fc-fused protein (e.g., comprising a first polypeptide comprising the amino acid sequence of SEQ ID NO:290 and a second polypeptide comprising the amino acid sequence of SEQ ID NO:291) is a metastatic cancer. In certain embodiments, the metastatic cancer is a local, regional, or distant metastatic cancer. In certain embodiments, a single or multiple dose of a heterodimeric IL-12-Fc-fused protein (e.g., comprising a first polypeptide comprising the amino acid sequence of SEQ ID NO:290 and a second polypeptide comprising the amino acid sequence of SEQ ID NO:291) treats a distant cancer, which is not the primary cancer of the source organ or tissue and/or the direct target of a treatment regimen, by an abscopal effect. In certain embodiments the abscopal effect of a heterodimeric IL-12-Fc-fused protein is enhanced during and/or after a treatment plan including radiation and/or chemotherapy. In certain embodiments, a single or multiple dose of a heterodimeric IL-12-Fc-fused protein (e.g., comprising a first polypeptide comprising the amino acid sequence of SEQ ID NO:290 and a second polypeptide comprising the amino acid sequence of SEQ ID NO:291) treats cancer in a patient by inducing a systemic anti-tumor response, determined, for example, by increased expression of IFNγ, CXCL9, and/or CXCL10 in the serum and/or the tumor of the patient.

V. Combination Therapy

Another aspect of the invention provides for combination therapy. A multi-specific binding protein described herein can be used in combination with additional therapeutic agents to treat the cancer.

In certain embodiments, the heterodimeric Fc-fused protein of the present invention (e.g., a heterodimeric Fc-fused protein comprising IL-12 subunits) is administered as a combination therapy to treat a subject diagnosed with cancer. In certain embodiments, the cancer is bladder cancer, breast cancer, cervical cancer, colorectal cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, non-small cell lung cancer, small cell lung cancer, brain cancer, sarcoma, neuroblastoma, or squamous cell carcinoma of the head and neck cancerous cells. In certain embodiments, the cancer is colon cancer. In certain embodiments, the heterodimeric Fc-fused protein is administered as a combination therapy to a subject diagnosed with colon cancer. In certain embodiments, the cancer is melanoma. In certain embodiments, the heterodimeric Fc-fused protein is administered as a combination therapy to a subject diagnosed with melanoma. In certain embodiments, the cancer is breast cancer. In certain embodiments, the heterodimeric Fc-fused protein is administered as a combination therapy to a subject diagnosed with breast cancer.

In some embodiments, a heterodimeric Fc-fused protein of the present invention (e.g., a heterodimeric Fc-fused protein comprising IL-12 subunits) is used in treating an advanced malignancy in combination with another therapeutic agent selected from: cytotoxic chemotherapy; radiotherapy; an antibody that targets a molecule involved in an anti-tumor immune response, such as CTLA-4, PD-1, PD-L1, or TGF-β; an antibody that acts by ADCC on a tumor-associated antigen; a multispecific antibody binding NKG2D, CD16, and a tumor-associated antigen, optionally administered in combination with an antibody that targets PD-1 or PD-L1; a personalized cancer vaccine; an oncolytic cancer vaccine; and a personalized vaccine administered in combination with an antibody that targets PD-1 or PD-L1.

In some embodiments, a heterodimeric Fc-fused protein of the present invention (e.g., a heterodimeric Fc-fused protein comprising IL-12 subunits) is used in treating malignancy (e.g., an advanced malignancy) in combination with another therapy including, but not limited to, an NK-targeting therapy (e.g., CAR-NK therapy), an antibody therapy, a checkpoint inhibitor therapy, an additional cytokine therapy, an innate immune system agonist therapy, a chemotherapy, a target agent therapy, a radiotherapy, an adoptive NK therapy, a stem cell transplant (SCT) therapy, an agonistic antibody, a chimeric antigen receptor (CAR) T cell therapy, a T-cell receptor (TCR) engineered therapy, a multi-specific binding protein (TriNKET), an agent that induces cellular senescence, and a vaccine and/or oncolytic virus therapy. In some embodiments, a heterodimeric Fc-fused protein of the present invention is used in treating malignancy (e.g., an advanced malignancy) in combination with two or more additional therapies selected from an NK-targeting therapy (e.g., CAR-NK therapy), an antibody therapy, a checkpoint inhibitor therapy, an additional cytokine therapy, an innate immune system agonist therapy, a chemotherapy, a target agent therapy, a radiotherapy, an adoptive NK therapy, a stem cell transplant (SCT) therapy, an agonistic antibody, a chimeric antigen receptor (CAR) T cell therapy, a T-cell receptor (TCR) engineered therapy, a multi-specific binding protein (TriNKET), an agent that induces cellular senescence, and a vaccine and/or oncolytic virus therapy.

In some embodiments, a heterodimeric Fc-fused protein of the present invention (e.g., a heterodimeric Fc-fused protein comprising IL-12) is used in treating locally advanced malignancy that can be fully resected, in combination with a cancer vaccine or an antibody that targets PD-1 or PD-L1.

Proteins of the invention can also be used as an adjunct to surgical removal of the primary lesion.

The amount of heterodimeric Fc-fused protein of the present invention (e.g., a heterodimeric Fc-fused protein comprising IL-12) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a heterodimeric Fc-fused protein may be administered during a time when the additional therapeutic agent(s) exerts its prophylactic or therapeutic effect, or vice versa.

As disclosed herein, the methods of the invention include coadministration of the combination of a heterodimeric Fc-fused protein (e.g., a heterodimeric Fc-fused protein comprising IL-12 subunits) and an additional therapeutic agent. As disclosed herein, the methods of the invention include coadministration of the combination of a heterodimeric Fc-fused protein comprising IL-12 subunits and an additional therapeutic agent.

Coadministered encompasses methods where a heterodimeric Fc-fused protein (e.g., a heterodimeric Fc-fused protein comprising IL-12 subunits) and an additional therapeutic agent are given simultaneously, where a heterodimeric Fc-fused protein and an additional therapeutic agent are given sequentially, and where either one of, or both of, a heterodimeric Fc-fused protein and an additional therapeutic agent are given intermittently or continuously, or any combination of: simultaneously, sequentially, intermittently and/or continuously. The skilled artisan will recognize that intermittent administration is not necessarily the same as sequential because intermittent also includes a first administration of an agent and then another administration later in time of that very same agent. Moreover, the skilled artisan understands that intermittent administration also encompasses sequential administration in some embodiments because intermittent administration does include interruption of the first administration of an agent with an administration of a different agent before the first agent is administered again. Further, the skilled artisan will also know that continuous administration can be accomplished by a number of routes including intravenous drip (IV infusion) or feeding tubes, etc.

Furthermore, and in a more general way, the term "coadministered" encompasses any and all methods where the individual administration of a heterodimeric Fc-fused protein and the individual administration of an additional therapeutic agent to a subject overlap during any timeframe.

The frequency of administration of a heterodimeric Fc-fused protein or an additional therapeutic agent to a subject is known in the art as Qnd or qnd where n is the frequency in days for successive administration of that agent. For example, Q3d would be an administration of an agent once every three (3) days. In certain embodiments, the method comprises administering either one of, or both of, or any combinations thereof, a heterodimeric Fc-fused protein and/or an additional therapeutic agent to a subject for Q1d, Q2d, Q3d, Q4d, Q5d, Q6d, Q7d, Q8d, Q9d, Q10d, Q14d, Q21d, Q28d, Q30d, Q90d, Q120d, Q240d, or Q365d.

In certain embodiments, either one of or both of a heterodimeric Fc-fused protein and/or an additional therapeutic agent are administered intermittently. In certain embodiments, the method includes administering either one of, or both of a heterodimeric Fc-fused protein or an additional therapeutic agent to a subject with a delay of at least ten (10) minutes, fifteen (15) minutes, twenty (20) minutes, thirty (30) minutes, forty (40) minutes, sixty (60) minutes, two (2) hours, three (3) hour, four (4) hours, six (6) hours, eight (8) hours, ten (10) hours, twelve (12) hours, fourteen (14) hours, eighteen (18) hours, twenty-four (24) hours, thirty-six (36) hours, forty-eight (48) hours, three (3) days, four (4) days, five (5) days, six (6) days, seven (7) days, eight (8) days, nine (9) days, ten (10) days, eleven (11) days, twelve (12) days, thirteen (13) days, fourteen (14) days, three (3) weeks, or four (4) weeks between administrations. In certain embodiments, the administration with a delay follows a pattern where one of, or both of, or any combination thereof, of a heterodimeric Fc-fused protein and/or an additional therapeutic agent are administered continuously for a given period of time from about ten (10) minutes to about three hundred and sixty five (365) days and then is not administered for a given period of time from about ten (10) minutes to about thirty (30) days.

In certain embodiments, either one of, or any combination of, a heterodimeric Fc-fused protein and/or an additional therapeutic agent are administered intermittently while the other is given continuously. In certain embodiments, the combination of the first effective amount of a heterodimeric Fc-fused protein is administered sequentially with the second effective amount of an additional therapeutic agent.

In certain embodiments, a heterodimeric Fc-fused protein and an additional therapeutic agent are administered simultaneously. In certain embodiments, the combination of the first effective amount of a heterodimeric Fc-fused protein is administered sequentially with the second effective amount of an additional therapeutic agent. In such embodiments, the combination is also said to be "coadministered" since the term includes any and all methods where the subject is exposed to both components in the combination. However, such embodiments are not limited to the combination being given just in one formulation or composition. It may be that certain concentrations of a heterodimeric Fc-fused protein and the additional therapeutic agent are more advantageous to deliver at certain intervals and as such, the first effective amount and second effective amount may change according to the formulation being administered.

In certain embodiments, a heterodimeric Fc-fused protein and the additional therapeutic agent are administered simultaneously or sequentially. In certain embodiments, the first effective amount of a heterodimeric Fc-fused protein is administered sequentially after the second effective amount of an additional therapeutic agent. In certain embodiments, the second effective amount of an additional therapeutic agent is administered sequentially after the first effective amount of a heterodimeric Fc-fused protein.

In certain embodiments, the combination of a heterodimeric Fc-fused protein (e.g., a heterodimeric Fc-fused protein comprising IL-12 subunits) and an additional therapeutic agent is administered in one formulation. In certain embodiments, the combination is administered in two (2) compositions where the first effective amount of a heterodimeric Fc-fused protein is administered in a separate formulation from the formulation of the second effective amount of an additional therapeutic agent. In certain embodiments, the combination is administered in two (2) compositions where the first effective amount of the heterodimeric Fc-fused protein is administered in a separate formulation from the formulation of the second effective amount of an additional therapeutic agent. In certain embodiments, the first effective amount of a heterodimeric Fc-fused protein is administered sequentially after the second effective amount of an additional therapeutic agent. In certain embodiments, the second effective amount of an additional therapeutic agent is administered sequentially after the first effective amount of a heterodimeric Fc-fused protein. In certain embodiments, a heterodimeric Fc-fused protein and the additional therapeutic agent are administered; and subsequently both the heterodimeric Fc-fused protein and the additional therapeutic agent are administered intermittently for at least twenty-four (24) hours. In certain embodiments, the heterodimeric Fc-fused protein and the additional therapeutic agent are administered on a non-overlapping every other day schedule.

In certain embodiments, the first effective amount of a heterodimeric Fc-fused protein is administered no less than four (4) hours after the second effective amount of an additional therapeutic agent. In certain embodiments, the first effective amount of a heterodimeric Fc-fused protein is administered no less than ten (10) minutes, no less than fifteen (15) minutes, no less than twenty (20) minutes, no less than thirty (30) minutes, no less than forty (40) minutes, no less than sixty (60) minutes, no less than one (1) hour, no less than two (2) hours, no less than four (4) hours, no less than six (6) hours, no less than eight (8) hours, no less than ten (10) hours, no less than twelve (12) hours, no less than twenty four (24) hours, no less than two (2) days, no less than four (4) days, no less than six (6) days, no less than eight (8) days, no less than ten (10) days, no less than twelve (12) days, no less than fourteen (14) days, no less than twenty one (21) days, or no less than thirty (30) days after the second effective amount of an additional therapeutic agent. In certain embodiments, the second effective amount of an additional therapeutic agent is administered no less than ten (10) minutes, no less than fifteen (15) minutes, no less than twenty (20) minutes, no less than thirty (30) minutes, no less than forty (40) minutes, no less than sixty (60) minutes, no less than one (1) hour, no less than two (2) hours, no less than four (4) hours, no less than six (6) hours, no less than eight (8) hours, no less than ten (10) hours, no less than twelve (12) hours, no less than twenty four (24) hours, no less than two (2) days, no less than four (4) days, no less than six (6) days, no less than eight (8) days, no less than ten (10) days, no less than twelve (12) days, no less than fourteen (14) days, no less than twenty one (21) days, or no less than thirty (30) days after the first effective amount of a heterodimeric Fc-fused protein.

In certain embodiments, either one of, or both of a heterodimeric Fc-fused protein and/or additional therapeutic agent are administered by a route selected from the group consisting of: intravenous, subcutaneous, cutaneous, oral, intramuscular, and intraperitoneal. In certain embodiments, either one of, or both of a heterodimeric Fc-fused protein and/or additional therapeutic agent are administered by intravenously. In certain embodiments, either one of, or both of, or any combination thereof, a heterodimeric Fc-fused protein and/or additional therapeutic agent are administered orally.

It is understood by the skilled artisan that the unit dose forms of the present disclosure may be administered in the same or different physical forms, i.e. orally via capsules or tablets and/or by liquid via IV infusion, and so on. Moreover, the unit dose forms for each administration may differ by the particular route of administration. Several various dosage forms may exist for either one of, or both of, the combination of a heterodimeric Fc-fused protein and additional therapeutic agents. Because different medical conditions can warrant different routes of administration, the same components of the combination described herein may be exactly alike in composition and physical form and yet may need to be given in differing ways and perhaps at differing times to alleviate the condition. For example, a condition such as persistent nausea, especially with vomiting, can make it difficult to use an oral dosage form, and in such a case, it may be necessary to administer another unit dose form, perhaps even one identical to other dosage forms used previously or afterward, with an inhalation, buccal, sublingual, or suppository route instead or as well. The specific dosage form may be a requirement for certain combinations of a heterodimeric Fc-fused protein and additional therapeutic agents, as there may be issues with various factors like chemical stability or pharmacokinetics.

NK-Targeting Therapy

In certain embodiments, the heterodimeric Fc-fused protein therapy is combined with NK targeting therapies. For example, in an embodiment, the heterodimeric Fc-fused protein is coadministered with a therapeutic agent that targets NKp46. In certain embodiments, the therapeutic agent that targets NKp46 also binds CD16, one or more tumor-associated antigens, or a combination thereof. Exemplary therapeutic agents that target NKp46 are described in more detail in U.S. Application No. US20170198038A1, herein incorporated by reference for all purposes.

In certain embodiments, the heterodimeric Fc-fused protein therapy is combined with bi- and tri-specific killer engagers (BiKEs and TriKEs) therapies, including BiKE and TriKE therapies targeting NK cells. BiKEs and TriKEs are constructed from a single heavy (VH) and light (VL) chain of the variable region of each antibody of interest. VH and VL domains are joined by a short flexible polypeptide linker to prevent dissociation. BiKEs and TriKEs are described in more detail in U.S. Application Nos. US20180282386A1 and US20180258396A1, herein incorporated by reference for all purposes. BiKEs and TriKEs can contain a binding domain specific for an NK cell.

In certain embodiments, BiKE and TriKE therapies are used in combination with the heterodimeric Fc-fused protein therapy to treat subjects known or suspected of having High-risk Myelodysplastic Syndrome, Acute Myelogenous Leukemia, Systemic Mastocytosis, or Mast Cell Leukemia. In certain embodiments, BiKE and TriKE therapies are administered as a single course of 3 weekly treatment blocks. In certain embodiments, a treatment block comprises 4 consecutive 24-hour continuous infusions (approximately 96 hours) followed by a 72 hour break. In certain embodiments, BiKE and TriKE therapies are administered at a dose of 5 µg/kg/day, 10 µg/kg/day, 25 µg/kg/day, 50 µg/kg/day, 100 µg/kg/day, or 200 µg/kg/day. In certain embodiments, BiKE and TriKE therapies are administered at a dose of at least 5 µg/kg/day, at least 10 µg/kg/day, at least 25 µg/kg/day, at least 50 µg/kg/day, at least 100 µg/kg/day, or at least 200 µg/kg/day. In certain embodiments, BiKE and TriKE therapies are administered at a dose of at least 1 µg/kg/day. In certain embodiments, BiKE and TriKE therapies are administered at a dose of at least 5 µg/kg/day. In certain embodiments, BiKE and TriKE therapies are administered at a dose of at least 200 µg/kg/day. In certain embodiments, BiKE and TriKE therapies are administered at a dose of at least 500 µg/kg/day. In certain embodiments, BiKE and TriKE therapies are administered at a dose of at least 1000 µg/kg/day. In certain embodiments, BiKE and TriKE therapies are administered at a dose of 200 µg/kg/day or less. In certain embodiments, BiKE and TriKE therapies are administered at a dose of 500 µg/kg/day or less. In certain embodiments, BiKE and TriKE therapies are administered at a dose of 1000 µg/kg/day or less. In certain embodiments, BiKE and TriKE therapies are administered at a dose of 1-200 µg/kg/day. In certain embodiments, BiKE and TriKE therapies are administered at a dose of 5-200 µg/kg/day. In certain embodiments, BiKE and TriKE therapies are administered at a dose of 1-500 µg/kg/day. In certain embodiments, BiKE and TriKE therapies are administered at a dose of 1-1000 µg/kg/day. In certain embodiments, BiKE and TriKE therapies are administered at a dose of 5-500 µg/kg/day. In certain embodiments, BiKE and TriKE therapies are administered at a dose of 5-1000 µg/kg/day. In certain embodiments, BiKE and TriKE therapies are administered at a maximum-tolerated dose. In certain embodiments, BiKE and TriKE therapies are administered at less than maximum-tolerated dose.

Multi-Specific Binding Protein ("TriNKET") Therapy

In certain embodiments, the heterodimeric Fc-fused protein therapy is combined with a therapy comprising a multi-specific binding protein, which comprises: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16 ("TriNKET") (for example, multi-specific binding proteins comprising various NKG2D-binders and tumor-associated antigen-binding sites described in international publication no. WO 2019/157332, whose contents relating to the multi-specific binding proteins described therein are incorporated by reference herein), to treat subjects known or suspected of having cancer. Exemplary tumor-associated antigens include, but are not limited to, HER2, CD20, CD33, B-cell maturation antigen (BCMA), EpCAM, CD2, CD19, CD25, CD30, CD38, CD40, CD52, CD70, CLL1/CLEC12A, FLT3, EGFR/ERBB1, IGF1R, HER3/ERBB3, HER4/ERBB4, MUC1, cMET, SLAMF7, PSCA, MICA, MICB, TRAILR1, TRATLR2, MAGE-A3, B7.1, B7.2, CTLA4, HLA-E, and PD-L1.

In certain embodiments, the heterodimeric Fc-fused protein therapy is combined with a therapy comprising a dose of a multi-specific binding protein based on body weight. For example, doses of a multi-specific binding protein based on body weight are from about 0.01 µg to about 100 mg per kg of body weight, such as about 0.01 µg to about 100 mg/kg of body weight, about 0.01 µg to about 50 mg/kg of body weight, about 0.01 µg to about 10 mg/kg of body weight, about 0.01 µg to about 1 mg/kg of body weight, about 0.01 µg to about 100 µg/kg of body weight, about 0.01 µg to about 50 µg/kg of body weight, about 0.01 µg to about 10 µg/kg of body weight, about 0.01 µg to about 1 µg/kg of body weight, about 0.01 µg to about 0.1 µg/kg of body weight, about 0.1 µg to about 100 mg/kg of body weight, about 0.1 µg to about 50 mg/kg of body weight, about 0.1 µg to about 10 mg/kg of body weight, about 0.1 µg to about 1 mg/kg of body weight, about 0.1 µg to about 100 µg/kg of body weight, about 0.1 µg to about 10 µg/kg of body weight, about 0.1 µg to about 1 µg/kg of body weight, about 1 µg to about 100 mg/kg of body weight, about 1 µg to about 50 mg/kg of body weight, about 1 µg to about 10 mg/kg of body weight, about 1 µg to about 1 mg/kg of body weight, about 1 µg to about 100 µg/kg of body weight, about 1 µg to about 50 µg/kg of body weight, about 1 µg to about 10 µg/kg of body weight, about 10 µg to about 100 mg/kg of body weight, about 10 µg to about 50 mg/kg of body weight, about 10 µg to about 10 mg/kg of body weight, about 10 µg to about 1 mg/kg of body weight, about 10 µg to about 100 µg/kg of body weight, about 10 µg to about 50 µg/kg of body weight, about 50 µg to about 100 mg/kg of body weight, about 50 µg to about 50 mg/kg of body weight, about 50 µg to about 10 mg/kg of body weight, about 50 µg to about 1 mg/kg of body weight, about 50 µg to about 100 µg/kg of body weight, about 100 µg to about 100 mg/kg of body weight, about 100 µg to about 50 mg/kg of body weight, about 100 µg to about 10 mg/kg of body weight, about 100 µg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

In certain embodiments, the heterodimeric Fc-fused protein therapy is combined with a therapy comprising doses of a multi-specific binding protein given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of a multi-specific binding protein could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

Chimeric Antigen Receptors (CARs) Therapy

In certain embodiments, the heterodimeric Fc-fused protein therapy is combined with a CAR therapy. The term "chimeric antigen receptor" or alternatively a "CAR" refers to a recombinant polypeptide construct comprising at least an extracellular antigen binding domain, a transmembrane domain and an intracellular signaling domain comprising a functional signaling domain derived from a stimulatory molecule (also referred to herein as a "primary signaling domain").

Accordingly, in certain embodiments, the CAR comprises an extracellular antigen-binding site that binds tumor-associated antigen, a transmembrane domain, and an intracellular signaling domain comprising a primary signaling domain. In certain embodiments, the CAR further comprises one or more functional signaling domains derived from at least one costimulatory molecule (also referred to as a "costimulatory signaling domain").

In one embodiment, the CAR comprises a chimeric fusion protein comprising a tumor-associated antigen-binding domain (e.g., tumor-associated antigen-binding scFv domain) comprising a heavy chain variable domain and a light chain variable domain as an extracellular antigen binding domain, a transmembrane domain, and an intracellular signaling domain comprising a primary signaling domain. In one embodiment, the CAR comprises a chimeric fusion protein comprising a tumor-associated antigen-binding domain (e.g., tumor-associated antigen-binding scFv domain) comprising a heavy chain variable domain and a light chain variable domain as an extracellular antigen binding domain, a transmembrane domain, and an intracellular signaling domain comprising a costimulatory signaling domain and a primary signaling domain. In certain embodiments, the CAR comprises a chimeric fusion protein comprising a tumor-associated antigen-binding domain (e.g., tumor-associated antigen-binding scFv domain) comprising a heavy chain variable domain and a light chain variable domain as an extracellular antigen binding domain, a transmembrane domain, and an intracellular signaling domain comprising two costimulatory signaling domains and a primary signaling domain. In one embodiment, the CAR comprises a chimeric fusion protein comprising a tumor-associated antigen-binding domain comprising a heavy chain variable domain and a light chain variable domain as an extracellular antigen binding domain, a transmembrane domain, and an intracellular signaling domain comprising at least two costimulatory signaling domains and a primary signaling domain.

With respect to the transmembrane domain, in various embodiments, the CAR is designed to comprise a transmembrane domain that is fused to the extracellular domain of the CAR. In one embodiment, the transmembrane domain is one that naturally is associated with one of the domains in the CAR. In some instances, the transmembrane domain can be selected or modified by amino acid substitution to avoid binding of such domains to the transmembrane domains of the same or different surface membrane proteins to minimize interactions with other members of the receptor complex. In another embodiment, the transmembrane domain is capable of homodimerization with another CAR on the CAR T cell surface. In another embodiment, the amino acid sequence of the transmembrane domain may be modified or substituted so as to minimize interactions with the binding domains of the native binding partner present in the same CAR T cell.

The transmembrane domain may be derived from any naturally occurring membrane-bound or transmembrane protein. In one embodiment, the transmembrane region is capable of signaling to the intracellular domain(s) whenever the CAR has bound to a target. In some embodiments, the transmembrane domain comprises the transmembrane region(s) of one or more proteins selected from the group consisting of TCR α chain, TCR β chain, TCR (chain, CD28, CD3F, CD45, CD4, CD5, CD8, CD9, CD16, CD22, CD33, CD37, CD64, CD80, CD86, CD134, CD137, and CD154. In some embodiments, the transmembrane domain comprises the transmembrane region(s) of one or more protein(s) selected from the group consisting of KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2Rβ, IL2Rγ, IL7Rα, ITGA1, VLA1, CD49a, ITGA4, IA4, CD49D, ITGA6, VLA-6, CD49f, ITGAD, CD11 d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKG2D, and NKG2C.

The extracellular tumor-associated antigen-binding domain (e.g., tumor-associated antigen-binding scFv domain) can be connected to the transmembrane domain by a hinge region. A variety of hinges can be employed, including but not limited to the human Ig hinge (e.g., an IgG4 hinge, an IgD hinge), a Gly-Ser linker, a $(G_4S)_4$ linker, a KIR2DS2 hinge, and a CD8α hinge.

The intracellular signaling domain of the CAR is responsible for activation of at least one of the specialized functions of the immune cell (e.g., cytolytic activity or helper activity, including the secretion of cytokines, of a T cell) in which the CAR has been placed in. Thus, as used herein, the term "intracellular signaling domain" refers to the portion of a protein which transduces an effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

The intracellular signaling domain of the CAR comprises a primary signaling domain (i.e. a functional signaling domain derived from a stimulatory molecule) and one or more costimulatory signaling domains (i.e. functional signaling domains derived from at least one costimulatory molecule).

As used herein, the term "stimulatory molecule" refers to a molecule expressed by an immune cell, e.g., a T cell, an NK cell, or a B cell, that provide the cytoplasmic signaling sequence(s) that regulate activation of the immune cell in a stimulatory way for at least some aspect of the immune cell signaling pathway. In one embodiment, the signal is a primary signal that is initiated by, for instance, binding of a TCR/CD3 complex with an MHC molecule loaded with a peptide, and which leads to mediation of a T cell response, including, but not limited to, proliferation, activation, differentiation, and the like.

Primary signaling domains that act in a stimulatory manner may contain signaling motifs which are known as immunoreceptor tyrosine-based activation motifs or ITAMs. Examples of ITAM containing cytoplasmic signaling sequences that are of particular use in the present disclosure include those derived from CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and DAP12. In one embodiment, the primary signaling domain in any one or more CARs comprises a cytoplasmic signaling sequence derived from CD3-zeta.

In some embodiments, the primary signaling domain is a functional signaling domain of TCR zeta, FcR gamma, FcR beta, CD3 gamma, CD3 delta, CD3 epsilon, CD5, CD22, CD79a, CD79b, CD66d, 4-1BB, and/or CD3-zeta. In an embodiment, the intracellular signaling domain comprises a functional signaling domain of CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and/or DAP12. In a particular embodiment, the primary signaling domain is a functional signaling domain of the zeta chain associated with the T cell receptor complex.

As used herein, the term "costimulatory molecule" refers to a cognate binding partner on a T cell that specifically binds with a costimulatory ligand, thereby mediating a costimulatory response by the T cell, such as, but not limited to, proliferation. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1, CD11a/CD18), CD2, CD7, CD258 (LIGHT), NKG2C, B7-H3, and a ligand that specifically binds with CD83, and the like. Further examples of such costimulatory molecules include CD5, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, and a ligand that specifically binds with CD83. In some embodiments, the costimulatory signaling domain of the CAR is a functional signaling domain of a costimulatory molecule described herein, e.g., OX40, CD27, CD28, CD30, CD40, PD-1, CD2, CD7, CD258, NKG2C, B7-H3, a ligand that binds to CD83, ICAM-1, LFA-1 (CD11a/CD18), ICOS and 4-1BB (CD137), or any combination thereof.

As used herein, the term "signaling domain" refers to the functional portion of a protein which acts by transmitting information within the cell to regulate cellular activity via defined signaling pathways by generating second messengers or functioning as effectors by responding to such messengers.

The cytoplasmic signaling sequences within the cytoplasmic signaling portion of the CAR may be linked to each other in a random or specified order. Optionally, a short oligo- or polypeptide linker, for example, between 2 and 10 amino acids in length may form the linkage.

Antibody Therapy

In certain embodiments, the heterodimeric Fc-fused protein therapy is combined with an antibody-therapy to treat subjects known or suspected of having cancer.

In certain embodiments, the heterodimeric Fc-fused protein is combined with a therapy comprising an anti-HER2 binding domain, such as an anti-HER2 antibody or anti-HER2 antibody platforms (e.g., a bi-specific or tri-specific antibody comprising an anti-HER2 binding domain, anti-HER2 antibody-drug conjugates, or anti-HER2 CAR). Anti-HER2 antibodies include, but are not limited to, trastuzumab (HERCEPTIN®—Roche/Genentech; Kanjinti—Amgen), pertuzumab (PERJETA®—Roche/Genentech), and MGAH22 (described in detail in U.S. Pat. No. 8,802,093, herein incorporated by reference for all purposes). Anti-HER2 antibody platforms include, but are not limited to, ertumaxomab (REXOMUN®—Creative Biolabs) and trastuzumab emtansine (ado-trastuzumab emtansine/T-DM1; KADCYLA®—Roche/Genentech). In certain embodiments, the anti-HER2 binding domain therapy is used in combination with the heterodimeric Fc-fused protein therapy to treat subjects known or suspected of having cancer. In certain embodiments, the anti-HER2 binding domain therapy is administered by IV infusion. In certain embodiments, the anti-HER2 binding domain therapy is administered at a dose of 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, 10 mg/kg/day. In certain embodiments, the anti-HER2 binding domain therapy is administered at a dose of at least 1 mg/kg/day, at least 2 mg/kg/day, at least 3 mg/kg/day, at least 4 mg/kg/day, at least 5 mg/kg/day, at least 6 mg/kg/day, at least 7 mg/kg/day, at least 8 mg/kg/day, at least 9 mg/kg/day, at least 10 mg/kg/day. In certain embodiments, the anti-HER2 binding domain therapy is administered at a dose of less than 1 mg/kg/day.

In certain embodiments, the anti-HER2 binding domain therapy is used in combination with the heterodimeric Fc-fused protein therapy to treat subjects known or suspected of having breast cancer, e.g., a subject diagnosed with netastatic HER2-overexpressing breast cancer. In certain embodiments, the anti-HER2 binding domain therapy is administered at 4 mg/kg/day. In certain embodiments, the anti-HER2 binding domain therapy is administered at 4 mg/kg/day by IV infusion over 90 minutes. In certain embodiments, the anti-HER2 binding domain therapy is administered at 2 mg/kg/day. In certain embodiments, the anti-HER2 binding domain therapy is administered at 2 mg/kg/day by IV infusion over 30 minutes. In certain embodiments, the anti-HER2 binding domain therapy is administered at an initial dose of 4 mg/kg/day, then subsequently administered weekly at 2 mg/kg/day. In certain embodiments, the anti-HER2 binding domain therapy is administered at an initial dose of 4 mg/kg/day, then subsequently administered weekly at 2 mg/kg/day for 52 weeks.

In certain embodiments, the anti-HER2 binding domain therapy is used in combination with the heterodimeric Fc-fused protein therapy to treat subjects known or suspected of having gastric cancer, e.g., a subject diagnosed with metastatic HER2-overexpressing gastric cancer. In certain embodiments, the anti-HER2 binding domain therapy is administered at 8 mg/kg/day. In certain embodiments, the anti-HER2 binding domain therapy is administered at 8 mg/kg/day by IV infusion over 90 minutes. In certain embodiments, the anti-HER2 binding domain therapy is administered at 6 mg/kg/day. In certain embodiments, the anti-HER2 binding domain therapy is administered at 6 mg/kg/day by IV infusion over 30-90 minutes. In certain embodiments, the anti-HER2 binding domain therapy is administered at an initial dose of 8 mg/kg/day, then subsequently administered weekly at 6 mg/kg/day. In certain embodiments, the anti-HER2 binding domain therapy is administered at an initial dose of 8 mg/kg/day, then subsequently administered weekly at 6 mg/kg/day for 52 weeks.

In certain embodiments, the heterodimeric Fc-fused protein therapy is combined with a therapy comprising an anti-CD20 binding domain, such as an anti-CD20 antibody or anti-CD20 antibody platforms (e.g., a bi-specific or tri-specific antibody comprising an anti-CD20 binding domain, anti-CD20 antibody-drug conjugates, or anti-CD20 CAR). Anti-CD20 antibodies include, but are not limited to, rituximab (RITUXAN®—Roche/Genentech), ocrelizumab (OCREVUS®—Roche/Genentech), obinutuzumab (GAZYVA®—Roche/Genentech), ofatumumab (ARZERRA®—Novartis), and veltuzumab. In certain embodiments, the anti-CD20 binding domain therapy is used in combination with the heterodimeric Fc-fused protein therapy to treat subjects known or suspected of having cancer. In certain embodiments, the anti-CD20 binding domain therapy is administered by IV infusion. In certain embodiments, the anti-CD20 binding domain therapy is administered at a dose of 100 mg/m$^2$, 200 mg/m$^2$, 300 mg/m$^2$, 400 mg/m$^2$, 500 mg/m$^2$, 600 mg/m$^2$, 700 mg/m$^2$, 800 mg/m$^2$, 900 mg/m$^2$, or 1000 mg/m$^2$. In certain embodiments, the anti-CD20 binding domain therapy is administered at a dose of 375 mg/m$^2$. In certain embodiments, the anti-CD20 binding domain therapy is administered at a dose of at least 100 mg/m$^2$, at least 200 mg/m$^2$, at least 300 mg/m$^2$, at least 400 mg/m$^2$, at least 500 mg/m$^2$, at least 600 mg/m$^2$, at least 700 mg/m$^2$, at least 800 mg/m$^2$, at least 900 mg/m$^2$, or at least 1000 mg/m$^2$. In certain embodiments, the anti-CD20 binding domain therapy is administered at a dose of less than 400 mg/m$^2$. In certain embodiments, the anti-CD20 binding domain therapy is administered at a dose of less than 375 mg/m$^2$.

In certain embodiments, the anti-CD20 binding domain therapy is used in combination with the heterodimeric Fc-fused protein therapy to treat subjects known or suspected of having Non-Hodgkin's Lymphoma (NHL). In certain embodiments, the anti-CD20 binding domain therapy is administered at a dose of 375 mg/m$^2$ by IV-infusion. In certain embodiments, the anti-CD20 binding domain therapy is administered at a dose less than 375 mg/m$^2$ by IV-infusion.

In certain embodiments, the anti-CD20 binding domain therapy is used in combination with the heterodimeric Fc-fused protein therapy to treat subjects known or suspected of having Chronic Lymphocytic Leukemia (CLL). In certain embodiments, the anti-CD20 binding domain therapy is administered at a dose of 375 mg/m$^2$ by IV-infusion in a first cycle, and at a dose of 500 mg/m$^2$ by IV-infusion per cycle in an additional 2-6 cycles. In certain embodiments, the anti-CD20 binding domain therapy is administered at a dose less than 375 mg/m$^2$ by IV-infusion. The combined anti-CD20 binding domain and heterodimeric Fc-fused protein therapy can be used in combination with fludarabine and cyclophosphamide (FC).

In certain embodiments, the anti-CD20 binding domain therapy is used in combination with the heterodimeric Fc-fused protein therapy to treat subjects known or suspected of having Rheumatoid Arthritis (RA). In certain embodiments, the anti-CD20 binding domain therapy is administered as two doses of 1000 mg, doses separated 2 weeks, by IV-infusion. In certain embodiments, the anti-CD20 binding domain therapy is administered as two doses of 1000 mg, doses separated 2 weeks, by IV-infusion up to 24 weeks. In certain embodiments, the combined anti-CD20 binding domain and heterodimeric Fc-fused protein therapy is coadministered with methotrexate.

In certain embodiments, the heterodimeric Fc-fused protein therapy is combined with a therapy comprising an antibody therapy comprising an agonist antibody. In certain embodiments, the agonist antibody is an anti-4-1BB antibody, an anti-CD137 antibody, an anti-FAP antibody, an anti-OX40 antibody, an anti-CD40 antibody, an anti-GITR antibody, or an anti-CD27 antibody. In certain embodiments, the agonist antibody is a bispecific antibody. In certain embodiments, the agonist antibody is a multispecific antibody, e.g., a bispecific antibody, comprising two or more antigen binding domains selected from an anti-4-1BB antibody, an anti-CD137 antibody, an anti-FAP antibody, an anti-OX40 antibody, an anti-CD40 antibody, an anti-GITR antibody, or an anti-CD27 antibody. An illustrative example is a bispecific agonist antibody targeting 4-1BB and CD137, such as utomilumab (Pfizer).

Checkpoint Inhibitor Therapy

In certain embodiments, the heterodimeric Fc-fused protein therapy can be combined with a checkpoint inhibitor therapy. Illustrative immune checkpoint molecules that can be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory CD8+ (αβ) T cells), CD160 (also referred to as BY55), and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160, and CGEN-15049. Illustrative immune checkpoint inhibitors include Illustrative immune checkpoint inhibitors include nivolumamb (anti-PD-1; OPDIVO®—BMS), AMP224 (anti-PD-1; NCI), pembrolizumab (anti-PD-1; MK-3475/KEYTRUDA®—Merck), pidilizumab (anti-PD-1 antibody; CT-O11-Teva/CureTech), atezolizumab (anti-PD-L1; TECENTRIQ®—Roche/Genentech), durvalumab (anti-PD-L1; MEDI4736/IMFINZI®—Medimmune/AstraZeneca), avelumab (anti-PD-L1; BAVENCIO®—Pfizer), BMS-936559 (anti-PD-L1-BMS), ipilimumab (anti-CTLA-4; YERVOY®—BMS), tremelimumab (anti-CTLA-4; Medimmune/AstraZeneca), lirilumab (anti-KIR; BMS), monalizumab (anti-NKG2A; Innate Pharma/AstraZeneca), BY55 (anti-CD160), anti-OX40. anti-TIM3, and anti-LAG3.

In certain embodiments, the checkpoint inhibitor therapy is used in combination with the heterodimeric Fc-fused protein therapy to treat subjects known or suspected of having cancer. In certain embodiments, the checkpoint inhibitor therapy is administered by IV infusion. In certain embodiments, the checkpoint inhibitor therapy is administered by IV infusion over 30 minutes. In certain embodiments, the checkpoint inhibitor therapy is administered every 3 weeks. In certain embodiments, the checkpoint inhibitor therapy is administered at a dose of 100 mg, 200 mg, 300 mg, 400 mg, 500 mg, 600 mg, 700 mg, 800 mg, 900 mg, or 1000 mg. In certain embodiments, the checkpoint inhibitor therapy is administered at a dose of 200 mg. In certain embodiments, the checkpoint inhibitor therapy is administered at a dose of at least 100 mg, at least 200 mg, at least 300 mg, at least 400 mg, at least 500 mg, at least 600 mg, at least 700 mg, at least 800 mg, at least 900 mg, or at least 1000 mg. In certain embodiments, the checkpoint inhibitor therapy is administered at a dose of less than 200 mg. In certain embodiments, the checkpoint inhibitor therapy is used in combination with the heterodimeric Fc-fused protein therapy to treat subjects known or suspected of having Melanoma, Non-Small Cell Lung Cancer (NSCLC), Head and Neck Squamous Cell Cancer (HN-SCC), Classical Hodgkin Lymphoma (cHL), Primary Mediastinal Large B-Cell Lymphoma (PMBCL), Urothelial Carcinoma, Microsatellite Instability-High Cancer, Gastric Cancer, Cervical Cancer, Hepatocellular Carcinoma (HCC), Merkel Cell Carcinoma (MCC), Renal Cell Carcinoma (RCC).

Additional Cytokine Therapy

In some embodiments, the heterodimeric Fc-fused protein therapy is combined with one or more additional cytokine therapies, one or more chemokine therapies, or combinations thereof. In some embodiments, the heterodimeric Fc-fused protein therapy is combined with one or more additional cytokine therapies. In some embodiments, the heterodimeric Fc-fused protein therapy is combined with one or more chemokine therapies. In some embodiments, the cytokine therapy comprises a pro-inflammatory cytokine, a Th1 cytokine, or a Th2 cytokine. In some embodiments, the cytokine therapy comprises a recombinant human cytokine or chemokine.

In some embodiments, the cytokine therapy includes a cytokine that is an interleukin (e.g., IL-1, IL-2, IL-6, IL-7, IL-8, IL-12, IL-13, IL-15, IL-16, IL-18, IL-21 and IL-22). In some embodiments, the cytokine therapy includes a cytokine that is growth factor (e.g., tumor necrosis factor (TNF), LT, EMAP-II, GM-CSF, FGF and PDGF) In some embodiments, the cytokine therapy comprises an anti-inflammatory cytokine (e.g., IL-4, IL-10, IL-11, IL-13 and TGF).

In some embodiments, the chemokine therapy includes a pro-inflammatory chemokine (e.g., GRO-α, GRO-b, LIX, GCP-2, MIG, IP10, I-TAC, and MCP-1, RANTES, Eotaxin, SDF-1, and MIP3a). In some embodiments, the chemokine therapy includes a chemokine receptor. In some embodiments, the chemokine therapy includes a CXC chemokine receptor (e.g., CXCR1, CXCR2, CXCR3, CXCR4, CXCR5, CXCR6, and CXCR7), a CC chemokine receptor (e.g., CCR1, CCR2, CCR3, CCR4, CCR5, CCR6, CCR7, CCR8, CCR9, CCR10, and CCR11), a CX3C chemokine receptor (e.g., CX3C11), or a XC chemokine receptor (e.g., XCR1). In some embodiments, the chemokine therapy comprises a G protein-linked transmembrane receptor.

In some embodiments, the cytokine therapy comprises a cytokine therapy that synergizes with the IL-12 signaling. In some embodiments, the cytokine therapy comprises an IL-2 cytokine or a derivative thereof. In some embodiments, the IL-2 therapy is aldesleukin (Proleukin—Prometheus Therapeutics). In some embodiments, the IL-2 therapy and/or aldesleukin is administered intravenously. In some embodiments, the cytokine therapy comprises an IL-15 cytokine or a derivative thereof. In some embodiments, the IL-15 therapy is ALT-803 (Altor Bioscience) or NKTR-255 (Nektar). In some embodiments, the IL-15 therapy, NKTR-255, and/or ALT-803 is administered subcutaneously. In some embodiments, the chemokine therapy comprises a CXCL9 chemokine, a CXCL10 chemokine, or derivatives thereof.

In some embodiments, the cytokine or chemokine therapy includes administering a cytokine or chemokine to a subject. In some embodiments, the cytokine or chemokine therapy includes administering a recombinant cytokine or chemokine to a subject. In some embodiments, the cytokine or chemokine therapy includes engineering a cell to produce the cytokine or chemokine. In some embodiments, the cytokine or chemokine therapy includes engineering a cell ex vivo, in vitro, or in vivo to produce the cytokine or chemokine.

In some embodiments, the cytokine or chemokine therapy includes engineering a cell to produce the cytokine or chemokine using a viral vector-based delivery platform such as vaccinia, fowlpox, self-replicating alphavirus, marabavirus, adenovirus (See, e.g., Tatsis et al., Adenoviruses, Molecular Therapy (2004) 10, 616-629), a lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, Immunol Rev. (2011) 239(1): 45-61, Sakuma et al., Lentiviral vectors: basic to translational, Biochem J. (2012) 443(3):603-18, Cooper et al., Rescue of splicing-mediated intron loss maximizes expression in lentiviral vectors containing the human ubiquitin C promoter, Nucl. Acids Res. (2015) 43 (1): 682-690, Zufferey et al., Self-Inactivating Lentivirus Vector for Safe and Efficient In Vivo Gene Delivery, J. Virol. (1998) 72 (12): 9873-9880), or an adeno-associated virus ("AAV") vector, as described in more detail in U.S. Pat. No. 5,173, 414; Tratschin et al, Mol. Cell. Biol. 5:3251-3260 (1985); Tratschin, et al, Mol. Cell, Biol. 4:2072-2081 (1984); Hermonat & amp; Muzyczka, PNAS 81:64666470 (1984); and Samuiski et al, J. Virol. 63:03822-3828 (1989)). In some embodiments, the cytokine or chemokine therapy includes engineering a cell to produce the cytokine or chemokine using a LNP, liposome, or an exosome. In some embodiments, the cytokine or chemokine therapy includes engineering a cell to produce the cytokine or chemokine using genome editing, such as using a nuclease-based genome editing systems (e.g., a Clustered Regularly Interspaced Short Palindromic Repeats (CRISPR) family, a Transcription activator-like effector nuclease (TALEN), a zinc-finger nuclease (ZFN), and a homing endonuclease (HE) based genome editing system or a derivative thereof). In some embodiments, the cytokine or chemokine therapy includes engineering a cell to produce the cytokine or chemokine using electroporation.

Innate Immune System Agonist Therapy

In some embodiments, the heterodimeric Fc-fused protein therapy is combined with one or more innate immune system agonists.

In some embodiments, the innate immune system agonist comprises a toll-like receptor (TLR) agonist. In some embodiments, the TLR agonist comprises a TLR1/2, TLR2/6, TLR3, TLR4, TLR7, TLR8, TLR7/8, or TLR9 agonist. In some embodiments, a TLR2/6 agonist comprises lipoproteins, such as bacterial lipoproteins or derivatives, such as Pam2CSK4. In some embodiments, a TLR1/2 agonist comprises lipoproteins. In some embodiments, a TLR3 agonist comprises a dsRNA analog, such as rintatolimod (AMPLIGEN®—Hemispherx Biopharma) or poly IC-LC (e.g., HILTONOL®). In some embodiments, a TLR4 agonist comprises lipopolysaccharide (LPS, also referred to as endotoxin) or derivatives, such as lipid A. In some embodiments, a TLR7 agonist comprises a ssRNA or derivatives or imidazoquinoline derivatives including, but not limited to, resiquimod (also referred to as R848), imiquimod (ZYCLARA®, Aldara—Medicis), and gardiquimod. In some embodiments, a TLR7 agonist is also a TLR8 agonist, such as imiquimod or Medi-9197 (AstraZeneca/MedImmune). In some embodiments, a TLR9 agonist comprises a CpG-containing oligodeoxynucleotide (CpG-ODN) or SD-101 (Dynavax).

In some embodiments, the innate immune system agonist comprises a Stimulator of interferon genes (STING) agonist. In some embodiments, the STING agonist comprises a cyclic-di-nucleotide (CDN). Is some embodiments, the CDN comprises a cyclic-di-AMP, a cyclic-di-GMP, or a cyclic-GMP-AMP (cGAMP). In some embodiments, the STING agonist comprises a nucleic acid (e.g., DNA or RNA) that stimulates cGAS. In some embodiments, the STING agonist is ADU-S100 (also referred to as MIW815—Aduro/Novartis).

Chemotherapy

In certain embodiments, the heterodimeric Fc-fused protein therapy is combined with one or more chemotherapies. In certain embodiments, the heterodimeric Fc-fused protein therapy is combined with one or more chemotherapies to treat a subject diagnosed with cancer. Examples of chemotherapy agents include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, ABT-199, BMS-345541, bortezomib (VELCADE®), bryostatin 1, busulfan, carboplatin, campath-1H, CC-5103, carmustine, caspofungin acetate, clofarabine, cisplatin, Cladribine (LEUSTARIN®), Chlorambucil (LEUKERAN®), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (ADRIAMYCIN®, ADRIBLASTINE®), doxorubicin hydrochloride, enzastaurin, epoetin alfa, etoposide, Everolimus (RAD001), fenretinide, filgrastim, melphalan, mesna, Flavopiridol, Fludarabine (FLUDARA®), Geldanamycin (17-AAG), ifosfamide, irinotecan hydrochloride, ixabepilone, Lenalidomide (REVLIMID®, CC-5013), lymphokine-activated killer cells, melphalan, methotrexate, mitoxantrone hydrochloride, motexafin gadolinium, mycophenolate mofetil, nelarabine, oblimersen (GENASENSE®) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (NIPENT®), perifosine, Prednisolone, Prednisone, R-roscovitine (SELICILIB®, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CC1-779), Thalidomide, therapeutic allogeneic lymphocytes, thiotepa, tipifarnib, VELCADE® (BORTEZOMIB® or PS-341), Vincristine (ONCOVIN®), vincristine sulfate, vinorelbine ditartrate, Vorinostat (SAHA), and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (R-MCP).

In certain embodiments, the heterodimeric Fc-fused protein therapy is combined with one or more chemotherapies to treat a subject diagnosed with colon cancer, rectal cancer, or colorectal cancer (CRC). In certain embodiments, the chemotherapy comprises FOLFOX (5-FU, leucovorin, and oxaliplatin/Eloxatin), FOLFIRI (leucovorin, 5-FU, and irinotecan/Camptosar), FOLFOXIRI (leucovorin, 5-FU, oxaliplatin, and irinotecan), CapeOx (capecitabine and oxaliplatin), 5-FU coadministered with leucovorin, capecitabine (XELODA®) alone, or Trifluridine and tipiracil (LONSURF®). In certain embodiments, the chemotherapy comprises a VEGF targeting agent, such as bevacizumab (AVASTIN®), ziv-aflibercept (ZALTRAP®), ramucirumab (CYRAMZA®), or Regorafenib (STIVARGA®), or an EGFR targeting agent such as cetuximab (ERBITUX) or panitumumab (VECTIBIX®). In certain embodiments, the chemotherapy coadministers a chemotherapy selected from FOLFOX, FOLFIRI, FOLFOXIRI, CapeOx, 5-FU coadministered with leucovorin, capecitabine alone, and Trifluridine/tipiracil together with a VEGF targeting agent or an EGFR targeting agent.

In certain embodiments, the heterodimeric Fc-fused protein therapy is combined with one or more chemotherapies to treat a subject diagnosed with breast cancer. In certain embodiments, the chemotherapy comprises doxorubicin (ADRIAMYCIN®), pegylated liposomal doxorubicin, epirubicin (ELLENCE®), paclitaxel (Taxol), docetaxel (TAXOTERE®), albumin-bound paclitaxel (ABRAXANE®), 5-fluorouracil (5-FU), cyclophosphamide (CYTOXAN®), carboplatin (PARAPLATIN®), cisplatin, vinorelbine (NAVELBINE®), capecitabine (XELODA), gemcitabine (GEMZAR®), ixabepilone (IXEMPRA®), or eribulin (HALAVEN). In certain embodiments, the chemotherapy comprises a combination of two or more chemotherapies selected from doxorubicin (ADRIAMYCIN®), pegylated liposomal doxorubicin, epirubicin (ELLENCE®), paclitaxel (Taxol), docetaxel (TAXOTERE®), albumin-bound paclitaxel (ABRAXANE®), 5-fluorouracil (5-FU), cyclophosphamide (CYTOXAN®), carboplatin (PARAPLATIN®), cisplatin, vinorelbine (NAVELBINE®), capecitabine (XELODA®), gemcitabine (GEMZAR®), ixabepilone (IXEMPRA®), and eribulin (HALAVEN®).

In certain embodiments, the heterodimeric Fc-fused protein therapy is combined with one or more chemotherapies to treat a subject diagnosed with melanoma/skin-cancer. In certain embodiments, the chemotherapy comprises dacarbazine (also called DTIC), temozolomide, nab-paclitaxel, paclitaxel, cisplatin, carboplatin, or vinblastine.

Targeted Agent Therapy

In certain embodiments, the heterodimeric Fc-fused protein therapy is combined with one or more targeted agents. In general, targeted agents act on specific molecular targets, such as targets associated with cancer. Targeted agents are differentiated from standard chemotherapies in that standard chemotherapies act on all rapidly dividing normal and cancerous cells. Targeted agents include, but are not limited to, a hormone therapy, a signal transduction inhibitor, a gene expression modulator, an apoptosis inducer, an angiogenesis inhibitor, an immunotherapy, a toxin delivery molecule (e.g., an antibody drug-conjugate), and a kinase inhibitor. In certain embodiments, a targeted agent comprises a receptor agonist or ligand.

In certain embodiments, the heterodimeric Fc-fused protein therapy is combined with one or more targeted agents to treat a subject diagnosed with colon cancer, rectal cancer, or colorectal cancer (CRC). In certain embodiments, the targeted agent comprises cetuximab (ERBITUX®), panitumumab (VECTIBIX®), bevacizumab (AVASTIN®), ziv-aflibercept (ZALTRAP®), regorafenib (STIVARGA®), ramucirumab (CYRAMZA®), nivolumab (OPDIVO®), or ipilimumab (YERVOY®).

In certain embodiments, the heterodimeric Fc-fused protein therapy is combined with one or more targeted agents to treat a subject diagnosed with breast cancer. In certain embodiments, the targeted agent comprises everolimus (AFINITOR®), tamoxifen (NOLVADEX®), toremifene (FARESTON®), trastuzumab (HERCEPTIN®), fulvestrant (FASLODEX®), anastrozole (ARIMIDEX®), exemestane (AROMASIN®), lapatinib (TYKERB®), letrozole (FEMARA®), pertuzumab (PERJETA®), ado-trastuzumab emtansine (KADCYLA®), palbociclib (IBRANCE®), ribociclib (KISQALI®), neratinib maleate (NERLYNX™), abemaciclib (VERZENIO™), olaparib (LYNPARZA™) atezolizumab (TECENTRIQ®), or alpelisib (PIQRAY®).

In certain embodiments, the heterodimeric Fc-fused protein therapy is combined with one or more targeted agents to treat a subject diagnosed with melanoma/skin-cancer. In certain embodiments, the targeted agent comprises Vismodegib (ERIVEDGE®), sonidegib (ODOMZO®), ipilimumab (YERVOY®), vemurafenib (ZELBORAF®), trametinib (MEKINIST®), dabrafenib (TAFINLAR®), pembrolizumab (KEYTRUDA®), nivolumab (OPDIVO®), cobimetinib (COTELLIC™), alitretinoin (PANRETIN®), avelumab (BAVENCIO®), encorafenib (BRAFTOVI™), binimetinib (MEKTOVI®), or cemiplimab-rwlc (LIBTAYO®).

In certain embodiments, the heterodimeric Fc-fused protein therapy is combined with a receptor agonist or ligand therapy. In certain embodiments, the receptor agonist or ligand therapy comprises an agonist antibody. In certain embodiments, the receptor agonist or ligand therapy comprises a receptor ligand, such as 4-1BBL or CD40L.

Radiotherapy

In some embodiments, the heterodimeric Fc-fused protein therapy is combined with radiotherapy. In certain embodiments, the heterodimeric Fc-fused protein therapy is combined with a radioisotope particle, such as indium In-111, yttrium Y-90, or iodine I-131. Examples of combination therapies include, but are not limited to, Iodine-131 tositumomab (BEXXAR®), Yttrium-90 ibritumomab tiuxetan (ZEVALIN®), and BEXXAR® with CHOP. In certain embodiments, the radiotherapy comprises external-beam radiation therapy (EBRT), internal radiation therapy (brachytherapy), endocavitary radiation therapy, interstitial brachytherapy, radioembolization, hypofractionated radiation therapy, intraoperative radiation therapy (IORT), 3D-conformal radiotherapy, stereotactic radiosurgery (SRS), or stereotactic body radiation therapy (SBRT).

In certain embodiments, the heterodimeric Fc-fused protein therapy is combined with one or more radiotherapies to treat a subject diagnosed with colon cancer, rectal cancer, or colorectal cancer (CRC). In certain embodiments, the radiotherapy comprises external-beam radiation therapy (EBRT), internal radiation therapy (brachytherapy), endocavitary radiation therapy, interstitial brachytherapy, or radioembolization.

In certain embodiments, the heterodimeric Fc-fused protein therapy is combined with one or more radiotherapies to treat a subject diagnosed with breast cancer. In certain embodiments, the radiotherapy comprises external-beam radiation therapy, hypofractionated radiation therapy, intraoperative radiation therapy (IORT), or 3D-conformal radiotherapy.

In certain embodiments, the heterodimeric Fc-fused protein therapy is combined with one or more radiotherapies to treat a subject diagnosed with melanoma/skin-cancer. In certain embodiments, the radiotherapy comprises stereotactic radiosurgery (SRS; e.g., using a Gamma Knife or linear accelerator) or stereotactic body radiation therapy (SBRT).

Vaccine and Oncolytic Viruses Therapy

In some embodiments, the heterodimeric Fc-fused protein therapy is combined with one or more immunogenic compositions, e.g., a vaccine composition or an oncolytic virus, capable of raising a specific immune response, e.g., a tumor-specific immune response.

In some embodiments, the heterodimeric Fc-fused protein therapy is combined with a vaccine composition. Vaccine compositions typically comprise a plurality of antigens and or neoantigens specific for the tumor to be targeted. Vaccine compositions can also be referred to as vaccines.

In some embodiments, a vaccine composition further comprises an adjuvant and/or a carrier. In some embodiments, a vaccine composition associates with a carrier such as a protein or an antigen-presenting cell such as a dendritic cell (DC) capable of presenting the peptide to a T-cell. In some embodiments, carriers are scaffold structures, for example a polypeptide or a polysaccharide, to which an antigen or neoantigen, is capable of being associated.

In general, adjuvants are any substance whose admixture into a vaccine composition increases or otherwise modifies the immune response to an antigen or neoantigen. Optionally, adjuvants are conjugated covalently or non-covalently. The ability of an adjuvant to increase an immune response to an antigen is typically manifested by a significant or substantial increase in an immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response. Suitable adjuvants include, but are not limited to 1018 ISS, alum, aluminium salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are useful. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11).

Cytokines can also be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418). In some embodiments, an adjuvant comprises a CpG immunostimulatory oligonucleotide. In some embodiments, an adjuvant comprises a TLR agonist.

Other examples of useful adjuvants include, but are not limited to, chemically modified CpGs (e.g. CpR, Idera), Poly(I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives can readily be determined by the skilled artisan without undue experimentation. Additional adjuvants include colony-stimulating factors, such as Granulocyte Macrophage Colony Stimulating Factor (GM-CSF, sargramostim).

In some embodiments, a vaccine composition comprises more than one different adjuvant. In some embodiments, a vaccine composition comprises any adjuvant substance including any of the above or combinations thereof. It is also contemplated that a vaccine and an adjuvant can be administered together or separately in any appropriate sequence.

In some embodiments, a carrier (or excipient) is present independently of an adjuvant. In some embodiments, the function of a carrier is to increase the molecular weight, increase activity or immunogenicity, to confer stability, to increase the biological activity, or to increase serum half-life. In some embodiments, a carrier aids presenting peptides to T-cells. In some embodiments, a carrier comprises any suitable carrier known to the person skilled in the art, for example a protein or an antigen presenting cell. Examples of carrier proteins include, but are not limited to, keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier is generally a physiologically acceptable carrier acceptable to humans and safe. However, tetanus toxoid and/or diptheria toxoid are suitable carriers. Alternatively, the carrier can be dextrans, for example sepharose.

In some embodiments, a vaccine comprises a viral vector-based vaccine platform, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). In general, upon introduction into a host, infected cells express the antigen or neoantigen and thereby elicits a host immune (e.g., CTL) response against the peptide(s).

Dependent on the packaging capacity of the above mentioned viral vector-based vaccine platforms, in some embodiments, the vaccine composition comprises one or more viral-vectors. In some embodiments, viral-vectors comprise sequences flanked by non-mutated sequences, separated by linkers, or preceded with one or more sequences targeting a subcellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, *Science.* (2016) 352 (6291):1337-41, Lu et al., Efficient identification of mutated cancer antigens recognized by T cells associated with durable tumor regressions, *Clin Cancer Res.* (2014) 20(13):3401-10). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of neoantigens, e.g., *Salmonella typhi* vectors, and the like will be apparent to those skilled in the art from the description herein.

In some embodiments, the heterodimeric Fc-fused protein therapy is combined with an oncolytic virus therapy. In general, an oncolytic virus is a virus engineered to infect and kill mainly cancer cells. In some embodiments, in addition to an oncolytic virus killing a cancer cell, the oncolytic virus induces an immune response to the cancer cell.

In certain embodiments, the heterodimeric Fc-fused protein therapy is combined with oncolytic virus therapy to treat a subject diagnosed with melanoma/skin-cancer. In certain embodiments, the oncolytic virus comprises talimogene laherparepvec (IMLYGIC®), also referred to as T-VEC. In some embodiments, a heterodimeric Fc-fused protein comprising subunits of IL-12 is used for treating cancer (e.g., an advanced malignancy) in combination with an oncolytic virus (for example, Talimogene Laherparepvec (IMLYGIC©) or T-VEC).

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and is not intended to limit the invention.

Example 1—Method of Preparation

The proteins of the present invention are typically made using recombinant DNA technology. In one exemplary embodiment, a first nucleic acid sequence encoding the first polypeptide comprising a first subunit of a multisubunit protein (p40 subunit of human IL-12) fused to a first antibody Fc domain polypeptide was cloned into a first expression vector (pET-pSURE-Puro); a second nucleic acid sequence encoding a second polypeptide comprising a second, different subunit of a multisubunit protein (p35 subunit of human IL-12) fused to a second antibody Fc domain polypeptide was cloned into a second expression vector (pET-pSURE-Puro); and the first and the second expression vectors were stably transfected together into host cells to produce the heterodimeric Fc-fused proteins.

Exemplary amino acid sequence encoded by the first expression vector is shown in SEQ ID NO:292. The first expression vector encoded a first polypeptide comprising a p40 subunit of human IL-12 fused to a human IgG1 Fc sequence comprising a Y349C mutation. The first polypeptide also included K360E and K409W mutations that promote heterodimerization, and LALAPA (L234A, L235A, and P329A) mutations that reduce effector functions. In SEQ ID NO:292, leader sequence is shown in italics, the p40 subunit sequence of human IL-12 is underlined, and the mutations are shown in bold.

(SEQ ID NO: 292)
MDMRVPAQLLGLLLLWLPGARCIWELKKDVYVVEL

DWYPDAPGEMVVLTCDTPEEDGITWTLDQSSEVLG

SGKTLTIQVKEFGDAGQYTCHKGGEVLSHSLLLLH

KKEDGIWSTDILKDQKEPKNKTFLRCEAKNYSGRF

TCWWLTTISTDLTFSVKSSRGSSDPQGVTCGAATL

SAERVRGDNKEYEYSVECQEDSACPAAEESLPIEV

MVDAVHKLKYENYTSSFFIRDIIKPDPPKNLQLKP

LKNSRQVEVSWEYPDTWSTPHSYFSLTFCVQVQGK

SKREKKDRVFTDKTSATVICRKNASISVRAQDRYY

SSSWSEWASVPCSPKSSDKTHTCPPCPAPEAAGGP

SVFLFPPKPKDTLMISRTPEVTCVVVDVSHEDPEV

KFNWYVDGVEVHNAKTKPREEQYNSTYRVVSVLTV

LHQDWLNGKEYKCKVSNKALAAPIEKTISKAKGQP

REPQVCTLPPSRDELTENQVSLTCLVKGFYPSDIA

VEWESNGQPENNYKTTPPVLDSDGSFFLYSWLTVD

KSRWQQGNVFSCSVMHEALHNHYTQKSLSLSPG

Exemplary amino acid sequence encoded from the second expression vector is shown in SEQ ID NO:293. The second expression vector encoded a second polypeptide comprising a p35 subunit of human IL-12 fused to a human IgG1 Fc sequence comprising a S354C mutation. The second polypeptide also included Q347R, D399V, and F405T mutations that promote heterodimerization, and LALAPA (L234A, L235A, and P329A) mutations that reduce effector functions. In SEQ ID NO:293, leader sequence is shown in italics, the p35 subunit sequence of human IL-12 is underlined, and mutations are shown in bold.

(SEQ ID NO: 293)
MDMRVPAQLLGLLLLWLPGARCRNLPVATPDPGMF

PCLHHSQNLLRAVSNMLQKARQTLEFYPCTSEEID

HEDITKDKTSTVEACLPLELTKNESCLNSRETSFI

TNGSCLASRKTSFMMALCLSSIYEDLKMYQVEFKT

MNAKLLMDPKRQIFLDQNMLAVIDELMQALNFNSE

TVPQKSSLEEPDFYKTKIKLCILLHAFRIRAVTID

RVMSYLNASGGGGSGGGGSGGGGSEPKSSDKTHTC

PPCPAPEAAGGPSVFLFPPKPKDTLMISRTPEVTC

VVVDVSHEDP EVKFNWYVDGVEVHNAKTKPREEQY

NSTYRVVSVLTVLHQDWLNGKEYKCKVSNKALAAP

IEKTISKAKGQPREPRVYTLPPCRDELTKNQVSLT

CLVKGFYPSDIAVEWESNGQPENNYKTTPPVLVSD

GSFTLYSKLTVDKSRWQQGNVFSCSVMHEALHNHY

TQKSLSLSPG

To achieve the highest yield of the protein, different ratios of the first and second expression vectors are explored to determine the optimal ratio for transfection into the host cells. After transfection, single clones are isolated for cell bank generation using methods known in the art, such as limited dilution, ELISA, FACS, microscopy, or Clonepix.

Clones are cultured under conditions suitable for bioreactor scale-up and maintained expression of the proteins. The proteins are isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

Example 2—Tumor Suppression by IL-12 Fused with a Silent Fc Domain Polypeptide in a CT26 Tumor Model This example describes relative abilities of two IL-12-Fc fusion constructs of recombinant murine IL-12 (rmIL-12) to control tumor progression in a mouse colon cancer model. The two IL-12-Fc fusion variants used in this example were mIL-12-Fc wildtype (DF-mIL-12-Fc wt), which includes wild-type murine IL-12 p40 and p35 subunits fused to the N-termini of wild-type murine IgG2a Fc domain polypeptides, and mIL-12-Fc silent (DF-mIL-12-Fc si), which includes wild-type murine IL-12 p40 and p35 subunits fused to the N-termini of murine IgG2a Fc domain polypeptides with mutations L234A, L235A, and P329G. The amino acid sequences of the proteins are shown below:

mIL-12-p40-mIgG2A-EW
(first chain of DF-mIL-12-Fc wt)
(SEQ ID NO: 286)
MWELEKDVYVVEVDWTPDAPGETVNLTCDTPEEDD

ITWTSDQRHGVIGSGKTLTITVKEFLDAGQYTCHK

GGETLSHSHLLLHKKENGIWSTEILKNFKNKTFLK

CEAPNYSGRFTCSWLVQRNMDLKFNIKSSSSSPDS

RAVTCGMASLSAEKVTLDQRDYEKYSVSCQEDVTC

PTAEETLPIELALEARQQNKYENYSTSFFIRDIIK

PDPPKNLQMKPLKNSQVEVSWEYPDSWSTPHSYFS

LKFFVRIQRKKEKMKETEEGCNQKGAFLVEKTSTE

VQCKGGNVCVQAQDRYYNSSCSKWACVPCRVRSPR

GPTIKPCPPCKCPAPNLLGGPSVFIFPPKIKDVLM

ISLSPIVTCVVVDVSEDDPDVQISWFVNNVEVHTA

QTQTHREDYNSTLRVVSALPIQHQDWMSGKEFKCK

VNNKDLPAPIERTISKPKGSVRAPQVYVLPPPEEE

MTEKQVTLTCMVTDFMPEDIYVEWTNNGKTELNYK

NTEPVLDSDGSYFMYSWLRVEKKNWVERNSYSCSV

VHEGLHNHHTTKSFSRTPG mIL-12-p35-mIgG2A-RVT
(second chain of DF-mIL-12-Fc wt)
(SEQ ID NO: 287)
RVIPVSGPARCLSQSRNLLKTTDDMVKTAREKLKH

YSCTAEDIDHEDITRDQTSTLKTCLPLELHKNESC

LATRETSSTTRGSCLPPQKTSLMMTLCLGSIYEDL

KMYQTEFQAINAALQNHNHQQIILDKGMLVAIDEL

-continued

MQSLNHNGETLRQKPPVGEADPYRVKMKLCILLHA

FSTRVVTINRVMGYLSSAGGGGSGGGGSGGGGSPR

GPTIKPCPPCKCPAPNLLGGPSVFIFPPKIKDVLM

ISLSPIVTCVVVDVSEDDPDVQISWFVNNVEVHTA

QTQTHREDYNSTLRVVSALPIQHQDWMSGKEFKCK

VNNKDLPAPIERTISKPKGSVRAPRVYVLPPPEEE

MTKKQVTLTCMVTDFMPEDIYVEWTNNGKTELNYK

NTEPVLVSDGSYTMYSKLRVEKKNWVERNSYSCSV

VHEGLHNHHTTKSFSRTPG mIL-12-p40-mIgG2A-EW-LALAPG
(first chain of DF-mIL-12-Fc si)
(SEQ ID NO: 288)
MWELEKDVYVVEVDWTPDAPGETVNLTCDTPEEDD

ITWTSDQRHGVIGSGKTLTITVKEFLDAGQYTCHK

GGETLSHSHLLLHKKENGIWSTEILKNFKNKTFLK

CEAPNYSGRFTCSWLVQRNMDLKFNIKSSSSSPDS

RAVTCGMASLSAEKVTLDQRDYEKYSVSCQEDVTC

PTAEETLPIELALEARQQNKYENYSTSFFIRDIIK

PDPPKNLQMKPLKNSQVEVSWEYPDSWSTPHSYFS

LKFFVRIQRKKEKMKETEEGCNQKGAFLVEKTSTE

VQCKGGNVCVQAQDRYYNSSCSKWACVPCRVRSPR

GPTIKPCPPCKCPAPNAAGGPSVFIFPPKIKDVLM

ISLSPIVTCVVVDVSEDDPDVQISWFVNNVEVHTA

QTQTHREDYNSTLRVVSALPIQHQDWMSGKEFKCK

VNNKDLGAPIERTISKPKGSVRAPQVYVLPPPEEE

MTEKQVTLTCMVTDFMPEDIYVEWTNNGKTELNYK

NTEPVLDSGSYFMYSWLRVEKKNWVERNSYSCSV

VHEGLHNHHTTKSFSRTPG mIL-12-p35-mIgG2A-RVT-LALAPG
(second chain of DF-mIL-12-Fc si)
(SEQ ID NO: 289)
RVIPVSGPARCLSQSRNLLKTTDDMVKTAREKLKH

YSCTAEDIDHEDITRDQTSTLKTCLPLELHKNESC

LATRETSSTTRGSCLPPQKTSLMMTLCLGSIYEDL

KMYQTEFQAINAALQNHNHQQIILDKGMLVAIDEL

MQSLNHNGETLRQKPPVGEADPYRVKMKLCILLHA

FSTRVVTINRVMGYLSSAGGGGSGGGGSGGGGSPR

GPTIKPCPPCKCPAPNAAGGPSVFIFPPKIKDVLM

ISLSPIVTCVVVDVSEDDPDVQISWFVNNVEVHTA

QTQTHREDYNSTLRVVSALPIQHQDWMSGKEFKCK

VNNKDLGAPIERTISKPKGSVRAPRVYVLPPPEEE

-continued

MTKKQVTLTCMVTDFMPEDIYVEWTNNGKTELNYK

NTEPVLVSDGSYTMYSKLRVEKKNWVERNSYSCSV

VHEGLHNHHTTKSFSRTPG

Briefly, $10^6$ CT26-Tyrp1 colon carcinoma cells were injected subcutaneously into the flank of Balb/c mice. On Day 14 after tumor inoculation, when tumor volume reached 270 mm$^3$, the mice were randomized into different treatment groups (n=10 per group) and treated intraperitoneally with 1 μg of rmIL-12, DF-mIL-12-Fc wt at a molar dose equivalent to 1 μg rmIL-12, DF-mIL-12-Fc si at a molar dose equivalent to 1 μg rmIL-12, or 1 μg of mIgG2a isotype control once a week. Tumor growth was assessed for 60 days.

Figure 5A:
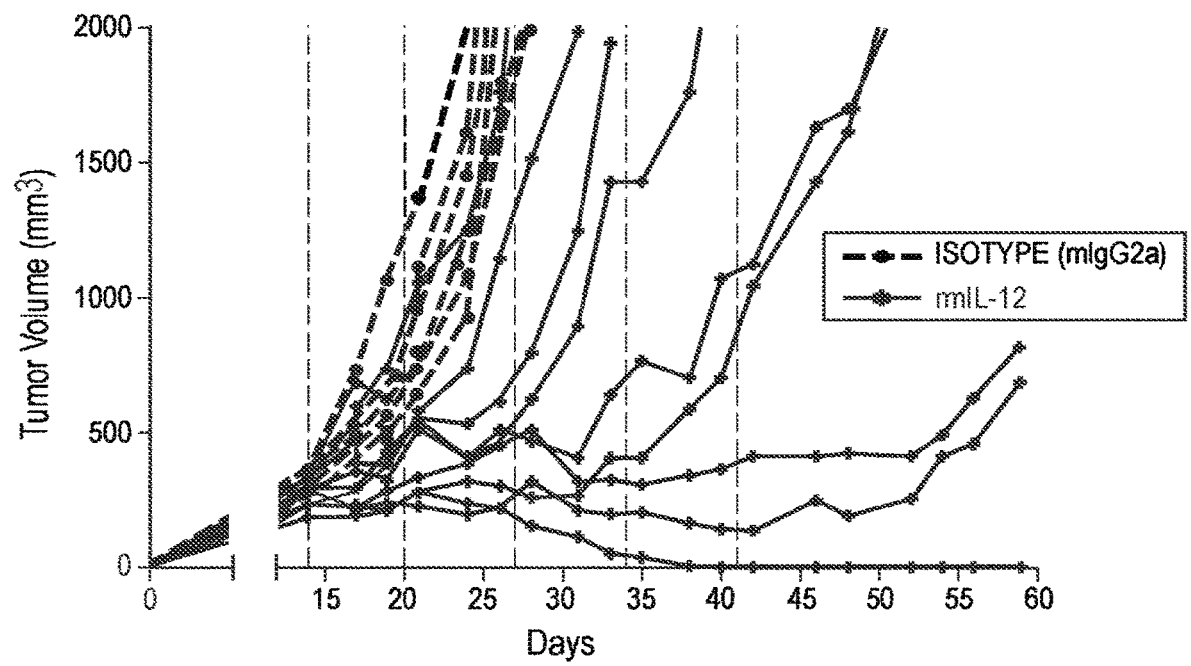
FIGS. 5A-5C are graphs showing tumor growth curves of individual mice inoculated with CT26 tumor cells and treated with recombinant mouse IL-12 (rmIL-12)(FIG. 5A), DF-mIL-12-Fc wt (FIG. 5B), DF-mIL-12-Fc si (FIG. 5C), or mIgG2a isotype control once a week.
Figure 5B:
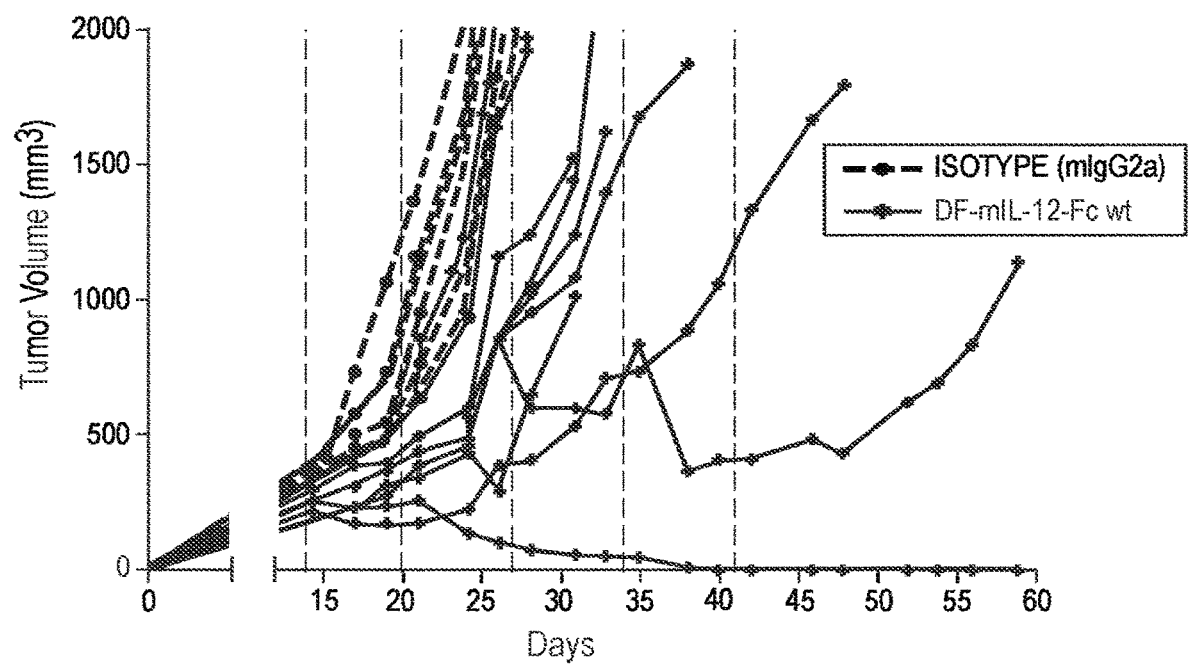
Figure 5C:
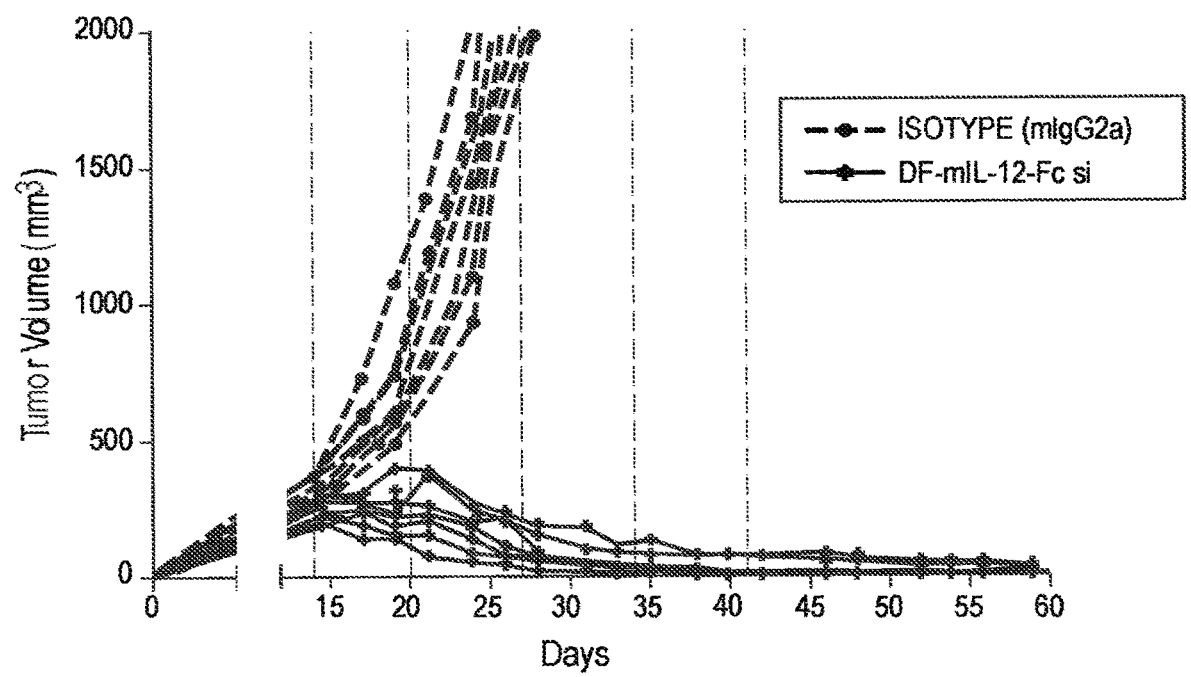
Figure 6:
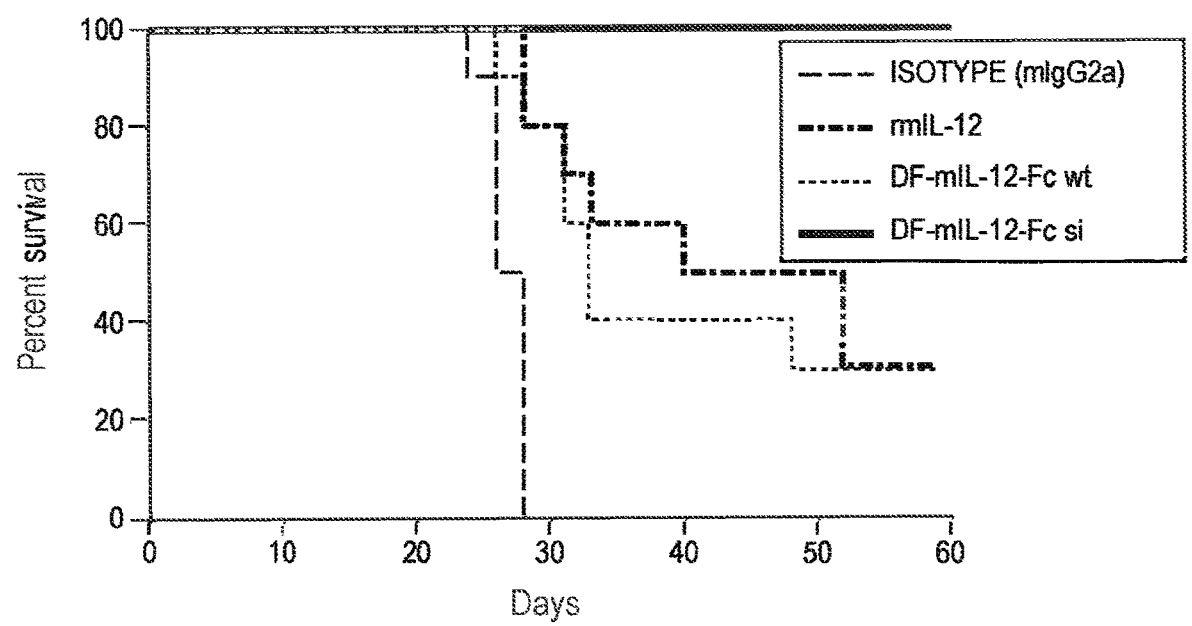
FIG. 6 is a graph showing Kaplan-Meier survival curves of mice inoculated with CT26 tumor cells and treated with rmIL-12, DF-mIL-12-Fc wt, DF-mIL-12-Fc si, or mIgG2a isotype control once a week.

As shown in FIGS. 5A-5C, although IL-12 (FIG. 5A) and DF-mIL-12-Fc wt (FIG. 5B) were efficient in controlling tumor progression in some mice, only DF-mIL-12-Fc si induced robust tumor regression and yielded 100% complete tumor regression (FIG. 5C). Moreover, overall survival was significantly extended by the treatment of DF-mIL-12-Fc si therapy—100% of treated mice were still alive at day 60, whereas median survival times of the mice treated with isotype control, DF-mIL-12-Fc wt, and IL-12 were 27 days, 33 days, and 46 days, respectively (FIG. 6).

Next, different doses of DF-mIL-12-Fc wt and DF-mIL-12-Fc si in controlling tumor progression were compared. Briefly, $10^6$ CT26-Tyrp1 colon carcinoma cells were injected subcutaneously into the flank of Balb/c mice. On Day 14 after tumor inoculation, when tumor volume reached 300 mm$^3$, the mice were randomized into different treatment groups (n=10 per group) and treated intraperitoneally with DF-mIL-12-Fc wt at molar doses equivalent to 1 μg or 0.1 μg rmIL-12, or DF-mIL-12-Fc si at molar doses equivalent to 1 μg or 0.1 μg IL-12 once a week. Tumor growth was assessed for 55 days.

Figure 7A:
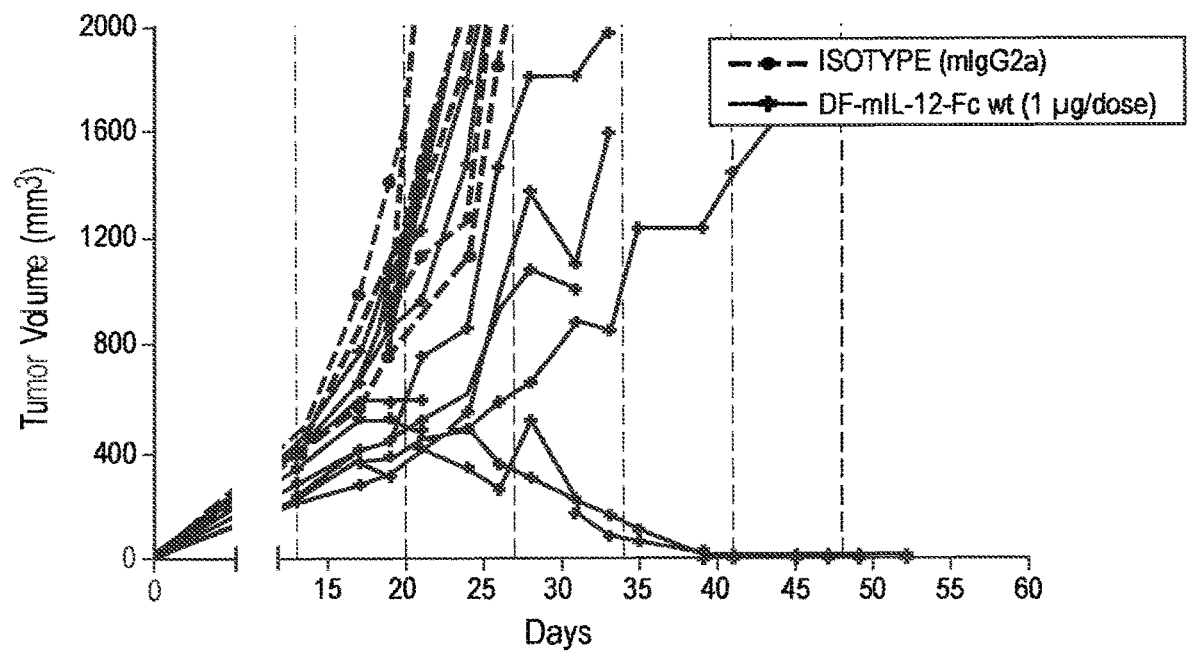
FIGS. 7A-7D are graphs showing tumor growth curves of individual mice inoculated with CT26 tumor cells and treated with DF-mIL-12-Fc wt at a molar equivalent of 1 μg rmIL-12 (FIG. 7A), DF-mIL-12-Fc si at a molar equivalent of 1 μg rmIL-12 (FIG. 7B), DF-mIL-12-Fc wt at a molar equivalent of 0.1 μg rmIL-12 (FIG. 7C), DF-mIL-12-Fc si at a molar equivalent of 0.1 μg rmIL-12 (FIG. 7D), or mIgG2a isotype control once a week.
Figure 7B:
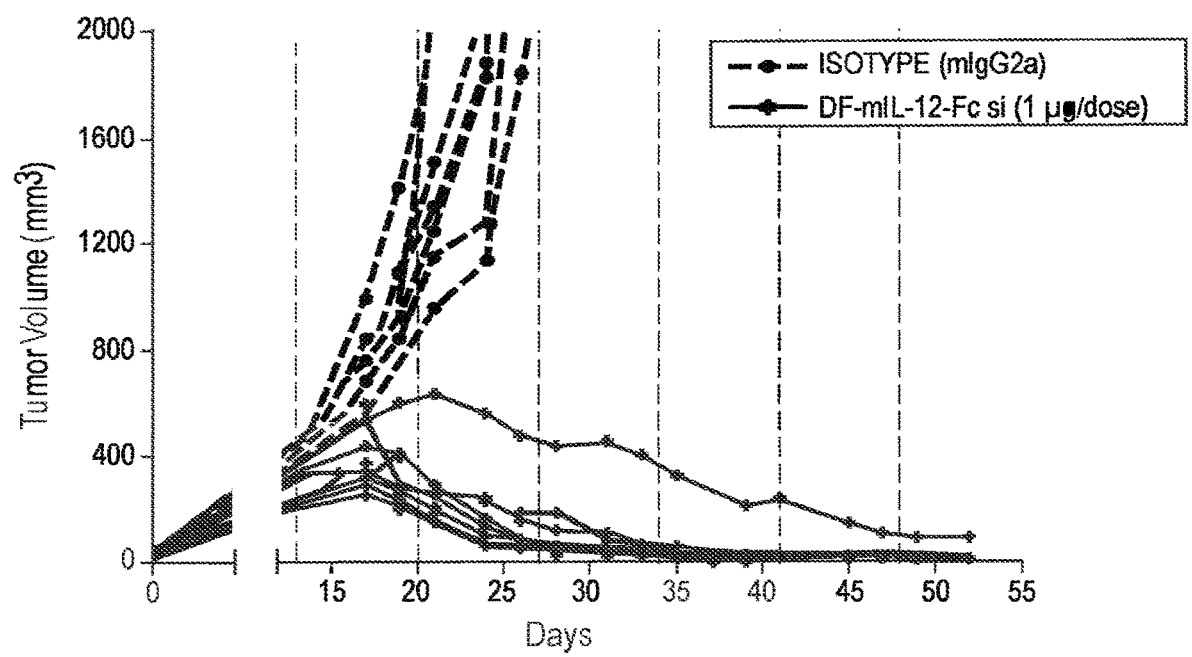
Figure 7C:
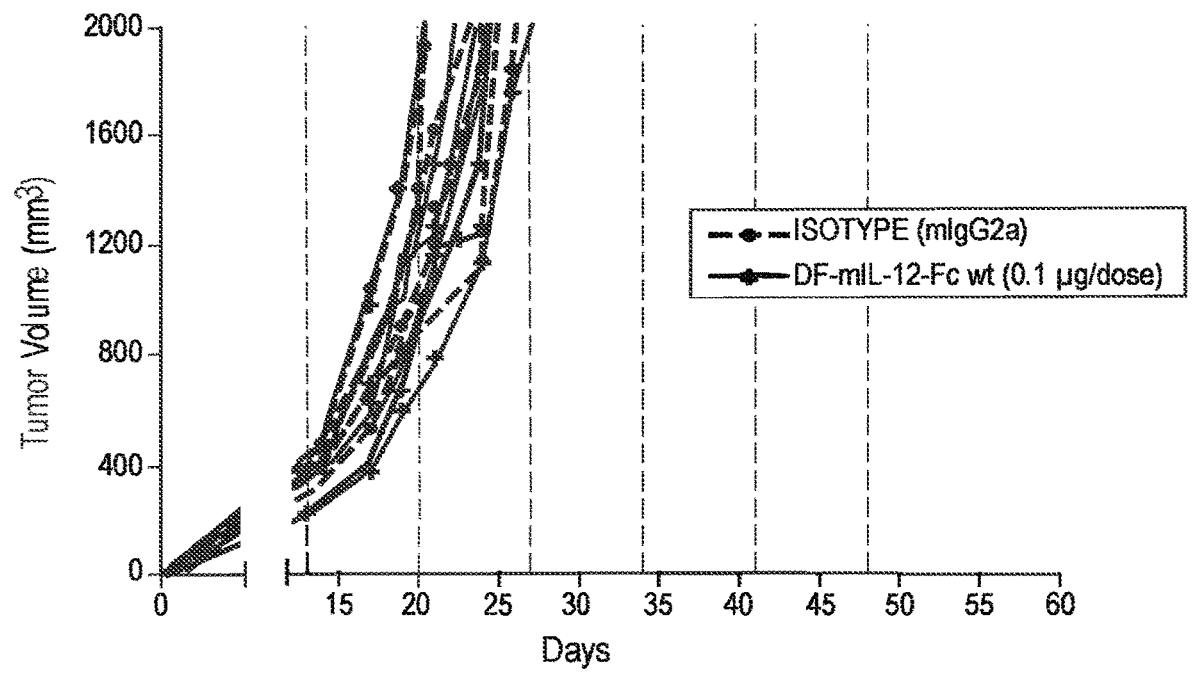
Figure 7D:
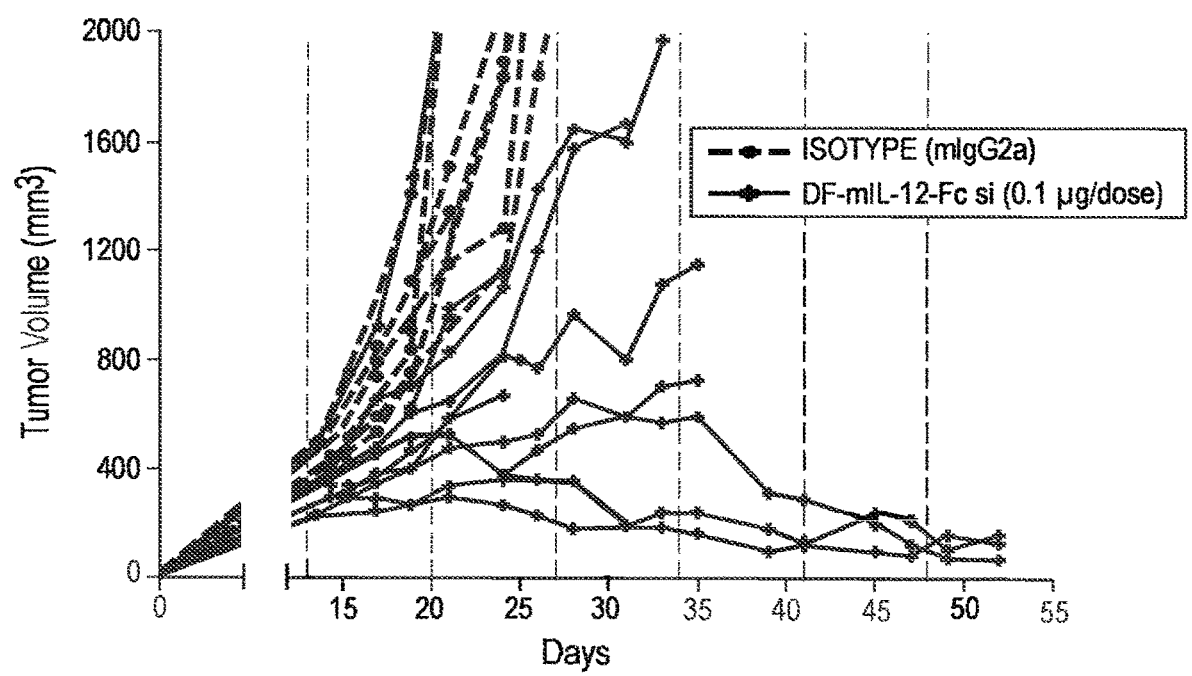
Figure 8:
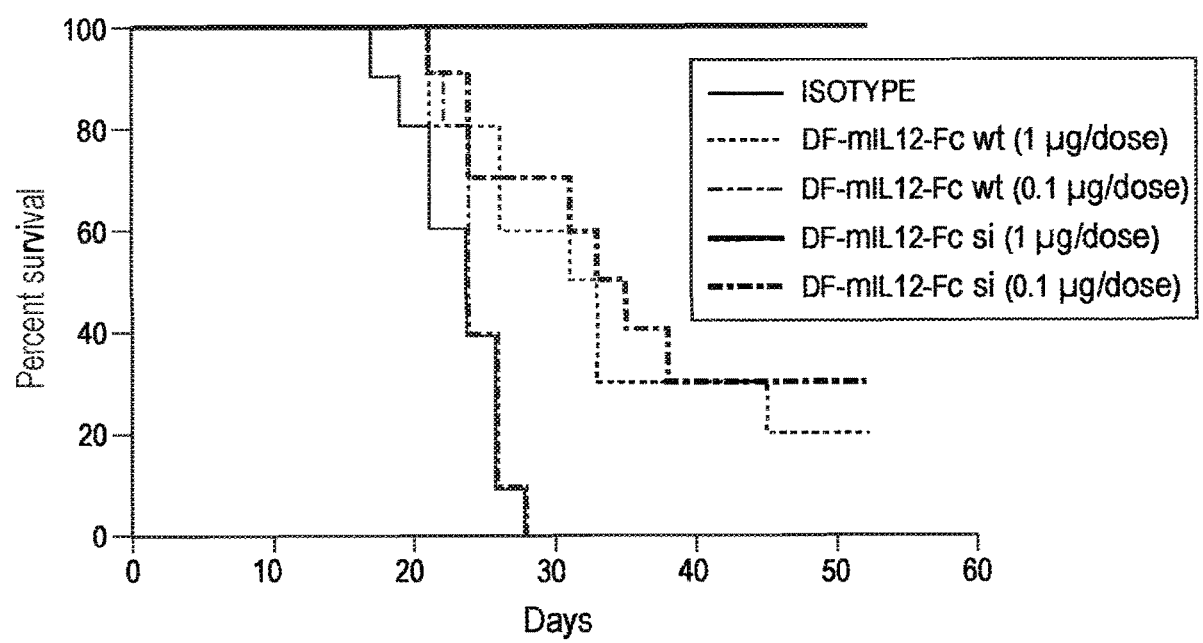
FIG. 8 is a graph showing Kaplan-Meier survival curves of mice inoculated with CT26 tumor cells and treated with DF-mIL-12-Fc wt at a molar equivalent of 1 μg rmIL-12, DF-mIL-12-Fc si at a molar equivalent of 1 μg rmIL-12, DF-mIL-12-Fc wt at a molar equivalent of 0.1 μg rmIL-12, DF-mIL-12-Fc si at a molar equivalent of 0.1 μg rmIL-12, or mIgG2a isotype control once a week.

As shown in FIGS. 7A-7D, treatment with DF-mIL-12-Fc wt led to reduced tumor progression in some mice and complete regression in two mice at the 1 μg rmIL-12 molar equivalents dose (FIG. 7A), but no tumor suppression was observed at the 0.1 μg IL-12 molar equivalents dose (FIG. 7C). By contrast, the DF-mIL-12-Fc si treatment at the 1 μg IL-12 molar equivalents dose yielded 100% complete tumor regression (FIG. 7B) and induced a robust delay in tumor growth at the lower dose of 0.1 μg IL-12 molar equivalents (FIG. 7D). The median survival of the mice treated with 1 μg IL-12 molar equivalents of DF-mIL-12-Fc wt was 32 days, similar to the 34 days of median survival of the mice treated with 0.1 μg IL-12 molar equivalents of DF-mIL-12-Fc si, suggesting that DF-mIL-12-Fc si was 10-fold more potent than its wildtype variant (FIG. 8). DF-mIL-12-Fc wt was not efficient at the dose of 0.1 μg IL-12 molar equivalents, and showed the same median survival of 24 days as the isotype treated group.

Next, in vivo efficacy for different routes of administering DF-mIL-12-Fc si were compared. Briefly, $10^6$ CT26-Tyrp1 colon carcinoma cells were injected subcutaneously into the flank of Balb/c mice. On Day 14 after tumor inoculation, when tumor volume reached 270 mm$^3$, the mice were randomized into different treatment groups (n=10 per group) and treated either intraperitoneally or subcutaneously with DF-mIL-12-Fc si at a molar dose equivalent to 1 μg IL-12 or molar equivalent of mIgG2a isotype control once a week. Tumor growth was assessed for over 60 days.

Figure 22A:
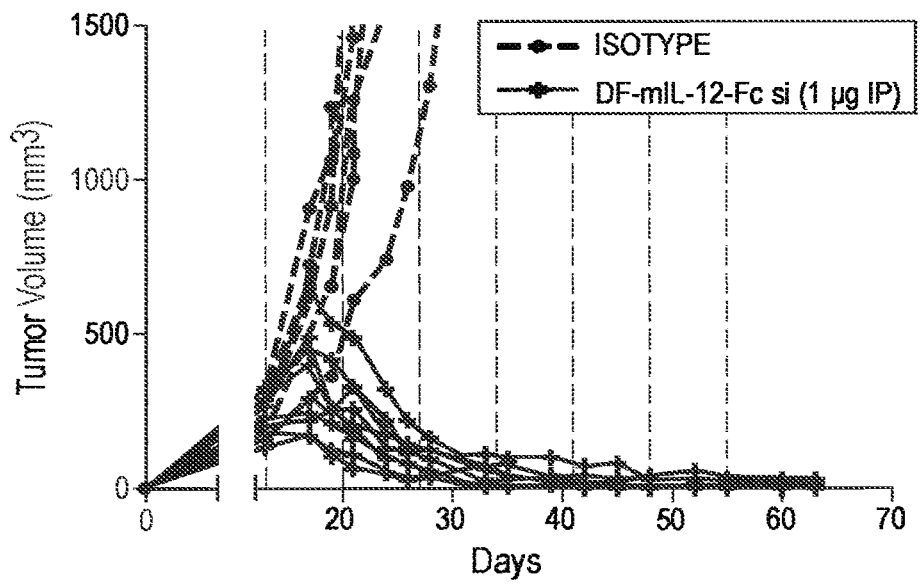
FIGS. 22A-22B are graphs showing tumor growth curves of individual mice inoculated with CT26 tumor cells and administered a weekly dose of DF-mIL-12-Fc si or mIgG2a isotype either intraperitoneally (IP)(FIG. 22A) or subcutaneously (SC) (FIG. 22B).
Figure 22B:
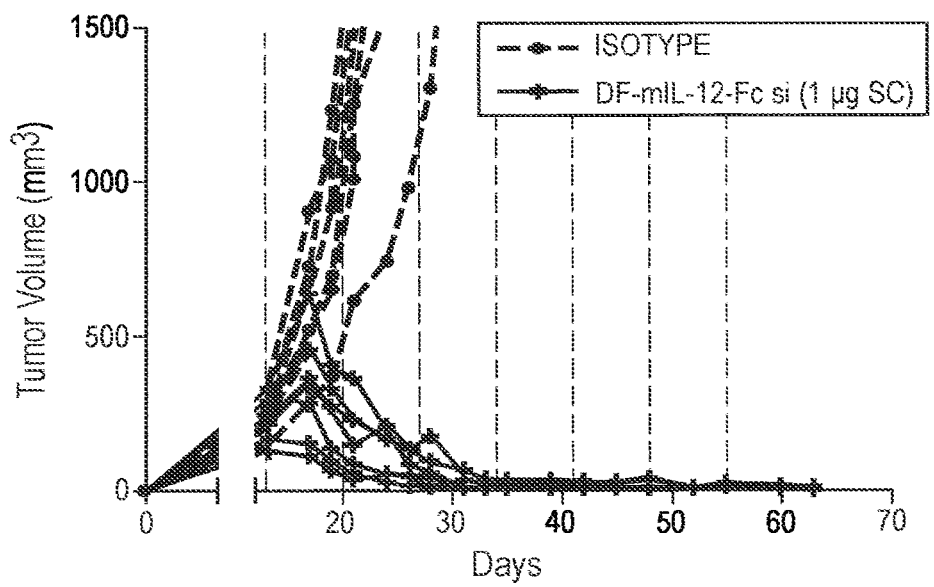

As shown in FIGS. 22A-22B, both intraperitoneal (FIG. 22A) and subcutaneous (FIG. 22B) administration of DF-mIL-12-Fc si induced robust tumor regression and yielded 100% complete tumor regression. Thus, DF-mIL-12-Fc si treatment demonstrated efficacy using various routes of administration.

Example 3—Tumor Suppression by IL-12 Fused with a Silent Fc Domain Polypeptide in a B16F10 Tumor Model This example describes relative abilities of DF-mIL-12-Fc wt and DF-mIL-12-Fc si in controlling tumor progression in a mouse melanoma model. Briefly, $10^6$ B16F10 melanoma cells were injected subcutaneously into C57BL/6 mice. On Day 8 after tumor inoculation, when tumor volume reached 250 mm$^3$, the mice were randomized into different treatment groups (n=10) and treated with 0.5 µg of IL-12, DF-mIL-12-Fc wt at a molar dose equivalent to 0.5 µg IL-12, DF-mIL-12-Fc si at a molar dose equivalent to 0.5 µg IL-12, or 0.5 µg of mIgG2a isotype control once a week. Tumor growth was assessed for 32 days.

Figure 9A:
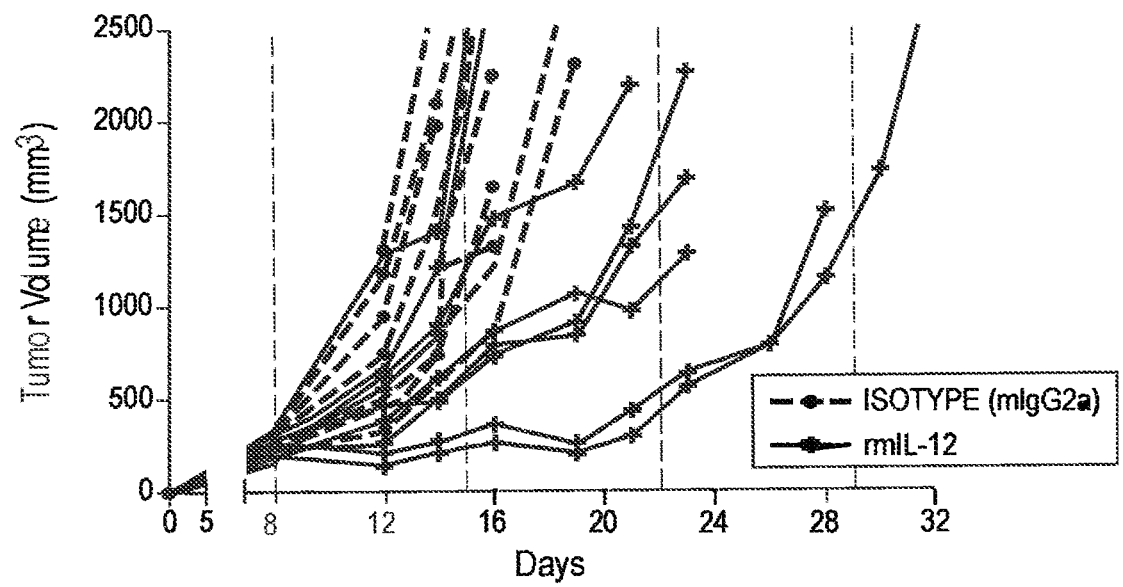
FIGS. 9A-9C are graphs showing tumor growth curves of individual mice inoculated with B16F10 melanoma cells and treated with rmIL-12 (FIG. 9A), DF-mIL-12-Fc wt (FIG. 9B), DF-mIL-12-Fc si (FIG. 9C), or mIgG2a isotype control once a week.
Figure 9B:
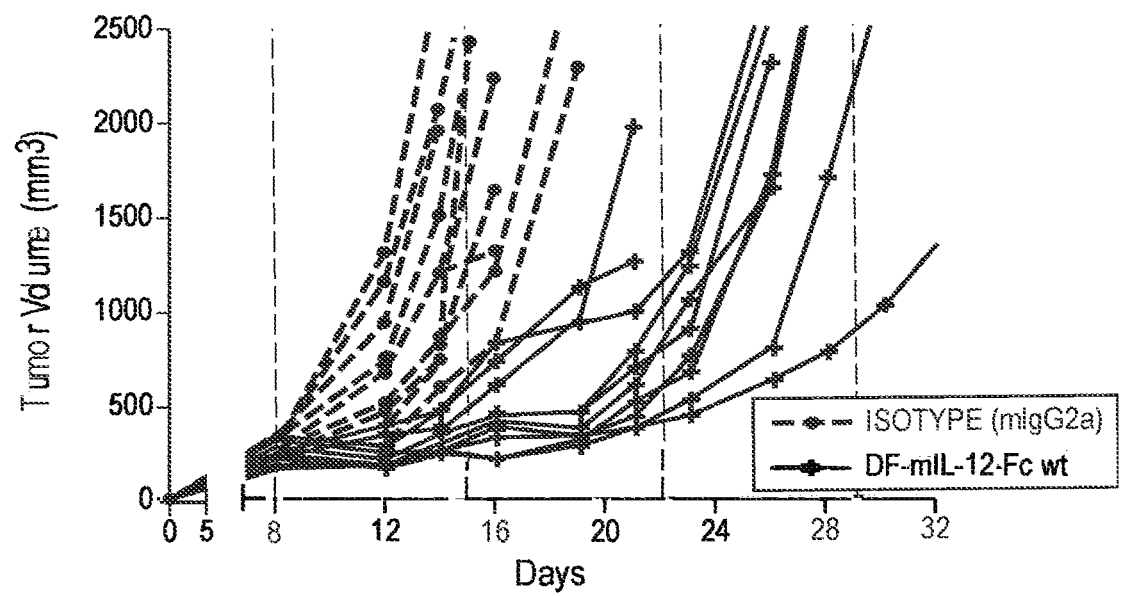
Figure 9C:
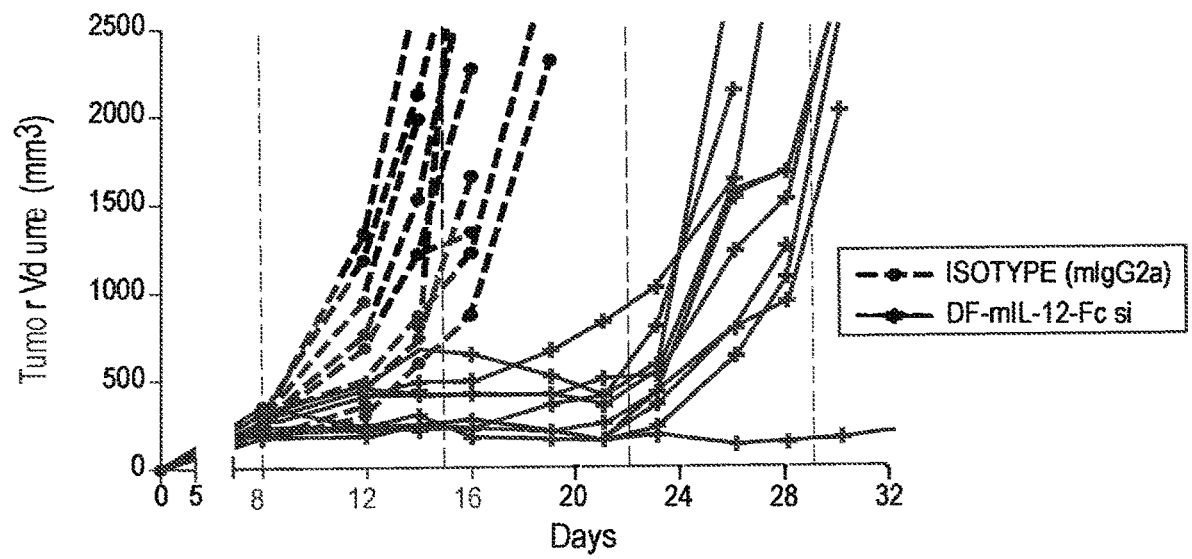
Figure 10:
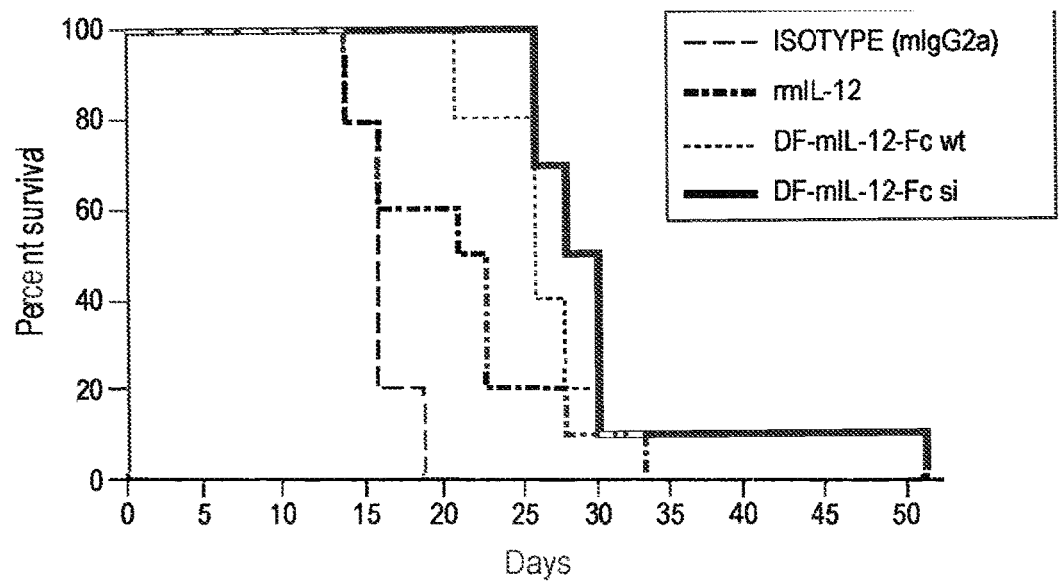
FIG. 10 is a graph showing Kaplan-Meier survival curves of mice inoculated with B16F10 melanoma cells and treated with rmIL-12, DF-mIL-12-Fc wt, DF-mIL-12-Fc si, or mIgG2a isotype control once a week.
Figure 11A:
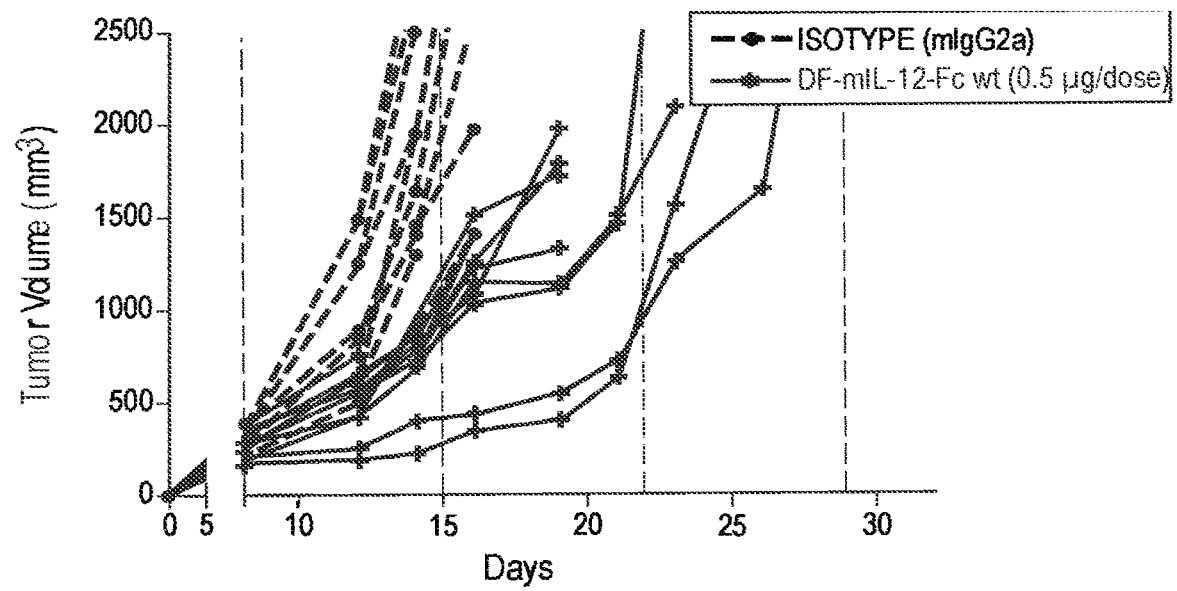
FIGS. 11A-11D are graphs showing tumor growth curves of individual mice inoculated with B16F10 melanoma cells and treated with DF-mIL-12-Fc wt at a molar equivalent of 0.5 μg rmIL-12 (FIG. 11A), DF-mIL-12-Fc si at a molar equivalent of 0.5 μg rmIL-12 (FIG. 11B), DF-mIL-12-Fc wt at a molar equivalent of 0.1 μg rmIL-12 (FIG. 11C), DF-mIL-12-Fc si at a molar equivalent of 0.1 μg rmIL-12 (FIG. 11D), or mIgG2a isotype control once a week.
Figure 11B:
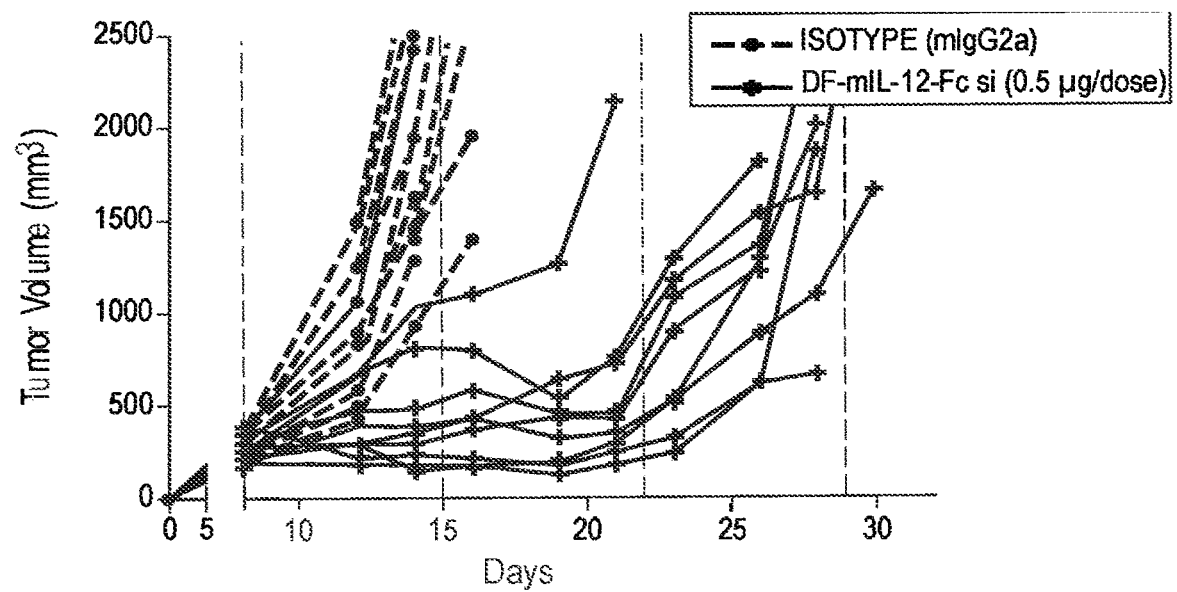
Figure 11C:
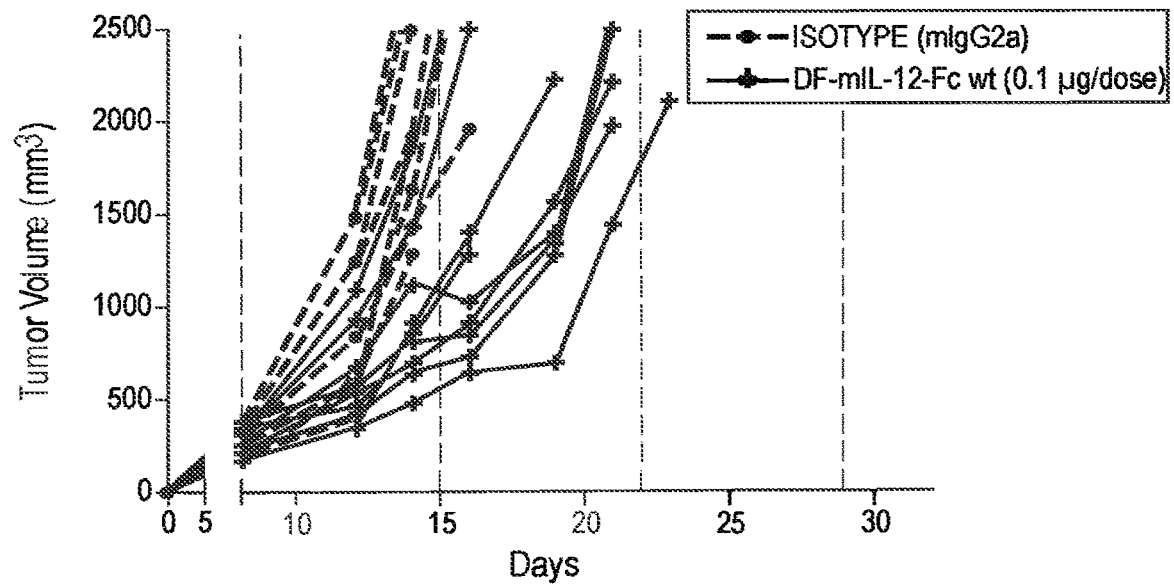
Figure 11D:
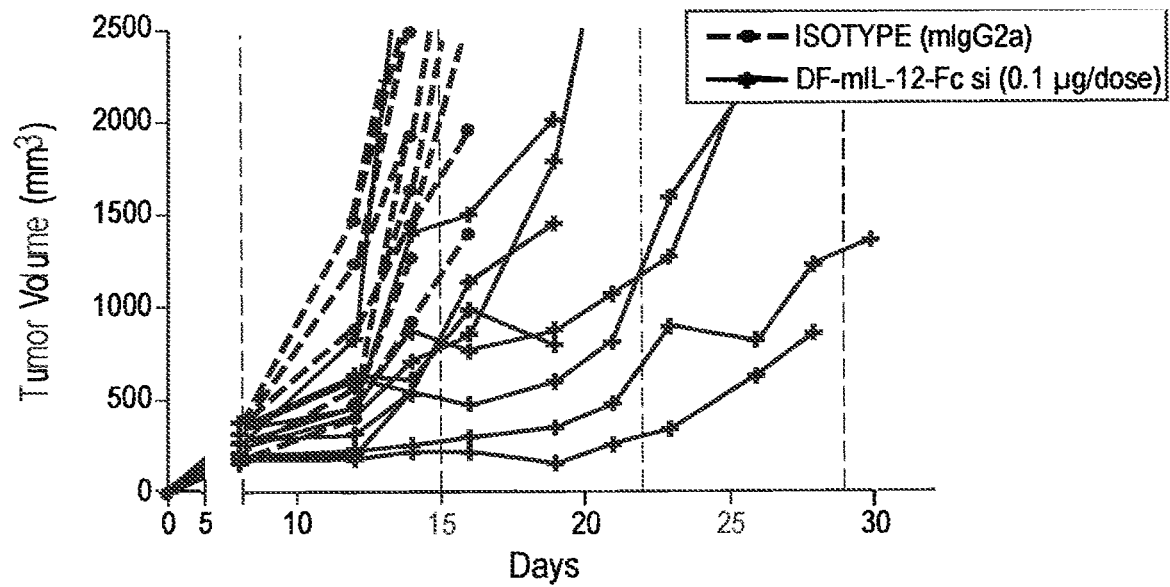

As shown in FIGS. 9A-9C, although each of the IL-12-Fc constructs tested delayed tumor progression, DF-mIL-12-Fc si was the most efficient in controlling tumor growth. Median survival time of the mice treated with DF-mIL-12-Fc si was 29 days, which was longer than the median survival times of the mice treated with isotype control, DF-mIL-12-Fc wt, and IL-12, which were 16 days, 26 days, and 22 days, respectively (FIG. 10).

Next, different doses of DF-mIL-12-Fc wt and DF-mIL-12-Fc si in controlling tumor progression were compared. Briefly, $10^6$ B16F10 melanoma cells were injected subcutaneously into the flank of C57BL/6 mice. On Day 8 after tumor inoculation, the mice were randomized into different treatment groups (n=10 per group) and treated intraperitoneally with 0.5 µg or 0.1 µg IL-12 molar equivalents of DF-mIL-12-Fc wt, or 0.5 µg or 0.1 µg IL-12 molar equivalents of DF-mIL-12-Fc si once a week. Tumor growth was assessed for 30 days.

Figure 12:
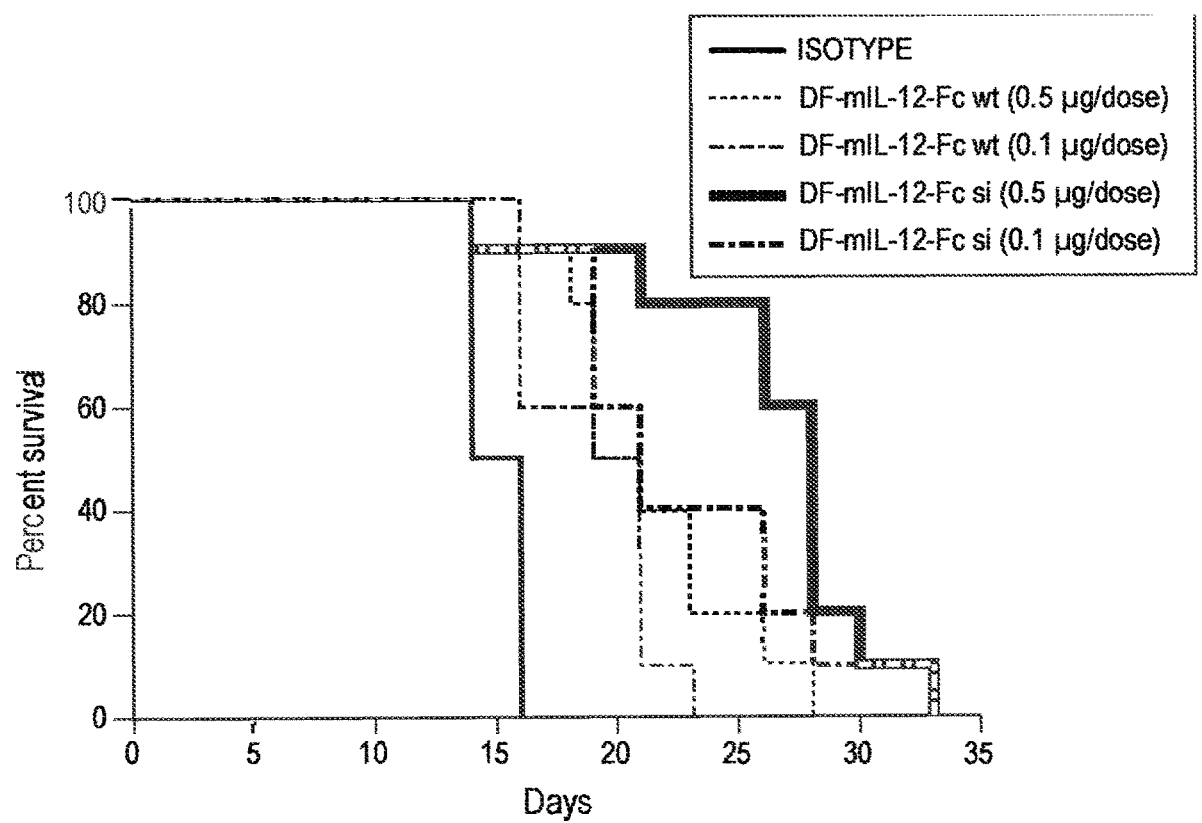
FIG. 12 is a graph showing Kaplan-Meier survival curves of mice inoculated with B16F10 melanoma cells and treated with DF-mIL-12-Fc wt at a molar equivalent of 0.5 μg rmIL-12, DF-mIL-12-Fc si at a molar equivalent of 0.5 μg rmIL-12, DF-mIL-12-Fc wt at a molar equivalent of 0.1 μg rmIL-12, DF-mIL-12-Fc si at a molar equivalent of 0.1 μg rmIL-12, or mIgG2a isotype control once a week.

As shown in FIGS. 11A-11D, DF-mIL-12-Fc si was superior to DF-mIL-12-Fc wt in suppression of tumor growth at both doses. Moreover, at each dose, the median survival of the mice treated with DF-mIL-12-Fc wt was 20 days. By contrast, the median survival of the mice treated with 0.1 µg IL-12 molar equivalents of DF-mIL-12-Fc si was 21 days, and the median survival of the mice treated with 0.5 µg IL-12 molar equivalents of DF-mIL-12-Fc si was 28 days (FIG. 12). These results demonstrated that a high dose (0.5 µg IL-12 molar equivalents) of DF-mIL-12-Fc si significantly increased the survival of mice compared to its wildtype counterpart or isotype control.

Next, single dose administrations of the DF-mIL-12-Fc si treatment was compared to the weekly treatments previously described. Briefly, $10^6$ B16F10 melanoma cells were injected subcutaneously into C57BL/6 mice. On Day 8 after tumor inoculation, when tumor volume reached 200 mm$^3$, the mice were randomized into different treatment groups (n=10) and treated with DF-mIL-12-Fc si at a molar dose equivalent to 0.5 µg IL-12 or molar equivalent of mIgG2a isotype control once a week. Tumor growth was assessed for 39 days.

Figure 23:
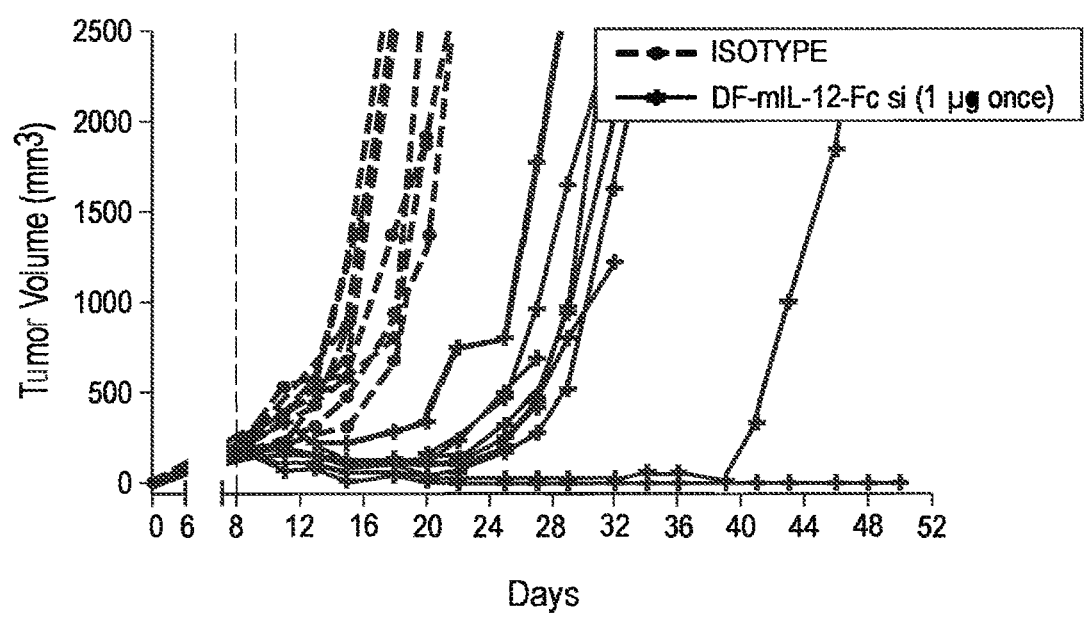
FIG. 23 is a graph showing tumor growth curves of individual mice inoculated with B16F10 melanoma cells and administered a single dose of DF-mIL-12-Fc si or mIgG2a isotype.

As shown in FIG. 23, a single administration of DF-mIL-12-Fc si resulted in reduced tumor outgrowth in 100% of mice, although tumor outgrowth occurred sooner when compared to weekly administrations (FIG. 9C). Additionally, mice demonstrated transient weight loss, but after the first dose only (data not shown). Accordingly, a single administration of DF-mIL-12-Fc si demonstrated initial efficacy in a hard-to-treat tumor model, although subsequent weekly administrations are better at delaying tumor outgrowth in this model.

Next, in vivo efficacy for different routes of administering DF-mIL-12-Fc si were compared. Briefly, $10^6$ B16F10 melanoma cells were injected subcutaneously into C57BL/6 mice. On Day 7 after tumor inoculation, when tumor volume reached 260 mm$^3$, the mice were randomized into different treatment groups (n=10) and treated either intraperitoneally or subcutaneously with DF-mIL-12-Fc si at a molar dose equivalent to 1 µg IL-12 or molar equivalent of mIgG2a isotype control once a week. Tumor growth was assessed for 40 days.

Figure 24A:
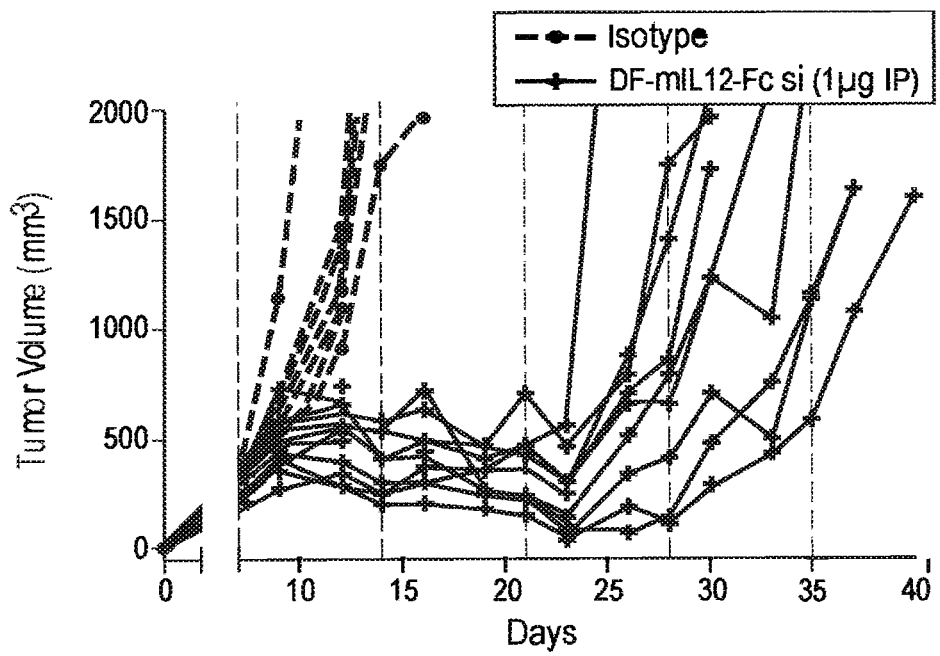
FIGS. 24A-24B are graphs showing tumor growth curves of individual mice inoculated with B16F10 melanoma cells and administered a weekly dose of DF-mIL-12-Fc si or mIgG2a isotype either intraperitoneally (TP) (FIG. 24A) or subcutaneously (SC) (FIG. 24B).
Figure 24B:
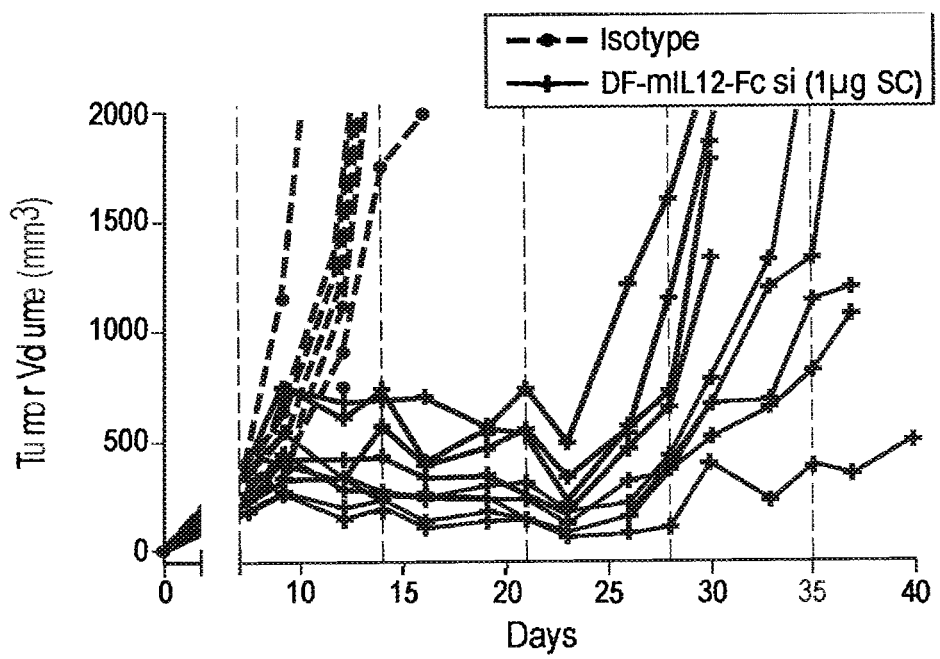

As shown in FIGS. 24A-24B, both intraperitoneal (FIG. 24A) and subcutaneous (FIG. 24B) administration of DF-mIL-12-Fc si induced tumor regression in 100% of mice. Thus, DF-mIL-12-Fc si treatment demonstrated efficacy using various routes of administration.

Example 4—In Vitro Potency of DF-hIL-12-Fc Wt and rhIL-12

The potency of DF-hIL-12-Fc si in comparison to rhIL-12 was assessed using in vitro bioassays.

IL-12 potency was assessed using a HEK-Blue IL-12 reporter assay. IL-12R+ HEK-Blue reporter cells (InvivoGen) were harvested from culture and adjusted to $1\times10^6$ cells/mL in culture media. DF-hIL-12-Fc si (DF IL-12-Fc) and recombinant human IL-12 (rhIL-12; PeproTech) were diluted in media. 100 µL of PBMC suspension was mixed with 100 µL of diluted test article and incubated for 48 hours. The supernatant was harvested and engagement of IL-12 receptor and signaling components stably expressed by the reporter cells was detected by measurement of secreted embryonic alkaline phosphatase from the cells following manufacturer instructions. Briefly, 25 µL of sample supernatant was mixed with 200 µL of QUANTI-Blue reagent and incubated in the dark at RT for 10 minutes. The plate was then read with a SpectraMax i3x plate-reader at 620 nM and optical density reported to represent relative IL-12 activity.

Figure 13A:
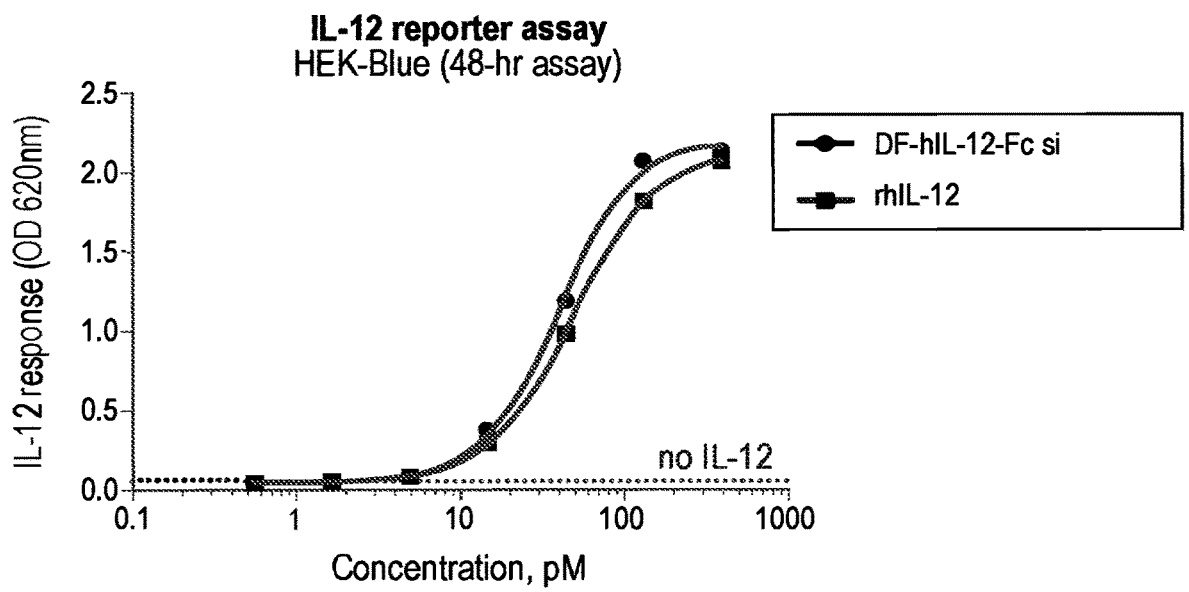
FIG. 13A is a graph showing IL-12 response to treatment with DF-hIL-12-Fc si (DF IL-12-Fc) or recombinant human IL-12 (rhIL-12) using a HEK-Blue IL-12 reporter assay.

As shown in FIG. 13A, production of SEAP by IL-12R+ HEK reporter cells increased with increasing concentrations of DF-hIL-12-Fc si or rhIL-12. The measured IL-12 responses in the HEK-Blue reporter assay were comparable between DF-hIL-12-Fc si and rhIL-12 at the concentrations examined.

Next, IL-12 potency was assessed by quantifying IFNγ production from human PBMCs. PBMCs were isolated from human peripheral blood buffy coats using density gradient centrifugation and adjusted to $1\times10^6$ cells/mL in culture media. DF-hIL-12-Fc si and recombinant human IL-12 (rhIL-12) were diluted in media. 100 µL of PBMC suspension was mixed with 100 µL of diluted test article and incubated for 48 hrs. The supernatant was harvested and IFNγ was quantified using a Human IFN-γ ELISA MAX kit (BioLegend). After development of the IFNγ ELISA plates, they were read using a SpectraMax i3x instrument at 450 nm with a background subtraction at 540 nm. IFNγ content in sample wells was approximated by interpolating sample readings from the assay standard curve.

Figure 13B:
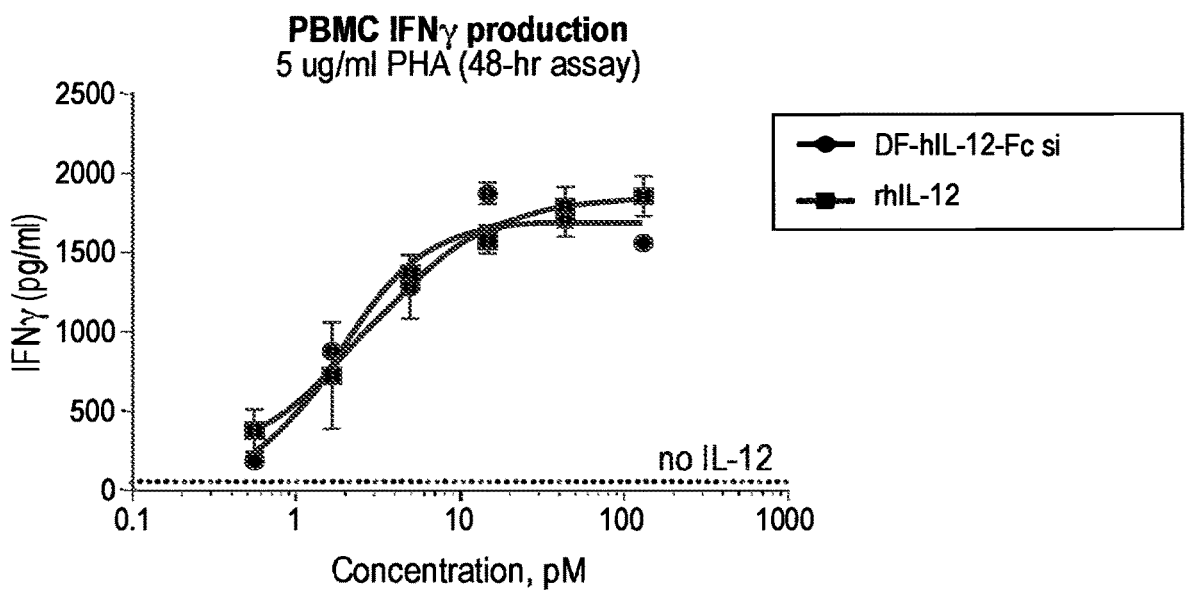
FIG. 13B is a graph showing IFNγ production by peripheral blood mononuclear cells (PBMCs) in response to treatment with DF-hIL-12-Fc si (DF IL-12-Fc) and rhIL-12.

As shown in FIG. 13B, IFNγ production increased when human PBMCs were cultured with DF-hIL-12-Fc si or rhIL-12, with concurrent treatment with 5 µg/ml of PHA to amplify the magnitude of IFNγ responses. IFN-γ production following IL-12 stimulation was comparable between DF-hIL-12-Fc si and rhIL-12 at the concentrations examined.

Accordingly, although the EC50 values with the two cell types and stimulation conditions differed by over an order of magnitude, comparable activity of DF-hIL-12-Fc si and rhIL-12 was demonstrated in both assays suggesting the potency of the DF-hIL-12-Fc si construct exhibits similar potency to that of native recombinant human IL-12.

Example 5—IL-12, DF-hIL-12-Fc Si and IFNγ Concentrations in Monkey Plasma Following IV Infusion of DF-hIL-12-Fc Si or rhIL-12

The pharmacodynamics (PD) and pharmacokinetics (PK) were assessed in cynomolgus monkeys following IV infusion of DF-hIL-12-Fc si or rhIL-12.

Cynomolgus monkeys were administered DF-hIL-12-Fc si and recombinant human IL-12 at 10 µg/kg by IV-infusion.

An immunoassay was used to detect DF-hIL-12-Fc si and Human IL-12 based on a Quantikine ELISA Human IL-12 p70 Immunoassay kit: This assay employed the quantitative sandwich enzyme immunoassay technique. A monoclonal antibody specific for human IL-12 p70 was used as a solid phase capture and detection was accomplished using an antibody HRP-tagged reporter. Standards and QCs spiked with rhIL-12 or DF-hIL-12-Fc si reference standard, along with test samples were pipetted into the wells of microtiter plate and any IL-12 p70 present in the samples were bound by the immobilized antibody, on the solid phase. Unbound substances were washed away and the enzyme-linked polyclonal antibody specific for human IL-12 p70 was added to the wells. Unbound antibody-enzyme reagents were washed away and TMB substrate was added to each well. The resulting enzyme reaction yields a blue product that turns yellow when an acid stop solution is added. The intensity of the color measured in each well is directly proportional to the amount of rhIL-12 or DF-hIL-12-Fc si is bound in the initial step. Plates were read at 450 nm with a reference of 540 nm on a SpectraMax microplate reader with data collection software, SoftMax Pro Enterprise version 4.6. Data was converted into a text file and imported/processed in Watson LIMS v.7.2.0.02. Regression was performed using a Logistic (Auto Estimate) curve fitting with a weighting factor of 1.

An immunoassay (meso scale discovery (MSD)—an ELISA like immunoassay) was also used to detect DF-hIL-12-Fc si that involved coating an untreated MSD microtiter plate with monkey-adsorbed goat anti-human IgG and incubating at room temperature. The plate was washed, blocked, washed, and incubated with standard curve and quality control samples spiked with DF-hIL-12-Fc si reference standard, along with test samples. After this incubation, the plate was washed and biotin anti-human IL-12/IL-23 p40 was added to the plate as the primary detection antibody. After another wash step, streptavidin-conjugated Sulfo-Tag was added as the secondary detection antibody. The plate was washed a final time, MSD Read Buffer T was added to the plate, and the plate was read using a MSD Sector Imager S600. Raw MSD data was exported into a text file, which was then converted into a Watson LIMS compatible file using a programmed Excel spreadsheet, which was custom designed at Envigo. Data was imported and regressed in Watson LIMS Software v.7.2.0.02.

A meso scale discovery method was performed for the relative quantitative measurement of NHP proinflammatory biomarkers in cynomolgus monkey plasma. The method used a sandwich immunoassay procedure for the relative quantitative measurement of Pro-inflammatory Panel 1 Biomarkers: IFNγ, IL-1β, IL-2, IL-6 IL-8, and IL-10 in cynomolgus monkey K2 EDTA plasma (referred to as monkey plasma). The method is based on MSD non-human primate (NHP) kits for V-PLEX and V-PLEX Plus, Catalog No. K15056D-1, K15056D-2, K15056D-4, K15056D-6, K15056G-1, K15056G-2, K15056G-4, K15056G-6. The method employs human capture and detection antibodies that react with cynomolgus monkeys. The kit provides plates pre-coated with capture antibodies on independent well-defined spots in each well of a 96-well multi-spot plate. The plate was incubated with monkey plasma samples, washed and then incubated with detection antibodies (specific for each analyte) that are conjugated with electrochemiluminescent (ECL) labels (MSD SULFO-TAG). Analytes in the sample bind to capture antibodies immobilized on the working electrode surface; recruitment of the detection antibodies by the bound analytes completes the sandwich. The plate was washed and an MSD Read Buffer was added to create the appropriate chemical environment for electrochemiluminescence (ECL). The plate was loaded into an MSD Sector Imager 600 (SI600) instrument where a voltage was applied to the plate electrodes causing the captured labels to emit light. The instrument measures the intensity of emitted light in terms of Relative Light Units (RLU) to provide a relative quantitative measure of analytes in the sample. Raw RLU data was exported into a text file, which then was converted into a Watson LIMS compatible file using a programmed Excel spread sheet, which was custom designed at Envigo. Data was subsequently imported and regressed in Watson LIMS Software v.7.2.0.02.

Figure 14:
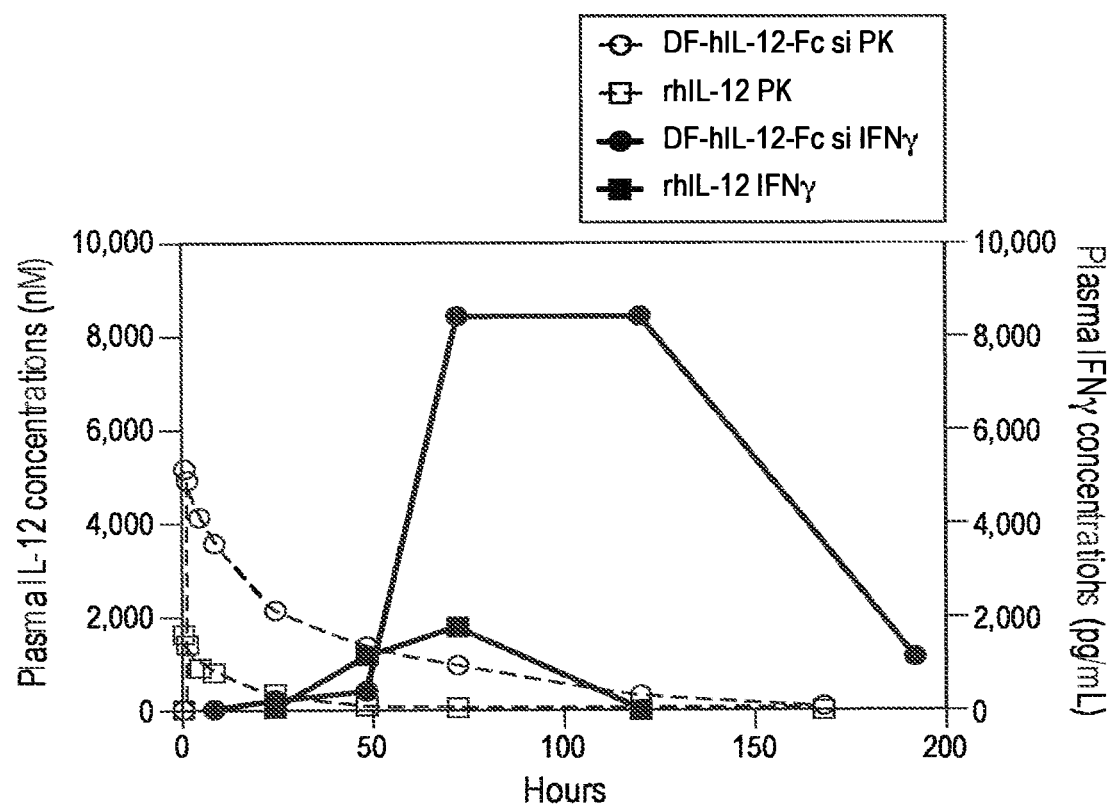
FIG. 14 is a graph showing the relative plasma concentrations of DF-hIL-12-Fc si, rhIL-12, and IFNγ in cynomolgus monkey K2 EDTA plasma following a single intravenous dose of equimolar amounts of DF-hIL-12-Fc si or wild type rhIL-12 at 10 μg/kg.

FIG. 14 shows the relative plasma concentrations of DF-hIL-12-Fc si and recombinant human IL-12 over time following IV-administration. The data indicate that concentrations of DF-hIL-12-Fc si and rhIL-12 decreased over time, as expected. However, DF-hIL-12-Fc si demonstrated a prolonged half-life and overall greater exposure compared to rhIL-12 over the time course.

FIG. 14 also shows the relative concentrations of IFNγ (PD) in monkey plasma following IV-administration. The data indicate that the pharmacodynamics of DF-hIL-12-Fc si and rhIL-12, as assessed by IFNγ production, both demonstrated activity following IV-administration. However, DF-hIL-12-Fc si demonstrated a higher peak activity and a longer duration compared to rhIL-12.

Example 6—Pharmacological Characterization of the Mouse Surrogate DF-mIL-12-Fc Si The serum half-life and in vivo pharmacodynamics of a half-life prolonged murine IL-12 variant, designated DF-mIL-12-Fc si, was examined.

An equivalent molar amount of DF-mIL-12-Fc si, corresponding to 1 µg IL-12, was intravenously injected in non-tumor bearing Balb/c mice and PK/PD characteristics were compared to IL-12. Naïve Balb/c (n=6) were injected intravenously with 1 µg DF-mIL-12-Fc si and IL-12 (equivalent molar to 1 µg IL-12). Blood was sampled at 0.017, 0.5, 3, 6, 24, 48, 72, 96, 144 and 219 hours post-injection. IL-12 and IFNγ levels in serum were analyzed by ELISA, as previously described.

Figure 15A:
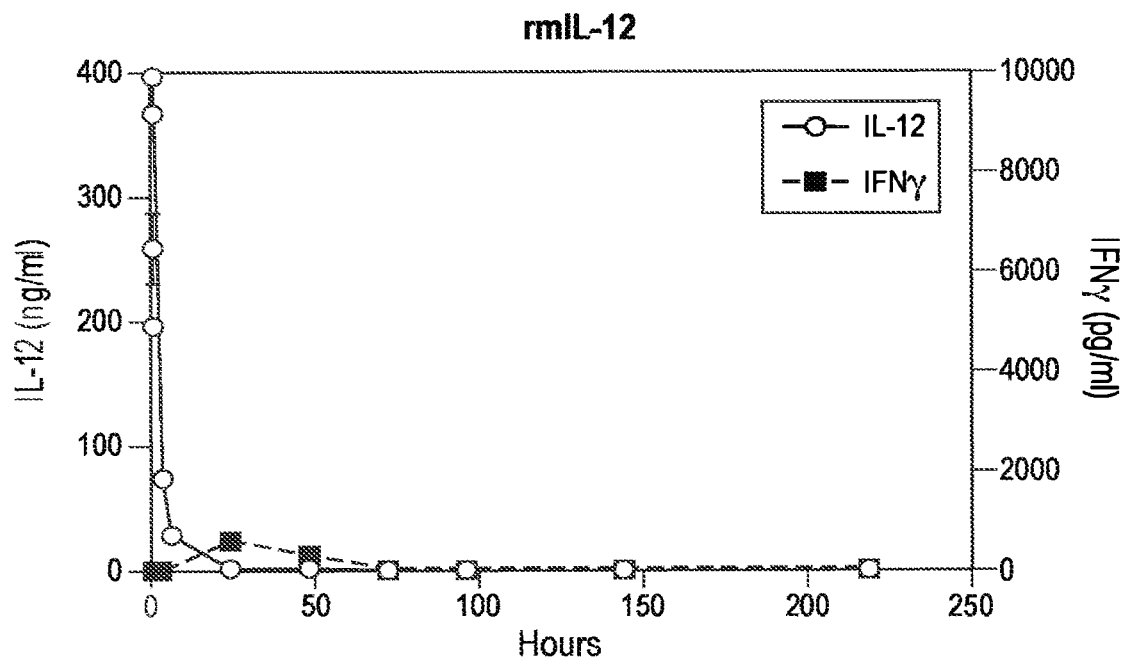
FIGS. 15A-15B are graphs showing the PK/PD profile of rmIL-12 (FIG. 15A) and DF-mIL-12-Fc si (FIG. 15B) in naïve Balb/c mice.
Figure 15B:
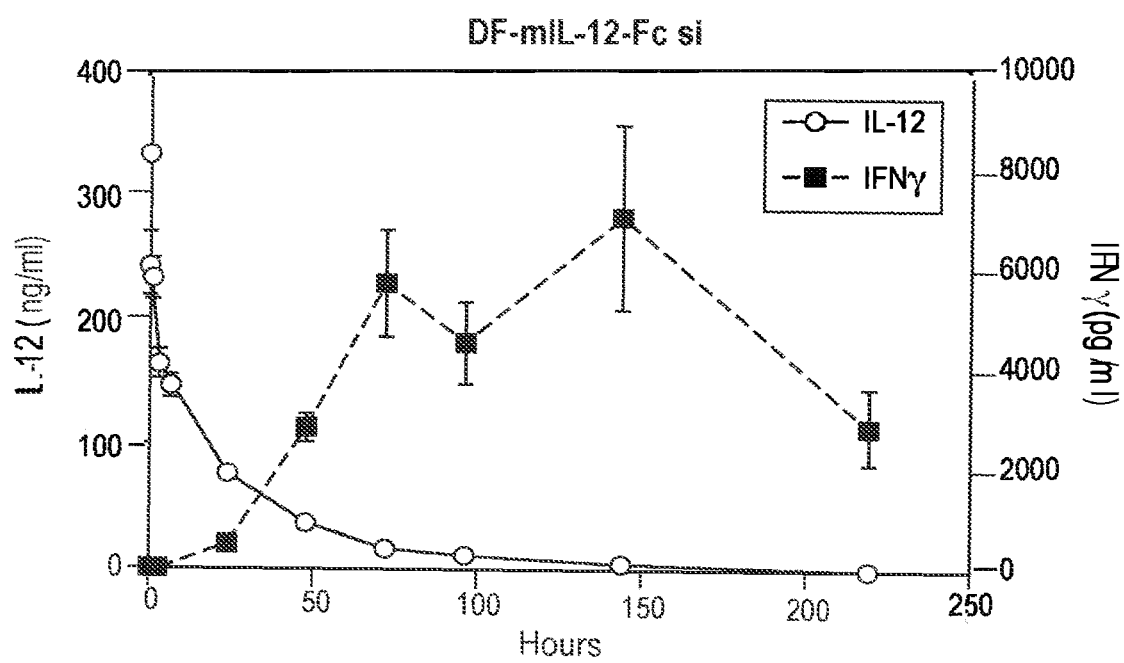

As shown in FIGS. 15A and 15B and quantified in Table 15, DF-mIL-12-Fc si showed protracted serum half-life of approximately 30 hours (FIG. 15B, DF-mIL-12-Fc si $T_{1/2}$=29.85 hours), which was 5 times longer than that of IL-12 (FIG. 15A; IL-12 $T_{1/2}$=6.05 hours). In addition to an extended half-life, DF-mIL-12-Fc si-mediated IFNγ production (AUC=916654) was also prolonged compared to IL-12 (AUC=20304).

Next, the PK/PD properties for different routes of administering DF-mIL-12-Fc si were compared. An equivalent molar amount of DF-mIL-12-Fc si, corresponding to 1 μg IL-12, was injected as a single dose in non-tumor bearing Balb/c mice by intravenous, intraperitoneal, or subcutaneous administration and PK/PD characteristics were assessed, as described.

Figure 15C:
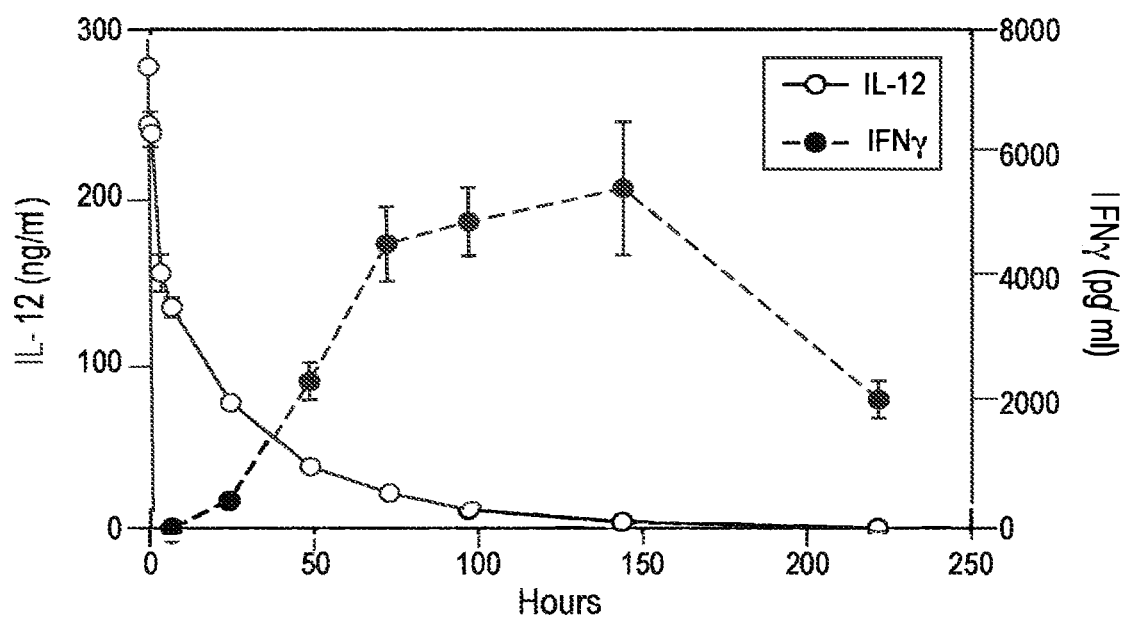
FIG. 15C is a graph showing the PK/PD profile of DF-mIL-12-Fc si administered intravenously in naïve Balb/c mice.
Figure 15D:
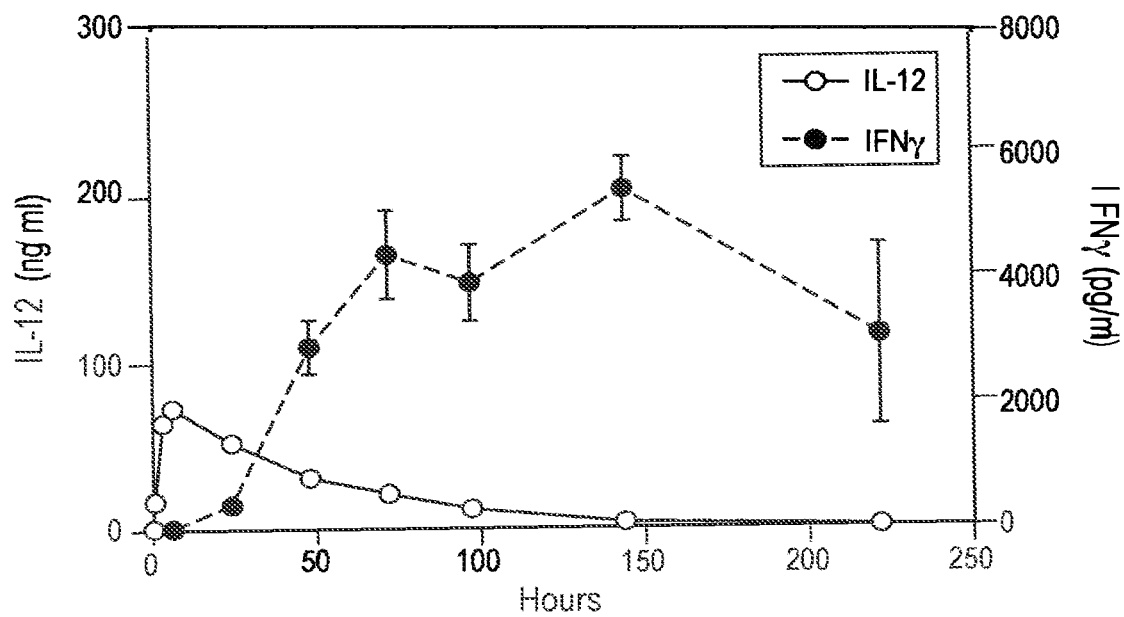
FIG. 15D is a graph showing the PK/PD profile of DF-mIL-12-Fc si administered intraperitoneally in naïve Balb/c mice.
Figure 15E:
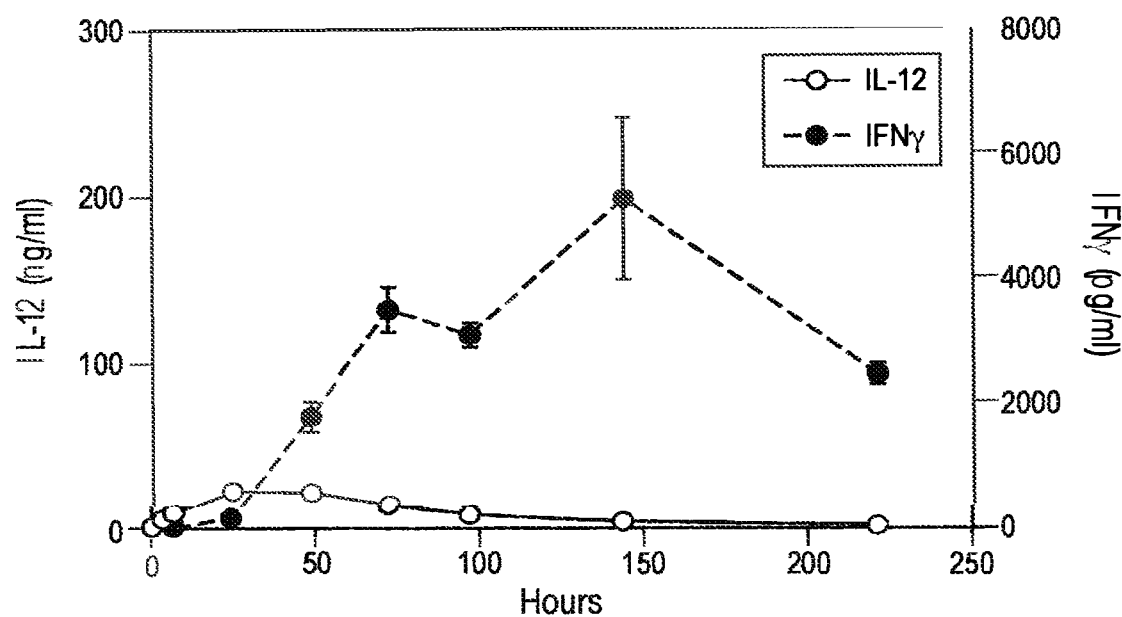
FIG. 15E is a graph showing the PK/PD profile of DF-mIL-12-Fc si administered subcutaneously in naïve Balb/c mice. Average serum levels represent the mean±SEM.

As shown in FIGS. 15C-15E and quantified in Table 16, intravenous (FIG. 15C), intraperitoneal (FIG. 15D), or subcutaneous (FIG. 15E) administration all resulted in DF-mIL-12-Fc si-mediated IFNγ production comparable across the different routes of administration. Notably, subcutaneous administration resulted in a lower IL-12 Cmax. Accordingly, the pharmacokinetic properties (e.g., IL-12 concentration) of DF-mIL-12-Fc si administration varied depending on the route of administration, while the pharmacodynamic properties (IFNγ production) remained protracted and relatively comparable across the different routes.

TABLE 15

Pharmacological characteristics of DF-mIL-12-Fc si and rmIL-12

|  | IL-12 | | | | | IFNγ |
|---|---|---|---|---|---|---|
|  | $T_{1/2}$ | Span | $T_{max}$ | $C_{max}$ | AUC | AUC |
| rmIL-12 | 6.05 | 9.15 | 0.13 | 358.65 | 999.81 | 20304 |
| DF-mIL-12-Fc | 29.85 | 6.92 | 0.19 | 258.20 | 5636.49 | 916654 |

TABLE 16

Pharmacological characteristics of DF-mIL-12-Fc si via IV, IP, and SC

|  | T½ | Span | Tmax | Cmax | AUC |
|---|---|---|---|---|---|
| Intravenous | 31.5 | 6.4 | 0.2 | 257.2 | 5985.6 |
| Intraperitoneal | 34.70 | 5.19 | N/A | 75.09 | 3964.21 |
| Subcutaneous | 37.5 | 4.1 | 36.0 | 23.1 | 1938.1 |

Example 7—Combination of DF-mIL-12-Fc Si and PD-1 Blockade in B16F10 Mouse Model Combination therapy of DF-mIL-12-Fc si and PD-1 blockade was performed to analyze whether anti-tumor immune response can be amplified in established B16F10 tumors.

C57BL/6 mice were injected with $10^6$ B16F10 melanoma cells subcutaneously into the flank of mice. On Day 8 after tumor inoculation, mice were randomized (n=10 per group). When average tumor volume reached ~245 mm$^3$, mice were treated intraperitoneally with 0.5 μg isotype control, 0.5 μg DF-mIL-12-Fc si, 200 μg anti-PD-1 clone RMP1-14, or combined DF-mIL-12-Fc si/anti-PD-1. Animals were injected once a week with DF-mIL-12-Fc si and twice weekly with anti-PD-1. Tumor growth was assessed for 60 days, and survival and body weight was monitored.

Figure 16A:
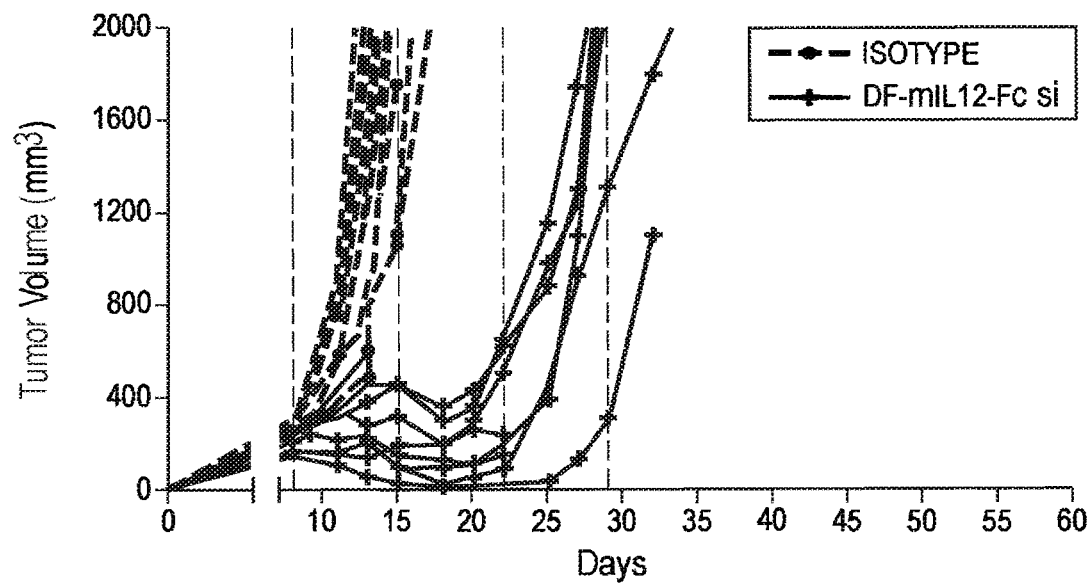
FIGS. 16A-16C are graphs showing tumor growth curves of B16F10 tumor-bearing mice treated with DF-mIL-12-Fc si, anti-PD-1, or a combination thereof. Mice were treated intraperitoneally with 0.5 μg isotype control or 0.5 μg DF-mIL-12-Fc si (FIG. 16A), isotype control or anti-PD-1 (FIG. 16B), and isotype control or DF-mIL-12-Fc si/anti-PD-1 (FIG. 16C). Animals were injected once a week with DF-mIL-12-Fc si and twice weekly with anti-PD-1 as indicated above. Tumor growth was assessed for 60 days. Graphs show tumor growth curves of individual mice.
Figure 16B:
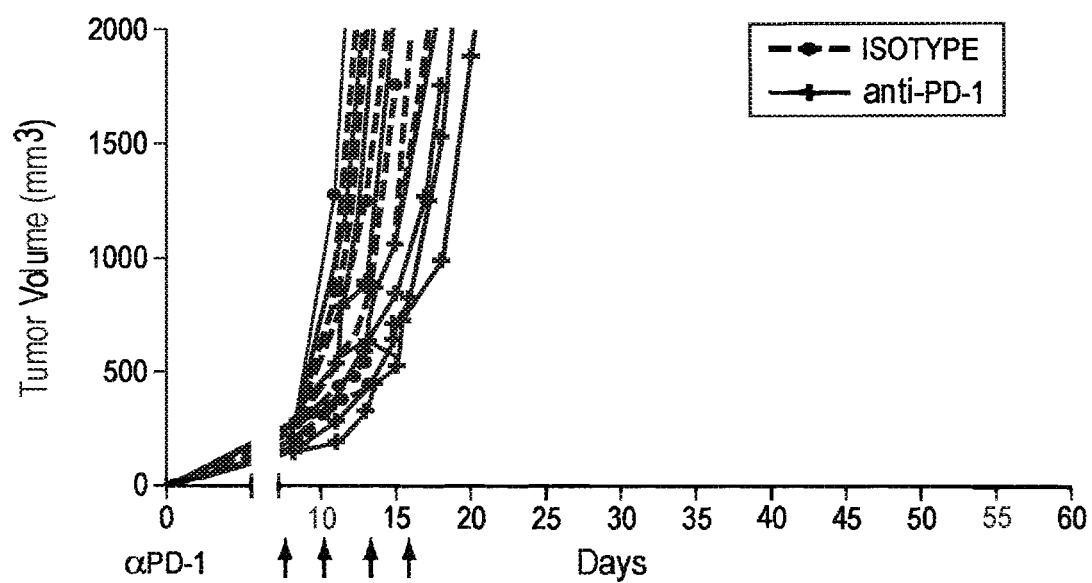
Figure 16C:
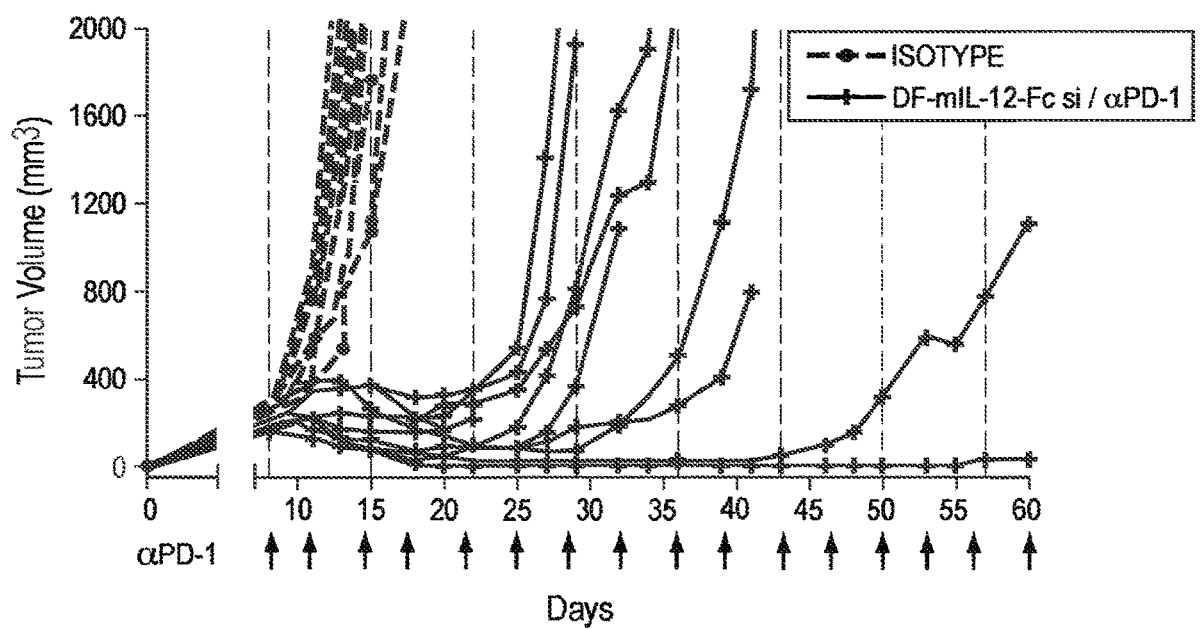

As shown in FIGS. 16A-16C, while administration of DF-mIL-12-Fc si alone delayed tumor regression (FIG. 16A) and PD-1 alone had a minimal effect on tumor growth (FIG. 16B), the combination of DF-mIL-12-Fc si with PD-1 blockade further delayed tumor growth (FIG. 16C), suggesting anti-PD-1 treatment further amplified anti-tumor responses to DF-mIL-12-Fc si treatment.

Figure 17A:
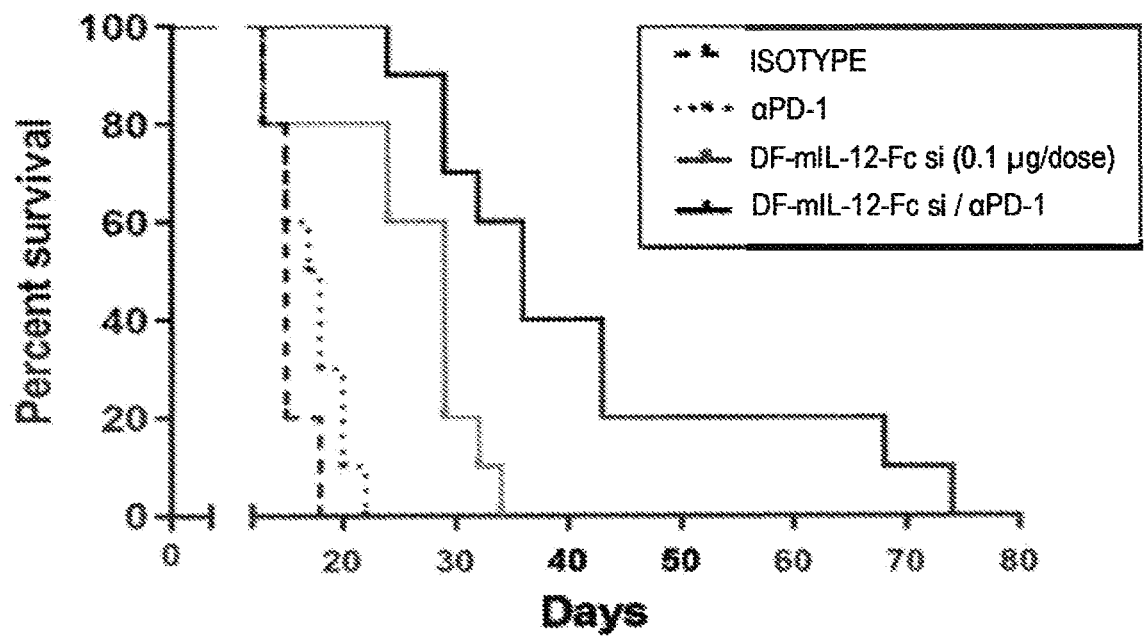
FIGS. 17A-17B are graphs showing survival and body weights of B16F10 tumor-bearing mice treated DF-mIL-12-Fc si, anti-PD-1, or a combination thereof. Mice were treated with isotype, DF-mIL-12-Fc si, anti-PD-1 or in combination of DF-mIL-12-Fc si and anti-PD-1. Animals were injected once a week with 0.5 μg DF-mIL-12-Fc si and twice weekly with 200 μg anti-PD-1 or isotype.
Figure 17B:
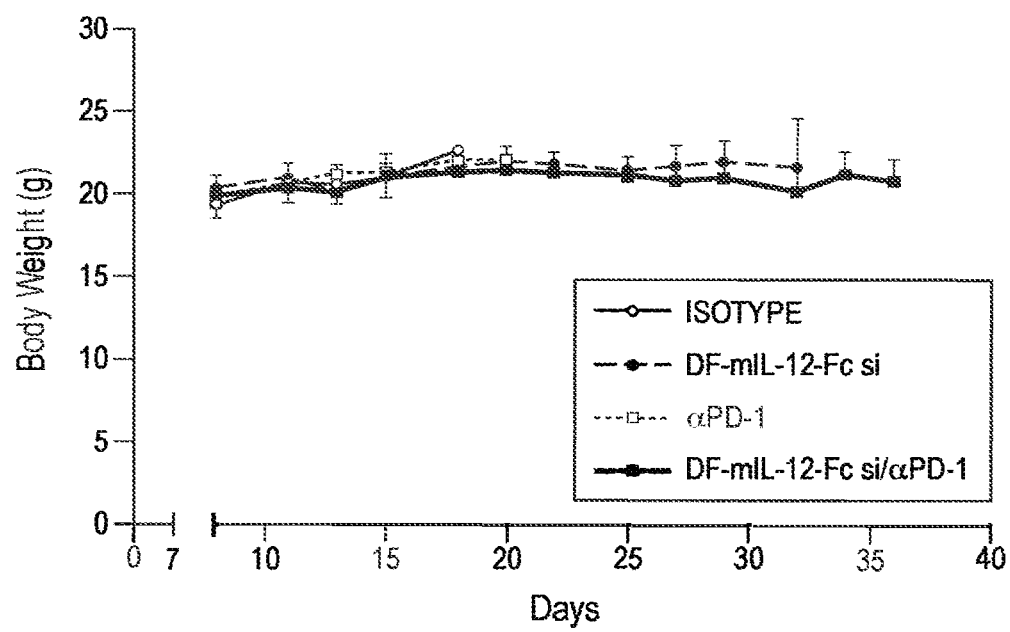

As shown in FIGS. 17A and 17B, overall survival with DF-mIL-12-Fc si therapy and in combination with PD-1 blockade was extended showing a median survival of 29 days (DF-mIL-12-Fc si monotherapy) and 36 days (combination) compared to 15 days of isotype and 17.5 days of 200 μg anti-PD-1 treated mice (FIG. 17A). Notably, despite the high response rate, the regimen of DF-mIL-12-Fc si and combination therapy appeared to be well tolerated by B16F10 tumor-bearing mice (FIG. 17B).

Accordingly, a combination therapy of DF-mIL-12-Fc si and PD-1 blockade demonstrated improved efficacy compared to either treatment alone.

Example 8—Combination of DF-mIL-12-Fc Si and with mcFAE-C26.99 TriNKETs in B16F10 Mouse Model Combination therapy of DF-mIL-12-Fc si and mcFAE-C26.99 TriNKETs was performed to analyze whether anti-tumor immune response can be amplified in established B16F10 tumors.

C57BL/6 mice were injected with $10^6$ B16F10 melanoma cells subcutaneously into the flank of the mice. On Day 7 after tumor inoculation mice were randomized (n=10 per group). When tumor average reached 200 mm$^3$, mice were treated intraperitoneally with 150 μg isotype control, or 0.5 μg DF-mIL-12-Fc si, 150 μg TriNKET, or the combination DF-mIL-12-Fc si/TriNKET. Tumor growth was assessed for 60 days, and survival and body weight was monitored.

Figure 18A:
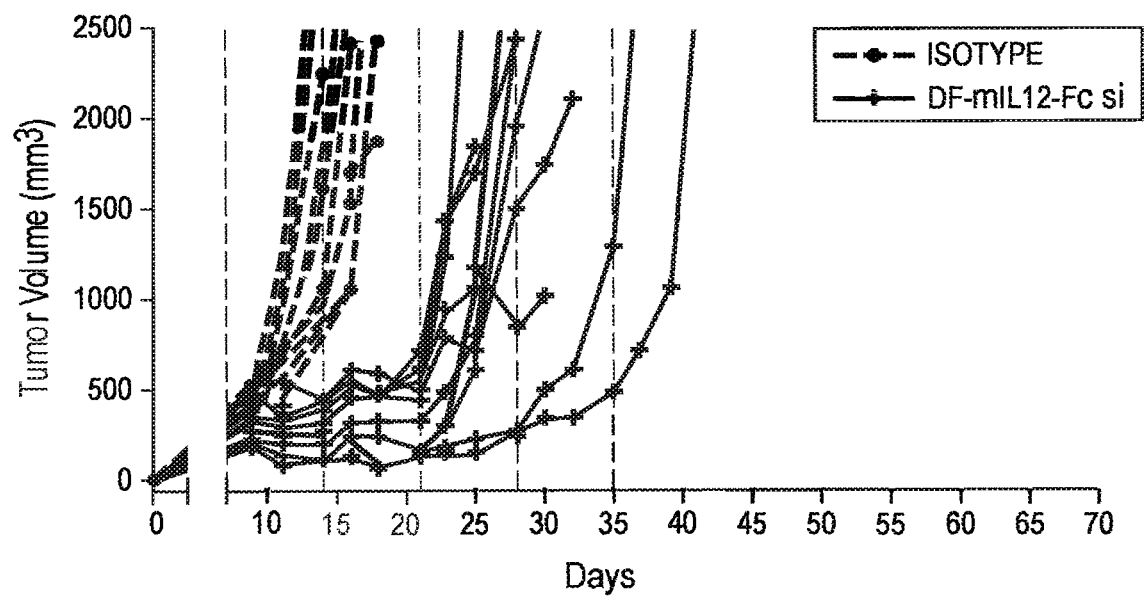
FIGS. 18A-18C are graphs showing tumor growth curves of B16F10 tumor-bearing mice treated DF-mIL-12-Fc si, mcFAE-C26.99 TriNKETs, or a combination thereof. Mice were treated intraperitoneally with 150 μg isotype control or 0.5 μg DF-mIL-12-Fc si (FIG. 18A), isotype control or 150 μg TriNKET (FIG. 18B), and isotype control or DF-mIL-12-Fc si/TriNKET (FIG. 18C). Animals were injected once a week with DF-mIL-12-Fc si and thrice weekly with TriNKET as indicated above. Tumor growth was assessed for 72 days. Graphs show tumor growth curves of individual mice.
Figure 18B:
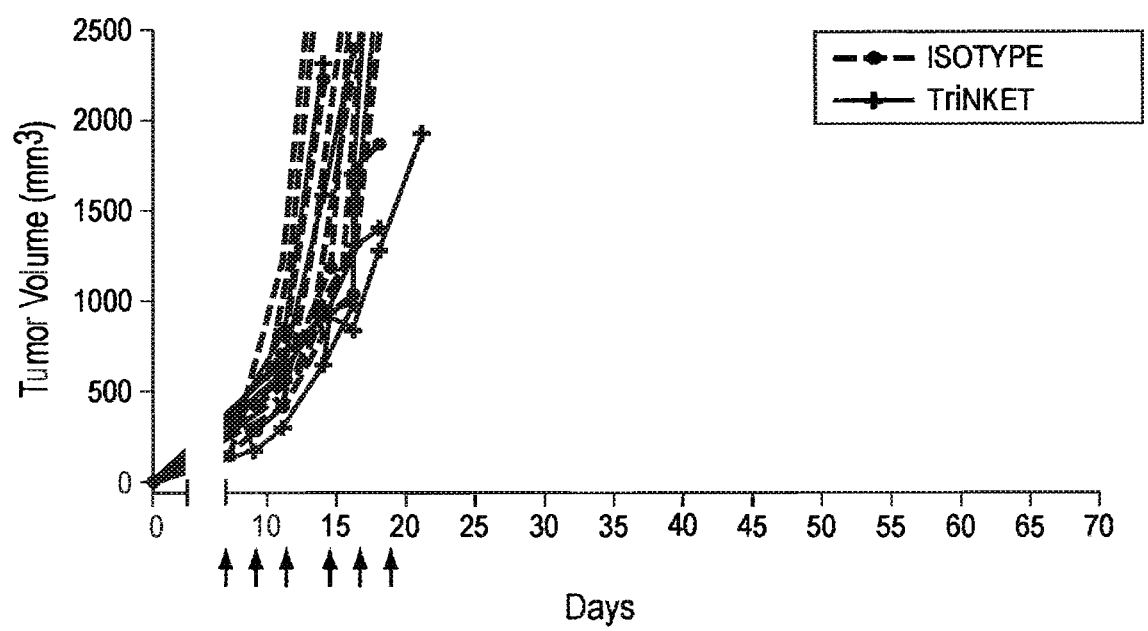
Figure 18C:
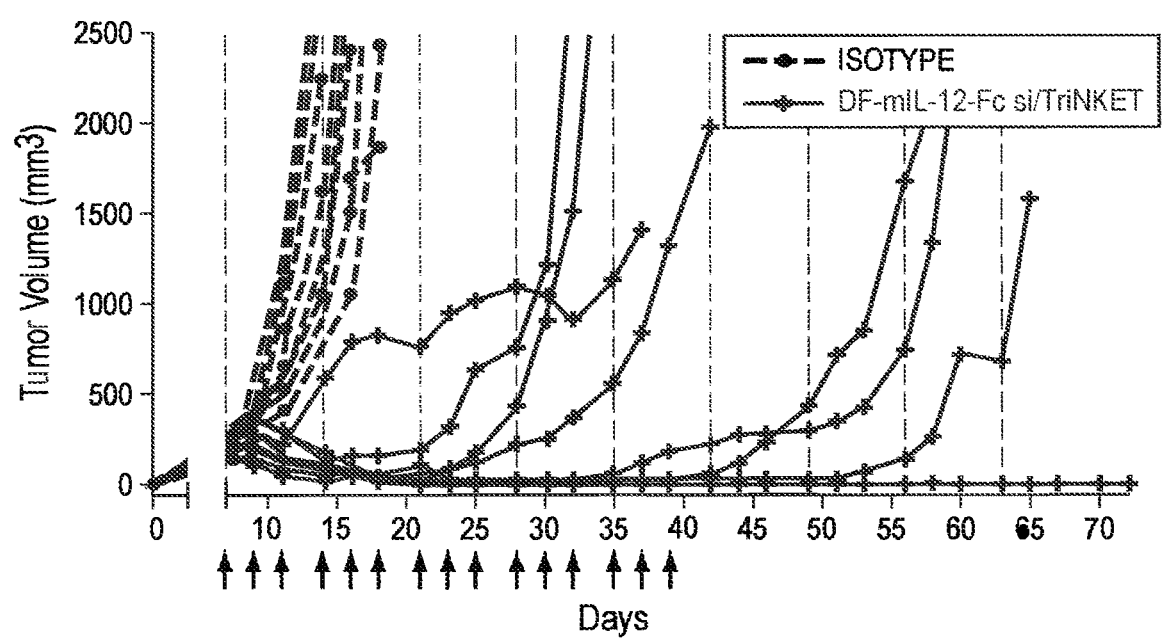

As shown in FIG. 18A, monotherapy with DF-mIL-12-Fc si led to reduced tumor growth. Treatment with mcFAE-C26.99 TriNKET as single agent at a starting tumor volume of 200 mm$^3$ did not result in delayed tumor progression (FIG. 18B). In contrast, the combination of DF-mIL-12-Fc si with mcFAE-C26.99 further enhanced anti-tumor responses in comparison to DF-mIL-12-Fc si alone (FIG. 18C) and resulted in 30% complete responders (CR) (n=3), suggesting TriNKET treatment further amplified anti-tumor responses to DF-mIL-12-Fc si treatment.

Figure 19A:
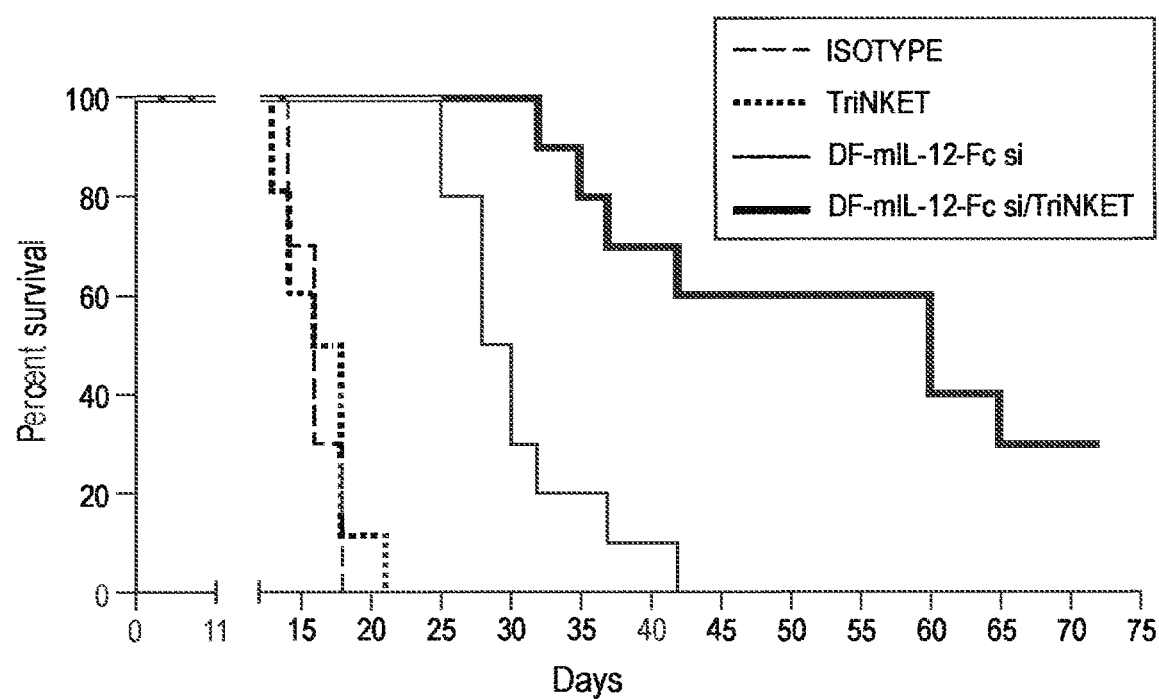
FIGS. 19A-19B are graphs showing survival and body weights of B16F10 tumor-bearing mice treated with DF-mIL-12-Fc si, mcFAE-C26.99 TriNKETs, or a combination thereof. Mice were treated with isotype, DF-mIL-12-Fc si, TriNKET, or a combination of DF-mIL-12-Fc si and TriNKET. Animals were injected once a week with 0.5 μg DF-mIL-12-Fc si and thrice weekly with 150 μg TriNKET or isotype.
Figure 19B:
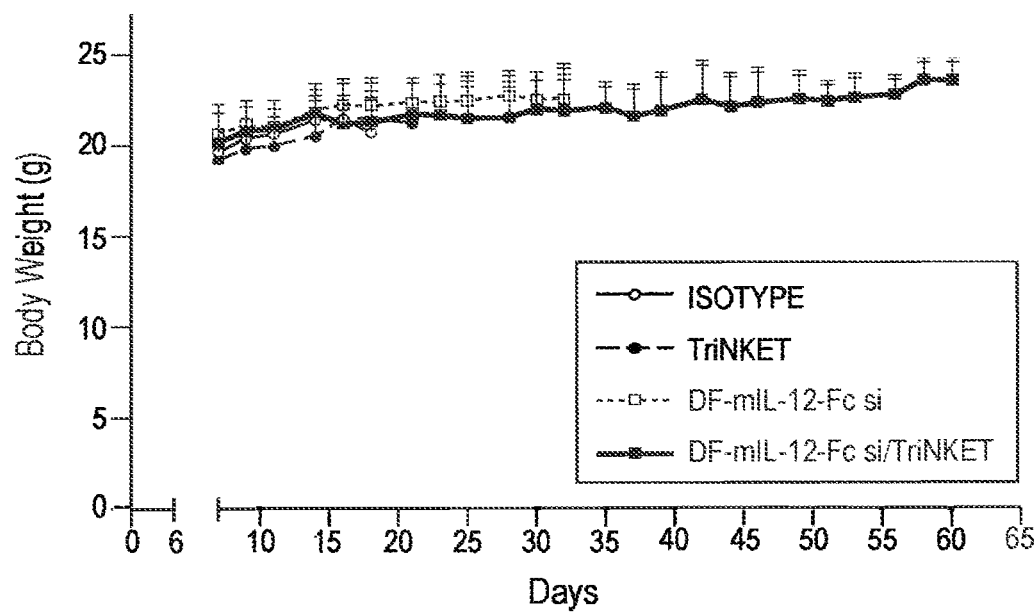

As shown in FIG. 19A, overall survival with DF-mIL-12-Fc si therapy and in combination with mcFAE-C26.99 TriNKET was extended showing a median survival of 29 days (DF-mIL-12-Fc si monotherapy) and 60 days (TriNKET combination) compared to 16 days of isotype and 17 days of TriNKET treated mice. Notably, despite the high response rate, the regimen of DF-mIL-12-Fc si and combination therapy appeared to be well tolerated by B16F10 tumor-bearing mice (FIG. 19B).

Figure 20:
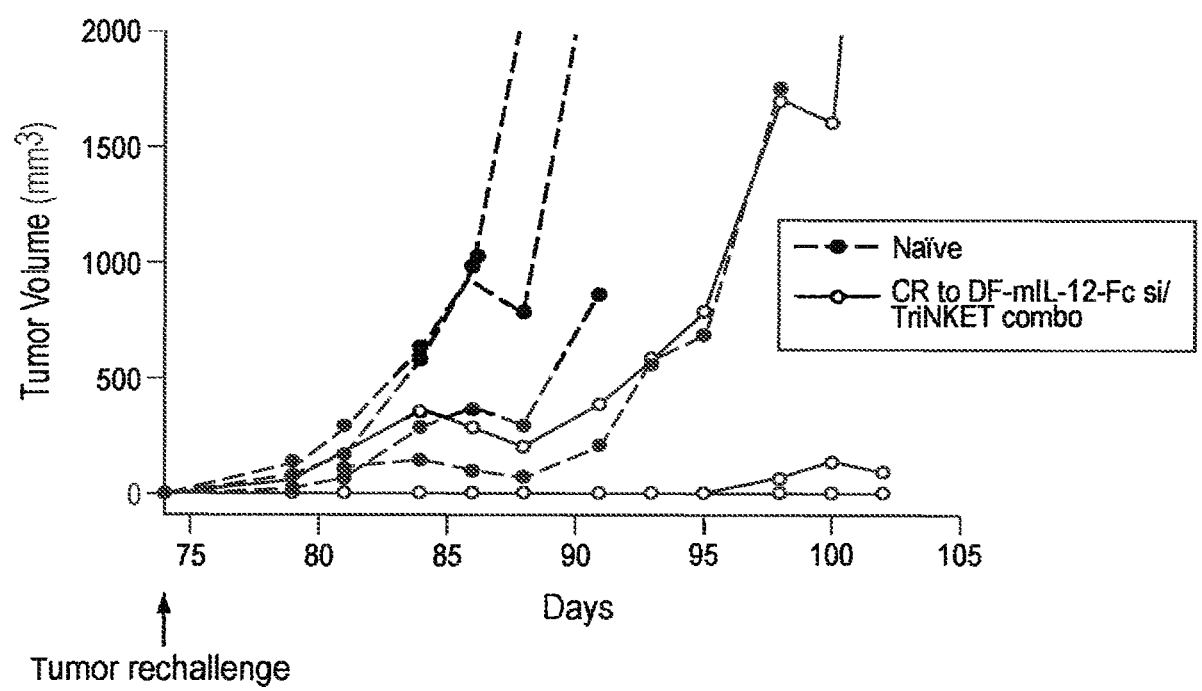
FIG. 20 is a graph showing tumor growth curves of complete responder (CR) mice from the B16F10 tumor model experiment of FIG. 18 treated with DF-mIL-12-Fc si/TriNKET combination therapy (n=3), re-challenged by engraftment with 2×10⁵ B16F10 melanoma cells.

The three complete responders (the CRs from the experiment described above and the data presented in FIG. 18C) were re-challenged with 2×10$^6$ B16F10 melanoma cells 72 days after first tumor inoculation. Age-matched naïve C57BL/6 mice were used as control group. 1 out of 3 mice from the initial DF-mIL-12-Fc si/TriNKET combo treated group remained tumor-free, another mouse showed tumor formation starting at day 95 and the tumor progression of the third mouse was similar to the age-matched control group (FIG. 20), suggesting the formation of immunological memory with combination therapy.

Accordingly, a combination therapy of DF-mIL-12-Fc si and TriNKETs demonstrated improved efficacy compared to either treatment alone, including demonstrating a complete, durable response in a population of mice.

Example 9—Treatment with DF-mIL-12-Fc Si Promotes Complete Recovery in CT26 Tumor Model This example shows that treatment with DF-mIL-12-Fc si promotes recovery in mice bearing CT26 tumors.

Briefly, $10^6$ CT26-Tyrp1 colon carcinoma cells were injected subcutaneously into the flank of Balb/c mice. On Day 14 after tumor inoculation, when tumor volume reached 270 mm$^3$, the mice were randomized into different treatment groups and intraperitoneally injected with 1 µg of DF-mIL-12-Fc si at a molar dose equivalent to 1 µg rmIL-12 or 1 µg of mIgG2a isotype control once a week. Tumor growth was assessed for 60 days. The complete responders were re-challenged with $10^6$ CT26 cells 72 days after first tumor inoculation. Age-matched naïve Balb/C mice were used as control group.

Figure 21A:
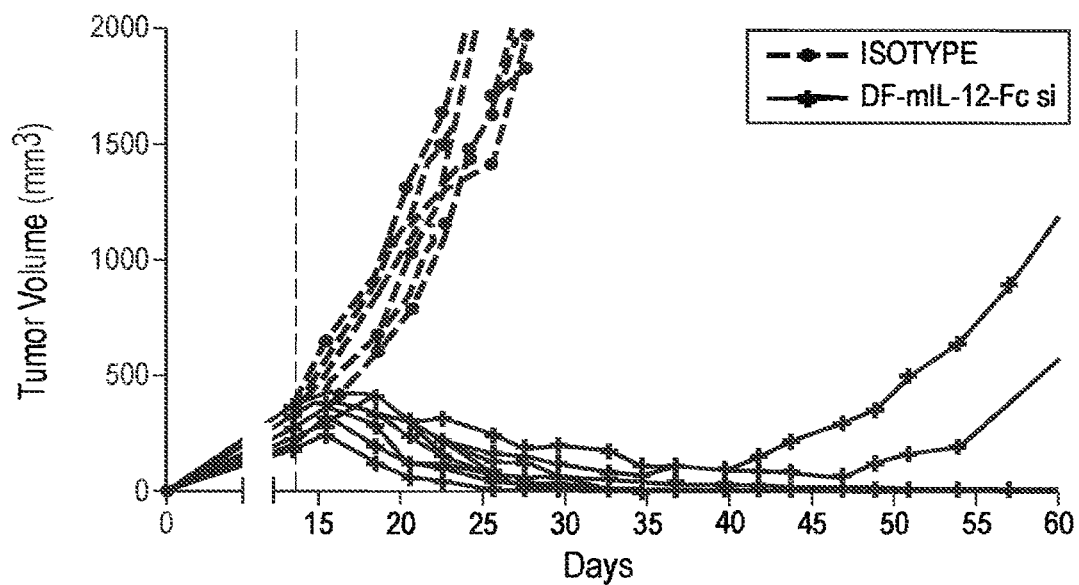
FIG. 21A is a graph showing tumor growth curves of individual mice inoculated with CT26 tumor cells and administered a single dose of DF-mIL-12-Fc si or mIgG2a isotype.
Figure 21B:
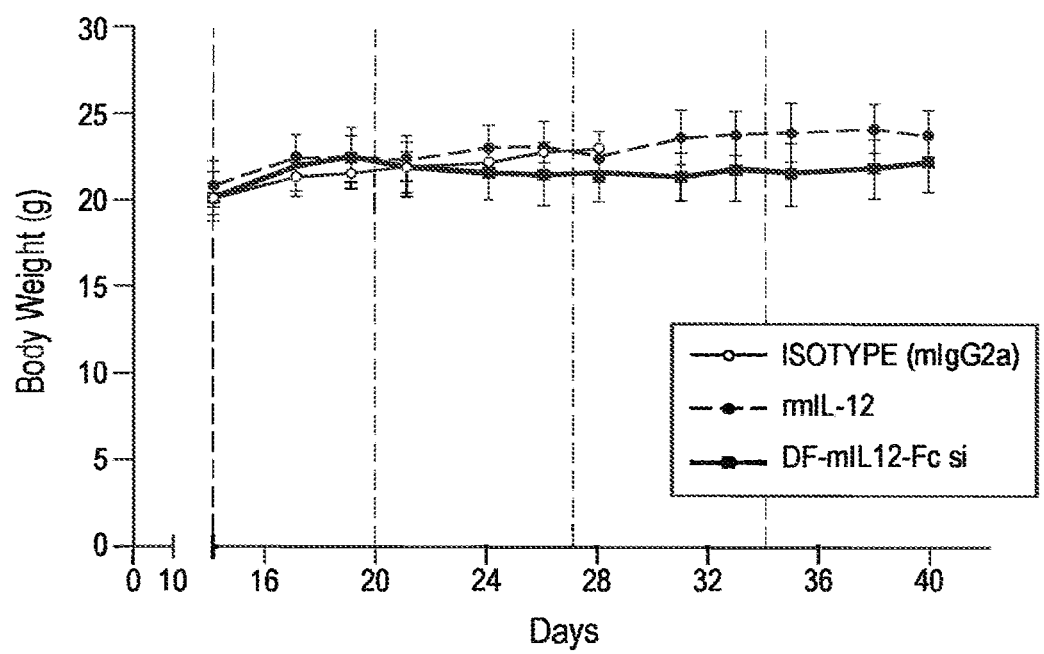
FIG. 21B is a graph showing body weights±standard deviation of mice inoculated with CT26 tumor cells and administered a weekly dose of DF-mIL-12-Fc si, mIgG2a isotype, or rmIL-12.
Figure 21C:
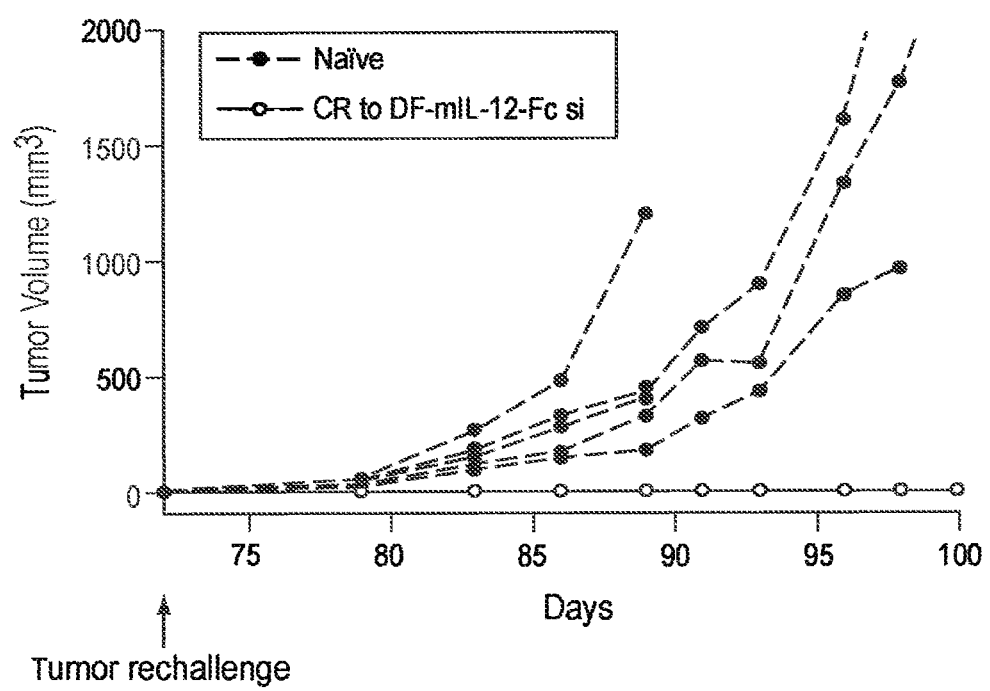
FIG. 21C is a graph showing tumor growth curves of re-challenged individual mice that were either naïve or complete responders (CR) when previously administered a single dose of DF-mIL-12-Fc si in a CT26 tumor model.

FIG. 21A is a graph showing tumor growth curves of individual mice inoculated with CT26 tumor cells and administered a single dose of 1 µg of DF-mIL-12-Fc si or mIgG2a isotype. FIG. 21B is a graph showing body weights of individual mice inoculated with CT26 tumor cells and administered a weekly dose of 1 µg of DF-mIL-12-Fc si or mIgG2a isotype. FIG. 21C is a graph showing tumor growth curves of individual mice re-challenged with inoculation of CT26 tumor cells.

As shown in FIGS. 21A-B, administration of DF-mIL-12-Fc si resulted in robust tumor regression in comparison to mIgG2a isotype with no observable toxicity affecting the body weight of treatment animals. As shown in FIG. 21C, the initial DF-mIL-12-Fc si treated mice remained tumor-free suggesting the formation of immunological memory with DF-mIL-12-Fc si treatment.

Example 10-DF mIL-12-Fc Si Delivered Intraperitoneally or Subcutaneously is Effective to Reduce Tumor Volume in CT26 Tumor Model This example shows that intraperitoneal or subcutaneous administration of DF-mIL-12-Fc si ensures 100% complete recovery in mice bearing CT26 tumors.

Briefly, $10^6$ CT26-Tyrp1 colon carcinoma cells were injected subcutaneously into the flank of Balb/c mice. On Day 14 after tumor inoculation, when tumor volume reached 270 mm$^3$, the mice were randomized into different treatment groups and intraperitoneally injected with 1 µg of DF-mIL-12-Fc si at a molar dose equivalent to 1 µg IL-12 or 1 µg of mIgG2a isotype control once a week, or subcutaneously injected with 1 µg of DF-mIL-12-Fc si at a molar dose equivalent to 1 µg IL-12 or 1 µg of mIgG2a isotype control once a week. Tumor growth was assessed for more than 60 days.

FIG. 22A is a graph showing tumor growth curve of individual mice inoculated with CT26 tumor cells and administered a weekly dose of 1 µg of DF-mIL-12-Fc si or mIgG2a isotype delivered intraperitoneally. FIG. 22B is a graph showing tumor growth curve of individual mice inoculated with CT26 tumor cells and administered a weekly dose of 1 µg of DF-mIL-12-Fc si or mIgG2a isotype delivered subcutaneously.

As shown in FIGS. 22A-B, either intraperitoneal or subcutaneous delivery of DF-mIL-12-Fc si was effective at reducing CT26 tumor volume.

Example 11—Single Dose Administration of DF-mIL-12-Fc Si is Effective to Reduce Tumor Volume in B16F10 Mouse Model This example shows that a single dose of DF-mIl2-Fc si is effective at reducing tumor volume in mice bearing B16F10 melanoma tumors.

In brief, C57BL/6 mice were injected with $10^6$ B16F10 melanoma cells subcutaneously into the flank of the mice. On Day 7 after tumor inoculation mice were randomized. When tumor average reached 200 mm$^3$, mice were treated intraperitoneally with a single dose of isotype control, or 1 µg of DF-mIL-12-Fc si. Tumor growth was assessed for 50 days.

As shown in FIG. 23, a single administration of µg of DF-mIL-12-Fc si is effective to reduce tumor volume in B16F10 tumor-bearing mice.

Example 12—DF-mIL-12-Fc Si Delivered Intraperitoneally or Subcutaneously is Effective to Reduce Tumor Volume in B16F10 Mouse Model This example shows that intraperitoneal or subcutaneous administration of DF-mIL-12-Fc si led to 100% complete recovery in mice bearing B16F10 melanoma tumors.

Briefly, $10^6$ B16F10 melanoma cells were injected subcutaneously into the flank of C57BL/6 mice. On Day 7 after tumor inoculation, mice were randomized. When tumor average reached 200 mm$^3$, mice were intraperitoneally injected with 1 µg of DF-mIL-12-Fc si at a molar dose equivalent to 1 µg IL-12 or 1 µg of mIgG2a isotype control once a week, or subcutaneously injected with 1 µg of DF-mIL-12-Fc si at a molar dose equivalent to 1 µg IL-12 or 1 µg of mIgG2a isotype control once a week. Tumor growth was assessed for 40 days.

As shown in FIGS. 24A-B, either intraperitoneal or subcutaneous delivery of DF-mIL-12-Fc si was effective at reducing B16F10 tumor volume as compared to isotype control.

Example 13—DF-mIL-12-Fc Si is Efficacious as a Single Dose

This example shows that DF-mIL-12-Fc si is effective at reducing CT26 tumor volume when administered as a single dose, and when administered via repeat dosing, is even more effective.

Briefly, $10^6$ CT26-Tyrp1 colon carcinoma cells were injected subcutaneously into the flank of Balb/c mice. On Day 14 after tumor inoculation, when tumor volume reached 270 mm$^3$, the mice were randomized into different treatment groups (n=10 per group) and intraperitoneally injected with a single dose of 1 µg of DF-mIL-12-Fc si at a molar dose equivalent to 0.1 µg IL-12 or 1 µg of mIgG2a isotype control once a week. Alternatively, mice were intraperitoneally injected with 1 µg of DF-mIL-12-Fc si at a molar dose equivalent to 1 µg IL-12 or 1 µg of mIgG2a isotype control once a week. Tumor growth was assessed for more than 60 days.

Figure 25A:
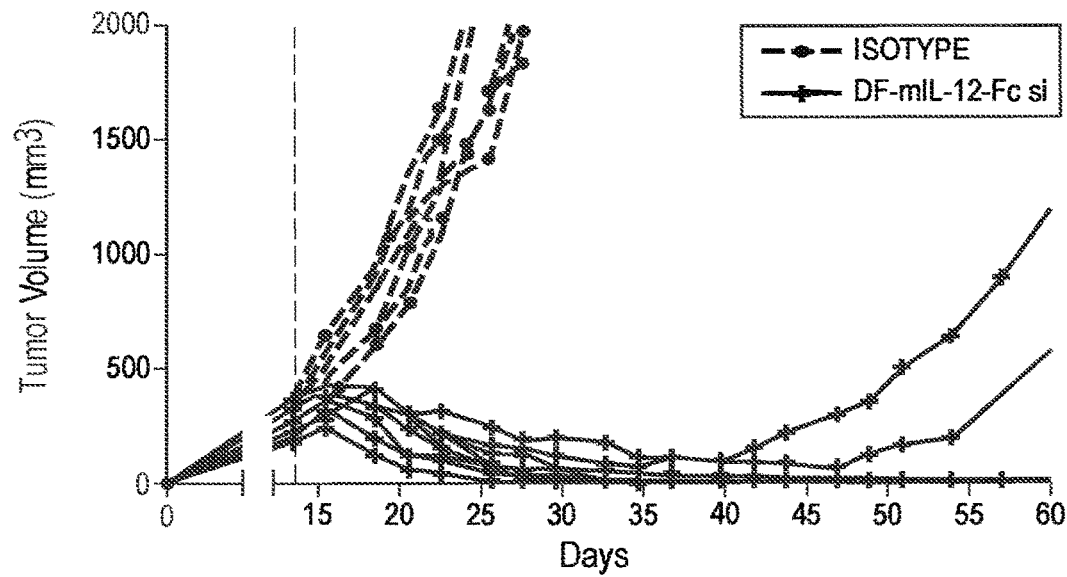
FIGS. 25A-25B are graphs showing tumor growth curves of individual mice inoculated with CT26 tumor cells and administered a single dose (FIG. 25A) or once weekly dose (FIG. 25B) of DF-mIL-12-Fc si or mIgG2A isotype intraperitoneally at a molar equivalent of 1 μg of rmIL-12.
Figure 25B:
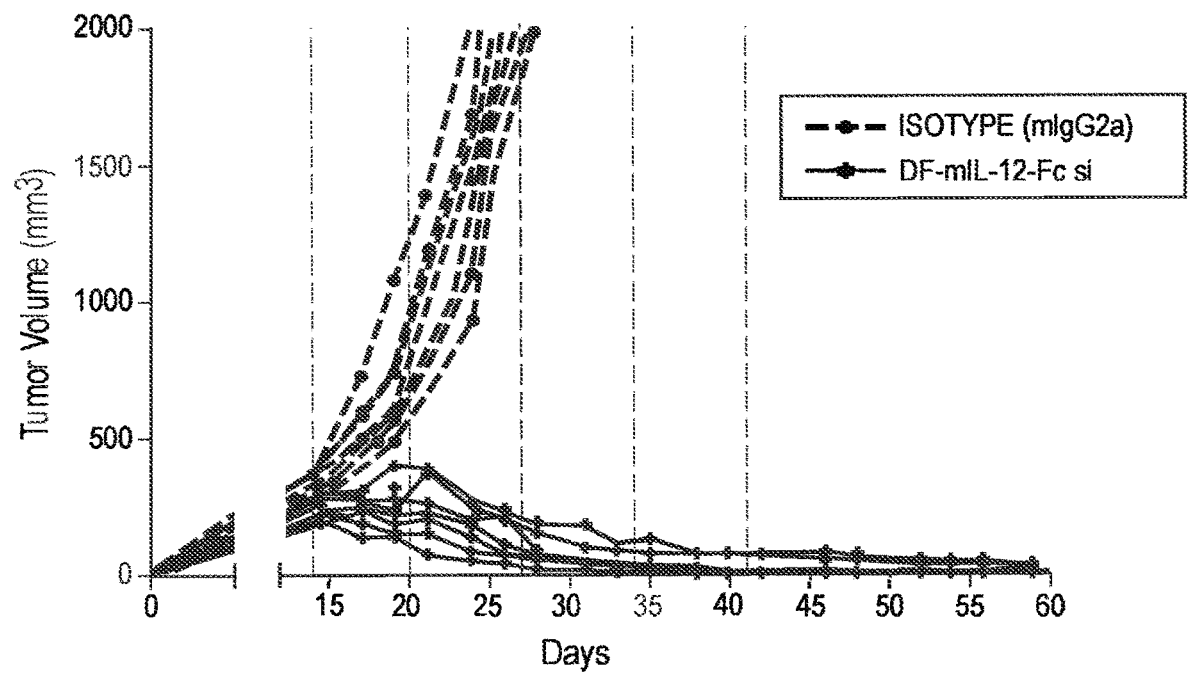

FIG. 25A is a graph showing tumor growth curve of individual mice inoculated with CT26 tumor cells and administered a single dose of 1 µg of DF-mIL-12-Fc si or mIgG2a isotype. FIG. 25B is a graph showing tumor growth curve of individual mice inoculated with CT26 tumor cells and administered a weekly dose of 1 µg of DF-mIL-12-Fc si or mIgG2a isotype.

As shown in FIG. 21A and FIG. 25A, a single administration of 1 µg of DF-mIL-12-Fc si resulted in robust 70% complete recovery of tumor-bearing mice as compared to mIgG2a isotype. However, as shown in FIG. 5C and FIG. 25B, repeat weekly dosing of 1 µg of DF-mIL-12-Fc si ensured 100% complete recovery of tumor-bearing mice as compared to mIgG2a isotype. As shown in FIG. 21B, even repeat administration of DF-mIL-12-Fc si was well-tolerated with no toxicities observed, as assessed by body weight.

Additionally, complete responders (CR) were re-challenged with 5×10⁵ CT26-Tyrp1 colon carcinoma cells at the opposite flank and tumor progression was compared to naïve mice challenged at the same tumor dose. As shown in FIG. 21C, while tumors grew in naïve mice, 100% of complete responders remained tumor-free following re-challenge. Accordingly, a single administration of DF-mIL-12-Fc si demonstrated a complete, durable response in a population of mice.

Example 14—Pharmacokinetics in Cynomolgus Monkeys Treated with a Single Subcutaneous Dose of DF-hIL-12-Fc Si Pharmacokinetics were determined following a subcutaneous injection of DF-hIL-12-Fc si at 1 µg/kg (FIG. 28A), 2 µg/kg (FIG. 28B), or 4 µg/kg (FIG. 28C) in cynomolgus monkeys utilizing an ELISA like immunoassay-Meso Scale Discovery (MSD) immunoassay method. Briefly, an untreated MSD microtiter plate was coated with monkey-adsorbed goat anti-human IgG and incubated at room temperature. Following coating and incubation, the plate was washed, blocked, washed, and incubated with standard curve and quality control samples spiked with a DF-hIL-12-Fc si reference standard, along with test samples. Following incubation, the plate was washed and biotin anti-human IL-12/IL-23 p40 was added to the plate as the primary detection antibody. Following another wash step, streptavidin-conjugated Sulfo-Tag was added as the secondary detection antibody. The plate was washed a final time before adding MSD read buffer T to the plate. The plate was read using an MSD Sector Imager S6000.

Figure 28A:
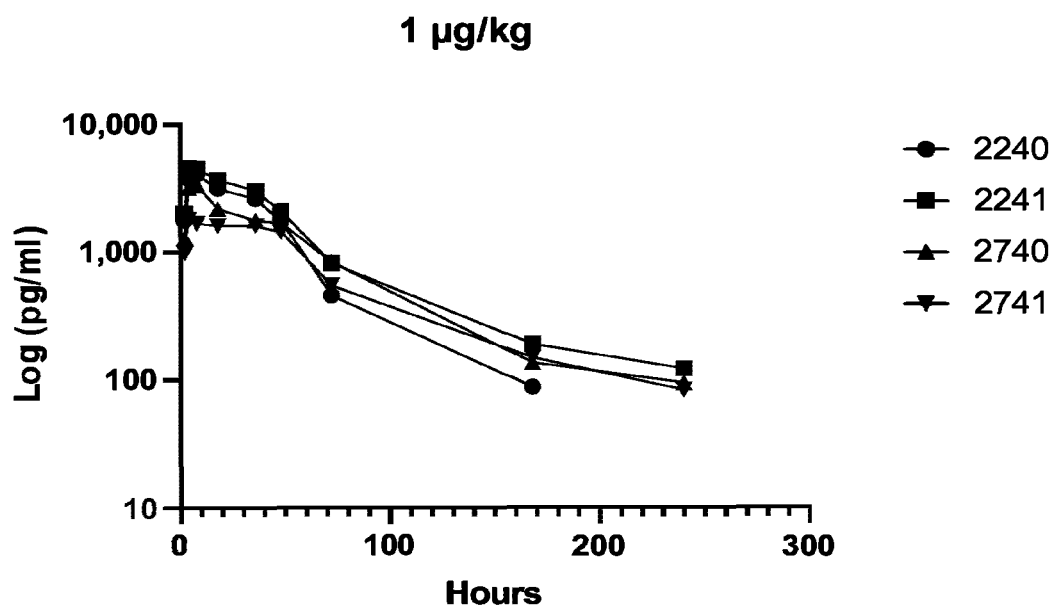
FIGS. 28A-28C are line graphs showing pharmacokinetics of DF-hIL-12-Fc si in cynomolgus monkeys treated with a single subcutaneous dose of 1 µg/kg (FIG. 28A), 2 µg/kg (FIG. 28B), or 4 µg/kg (FIG. 28C) of DF-hIL-12-Fc si. 2240, 2241, 2740, 2741 denote individual cynomolgus monkey subjects.
Figure 28B:
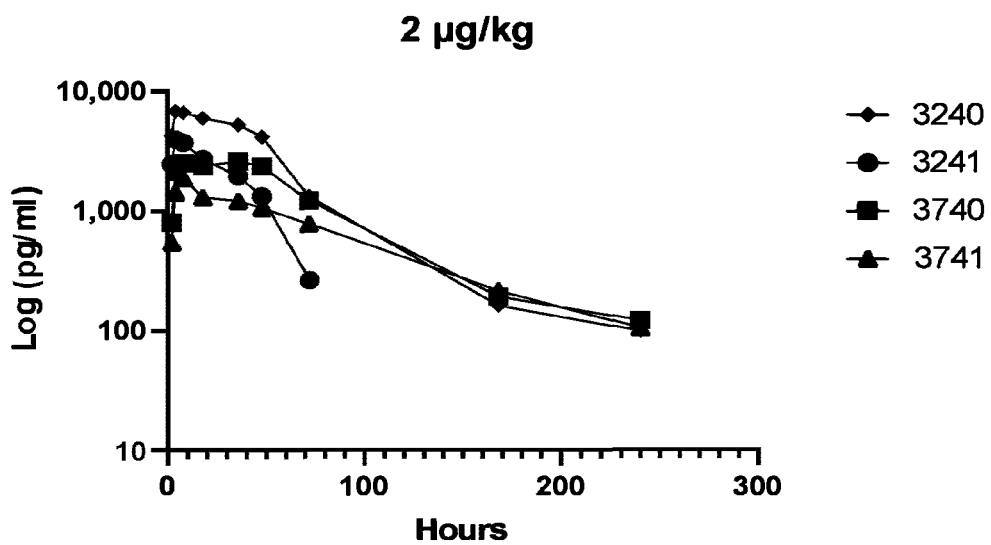
Figure 28C:
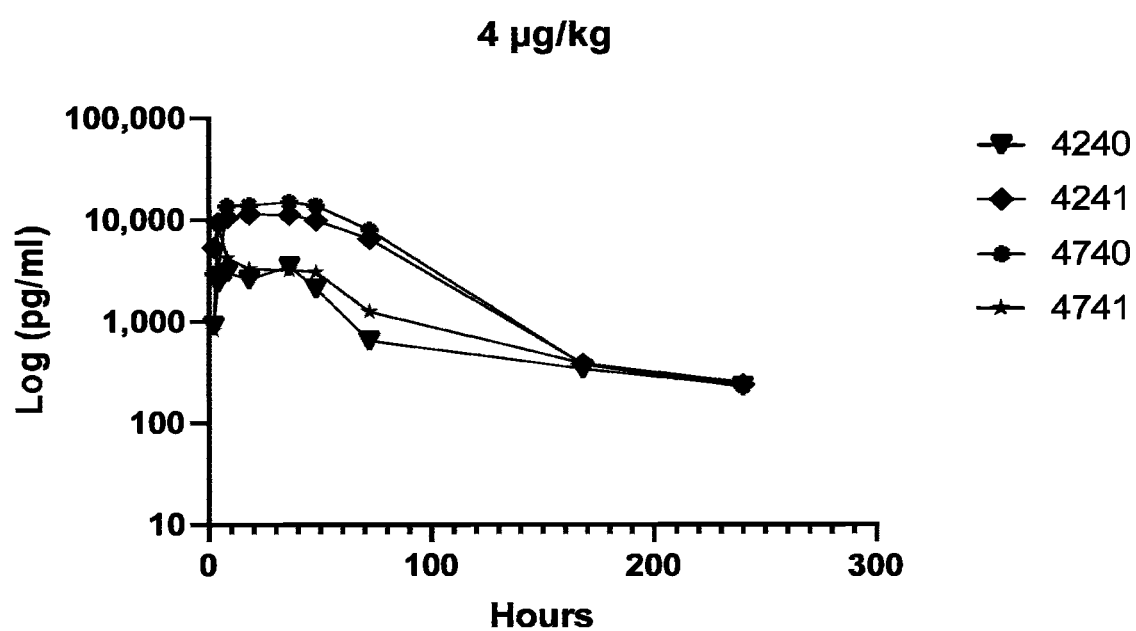

FIGS. 28A-28C are line graphs showing pharmacokinetics in cynomolgus monkeys treated with a single subcutaneous dose of 1 µg/kg (FIG. 28A), 2 µg/kg (FIG. 28B), or 4 µg/kg (FIG. 28C) of DF-hIL-12-Fc si.

The data indicate that concentrations of DF-hIL-12-Fc si and rhIL-12 decreased over time, as expected, with similar pharmacokinetic profiles at all doses tested.

Example 15—Cytokine Release in Cynomolgus Monkeys Treated with a Single Subcutaneous Dose of DF-hIL-12-Fc Si Quantitative measurements of cytokines following a subcutaneous injection of DF-hIL-12-Fc si at 1 µg/kg (FIGS. 29A and 29B), 2 µg/kg (FIGS. 29C and 29D), or 4 µg/kg (FIGS. 29E and 29F) in cynomolgus monkeys were determined using MSD immunoassay kits. The method used sandwich immunoassay kits (Pro-inflammatory Panel 1 Biomarkers and V-PLEX Plus Chemokine Panel 1 NHP Kit) for the relative quantitative measurement of Pro-inflammatory Panel 1 Biomarkers: IFNγ, IL-1β, IL-2, IL-6 IL-8, and IL-10 in cynomolgus monkey K2 EDTA plasma (referred to as monkey plasma). The method is based on MSD non-human primate (NHP) kits for V-PLEX and V-PLEX Plus, Catalog No. K15056D-1, K15056D-2, K15056D-4, K15056D-6, K15056G-1, K15056G-2, K15056G-4, K15056G-6. The method employs human capture and detection antibodies that react with cynomolgus monkeys. The kit provides plates pre-coated with capture antibodies on independent, well-defined spots within each well of a 96-well multi-spot plate. The plate was incubated with monkey plasma samples, washed and then incubated with detection antibodies (specific for each analyte) that are conjugated with electrochemiluminescent (ECL) labels (MSD SULFO-TAG). Analytes in the sample bind to capture antibodies immobilized on the working electrode surface; recruitment of the detection antibodies by the bound analytes completes the sandwich. The plate was washed and an MSD Read Buffer was added to create the appropriate chemical environment for electrochemiluminescence (ECL). The plate was loaded into an MSD Sector Imager 600 (SI600) instrument where a voltage was applied to the plate electrodes causing the captured labels to emit light. The instrument measures the intensity of emitted light in terms of Relative Light Units (RLU) to provide a relative quantitative measure of analytes in the sample. Raw RLU data was exported into a text file, which then was converted into a Watson LIMS compatible file using a programmed Excel spread sheet, which was custom designed at Envigo. Data was subsequently imported and regressed in Watson LIMS Software v.7.2.0.02.

FIGS. 29A-29F are line graphs showing concentrations of IFNγ (FIGS. 29A, 29C, and 29E) and IP10/CXCL10 (FIGS. 29B, 29D, and 29F) in cynomolgus monkeys treated with a single subcutaneous dose of 1 µg/kg (FIGS. 29A and 29B), 2 µg/kg (FIGS. 29C and 29D), or 4 µg/kg (FIGS. 29E and 29F) of DF-hIL-12-Fc si.

Figure 29A:
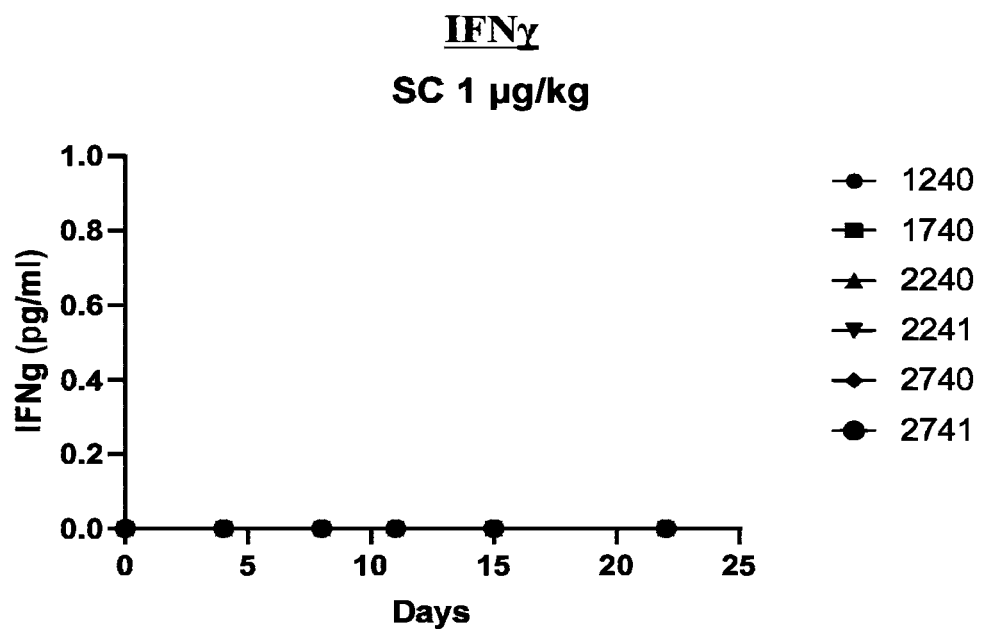
FIGS. 29A-29F are line graphs showing concentrations of IFNγ and IP10/CXCL10 in cynomolgus monkeys treated with a single subcutaneous dose of DF-hIL-12-Fc si.
Figure 29B:
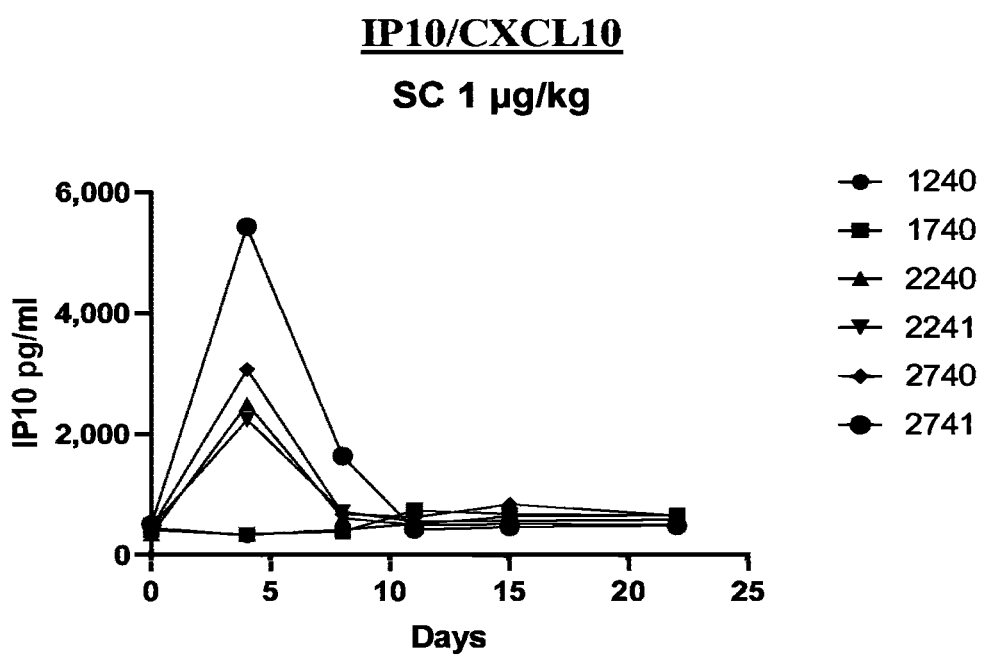
Figure 29C:
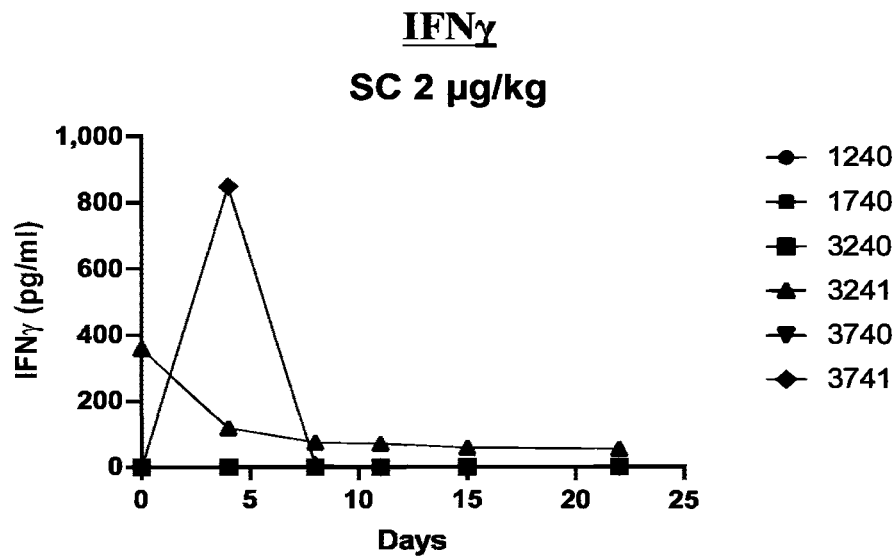
Figure 29D:
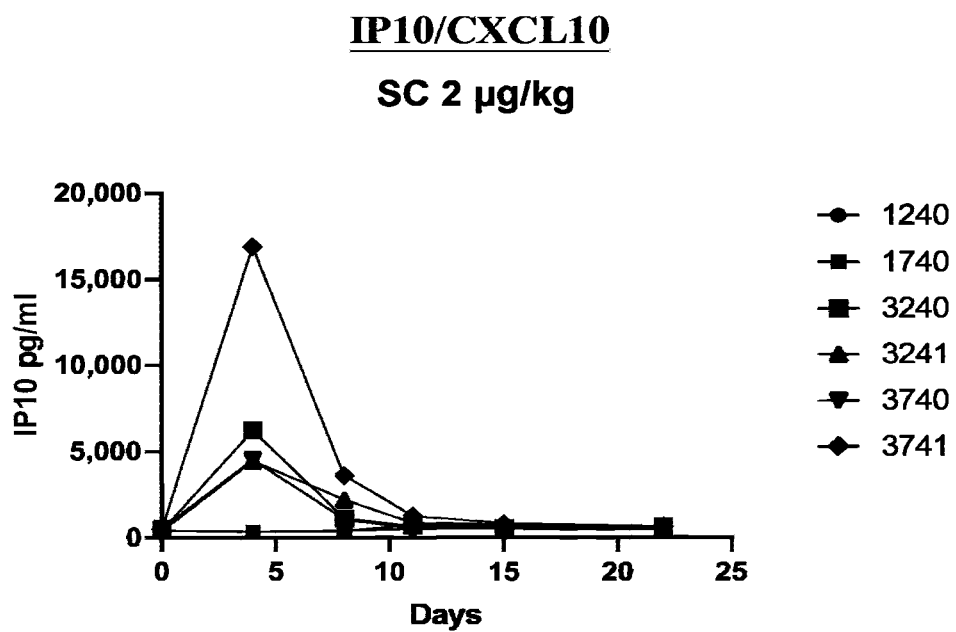
Figure 29E:
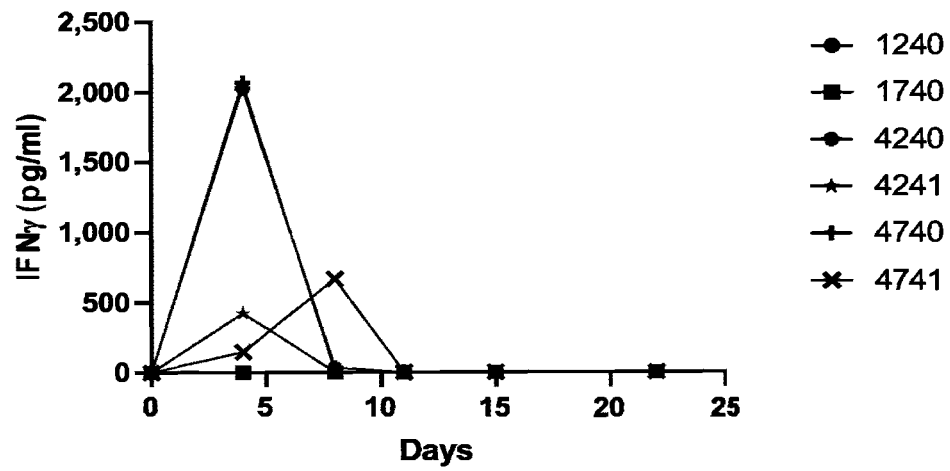
Figure 29F:
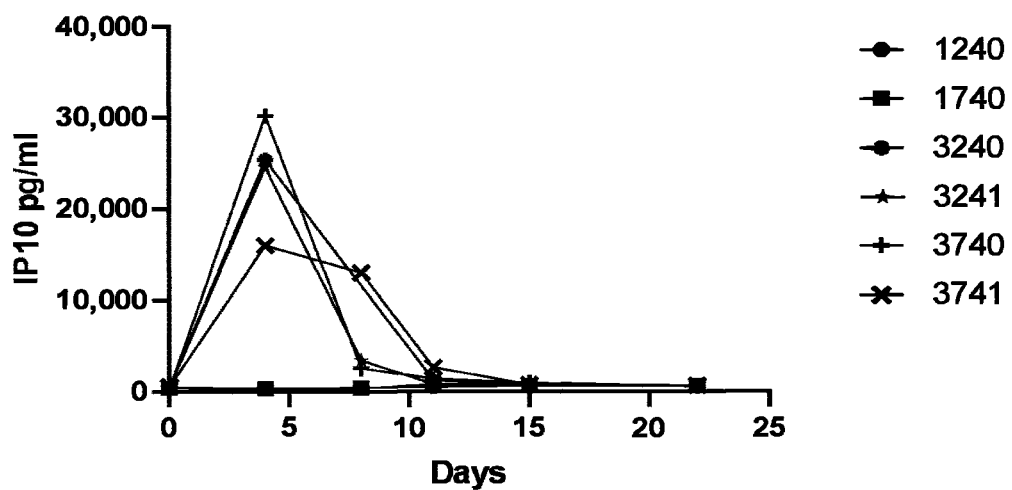

As shown in FIG. 29A, a single subcutaneous dose of DF-hIL-12-Fc si at 1 µg/kg did not result in detectable levels of IFNγ. Subcutaneous doses of DF-hIL-12-Fc si at 2 µg/kg and 4 µg/kg, resulted in an increase in IFNγ levels in some animals that peaked at day 4 post-dosing (FIGS. 29C and 29E). Subcutaneous doses of DF-hIL-12-Fc si at 1 µg/kg, 2 µg/kg, and 4 µg/kg all resulted in elevated IP10/CXCL10 levels that peaked at day 4 post-dosing (FIGS. 29B, 29D, and 29F).

Figure 30:
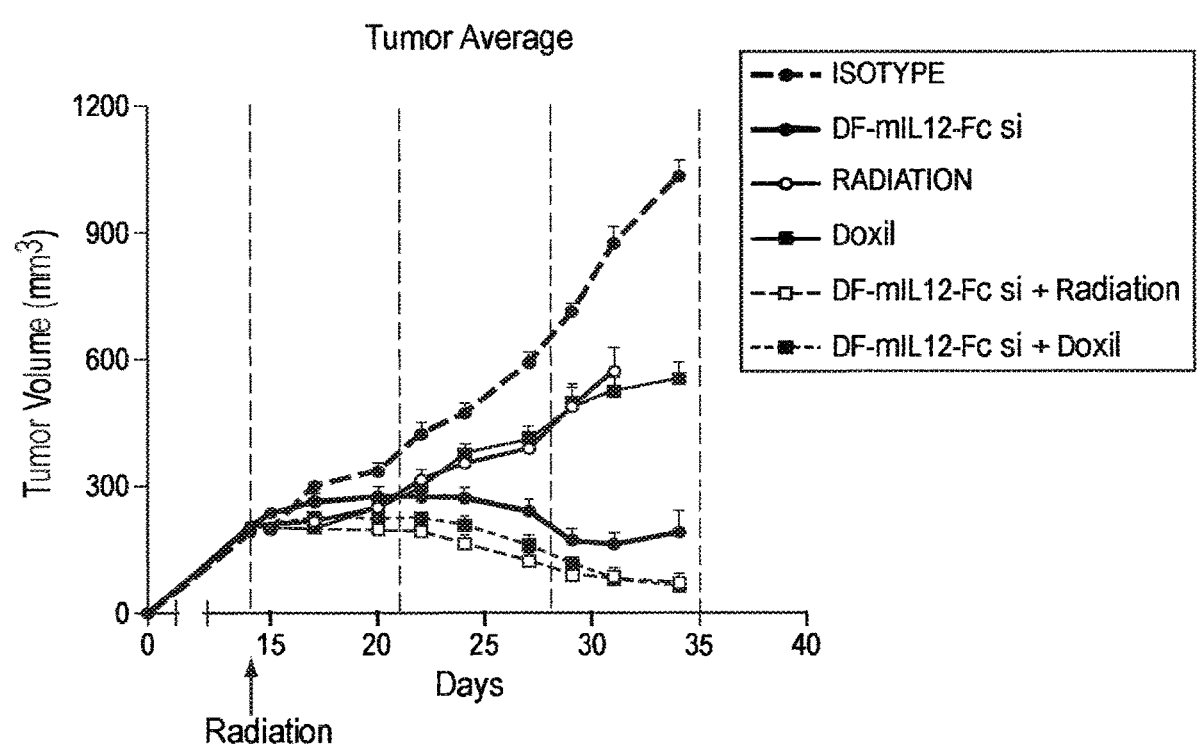
FIG. 30 is a graph showing tumor growth curves of individual mice inoculated with breast cancer cells and administered a weekly dose of a monotherapy (isotype control, DF-mIL-12-Fc si, Doxil® (chemotherapy), or irradiated with 10 Gy) or combination therapy (DF-mIL-12-Fc si in combination with Doxil® or radiation).

Example 16—DF-mIL-12-Fc Si Combination Therapy Using Radiation or Chemotherapy in 4T1 Orthotopic Mouse Model In order to show whether anti-tumor activity elicited by administration of DF-mIL-12-Fc si can be amplified, combination studies using radiation or chemotherapy were performed. Briefly, Balb/c mice were injected orthotopically into the mammary fat pad with 5×10⁵ 4T1-luc tumor cells. On Day 14 after tumor inoculation, mice were randomized (n=10 per group). Mice were treated subcutaneously with either isotype, DF-mIL-12-Fc si (both equimolar to 1 µg IL-12), 5 mg/kg Doxil® (chemotherapy) intravenously, or irradiated with 10 Gy as monotherapy, or DF-mIL-12-Fc si in combination with Doxil® or radiation. Tumor growth was assessed over time. FIG. 30 is a graph showing tumor growth curves of individual mice inoculated with breast cancer cells and administered a weekly dose of isotype control, DF-mIL-12-Fc si, Doxil (chemotherapy), or irradiated with 10 Gy as monotherapy or DF-mIL-12-Fc si in combination with Doxil® or radiation. Graph shows group averages of tumor growth±standard error mean.

As seen in FIG. 30, although monotherapy with DF-mIL-12-Fc si was effective by itself in 4T1 tumor-bearing mice, combination therapy amplified anti-tumor immune responses leading to full tumor regression in 10-30% of mice.

Figure 31A:
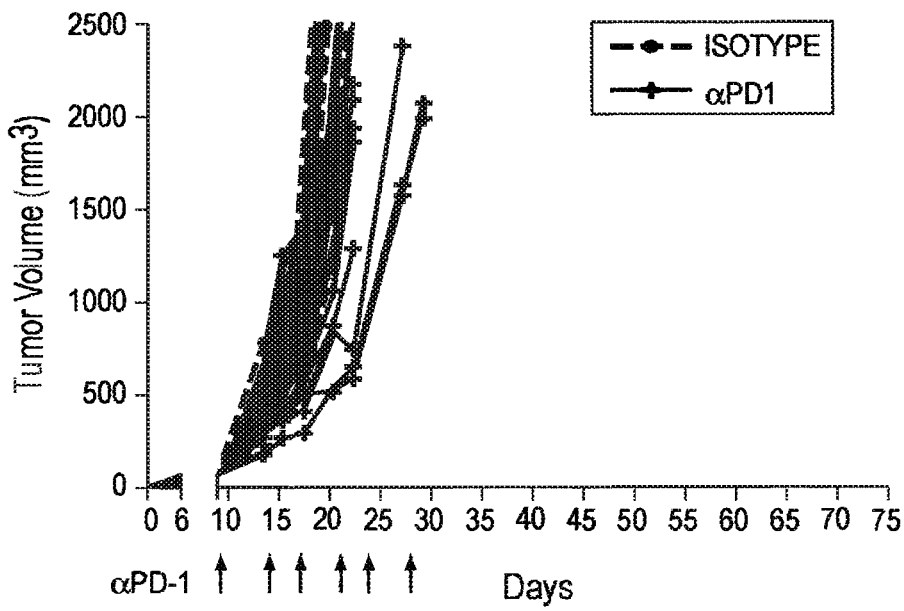
FIG. 31A is a graph showing tumor growth curves of individual mice inoculated with CT26-Tyrp1 tumor cells and treated (bi-weekly) either with isotype control or anti-PD-1 antibody.
Figure 31B:
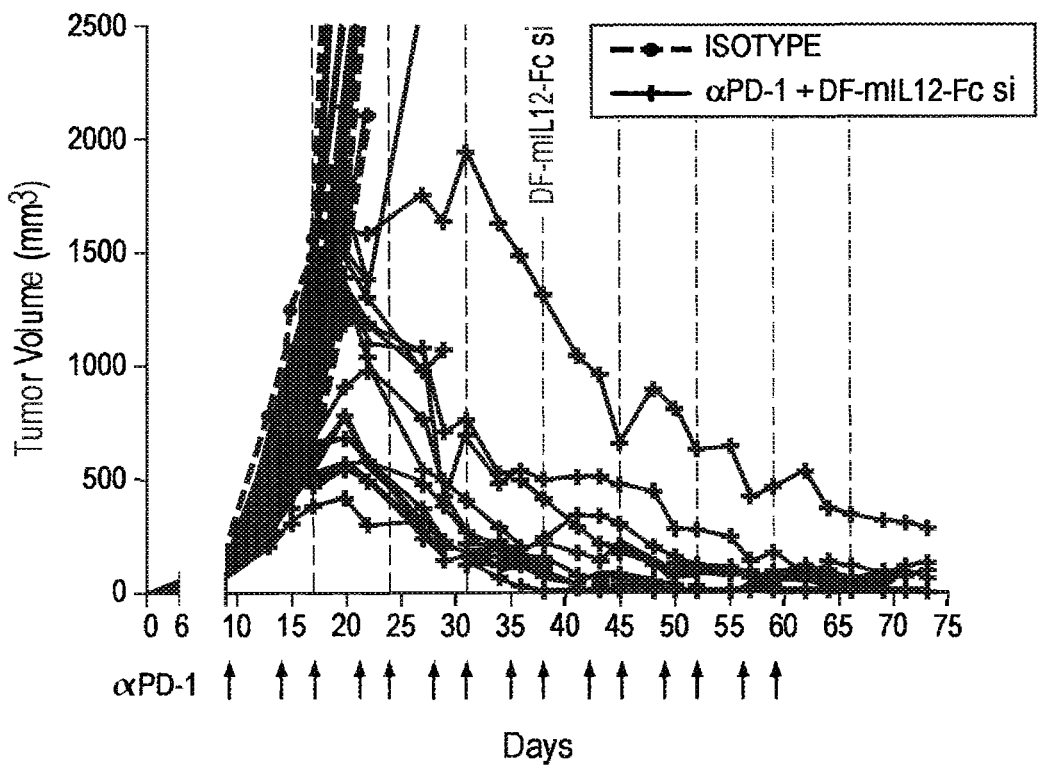
FIG. 31B is a graph showing tumor growth curve of Balb/c mice inoculated with CT26-Tyrp1 tumor cells and treated (bi-weekly) either with isotype control or anti-PD-1 antibody.

Example 17—DF-mIL-12-Fc Si Mediated Anti-Tumor Efficacy Against Large, PD-1 Blockade-Resistant CT26 Colon Carcinoma Tumors This example analyzes whether DF-mIL-12-Fc si elicited potent, anti-tumor responses against PD-1 blockade-resistant CT26-Tyrp1 tumors. Briefly, Balb/c mice were injected with 0.5×10⁶ CT26-Tyrp1 tumor cells. Following inoculation when average tumor volume reached ~120 mm³, mice were randomized on Day 9. Mice were either treated with 200 µg isotype or anti-PD-1 antibody (twice weekly). FIG. 31A is a graph showing tumor growth curve of Balb/c mice inoculated with CT26-Tyrp1 tumor cells and treated (bi-weekly) either with isotype control or anti-PD-1 antibody. On day 17, the group previously treated with anti-PD-1 (with an average tumor volume ~800 mm³) was subdivided into two treatment groups. Group 1 continued to receive PD-1 blockade treatment twice weekly, Group 2 received PD-1 blockade (twice weekly) along with DF-mIL-12-Fc si (1 µg weekly). FIG. 31B is a graph showing tumor growth curve of the previously anti-PD-1 antibody-treated Balb/c mice treated with anti-PD-1 antibody (bi-weekly) along with weekly treatment with 1 µg of DF-mIL-12-Fc si.

As shown in FIG. 31A, anti-PD-1 monotherapy failed to control tumor progression. However, as shown in FIG. 31B, the addition of DF-mIL-12-Fc si resulted in effective tumor regression.

Figure 32A:
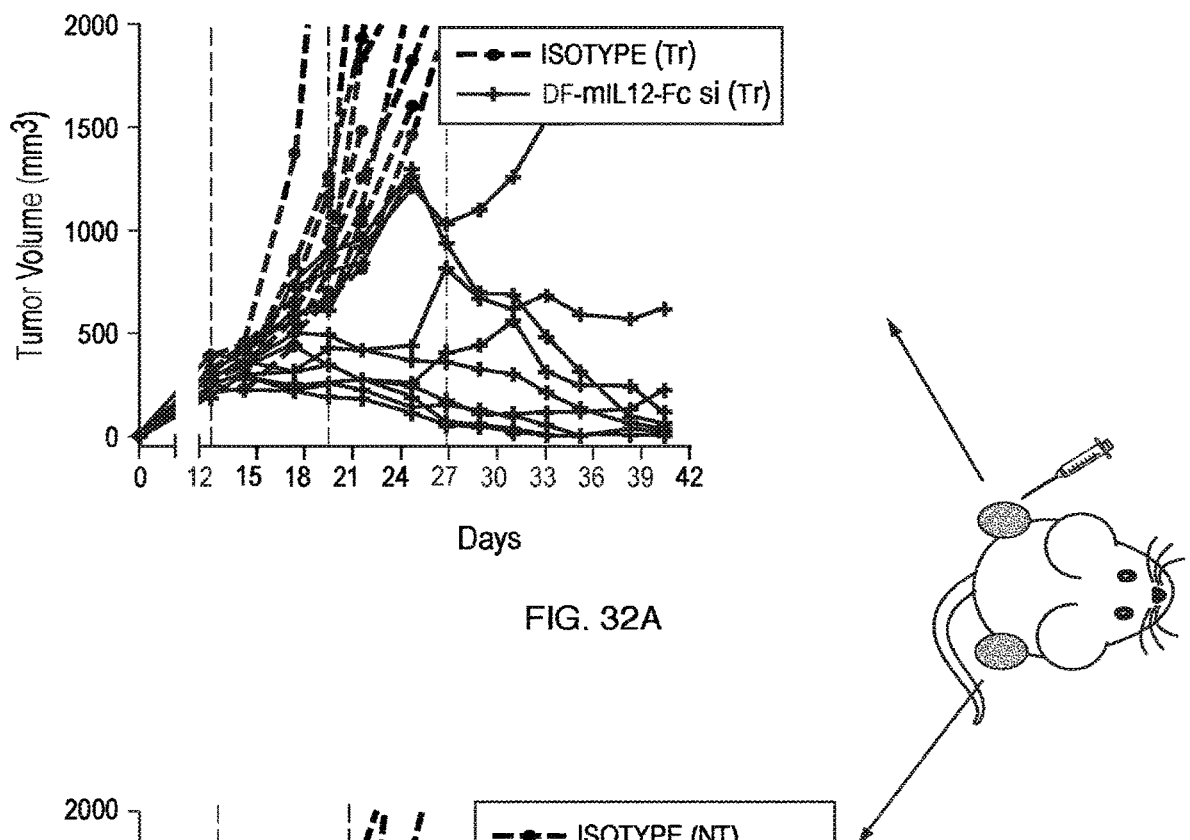
FIG. 32A is a graph showing tumor growth curves of treated (Tr) tumors in individual mice inoculated with CT26-Tyrp1 tumor cells and intratumorally treated once (weekly) with either isotype control or DF-mIL-12-Fc si.

Example 18—Local Treatment of DF-mIL-12-Fc Si Against Large CT26 Colon Carcinoma Tumors Induces Abscopal Anti-Tumor Responses This example shows whether DF-mIL-12-Fc si treatment can induce abscopal therapeutic effects. Briefly, Balb/c were implanted subcutaneously with CT26-Tyrp1 colon carcinoma cells on both the left (0.8×10⁶ tumor cells) and right (0.4×10⁶ tumor cells) flank. On Day 13 after tumor inoculation, left tumors were injected either with 0.1 µg isotype control or 0.1 µg DF-mIL-12-Fc si once weekly for 2-3 weeks. FIG. 32A is a graph showing tumor growth curve of the treated (Tr) tumor in Balb/c mice inoculated with CT26-Tyrp1 tumor cells and treated once (weekly) with either isotype control or DF-mIL-12-Fc si. Right tumors were left untreated (NT).

Figure 32B:
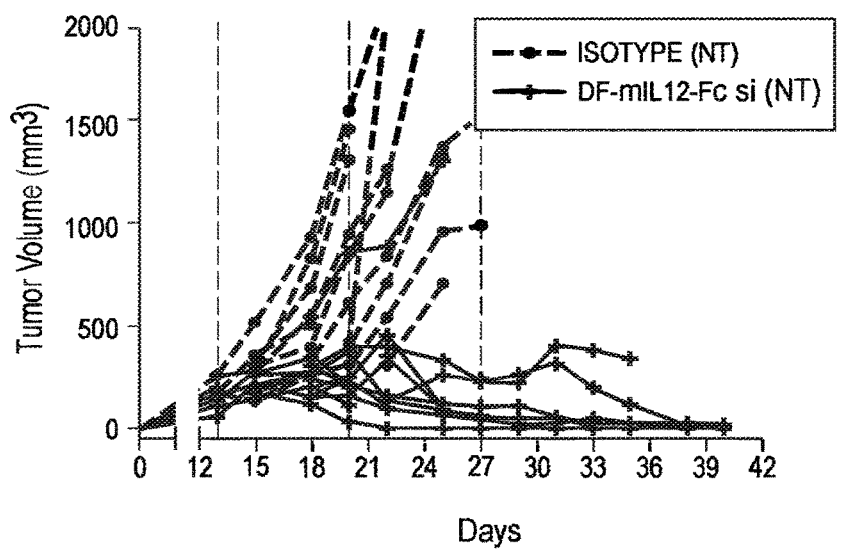
FIG. 32B is a graph showing tumor growth curves of non-treated (NT) CT26-Tyrp1 tumors in the individual mice described in FIG. 32A.

FIG. 32B is a graph showing tumor growth curves of the untreated (NT) tumors in Balb/c mice inoculated with CT26-Tyrp1 tumor cells.

As shown in FIGS. 32A-32B, control isotype-treated tumors grew progressively at both right and left sites. As shown in FIGS. 32A-32B, DF-mIL-12-Fc si caused effective anti-tumor responses at the local injected site (FIG. 32A) and the distant non-treated tumor (FIG. 32B) indicating abscopal therapeutic effects.

Example 19—DF-mIL-12-Fc Si Mediated Anti-Tumor Efficacy Against Large CT26 Colon Carcinoma Tumors This example shows that DF-mIL-12-Fc si which includes wild-type murine IL-12 p40 and p35 subunits fused to the N-termini of murine IgG2a Fc domain polypeptides with mutations L234A, L235A, and P329G (discussed in Example 2) is efficacious against larger tumor volumes.

DF-mIL-12-Fc si-mediated anti-tumor efficacy against large CT26 colon carcinoma tumors was tested. Briefly, Balb/c mice were injected subcutaneously with 10⁶ CT26-Tyrp1 colon carcinoma cells. On Day 18 after tumor inoculation, when tumor volume reached 800 mm³, the mice were randomized into different treatment groups (n=10 per group) and treated intraperitoneally with DF-mIL-12-Fc si at a molar dose equivalent to 1 µg or 2 µg IL-12, or molar equivalent of mIgG2a isotype once or once weekly.

Figure 26A:
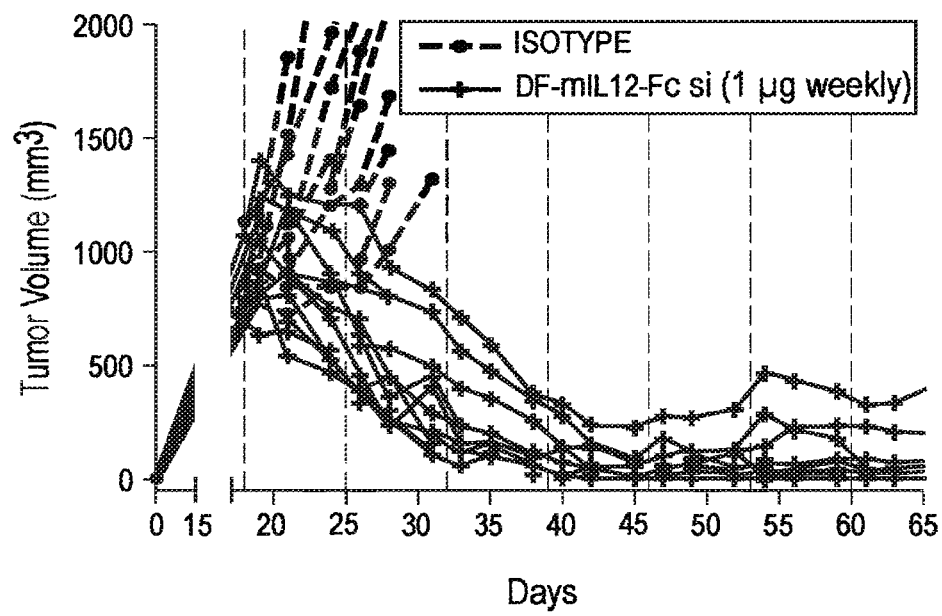
FIGS. 26A-26B are graphs showing tumor growth curves of individual mice inoculated with CT26 tumor cells and administered a once weekly dose of DF-mIL-12-Fc si subcutaneously.
Figure 26B:
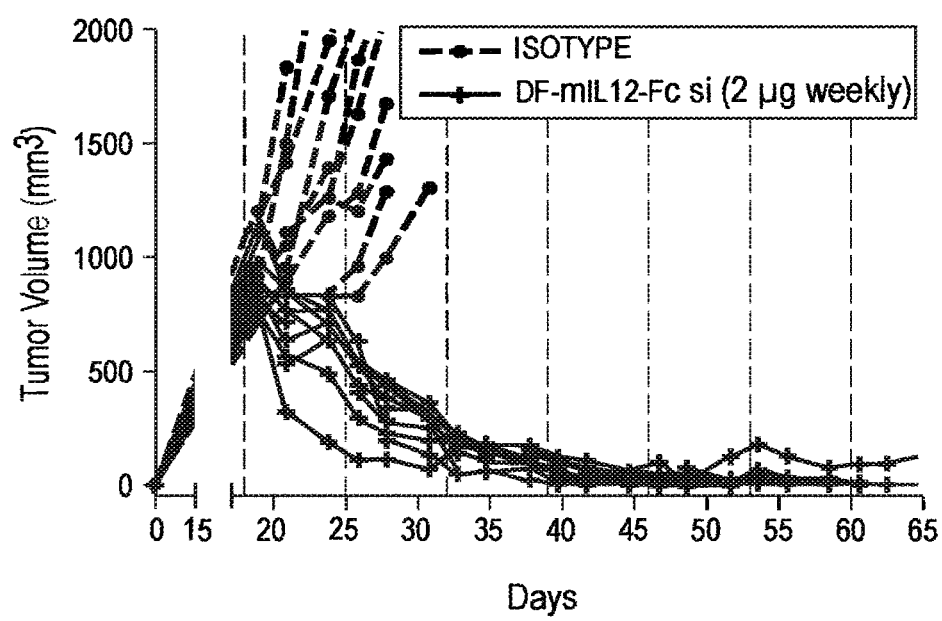
Figure 33A:
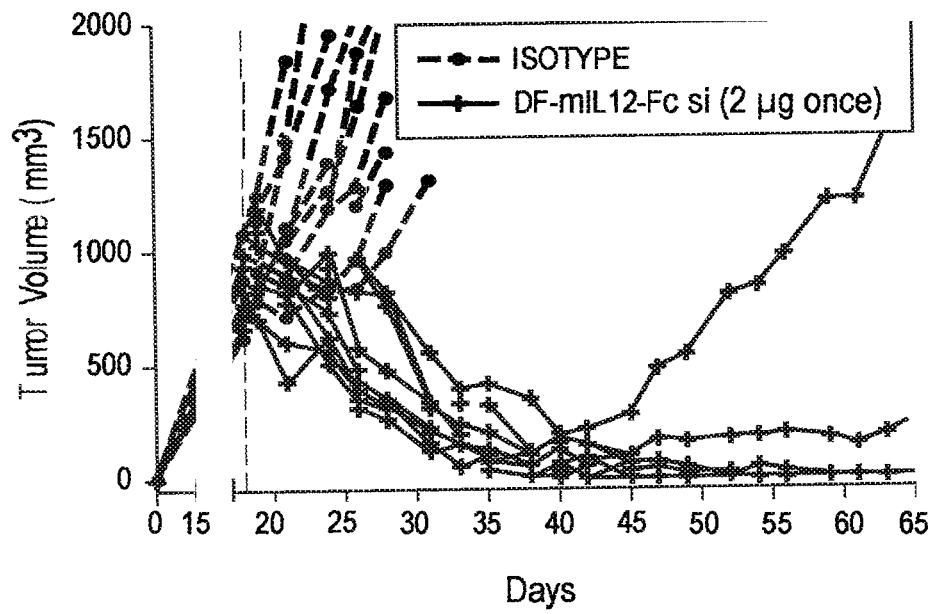
FIG. 33A is a graph showing tumor growth curves of individual mice inoculated with CT26-Tyrp1 tumor cells and treated once with either 2 µg mIgG2a isotype control or 2 µg DF-mIL-12-Fc si.
Figure 33B:
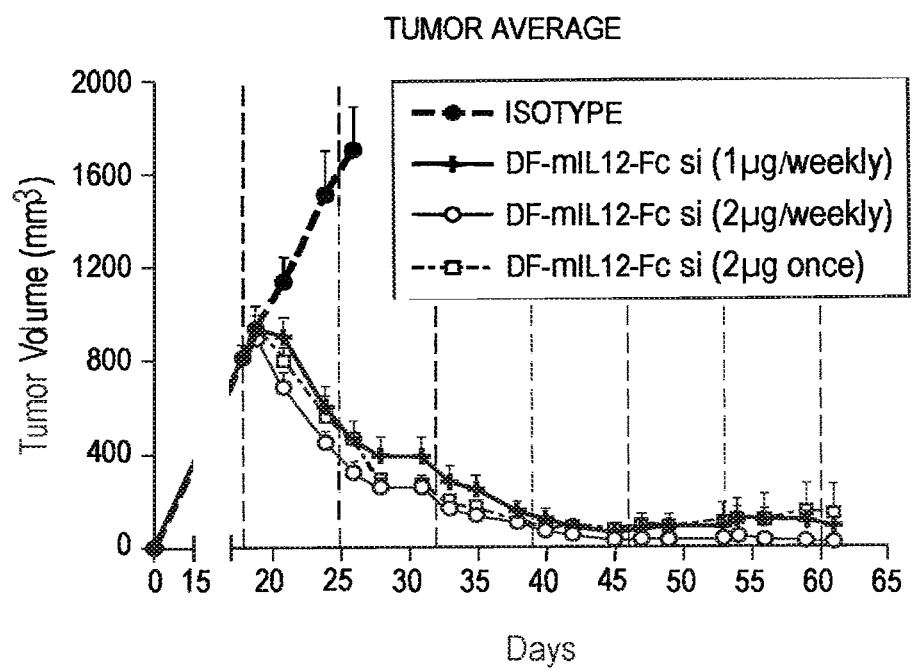
FIG. 33B is a graph showing average tumor growth curves of individual mice inoculated with CT26-Tyrp1 tumor cells and treated with 2 µg mIgG2a isotype control, 1 µg DF-mIL-12-Fc si (weekly administration), 2 µg DF-mIL-12-Fc si (weekly administration), or 2 µg DF-mIL-12-Fc si (once)

Tumor growth was assessed for 65 days. FIG. 26A is a graph showing tumor growth curves of Balb/c mice inoculated with CT26-Tyrp1 tumor cells and treated once (weekly) with either 2 µg mIgG2a isotype control or 1 µg DF-mIL-12-Fc si. FIG. 26B is a graph showing tumor growth curves of Balb/c mice inoculated with CT26-Tyrp1 tumor cells and treated once (weekly) with either 2 µg mIgG2a isotype control or 2 µg DF-mIL-12-Fc si. FIG. 33A is a graph showing tumor growth curves of Balb/c mice inoculated with CT26-Tyrp1 tumor cells and treated once with either 2 µg mIgG2a isotype control or 2 µg DF-mIL-12-Fc si. FIG. 33B is a graph showing average tumor growth curves of Balb/c mice inoculated with CT26-Tyrp1 tumor cells and treated with 2 µg mIgG2a isotype control, 1 µg DF-mIL-12-Fc si (weekly administration), 2 µg DF-mIL-12-Fc si (weekly administration), or 2 µg DF-mIL-12-Fc si (once). FIGS. 26A, 26B, and 33A show tumor growth curves of individual mice. FIG. 33B shows tumor average±standard error mean.

As shown in FIGS. 26A, 26B, and 33B, weekly doses (1 µg or 2 µg) of DF-mIL-12-Fc si were efficient in controlling tumor progression and 100% of mice responded to DF-mIL-12-Fc si treatment. Additionally, as shown in FIG. 33A, a single treatment with 2 µg DF-mIL-12-Fc si showed tumor regression yielding a 100% response rate. The data and figures described in this example show that DF-mIL-12-Fc si is not only effective at reducing larger CT26 tumor volume but also effective at reducing CT26 tumor volume when administered as a single dose.

Example 20—DF-mIL-12-Fc Si Treatment Against B16F10 Melanomas Induces Production of Cytokines and Chemokines in Serum and in Tumors This example shows that DF-mIL-12-Fc si treatment results in elevated levels of IFNγ, CXCL9, and CXCL10 in blood and tumors of C57BL/6 mice bearing B16F10 tumors. Briefly, C57BL/6 mice were injected subcutaneously with 10⁶ B16F10 melanoma cells. On Day 7 after tumor inoculation (when average tumor volume reached 150 mm³), mice were randomized (n=8 per group). Mice were treated intraperitoneally with isotype control, IL-12, or DF-mIL-12-Fc equimolar to 1 µg IL-12.

Figure 34A:
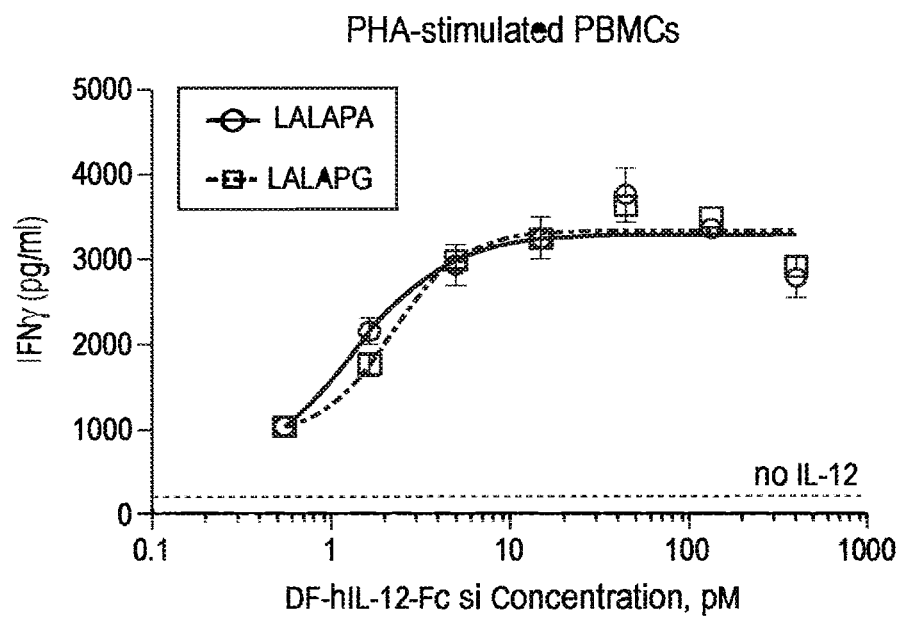
FIG. 34A is a graph showing IFNγ production of PHA-stimulated PBMCs treated with DF hIL-12-Fc-si having L234A, L235A, and P329A mutations (LALAPA), or L234A, L235A, P329G mutations (LALAPG).
Figure 34B:
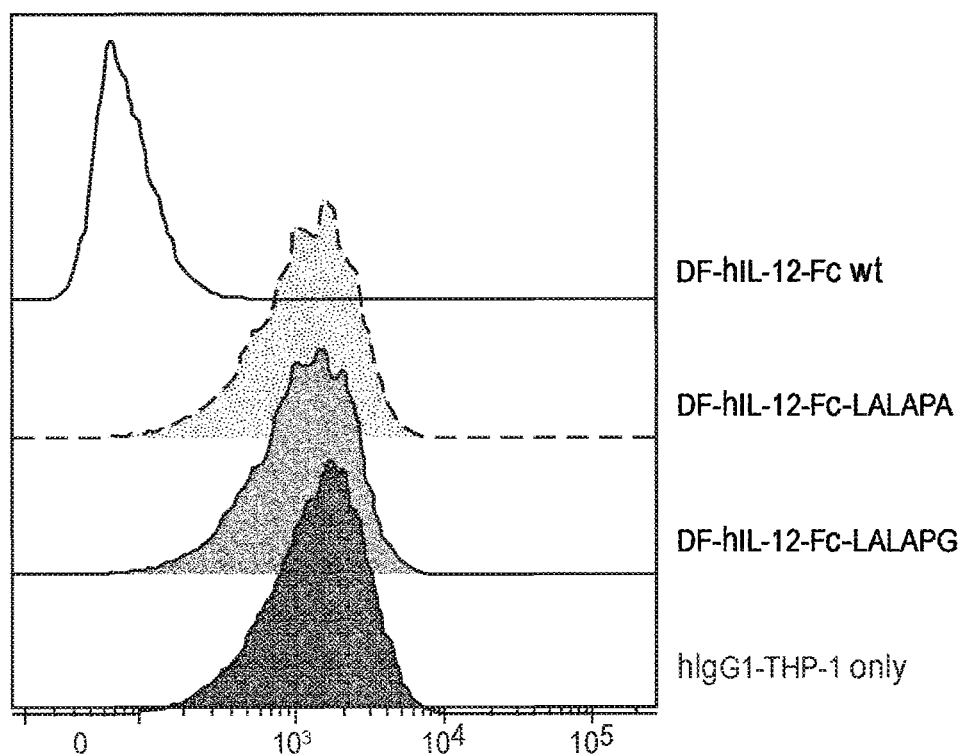
FIG. 34B shows flow cytometry histograms of fluorophore-conjugated hIgG1 binding to THP-1 cells in the presence or absence of DF hIL-12-Fc-si having LALAPA mutations, or LALAPG mutations.

After 72 hours post-treatment, serum and tumor lysates were prepared and analyzed for IFNγ (FIG. 27A), CXCL9 (FIG. 27B), and CXCL10 (FIG. 27C) expression using multiplex technology. FIGS. 34A-C show average cytokine/chemokine levels in mice.

Figure 27A:
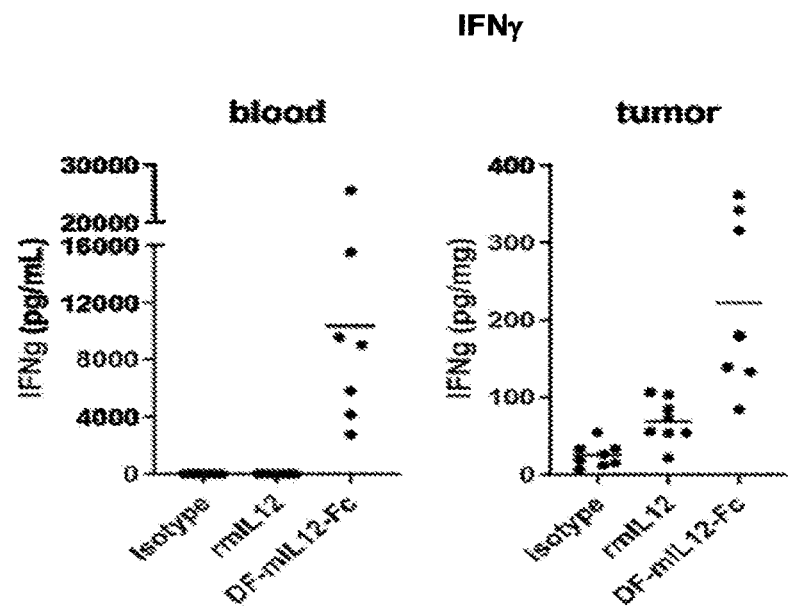
FIGS. 27A-27C are graphs showing IFNγ (FIG. 27A), CXCL9 (FIG. 27B), and CXCL10 (FIG. 27C) levels in blood (left) and tumor (right) samples at 72 hours following a single dose of DF-mIL-12-Fc si in C57BL/6 mice bearing B16F10 tumors.
Figure 27B:
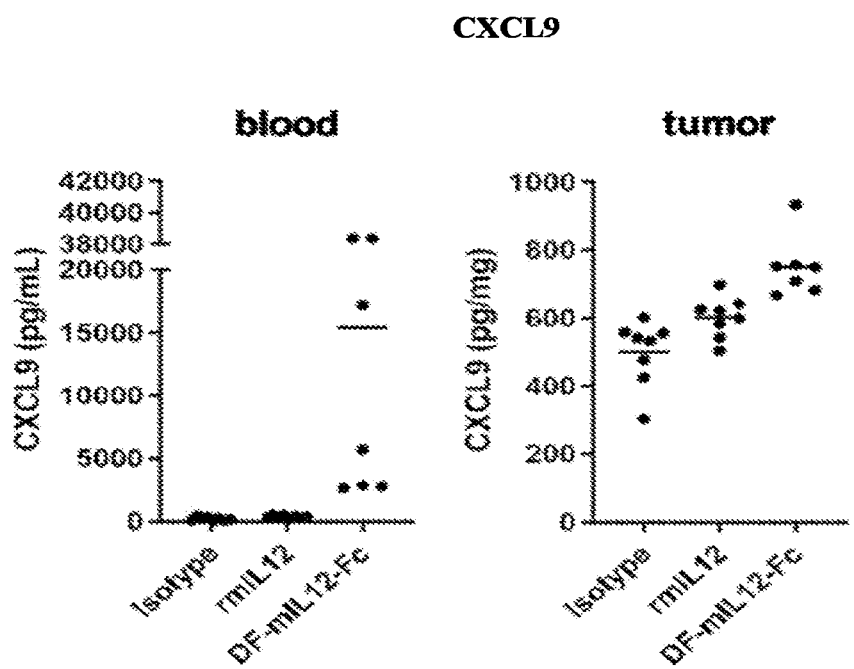
Figure 27C:
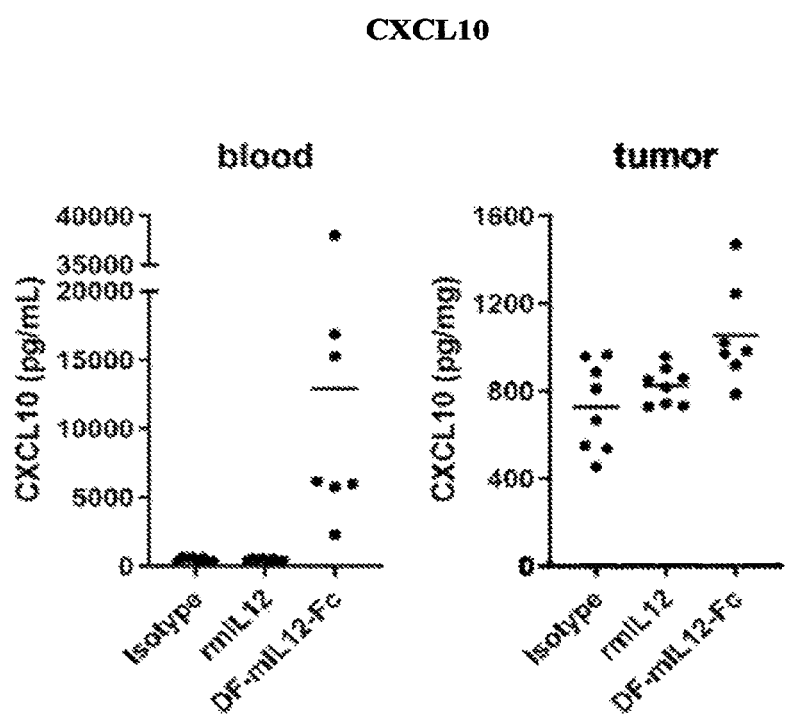

As shown in FIGS. 27A-27C, a single administration of 0.5 µg of DF-mIL-12-Fc si resulted in increased expression of IFNγ (FIG. 27A), CXCL9 (FIG. 27B), and CXCL10 (FIG. 27C) in serum (left panel) and within tumors (right panel), whereas IL-12 treatment had little or no effect.

Example 21—DF hIL-12-Fc Si Having LALAPA and LALAPG Mutations have Similar IFNγ-Stimulating Activity and Abrogated FcγR Binding This example shows the IFNγ-stimulating and FcγR-binding activities of DF hIL-12-Fc si with IgG1 Fc having LALAPA (L234A, L235A, and P329A) mutations, or LALAPG (L234A, L235A, and P329G) mutations. In brief, human PBMCs were cultured for 2 days with both 5 µg/ml phytohemagglutinin (PHA) and a dose-titration of DF hIL-12-Fc-si, having LALAPA or LALAPG mutations. After 2-day stimulation, supernatants were harvested and IFNγ content measured by ELISA. For determining FcγR-binding activities, fluorophore-conjugated hIgG1 isotype antibody (83 nM) bound to THP-1 cells that express high affinity FcγRs CD32 and CD64 was detected by flow cytometry.

As shown in FIG. 34A, hIL-12-Fc-LALAPA and hIL-12-Fc-LALAPG have similar abilities to stimulate IFNγ production from PBMCs concurrently with PHA, well above the amount produced with PHA alone.

As shown in FIG. 34B, Simultaneous inclusion of 16-fold molar excess of hIL-12-Fc-wt (1.3 µM) in a mixture with the labeled hIgG1 isotype antibody resulted in substantial reduction of binding signal, likely due to competition for IgG1 binding to CD32 and CD64. In contrast, at the same concentration, neither incubation with hIL-12-Fc-LALAPA nor hIL-12-Fc-LALAPG resulted in detectable IgG1 isotype binding, suggesting abrogated FcγR engagement for both proteins attributable to the LALAPA and LALAPG mutations.

NUMBERED EMBODIMENTS

Embodiments disclosed herein include embodiments P1 to P121 as provided in the numbered embodiments of the disclosure.

Embodiment P1: A heterodimeric Fc-fused protein comprising:
- a first polypeptide comprising a first antibody Fc sequence and a second polypeptide comprising a second, different antibody Fc sequence,
- wherein the first polypeptide further comprises a protein sequence of a subunit of a multisubunit protein,
- wherein the protein sequence is fused by a linker comprising amino acid sequence RVESKYGPPCPPCPAPEFXGG (SEQ ID NO:1) to the first antibody Fc sequence, wherein X represents L or E; and
- an additional subunit of the multisubunit protein is fused to the second, different antibody Fc sequence, and the subunits of the multisubunit protein are bound to each other,
- wherein the first antibody Fc sequence and the second, different antibody Fc sequence each comprise different mutations promoting heterodimerization,
- wherein the first antibody Fc sequence and the second, different antibody Fc sequence are bound to each other.

Embodiment P2: The heterodimeric Fc-fused protein of embodiment P1, wherein the linker comprises amino acid sequence RVESKYGPPCPPCPAPEFLGG (SEQ ID NO:2).

Embodiment P3: The heterodimeric Fc-fused protein of embodiment P2, wherein the additional subunit of the multisubunit protein is fused to the second, different antibody Fc sequence by a linker comprising amino acid sequence (SEQ ID NO: 3)
GGGGSGGGGSGGGGSRVESKYGPPCPPCPAPEFLGG.

Embodiment P4: The heterodimeric Fc-fused protein of embodiment P3, wherein the additional subunit of the multisubunit protein is fused to the second, different antibody Fc sequence by a linker consisting of amino acid sequence (SEQ ID NO: 3)
GGGGSGGGGSGGGGSRVESKYGPPCPPCPAPEFLGG.

Embodiment P5: The heterodimeric Fc-fused protein of embodiment P2, wherein the additional subunit of the multisubunit protein is fused to the second, different antibody Fc sequence by a linker comprising amino acid sequence (SEQ ID NO: 13)
GGGGSRVESKYGPPCPPCPAPEFLGG.

Embodiment P6: The heterodimeric Fc-fused protein of embodiment P5, wherein the additional subunit of the multisubunit protein is fused to the second, different antibody Fc sequence by a linker consisting of amino acid sequence (SEQ ID NO: 13)
GGGGSRVESKYGPPCPPCPAPEFLGG.

Embodiment P7: The heterodimeric Fc-fused protein of embodiment P2, wherein the additional subunit of the multisubunit protein is fused to the second, different antibody Fc sequence by a linker comprising amino acid sequence (SEQ ID NO: 14)
GGGGSGGGGSRVESKYGPPCPPCPAPEFLGG.

Embodiment P8: The heterodimeric Fc-fused protein of embodiment P7, wherein the additional subunit of the multisubunit protein is fused to the second, different antibody Fc sequence by a linker consisting of amino acid sequence (SEQ ID NO: 14)
GGGGSGGGGSRVESKYGPPCPPCPAPEFLGG.

Embodiment P9: A heterodimeric Fc-fused protein according to any one of embodiments P2 to P8, wherein the linker fusing the protein sequence to the first antibody Fc sequence consists of amino acid sequence RVESKYGPPCPPCPAPEFLGG (SEQ ID NO:2).

Embodiment P10: The heterodimeric Fc-fused protein of embodiment P1, wherein the linker comprises amino acid sequence RVESKYGPPCPPCPAPEFEGG (SEQ ID NO:4).

Embodiment P11: The heterodimeric Fc-fused protein of embodiment P10, wherein the additional subunit of the multisubunit protein is fused to the second, different antibody Fc sequence by a linker comprising amino acid sequence (SEQ ID NO: 5)
GGGGSGGGGSGGGGSRVESKYGPPCPPCPAPEFEGG.

Embodiment P12: The heterodimeric Fc-fused protein of embodiment P11, wherein the additional subunit of the multisubunit protein is fused to the second, different antibody Fc sequence by a linker consisting of amino acid sequence (SEQ ID NO: 5)
GGGGSGGGGSGGGGSRVESKYGPPCPPCPAPEFEGG.

Embodiment P13: The heterodimeric Fc-fused protein of embodiment P10, wherein the additional subunit of the multisubunit protein is fused to the second, different antibody Fc sequence by a linker comprising amino acid sequence

```
                                         (SEQ ID NO: 63)
    GGGGSRVESKYGPPCPPCPAPEFEGG.
```

Embodiment P14: The heterodimeric Fc-fused protein of embodiment P13, wherein the additional subunit of the multisubunit protein is fused to the second, different antibody Fc sequence by a linker consisting of amino acid sequence

```
                                         (SEQ ID NO: 63)
    GGGGSRVESKYGPPCPPCPAPEFEGG.
```

Embodiment P15: The heterodimeric Fc-fused protein of embodiment P10, wherein the additional subunit of the multisubunit protein is fused to the second, different antibody Fc sequence by a linker comprising amino acid sequence

```
                                         (SEQ ID NO: 64)
    GGGGSGGGGSRVESKYGPPCPPCPAPEFEGG.
```

Embodiment P16: The heterodimeric Fc-fused protein of embodiment P15, wherein the additional subunit of the multisubunit protein is fused to the second, different antibody Fc sequence by a linker consisting of amino acid sequence

```
                                         (SEQ ID NO: 64)
    GGGGSGGGGSRVESKYGPPCPPCPAPEFEGG.
```

Embodiment P17: A heterodimeric Fc-fused protein according to any one of embodiments P10 to P16, wherein the linker fusing the protein sequence to the first antibody Fc sequence consists of amino acid sequence RVESKYGPPCPPCPAPEFEGG (SEQ ID NO:4).

Embodiment P18: A heterodimeric Fc-fused protein comprising:
- a first polypeptide comprising a first antibody Fc sequence and a second polypeptide comprising a second, different antibody Fc sequence,
- wherein the first polypeptide further comprises a protein sequence of a subunit of a multisubunit protein,
- wherein the protein sequence is fused by a linker comprising amino acid sequence EPKSSDKTHTCPPCPAPEX$_1$X$_2$GX$_3$ (SEQ ID NO:6) or PKSSDKTHTCPPCPAPEX$_1$X$_2$GX$_3$ (SEQ ID NO:237) to the first antibody Fc sequence, wherein X$_1$ represents L or A, X$_2$ represents L, E, or A, and X$_3$ represents A or G; and
- an additional subunit of the multisubunit protein is fused to the second, different antibody Fc sequence, and the subunits of the multisubunit protein are bound to each other, and
- wherein when the X$_1$ represents L and/or X$_2$ represents L, at least one of the first antibody Fc sequence, and the second, different antibody Fc sequence comprises a Q347R mutation for promoting heterodimerization, wherein the first antibody Fc sequence and the second, different antibody Fc sequence are bound to each other.

Embodiment P19: The heterodimeric Fc-fused protein of embodiment P18, wherein the linker comprises amino acid sequence EPKSSDKTHTCPPCPAPELLGG (SEQ ID NO:7) or PKSSDKTHTCPPCPAPELLGG (SEQ ID NO:238).

Embodiment P20: The heterodimeric Fc-fused protein of embodiment P19, wherein the additional subunit of the multisubunit protein is fused to the second, different antibody Fc sequence by a linker comprising amino acid sequence

```
                                         (SEQ ID NO: 8)
    GGGGSGGGGSGGGGSEPKSSDKTHTCPPCPAPELLGG
or
                                         (SEQ ID NO: 241)
    GGGGSGGGGSGGGGSPKSSDKTHTCPPCPAPELLGG.
```

Embodiment P21: The heterodimeric Fc-fused protein of embodiment P20, wherein the additional subunit of the multisubunit protein is fused to the second, different antibody Fc sequence by a linker consisting of amino acid sequence

```
                                         (SEQ ID NO: 8)
    GGGGSGGGGSGGGGSEPKSSDKTHTCPPCPAPELLGG
or
                                         (SEQ ID NO: 241)
    GGGGSGGGGSGGGGSPKSSDKTHTCPPCPAPELLGG.
```

Embodiment P22: The heterodimeric Fc-fused protein of embodiment P19, wherein the additional subunit of the multisubunit protein is fused to the second, different antibody Fc sequence by a linker comprising amino acid sequence

```
                                         (SEQ ID NO: 15)
    GGGGSEPKSSDKTHTCPPCPAPELLGG
or
                                         (SEQ ID NO: 242)
    GGGGSPKSSDKTHTCPPCPAPELLGG.
```

Embodiment P23: The heterodimeric Fc-fused protein of embodiment P22, wherein the additional subunit of the multisubunit protein is fused to the second, different antibody Fc sequence by a linker consisting of amino acid sequence

```
                                         (SEQ ID NO: 15)
    GGGGSEPKSSDKTHTCPPCPAPELLGG
or
                                         (SEQ ID NO: 242)
    GGGGSPKSSDKTHTCPPCPAPELLGG.
```

Embodiment P24: The heterodimeric Fc-fused protein of embodiment P19, wherein the additional subunit of the multisubunit protein is fused to the second, different antibody Fc sequence by a linker comprising amino acid sequence

```
                                        (SEQ ID NO: 16)
    GGGGSGGGGSEPKSSDKTHTCPPCPAPELLGG
or
                                       (SEQ ID NO: 243)
    GGGGSGGGGSPKSSDKTHTCPPCPAPELLGG.
```

Embodiment P25: The heterodimeric Fc-fused protein of embodiment P24, wherein the additional subunit of the multisubunit protein is fused to the second, different antibody Fc sequence by a linker consisting of amino acid sequence

```
                                        (SEQ ID NO: 16)
    GGGGSGGGGSEPKSSDKTHTCPPCPAPELLGG
or
                                       (SEQ ID NO: 243)
    GGGGSGGGGSPKSSDKTHTCPPCPAPELLGG.
```

Embodiment P26: A heterodimeric Fc-fused protein according to any one of embodiments P19 to P25, wherein the linker fusing the protein sequence to the first antibody Fc sequence consists of amino acid sequence EPKSSDKTHTCPPCPAPELLGG (SEQ ID NO:7) or PKSSDKTHTCPPCPAPELLGG (SEQ ID NO:238).

Embodiment P27: The heterodimeric Fc-fused protein of embodiment P18, wherein the linker comprises amino acid sequence EPKSSDKTHTCPPCPAPEAAGG (SEQ ID NO:9) or PKSSDKTHTCPPCPAPEAAGG (SEQ ID NO:239).

Embodiment P28: The heterodimeric Fc-fused protein of embodiment P27, wherein the additional subunit of the multisubunit protein is fused to the second, different antibody Fc sequence by a linker comprising amino acid sequence

```
                                        (SEQ ID NO: 10)
    GGGGSGGGGSGGGGSEPKSSDKTHTCPPCPAPEAAGG
or
                                       (SEQ ID NO: 244)
    GGGGSGGGGSGGGGSPKSSDKTHTCPPCPAPEAAGG.
```

Embodiment P29: The heterodimeric Fc-fused protein of embodiment P28, wherein the additional subunit of the multisubunit protein is fused to the second, different antibody Fc sequence by a linker consisting of amino acid sequence

```
                                        (SEQ ID NO: 10)
    GGGGSGGGGSGGGGSEPKSSDKTHTCPPCPAPEAAGG
or
                                       (SEQ ID NO: 244)
    GGGGSGGGGSGGGGSPKSSDKTHTCPPCPAPEAAGG.
```

Embodiment P30: The heterodimeric Fc-fused protein of embodiment P27, wherein the additional subunit of the multisubunit protein is fused to the second, different antibody Fc sequence by a linker comprising amino acid sequence

```
                                        (SEQ ID NO: 65)
    GGGGSEPKSSDKTHTCPPCPAPEAAGG
or
                                       (SEQ ID NO: 245)
    GGGGSPKSSDKTHTCPPCPAPEAAGG.
```

Embodiment P31: The heterodimeric Fc-fused protein of embodiment P30, wherein the additional subunit of the multisubunit protein is fused to the second, different antibody Fc sequence by a linker consisting of amino acid sequence

```
                                        (SEQ ID NO: 65)
    GGGGSEPKSSDKTHTCPPCPAPEAAGG
or
                                       (SEQ ID NO: 245)
    GGGGSPKSSDKTHTCPPCPAPEAAGG.
```

Embodiment P32: The heterodimeric Fc-fused protein of embodiment P27, wherein the additional subunit of the multisubunit protein is fused to the second, different antibody Fc sequence by a linker comprising amino acid sequence

```
                                        (SEQ ID NO: 66)
    GGGGSGGGGSEPKSSDKTHTCPPCPAPEAAGG
or
                                       (SEQ ID NO: 246)
    GGGGSGGGGSPKSSDKTHTCPPCPAPEAAGG.
```

Embodiment P33: The heterodimeric Fc-fused protein of embodiment P32, wherein the additional subunit of the multisubunit protein is fused to the second, different antibody Fc sequence by a linker consisting of amino acid sequence

```
                                        (SEQ ID NO: 66)
    GGGGSGGGGSEPKSSDKTHTCPPCPAPEAAGG
or
                                       (SEQ ID NO: 246)
    GGGGSGGGGSPKSSDKTHTCPPCPAPEAAGG.
```

Embodiment P34: A heterodimeric Fc-fused protein according to any one of embodiments P27 to P33, wherein the linker fusing the protein sequence to the first antibody Fc sequence consists of amino acid sequence EPKSSDKTHTCPPCPAPEAAGG (SEQ ID NO:9) or PKSSDKTHTCPPCPAPEAAGG (SEQ ID NO:239).

Embodiment P35: The heterodimeric Fc-fused protein of embodiment P18, wherein the linker comprises amino acid sequence EPKSSDKTHTCPPCPAPEAEGA (SEQ ID NO:11) or PKSSDKTHTCPPCPAPEAEGA (SEQ ID NO:240).

Embodiment P36: The heterodimeric Fc-fused protein of embodiment P35, wherein the additional subunit of the multisubunit protein is fused to the second, different antibody Fc sequence by a linker comprising amino acid sequence GGGGSGGGGSGGGGSEPKSSDKTHTCPPCPAPEAEGA (SEQ ID NO: 12)
or
GGGGSGGGGSGGGGSPKSSDKTHTCPPCPAPEAEGA (SEQ ID NO: 247).

Embodiment P37: The heterodimeric Fc-fused protein of embodiment P36, wherein the additional subunit of the multisubunit protein is fused to the second, different antibody Fc sequence by a linker consisting of amino acid sequence GGGGSGGGGSGGGGSEPKSSDKTHTCPPCPAPEAEGA (SEQ ID NO: 12)
or
GGGGSGGGGSGGGGSPKSSDKTHTCPPCPAPEAEGA (SEQ ID NO: 247).

Embodiment P38: The heterodimeric Fc-fused protein of embodiment P35, wherein the additional subunit of the multisubunit protein is fused to the second, different antibody Fc sequence by a linker comprising amino acid sequence GGGGSEPKSSDKTHTCPPCPAPEAEGA (SEQ ID NO: 67)
or
GGGGSPKSSDKTHTCPPCPAPEAEGA (SEQ ID NO: 248).

Embodiment P39: The heterodimeric Fc-fused protein of embodiment P38, wherein the additional subunit of the multisubunit protein is fused to the second, different antibody Fc sequence by a linker consisting of amino acid sequence GGGGSEPKSSDKTHTCPPCPAPEAEGA (SEQ ID NO: 67)
or
GGGGSPKSSDKTHTCPPCPAPEAEGA (SEQ ID NO: 248).

Embodiment P40: The heterodimeric Fc-fused protein of embodiment P35, wherein the additional subunit of the multisubunit protein is fused to the second, different antibody Fc sequence by a linker comprising amino acid sequence GGGGSGGGGSEPKSSDKTHTCPPCPAPEAEGA (SEQ ID NO: 68)
or
GGGGSGGGGSPKSSDKTHTCPPCPAPEAEGA (SEQ ID NO: 249).

Embodiment P41: The heterodimeric Fc-fused protein of embodiment P40, wherein the additional subunit of the multisubunit protein is fused to the second, different antibody Fc sequence by a linker consisting of amino acid sequence GGGGSGGGGSEPKSSDKTHTCPPCPAPEAEGA (SEQ ID NO: 68)
or
GGGGSGGGGSPKSSDKTHTCPPCPAPEAEGA (SEQ ID NO: 249).

Embodiment P42: A heterodimeric Fc-fused protein according to any one of embodiments P35 to P41, wherein the linker fusing the protein sequence to the first antibody Fc sequence consists of amino acid sequence EPKSSDKTHTCPPCPAPEAEGA (SEQ ID NO:11) or PKSSDKTHTCPPCPAPEAEGA (SEQ ID NO:240).

Embodiment P43: A heterodimeric Fc-fused protein according to any one of embodiments P1 to P17, wherein the first antibody Fc sequence and the second, different antibody Fc sequence are IgG4 Fc sequences mutated to promote heterodimerization with each other.

Embodiment P44: The heterodimeric Fc-fused protein of embodiment P43, wherein the first antibody Fc sequence comprises one or more mutation(s) selected from the group consisting of K370E, R409W, and a combination thereof, and the second, different antibody Fc sequence comprises one or more mutation(s) selected from the group consisting of E357N, D399V, F405T, and any combination(s) thereof.

Embodiment P45: The heterodimeric Fc-fused protein of embodiment P43, wherein the first antibody Fc sequence comprises one or more mutation(s) selected from the group consisting of E357N, D399V, F405T, and any combination(s) thereof, and the second, different antibody Fc sequence comprises one or more mutation(s) selected from the group consisting of K370E, R409W, and a combination thereof.

Embodiment P46: The heterodimeric Fc-fused protein of embodiment P43, wherein the first antibody Fc sequence comprises mutations K370E and R409W, and the second, different antibody Fc sequence comprises mutations E357N, D399V, and F405T.

Embodiment P47: The heterodimeric Fc-fused protein of embodiment P43, wherein the first antibody Fc sequence comprises mutations E357N, D399V, and F405T, and the second, different antibody Fc sequence comprises mutations K370E and R409W.

Embodiment P48: The heterodimeric Fc-fused protein of embodiment P43, wherein the first antibody Fc sequence comprises one or more mutation(s) selected from the group consisting of K360E, R409W, and a combination thereof, and the second, different antibody Fc sequence comprises one or more mutation(s) selected from the group consisting of Q347R, D399V, F405T, and any combination(s) thereof.

Embodiment P49 The heterodimeric Fc-fused protein of embodiment P43, wherein the first antibody Fc sequence comprises one or more mutation(s) selected from the group consisting of Q347R, D399V, F405T, and any combination(s) thereof, and the second, different antibody Fc sequence comprises one or more mutation(s) selected from the group consisting of K360E, R409W, and a combination thereof.

Embodiment P50: The heterodimeric Fc-fused protein of embodiment P43, wherein the first antibody Fc sequence comprises mutations K360E and R409W, and the second, different antibody Fc sequence comprises mutations Q347R, D399V, and F405T.

Embodiment P51: The heterodimeric Fc-fused protein of embodiment P43, wherein the first antibody Fc sequence comprises mutations Q347R, D399V, and F405T, and the second, different antibody Fc sequence comprises mutations K360E and R409W.

Embodiment P52: A heterodimeric Fc-fused protein according to any one of embodiments P18 to P42, wherein the first antibody Fc sequence and the second, different antibody Fc sequence are IgG1 Fc sequence are mutated to promote heterodimerization with each other.

Embodiment P53: The heterodimeric Fc-fused protein of embodiment P52, wherein the first antibody Fc sequence comprises one or more mutation(s) selected from the group consisting of K360E, K409W, and a combination thereof, and the second, different antibody Fc sequence comprises one or more mutation(s) selected from the group consisting of Q347R, D399V, F405T, and any combination(s) thereof.

Embodiment P54: The heterodimeric Fc-fused protein of embodiment P52, wherein the first antibody Fc sequence comprises one or more mutation(s) selected from the group consisting of Q347R, D399V, F405T, and any combination(s) thereof, and the second, different antibody Fc sequence comprises one or more mutation(s) selected from the group consisting of K360E, K409W, and a combination thereof.

Embodiment P55: The heterodimeric Fc-fused protein of embodiment P52, wherein the first antibody Fc sequence comprises mutations K360E and K409W, and the second, different antibody Fc sequence comprises mutations Q347R, D399V, and F405T.

Embodiment P56: The heterodimeric Fc-fused protein of embodiment P52, wherein the first antibody Fc sequence comprises mutations Q347R, D399V, and F405T, and the second, different antibody Fc sequence comprises mutations K360E and K409W.

Embodiment P57: A heterodimeric Fc-fused protein according to any one of embodiments P43 to P56, wherein the IgG4 or IgG1 Fc sequences are further mutated to reduce effector functions.

Embodiment P58: The heterodimeric Fc-fused protein of embodiment P57, wherein the first antibody Fc sequence and the second, different antibody Fc sequence each comprise the mutation L234A, L235A or L235E, and/or P329A.

Embodiment P59: The heterodimeric Fc-fused protein of embodiment P57 or embodiment P58, wherein the first antibody Fc sequence and the second, different antibody Fc sequence each comprise one or more mutation(s) selected from the group consisting of G237A, A330S, P331S, and any combination(s) thereof.

Embodiment P60: The heterodimeric Fc-fused protein of embodiment P57 or embodiment P58, wherein the first antibody Fc sequence and the second, different antibody Fc sequence each comprise the mutations G237A, A330S, and P331S.

Embodiment P61: A heterodimeric Fc-fused protein according to any one of embodiments P43 to P60, wherein the IgG4 or IgG1 Fc sequences are further mutated to introduce an inter-chain disulfide bridge.

Embodiment P62: The heterodimeric Fc-fused protein of embodiment P61, wherein the first antibody Fc sequence comprises mutation Y349C, and the second, different antibody Fc sequence comprises mutation S354C.

Embodiment P63: The heterodimeric Fc-fused protein of embodiment P61, wherein the first antibody Fc sequence comprises mutation S354C, and the second, different antibody Fc sequence comprises mutation Y349C.

Embodiment P64: The heterodimeric Fc-fused protein of any one of embodiments P1 to P63, wherein the subunit of a multisubunit protein is a subunit of a multisubunit cytokine.

Embodiment P65 The heterodimeric Fc-fused protein of embodiment P64, wherein the cytokine is IL-12.

Embodiment P66: A heterodimeric Fc-fusion protein according to any one of embodiments P1 to P65, further comprising at least one antibody variable domain.

Embodiment P67: The heterodimeric Fc-fusion protein according to embodiment P66, wherein the at least one antibody heavy chain variable region is connected to an antibody light chain variable region to form an Fab, wherein the Fab is connected at the N-terminus of the first antibody Fc sequence and/or the second, different antibody Fc sequence.

Embodiment P68: The heterodimeric Fc-fusion protein according to embodiment P67, wherein the protein sequence of a subunit of a multisubunit protein and the additional subunit of the multisubunit protein are connected to the C-terminus of the first antibody Fc sequence and the second, different antibody Fc sequence, respectively.

Embodiment P69: The heterodimeric Fc-fusion protein according to embodiment P67, wherein the protein sequence of a subunit of a multisubunit protein and the additional subunit of the multisubunit protein are connected to the C-terminus of the second, different antibody Fc sequence and the first antibody Fc sequence, respectively.

Embodiment P70: A heterodimeric Fc-fusion protein according to embodiment P66, wherein the first polypeptide comprises an antibody heavy chain variable domain positioned C-terminal to the first antibody Fc sequence.

Embodiment P71: A heterodimeric Fc-fusion protein according to embodiment P66 or embodiment P70, wherein the second polypeptide comprises an antibody heavy chain variable domain positioned C-terminal to the second, different antibody Fc sequence.

Embodiment P72: The heterodimeric Fc-fusion protein according to embodiment P70 or embodiment P71, wherein the antibody heavy chain variable region is connected to an antibody light chain variable region to form an scFv.

Embodiment P73: The heterodimeric Fc-fusion protein according to any one of embodiments P70 to 72, wherein the protein sequence of a subunit of a multisubunit protein and the additional subunit of the multisubunit protein are connected to the N-terminus of the first antibody Fc sequence and the second, different antibody Fc sequence, respectively.

Embodiment P74: The heterodimeric Fc-fusion protein according to any one of embodiments P70 to P72, wherein the protein sequence of a subunit of a multisubunit protein and the additional subunit of the multisubunit protein are connected to the N-terminus of the second, different antibody Fc sequence and the first antibody Fc sequence, respectively.

Embodiment P75: A heterodimeric Fc-fusion protein according to any one of embodiments P1 to P65 not comprising an antibody variable domain.

Embodiment P76: The heterodimeric Fc-fusion protein according to any one of embodiments P1 to P65 or embodiment P75, further comprising a proteoglycan-binding domain.

Embodiment P77: The heterodimeric Fc-fusion protein according to embodiment P76, wherein the proteoglycan-binding domain binds one or more proteoglycans that are specifically expressed in a tumor.

Embodiment P78: The heterodimeric Fc-fusion protein according to embodiment P77, wherein the proteoglycan-binding domain binds one or more proteoglycans selected from syndecan, serglycin, CSPG4, betaglycan, glypican, perlecan, versican, brevican, and small leucine-rich proteoglycans (SLRPs).

Embodiment P79: The heterodimeric Fc-fusion protein according to embodiment P78, wherein the SLRPs are selected from decorin, biglycan, asporin, fibrodulin, and lumican.

Embodiment P80: The heterodimeric Fc-fusion protein according to any one of embodiments P1 to P65 or embodiments P75 to P79, further comprising a collagen-binding domain.

Embodiment P81: The heterodimeric Fc-fusion protein according to embodiment P80, wherein the collagen-binding domain binds one or more collagens that are specifically expressed in a tumor.

Embodiment P82: The heterodimeric Fc-fusion protein according to any one of embodiments P1 to P65 or embodiments P75 to P81, further comprising a hyaluronic acid-binding domain.

Embodiment P83: The heterodimeric Fc-fusion protein according to any one of embodiments P76 to P82, wherein the proteoglycan-binding domain, collagen-binding domain, or hyaluronic acid-binding domain is fused to the C-terminus of the first antibody Fc domain polypeptide or the second antibody Fc domain polypeptide.

Embodiment P84: A formulation comprising a heterodimeric Fc-fused protein according to any one of the preceding embodiments and a pharmaceutically acceptable carrier.

Embodiment P85: A cell comprising one or more nucleic acid(s) encoding a heterodimeric Fc-fused protein according to any one of embodiments P1 to P83.

Embodiment P86: A method of treating cancer, wherein the method comprises administering a heterodimeric Fc-fused protein according to any one of embodiments P1to P83 or a formulation according to embodiment P84 to a patient.

Embodiment P87: A method of treating acute radiation syndrome, wherein the method comprises administering a heterodimeric Fc-fused protein according to any one of embodiments P1 to P83 or a formulation according to embodiment P84 to a patient.

Embodiment P88: The method of embodiment P87, wherein the acute radiation syndrome comprises one or more syndrome(s) selected from the group consisting of hematopoietic radiation syndrome, gastrointestinal radiation syndrome, neurovascular radiation syndrome, cutaneous radiation syndrome, and any combination(s) thereof.

Embodiment P89: A heterodimeric Fc-fused protein comprising a first polypeptide comprising the amino acid sequence of SEQ ID NO:290 and a second polypeptide comprising the amino acid sequence of SEQ ID NO:291.

Embodiment P90: A polypeptide comprising a subunit of a multisubunit cytokine and an immunoglobulin Fc domain polypeptide, wherein the Fc domain polypeptide comprises mutations for promoting heterodimerization with a different immunoglobulin Fc domain polypeptide, and one or more mutation(s) that reduce(s) an effector function of an Fc.

Embodiment P91: The polypeptide of embodiment P90, wherein the Fc domain is a human IgG1 antibody Fc domain.

Embodiment P92: The polypeptide of embodiment P91, wherein the one or more mutation(s) that reduce(s) an effector function of an Fc is selected from L234A, L235A or L235E, G237A, P329A, A330S, and P331S, numbered according to the EU numbering system.

Embodiment P93: The polypeptide of embodiment P91 or embodiment P92, wherein the mutations that reduce an effector function of an Fc are L234A, L235A, and P329A, numbered according to the EU numbering system.

Embodiment P94: The polypeptide of any one of embodiments P91-P93, wherein the mutations for promoting heterodimerization are K360E and K409W, numbered according to the EU numbering system.

Embodiment P95: The polypeptide of any one of embodiments P91-P93, wherein the mutations for promoting heterodimerization are Q347R, D399V, and F405T, numbered according to the EU numbering system.

Embodiment P96: The polypeptide of embodiment P94 or P95, wherein the Fc domain further comprises a mutation for promoting disulfide bond formation with a different immunoglobulin Fc domain polypeptide.

Embodiment P97: The polypeptide of embodiment P96, wherein when the heterodimerization mutations are K360E and K409W, the mutation for promoting disulfide bond formation is Y349C, numbered according to the EU numbering system.

Embodiment P98: The polypeptide of embodiment P96, wherein when the heterodimerization mutations are Q347R, D399V, and F405T, the mutation for promoting disulfide bond formation is S354C, numbered according to the EU numbering system.

Embodiment P99: The polypeptide of embodiment P97 comprising an amino acid sequence of SEQ ID NO:290.

Embodiment P100: The polypeptide of embodiment P98 comprising an amino acid sequence of SEQ ID NO:291.

Embodiment P101: The polypeptide of any one of embodiments P90-P100 further comprising an antibody variable domain.

Embodiment P102: The polypeptide of embodiment P101, wherein the antibody variable domain comprises an antibody heavy chain variable domain.

Embodiment P103: The polypeptide of embodiment P102, wherein the antibody heavy chain variable domain is fused to the N-terminus of the polypeptide.

Embodiment P104: The polypeptide of embodiment P103, wherein the antibody heavy chain variable domain binds an antibody light chain variable domain to form an Fab.

Embodiment P105: The polypeptide of embodiment P103, wherein the antibody heavy chain variable domain is further fused to an antibody light chain variable domain to form an scFv.

Embodiment P106: The polypeptide of any one of embodiments P101-P105, wherein the subunit of the multisubunit cytokine is fused to the C-terminus of the immunoglobulin Fc domain.

Embodiment P107: The polypeptide of embodiment P101, wherein the antibody heavy chain variable domain is fused to the C-terminus of the polypeptide.

Embodiment P108: The polypeptide of embodiment P107, wherein the antibody heavy chain variable domain is further fused to an antibody light chain variable domain to form an scFv.

Embodiment P109: The polypeptide of embodiment P107 or P108, wherein the subunit of the multi-subunit cytokine is fused to the N-terminus of the immunoglobulin Fc domain.

Embodiment P110: A polypeptide of any one of embodiments P90-P100 not comprising an antibody variable domain.

Embodiment P111: A polypeptide of any one of embodiments P90-P100 or P110, further comprising a proteoglycan-binding domain.

Embodiment P112: The polypeptide of embodiment P111, wherein the proteoglycan-binding domain binds one or more proteoglycan(s) specifically expressed in a tumor.

Embodiment P113: The polypeptide of embodiment P112, wherein the proteoglycan-binding domain binds one or more proteoglycan(s) selected from syndecan, serglycin, CSPG4, betaglycan, glypican, perlecan, versican, brevican, and small leucine-rich proteoglycans (SLRPs).

Embodiment P114: The polypeptide of embodiment P113, wherein the SLRPs are selected from decorin, biglycan, asporin, fibrodulin, and lumican.

Embodiment P115: The polypeptide of any one of embodiments P90-P100, or 110-114, further comprising a collagen-binding domain.

Embodiment P116: The polypeptide of embodiment P115, wherein the collagen-binding domain binds one or more collagen(s) specifically expressed in a tumor.

Embodiment P117: The polypeptide of any one of embodiments P90-P100, or 110-116, further comprising a hyaluronic acid-binding domain.

Embodiment P118: The polypeptide of any one of embodiments P111-P117, wherein the proteoglycan-binding domain, collagen-binding domain, or hyaluronic acid-binding domain is fused to the C-terminus of the polypeptide.

Embodiment P119: A nucleic acid encoding a polypeptide comprising the amino acid sequence of SEQ ID NO:290 or SEQ ID NO:291 according to any one of embodiments P89-P118.

Embodiment P120: An expression vector comprising a nucleic acid comprising a sequence encoding a polypeptide comprising the amino acid sequence of SEQ ID NO:290 or SEQ ID NO:291, according to any one of embodiments P89-P118.

Embodiment P121: A cell comprising a nucleic acid of embodiment P119 or an expression vector of embodiment P120.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A heterodimeric Fc-fused protein comprising:
   (a) a first polypeptide comprising a first human IgG1 Fc domain polypeptide and a first subunit of a multisubunit protein,
   wherein the first human IgG1 Fc domain polypeptide comprises CH3 domain substitutions Y349C, K360E, and K409W, numbered according to the EU numbering system,
   wherein the first subunit of the multisubunit protein is a p40 subunit of human IL-12,
   wherein the first polypeptide comprises a linker connecting the first human IgG1 Fc domain polypeptide and the first subunit of the multisubunit protein,
   wherein the linker of the first polypeptide comprises amino acid sequence PKSSDKTHTCPPCPAPEAAGG (SEQ ID NO:239), and
   wherein the first polypeptide comprises amino acid sequence SEQ ID NO:290; and
   (b) a second polypeptide comprising a second human IgG1 Fc domain polypeptide and a second, different subunit of the multisubunit protein,
   wherein the second human IgG1 Fc domain polypeptide comprises CH3 domain substitutions Q347R, D399V, F405T, and S354C, numbered according to the EU numbering system,
   wherein the second, different subunit of the multisubunit protein is a p35 subunit of human IL-12,
   wherein the second polypeptide comprises a linker connecting the second human IgG1 Fc domain polypeptide and the second, different subunit of the multisubunit protein,
   wherein the linker of the second polypeptide comprises amino acid sequence

GGGGSGGGGSGGGGSEPKSSDKTHTCPPCPAPEAAGG; (SEQ ID NO: 10)

and
   wherein the second polypeptide comprises amino acid sequence SEQ ID NO:291;
   wherein the first human IgG1 Fc domain polypeptide and the second human IgG1 Fc domain polypeptide each comprise CH2 domain substitutions L234A, L235A, and P329A, numbered according to the EU numbering system, and
   wherein the first subunit and the second, different subunit of the multisubunit protein are bound to each other.

2. The heterodimeric Fc-fused protein of claim 1, wherein
   (a) the first polypeptide consists of amino acid sequence SEQ ID NO:290; and
   (b) the second polypeptide consists of amino acid sequence SEQ ID NO:291.

3. The heterodimeric Fc-fused protein of claim 1, wherein the second polypeptide consists of amino acid sequence SEQ ID NO:291.

4. The heterodimeric Fc-fused protein of claim 1, wherein the first polypeptide consists of amino acid sequence SEQ ID NO:290.

5. A pharmaceutical composition comprising a heterodimeric Fc-fused protein and a pharmaceutically acceptable carrier, wherein the heterodimeric Fc-fused protein comprises:
   (a) a first polypeptide comprising a first human IgG1 Fc domain polypeptide and a first subunit of a multisubunit protein,
   wherein the first human IgG1 Fc domain polypeptide comprises CH3 domain substitutions Y349C, K360E, and K409W, numbered according to the EU numbering system,
   wherein the first subunit of the multisubunit protein is a p40 subunit of human IL-12,
   wherein the first polypeptide comprises a linker connecting the first human IgG1 Fc domain polypeptide and the first subunit of the multisubunit protein,
   wherein the linker of the first polypeptide comprises amino acid sequence PKSSDKTHTCPPCPAPEAAGG (SEQ ID NO:239), and
   wherein the first polypeptide comprises amino acid sequence SEQ ID NO:290; and
   (b) a second polypeptide comprising a second human IgG1 Fc domain polypeptide and a second, different subunit of the multisubunit protein,
   wherein the second human IgG1 Fc domain polypeptide comprises CH3 domain substitutions Q347R, D399V, F405T, and S354C, numbered according to the EU numbering system, wherein the second, different subunit of the multisubunit protein is a p35 subunit of human IL-12, wherein the second polypeptide comprises a linker connecting the second human IgG1 Fc domain polypeptide and the second, different subunit of the multisubunit protein, wherein the linker of the second polypeptide comprises amino acid sequence

```
                                          (SEQ ID NO: 10)
GGGGSGGGGSGGGGSEPKSSDKTHTCPPCPAPEAAGG;
``` and wherein the second polypeptide comprises amino acid sequence SEQ ID NO:291;

wherein the first human IgG1 Fc domain polypeptide and the second human IgG1 Fc domain polypeptide each comprise CH2 domain substitutions L234A, L235A, and P329A, numbered according to the EU numbering system, and wherein the first subunit and the second, different subunit of the multisubunit protein are bound to each other.

6. The pharmaceutical composition of claim 5, wherein
(a) the first polypeptide consists of amino acid sequence SEQ ID NO:290; and
(b) the second polypeptide consists of amino acid sequence SEQ ID NO:291.

7. The pharmaceutical composition of claim 5, wherein the composition is suitable for intravenous, subcutaneous, intraperitoneal, or intratumoral administration.

8. The pharmaceutical composition of claim 5, wherein the second polypeptide consists of amino acid sequence SEQ ID NO:291.

9. The pharmaceutical composition of claim 5, wherein the first polypeptide consists of amino acid sequence SEQ ID NO:290.

10. The pharmaceutical composition of claim 5, wherein the composition is suitable for intravenous administration.

11. The pharmaceutical composition of claim 5, wherein the composition is suitable for subcutaneous administration.

12. The pharmaceutical composition of claim 5, wherein the composition is suitable for intraperitoneal administration.

13. The pharmaceutical composition of claim 5, wherein the composition is suitable for intratumoral administration.

* * * * *